(12) United States Patent
Montgomery et al.

(10) Patent No.: US 7,956,237 B2
(45) Date of Patent: Jun. 7, 2011

(54) GENE DISRUPTIONS, COMPOSITIONS AND METHODS RELATING THERETO

(75) Inventors: Charles Montgomery, Jay, OK (US); Zheng-Zheng Shi, The Woodlands, TX (US); Mary Jean Sparks, Magnolia, TX (US)

(73) Assignee: Genentech, Inc., South San Francisco, CA (US)

( * ) Notice: Subject to any disclaimer, the term of this patent is extended or adjusted under 35 U.S.C. 154(b) by 205 days.

(21) Appl. No.: 11/572,702

(22) PCT Filed: Aug. 23, 2005

(86) PCT No.: PCT/US2005/029782
§ 371 (c)(1),
(2), (4) Date: Jan. 25, 2007

(87) PCT Pub. No.: WO2006/026222
PCT Pub. Date: Mar. 9, 2006

(65) Prior Publication Data
US 2008/0160034 A1 Jul. 3, 2008

Related U.S. Application Data

(60) Provisional application No. 60/604,323, filed on Aug. 25, 2004.

(51) Int. Cl.
*G01N 33/00* (2006.01)
*A01K 67/027* (2006.01)

(52) U.S. Cl. ............................................. 800/3; 800/18
(58) Field of Classification Search .................. 800/3, 18
See application file for complete search history.

(56) References Cited

U.S. PATENT DOCUMENTS

| | | | |
|---|---|---|---|
| 7,378,507 B2 * | 5/2008 | Ferrara et al. ................. | 530/399 |
| 2003/0104558 A1 | 6/2003 | Ashkenazi et al. | |

FOREIGN PATENT DOCUMENTS

| | | |
|---|---|---|
| WO | WO 00/53753 | 9/2000 |
| WO | 02/40662 | 5/2002 |
| WO | 2005/112619 A2 | 1/2005 |
| WO | 2005/112619 A3 | 1/2005 |
| WO | WO2005/058028 | 6/2005 |
| WO | WO2005/079566 | 9/2005 |

OTHER PUBLICATIONS

Wall, R. J., 1996, Theriogenology, vol. 45, p. 45-68.*
Houdebine, L-M., 2002, Journal of Biotechnology, vol. 98, p. 145-160.*
Sigmund, C., Jun. 2000, Arterioscler. Thromb. Vasc. Biol., p. 1425-1429.*
Rescher et al., 2004, Journal of Cell Science, vol. 117, p. 2631-2639.*
Mogil et al., 1999, Pain, vol. 80, pp. 67-82.*
Schalkwyk et al., 2007, Genes, Brain and Behavior, vol. 6, p. 299-303.*
Olsen et al., 2000, GABA in the Nervous System: the View at Fifty Years/ Editors, David I. Martin, Richard W. Olsen, Chapter 6: Function of GABA Receptors, Insight from Mutant and Knockout Mice, p. 81-95, Lippincott Williams & Wilkins, Philadelphia.*
Abu-Elheiga, L. et al., "Continuous Fatty Acid Oxidation and Reduced Fat Storage in Mice Lacking Acetyl-CoA Carboxylase 2" *Science* 291(5513) :2613-16 (Mar. 30, 2001).
Bouillet et al., "Developmental expression pattern of Stra6, a retinoic acid-responsive gene encoding a new type of membrane protein" *Mech Dev*. 63(2) :173-86 (May 1997).
Chazaud et al., "Restricted expression of a novel retinoic acid responsive gene during limb bud dorsoventral patterning and endochondral ossification" *Dev Genet*. 19(1) :66-73 (1996).
Chinnaiyan et al., "Signal transduction by DR3, a death domain-containing receptor related to TNFR-1 and CD95" *Science* 274(5289) :990-2 (Nov. 8, 1996).
DeLorey, T.M. et al., "Mice lacking the β3 subunit of the GABBA receptor have the epilepsy phenotype and many of the behavorial characteristics of Angelman syndrome." *J Neurosci*. 18(20):8505-14 (Oct. 15, 1998).
Eerdewegh et al., "Association of the ADAM33 gene with asthma and bronchial hyperresponsiveness" *Nature* 418(6896):426-30 (Jul. 25, 2002).
Esther, R.C. et al., "Mice Lacking angiotensin-converting enzyme have low blood pressure, renal pathology, and reduced male fertility." *Laboratory Investigation* 74(5):953-65 (May 1996).
Fisher et al., "Counteracting the Nogo receptor enhances optic nerve regeneration if retinal ganglion cells are in an active growth state" *J Neurosci*. 24(7):1646-51 (Feb. 18, 2004).
Fournier et al., "Identification of a receptor mediating Nogo-66 inhibition of axonal regeneration" *Nature* 409(6818):341-6 (Jan. 18, 2001).
Fukami et al., "Isolation of the mouse Tsll1 and Tsll2 genes, orthologues of the human TSLC1-like genes 1 and 2 (TSLL1 and TSLL2)" *Gene* 323:11-8 (Dec. 24, 2003). Fukuhara et al., "Isolation of the TSLL1 and TSLL2 genes, members of the tumor suppressor TSLC1 gene family encoding transmembrane proteins" *Oncogene* 20(38):5401-7 (Aug. 30, 2001).
Ganz, "Hepcidin, a key regulator of iron metabolism and mediator of anemia of inflammation" *Blood* 102(3):783-8 (Aug. 1, 2003).
Garlisi et al., "Human ADAM33: protein maturation and localization" *Biochem Biophys Res Commun*. 301(1):35-43 (Jan. 31, 2003).
Gelius et al., "A mammalian peptidoglycan recognition protein with N-acetylmuramoyl-L-alanine amidase activity" *Biochem Biophys Res Commun*. 306(4):988-94 (Jul. 11, 2003).

(Continued)

Primary Examiner — Shin-Lin Chen
(74) Attorney, Agent, or Firm — Bonny Yeung; James A. Fox; Ginger R. Dreger

(57) ABSTRACT

The present invention relates to transgenic animals, as well as compositions and methods relating to the characterization of gene function. Specifically, the present invention provides transgenic mice comprising disruptions in PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 genes. Such in vivo studies and characterizations may provide valuable identification and discovery of therapeutics and/or treatments useful in the prevention, amelioration or correction of diseases or dysfunctions associated with gene disruptions such as neurological disorders; cardiovascular, endothelial or angiogenic disorders; eye abnormalities; immunological disorders; oncological disorders; bone metabolic abnormalities or disorders; lipid metabolic disorders; or developmental abnormalities.

2 Claims, 73 Drawing Sheets

OTHER PUBLICATIONS

Glozak et al., "Trapping and characterization of novel retinoid response elements" *Mol Endocrinol.* 17(1):27-41 (Jan. 2003).

Gress et al., "Identification of genes with specific expression in pancreatic cancer by cDNA representational difference analysis" *Genes Chromosomes Cancer* 19(2):97-103 (Jun. 1997).

Grossman et al., "Identification of a ubiquitous family of membrane proteins and their expression in mouse brain" *J Exp Biol.* 203(Pt 3):447-57 (Feb. 2000).

Hirara et al., "Cloning of an immunoglobulin family adhesion molecule selectively expressed by endothelial cells" *J Biol Chem.* 276(19):16223-31 (May 11, 2001).

Ishida et al., "Targeted disruption of endothelial cell-selective adhesion molecule inhibits angiogenic processes in vitro and in vivo" *J Biol Chem.* 278(36):34598-604 (Sep. 5, 2003).

Kibardin et al., "The differentially spliced mouse tagL gene, homolog of tag7/PGRP gene family in mammals and Drosophila, can recognize Gram-positive and Gram-negative bacterial cell wall independently of T phage lysozyme homology domain" *J Mol Biol.* 326(2):467-74 (Feb. 14, 2003).

Kitson et al., "A death-domain-containing receptor that mediates apoptosis" *Nature* 384(6607):372-5 (Nov. 28, 1996).

Knauer and Lehle, "The oligosaccharyltransferase complex from *Saccharomyces cerevisiae*. Isolation of the OST6 gene, its synthetic interaction with OST3, and analysis of the native complex" *J Biol Chem.* 274(24):17249-56 (Jun. 11, 1999).

Krause et al., "Molecular cloning and characterization of murine Mpgc60, a gene predominantly expressed in the intestinal tract" *Differentiation* 63(5):285-94 (Sep. 1998).

Lai et al., "hSulf1 Sulfatase promotes apoptosis of hepatocellular cancer cells by decreasing heparin-binding growth factor signaling" *Gastroenterology* 126(1):231-48 (Jan. 2004).

Lai et al., "Loss of HSulf-1 up-regulates heparin-binding growth factor signaling in cancer" *J Biol Chem.* 278(25):23107-17 (Jun. 20, 2003).

Langenbach, R. et al., "Prostaglandin Synthase 1 Gene Disruption in Mice Reduces Arachidonic Acid-Induced Inflammation and Indomethancin-Induced Gastric Ulceration" *Cell* 83(3):483-92 (Nov. 3, 1995).

Lee et al., "Targeting the Nogo receptor to treat central nervous system injuries" *Nat Rev Drug Discov.* 2(11):872-8 (Nov. 2003).

Liu et al., "Myelin-associated glycoprotein as a functional ligand for the Nogo-66 receptor" *Science* 297(5584):1190-3 (Aug. 16, 2002).

Marchler-Bauer et al., "CDD: a curated Entrez database of conserved domain alignments" *Nucleic Acids Research* 31(1):383-7 (Jan. 1, 2003).

Margolis et al., "cDNAs with long CAG trinucleotide repeats from human brain" *Hum Genet.* 100(1):114-22 (Jul. 1997).

Mi et al., "LINGO-1 is a component of the Nogo-66 receptor/p75 signaling complex" *Nat Neurosci.* 7(3):221-8 (Mar. 2004).

Migone et al., "TL1A is a TNF-like ligand for DR3 and TR6/DcR3 and functions as a T cell costimulator" *Immunity* 16(3):479-92 (Mar. 2002).

Morimoto-Tomita at al., "Cloning and characterization of two extracellular heparin-degrading endosulfatases in mice and humans" *J Biol Chem.* 277(51):49175-85 (Dec. 20, 2002).

Naeve et al., "Neuritin: a gene induced by neural activity and neurotrophins that promotes neuritogenesis" *Proc Natl Acad Sci U S A.* 94(6):2648-53 (Mar. 18, 1997).

Nasdala, "A transmembrane tight junction protein selectively expressed on endothelial cells and platelets" *J Biol Chem.* 277(18):16294-303 (May 3, 2002).

Nicolas et al., "Constitutive hepcidin expression prevents iron overload in a mouse model of hemochromatosis" *Nat Genet.* 34(1):97-101 (May 2003).

Nicolas et al., "Lack of hepcidin gene expression and severe tissue iron overload in upstream stimulatory factor 2 (USF2) knockout mice" *Proc Natl Acad Sci U S A.* 98(15):8780-5 (Jul. 17, 2001).

Nicolas et al., "Severe iron deficiency anemia in transgenic mice expressing liver hepcidin" *Proc Natl Acad Sci U S A.* 99(7):4596-601 (Apr. 2, 2002).

Norberg et al., "Identification of the bioactive peptide PEC-60 in brain" *Cell Mol Life Sci.* 60(2):378-81 (Feb. 2003).

Piper and Little, "Movement through Slits: cellular migration via the Slit family" *Bioessays* 25(1):32-8 (Jan. 2003).

Player et al., "Identification of TDE2 gene and its expression in non-small cell lung cancer" *Int J Cancer.* 107(2):238-43 (Nov. 1, 2003).

Primakoff et al., "The ADAM gene family: surface proteins with adhesion and protease activity" *Trends Genet.* 16(2):83-7 (Feb. 2000).

Roetto et al., "Mutant antimicrobial peptide hepcidin is associated with severe juvenile hemochromatosis" *Nat Genet.* 33(1):21-2 (Jan. 2003).

Shingai et al., "Implications of nectin-like molecule-2/IGSF4/RA175/SgIGSF/TSLC1/SynCAM1 in cell-cell adhesion and transmembrane protein localization in epithelial cells" *J Biol Chem.* 278(37):35421-7 (Sep. 12, 2003).

Song et al., "Suppression of p75NTR does not promote regeneration of injured spinal cord in mice" *J Neurosci.* 24(2):542-6 (Jan. 14, 2004).

Steiglitz et al., "PCOLCE2 encodes a functional procollagen C-proteinase enhancer (PCPE2) that is a collagen-binding protein differing in distribution of expression and post-translational modification from the previously described PCPE1" *J Biol Chem.* 277(51):49820-30 (Dec. 20, 2002).

Sugiyama et al., "A novel low-density lipoprotein receptor-related protein mediating cellular uptake of apolipoprotein E-enriched beta-VLDL in vitro" *Biochemistry* 39(51):15817-25 (Dec. 26, 2000).

Szeto et al., "Overexpression of the retinoic acid-responsive gene Stra6 in human cancers and its synergistic induction by Wnt-1 and retinoic acid" *Cancer Research* 61(10):4197-205 (May 15, 2001).

Telo et al., "Identification of a novel cadherin (vascular endothelial cadherin-2) located at intercellular junctions in endothelial cells" *J Biol Chem.* 273(28):17565-72 (Jul. 10, 1998).

Thiel et al., "A new type of congenital disorders of glycosylation (CDG-Ii) provides new insights into the early steps of dolichol-linked oligosaccharide biosynthesis" *J Biol Chem.* 278(25):22498-505 (Jun. 20, 2003).

Tice et al., "Synergistic induction of tumor antigens by Wnt-1 signaling and retinoic acid revealed by gene expression profiling" *J Biol Chem.* 277(16):14329-35 (Apr. 19, 2002).

Wallrapp et al., "A novel transmembrane serine protease (TMPRSS3) overexpressed in pancreatic cancer" *Cancer Research* 60(10):2602-6 (May 15, 2000).

Wang et al., "DR3 regulates negative selection during thymocyte development" *Mol Cell Biol.* 21(10):3451-61 (May 2001).

Wang et al., "Oligodendrocyte-myelin glycoprotein is a Nogo receptor ligand that inhibits neurite outgrowth" *Nature* 417(6892):941-4 (Jun. 27, 2002).

Wang et al., "P75 interacts with the Nogo receptor as a co-receptor for Nogo, MAG and OMgp" *Nature* 420(6911):74-8 (Nov. 7, 2002).

Wen et al., "TL1A-induced NF-kappaB activation and c-IAP2 production prevent DR3-mediated apoptosis in TF-1 cells" *J Biol Chem.* 278(40):39251-8 (Oct. 3, 2003).

Wong et al., "A p75 (NTR) and Nogo receptor complex mediates repulsive signaling by myelin-associated glycoprotein" *Nat Neurosci.* 5(12):1302-8 (Dec. 2002).

Wu and Maniatis, "Large exons encoding multiple ectodomains are a characteristic feature of protocadherin genes" *Proc Natl Acad Sci U S A.* 97(7):3124-9 (Mar. 28, 2000).

Wu, H. et al., "Generation of Committed Erythroid BFU-E and CFU-E Progenitors Does Not Require Erythropoietin or the Erythropoietin Receptor" *Cell* 83(1):59-67 (Oct. 6, 1995).

Xu et al., "Identification and expression of a novel type I procollagen C-proteinase enhancer protein gene from the glaucoma candidate region on 3q21-q2" *Genomics* 66(3):264-73 (Jun. 15, 2000).

Yamakawa et al., "cDNA cloning of a novel trypsin inhibitor with similarity to pathogenesis-related proteins, and its frequent expression in human brain cancer cells" *Biochim Biophys Acta.* 1395(2):202-8 (Jan. 21, 1998).

Yoshinaka et al., "Identification and characterization of novel mouse and human ADAM33s with potential metalloprotease activity" *Gene* 282(1-2):227-36 (Jan. 9, 2002).

Capecchi, "Targeted Gene Replacement" *Scientific American* pp. 52-59 (Mar. 1994).

Capecchi, "Targeted Gene Replacement" Scientific American, Scientific American Inc., New York, NY, pp. 52-59 (1994).

\* cited by examiner

FIGURE 1

GGCTGAGGGGAGGCCCGGAGCCTTTCTGGGGCCTGGGGGATCCTCTTGCACTGGTGGGTGGAGAGAAGCGCCTG
CAGCCAACCAGGGTCAGGCTGTGCTCACAGTTTCCTCTGGCGGCATGTAAAGGCTCCACAAAGGAGTTGGGAGT
TCAAATGAGGCTGCTGCGGACGGCCTGAGGATGGACCCCAAGCCCTGGACCTGCCGAGCGTGGCACTGAGGCAG
CGGCTGACGCTACTGTGAGGGAAAGAAGGTTGTGAGCAGCCCCGCAGGACCCCTGGCCAGCCCTGGCCCCAGCC
TCTGCCGGAGCCCTCTGTGGAGGCAGAGCCAGTGGAGCCCAGTGAGGCAGGGCTGCTTGGCAGCCACCGGCCTG
CAACTCAGGAACCCCTCCAGAGGCCATGGACAGGCTGCCCCGCTGACGGCCAGGGTGAAGCATGTGAGGAGCCG
CCCCGGAGCCAAGCAGGAGGGAAGAGGCTTTCATAGATTCTATTCACAAAGAATAACCACCATTTTGCAAGGAC
CATGAGGCCACTGTGCGTGACATGCTGGTGGCTCGGACTGCTGGCTGCCATGGGAGCTGTTGCAGGCAGGAGG
ACGGTTTTGAGGGCACTGAGGAGGGCTCGCCAAGAGAGTTCATTTACCTAAACAGGTACAAGCGGGCGGGCGAG
TCCCAGGACAAGTGCACCTACACCTTCATTGTGCCCCAGCAGCGGGTCACGGGTGCCATCTGCGTCAACTCCAA
GGAGCCTGAGGTGCTTCTGGAGAACCGAGTGCATAAGCAGGAGCTAGAGCTGCTCAACAATGAGCTGCTCAAGC
AGAAGCGGCAGATCGAGACGCTGCAGCAGCTGGTGGAGGTGGACGGCGGCATTGTGAGCGAGGTGAAGCTGCTG
CGCAAGGAGAGCCGCAACATGAACTCGCGGGTCACGCAGCTCTACATGCAGCTCCTGCACGAGATCATCCGCAA
GCGGGACAACGCGTTGGAGCTCTCCCAGCTGGAGAACAGGATCCTGAACCAGACAGCCGACATGCTGCAGCTGG
CCAGCAAGTACAAGGACCTGGAGCACAAGTACCAGCACCTGGCCACACTGGCCCACAACCAATCAGAGATCATC
GCGCAGCTTGAGGAGCACTGCCAGAGGGTGCCCTCGGCCAGGCCCGTCCCCCAGCCACCCCCCGCTGCCCCGCC
CCGGGTCTACCAACCACCCACCTACAACCGCATCATCAACCAGATCTCTACCAACGAGATCCAGAGTGACCAGA
ACCTGAAGGTGCTGCCACCCCCTCTGCCCACTATGCCCACTCTCACCAGCCTCCCATCTTCCACCGACAAGCCG
TCGGGCCCATGGAGAGACTGCCTGCAGGCCCTGGAGGATGGCCACGACACCAGCTCCATCTACCTGGTGAAGCC
GGAGAACACCAACCGCCTCATGCAGGTGTGGTGCGACCAGAGACACGACCCCGGGGGCTGGACCGTCATCCAGA
GACGCCTGGATGGCTCTGTTAACTTCTTCAGGAACTGGGAGACGTACAAGCAAGGGTTTGGGAACATTGACGGC
GAATACTGGCTGGGCCTGGAGAACATTTACTGGCTGACGAACCAAGGCAACTACAAACTCCTGGTGACCATGGA
GGACTGGTCCGGCCGCAAAGTCTTTGCAGAATACGCCAGTTTCCGCCTGGAACCTGAGAGCGAGTATTATAAGC
TGCGGCTGGGGCGCTACCATGGCAATGCGGGTGACTCCTTTACATGGCACAACGGCAAGCAGTTCACCACCCTG
GACAGAGATCATGATGTCTACACAGGAAACTGTGCCCACTACCAGAAGGGAGGCTGGTGGTATAACGCCTGTGC
CCACTCCAACCTCAACGGGGTCTGGTACCGCGGGGGCCATTACCGGAGCCGCTACCAGGACGGAGTCTACTGGG
CTGAGTTCCGAGGAGGCTCTTACTCACTCAAGAAAGTGGTGATGATGATCCGACCGAACCCCAACACCTTCCAC
TAAGCCAGCTCCCCTCCTGACCTCTCGTGGCCATTGCCAGGAGCCCACCCTGGTCACGCTGGCCACAGCACAA
AGAACAACTCCTCACCAGTTCATCCTGAGGCTGGAGGACCGGGATGCTGGATTCTGTTTTCCGAAGTCACTGC
AGCGGATGATGGAACTGAATCGATACGGTGTTTTCTGTCCCTCCTACTTTCCTTCACACCAGACAGCCCCTCAT
   GTCTCCAGGACAGGACAGGACTACAGACAACTCTTTCTTTAAATAAATTAAGTCTCTACAATAAAAAAAA

FIGURE 2

></usr/seqdb2/sst/DNA/Dnaseqs.min/ss.DNA22779
><subunit 1 of 1, 493 aa, 1 stop
><MW: 57104, pI: 7.67, NX(S/T): 2
MRPLCVTCWWLGLLAAMGAVAGQEDGFEGTEEGSPREFIYLNRYKRAGESQDKCTYTFIVPQQRVTGAICVNSK
EPEVLLENRVHKQELELLNNELLKQKRQIETLQQLVEVDGGIVSEVKLLRKESRNMNSRVTQLYMQLLHEIIRK
RDNALELSQLENRILNQTADMLQLASKYKDLEHKYQHLATLAHNQSEIIAQLEEHCQRVPSARPVPQPPPAAPP
RVYQPPTYNRIINQISTNEIQSDQNLKVLPPPLPTMPTLTSLPSSTDKPSGPWRDCLQALEDGHDTSSIYLVKP
ENTNRLMQVWCDQRHDPGGWTVIQRRLDGSVNFFRNWETYKQGFGNIDGEYWLGLENIYWLTNQGNYKLLVTME
DWSGRKVFAEYASFRLEPESEYYKLRLGRYHGNAGDSFTWHNGKQFTTLDRDHDVYTGNCAHYQKGGWWYNACA
HSNLNGVWYRGGHYRSRYQDGVYWAEFRGGSYSLKKVVMMIRPNPNTFH
Important features of the protein:
Signal peptide:
amino acids 1-22
N-glycosylation sites.
amino acids 164-168, 192-196
cAMP- and cGMP-dependent protein kinase phosphorylation site.
amino acids 124-128
Tyrosine kinase phosphorylation sites.
amino acids 177-184, 385-393, 385-394, 461-468
N-myristoylation sites.
amino acids 12-18, 18-24, 22-28, 29-35, 114-120, 341-347, 465-471, 473-479
Amidation site.
amino acids 373-377
Fibrinogen beta and gamma chains C-terminal domain signature.
amino acids 438-451
Fibrinogen beta and gamma chains C-terminal domain proteins.
amino acids 305-343, 365-402, 411-424, 428-458
Trehalase proteins.
amino acids 275-292

FIGURE 3

CCAGGCCGGGAGGCGACGCGCCCAGCCGTCTAAACGGGAACAGCCCTGGCTGAGGGAGCTGCAGCGCAGCAGAG
TATCTGACGGCGCCAGGTTGCGTAGGTGCGGCACGAGGAGTTTTCCCGGCAGCGAGGAGGTCCTGAGCAGATG
GCCCGGAGGAGCGCCTTCCCTGCCGCCGCGCTCTGGCTCTGGAGCATCCTCCTGTGCCTGCTGGCACTGCGGGC
GGAGGCCGGGCCGCCGCAGGAGGAGAGCCTGTACCTATGGATCGATGCTCACCAGGCAAGAGTACTCATAGGAT
TTGAAGAAGATATCCTGATTGTTTCAGAGGGGAAAATGGCACCTTTTACACATGATTTCAGAAAAGCGCAACAG
AGAATGCCAGCTATTCCTGTCAATATCCATTCCATGAATTTTACCTGGCAAGCTGCAGGGCAGGCAGAATACTT
CTATGAATTCCTGTCCTTGCGCTCCCTGGATAAAGGCATCATGGCAGATCCAACCGTCAATGTCCCTCTGCTGG
GAACAGTGCCTCACAAGGCATCAGTTGTTCAAGTTGGTTTCCCATGTCTTGGAAAACAGGATGGGGTGGCAGCA
TTTGAAGTGGATGTGATTGTTATGAATTCTGAAGGCAACACCATTCTCCAAACACCTCAAAATGCTATCTTCTT
TAAAACATGTCAACAAGCTGAGTGCCCAGGCGGGTGCCGAAATGGAGGCTTTTGTAATGAAAGACGCATCTGCG
AGTGTCCTGATGGGTTCCACGGACCTCACTGTGAGAAAGCCCTTTGTACCCCACGATGTATGAATGGTGGACTT
TGTGTGACTCCTGGTTTCTGCATCTGCCCACCTGGATTCTATGGAGTGAACTGTGACAAAGCAAACTGCTCAAC
CACCTGCTTTAATGGAGGGACCTGTTTCTACCCTGGAAAATGTATTTGCCCTCCAGGACTAGAGGGAGAGCAGT
GTGAAATCAGCAAATGCCCACAACCCTGTCGAAATGGAGGTAAATGCATTGGTAAAAGCAAATGTAAGTGTTCC
AAAGGTTACCAGGGAGACCTCTGTTCAAAGCCTGTCTGCGAGCCTGGCTGTGGTGCACATGGAACCTGCCATGA
ACCCAACAAATGCCAATGTCAAGAAGGTTGGCATGGAAGACACTGCAATAAAAGGTACGAAGCCAGCCTCATAC
ATGCCCTGAGGCCAGCAGGCGCCCAGCTCAGGCAGCACACGCCTTCACTTAAAAAGGCCGAGGAGCGGCGGGAT
CCACCTGAATCCAATTACATCTGGTGAACTCCGACATCTGAAACGTTTTAAGTTACACCAAGTTCATAGCCTTT
GTTAACCTTTCATGTGTTGAATGTTCAAATAATGTTCATTACACTTAAGAATACTGGCCTGAATTTTATTAGCT
TCATTATAAATCACTGAGCTGATATTTACTCTTCCTTTTAAGTTTTCTAAGTACGTCTGTAGCATGATGGTATA
GATTTCTTGTTTCAGTGCTTTGGGACAGATTTTATATTATGTCAATTGATCAGGTTAAAATTTTCAGTGTGTA
GTTGGCAGATATTTTCAAAATTACAATGCATTTATGGTGTCTGGGGCAGGGGAACATCAGAAAGGTTAAATTG
GGCAAAAATGCGTAAGTCACAAGAATTTGGATGGTGCAGTTAATGTTGAAGTTACAGCATTTCAGATTTTATTG
TCAGATATTTAGATGTTTGTTACATTTTTAAAAATTGCTCTTAATTTTTAAACTCTCAATACAATATATTTGA
CCTTACCATTATTCCAGAGATTCAGTATTAAAAAAAAAAAAATTACACTGTGGTAGTGGCATTTAAACAATATA
ATATATTCTAAACACAATGAAATAGGGAATATAATGTATGAACTTTTTGCATTGGCTTGAAGCAATATAATATA
TTGTAAACAAAACACAGCTCTTACCTAATAAACATTTTATACTGTTTGTATGTATAAAATAAAGGTGCTGCTTT
AGTTTTTTGGAAAAAAAAAAAAAAAAAAAAAAAAAA

FIGURE 4

Signal sequence:                              Amino acids 1-28

N-glycosylation sites:                        Amino acids 88-92;245-249

Tyrosine kinase phosphorylation site:         Amino acids 370-378

N-myristoylation sites:                       Amino acids 184-190;185-191;
                                              189-195;315-321

ATP/GTP-binding site motif A (P-loop):        Amino acids 285-293

EGF-like domain cysteine pattern signatures:
                                              Amino acids 198-210;230-242;
                                              262-274;294-306;326-338

MARRSAFPAAALWLWSILLCLLALRAEAGPPQEESLYLWIDAHQARVLIGFEEDILIVSEGKMAPFTHDFRKAQ
QRMPAIPVNIHSMNFTWQAAGQAEYFYEFLSLRSLDKGIMADPTVNVPLLGTVPHKASVVQVGFPCLGKQDGVA
AFEVDVIVMNSEGNTILQTPQNAIFFKTCQQAECPGGCRNGGFCNERRICECPDGFHGPHCEKALCTPRCMNGG
LCVTPGFCICPPGFYGVNCDKANCSTTCFNGGTCFYPGKCICPPGLEGEQCEISKCPQPCRNGGKCIGKSKCKC
SKGYQGDLCSKPVCEPGCGAHGTCHEPNKCQCQEGWHGRHCNKRYEASLIHALRPAGAQLRQHTPSLKKAEERR
DPPESNYIW

FIGURE 5

GGGGTCTCCCTCAGGGCCGGGAGGCACAGCGGTCCCTGCTTGCTGAAGGGCTGGATGTACGCATCCGCAGGTTC
CCGCGGACTTGGGGGCGCCCGCTGAGCCCCGGCGCCCGCAGAAGACTTGTGTTTGCCTCCTGCAGCCTCAACCC
GGAGGGCAGCGAGGGCCTACCACCATGATCACTGGTGTGTTCAGCATGCGCTTGTGGACCCCAGTGGGCGTCCT
GACCTCGCTGGCGTACTGCCTGCACCAGCGGCGGGTGGCCCTGGCCGAGCTGCAGGAGGCCGATGGCCAGTGTC
CGGTCGACCGCAGCCTGCTGAAGTTGAAAATGGTGCAGGTCGTGTTTCGACACGGGGCTCGGAGTCCTCTCAAG
CCGCTCCCGCTGGAGGAGCAGGTAGAGTGGAACCCCCAGCTATTAGAGGTCCCACCCCAAACTCAGTTTGATTA
CACAGTCACCAATCTAGCTGGTGGTCCGAAACCATATTCTCCTTACGACTCTCAATACCATGAGACCACCCTGA
AGGGGGGCATGTTTGCTGGGCAGCTGACCAAGGTGGGCATGCAGCAAATGTTTGCCTTGGGAGAGAGACTGAGG
AAGAACTATGTGGAAGACATTCCCTTTCTTTCACCAACCTTCAACCCACAGGAGGTCTTTATTCGTTCCACTAA
CATTTTTCGGAATCTGGAGTCCACCCGTTGTTTGCTGGCTGGGCTTTTCCAGTGTCAGAAAGAAGGACCCATCA
TCATCCACACTGATGAAGCAGATTCAGAAGTCTTGTATCCCAACTACCAAAGCTGCTGGAGCCTGAGGCAGAGA
ACCAGAGGCCGGAGGCAGACTGCCTCTTTACAGCCAGGAATCTCAGAGGATTTGAAAAAGGTGAAGGACAGGAT
GGGCATTGACAGTAGTGATAAAGTGGACTTCTTCATCCTCCTGGACAACGTGGCTGCCGAGCAGGCACACAACC
TCCCAAGCTGCCCCATGCTGAAGAGATTTGCACGGATGATCGAACAGAGAGCTGTGGACACATCCTTGTACATA
CTGCCCAAGGAAGACAGGGAAAGTCTTCAGATGGCAGTAGGCCCATTCCTCCACATCCTAGAGAGCAACCTGCT
GAAAGCCATGGACTCTGCCACTGCCCCCGACAAGATCAGAAAGCTGTATCTCTATGCGGCTCATGATGTGACCT
TCATACCGCTCTTAATGACCCTGGGGATTTTTGACCACAAATGGCCACCGTTTGCTGTTGACCTGACCATGGAA
CTTTACCAGCACCTGGAATCTAAGGAGTGGTTTGTGCAGCTCTATTACCACGGGAAGGAGCAGGTGCCGAGAGG
TTGCCCTGATGGGCTCTGCCCGCTGGACATGTTCTTGAATGCCATGTCAGTTTATACCTTAAGCCCAGAAAAAT
ACCATGCACTCTGCTCTCAAACTCAGGTGATGGAAGTTGGAAATGAAGAGTAACTGATTTATAAAAGCAGGATG
TGTTGATTTTAAAATAAAGTGCCTTTATACAATG

FIGURE 6

MITGVFSMRLWTPVGVLTSLAYCLHQRRVALAELQEADGQCPVDRSLLKLKMVQVVFRHGARSPLKPLPLEEQV
EWNPQLLEVPPQTQFDYTVTNLAGGPKPYSPYDSQYHETTLKGGMFAGQLTKVGMQQMFALGERLRKNYVEDIP
FLSPTFNPQEVFIRSTNIFRNLESTRCLLAGLFQCQKEGPIIIHTDEADSEVLYPNYQSCWSLRQRTRGRRQTA
SLQPGISEDLKKVKDRMGIDSSDKVDFFILLDNVAAEQAHNLPSCPMLKRFARMIEQRAVDTSLYILPKEDRES
LQMAVGPFLHILESNLLKAMDSATAPDKIRKLYLYAAHDVTFIPLLMTLGIFDHKWPPFAVDLTMELYQHLESK
EWFVQLYYHGKEQVPRGCPDGLCPLDMFLNAMSVYTLSPEKYHALCSQTQVMEVGNEE

Signal sequence:
amino acids 1-23 cAMP- and cGMP-dependent protein kinase phosphorylation site.
amino acids 218-222

Casein kinase II phosphorylation site.
amino acids 87-91, 104-108, 320-324

Tyrosine kinase phosphorylation site.
amino acids 280-288

N-myristoylation site.
amino acids 15-21, 117-123, 118-124, 179-185, 240-246, 387-393

Amidation site.
amino acids 216-220

Leucine zipper pattern.
amino acids 10-32

Histidine acid phosphatases phosphohistidine signature.
amino acids 50-65

FIGURE 7

```
AGGCTCCCGCGCGCGGCTGAGTGCGGACTGGAGTGGGAACCCGGGTCCCCGCGCTTAGAGAACACGCGATGACC
ACGTGGAGCCTCCGGCGGAGGCCGGCCCGCACGCTGGGACTCCTGCTGCTGGTCGTCTTGGGCTTCCTGGTGCT
CCGCAGGCTGGACTGGAGCACCCTGGTCCCTCTGCGGCTCCGCCATCGACAGCTGGGGCTGCAGGCCAAGGGCT
GGAACTTCATGCTGGAGGATTCCACCTTCTGGATCTTCGGGGGCTCCATCCACTATTTCCGTGTGCCCAGGGAG
TACTGGAGGGACCGCCTGCTGAAGATGAAGGCCTGTGGCTTGAACACCCTCACCACCTATGTTCCGTGGAACCT
GCATGAGCCAGAAAGAGGCAAATTTGACTTCTCTGGGAACCTGGACCTGGAGGCCTTCGTCCTGATGGCCGCAG
AGATCGGGCTGTGGGTGATTCTGCGTCCAGGCCCCTACATCTGCAGTGAGATGGACCTCGGGGGCTTGCCCAGC
TGGCTACTCCAAGACCCTGGCATGAGGCTGAGGACAACTTACAAGGGCTTCACCGAAGCAGTGGACCTTTATTT
TGACCACCTGATGTCCAGGGTGGTGCCACTCCAGTACAAGCGTGGGGGACCTATCATTGCCGTGCAGGTGGAGA
ATGAATATGGTTCCTATAATAAAGACCCCGCATACATGCCCTACGTCAAGAAGGCACTGGAGGACCGTGGCATT
GTGGAACTGCTCCTGACTTCAGACAACAAGGATGGGCTGAGCAAGGGGATTGTCCAGGGAGTCTTGGCCACCAT
CAACTTGCAGTCAACACACGAGCTGCAGCTACTGACCACCTTTCTCTTCAACGTCCAGGGGACTCAGCCCAAGA
TGGTGATGGAGTACTGGACGGGGTGGTTTGACTCGTGGGGAGGCCCTCACAATATCTTGGATTCTTCTGAGGTT
TTGAAAACCGTGTCTGCCATTGTGGACGCCGGCTCCTCCATCAACCTCTACATGTTCCACGGAGGCACCAACTT
TGGCTTCATGAATGGAGCCATGCACTTCCATGACTACAAGTCAGATGTCACCAGCTATGACTATGATGCTGTGC
TGACAGAAGCCGGCGATTACACGGCCAAGTACATGAAGCTTCGAGACTTCTTCGGCTCCATCTCAGGCATCCCT
CTCCCTCCCCCACCTGACCTTCTTCCCAAGATGCCGTATGAGCCCTTAACGCCAGTCTTGTACCTGTCTCTGTG
GGACGCCCTCAAGTACCTGGGGGAGCCAATCAAGTCTGAAAAGCCCATCAACATGGAGAACCTGCCAGTCAATG
GGGGAAATGGACAGTCCTTCGGGTACATTCTCTATGAGACCAGCATCACCTCGTCTGGCATCCTCAGTGGCCAC
GTGCATGATCGGGGGCAGGTGTTTGTGAACACAGTATCCATAGGATTCTTGGACTACAAGACAACGAAGATTGC
TGTCCCCCTGATCCAGGGTTACACCGTGCTGAGGATCTTGGTGGAGAATCGTGGGCGAGTCAACTATGGGGAGA
ATATTGATGACCAGCGCAAAGGCTTAATTGGAAATCTCTATCTGAATGATTCACCCCTGAAAAACTTCAGAATC
TATAGCCTGGATATGAAGAAGAGCTTCTTTCAGAGGTTCGGCCTGGACAAATGGNGTTCCCTCCCAGAAACACC
CACATTACCTGCTTTCTTCTTGGGTAGCTTGTCCATCAGCTCCACGCCTTGTGACACCTTTCTGAAGCTGGAGG
GCTGGGAGAAGGGGGTTGTATTCATCAATGGCCAGAACCTTGGACGTTACTGGAACATTGGACCCCAGAAGACG
CTTTACCTCCCAGGTCCCTGGTTGAGCAGCGGAATCAACCAGGTCATCGTTTTTGAGGAGACGATGGCGGGCCC
TGCATTACAGTTCACGGAAACCCCCCACCTGGGCAGGAACCAGTACATTAAGTGAGCGGTGGCACCCCCTCCTG
CTGGTGCCAGTGGGAGACTGCCGCCTCCTCTTGACCTGAAGCCTGGTGGCTGCTGCCCCACCCCTCACTGCAAA
AGCATCTCCTTAAGTAGCAACCTCAGGGACTGGGGGCTACAGTCTGCCCCTGTCTCAGCTCAAAACCCTAAGCC
TGCAGGGAAAGGTGGGATGGCTCTGGGCCTGGCTTTGTTGATGATGGCTTTCCTACAGCCCTGCTCTTGTGCCG
AGGCTGTCGGGCTGTCTCTAGGGTGGGAGCAGCTAATCAGATCGCCCAGCCTTTGGCCCTCAGAAAAAGTGCTG
AAACGTGCCCTTGCACCGGACGTCACAGCCCTGCGAGCATCTGCTGGACTCAGGCGTGCTCTTTGCTGGTTCCT
GGGAGGCTTGGCCACATCCCTCATGGCCCCATTTTATCCCCGAAATCCTGGGTGTGTCACCAGTGTAGAGGGTG
GGGAAGGGGTGTCTCACCTGAGCTGACTTTGTTCTTCCTTCACAACCTTCTGAGCCTTCTTTGGGATTCTGGAA
GGAACTCGGCGTGAGAAACATGTGACTTCCCCTTTCCCTTCCCACTCGCTGCTTCCCACAGGGTGACAGGCTGG
GCTGGAGAAACAGAAATCCTCACCCTGCGTCTTCCCAAGTTAGCAGGTGTCTCTGGTGTTCAGTGAGGAGGACA
TGTGAGTCCTGGCAGAAGCCATGGCCCATGTCTGCACATCCAGGGAGGAGGACAGAAGGCCCAGCTCACATGTG
AGTCCTGGCAGAAGCCATGGCCCATGTCTGCACATCCAGGGAGGAGGACAGAAGGCCCAGCTCACATGTGAGTC
CTGGCAGAAGCCATGGCCCATGTCTGCACATCCAGGGAGGAGGACAGAAGGCCCAGCTCACATGTGAGTCCTGG
CAGAAGCCATGGCCCATGTCTGCACATCCAGGGAGGAGGACAGAAGGCCCAGCTCAGTGGCCCCGCTCCCCAC
CCCCCACGCCCGAACAGCAGGGGCAGAGCAGCCCTCCTTCGAAGTGTGTCCAAGTCCGCATTTGAGCCTTGTTC
TGGGGCCCAGCCCAACACCTGGCTTGGGCTCACTGTCCTGAGTTGCAGTAAAGCTATAACCTTGAATCACAA
```

FIGURE 8

MTTWSLRRRPARTLGLLLLVVLGFLVLRRLDWSTLVPLRLRHRQLGLQAKGWNFMLEDSTFWIFGGSIHYFRVP
REYWRDRLLKMKACGLNTLTTYVPWNLHEPERGKFDFSGNLDLEAFVLMAAEIGLWVILRPGPYICSEMDLGGL
PSWLLQDPGMRLRTTYKGFTEAVDLYFDHLMSRVVPLQYKRGGPIIAVQVENEYGSYNKDPAYMPYVKKALEDR
GIVELLLTSDNKDGLSKGIVQGVLATINLQSTHELQLLTTFLFNVQGTQPKMVMEYWTGWFDSWGGPHNILDSS
EVLKTVSAIVDAGSSINLYMFHGGTNFGFMNGAMHFHDYKSDVTSYDYDAVLTEAGDYTAKYMKLRDFFGSISG
IPLPPPPDLLPKMPYEPLTPVLYLSLWDALKYLGEPIKSEKPINMENLPVNGGNGQSFGYILYETSITSSGILS
GHVHDRGQVFVNTVSIGFLDYKTTKIAVPLIQGYTVLRILVENRGRVNYGENIDDQRKGLIGNLYLNDSPLKNF
RIYSLDMKKSFFQRFGLDKWXSLPETPTLPAFFLGSLSISSTPCDTFLKLEGWEKGVVFINGQNLGRYWNIGPQ
KTLYLPGPWLSSGINQVIVFEETMAGPALQFTETPHLGRNQYIK

Signal sequence:
amino acids 1-27

Casein kinase II phosphorylation site.
amino acids 141-118, 253-257, 340-344, 395-399, 540-544, 560-564

N-myristoylation site.
amino acids 146-152, 236-242, 240-246, 244-250, 287-293, 309-315, 320-326, 366-372, 423-429, 425-431, 441-447, 503-509, 580-586

FIGURE 9

CCCAGAAGTTCAAGGGCCCCCGGCCTCCTGCGCTCCTGCCGCCGGGACCCTCGACCTCCTCAGAGCAGCCGGCT
GCCGCCCCGGGAAGATGGCGAGGAGGAGCCGCCACCGCCTCCTCCTGCTGCTGCTGCGCTACCTGGTGGTCGCC
CTGGGCTATCATAAGGCCTATGGGTTTTCTGCCCCAAAAGACCAACAAGTAGTCACAGCAGTAGAGTACCAAGA
GGCTATTTTAGCCTGCAAAACCCCAAAGAAGACTGTTTCCTCCAGATTAGAGTGGAAGAAACTGGGTCGGAGTG
TCTCCTTTGTCTACTATCAACAGACTCTTCAAGGTGATTTTAAAAATCGAGCTGAGATGATAGATTTCAATATC
CGGATCAAAAATGTGACAAGAAGTGATGCGGGGAAATATCGTTGTGAAGTTAGTGCCCCATCTGAGCAAGGCCA
AAACCTGGAAGAGGATACAGTCACTCTGGAAGTATTAGTGGCTCCAGCAGTTCCATCATGTGAAGTACCCTCTT
CTGCTCTGAGTGGAACTGTGGTAGAGCTACGATGTCAAGACAAAGAAGGGAATCCAGCTCCTGAATACACATGG
TTTAAGGATGGCATCCGTTTGCTAGAAAATCCCAGACTTGGCTCCCAAAGCACCAACAGCTCATACACAATGAA
TACAAAAACTGGAACTCTGCAATTTAATACTGTTTCCAAACTGGACACTGGAGAATATTCCTGTGAAGCCCGCA
ATTCTGTTGGATATCGCAGGTGTCCTGGGAAACGAATGCAAGTAGATGATCTCAACATAAGTGGCATCATAGCA
GCCGTAGTAGTTGTGGCCTTAGTGATTTCCGTTTGTGGCCTTGGTGTATGCTATGCTCAGAGGAAAGGCTACTT
TTCAAAAGAAACCTCCTTCCAGAAGAGTAATTCTTCATCTAAAGCCACGACAATGAGTGAAAATGTGCAGTGGC
TCACGCCTGTAATCCCAGCACTTTGGAAGGCCGCGGCGGGCGGATCACGAGGTCAGGAGTTCTAGACCAGTCTG
GCCAATATGGTGAAACCCCATCTCTACTAAAATACAAAAATTAGCTGGGCATGGTGGCATGTGCCTGCAGTTCC
AGCTGCTTGGGAGACAGGAGAATCACTTGAACCCGGGAGGCGGAGGTTGCAGTGAGCTGAGATCACGCCACTGC
AGTCCAGCCTGGGTAACAGAGCAAGATTCCATCTCAAAAAATAAAATAAATAAATAAATAAATACTGGTTTTTA
CCTGTAGAATTCTTACAATAAATATAGCTTGATATTC

FIGURE 10

MARRSRHRLLLLLLRYLVVALGYHKAYGFSAPKDQQVVTAVEYQEAILACKTPKKTVSSRLEWKKLGRSVSFVY
YQQTLQGDFKNRAEMIDFNIRIKNVTRSDAGKYRCEVSAPSEQGQNLEEDTVTLEVLVAPAVPSCEVPSSALSG
TVVELRCQDKEGNPAPEYTWFKDGIRLLENPRLGSQSTNSSYTMNTKTGTLQFNTVSKLDTGEYSCEARNSVGY
RRCPGKRMQVDDLNISGIIAAVVVVALVISVCGLGVCYAQRKGYFSKETSFQKSNSSSKATTMSENVQWLTPVI
PALWKAAAGGSRGQEF

Signal peptide:
amino acids 1-20

Transmembrane domain:
amino acids 130-144, 238-258

N-glycosylation site.
amino acids 98-102, 187-191, 236-240, 277-281

Casein kinase II phosphorylation site.
amino acids 39-43, 59-63, 100-104, 149-153, 205-209, 284-288

N-myristoylation site.
amino acids 182-188, 239-245, 255-261, 257-263, 305-311

Amidation site.
amino acids 226-230

FIGURE 11

GGAGCCGCCCTGGGTGTCAGCGGCTCGGCTCCCGCGCACGCTCCGGCCGTCGCGCAGCCTC
GGCACCTGCAGGTCCGTGCGTCCCGCGGCTGGCGCCCCTGACTCCGTCCCGGCCAGGGAGG
GCCATGATTTCCCTCCCGGGGCCCCTGGTGACCAACTTGCTGCGGTTTTTGTTCCTGGGGC
TGAGTGCCCTCGCGCCCCCTCGCGGGCCCAGCTGCAACTGCACTTGCCCGCCAACCGGTT
GCAGGCGGTGGAGGGAGGGGAAGTGGTGCTTCCAGCGTGGTACACCTTGCACGGGGAGGTG
TCTTCATCCCAGCCATGGGAGGTGCCCTTTGTGATGTGGTTCTTCAAACAGAAAGAAAAGG
AGGATCAGGTGTTGTCCTACATCAATGGGGTCACAACAAGCAAACCTGGAGTATCCTTGGT
CTACTCCATGCCCTCCCGGAACCTGTCCCTGCGGCTGGAGGGTCTCCAGGAGAAAGACTCT
GGCCCCTACAGCTGCTCCGTGAATGTGCAAGACAAACAAGGCAAATCTAGGGGCCACAGCA
TCAAAACCTTAGAACTCAATGTACTGGTTCCTCCAGCTCCTCCATCCTGCCGTCTCCAGGG
TGTGCCCCATGTGGGGGCAAACGTGACCCTGAGCTGCCAGTCTCCAAGGAGTAAGCCCGCT
GTCCAATACCAGTGGGATCGGCAGCTTCCATCCTTCCAGACTTTCTTTGCACCAGCATTAG
ATGTCATCCGTGGGTCTTTAAGCCTCACCAACCTTTCGTCTTCCATGGCTGGAGTCTATGT
CTGCAAGGCCCACAATGAGGTGGGCACTGCCCAATGTAATGTGACGCTGGAAGTGAGCACA
GGGCCTGGAGCTGCAGTGGTTGCTGGAGCTGTTGTGGGTACCCTGGTTGGACTGGGGTTGC
TGGCTGGGCTGGTCCTCTTGTACCACCGCCGGGGCAAGGCCCTGGAGGAGCCAGCCAATGA
TATCAAGGAGGATGCCATTGCTCCCCGGACCCTGCCCTGGCCCAAGAGCTCAGACACAATC
TCCAAGAATGGGACCCTTTCCTCTGTCACCTCCGCACGAGCCCTCCGGCCACCCCATGGCC
CTCCCAGGCCTGGTGCATTGACCCCCACGCCCAGTCTCTCCAGCCAGGCCCTGCCCTCACC
AAGACTGCCCACGACAGATGGGGCCCACCCTCAACCAATATCCCCCATCCCTGGTGGGGTT
TCTTCCTCTGGCTTGAGCCGCATGGGTGCTGTGCCTGTGATGGTGCCTGCCCAGAGTCAAG
CTGGCTCTCTGGTATGATGACCCCACCACTCATTGGCTAAAGGATTTGGGGTCTCTCCTTC
CTATAAGGGTCACCTCTAGCACAGAGGCCTGAGTCATGGGAAAGAGTCACACTCCTGACCC
TTAGTACTCTGCCCCCACCTCTCTTTACTGTGGGAAAACCATCTCAGTAAGACCTAAGTGT
CCAGGAGACAGAAGGAGAAGAGGAAGTGGATCTGGAATTGGGAGGAGCCTCCACCCACCCC
TGACTCCTCCTTATGAAGCCAGCTGCTGAAATTAGCTACTCACCAAGAGTGAGGGCAGAG
ACTTCCAGTCACTGAGTCTCCCAGGCCCCCTTGATCTGTACCCCACCCCTATCTAACACCA
CCCTTGGCTCCCACTCCAGCTCCCTGTATTGATATAACCTGTCAGGCTGGCTTGGTTAGGT
TTTACTGGGGCAGAGGATAGGGAATCTCTTATTAAAACTAACATGAAATATGTGTTGTTTT
CATTTGCAAATTTAAATAAAGATACATAATGTTTGTATGAAAAA

FIGURE 12

MISLPGPLVTNLLRFLFLGLSALAPPSRAQLQLHLPANRLQAVEGGEVVLPAWYTLHGEVS
SSQPWEVPFVMWFFKQKEKEDQVLSYINGVTTSKPGVSLVYSMPSRNLSLRLEGLQEKDSG
PYSCSVNVQDKQGKSRGHSIKTLELNVLVPPAPPSCRLQGVPHVGANVTLSCQSPRSKPAV
QYQWDRQLPSFQTFFAPALDVIRGSLSLTNLSSSMAGVYVCKAHNEVGTAQCNVTLEVSTG
PGAAVVAGAVVGTLVGLGLLAGLVLLYHRRGKALEEPANDIKEDAIAPRTLPWPKSSDTIS
KNGTLSSVTSARALRPPHGPPRPGALTPTPSLSSQALPSPRLPTTDGAHPQPISPIPGGVS
SSGLSRMGAVPVMVPAQSQAGSLV

Signal peptide:

amino acids 1-29

Transmembrane domain:

amino acids 245-267

N-glycosylation site.

amino acids 108-112, 169-173, 213-217, 236-240, 307-311

N-myristoylation site.

amino acids 90-96, 167-173, 220-226, 231-237, 252-258, 256-262,
262-268, 308-314, 363-369, 364-370

Prokaryotic membrane lipoprotein lipid attachment site.

amino acids 164-175

FIGURE 13

CCCACGCGTCCGCACCTCGGCCCCGGGCTCCGAAGCGGCTCGGGGGCGCCCTTTCGGTCAACATCGTAGTCCAC
CCCCTCCCCATCCCCAGCCCCGGGGATTCAGGCTCGCCAGCGCCCAGCCAGGGAGCCGGCCGGGAAGCGCGAT
GGGGGCCCCAGCCGCCTCGCTCCTGCTCCTGCTCCTGCTGTTCGCCTGCTGCTGGGCGCCCGGCGGGGCCAACC
TCTCCCAGGACGACAGCCAGCCCTGGACATCTGATGAAACAGTGGTGGCTGGTGGCACCGTGGTGCTCAAGTGC
CAAGTGAAAGATCACGAGGACTCATCCCTGCAATGGTCTAACCCTGCTCAGCAGACTCTCTACTTTGGGGAGAA
GAGAGCCCTTCGAGATAATCGAATTCAGCTGGTTACCTCTACGCCCACGAGCTCAGCATCAGCATCAGCAATG
TGGCCCTGGCAGACGAGGGCGAGTACACCTGCTCAATCTTCACTATGCCTGTGCGAACTGCCAAGTCCCTCGTC
ACTGTGCTAGGAATTCCACAGAAGCCCATCATCACTGGTTATAAATCTTCATTACGGGAAAAAGACACAGCCAC
CCTAAACTGTCAGTCTTCTGGGAGCAAGCCTGCAGCCCGGCTCACCTGGAGAAAGGGTGACCAAGAACTCCACG
GAGAACCAACCCGCATACAGGAAGATCCCAATGGTAAAACCTTCACTGTCAGCAGCTCGGTGACATTCCAGGTT
ACCCGGGAGGATGATGGGGCGAGCATCGTGTGCTCTGTGAACCATGAATCTCTAAAGGGAGCTGACAGATCCAC
CTCTCAACGCATTGAAGTTTTATACACACCAACTGCGATGATTAGGCCAGACCCTCCCCATCCTCGTGAGGGCC
AGAAGCTGTTGCTACACTGTGAGGGTCGCGGCAATCCAGTCCCCCAGCAGTACCTATGGGAGAAGGAGGGCAGT
GTGCCACCCCTGAAGATGACCCAGGAGAGTGCCCTGATCTTCCCTTTCCTCAACAAGAGTGACAGTGGCACCTA
CGGCTGCACAGCCACCAGCAACATGGGCAGCTACAAGGCCTACTACACCCTCAATGTTAATGACCCCAGTCCGG
TGCCCTCCTCCTCCAGCACCTACCACGCCATCATCGGTGGGATCGTGGCTTTCATTGTCTTCCTGCTGCTCATC
ATGCTCATCTTCCTTGGCCACTACTTGATCCGGCACAAAGGAACCTACCTGACACATGAGGCAAAAGGCTCCGA
CGATGCTCCAGACGCGGACACGGCCATCATCAATGCAGAAGGCGGGCAGTCAGGAGGGGACGACAAGAAGGAAT
ATTTCATCTAGAGGCGCCTGCCCACTTCCTGCGCCCCCAGGGGCCCTGTGGGGACTGCTGGGGCCGTCACCAA
CCCGGACTTGTACAGAGCAACCGCAGGGCCGCCCCTCCCGCTTGCTCCCCAGCCCACCCACCCCCCTGTACAGA
ATGTCTGCTTTGGGTGCGGTTTTGTACTCGGTTTGGAATGGGGAGGGAGGAGGGCGGGGGAGGGGAGGGTTGC
CCTCAGCCCTTTCCGTGGCTTCTCTGCATTTGGGTTATTATTATTTTTGTAACAATCCCAAATCAAATCTGTCT
CCAGGCTGGAGAGGCAGGAGCCCTGGGGTGAGAAAAGCAAAAAACAAACAAAAAACA

FIGURE 14

MGAPAASLLLLLLLLFACCWAPGGANLSQDDSQPWTSDETVVAGGTVVLKCQVKDHEDSSLQWSNPAQQTLYFGE
KRALRDNRIQLVTSTPHELSISISNVALADEGEYTCSIFTMPVRTAKSLVTVLGIPQKPIITGYKSSLREKDTA
TLNCQSSGSKPAARLTWRKGDQELHGEPTRIQEDPNGKTFTVSSSVTFQVTREDDGASIVCSVNHESLKGADRS
TSQRIEVLYTPTAMIRPDPPHPREGQKLLLHCEGRGNPVPQQYLWEKEGSVPPLKMTQESALIFPFLNKSDSGT
YGCTATSNMGSYKAYYTLNVNDPSPVPSSSSTYHAIIGGIVAFIVFLLLIMLIFLGHYLIRHKGTYLTHEAKGS
DDAPDADTAIINAEGGQSGGDDKKEYFI

Signal sequence:

amino acids 1-20

Transmembrane domain:

amino acids 331-352

N-glycosylation site.

amino acids 25-29, 290-294

Casein kinase II phosphorylation site.

amino acids 27-31, 35-39, 89-93, 141-145, 199-203, 388-392

N-myristoylation site.

amino acids 2-8, 23-29, 156-162, 218-224, 295-301, 298-304, 306-310, 334-340, 360-364, 385-389, 386-390

Prokaryotic membrane lipoprotein lipid attachment site.

amino acids 7-18

FIGURE 15

CGGACGCGTGGGATTCAGCAGTGGCCTGTGGCTGCCAGAGCAGCTCCTCAGGGGAAACTAAGCGTCGAGTCAGA
CGGCACCATAATCGCCTTTAAAAGTGCCTCCGCCCTGCCGGCCGCGTATCCCCCGGCTACCTGGGCCGCCCCGC
GGCGGTGCGCGCGTGAGAGGGAGCGCGCGGGCAGCCGAGCGCCGGTGTGAGCCAGCGCTGCTGCCAGTGTGAGC
GGCGGTGTGAGCGCGGTGGGTGCGGAGGGGCGTGTGTGCCGGCGCGCGCCGTGGGGTGCAAACCCCGAGCGT
CTACGCTGCCATGAGGGGCGCGAACGCCTGGGCGCCACTCTGCCTGCTGCTGGCTGCCGCCACCCAGCTCTCGC
GGCAGCAGTCCCCAGAGAGACCTGTTTTCACATGTGGTGGCATTCTTACTGGAGAGTCTGGATTTATTGGCAGT
GAAGGTTTTCCTGGAGTGTACCCTCCAAATAGCAAATGTACTTGGAAAATCACAGTTCCCGAAGGAAAAGTAGT
CGTTCTCAATTTCCGATTCATAGACCTCGAGAGTGACAACCTGTGCCGCTATGACTTTGTGGATGTGTACAATG
GCCATGCCAATGGCCAGCGCATTGGCCGCTTCTGTGGCACTTTCCGGCCTGGAGCCCTTGTGTCCAGTGGCAAC
AAGATGATGGTGCAGATGATTTCTGATGCCAACACAGCTGGCAATGGCTTCATGGCCATGTTCTCCGCTGCTGA
ACCAAACGAAAGAGGGGATCAGTATTGTGGAGGACTCCTTGACAGACCTTCCGGCTCTTTTAAAACCCCCAACT
GGCCAGACCGGGATTACCCTGCAGGAGTCACTTGTGTGTGGCACATTGTAGCCCCAAAGAATCAGCTTATAGAA
TTAAAGTTTGAGAAGTTTGATGTGGAGCGAGATAACTACTGCCGATATGATTATGTGGCTGTGTTTAATGGCGG
GGAAGTCAACGATGCTAGAAGAATTGGAAAGTATTGTGGTGATAGTCCACCTGCGCCAATTGTGTCTGAGAGAA
ATGAACTTCTTATTCAGTTTTTATCAGACTTAAGTTTAACTGCAGATGGGTTTATTGGTCACTACATATTCAGG
CCAAAAAAACTGCCTACAACTACAGAACAGCCTGTCACCACCACATTCCCTGTAACCACGGGTTTAAAACCCAC
CGTGGCCTTGTGTCAACAAAAGTGTAGACGGACGGGGACTCTGGAGGGCAATTATTGTTCAAGTGACTTTGTAT
TAGCCGGCACTGTTATCACAACCATCACTCGCGATGGGAGTTTGCACGCCACAGTCTCGATCATCAACATCTAC
AAAGAGGGAAATTTGGCGATTCAGCAGGCGGGCAAGAACATGAGTGCCAGGCTGACTGTCGTCTGCAAGCAGTG
CCCTCTCCTCAGAAGAGGTCTAAATTACATTATTATGGGCCAAGTAGGTGAAGATGGGCGAGGCAAATCATGC
CAAACAGCTTTATCATGATGTTCAAGACCAAGAATCAGAAGCTCCTGGATGCCTTAAAAAATAAGCAATGTTAA
CAGTGAACTGTGTCCATTTAAGCTGTATTCTGCCATTGCCTTTGAAAGATCTATGTTCTCTCAGTAGAAAAAAA
AATACTTATAAAATTACATATTCTGAAAGAGGATTCCGAAAGATGGGACTGGTTGACTCTTCACATGATGGAGG
TATGAGGCCTCCGAGATAGCTGAGGGAAGTTCTTTGCCTGCTGTCAGAGGAGCAGCTATCTGATTGGAAACCTG
CCGACTTAGTGCGGTGATAGGAAGCTAAAAGTGTCAAGCGTTGACAGCTTGGAAGCGTTTATTTATACATCTCT
GTAAAAGGATATTTTAGAATTGAGTTGTGTGAAGATGTCAAAAAAAGATTTTAGAAGTGCAATATTTATAGTGT
TATTTGTTTCACCTTCAAGCCTTTGCCCTGAGGTGTTACAATCTTGTCTTGCGTTTTCTAAATCAATGCTTAAT
AAAATATTTTTAAAGGAAAAAAAAAAAA

FIGURE 16

MRGANAWAPLCLLLAAATQLSRQQSPERPVFTCGGILTGESGFIGSEGFPGVYPPNSKCTWKITVPEGKVVVLN
FRFIDLESDNLCRYDFVDVYNGHANGQRIGRFCGTFRPGALVSSGNKMMVQMISDANTAGNGFMAMFSAAEPNE
RGDQYCGGLLDRPSGSFKTPNWPDRDYPAGVTCVWHIVAPKNQLIELKFEKFDVERDNYCRYDYVAVFNGGEVN
DARRIGKYCGDSPPAPIVSERNELLIQFLSDLSLTADGFIGHYIFRPKKLPTTTEQPVTTTFPVTTGLKPTVAL
CQQKCRRTGTLEGNYCSSDFVLAGTVITTITRDGSLHATVSIINIYKEGNLAIQQAGKNMSARLTVVCKQCPLL
RRGLNYIIMGQVGEDGRGKIMPNSFIMMFKTKNQKLLDALKNKQC

Signal sequence:
amino acids 1-23

N-glycosylation site.
amino acids 355-359

Casein kinase II phosphorylation site.
amino acids 64-68, 142-146, 274-278

Tyrosine kinase phosphorylation site.
amino acids 199-208

N-myristoylation site.
amino acids 34-40, 35-41, 100-106, 113-119, 218-224, 289-295, 305-311, 309-315, 320-326, 330-336

Cell attachment sequence.
amino acids 149-152

FIGURE 17

GACGGCTGGCCACCATGCACGGCTCCTGCAGTTTCCTGATGCTTCTGCTGCCGCTACTGCT
ACTGCTGGTGGCCACCACAGGCCCCGTTGGAGCCCTCACAGATGAGGAGAAACGTTTGATG
GTGGAGCTGCACAACCTCTACCGGGCCCAGGTATCCCCGACGGCCTCAGACATGCTGCACA
TGAGATGGGACGAGGAGCTGGCCGCCTTCGCCAAGGCCTACGCACGGCAGTGCGTGTGGGG
CCACAACAAGGAGCGCGGGCGCCGCGGCGAGAATCTGTTCGCCATCACAGACGAGGGCATG
GACGTGCCGCTGGCCATGGAGGAGTGGCACCACGAGCGTGAGCACTACAACCTCAGCGCCG
CCACCTGCAGCCCAGGCCAGATGTGCGGCCACTACACGCAGGTGGTATGGGCCAAGACAGA
GAGGATCGGCTGTGGTTCCCACTTCTGTGAAGCTCCAGGGTGTTGAGGAGACCAACATC
GAATTACTGGTGTGCAACTATGAGCCTCCGGGGAACGTGAAGGGGAAACGGCCCTACCAGG
AGGGGACTCCGTGCTCCCAATGTCCCTCTGGCTACCACTGCAAGAACTCCCTCTGTGAACC
CATCGGAAGCCCGGAAGATGCTCAGGATTTGCCTTACCTGGTAACTGAGGCCCCATCCTTC
CGGGCGACTGAAGCATCAGACTCTAGGAAAATGGGTACTCCTTCTTCCCTAGCAACGGGGA
TTCCGGCTTTCTTGGTAACAGAGGTCTCAGGCTCCCTGGCAACCAAGGCTCTGCCTGCTGT
GGAAACCCAGGCCCCAACTTCCTTAGCAACGAAAGACCCGCCCTCCATGGCAACAGAGGCT
CCACCTTGCGTAACAACTGAGGTCCCTTCCATTTTGGCAGCTCACAGCCTGCCCTCCTTGG
ATGAGGAGCCAGTTACCTTCCCCAAATCGACCCATGTTCCTATCCCAAAATCAGCAGACAA
AGTGACAGACAAAACAAAAGTGCCCTCTAGGAGCCCAGAGAACTCTCTGGACCCCAAGATG
TCCCTGACAGGGGCAAGGGAACTCCTACCCCATGCCCAGGAGGAGGCTGAGGCTGAGGCTG
AGTTGCCTCCTTCCAGTGAGGTCTTGGCCTCAGTTTTTCCAGCCCAGGACAAGCCAGGTGA
GCTGCAGGCCACACTGGACCACACGGGGCACACCTCCTCCAAGTCCCTGCCCAATTTCCCC
AATACCTCTGCCACCGCTAATGCCACGGGTGGGCGTGCCCTGGCTCTGCAGTCGTCCTTGC
CAGGTGCAGAGGGCCCTGACAAGCCTAGCGTTGTGTCAGGGCTGAACTCGGGCCCTGGTCA
TGTGTGGGGCCCTCTCCTGGGACTACTGCTCCTGCCTCCTCTGGTGTTGGCTGGAATCTTC
TGAATGGGATACCACTCAAAGGGTGAAGAGGTCAGCTGTCCTCCTGTCATCTTCCCCACCC
TGTCCCCAGCCCCTAAACAAGATACTTCTTGGTTAAGGCCCTCCGGAAGGGAAAGGCTACG
GGGCATGTGCCTCATCACACCATCCATCCTGGAGGCACAAGGCCTGGCTGGCTGCGAGCTC
AGGAGGCCGCCTGAGGACTGCACACCGGGCCCACACCTCTCCTGCCCCTCCCTCCTGAGTC
CTGGGGGTGGGAGGATTTGAGGGAGCTCACTGCCTACCTGGCCTGGGGCTGTCTGCCCACA
CAGCATGTGCGCTCTCCCTGAGTGCCTGTGTAGCTGGGGATGGGGATTCCTAGGGGCAGAT
GAAGGACAAGCCCCACTGGAGTGGGGTTCTTTGAGTGGGGAGGCAGGGACGAGGGAAGGA
AAGTAACTCCTGACTCTCCAATAAAAACCTGTCCAACCTGTGAAA

FIGURE 18

```
MHGSCSFLMLLLPLLLLLVATTGPVGALTDEEKRLMVELHNLYRAQVSPTASDMLHMRWDE
ELAAFAKAYARQCVWGHNKERGRRGENLFAITDEGMDVPLAMEEWHHEREHYNLSAATCSP
GQMCGHYTQVVWAKTERIGCGSHFCEKLQGVEETNIELLVCNYEPPGNVKGKRPYQEGTPC
SQCPSGYHCKNSLCEPIGSPEDAQDLPYLVTEAPSFRATEASDSRKMGTPSSLATGIPAFL
VTEVSGSLATKALPAVETQAPTSLATKDPPSMATEAPPCVTTEVPSILAAHSLPSLDEEPV
TFPKSTHVPIPKSADKVTDKTKVPSRSPENSLDPKMSLTGARELLPHAQEEAEAEAELPPS
SEVLASVFPAQDKPGELQATLDHTGHTSSKSLPNFPNTSATANATGGRALALQSSLPGAEG
PDKPSVVSGLNSGPGHVWGPLLGLLLLPPLVLAGIF
```

Signal sequence:

amino acids 1-22

N-glycosylation site.

amino acids 114-118, 403-407, 409-413

Glycosaminoglycan attachment site.

amino acids 439-443

Casein kinase II phosphorylation site.

amino acids 29-33, 50-54, 156-160, 195-199, 202-206, 299-303

N-myristoylation site.

amino acids 123-129, 143-149, 152-158, 169-175, 180-186, 231-237, 250-256

Amidation site.

amino acids 82-86, 172-176

Peroxidases proximal heme-ligand signature.

amino acids 287-298

Extracellular proteins SCP/Tpx-1/Ag5/PR-1/Sc7 signature 1.

amino acids 127-138

Extracellular proteins SCP/Tpx-1/Ag5/PR-1/Sc7 signature 2.

amino acids 160-172

FIGURE 19

GACTAGTTCTCTTGGAGTCTGGGAGGAGGAAAGCGGAGCCGGCAGGGAGCGAACCAGGACT
GGGGTGACGGCAGGGCAGGGGCGCCTGGCCGGGGAGAAGCGCGGGGGCTGGAGCACCACC
AACTGGAGGGTCCGGAGTAGCGAGCGCCCCGAAGGAGGCCATCGGGGAGCCGGGAGGGGGG
ACTGCGAGAGGACCCCGGCGTCCGGGCTCCCGGTGCCAGCGCTATGAGGCCACTCCTCGTC
CTGCTGCTCCTGGGCCTGGCGGCCGGCTCGCCCCACTGGACGACAACAAGATCCCCAGCC
TCTGCCCGGGGCACCCCGGCCTTCCAGGCACGCCGGGCCACCATGGCAGCCAGGGCTTGCC
GGGCCGCGATGGCCGCGACGGCCGCGACGGCGCGCCCGGGGCTCCGGGAGAGAAAGGCGAG
GCGGGAGGCCGGGACTGCCGGGACCTCGAGGGGACCCCGGGCCGCGAGGAGAGGCGGGAC
CCGCGGGGCCCACCGGGCCTGCCGGGGAGTGCTCGGTGCCTCCGCGATCCGCCTTCAGCGC
CAAGCGCTCCGAGAGCCGGGTGCCTCCGCCGTCTGACGCACCCTTGCCCTTCGACCGCGTG
CTGGTGAACGAGCAGGGACATTACGACGCCGTCACCGGCAAGTTCACCTGCCAGGTGCCTG
GGGTCTACTACTTCGCCGTCCATGCCACCGTCTACCGGGCCAGCCTGCAGTTTGATCTGGT
GAAGAATGGCGAATCCATTGCCTCTTTCTTCCAGTTTTTCGGGGGGTGGCCCAAGCCAGCC
TCGCTCTCGGGGGGGCCATGGTGAGGCTGGAGCCTGAGGACCAAGTGTGGGTGCAGGTGG
GTGTGGGTGACTACATTGGCATCTATGCCAGCATCAAGACAGACAGCACCTTCTCCGGATT
TCTGGTGTACTCCGACTGGCACAGCTCCCCAGTCTTTGCTTAGTGCCCACTGCAAAGTGAG
CTCATGCTCTCACTCCTAGAAGGAGGGTGTGAGGCTGACAACCAGGTCATCCAGGAGGGCT
GGCCCCCTGGAATATTGTGAATGACTAGGGAGGTGGGGTAGAGCACTCTCCGTCCTGCTG
CTGGCAAGGAATGGGAACAGTGGCTGTCTGCGATCAGGTCTGGCAGCATGGGGCAGTGGCT
GGATTTCTGCCCAAGACCAGAGGAGTGTGCTGTGCTGGCAAGTGTAAGTCCCCAGTTGCT
CTGGTCCAGGAGCCCACGGTGGGGTGCTCTCTTCCTGGTCCTCTGCTTCTCTGGATCCTCC
CCACCCCTCCTGCTCCTGGGGCCGGCCTTTTCTCAGAGATCACTCAATAAACCTAAGAA
CCCTCATAAAAAAAAAAAAAAAAAAAAAAAAAAA

FIGURE 20

```
></usr/seqdb2/sst/DNA/Dnaseqs.min/ss.DNA40592
><subunit 1 of 1, 243 aa, 1 stop
><MW: 25298, pI: 6.44, NX(S/T): 0
MRPLLVLLLLGLAAGSPPLDDNKIPSLCPGHPGLPGTPGHHGSQGLPGRDGRDGRDGAPGA
PGEKGEGGRPGLPGPRGDPGPRGEAGPAGPTGPAGECSVPPRSAFSAKRSESRVPPPSDAP
LPFDRVLVNEQGHYDAVTGKFTCQVPGVYYFAVHATVYRASLQFDLVKNGESIASFFQFFG
GWPKPASLSGGAMVRLEPEDQVWVQVGVGDYIGIYASIKTDSTFSGFLVYSDWHSSPVFA
```

Signal sequence.

amino acids 1-15

N-myristoylation sites.

amino acids 11-17, 68-74, 216-222

Cell attachment sequence.

amino acids 77-80

FIGURE 21

GGGGCGGGTGGACGCGGACTCGAACGCAGTTGCTTCGGGACCCAGGACCCCCTCGGGCCCGACCCGCCAGGAAA
GACTGAGGCCGCGGCCTGCCCCGCCCGGCTCCCTGCGCCGCCGCCGCCTCCCGGGACAGAAGATGTGCTCCAGG
GTCCCTCTGCTGCTGCCGCTGCTCCTGCTACTGGCCCTGGGGCCTGGGGTGCAGGGCTGCCCATCCGGCTGCCA
GTGCAGCCAGCCACAGACAGTCTTCTGCACTGCCCGCCAGGGGACCACGGTGCCCCGAGACGTGCCACCCGACA
CGGTGGGGCTGTACGTCTTTGAGAACGGCATCACCATGCTCGACGCAAGCAGCTTTGCCGGCCTGCCGGGCCTG
CAGCTCCTGGACCTGTCACAGAACCAGATCGCCAGCCTGCGCCTGCCCCGCCTGCTGCTGCTGGACCTCAGCCA
CAACAGCCTCCTGGCCCTGGAGCCCGGCATCCTGGACACTGCCAACGTGGAGGCGCTGCGGCTGGCTGGTCTGG
GGCTGCAGCAGCTGGACGAGGGGCTCTTCAGCCGCTTGCGCAACCTCCACGACCTGGATGTGTCCGACAACCAG
CTGGAGCGAGTGCCACCTGTGATCCGAGGCCTCCGGGGCCTGACGCGCCTGCGGCTGGCCGGCAACACCCGCAT
TGCCCAGCTGCGGCCCGAGGACCTGGCCGGCCTGGCTGCCCTGCAGGAGCTGGATGTGAGCAACCTAAGCCTGC
AGGCCCTGCCTGGCGACCTCTCGGGCCTCTTCCCCCGCCTGCGGCTGCTGGCAGCTGCCCGCAACCCCTTCAAC
TGCGTGTGCCCCCTGAGCTGGTTTGGCCCCTGGGTGCGCGAGAGCCACGTCACACTGGCCAGCCCTGAGGAGAC
GCGCTGCCACTTCCCGCCCAAGAACGCTGGCCGGCTGCTCCTGGAGCTTGACTACGCCGACTTTGGCTGCCCAG
CCACCACCACCACAGCCACAGTGCCCACCACGAGGCCCGTGGTGCGGGAGCCCACAGCCTTGTCTTCTAGCTTG
GCTCCTACCTGGCTTAGCCCCACAGCGCCGGCCACTGAGGCCCCAGCCCGCCCTCCACTGCCCCACCGACTGT
AGGGCCTGTCCCCCAGCCCCAGGACTGCCCACCGTCCACCTGCCTCAATGGGGGCACATGCCACCTGGGGACAC
GGCACCACCTGGCGTGCTTGTGCCCCGAAGGCTTCACGGGCCTGTACTGTGAGAGCCAGATGGGGCAGGGGACA
CGGCCCAGCCCTACACCAGTCACGCCGAGGCCACCACGGTCCCTGACCCTGGGCATCGAGCCGGTGAGCCCCAC
CTCCCTGCGCGTGGGGCTGCAGCGCTACCTCCAGGGGAGCTCCGTGCAGCTCAGGAGCCTCCGTCTCACCTATC
GCAACCTATCGGGCCCTGATAAGCGGCTGGTGACGCTGCGACTGCCTGCCTCGCTCGCTGAGTACACGGTCACC
CAGCTGCGGCCCAACGCCACTTACTCCGTCTGTGTCATGCCTTTGGGGCCCGGGCGGGTGCCGGAGGGCGAGGA
GGCCTGCGGGGAGGCCCATACACCCCCAGCCGTCCACTCCAACCACGCCCCAGTCACCCAGGCCCGCGAGGGCA
ACCTGCCGCTCCTCATTGCGCCCGCCCTGGCCGCGGTGCTCCTGGCCGCGCTGGCTGCGGTGGGGGCAGCCTAC
TGTGTGCGGCGGGGCGGGCCATGGCAGCAGCGGCTCAGGACAAAGGGCAGGTGGGGCCAGGGGCTGGGCCCCT
GGAACTGGAGGGAGTGAAGGTCCCCTTGGAGCCAGGCCCGAAGGCAACAGAGGGCGGTGGAGAGGCCCTGCCCA
GCGGGTCTGAGTGTGAGGTGCCACTCATGGGCTTCCCAGGGCCTGGCCTCCAGTCACCCCTCCACGCAAAGCCC
TACATCTAAGCCAGAGAGAGACAGGGCAGCTGGGGCCGGGCTCTCAGCCAGTGAGATGGCCAGCCCCCTCCTGC
TGCCACACCACGTAAGTTCTCAGTCCCAACCTCGGGGATGTGTGCAGACAGGGCTGTGTGACCACAGCTGGGCC
CTGTTCCCTCTGGACCTCGGTCTCCTCATCTGTGAGATGCTGTGGCCCAGCTGACGAGCCCTAACGTCCCCAGA
ACCGAGTGCCTATGAGGACAGTGTCCGCCCTGCCCTCCGCAACGTGCAGTCCCTGGGCACGGCGGGCCCTGCCA
TGTGCTGGTAACGCATGCCTGGGCCCTGCTGGGCTCTCCCACTCCAGGCGGACCCTGGGGGCCAGTGAAGGAAG
CTCCCGGAAAGAGCAGAGGGAGAGCGGGTAGGCGGCTGTGTGACTCTAGTCTTGGCCCCAGGAAGCGAAGGAAC
AAAAGAAACTGGAAAGGAAGATGCTTTAGGAACATGTTTTGCTTTTTTAAAATATATATATATTTATAAGAGAT
CCTTTCCCATTTATTCTGGGAAGATGTTTTTCAAACTCAGAGACAAGGACTTTGGTTTTTGTAAGACAAACGAT
GATATGAAGGCCTTTTGTAAGAAAAAATAAAAAAAAAAA

FIGURE 22

```
</usr/seqdb2/sst/DNA/Dnaseqs.min/ss.DNA44804
<subunit 1 of 1, 598 aa, 1 stop
<MW: 63030, pI: 7.24, NX(S/T): 3
MCSRVPLLLPLLLLLALGPGVQGCPSGCQCSQPQTVFCTARQGTTVPRDVPPDTVGLYVFE
NGITMLDASSFAGLPGLQLLDLSQNQIASLRLPRLLLLDLSHNSLLALEPGILDTANVEAL
RLAGLGLQQLDEGLFSRLRNLHDLDVSDNQLERVPPVIRGLRGLTRLRLAGNTRIAQLRPE
DLAGLAALQELDVSNLSLQALPGDLSGLFPRLRLLAAARNPFNCVCPLSWFGPWVRESHVT
LASPEETRCHFPPKNAGRLLLELDYADFGCPATTTTATVPTTRPVVREPTALSSSLAPTWL
SPTAPATEAPSPPSTAPPTVGPVPQPQDCPPSTCLNGGTCHLGTRHHLACLCPEGFTGLYC
ESQMGQGTRPSPTPVTPRPPRSLTLGIEPVSPTSLRVGLQRYLQGSSVQLRSLRLTYRNLS
GPDKRLVTLRLPASLAEYTVTQLRPNATYSVCVMPLGPGRVPEGEEACGEAHTPPAVHSNH
APVTQAREGNLPLLIAPALAAVLLAALAAVGAAYCVRRGRAMAAAAQDKGQVGPGAGPLEL
EGVKVPLEPGPKATEGGGEALPSGSECEVPLMGFPGPGLQSPLHAKPYI
```

Signal sequence.

amino acids 1-23

Transmembrane domain.

amino acids 501-522

N-glycosylation sites.

amino acids 198-202, 425-429, 453-457

Tyrosine kinase phosphorylation site.

amino acids 262-270

N-myristoylation sites.

amino acids 23-29, 27-33, 112-118, 273-279, 519-525, 565-571

Prokaryotic membrane lipoprotein lipid attachment site.

amino acids 14-25

EGF-like domain cysteine pattern signature.

amino acids 355-367

Leucine zipper pattern.

amino acids 122-144, 194-216

FIGURE 23

```
GGCGCCGGTGCACCGGGCGGGCTGAGCGCCTCCTGCGGCCCGGCCTGCGCGCCCCGGCCCGCCGCGCCGCCCAC
GCCCCAACCCCGGCCCGCGCCCCCTAGCCCCCGCCCGGGCCCGCGCCCGCGCCCGCGCCCAGGTGAGCGCTCCG
CCCGCCGCGAGGCCCCGCCCCGGCCCGCCCCCGCCCCGCCCCGGCCGGCGGGGGAACCGGGCGGATTCCTCGCG
CGTCAAACCACCTGATCCCATAAAACATTCATCCTCCCGGCGGCCCGCGCTGCGAGCGCCCCGCCAGTCCGCGC
CGCCGCCGCCCTCGCCCTGTGCGCCCTGCGCGCCCTGCGCACCCGCGGCCCGAGCCCAGCCAGAGCCGGGCGGA
GCGGAGCGCGCCGAGCCTCGTCCCGCGGCCGGGCCGGGCCGGGCCGTAGCGGCGGCGCCTGGATGCGGACCCG
GCCGCGGGGAGACGGGCGCCCGCCCCGAAACGACTTTCAGTCCCCGACGCGCCCCGCCCAACCCCTACGATGAA
GAGGGCGTCCGCTGGAGGGAGCCGGCTGCTGGCATGGGTGCTGTGGCTGCAGGCCTGGCAGGTGGCAGCCCCAT
GCCCAGGTGCCTGCGTATGCTACAATGAGCCCAAGGTGACGACAAGCTGCCCCCAGCAGGGCCTGCAGGCTGTG
CCCGTGGGCATCCCTGCTGCCAGCCAGCGCATCTTCCTGCACGGCAACCGCATCTCGCATGTGCCAGCTGCCAG
CTTCCGTGCCTGCCGCAACCTCACCATCCTGTGGCTGCACTCGAATGTGCTGGCCCGAATTGATGCGGCTGCCT
TCACTGGCCTGGCCCTCCTGGAGCAGCTGGACCTCAGCGATAATGCACAGCTCCGGTCTGTGGACCCTGCCACA
TTCCACGGCCTGGGCCGCCTACACACGCTGCACCTGGACCGCTGCGGCCTGCAGGAGCTGGGCCCGGGGCTGTT
CCGCGGCCTGGCTGCCCTGCAGTACCTCTACCTGCAGGACAACGCGCTGCAGGCACTGCCTGATGACACCTTCC
GCGACCTGGGCAACCTCACACACCTCTTCCTGCACGGCAACCGCATCTCCAGCGTGCCCGAGCGCGCCTTCCGT
GGGCTGCACAGCCTCGACCGTCTCCTACTGCACCAGAACCGCGTGGCCCATGTGCACCCGCATGCCTTCCGTGA
CCTTGGCCGCCTCATGACACTCTATCTGTTTGCCAACAATCTATCAGCGCTGCCCACTGAGGCCCTGGCCCCCC
TGCGTGCCCTGCAGTACCTGAGGCTCAACGACAACCCCTGGGTGTGTGACTGCCGGGCACGCCCACTCTGGGCC
TGGCTGCAGAAGTTCCGCGGCTCCTCCTCCGAGGTGCCCTGCAGCCTCCCGCAACGCCTGGCTGGCCGTGACCT
CAAACGCCTAGCTGCCAATGACCTGCAGGGCTGCGCTGTGGCCACCGGCCCTTACCATCCCATCTGGACCGGCA
GGGCCACCGATGAGGAGCCGCTGGGGCTTCCCAAGTGCTGCCAGCCAGATGCCGCTGACAAGGCCTCAGTACTG
GAGCCTGGAAGACCAGCTTCGGCAGGCAATGCGCTGAAGGGACGCGTGCCGCCCGGTGACAGCCCGCCGGGCAA
CGGCTCTGGCCCACGGCACATCAATGACTCACCCTTTGGGACTCTGCCTGGCTCTGCTGAGCCCCCGCTCACTG
CAGTGCGGCCCGAGGGCTCCGAGCCACCAGGGTTCCCCACCTCGGGCCCTCGCCGGAGGCCAGGCTGTTCACGC
AAGAACCGCACCCGCAGCCACTGCCGTCTGGGCCAGGCAGGCAGCGGGGGTGGCGGGACTGGTGACTCAGAAGG
CTCAGGTGCCCTACCCAGCCTCACCTGCAGCCTCACCCCCTGGGCCTGGCGCTGGTGCTGTGGACAGTGCTTG
GGCCCTGCTGACCCCCAGCGGACACAAGAGCGTGCTCAGCAGCCAGGTGTGTGTACATACGGGTCTCTCTCCA
CGCCGCCAAGCCAGCCGGGCGGCCGACCCGTGGGGCAGGCCAGGCCAGGTCCTCCCTGATGGACGCCTGCCGCC
CGCCACCCCCATCTCCACCCCATCATGTTTACAGGGTTCGGCGGCAGCGTTTGTTCCAGAACGCCGCCTCCCAC
CCAGATCGCGGTATATAGAGATATGCATTTTATTTTACTTGTGTAAAAATATCGGACGACGTGGAATAAAGAGC
TCTTTTCTTAAAAAAA
```

FIGURE 24

></usr/seqdb2/sst/DNA/Dnaseqs.min/ss.DNA44184
><subunit 1 of 1, 473 aa, 1 stop
><MW: 50708, pI: 9.28, NX(S/T): 6

MKRASAGGSRLLAWVLWLQAWQVAAPCPGACVCYNEPKVTTSCPQQGLQAVPVGIPAASQR
IFLHGNRISHVPAASFRACRNLTILWLHSNVLARIDAAAFTGLALLEQLDLSDNAQLRSVD
PATFHGLGRLHTLHLDRCGLQELGPGLFRGLAALQYLYLQDNALQALPDDTFRDLGNLTHL
FLHGNRISSVPERAFRGLHSLDRLLLHQNRVAHVHPHAFRDLGRLMTLYLFANNLSALPTE
ALAPLRALQYLRLNDNPWVCDCRARPLWAWLQKFRGSSSEVPCSLPQRLAGRDLKRLAAND
LQGCAVATGPYHPIWTGRATDEEPLGLPKCCQPDAADKASVLEPGRPASAGNALKGRVPPG
DSPPGNGSGPRHINDSPFGTLPGSAEPPLTAVRPEGSEPPGFPTSGPRRRPGCSRKNRTRS
HCRLGQAGSGGGGTGDSEGSGALPSLTCSLTPLGLALVLWTVLGPC

Important features:

Signal peptide:
amino acids 1-26

Leucine zipper pattern.
amino acids 135-156

Glycosaminoglycan attachment site.
amino acids 436-439

N-glycosylation site.
amino acids 82-85, 179-183, 237-240, 372-375 and 423-426

VWFC domain
amino acids 411-425

FIGURE 25

```
CGGACGCGTGGGCGGACGCGTGGGCCTGGGCAAGGGCCGGGGCGCCGGGCCGAGCCACCTCTTCCCCTCCCCCG
CTTCCCTGTCGCGCTCCGCTGGCTGGACGCGCTGGAGGAGTGGAGCAGCACCCGGCCGGCCCTGGGGGCTGACA
GTCGGCAAAGTTTGGCCCGAAGAGGAAGTGGTCTCAAACCCCGGCAGGTGGCGACCAGGCCAGACCAGGGGCGC
TCGCTGCCTGCGGGCGGGCTGTAGGCGAGGGCGCGCCCCAGTGCCGAGACCCGGGGCTTCAGGAGCCGGCCCCG
GGAGAGAAGAGTGCGGCGGCGGACGGAGAAAACAACTCCAAAGTTGGCGAAAGGCACCGCCCCTACTCCCGGGC
TGCCGCCGCCTCCCCGCCCCCAGCCCTGGCATCCAGAGTACGGGTCGAGCCCGGGCCATGGAGCCCCCTGGGG
AGGCGGCACCAGGGAGCCTGGGCGCCCGGGGCTCCGCCGCGACCCCATCGGGTAGACCACAGAAGCTCCGGGAC
CCTTCCGGCACCTCTGGACAGCCCAGGATGCTGTTGGCCACCCTCCTCCTCCTCCTCCTTGGAGGCGCTCTGGC
CCATCCAGACCGGATTATTTTTCCAAATCATGCTTGTGAGGACCCCCAGCAGTGCTCTTAGAAGTGCAGGGCA
CCTTACAGAGGCCCCTGGTCCGGGACAGCCGCACCTCCCCTGCCAACTGCACCTGGCTCATCCTGGGCAGCAAG
GAACAGACTGTCACCATCAGGTTCCAGAAGCTACACCTGGCCTGTGGCTCAGAGCGCTTAACCCTACGCTCCCC
TCTCCAGCCACTGATCTCCCTGTGTGAGGCACCTCCCAGCCCTCTGCAGCTGCCCGGGGGCAACGTCACCATCA
CTTACAGCTATGCTGGGGCCAGAGCACCCATGGGCCAGGGCTTCCTGCTCTCCTACAGCCAAGATTGGCTGATG
TGCCTGCAGGAAGAGTTTCAGTGCCTGAACCACCGCTGTGTATCTGCTGTCCAGCGCTGTGATGGGGTTGATGC
CTGTGGCGATGGCTCTGATGAAGCAGGTTGCAGCTCAGACCCCTTCCCTGGCCTGACCCCAAGACCCGTCCCCT
CCCTGCCTTGCAATGTCACCTTGGAGGACTTCTATGGGGTCTTCTCCTCTCCTGGATATACACACCTAGCCTCA
GTCTCCCACCCCCAGTCCTGCCATTGGCTGCTGGACCCCCATGATGGCCGGCGGCTGGCCGTGCGCTTCACAGC
CCTGGACTTGGGCTTTGGAGATGCAGTGCATGTGTATGACGGCCCTGGGCCCCCTGAGAGCTCCCGACTACTGC
GTAGTCTCACCCACTTCAGCAATGGCAAGGCTGTCACTGTGGAGACACTGTCTGGCCAGGCTGTTGTGTCCTAC
CACACAGTTGCTTGGAGCAATGGTCGTGGCTTCAATGCCACCTACCATGTGCGGGGCTATTGCTTGCCTTGGGA
CAGACCCTGTGGCTTAGGCTCTGGCCTGGGAGCTGGCGAAGGCCTAGGTGAGCGCTGCTACAGTGAGGCACAGC
GCTGTGACGGCTCATGGGACTGTGCTGACGGCACAGATGAGGAGGACTGCCCAGGCTGCCCACCTGGACACTTC
CCCTGTGGGGCTGCTGGCACCTCTGGTGCCACAGCCTGCTACCTGCCTGCTGACCGCTGCAACTACCAGACTTT
CTGTGCTGATGGAGCAGATGAGAGACGCTGTCGGCATTGCCAGCCTGGCAATTTCCGATGCCGGGACGAGAAGT
GCGTGTATGAGACGTGGGTGTGCGATGGGCAGCCAGACTGTGCGGACGGCAGTGATGAGTGGGACTGCTCCTAT
GTTCTGCCCCGCAAGGTCATTACAGCTGCAGTCATTGGCAGCCTAGTGTGCGGCCTGCTCCTGGTCATCGCCCT
GGGCTGCACCTGCAAGCTCTATGCCATTCGCACCCAGGAGTACAGCATCTTTGCCCCCCTCTCCCGGATGGAGG
CTGAGATTGTGCAGCAGCAGGCACCCCCTTCCTACGGCAGCTCATTGCCCAGGGTGCCATCCCACCTGTAGAA
GACTTTCCTACAGAGAATCCTAATGATAACTCAGTGCTGGGCAACCTGCGTTCTCTGCTACAGATCTTACGCCA
GGATATGACTCCAGGAGGTGGCCCAGGTGCCCGCCGTCGTCAGCGGGGCCGCTTGATGCGACGCCTGGTACGCC
GTCTCCGCCGCTGGGGCTTGCTCCCTCGAACCAACACCCCGGCTCGGGCCTCTGAGGCCAGATCCCAGGTCACA
CCTTCTGCTGCTCCCCTTGAGGCCCTAGATGGTGGCACAGGTCCAGCCCGTGAGGGCGGGGCAGTGGGTGGGCA
AGATGGGGAGCAGGCACCCCACTGCCCATCAAGGCTCCCCTCCCATCTGCTAGCACGTCTCCAGCCCCCACTA
CTGTCCCTGAAGCCCCAGGGCCACTGCCCTCACTGCCCCTAGAGCCATCACTATTGTCTGGAGTGGTGCAGGCC
CTGCGAGGCCGCCTGTTGCCCAGCCTGGGGCCCCAGGACCAACCCGGAGCCCCCTGGACCCCACACAGCAGT
CCTGGCCCTGGAAGATGAGGACGATGTGCTACTGGTGCCACTGGCTGAGCCGGGGGTGTGGGTAGCTGAGGCAG
AGGATGAGCCACTGCTTACCTGAGGGGACCTGGGGGCTCTACTGAGGCCTCTCCCCTGGGGGCTCTACTCATAG
TGGCACAACCTTTTAGAGGTGGGTCAGCCTCCCCTCCACCACTTCCTTCCCTGTCCCTGGATTTCAGGGACTTG
GTGGGCCTCCCGTTGACCCTATGTAGCTGCTATAAAGTTAAGTGTCCCTCAGGCAGGGAGAGGGCTCACAGAGT
CTCCTCTGTACGTGGCCATGGCCAGACACCCCAGTCCCTTCACCACCACCTGCTCCCACGCCACCACCATTTG
GGTGGCTGTTTTTAAAAAGTAAAGTTCTTAGAGGATCATAGGTCTGGACACTCCATCCTTGCCAAACCTCTACC
```

FIGURE 25 Continued

```
CAAAAGTGGCCTTAAGCACCGGAATGCCAATTAACTAGAGACCCTCCAGCCCCCAAGGGGAGGATTTGGGCAGA
ACCTGAGGTTTTGCCATCCACAATCCCTCCTACAGGGCCTGGCTCACAAAAAGAGTGCAACAAATGCTTCTATT
CCATAGCTACGGCATTGCTCAGTAAGTTGAGGTCAAAAATAAAGGAATCATACATCTC
```

FIGURE 26

</usr/seqdb2/sst/DNA/Dnaseqs.min/ss.DNA49631
<subunit 1 of 1, 713 aa, 1 stop
<MW: 76193, pI: 5.42, NX(S/T): 4

MLLATLLLLLLGGALAHPDRIIFPNHACEDPPAVLLEVQGTLQRPLVRDSRTSPANCTWLILGSKEQTVTIRFQ
KLHLACGSERLTLRSPLQPLISLCEAPPSPLQLPGGNVTITYSYAGARAPMGQGFLLSYSQDWLMCLQEEFQCL
NHRCVSAVQRCDGVDACGDGSDEAGCSSDPFPGLTPRPVPSLPCNVTLEDFYGVFSSPGYTHLASVSHPQSCHW
LLDPHDGRRLAVRFTALDLGFGDAVHVYDGPGPPESSRLLRSLTHFSNGKAVTVETLSGQAVVSYHTVAWSNGR
GFNATYHVRGYCLPWDRPCGLGSGLGAGEGLGERCYSEAQRCDGSWDCADGTDEEDCPGCPPGHFPCGAAGTSG
ATACYLPADRCNYQTFCADGADERRCRHCQPGNFRCRDEKCVYETWVCDGQPDCADGSDEWDCSYVLPRKVITA
AVIGSLVCGLLLVIALGCTCKLYAIRTQEYSIFAPLSRMEAEIVQQQAPPSYGQLIAQGAIPPVEDFPTENPND
NSVLGNLRSLLQILRQDMTPGGGPGARRRQRGRLMRRLVRRLRRWGLLPRTNTPARASEARSQVTPSAAPLEAL
DGGTGPAREGGAVGGQDGEQAPPLPIKAPLPSASTSPAPTTVPEAPGPLPSLPLEPSLLSGVVQALRGRLLPSL
GPPGPTRSPPGPHTAVLALEDEDDVLLVPLAEPGVWVAEAEDEPLLT

Important features:
Signal peptide:
amino acids 1-16

Transmembrane domain:
amino acids 442-462

LDL-receptor class A (LDLRA) domain proteins
amino acids 411-431, 152-171, 331-350 and 374-393

FIGURE 27

```
GTCCCACATCCTGCTCAACTGGGTCAGGTCCCTCTTAGACCAGCTCTTGTCCATCATTTGCTGAAGTGGACCAA
CTAGTTCCCCAGTAGGGGGTCTCCCCTGGCAATTCTTGATCGGCGTTTGGACATCTCAGATCGCTTCCAATGAA
GATGGCCTTGCCTTGGGGTCCTGCTTGTTTCATAATCATCTAACTATGGGACAAGGTTGTGCCGGCAGCTCTGG
GGGAAGGAGCACGGGGCTGATCAAGCCATCCAGGAAACACTGGAGGACTTGTCCAGCCTTGAAAGAACTCTAGT
GGTTTCTGAATCTAGCCCACTTGGCGGTAAGCATGATGCAACTTCTGCAACTTCTGCTGGGGCTTTTGGGGCCA
GGTGGCTACTTATTTCTTTTAGGGGATTGTCAGGAGGTGACCACTCTCACGGTGAAATACCAAGTGTCAGAGGA
AGTGCCATCTGGTACAGTGATCGGGAAGCTGTCCCAGGAACTGGGCCGGGAGGAGAGGCGGAGGCAAGCTGGGG
CCGCCTTCCAGGTGTTGCAGCTGCCTCAGGCGCTCCCCATTCAGGTGGACTCTGAGGAAGGCTTGCTCAGCACA
GGCAGGCGGCTGGATCGAGAGCAGCTGTGCCGACAGTGGGATCCCTGCCTGGTTTCCTTTGATGTGCTTGCCAC
AGGGGATTTGGCTCTGATCCATGTGGAGATCCAAGTGCTGGACATCAATGACCACCAGCCACGGTTTCCCAAAG
GCGAGCAGGAGCTGGAAATCTCTGAGAGCGCCTCTCTGCGAACCCGGATCCCCCTGGACAGAGCTCTTGACCCA
GACACAGGCCCTAACACCCTGCACACCTACACTCTGTCTCCCAGTGAGCACTTTGCCTTGGATGTCATTGTGGG
CCCTGATGAGACCAAACATGCAGAACTCATAGTGGTGAAGGAGCTGGACAGGGAAATCCATTCATTTTTTGATC
TGGTGTTAACTGCCTATGACAATGGGAACCCCCCCAAGTCAGGTACCAGCTTGGTCAAGGTCAACGTCTTGGAC
TCCAATGACAATAGCCCTGCGTTTGCTGAGAGTTCACTGGCACTGGAAATCCAAGAAGATGCTGCACCTGGTAC
GCTTCTCATAAAACTGACCGCCACAGACCCTGACCAAGGCCCCAATGGGGAGGTGGAGTTCTTCCTCAGTAAGC
ACATGCCTCCAGAGGTGCTGGACACCTTCAGTATTGATGCCAAGACAGGCCAGGTCATTCTGCGTCGACCTCTA
GACTATGAAAAGAACCCTGCCTACGAGGTGGATGTTCAGGCAAGGGACCTGGGTCCCAATCCTATCCCAGCCCA
TTGCAAAGTTCTCATCAAGGTTCTGGATGTCAATGACAACATCCCAAGCATCCACGTCACATGGGCCTCCCAGC
CATCACTGGTGTCAGAAGCTCTTCCCAAGGACAGTTTTATTGCTCTTGTCATGGCAGATGACTTGGATTCAGGA
CACAATGGTTTGGTCCACTGCTGGCTGAGCCAAGAGCTGGGCCACTTCAGGCTGAAAAGAACTAATGGCAACAC
ATACATGTTGCTAACCAATGCCACACTGGACAGAGAGCAGTGGCCCAAATATACCCTCACTCTGTTAGCCCAAG
ACCAAGGACTCCAGCCCTTATCAGCCAAGAAACAGCTCAGCATTCAGATCAGTGACATCAACGACAATGCACCT
GTGTTTGAGAAAAGCAGGTATGAAGTCTCCACGCGGGAAAACAACTTACCCTCTCTTCACCTCATTACCATCAA
GGCTCATGATGCAGACTTGGGCATTAATGGAAAAGTCTCATACCGCATCCAGGACTCCCCAGTTGCTCACTTAG
TAGCTATTGACTCCAACACAGGAGAGGTCACTGCTCAGAGGTCACTGAACTATGAAGAGATGGCCGGCTTTGAG
TTCCAGGTGATCGCAGAGGACAGCGGGCAACCCATGCTTGCATCCAGTGTCTCTGTGTGGGTCAGCCTCTTGGA
TGCCAATGATAATGCCCCAGAGGTGGTCCAGCCTGTGCTCAGCGATGGAAAAGCCAGCCTCTCCGTGCTTGTGA
ATGCCTCCACAGGCCACCTGCTGGTGCCCATCGAGACTCCCAATGGCTTGGGCCAGCGGGCACTGACACACCT
CCACTGGCCACTCACAGCTCCCGGCCATTCCTTTTGACAACCATTGTGGCAAGAGATGCAGACTCGGGGGCAAA
TGGAGAGCCCCTCTACAGCATCCGCAATGGAAATGAAGCCCACCTCTTCATCCTCAACCCTCATACGGGGCAGC
TGTTCGTCAATGTCACCAATGCCAGCAGCCTCATTGGGAGTGAGTGGGAGCTGGAGATAGTAGTAGAGGACCAG
GGAAGCCCCCCCTTACAGACCCGAGCCCTGTTGAGGGTCATGTTTGTCACCAGTGTGGACCACCTGAGGGACTC
AGCCCGCAAGCCTGGGGCCTTGAGCATGTCGATGCTGACGGTGATCTGCCTGGCTGTACTGTGGGCATCTTCG
GGTTGATCCTGGCTTTGTTCATGTCCATCTGCCGGACAGAAAAGAAGGACAACAGGGCCTACAACTGTCGGGAG
GCCGAGTCCACCTACCGCCAGCAGCCCAAGAGGCCCCAGAAACACATTCAGAAGGCAGACATCCACCTCGTGCC
TGTGCTCAGGGGTCAGGCAGGTGAGCCTTGTGAAGTCGGGCAGTCCCACAAAGATGTGGACAAGGAGGCGATGA
TGGAAGCAGGCTGGGACCCCTGCCTGCAGGCCCCCTTCCACCTCACCCCGACCCTGTACAGGACGCTGCGTAAT
CAAGGCAACCAGGGAGCACCGGCGGAGAGCCGAGAGGTGCTGCAAGACACGGTCAACCTCCTTTTCAACCATCC
CAGGCAGAGGAATGCCTCCCGGGAGAACCTGAACCTTCCCGAGCCCCAGCCTGCCACAGGCCAGCCACGTTCCA
GGCCTCTGAAGGTTGCAGGCAGCCCCACAGGGAGGCTGGCTGGAGACCAGGGCAGTGAGGAAGCCCCACAGAGG
```

FIGURE 27 Continued

CCACCAGCCTCCTCTGCAACCCTGAGACGGCAGCGACATCTCAATGGCAAAGTGTCCCCTGAGAAAGAATCAGG
GCCCCGTCAGATCCTGCGGAGCCTGGTCCGGCTGTCTGTGGCTGCCTTCGCCGAGCGGAACCCCGTGGAGGAGC
TCACTGTGGATTCTCCTCCTGTTCAGCAAATCTCCCAGCTGCTGTCCTTGCTGCATCAGGGCCAATTCCAGCCC
AAACCAAACCACCGAGGAAATAAGTACTTGGCCAAGCCAGGAGGCAGCAGGAGTGCAATCCCAGACACAGATGG
CCCAAGTGCAAGGGCTGGAGGCCAGACAGACCCAGAACAGGAGGAAGGGCCTTTGGATCCTGAAGAGGACCTCT
CTGTGAAGCAACTGCTAGAAGAAGAGCTGTCAAGTCTGCTGGACCCCAGCACAGGTCTGGCCCTGGACCGGCTG
AGCGCCCCTGACCCGGCCTGGATGGCGAGACTCTCTTTGCCCCTCACCACCAACTACCGTGACAATGTGATCTC
CCCGGATGCTGCAGCCACGGAGGAGCCGAGGACCTTCCAGACGTTCGGCAAGGCAGAGGCACCAGAGCTGAGCC
CAACAGGCACGAGGCTGGCCAGCACCTTTGTCTCGGAGATGAGCTCACTGCTGGAGATGCTGCTGGAACAGCGC
TCCAGCATGCCCGTGGAGGCCGCCTCCGAGGCGCTGCGGCGGCTCTCGGTCTGCGGGAGGACCCTCAGTTTAGA
CTTGGCCACCAGTGCAGCCTCAGGCATGAAAGTGCAAGGGGACCCAGGTGGAAAGACGGGGACTGAGGGCAAGA
GCAGAGGCAGCAGCAGCAGCAGCAGGTGCCTGTGAACATACCTCAGACGCCTCTGGATCCAAGAACCAGGGGCC
TGAGGATCTGTGGACAAGAGCTGGTTTCTAAAATCTTGTAACTCACTAGCTAGCGGCGGCCTGAGAACTTTAGG
GTGACTGATGCTACCCCCACAGAGGAGGCAAGAGCCCCAGGACTAACAGCTGACTGACCAAAGCAGCCCCTTGT
AAGCAGCTCTGAGTCTTTTGGAGGACAGGGACGGTTTGTGGCTGAGATAAGTGTTTCCTGGCAAAACATATGTG
GAGCACAAAGGGTCAGTCCTCTGGCAGAACAGATGCCACGGAGTATCACAGGCAGGAAAGGGTGGCCTTCTTGG
GTAGCAGGAGTCAGGGGGCTGTACCCTGGGGGTGCCAGGAAATGCTCTCTGACCTATCAATAAAGGAAAGCAG
TAAAAAAAAAAAAAAAAAAAAA

FIGURE 28

```
</usr/seqdb2/sst/DNA/Dnaseqs.min/ss.DNA48331
<subunit 1 of 1, 1184 aa, 1 stop
<MW: 129022, pI: 5.20, NX(S/T): 5
MMQLLQLLLGLLGPGGYLFLLGDCQEVTTLTVKYQVSEEVPSGTVIGKLSQELGREERRRQAGAAFQVLQLPQA
LPIQVDSEEGLLSTGRRLDREQLCRQWDPCLVSFDVLATGDLALIHVEIQVLDINDHQPRFPKGEQELEISESA
SLRTRIPLDRALDPDTGPNTLHTYTLSPSEHFALDVIVGPDETKHAELIVVKELDREIHSFFDLVLTAYDNGNP
PKSGTSLVKVNVLDSNDNSPAFAESSLALEIQEDAAPGTLLIKLTATDPDQGPNGEVEFFLSKHMPPEVLDTFS
IDAKTGQVILRRPLDYEKNPAYEVDVQARDLGPNPIPAHCKVLIKVLDVNDNIPSIHVTWASQPSLVSEALPKD
SFIALVMADDLDSGHNGLVHCWLSQELGHFRLKRTNGNTYMLLTNATLDREQWPKYTLTLLAQDQGLQPLSAKK
QLSIQISDINDNAPVFEKSRYEVSTRENNLPSLHLITIKAHDADLGINGKVSYRIQDSPVAHLVAIDSNTGEVT
AQRSLNYEEMAGFEFQVIAEDSGQPMLASSVSVWVSLLDANDNAPEVVQPVLSDGKASLSVLVNASTGHLLVPI
ETPNGLGPAGTDTPPLATHSSRPFLLTTIVARDADSGANGEPLYSIRNGNEAHLFILNPHTGQLFVNVTNASSL
IGSEWELEIVVEDQGSPPLQTRALLRVMFVTSVDHLRDSARKPGALSMSMLTVICLAVLLGIFGLILALFMSIC
RTEKKDNRAYNCREAESTYRQQPKRPQKHIQKADIHLVPVLRGQAGEPCEVGQSHKDVDKEAMMEAGWDPCLQA
PFHLTPTLYRTLRNQGNQGAPAESREVLQDTVNLLFNHPRQRNASRENLNLPEPQPATGQPRSRPLKVAGSPTG
RLAGDQGSEEAPQRPPASSATLRRQRHLNGKVSPEKESGPRQILRSLVRLSVAAFAERNPVEELTVDSPPVQQI
SQLLSLLHQGQFQPKPNHRGNKYLAKPGGSRSAIPDTGPSARAGGQTDPEQEEGPLDPEEDLSVKQLLEEELS
SLLDPSTGLALDRLSAPDPAWMARLSLPLTTNYRDNVISPDAAATEEPRTFQTFGKAEAPELSPTGTRLASTFV
SEMSSLLEMLLEQRSSMPVEAASEALRRLSVCGRTLSLDLATSAASGMKVQGDPGGKTGTEGKSRGSSSSSRCL
```

Important features:

Signal peptide:

amino acids 1-13

Transmembrane domain:

amino acids 719-739

N-glycosylation site.

amino acids 415-418, 582-585, 659-662, 662-665 amd 857-860

Cadherins extracellular repeated domain signature.

amino acids 123-133, 232-242, 340-350, 448-458 and 553-563

FIGURE 29

```
TCTCGCAGATAGTAAATAATCTCGGAAAGGCGAGAAAGAAGCTGTCTCCATCTTGTCTGTATCCGCTGCTCTTG
TGACGTTGTGGAGATGGGGAGCGTCCTGGGGCTGTGCTCCATGGCGAGCTGGATACCATGTTTGTGTGGAAGTG
CCCCGTGTTTGCTATGCCGATGCTGTCCTAGTGGAAACAACTCCACTGTAACTAGATTGATCTATGCACTTTTC
TTGCTTGTTGGAGTATGTGTAGCTTGTGTAATGTTGATACCAGGAATGGAAGAACAACTGAATAAGATTCCTGG
ATTTTGTGAGAATGAGAAAGGTGTTGTCCCTTGTAACATTTTGGTTGGCTATAAAGCTGTATATCGTTTGTGCT
TTGGTTTGGCTATGTTCTATCTTCTTCTCTCTTTACTAATGATCAAAGTGAAGAGTAGCAGTGATCCTAGAGCT
GCAGTGCACAATGGATTTTGGTTCTTTAAATTTGCTGCAGCAATTGCAATTATTATTGGGGCATTCTTCATTCC
AGAAGGAACTTTTACAACTGTGTGGTTTTATGTAGGCATGGCAGGTGCCTTTTGTTTCATCCTCATACAACTAG
TCTTACTTATTGATTTTGCACATTCATGGAATGAATCGTGGGTTGAAAAAATGGAAGAAGGGAACTCGAGATGT
TGGTATGCAGCCTTGTTATCAGCTACAGCTCTGAATTATCTGCTGTCTTTAGTTGCTATCGTCCTGTTCTTTGT
CTACTACACTCATCCAGCCAGTTGTTCAGAAAACAAGGCGTTCATCAGTGTCAACATGCTCCTCTGCGTTGGTG
CTTCTGTAATGTCTATACTGCCAAAAATCCAAGAATCACAACCAAGATCTGGTTTGTTACAGTCTTCAGTAATT
ACAGTCTACACAATGTATTTGACATGGTCAGCTATGACCAATGAACCAGAAACAAATTGCAACCCAAGTCTACT
AAGCATAATTGGCTACAATACAACAAGCACTGTCCCAAAGGAAGGGCAGTCAGTCCAGTGGTGGCATGCTCAAG
GAATTATAGGACTAATTCTCTTTTTGTTGTGTGTATTTTATTCCAGCATCCGTACTTCAAACAATAGTCAGGTT
AATAAACTGACTCTAACAAGTGATGAATCTACATTAATAGAAGATGGTGGAGCTAGAAGTGATGGATCACTGGA
GGATGGGGACGATGTTCACCGAGCTGTAGATAATGAAAGGGATGGTGTCACTTACAGTTATTCCTTCTTTCACT
TCATGCTTTTCCTGGCTTCACTTTATATCATGATGACCCTTACCAACTGGTCCAGGTATGAACCCTCTCGTGAG
ATGAAAAGTCAGTGGACAGCTGTCTGGGTGAAAATCTCTTCCAGTTGGATTGGCATCGTGCTGTATGTTTGGAC
ACTCGTGGCACCACTTGTTCTTACAAATCGTGATTTTGACTGAGTGAGACTTCTAGCATGAAAGTCCCACTTTG
ATTATTGCTTATTTGAAAACAGTATTCCCAACTTTTGTAAAGTTGTGTATGTTTTTGCTTCCCATGTAACTTCT
CCAGTGTTCTGGCATGAATTAGATTTTACTGCTTGTCATTTTGTTATTTTCTTACCAAGTGCATTGATATGTGA
AGTAGAATGAATTGCAGAGGAAAGTTTTATGAATATGGTGATGAGTTAGTAAAAGTGGCCATTATTGGGCTTAT
TCTCTGCTCTATAGTTGTGAAATGAAGAGTAAAAACAAATTTGTTTGACTATTTTAAAATTATATTAGACCTTA
AGCTGTTTTAGCAAGCATTAAAGCAAATGTATGGCTGCCTTTTGAAATATTTGATGTGTTGCCTGGCAGGATAC
TGCAAAGAACATGGTTTATTTTAAAATTTATAAACAAGTCACTTAAATGCCAGTTGTCTGAAAAATCTTATAAG
GTTTTACCCTTGATACGGAATTTACACAGGTAGGGAGTGTTTAGTGGACAATAGTGTAGGTTATGGATGGAGGT
GTCGGTACTAAATTGAATAACGAGTAAATAATCTTACTTGGGTAGAGATGGCCTTTGCCAACAAAGTGAACTGT
TTTGGTTGTTTTAAACTCATGAAGTATGGGTTCAGTGGAAATGTTTGGAACTCTGAAGGATTTAGACAAGGTTT
TGAAAAGGATAATCATGGGTTAGAAGGAAGTGTTTTGAAAGTCACTTTGAAAGTTAGTTTTGGGCCCAGCACGG
TAGCTCACCCTTGGTAATCCCAGCACTTTGGGAGCTTAAGTGGGTAGATTACTTGAGCCCAGGAATTCAGACCA
GCTTGGCACATGGTGAACCTGTTCTATAAAAATAATCTGGCTTTGAGCATATGCCTGTGGTCCAGCACTGAGAG
GCTAGTGAAGATTGCTGAGCCCAGAGCCAAAGGTTGCAGTGAGCAAGTCACGTCACTGCACTCTAGCTGGCACA
GAGTAAGCCAAAAAAATATATATATATTGAAATCAAGGAGGCAAAATTTTGACAGGGAAGGAAGTAACTGCAAA
ACCACTAGGCTTTAGTAGGTACTTATATAAAATCTAGTCCAGTTCTCTCATTTAAAAAAATGAAGACACTGAAA
TACAGACTTAAATAGCTCAGATAGCTAATTAGGAAATTTCAAGTTGGCCAATAATAGCATTCTCTCTGACATTT
AAAAATAATTTCTATTCAAAATACATGCATATTGATTTACACCTCATACTGTGATAATTAATGTGATGTGGATT
GCTGGTGTCCAGCATGACCCATAAACAGGTCAGAAGAATGATGGAATGTTTTAGAATAAACTCCTGCTTATAGT
ATACTACACAGTTCAAAAGATGTTTAAAATGCTTTTGTATTTACTGCCATGTAATTGAAATATATAGATTATTG
TAACCTTTCAACCTGAAAATCAAGCAGTATGAGAGTTTAGTTATTTGTATGTGTCACTAGTGTCTAATGAAGCT
TTTAAAATCTACAATTTCTTCTTTAAAAATATTTATTAATGTGAATGGAATATAACAATTCAGCTTAATTCCCC
AACCTTATTCTGTGTGTAGACATTGTATTCCACAATTTTGAATGGCTGTGTTTTACCTCTAAATAAATGAATTC
AGAGAAAAAAAAAAAAAA
```

FIGURE 30

MGSVLGLCSMASWIPCLCGSAPCLLCRCCPSGNNSTVTRLIYALFLLVGVCVACVMLIPGMEEQLNKIPGFCEN
EKGVVPCNILVGYKAVYRLCFGLAMFYLLLSLLMIKVKSSSDPRAAVHNGFWFFKFAAAIAIIIGAFFIPEGTF
TTVWFYVGMAGAFCFILIQLVLLIDFAHSWNESWVEKMEEGNSRCWYAALLSATALNYLLSLVAIVLFFVYYTH
PASCSENKAFISVNMLLCVGASVMSILPKIQESQPRSGLLQSSVITVYTMYLTWSAMTNEPETNCNPSLLSIIG
YNTTSTVPKEGQSVQWWHAQGIIGLILFLLCVFYSSIRTSNNSQVNKLTLTSDESTLIEDGGARSDGSLEDGDD
VHRAVDNERDGVTYSYSFFHFMLFLASLYIMMTLTNWSRYEPSREMKSQWTAVWVKISSSWIGIVLYVWTLVAP
LVLTNRDFD

FIGURE 31

GCTCAAGACCCAGCAGTGGGACAGCCAGACAGACGGCACGATGGCACTGAGCTCCCAGATC

TGGGCCGCTTGCCTCCTGCTCCTCCTCCTCCTCGCCAGCCTGACCAGTGGCTCTGTTTTCC

CACAACAGACGGGACAACTTGCAGAGCTGCAACCCCAGGACAGAGCTGGAGCCAGGGCCAG

CTGGATGCCCATGTTCCAGAGGCGAAGGAGGCGAGACACCCACTTCCCCATCTGCATTTTC

TGCTGCGGCTGCTGTCATCGATCAAAGTGTGGGATGTGCTGCAAGACGTAGAACCTACCTG

CCCTGCCCCCGTCCCCTCCCTTCCTTATTTATTCCTGCTGCCCCAGAACATAGGTCTTGGA

ATAAAATGGCTGGTTCTTTTGTTTTCCAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

FIGURE 32

MALSSQIWAACLLLLLLLLASLTSGSVFPQQTGQLAELQPQDRAGARASWMPMFQRRRRRDT
HFPICIFCCGCCHRSKCGMCCKT

FIGURE 33

GGCCTCGGTTCAAACGACCCGGTGGGTCTACAGCGGAAGGGAGGGAGCGAAGGTAGGAGGC
AGGGCTTGCCTCACTGGCCACCCTCCCAACCCCAAGAGCCCAGCCCCATGGTCCCCGCCGC
CGGCGCGCTGCTGTGGGTCCTGCTGCTGAATCTGGGTCCCCGGGCGGCGGGGCCCAAGGC
CTGACCCAGACTCCGACCGAAATGCAGCGGGTCAGTTTACGCTTTGGGGCCCCATGACCC
GCAGCTACCGGAGCACCGCCCGGACTGGTCTTCCCCGGAAGACAAGGATAATCCTAGAGGA
CGAGAATGATGCCATGGCCGACGCCGACCGCCTGGCTGGACCAGCGGCTGCCGAGCTCTTG
GCCGCCACGGTGTCCACCGGCTTTAGCCGGTCGTCCGCCATTAACGAGGAGGATGGGTCTT
CAGAAGAGGGGGTTGTGATTAATGCCGGAAAGGATAGCACCAGCAGAGAGCTTCCCAGTGC
GACTCCCAATACAGCGGGGAGTTCCAGCACGAGGTTTATAGCCAATAGTCAGGAGCCTGAA
ATCAGGCTGACTTCAAGCCTGCCGCGCTCCCCGGGAGGTCTACTGAGGACCTGCCAGGCT
CGCAGGCCACCCTGAGCCAGTGGTCCACACCTGGGTCTACCCCGAGCCGGTGGCCGTCACC
CTCACCCACAGCCATGCCATCTCCTGAGGATCTGCGGCTGGTGCTGATGCCCTGGGGCCCG
TGGCACTGCCACTGCAAGTCGGGCACCATGAGCCGGAGCCGGTCTGGGAAGCTGCACGGCC
TTTCCGGGCGCCTTCGAGTTGGGGCGCTGAGCCAGCTCCGCACGGAGCACAAGCCTTGCAC
CTATCAACAATGTCCCTGCAACCGACTTCGGGAAGAGTGCCCCTGGACACAAGTCTCTGT
ACTGACACCAACTGTGCCTCTCAGAGCACCACCAGTACCAGGACCACCACTACCCCCTTCC
CCACCATCCACCTCAGAAGCAGTCCCAGCCTGCCACCCGCCAGCCCCTGCCCAGCCCTGGC
TTTTTGGAAACGGGTCAGGATTGGCCTGGAGGATATTTGGAATAGCCTCTCTTCAGTGTTC
ACAGAGATGCAACCAATAGACAGAAACCAGAGGTAATGGCCACTTCATCCACATGAGGAGA
TGTCAGTATCTCAACCTCTCTTGCCCTTTCAATCCTAGCACCCACTAGATATTTTTAGTAC
AGAAAAACAAAACTGGAAAACACAA

FIGURE 34

MVPAAGALLWVLLLNLGPRAAGAQGLTQTPTEMQRVSLRFGGPMTRSYRSTARTGLPRKTR
IILEDENDAMADADRLAGPAAAELLAATVSTGFSRSSAINEEDGSSEEGVVINAGKDSTSR
ELPSATPNTAGSSSTRFIANSQEPEIRLTSSLPRSPGRSTEDLPGSQATLSQWSTPGSTPS
RWPSPSPTAMPSPEDLRLVLMPWGPWHCHCKSGTMSRSRSGKLHGLSGRLRVGALSQLRTE
HKPCTYQQCPCNRLREECPLDTSLCTDTNCASQSTTSTRTTTTPFPTIHLRSSPSLPPASP
CPALAFWKRVRIGLEDIWNSLSSVFTEMQPIDRNQR

FIGURE 35

```
CAGGAACCCTCTCTTTGGGTCTGGATTGGGACCCCTTTCCAGTACCATTTTTTCTAGTGAACCACGAAGGGACG
ATACCAGAAAACACCCTCAACCCAAAGGAAATAGACTACAGCCCCAATTGGCTGACTTTGGCTATAGAAAAAG
AAAGGAACGAAAAGAGACAGTTTTTTTTGGAAAGCTAAGTCTTCCCTTTATCGAGTCAAGAAACCCCCCCTTCT
TGAGCTATTTACAGCTTTTAACAATTGAGTAAAGTACGCTCCGGTCACCATGGTGACAGCCGCCCTGGGTCCCG
TCTGGGCAGCGCTCCTGCTCTTTCTCCTGATGTGTGAGATCCGTATGGTGGAGCTCACCTTTGACAGAGCTGTG
GCCAGCGGCTGCCAACGGTGCTGTGACTCTGAGGACCCCCTGGATCCTGCCCATGTATCCTCAGCCTCTTCCTC
CGGCCGCCCCACGCCCTGCCTGAGATCAGACCCTACATTAATATCACCATCCTGAAGGGTGACAAAGGGGACC
CAGGCCCAATGGGCCTGCCAGGGTACATGGGCAGGAGGGTCCCCAAGGGGAGCCTGGCCCTCAGGGCAGCAAG
GGTGACAAGGGGGAGATGGGCAGCCCCGGCGCCCCGTGCCAGAAGCGCTTCTTCGCCTTCTCAGTGGGCCGCAA
GACGGCCCTGCACAGCGGCGAGGACTTCCAGACGCTGCTCTTCGAAAGGGTCTTTGTGAACCTTGATGGGTGCT
TTGACATGGCGACCGGCCAGTTTGCTGCTCCCCTGCGTGGCATCTACTTCTTCAGCCTCAATGTGCACAGCTGG
AATTACAAGGAGACGTACGTGCACATTATGCATAACCAGAAAGAGGCTGTCATCCTGTACGCGCAGCCCAGCGA
GCGCAGCATCATGCAGAGCCAGAGTGTGATGCTGGACCTGGCCTACGGGGACGCGTCTGGGTGCGGCTCTTCA
AGCGCCAGCGCGAGAACGCCATCTACAGCAACGACTTCGACACCTACATCACCTTCAGCGGCCACCTCATCAAG
GCCGAGGACGACTGAGGGCCTCTGGGCCACCCTCCCGGCTGGAGAGCTCAGGTGCTGGTCCCGTCCCTGCAGG
GCTCAGTTTGCACTGCTGTGAAGCAGGAAGGCCAGGGAGGTCCCCGGGGACCTGGCATTCTGGGGAGACCCTGC
TTCTATCTTGGCTGCCATCATCCCTCCCAGCCTATTTCTGCTCCTCTCTTCTCTCTTGGACCTATTTTAAGAAG
CTTGCTAACCTAAATATTCTAGAACTTTCCCAGCCTCGTAGCCCAGCACTTCTCAAACTTGGAAATGCATGCGA
ATCACCCGGGGTTCGTGTTAAATGCAGATTCTGACTCAGCAGGTCTGAGTGGGTCCAGGATTCTGTGTTTCTCA
TATGTTCCTGGGTGATGCTGATGGGGTCAGTCTATGAACCACACTGGAGCAACCAGGTTCTAGGACTTTCTCAA
TATTCTAGTACTTTCTGAACATTCTGGAATCCTCCCCACATTCTAGAATTCTCCCAACATTTTTTTTCTTGAG
ACAGAGTCTTGCTCTGTTGCCCAGGCTAGAGTGCAGTGGTGCAATCTCAGTTCACTGCAACCTCTGCCTCCCGG
GTTCAAGCGATTCTTCTGCCTCAGCCTCCCTAGTGGCTGGGATTACAGGCGCCTGCTACCATGCCTGGCTAATT
TTTGTATTTTTAGTAGAGATGGGGTTTCACCATATTGGCCAGGCTGGTCTTGAACTCCTGACTTCAGGTGACCC
ACCCGCCTCGGCCTCTCAAAATGCTGGGATTACAGGTGTGAGCCACCGTGCCTGGCCAATTCCAACATTCTTAA
ATTCTCTCATCCCTCCAGGGCTCCCCGTGCTATGTTCTCTTTACCCCTTCCCCCTCTTCTCTTGCTCAGGCCTG
CACCACTGCAGCCACCGTTCATTTATTCATTCATTAAACACTGAGCACTCACTCTGTGCTGGGTCCCGGGAAGG
GTGAGGGGTCAGACACAGGCCCTGCCCCTGCCCTCAGTGACTGGCCAGTCCAGCCCAGGCGGGGAGAGATGTG
TACATAGGTTTTAAAGCAGACCCAGAGCTCATGGGGGCCTGTGTTCTGGGTGTTCAGGTGCTGCTGGTCCTCCA
TTACCCACTGCTCCCCAAGGCTGGTGGGACGGGGTCCCGGTGGCAGGGGCAGGTATCTCCTTCCCGTTCCTCAT
CCACCTGCCCAGTGCTCATCGTTACAGCAAACCCCAGGGGGCCTTGGCCAGGTCAAGGGTTCTGTGAGGAGAGG
ACCCAGGAGTGTGGGGGCATTTGGGGGTGAAGTGGCCCCCGAAGAATGGAACCCACACCCATAGCTCTCCCCA
CAGCTGATACGGCATCCTGCGAGAAGACCTGCCCTCCTCACTGGGATCCCCTTCCTGCCTCCTCCCAGGGCTCT
GCCAGGGCCTTGCTCAGTCCCTTCCACCAAAGTCATCTGAACTTCCGTTTCCCCAGGGCCTCCAGCTGCCCTCA
GACACTGATGTCTGTCCCCAGGTGCTCTCTGCCCCTCATGCCCCTCTCACCGGCCCAGTGCCCCGACTCTCCAG
GCTTTATCAAGGTGCTAAGGCCCGGGTGGGCAGCTCCTCGTCTCAGAGCCCTCCTCCGGCCTGGTGCTGCCTTT
ACAAACACCTGCAGGAGAAGGGCCACGGAAGCCCCAGGCTTTAGAGCCCTCAGCAGGTCTGGGGAGCTAGAGCA
AAGGAGGGACCTCAGGCCTTCCGTTTCTTCTTCCAGGGTGGGGTGGCCTGGTGTTCCCCTAGCCTTCCAAACCC
AGGTGGCCTGCCCTTCTCCCCAGAGGGAGGCGGCCTCCGCCCATTGGTGCTCATGCAGACTCTGGGGCTGAGGT
GCCCCGGGGGGTGATCTCTGGTGCTCACAGCCGAGGGAGCCGTGGCTCCATGGCCAGATGACGGAAACAGGGTC
TGACCAAGTGCCAGGAAGACCTGTGCTATAAACCACCCTGCCTGATCCTGCCCCTGCCTGACCCCGCCACGCCC
```

FIGURE 35 CONTINUED

TGCCGTCCAGCATGATTAAAGAATGCTGTCTCCTCTTGGAAAAAAAAAAAAAAAA

FIGURE 36

MVTAALGPVWAALLLFLLMCEIRMVELTFDRAVASGCQRCCDSEDPLDPAHVSSASSSGRPHALPEIRPYINIT
ILKGDKGDPGPMGLPGYMGREGPQGEPGPQGSKGDKGEMGSPGAPCQKRFFAFSVGRKTALHSGEDFQTLLFER
VFVNLDGCFDMATGQFAAPLRGIYFFSLNVHSWNYKETYVHIMHNQKEAVILYAQPSERSIMQSQSVMLDLAYG
DRVWVRLFKRQRENAIYSNDFDTYITFSGHLIKAEDD

Important features:
Signal peptide:
amino acids 1-20

N-glycosylation site.
amino acids 72-75

C1q domain proteins.
amino acids 144-178, 78-111 and 84-117

FIGURE 37

GAGCGAACATGGCAGCGCGTTGGCGGTTTTGGTGTGTCTCTGTGACCATGGTGGTGGCGCTGCTCATCGTTTGC
GACGTTCCCTCAGCCTCTGCCCAAAGAAAGAAGGAGATGGTGTTATCTGAAAAGGTTAGTCAGCTGATGGAATG
GACTAACAAAAGACCTGTAATAAGAATGAATGGAGACAAGTTCCGTCGCCTTGTGAAAGCCCCACCGAGAAATT
ACTCCGTTATCGTCATGTTCACTGCTCTCCAACTGCATAGACAGTGTGTCGTTTGCAAGCAAGCTGATGAAGAA
TTCCAGATCCTGGCAAACTCCTGGCGATACTCCAGTGCATTCACCAACAGGATATTTTTTGCCATGGTGGATTT
TGATGAAGGCTCTGATGTATTTCAGATGCTAAACATGAATTCAGCTCCAACTTTCATCAACTTTCCTGCAAAAG
GGAAACCCAAACGGGGTGATACATATGAGTTACAGGTGCGGGGTTTTTCAGCTGAGCAGATTGCCCGGTGGATC
GCCGACAGAACTGATGTCAATATTAGAGTGATTAGACCCCCAAATTATGCTGGTCCCCTTATGTTGGGATTGCT
TTTGGCTGTTATTGGTGGACTTGTGTATCTTCGAAGAAGTAATATGGAATTTCTCTTTAATAAAACTGGATGGG
CTTTTGCAGCTTTGTGTTTTGTGCTTGCTATGACATCTGGTCAAATGTGGAACCATATAAGAGGACCACCATAT
GCCCATAAGAATCCCCACACGGGACATGTGAATTATATCCATGGAAGCAGTCAAGCCCAGTTTGTAGCTGAAAC
ACACATTGTTCTTCTGTTTAATGGTGGAGTTACCTTAGGAATGGTGCTTTTATGTGAAGCTGCTACCTCTGACA
TGGATATTGGAAAGCGAAAGATAATGTGTGTGGCTGGTATTGGACTTGTTGTATTATTCTTCAGTTGGATGCTC
TCTATTTTTAGATCTAAATATCATGGCTACCCATACAGCTTTCTGATGAGTTAAAAAGGTCCCAGAGATATATA
GACACTGGAGTACTGGAAATTGAAAAACGAAAATCGTGTGTGTTTGAAAAGAAGAATGCAACTTGTATATTTTG
TATTACCTCTTTTTTTTCAAGTGATTTAAATAGTTAATCATTTAACCAAAGAAGATGTGTAGTGCCTTAACAAGC
AATCCTCTGTCAAAATCTGAGGTATTTGAAAATAATTATCCTCTTAACCTTCTCTTCCCAGTGAACTTTATGGA
ACATTTAATTTAGTACAATTAAGTATATTATAAAAATTGTAAAACTACTACTTTGTTTTAGTTAGAACAAAGCT
CAAAACTACTTTAGTTAACTTGGTCATCTGATTTTATATTGCCTTATCCAAAGATGGGGAAAGTAAGTCCTGAC
CAGGTGTTCCCACATATGCCTGTTACAGATAACTACATTAGGAATTCATTCTTAGCTTCTTCATCTTTGTGTGG
ATGTGTATACTTTACGCATCTTTCCTTTTGAGTAGAGAAATTATGTGTGTCATGTGGTCTTCTGAAAATGGAAC
ACCATTCTTCAGAGCACACGTCTAGCCCTCAGCAAGACAGTTGTTTCTCCTCCTCCTTGCATATTTCCTACTGC
GCTCCAGCCTGAGTGATAGAGTGAGACTCTGTCTCAAAAAAAAGTATCTCTAAATACAGGATTATAATTTCTGC
TTGAGTATGGTGTTAACTACCTTGTATTTAGAAAGATTTCAGATTCATTCCATCTCCTTAGTTTTCTTTTAAGG
TGACCCATCTGTGATAAAAATATAGCTTAGTGCTAAAATCAGTGTAACTTATACATGGCCTAAAATGTTTCTAC
AAATTAGAGTTTGTCACTTATTCCATTTGTACCTAAGAGAAAAATAGGCTCAGTTAGAAAAGGACTCCCTGGCC
AGGCGCAGTGACTTACGCCTGTAATCTCAGCACTTTGGGAGGCCAAGGCAGGCAGATCACGAGGTCAGGAGTTC
GAGACCATCCTGGCCAACATGGTGAAACCCCGTCTCTACTAAAAATATAAAAATTAGCTGGGTGTGGTGGCAGG
AGCCTGTAATCCCAGCTACACAGGAGGCTGAGGCACGAGAATCACTTGAACTCAGGAGATGGAGGTTTCAGTGA
GCCGAGATCACGCCACTGCACTCCAGCCTGGCAACAGAGCGAGACTCCATCTCAAAAAAAAAAAAAA

FIGURE 38

MAARWRFWCVSVTMVVALLIVCDVPSASAQRKKEMVLSEKVSQLMEWTNKRPVIRMNGDKFRRLVKAPPRNYSV
IVMFTALQLHRQCVVCKQADEEFQILANSWRYSSAFTNRIFFAMVDFDEGSDVFQMLNMNSAPTFINFPAKGKP
KRGDTYELQVRGFSAEQIARWIADRTDVNIRVIRPPNYAGPLMLGLLLAVIGGLVYLRRSNMEFLFNKTGWAFA
ALCFVLAMTSGQMWNHIRGPPYAHKNPHTGHVNYIHGSSQAQFVAETHIVLLFNGGVTLGMVLLCEAATSDMDI
GKRKIMCVAGIGLVVLFFSWMLSIFRSKYHGYPYSFLMS

Signal peptide:
amino acids 1-29

Transmembrane domains:
amino acids 183-205, 217-237, 217-287, 301-321

FIGURE 39

CAGGCCATTTGCATCCCACTGTCCTTGTGTTCGGAGCCAGGCCACACCGTCCTCAGCAGTGTCATGTGTTAAAA
ACGCCAAGCTGAATATATCATGCCCCTATTAAAACTTGTACATGGCTCCCCATTGGTTTTTGGAGAAAAGTTCA
AGCTTTTTACCTTGGTGTCTGCCTGTATCCCAGTGTTCAGGCTGGCTAGACGGCGGAAGAAGATCCTATTTTAC
TGTCACTTCCCAGATCTGCTTCTCACCAAGAGAGATTCTTTTCTTAAACGACTATACAGGGCCCCAATTGACTG
GATAGAGGAATACACCACAGGCATGGCAGACTGCATCTTAGTCAACAGCCAGTTCACAGCTGCTGTTTTTAAGG
AAACATTCAAGTCCCTGTCTCACATAGACCCTGATGTCCTCTATCCATCTCTAAATGTCACCAGCTTTGACTCA
GTTGTTCCTGAAAAGCTGGATGACCTAGTCCCCAAGGGGAAAAAATTCCTGCTGCTCTCCATCAACAGATACGA
AAGGAAGAAAAATCTGACTTTGGCACTGGAAGCCCTAGTACAGCTGCGTGGAAGATTGACATCCCAAGATTGGG
AGAGGGTTCATCTGATCGTGGCAGGTGGTTATGACGAGAGAGTCCTGGAGAATGTGGAACATTATCAGGAATTG
AAGAAAATGGTCCAACAGTCCGACCTTGGCCAGTATGTGACCTTCTTGAGGTCTTTCTCAGACAAACAGAAAAT
CTCCCTCCTCCACAGCTGCACGTGTGTGCTTTACACACCAAGCAATGAGCACTTTGGCATTGTCCCTCTGGAAG
CCATGTACATGCAGTGCCCAGTCATTGCTGTTAATTCGGGTGGACCCTTGGAGTCCATTGACCACAGTGTCACA
GGGTTTCTGTGTGAGCCTGACCCGGTGCACTTCTCAGAAGCAATAGAAAGTTCATCCGTGAACCTTCCTTAAA
AGCCACCATGGGCCTGGCTGGAAGAGCCAGAGTGAAGGAAAAATTTTCCCCTGAAGCATTTACAGAACAGCTCT
ACCGATATGTTACCAAACTGCTGGTATAATCAGATTGTTTTTAAGATCTCCATTAATGTCATTTTTATGGATTG
TAGACCCAGTTTTGAAACCAAAAAAGAAACCTAGAATCTAATGCAGAAGAGATCTTTTAAAAAATAAACTTGAG
TCTTGAATGTGAGCCACTTTCCTATATACCACACCTCCCTGTCCACTTTTCAGAAAAACCATGTCTTTTATGCT
ATAATCATTCCAAATTTTGCCAGTGTTAAGTTACAAATGTGGTGTCATTCCATGTTCAGCAGAGTATTTTAATT
ATATTTTCTCGGGATTATTGCTCTTCTGTCTATAAATTTTGAATGATACTGTGCCTTAATTGGTTTTCATAGTT
TAAGTGTGTATCATTATCAAAGTTGATTAATTTGGCTTCATAGTATAATGAGAGCAGGGCTATTGTAGTTCCCA
GATTCAATCCACCGAAGTGTTCACTGTCATCTGTTAGGGAATTTTTGTTTGTCCTGTCTTTGCCTGGATCCATA
GCGAGAGTGCTCTGTATTTTTTTAAGATAATTTGTATTTTTGCACACTGAGATATAATAAAAGGTGTTTATCA
TAAAAAAAAAAAAAAAAAAA

FIGURE 40

MPLLKLVHGSPLVFGEKFKLFTLVSACIPVFRLARRRKKILFYCHFPDLLLTKRDSFLKRLYRAPIDWIEEYTT
GMADCILVNSQFTAAVFKETFKSLSHIDPDVLYPSLNVTSFDSVVPEKLDDLVPKGKKFLLLSINRYERKKNLT
LALEALVQLRGRLTSQDWERVHLIVAGGYDERVLENVEHYQELKKMVQQSDLGQYVTFLRSFSDKQKISLLHSC
TCVLYTPSNEHFGIVPLEAMYMQCPVIAVNSGGPLESIDHSVTGFLCEPDPVHFSEAIEKFIREPSLKATMGLA
GRARVKEKFSPEAFTEQLYRYVTKLLV

Signal peptide:
amino acids 1-15

FIGURE 41

AAGACCCTCTCTTTCGCTGTTTGAGAGTCTCTCGGCTCAAGGACCGGGAGGTAAGAGGTT
TGGGACTGCCCCGGCAACTCCAGGGTGTCTGGTCCACGACCTATCCTAGGCGCCATGGGT
GTGATAGGTATACAGCTGGTTGTTACCATGGTGATGGCCAGTGTCATGCAGAAGATTATA
CCTCACTATTCTCTTGCTCGATGGCTACTCTGTAATGGCAGTTTGAGGTGGTATCAACAT
CCTACAGAAGAAGAATTAAGAATTCTTGCAGGGAAACAACAAAAGGGAAAACCAAAAAA
GATAGGAAATATAATGGTCACATTGAAAGTAAGCCATTAACCATTCCAAAGGATATTGAC
CTTCATCTAGAAACAAAGTCAGTTACAGAAGTGGATACTTTAGCATTGCATTACTTTCCA
GAATACCAGTGGCTGGTGGATTTCACAGTGGCTGCTACAGTTGTGTATCTAGTAACTGAA
GTCTACTACAATTTTATGAAGCCTACACAGGAAATGAATATCAGCTTAGTCTGGTGCCTA
CTTGTTTTGTCTTTTGCAATCAAAGTTCTATTTTCATTAACTACACACTATTTTAAAGTA
GAAGATGGTGGTGAAAGATCTGTTTGTGTCACCTTTGGATTTTTTTTCTTTGTCAAAGCA
ATGGCAGTGTTGATTGTAACAGAAAATTATCTGGAATTTGGACTTGAAACAGGGTTTACA
AATTTTTCAGACAGTGCGATGCAGTTTCTTGAAAAGCAAGGTTTAGAATCTCAGAGTCCT
GTTTCAAAACTTACTTTCAAATTTTTCCTGGCTATTTTCTGTTCATTCATTGGGGCTTTT
TTGACATTTCCTGGATTACGACTGGCTCAAATGCATCTGGATGCCCTGAATTTGGCAACA
GAAAAAATTACACAAACTTTACTTCATATCAACTTCTTGGCACCTTTATTTATGGTTTTG
CTCTGGGTAAAACCAATCACCAAAGACTACATTATGAACCCACCACTGGGCAAAGAAATT
TCCCCATCTGGAAGATGAAGATAATAGTATCTAACTCACAAGGTTATCATTGGAATAAAT
GAAAGAACACATGTAATGCAACCAGCTGGAATTAAGTGCTTAATAAATGTTCTTTTCACT
GCTTTGCCTCATCAGAATTAAAATAGAAATACTTGACTAGT

FIGURE 42

</usr/seqdb2/sst/DNA/Dnaseqs.full/ss.DNA64966

<subunit 1 of 1, 307 aa, 1 stop

<MW: 35098, pI: 8.11, NX(S/T): 3

MGVIGIQLVVTMVMASVMQKIIPHYSLARWLLCNGSLRWYQHPTEEELRILAGKQQ
KGKTKKDRKYNGHIESKPLTIPKDIDLHLETKSVTEVDTLALHYFPEYQWLVDFTVA
ATVVYLVTEVYYNFMKPTQEMNISLVWCLLVLSFAIKVLFSLTTHYFKVEDGGERS
VCVTFGFFFFVKAMAVLIVTENYLEFGLETGFTNFSDSAMQFLEKQGLESQSPVSKL
TFKFFLAIFCSFIGAFLTFPGLRLAQMHLDALNLATEKITQTLLHINFLAPLFMVLLWV
KPITKDYIMNPPLGKEISPSGR

Important features:

Signal peptide:

Amino acids          1-15

Transmembrane domains:

Amino acids          134-157;169-189;230-248;272-285

N-glycosylation sites:

Amino acids          34-38;135-139;203-207

ATP/GTP-binding site motif A (P-loop):

Amino acids          53-61

Tyrosine kinase phosphorylation site:

Amino acids          59-67

N-myristoylation sites:

Amino acids          165-171;196-202;240-246;247-253

FIGURE 43

GAGAGAGGCAGCAGCTTGCTCAGCGGACAAGGATGCTGGGCGTGAGGGACCAAGGCCTGCCCTGCACTCGGGCC
TCCTCCAGCCAGTGCTGACCAGGGACTTCTGACCTGCTGGCCAGCCAGGACCTGTGTGGGGAGGCCCTCCTGCT
GCCTTGGGGTGACAATCTCAGCTCCAGGCTACAGGGAGACCGGGAGGATCACAGAGCCAGCATGTTACAGGATC
CTGACAGTGATCAACCTCTGAACAGCCTCGATGTCAAACCCCTGCGCAAACCCCGTATCCCCATGGAGACCTTC
AGAAAGGTGGGGATCCCCATCATCATAGCACTACTGAGCCTGGCGAGTATCATCATTGTGGTTGTCCTCATCAA
GGTGATTCTGGATAAATACTACTTCCTCTGCGGGCAGCCTCTCCACTTCATCCCGAGGAAGCAGCTGTGTGACG
GAGAGCTGGACTGTCCCTTGGGGGAGGACGAGGAGCACTGTGTCAAGAGCTTCCCCGAAGGGCCTGCAGTGGCA
GTCCGCCTCTCCAAGGACCGATCCACACTGCAGGTGCTGGACTCGGCCACAGGGAACTGGTTCTCTGCCTGTTT
CGACAACTTCACAGAAGCTCTCGCTGAGACAGCCTGTAGGCAGATGGGCTACAGCAGAGCTGTGGAGATTGGCC
CAGACCAGGATCTGGATGTTGTTGAAATCACAGAAAACAGCCAGGAGCTTCGCATGCGGAACTCAAGTGGGCCC
TGTCTCTCAGGCTCCCTGGTCTCCCTGCACTGTCTTGCCTGTGGGAAGAGCCTGAAGACCCCCGTGTGGTGGG
TGGGGAGGAGGCCTCTGTGGATTCTTGGCCTTGGCAGGTCAGCATCCAGTACGACAAACAGCACGTCTGTGGAG
GGAGCATCCTGGACCCCCACTGGGTCCTCACGGCAGCCCACTGCTTCAGGAAACATACCGATGTGTTCAACTGG
AAGGTGCGGGCAGGCTCAGACAAACTGGGCAGCTTCCCATCCCTGGCTGTGGCCAAGATCATCATCATTGAATT
CAACCCCATGTACCCCAAAGACAATGACATCGCCCTCATGAAGCTGCAGTTCCCACTCACTTTCTCAGGCACAG
TCAGGCCCATCTGTCTGCCCTTCTTTGATGAGGAGCTCACTCCAGCCACCCCACTCTGGATCATTGGATGGGGC
TTTACGAAGCAGAATGGAGGGAAGATGTCTGACATACTGCTGCAGGCGTCAGTCCAGGTCATTGACAGCACACG
GTGCAATGCAGACGATGCGTACCAGGGGAAGTCACCGAGAAGATGATGTGTGCAGGCATCCCGGAAGGGGGTG
TGGACACCTGCCAGGGTGACAGTGGTGGGCCCCTGATGTACCAATCTGACCAGTGGCATGTGGTGGGCATCGTT
AGCTGGGGCTATGGCTGCGGGGGCCCGAGCACCCCAGGAGTATACACCAAGGTCTCAGCCTATCTCAACTGGAT
CTACAATGTCTGGAAGGCTGAGCTGTAATGCTGCTGCCCCTTTGCAGTGCTGGGAGCCGCTTCCTTCCTGCCCT
GCCCACCTGGGGATCCCCCAAAGTCAGACACAGAGCAAGAGTCCCCTTGGGTACACCCCTCTGCCCACAGCCTC
AGCATTTCTTGGAGCAGCAAAGGGCCTCAATTCCTGTAAGAGACCCTCGCAGCCCAGAGGCGCCCAGAGGAAGT
CAGCAGCCCTAGCTCGGCCACACTTGGTGCTCCCAGCATCCCAGGGAGAGACACAGCCCACTGAACAAGGTCTC
AGGGGTATTGCTAAGCCAAGAAGGAACTTTCCCACACTACTGAATGGAAGCAGGCTGTCTTGTAAAAGCCCAGA
TCACTGTGGGCTGGAGAGGAGAAGGAAAGGGTCTGCGCCAGCCCTGTCCGTCTTCACCCATCCCCAAGCCTACT
AGAGCAAGAAACCAGTTGTAATATAAAATGCACTGCCCTACTGTTGGTATGACTACCGTTACCTACTGTTGTCA
TTGTTATTACAGCTATGGCCACTATTATTAAAGAGCTGTGTAACATCTCTGGCAAAAAAAAAAAA

FIGURE 44

></usr/seqdb2/sst/DNA/Dnaseqs.min/ss.DNA68885
><subunit 1 of 1, 432 aa, 1 stop
><MW: 47644, pI: 5.18, NX(S/T): 2
MLQDPDSDQPLNSLDVKPLRKPRIPMETFRKVGIPIIIALLSLASIIIVVVLIKVILDKYYFLCGQPLHFIPRK
QLCDGELDCPLGEDEEHCVKSFPEGPAVAVRLSKDRSTLQVLDSATGNWFSACFDNFTEALAETACRQMGYSRA
VEIGPDQDLDVVEITENSQELRMRNSSGPCLSGSLVSLHCLACGKSLKTPRVVGGEEASVDSWPWQVSIQYDKQ
HVCGGSILDPHWVLTAAHCFRKHTDVFNWKVRAGSDKLGSFPSLAVAKIIIIEFNPMYPKDNDIALMKLQFPLT
FSGTVRPICLPFFDEELTPATPLWIIGWGFTKQNGGKMSDILLQASVQVIDSTRCNADDAYQGEVTEKMMCAGI
PEGGVDTCQGDSGGPLMYQSDQWHVVGIVSWGYGCGGPSTPGVYTKVSAYLNWIYNVWKAEL

Transmembrane domain:
amino acids 32-53 (typeII)

FIGURE 45

CGGACGCGTGGGTGGCAACCAGGAGAAGCCAAACTTGGTCCCCCGGCTCGCGGAGTGCCTGCGA
GCGGTGCTCATGGCGCTCTATGAGGTCTTCTCTCACCCGGTCGAGCGCAGTTACCGCGCGGGGCT
CTGCTCCAAAGCCGCGCTGTTCCTGCTGCTGGCCGCTGCGCTCACGTACATCCCGCCGCTGCTGGT
GGCCTTCCGGAGCCACGGGTTTTGGCTGAAGCGGAGCAGCTACGAGGAGCAGCCGACCGTGCGC
TTCCAACACCAGGTGCTGCTCGTGGCCCTGCTCGGACCCGAAAGCGACGGGTTCCTCGCCTGGAG
CACGTTCCCCGCCTTCAACCGGCTGCAAGGGGATCGCCTGCGCGTCCCGCTCGTTTCGACTAGAG
AAGAAGACAGGAACCAGGATGGGAAGACGGACATGTTACATTTTAAGCTGGAGCTTCCCCTGCA
GTCCACGGAGCACGTTCTCGGTGTGCAGCTCATCCTGACTTTCTCCTATCGATTACACAGGATGG
CGACCCTCGTGATGCAGAGCATGGCGTTTCTCCAGTCCTCCTTTCCTGTCCCGGGATCCCAGTTAT
ACGTGAACGGAGACCTGAGGCTGCAGCAGAAGCAGCCGCTGAGCTGTGGTGGCCTAGATGCCCG
ATACAACATATCCGTGATCAACGGGACCAGCCCCTTTGCCTATGACTACGACCTCACCCATATTG
TTGCTGCCTACCAGGAGAGGAACGTTACCACCGTCCTGAATGATCCCAACCCCATCTGGCTGGTG
GGCAGGGCCGCAGATGCTCCATTTGTGATTAATGCTATCATCCGATACCCTGTGGAAGTCATTTC
TTATCAGCCAGGATTCTGGGAGATGGTAAAGTTCGCCTGGGTACAGTATGTCAGCATCCTGCTTA
TCTTCCTCTGGGTGTTTGAAAGAATCAAGATCTTCGTGTTTCAGAATCAGGTGGTGACCACCATTC
CTGTGACAGTGACGCCCCGGGGAGACTTGTGTAAGGAGCACTTATCCTAGAAAGGCCATTTCTGA
AGACTCAGCAGGACCGTGGCTGCCTCATTGTCATCTTCTGGGAACATCTTAGGACCTTTTGAAAG
AGCCCAGCGGACACCTGCGGGCTTGTGTGCTTTTCCCTCAGAGACAACGGTTCTTTCCGGTTTTGC
TCTACACAGTTCCGTATCTTCAGAGCTCCTGCAGAATTGTCAGGGACTAGTTTGTGGAAAGGTCT
GAGAGTTCCTGGAGGCTATAATTAGCTTTTTGGGTTTTCCTTCTTTGCCTTAGCGTTGAATTTCAG
GAGAAAATTGCAGTCAGTTCAGACATCTTGGAAAGAGTCCCATCTCTGGTCAAGCAGAGACTTTT
CCTCTGTTGAACTGAGGAACACACTGTGCATTTCTTCCTTCTGTTGTGAGCCACTCTTACTCTTTT
CAGGGCTCTCTTGTGACAAACATGCCAATCACTAGCACTTTGCACCCCTGGGCTTCTCCATTTCCC
ATTCACAGCTTTGATTTCCAGAGCTGAGGCCTTTAACTGGAGACCTGGAGGGGCAGGGCCCAAGG
GCAAGGGCCGCATTAGCACAGGCAATCAGGGAGGGCCGCTGAAGGACACTTGGACCGTCCACCT
GCCCCAGCCCAACAGTCAGTCATCTGTCATCAGCTCAGCTGAGCAGCCCTGGATCTTTGCCGTAC
TGTGACTGGGCTCTTTGCCCTATTTTTCCCTCTGTCTGTGCCCCTGGATGGCAGGCTGAAGTCAGA
GGGGCTGTTTCATTCTCAGCCCCCTCAGCAGCACTGGGGGAAGAAAGCATTGTCACAACAGGTTC
TTTCTGGCCCTCACCCAACAGCCTGGGCACTTGGCCCTCCTCCTCCTTGACAGCCCTCCCCCTTCC
TGCAAAGGACAGGGGCGACAGGGGTTGGTGTTGGGATTGGCTCCCGCTGCCTGACAACCACAAG
TTTATTTGGAAGGCTAGCGGGAAGCCCAGCGGCTGGCGTTTCCCTTGACTAAGGAACAGGGTGCC
CATCAGAGTGGGGCGGGCAGCTTTGGGAAGGACACAAGAAGCAGTAAGAGTGTAAAGAGGATG
CTGGCCTGGGCAGGCCAGTCCAGCCTGGCCACTAGCAGAATACCAAGCAGTCCAGTGGATTACCC
TCGTGGCTAAGCAAGTGTCTGCAGGAGCAGAGATGGCTGGAAGGGGCCTCTGCACACGGAAGAT
GGCTTGTTCAGCCCATTCACCTCCTGAGGATGTGGGCAGTCTCCTCCAAGAACACATGGAGCTGC
TTCCTGATCCCAAGCAGGTCATTGCCACTGGAAGGACATGGCCCCGGTGATCCATGCTTCATGCC
CACCCAGAAACACACCCCTCAGTGTGTGCCTCAGTTTACTTTGGAGATCAGTTGTCGTTTTTAGTG

FIGURE 45 CONTINUED

CTCCTTTAGGCTTACTAAAACAGTTTTGGAAACAAAGCTATTTTGAAGTATTCAAGCAGAGGAAT
TCCCTAACACTGACCCCCTTGTCTTTTTTTAATATTCAGGCTGTTTTATATGCCTAAATTTTTTCT
TAAGATCTAAACGAAAAATAGTTTCTTGTTTAAATTCACATAAGGCAATGAGATATGGAAAGATG
ACAAGATACGTATAAACATTGGTTTGCATCTTATTAAATTATTCTAATGCAAATCTTGTATAAAG
AACCCATGATGTTTTGTAACTTTCTAATTAAAATGTTCAAAATGAG

FIGURE 46

MALYEVFSHPVERSYRAGLCSKAALFLLLAAALTYIPPLLVAFRSHGFWLKRSSYEEQPTVRFQHQVL
LVALLGPESDGFLAWSTFPAFNRLQGDRLRVPLVSTREEDRNQDGKTDMLHFKLELPLQSTEHVLGV
QLILTFSYRLHRMATLVMQSMAFLQSSFPVPGSQLYVNGDLRLQQKQPLSCGGLDARYNISVINGTSP
FAYDYDLTHIVAAYQERNVTTVLNDPNPIWLVGRAADAPFVINAIIRYPVEVISYQPGFWEMVKFAW
VQYVSILLIFLWVFERIKIFVFQNQVVTTIPVTVTPRGDLCKEHLS

Important features of the protein:

Signal peptide:

amino acids 1-34

Transmembrane domain:

amino acids 268-284

N-glycosylation sites.

amino acids 194-198, 199-203, 221-225 cAMP- and cGMP-dependent protein kinase phosphorylation site.

amino acids 51-55

Tyrosine kinase phosphorylation site.

amino acids 250-259

N-myristoylation site.

amino acids 187-193

Cell attachment sequence.

amino acids 307-310

FIGURE 47

```
CGGACGCGTGGGTCCGGCGGCCTGAGGCTGCACCGGGCACGGGTCGGCCGCAATCCAGCCTGGGCGGAGCCGGA
GTTGCGAGCCGCTGCCTAGAGGCCGAGGAGCTCACAGCTATGGGCTGGAGGCCCCGGAGAGCTCGGGGGACCCC
GTTGCTGCTGCTGCTACTACTGCTGCTGCTCTGGCCAGTGCCAGGCGCCGGGGTGCTTCAAGGACATATCCCTG
GGCAGCCAGTCACCCCGCACTGGGTCCTGGATGGACAACCCTGGCGCACCGTCAGCCTGGAGGAGCCGGTCTCG
AAGCCAGACATGGGGCTGGTGGCCCTGGAGGCTGAAGGCCAGGAGCTCCTGCTTGAGCTGGAGAAGAACCACAG
GCTGCTGGCCCCAGGATACATAGAAACCCACTACGGCCCAGATGGGCAGCCAGTGGTGCTGGCCCCCAACCACA
CGGATCATTGCCACTACCAAGGGCGAGTAAGGGGCTTCCCCGACTCCTGGGTAGTCCTCTGCACCTGCTCTGGG
ATGAGTGGCCTGATCACCCTCAGCAGGAATGCCAGCTATTATCTGCGTCCCTGGCCACCCCGGGGCTCCAAGGA
CTTCTCAACCCACGAGATCTTTCGGATGGAGCAGCTGCTCACCTGGAAAGGAACCTGTGGCCACAGGGATCCTG
GGAACAAAGCGGGCATGACCAGCCTTCCTGGTGGTCCCCAGAGCAGGGGCAGGCGAGAAGCGCGCAGGACCCGG
AAGTACCTGGAACTGTACATTGTGGCAGACCACACCCTGTTCTTGACTCGGCACCGAAACTTGAACCACACCAA
ACAGCGTCTCCTGGAAGTCGCCAACTACGTGGACCAGCTTCTCAGGACTCTGGACATTCAGGTGGCGCTGACCG
GCCTGGAGGTGTGGACCGAGCGGGACCGCAGCCGCGTCACGCAGGACGCCAACGCCACGCTCTGGGCCTTCCTG
CAGTGGCGCCGGGGCTGTGGGCGCAGCGGCCCCACGACTCCGCGCAGCTGCTCACGGGCCGCGCCTTCCAGGG
CGCCACAGTGGGCCTGGCGCCCGTCGAGGGCATGTGCCGCGCCGAGAGCTCGGGAGGCGTGAGCACGGACCACT
CGGAGCTCCCCATCGGCGCCGCAGCCACCATGGCCCATGAGATCGGCCACAGCCTCGGCCTCAGCCACGACCCC
GACGGCTGCTGCGTGGAGGCTGCGGCCGAGTCCGGAGGCTGCGTCATGGCTGCGGCCACCGGGCACCCGTTTCC
GCGCGTGTTCAGCGCCTGCAGCCGCCGCCAGCTGCGCGCCTTCTTCCGCAAGGGGGCGGCGCTTGCCTCTCCA
ATGCCCCGGACCCCGGACTCCCGGTGCCGCCGGCGCTCTGCGGGAACGGCTTCGTGGAAGCGGGCGAGGAGTGT
GACTGCGGCCCTGGCCAGGAGTGCCGCGACCTCTGCTGCTTTGCTCACAACTGCTCGCTGCGCCCGGGGGCCCA
GTGCGCCCACGGGGACTGCTGCGTGCGCTGCCTGCTGAAGCCGGCTGGAGCGCTGTGCCGCCAGGCCATGGGTG
ACTGTGACCTCCCTGAGTTTTGCACGGGCACCTCCTCCCACTGTCCCCAGACGTTTACCTACTGGACGGCTCA
CCCTGTGCCAGGGGCAGTGGCTACTGCTGGGATGGCGCATGTCCCACGCTGGAGCAGCAGTGCCAGCAGCTCTG
GGGGCCTGGCTCCCACCCAGCTCCCGAGGCCTGTTTCCAGGTGGTGAACTCTGCGGGAGATGCTCATGGAAACT
GCGGCCAGGACAGCGAGGGCACTTCCTGCCCTGTGCAGGGAGGGATGCCCTGTGTGGGAAGCTGCAGTGCCAG
GGTGGAAAGCCCAGCCTGCTCGCACCGCACATGGTGCCAGTGGACTCTACCGTTCACCTAGATGGCCAGGAAGT
GACTTGTCGGGGAGCCTTGGCACTCCCCAGTGCCCAGCTGGACCTGCTTGGCCTGGGCCTGGTAGAGCCAGGCA
CCCAGTGTGGACCTAGAATGGTGTGCCAGAGCAGGCGCTGCAGGAAGAATGCCTTCCAGGAGCTTCAGCGCTGC
CTGACTGCCTGCCACAGCCACGGGGTTTGCAATAGCAACCATAACTGCCACTGTGCTCCAGGCTGGGCTCCACC
CTTCTGTGACAAGCCAGGCTTTGGTGGCAGCATGGACAGTGGCCCTGTGCAGGCTGAAAACCATGACACCTTCC
TGCTGGCCATGCTCCTCAGCGTCCTGCTGCCTCTGCTCCCAGGGGCCGGCCTGGCCTGGTGTTGCTACCGACTC
CCAGGAGCCCATCTGCAGCGATGCAGCTGGGGCTGCAGAAGGGACCCTGCGTGCAGTGGCCCCAAAGATGGCCC
ACACAGGGACCACCCCCTGGGCGGCGTTCACCCCATGGAGTTGGGCCCCACAGCCACTGGACAGCCCTGGCCCC
TGGACCCTGAGAACTCTCATGAGCCCAGCAGCCACCCTGAGAAGCCTCTGCCAGCAGTCTCGCCTGACCCCCAA
GCAGATCAAGTCCAGATGCCAAGATCCTGCCTCTGGTGAGAGGTAGCTCCTAAAATGAACAGATTTAAAGACAG
GTGGCCACTGACAGCCACTCCAGGAACTTGAACTGCAGGGCAGAGCCAGTGAATCACCGGACCTCCAGCACCT
GCAGGCAGCTTGGAAGTTTCTTCCCCGAGTGGAGCTTCGACCCACCCACTCCAGGAACCCAGAGCCACATTAGA
AGTTCCTGAGGGCTGGAGAACACTGCTTGGGCACACTCTCCAGCTCAATAAACCATCAGTCCCAGAAGCAAAGG
TCACACAGCCCCTGACCTCCCTCACCAGTGGAGGCTGGGTAGTGCTGGCCATCCCAAAAGGGCTCTGTCCTGGG
AGTCTGGTGTGTCTCCTACATGCAATTTCCACGGACCCAGCTCTGTGGAGGGCATGACTGCTGGCCAGAAGCTA
GTGGTCCTGGGGCCCTATGGTTCGACTGAGTCCACACTCCCCTGCAGCCTGGCTGGCCTCTGCAAACAAACATA
```

FIGURE 47 Continued

```
ATTTTGGGGACCTTCCTTCCTGTTTCTTCCCACCCTGTCTTCTCCCCTAGGTGGTTCCTGAGCCCCACCCCCA
ATCCCAGTGCTACACCTGAGGTTCTGGAGCTCAGAATCTGACAGCCTCTCCCCCATTCTGTGTGTGTCCGGGGG
ACAGAGGGAACCATTTAAGAAAAGATACCAAAGTAGAAGTCAAAAGAAAGACATGTTGGCTATAGGCGTGGTGG
CTCATGCCTATAATCCCAGCACTTTGGGAAGCCGGGGTAGGAGGATCACCAGAGGCCAGCAGGTCCACACCAGC
CTGGGCAACACAGCAAGACACCGCATCTACAGAAAAATTTTAAAATTAGCTGGGCGTGGTGGTGTGTACCTGTA
GGCCTAGCTGCTCAGGAGGCTGAAGCAGGAGGATCACTTGAGCCTGAGTTCAACACTGCAGTGAGCTATGGTGG
CACCACTGCACTCCAGCCTGGGTGACAGAGCAAGACCCTGTCTCTAAAATAAATTTTAAAAGGACTTAAAAAAA
AAAAAAAAAAAAAAAAAAAAAAAGAAAA
```

FIGURE 48

></usr/seqdb2/sst/DNA/Dnaseqs.min/ss.DNA76788
><subunit 1 of 1, 813 aa, 1 stop
><MW: 87739, pI: 6.94, NX(S/T): 5

MGWRPRRARGTPLLLLLLLLLLWPVPGAGVLQGHIPGQPVTPHWVLDGQPWRTVSLEEPVSKPDMGLVALEAEG
QELLLELEKNHRLLAPGYIETHYGPDGQPVVLAPNHTDHCHYQGRVRGFPDSWVVLCTCSGMSGLITLSRNASY
YLRPWPPRGSKDFSTHEIFRMEQLLTWKGTCGHRDPGNKAGMTSLPGGPQSRGRREARRTRKYLELYIVADHTL
FLTRHRNLNHTKQRLLEVANYVDQLLRTLDIQVALTGLEVWTERDRSRVTQDANATLWAFLQWRRGLWAQRPHD
SAQLLTGRAFQGATVGLAPVEGMCRAESSGGVSTDHSELPIGAAATMAHEIGHSLGLSHDPDGCCVEAAAESGG
CVMAAATGHPFPRVFSACSRRQLRAFFRKGGGACLSNAPDPGLPVPPALCGNGFVEAGEECDCGPGQECRDLCC
FAHNCSLRPGAQCAHGDCCVRCLLKPAGALCRQAMGDCDLPEFCTGTSSHCPPDVYLLDGSPCARGSGYCWDGA
CPTLEQQCQQLWGPGSHPAPEACFQVVNSAGDAHGNCGQDSEGHFLPCAGRDALCGKLQCQGGKPSLLAPHMVP
VDSTVHLDGQEVTCRGALALPSAQLDLLGLGLVEPGTQCGPRMVCQSRRCRKNAFQELQRCLTACHSHGVCNSN
HNCHCAPGWAPPFCDKPGFGGSMDSGPVQAENHDTFLLAMLLSVLLPLLPGAGLAWCCYRLPGAHLQRCSWGCR
RDPACSGPKDGPHRDHPLGGVHPMELGPTATGQPWPLDPENSHEPSSHPEKPLPAVSPDPQADQVQMPRSCLW

Important features of the protein:
Signal peptide:
Amino acids 1-27

Transmembrane domain:
Amino acids 702-720

N-glycosylation sites:
Amino acids 109-113;145-149;231-235;276-280;448-452

Tyrosine kinase phosphorylation site:
Amino acids 236-244

N-myristoylation sites:
Amino acids 29-35;185-191;195-201;308-314;318-324;326-332;338-344;370-376;
           400-406;402-408;454-460;504-510;510-516;517-523;580-586;
           601-607;661-667;687-693;717-723;719-725

Amidation site:
Amino acids 200-204

Neutral zinc metallopeptidases, zinc-binding region signature:
Amino acids 342-352

FIGURE 49

GGCACGAGGGAGCCTCCGTTAGGGGGTGGGAAAGGACTTTGCCATAGGTCGCTGAGGCCAC
CATCTGCTCTCTTACTGGCCAAGGGCGTAAAAAGATAGTCTTCCCATTAGCTAGAGAGCAA
ACCCCAGAAAGCCTATTGGCTGCGCCGTCCGCGGGCCTTGGTCCGCTTTGAAGGCGGGCTG
CGGCTGCGAGAGGAGGGCGGGCGGGAGGCTAGCTGTTGTCGTGGTTGCTCGGAGGCACGTG
TGCAGTCCCGGAAGCGGCGAGGGGAAACTGCTCCGCGCGCCGCGGGAGGAGGAACCGCC
CGGTCCTTTAGGGTCCGGGCCCGGCCGGGCCATGGATTCAATGCCTGAGCCCGCGTCCCGC
TGTCTTCTGCTTCTTCCCTTGCTGCTGCTGCTGCTGCTGCTGCCGGCCCCGGAGCTGG
GCCCGAGCCAGGCCGGAGCTGAGGAGAACGACTGGGTTCGCCTGCCCAGCAAATGCGAAGT
GTGTAAATATGTTGCTGTGGAGCTGAAGTCAGCCTTTGAGGAAACCGGCAAGACCAAGGAG
GTGATTGGCACGGGCTATGGCATCCTGGACCAGAAGGCCTCTGGAGTCAAATACACCAAGT
CGGACTTGCGGTTAATCGAAGTCACTGAGACCATTTGCAAGAGGCTCCTGGATTATAGCCT
GCACAAGGAGAGGACCGGCAGCAATCGATTTGCCAAGGGCATGTCAGAGACCTTTGAGACA
TTACACAACCTGGTACACAAAGGGGTCAAGGTGGTGATGGACATCCCCTATGAGCTGTGGA
ACGAGACTTCTGCAGAGGTGGCTGACCTCAAGAAGCAGTGTGATGTGCTGGTGGAAGAGTT
TGAGGAGGTGATCGAGGACTGGTACAGGAACCACCAGGAGGAAGACCTGACTGAATTCCTC
TGCGCCAACCACGTGCTGAAGGGAAAAGACACCAGTTGCCTGGCAGAGCAGTGGTCCGGCA
AGAAGGGAGACACAGCTGCCCTGGGAGGGAAGAAGTCCAAGAAGAAGAGCAGCAGGGCCAA
GGCAGCAGGCGGCAGGAGTAGCAGCAGCAAACAAAGGAAGGAGCTGGGTGGCCTTGAGGGA
GACCCCAGCCCCGAGGAGGATGAGGGCATCCAGAAGGCATCCCTCTCACACACAGCCCCC
CTGATGAGCTCTGAGCCCACCCAGCATCCTCTGTCCTGAGACCCCTGATTTTGAAGCTGAG
GAGTCAGGGGCATGGCTCTGGCAGGCCGGGATGGCCCCGCAGCCTTCAGCCCCTCCTTGCC
TTGGCTGTGCCCTCTTCTGCCAAGGAAAGACACAAGCCCCAGGAAGAACTCAGAGCCGTCA
TGGGTAGCCCACGCCGTCCTTTCCCCTCCCCAAGTGTTTCTCTCCTGACCCAGGGTTCAGG
CAGGCCTTGTGGTTTCAGGACTGCAAGGACTCCAGTGTGAACTCAGGAGGGGCAGGTGTCA
GAACTGGGCACCAGGACTGGAGCCCCCTCCGGAGACCAAACTCACCATCCCTCAGTCCTCC
CCAACAGGGTACTAGGACTGCAGCCCCTGTAGCTCCTCTCTGCTTACCCCTCCTGTGGAC
ACCTTGCACTCTGCCTGGCCCTTCCCAGAGCCCAAAGAGTAAAAATGTTCTGGTTCTGATT
TCTGAAAAAAAAAAAAAAAAAAATTCCT

FIGURE 50

MDSMPEPASRCLLLLPLLLLLLLLLPAPELGPSQAGAEENDWVRLPSKCEVCKYVAVELKS
AFEETGKTKEVIGTGYGILDQKASGVKYTKSDLRLIEVTETICKRLLDYSLHKERTGSNRF
AKGMSETFETLHNLVHKGVKVVMDIPYELWNETSAEVADLKKQCDVLVEEFEEVIEDWYRN
HQEEDLTEFLCANHVLKGKDTSCLAEQWSGKKGDTAALGGKKSKKKSSRAKAAGGRSSSSK
QRKELGGLEGDPSPEEDEGIQKASPLTHSPPDEL

Important features of the protein:

Signal peptide:

amino acids 1-26

N-glycosylation site.

amino acids 153-157 cAMP- and cGMP-dependent protein kinase phosphorylation sites.

amino acids 227-231, 228-232

Tyrosine kinase phosphorylation site.

amino acids 142-150

N-myristoylation sites.

amino acids 36-42, 74-80, 86-92, 125-131, 222-228, 237-243, 250-256, 263-269

Amidation sites.

amino acids 212-216, 222-226

ATP/GTP-binding site motif A (P-loop).

amino acids 62-70

FIGURE 51

CTCCTGCACTAGGCTCTCAGCCAGGGATGATGCGCTGCTGCCGCCGCCGCTGCTGCTGCCG
GCAACCACCCCATGCCCTGAGGCCGTTGCTGTTGCTGCCCCTCGTCCTTTTACCTCCCCTG
GCAGCAGCTGCAGCGGGCCCAAACCGATGTGACACCATATACCAGGGCTTCGCCGAGTGTC
TCATCCGCTTGGGGGACAGCATGGGCCGCGGAGGCGAGCTGGAGACCATCTGCAGGTCTTG
GAATGACTTCCATGCCTGTGCCTCTCAGGTCCTGTCAGGCTGTCCGGAGGAGGCAGCTGCA
GTGTGGGAATCACTACAGCAAGAAGCTCGCCAGGCCCCCGTCCGAATAACTTGCACACTC
TGTGCGGTGCCCCGGTGCATGTTCGGGAGCGCGGCACAGGCTCCGAAACCAACCAGGAGAC
GCTGCGGGCTACAGCGCCTGCACTCCCCATGGCCCCTGCGCCCCACTGCTGGCGGCTGCT
CTGGCTCTGGCCTACCTCCTGAGGCCTCTGGCCTAGCTTGTTGGGTTGGGTAGCAGCGCCC
GTACCTCCAGCCCTGCTCTGGCGGTGGTTGTCCAGGCTCTGCAGAGCGCAGCAGGGCTTTT
CATTAAAGGTATTTATATTTGTA

FIGURE 52

></usr/seqdb2/sst/DNA/Dnaseqs.min/ss.DNA92265
><subunit 1 of 1, 165 aa, 1 stop
><MW: 17786, pI: 8.43, NX(S/T): 0
MMRCCRRRCCCRQPPHALRPLLLLPLVLLPPLAAAAAGPNRCDTIYQGFAECLIRLGDSM
GRGGELETICRSWNDFHACASQVLSGCPEEAAAVWESLQQEARQAPRPNNLHTLCGAPVH
VRERGTGSETNQETLRATAPALPMAPAPPLLAAALALAYLLRPLA

Important features of the protein:

Signal peptide:

Amino acids    1-35

Transmembrane domain:

Amino acids    141-157

N-myristoylation site:

Amino acids    127-133

Prokaryotic membrane lipoprotein lipid attachment site:

Amino acids    77-88

FIGURE 53

```
      ccaggatcag catggccgtc cgccagtggg taatcgccct ggccttggct gccctccttg
 61   ttgtggacag ggaagtgcca gtggcagcag gaaagctccc tttctcaaga atgcccatct
121   gtgaacacat ggtagagtct ccaacctgtt cccagatgtc caacctggtc tgcggcactg
181   atgggctcac atatacgaat gaatgccagc tctgcttggc ccggataaaa accaaacagg
241   acatccagat catgaaagat ggcaaatgct gatcccacag gagcacctca agccatgaag
301   tgtcagctgg agaacagtgg tgggcatgga gaggatatga catgaaataa aagatccagc
361   ccaactgaaa aaaaaaaaaa aaaaaa
```

FIGURE 54

></usr/seqdb2/sst/DNA/Dnaseqs.min/ss.DNA98591
39.    ><subunit 1 of 1, 86 aa, 1 stop
><MW: 9454, pI: 8.03, NX(S/T): 0

MAVRQWVIALALAALLVVDREVPVAAGKLPFSRMPICEHMVESPTCSQMSNLVCGTDGLT
YTNECQLCLARIKTKQDIQIMKDGKC

FIGURE 55

```
GTGGAGTTGGGTGGTGTCGGGAGCCTCTCCCTGAGGGGCACCGCGTCTTCAGGAGCTGGGCCTCCAGTGCGGCG
CGATGTCAGGCGCGGTGACAGCTCTGTGAGTCCGAGGCCGCGGCCGTGGCGCTGGGCGGCTGCGGGGCCTGACC
GGTCCGCTCATGGTGCCGCCACGACGCCATCGCGGGGCAGGAAGGCCAGGGGTGCTGAGTTCTTCACCTCCTTT
TAGACTGAGATCTGCCAAGTTTTCCGGCATTGCTCTTGAGGATCTCAGAAGGGCTCTTAAGACAAGACTGCAAA
TGGTGTGTGTATTTGTCATGAACCGAATGAATTCCCAGAACAGTGGTTTCACTCAGCGCAGGCGAATGGCTCTT
GGGATTGTTATTCTTCTGCTTGTTGATGTGATATGGGTTGCTTCCTCTGAACTTACTTCGTATGTTTTACCCA
GTACAACAAACCATTCTTCAGCACCTTTGCAAAAACATCTATGTTTGTTTTGTACCTTTTGGGCTTTATTATTT
GGAAGCCATGGAGACAACAGTGTACAAGAGGACTTCGCGGAAAGCATGCTGCTTTTTTTGCAGATGCTGAAGGT
TACTTTGCTGCTTGCACAACAGATACAACTATGAATAGTTCTTTGAGTGAACCTCTGTATGTGCCTGTGAAATT
CCATGATCTTCCAAGTGAAAAACCTGAGAGCACAAACATTGATACTGAAAAAACCCCCAAAAAGTCTCGTGTGA
GGTTCAGTAATATCATGGAGATTCGACAGCTTCCGTCAAGTCATGCATTGGAAGCAAAGTTGTCTCGCATGTCA
TATCCTGTGAAAGAACAAGAATCCATACTGAAAACTGTGGGGAAACTTACTGCAACTCAAGTAGCGAAAATTAG
CTTTTTTTTTTGCTTTGTGTGGTTTTTGGCAAATTTGTCATATCAAGAAGCACTTTCAGACACACAAGTTGCTA
TAGTTAATATTTTATCTTCAACTTCCGGACTTTTTACCTTAATCCTTGCTGCAGTATTTCCAAGTAACAGTGGA
GATAGATTTACCCTTTCTAAACTATTAGCTGTAATTTTAAGCATTGGAGGCGTTGTACTGGTAAACCTGGCAGG
GTCTGAAAAACCTGCTGGAAGAGACACAGTAGGTTCCATTTGGTCTCTTGCTGGAGCCATGCTCTATGCTGTCT
ATATTGTTATGATTAAGAGAAAAGTAGATAGAGAAGACAAGTTGGATATTCCAATGTTCTTTGGTTTTGTAGGT
TTGTTTAATCTGCTGCTCTTATGGCCAGGTTTCTTTTTACTTCATTATACTGGATTTGAGGACTTCGAGTTTCC
CAATAAAGTAGTATTAATGTGCATTATCATTAATGGCCTTATTGGAACAGTACTCTCAGAGTTCCTGTGGTTGT
GGGGCTGCTTTCTTACCTCATCATTGATAGGCACACTTGCACTAAGCCTTACAATACCTCTGTCCATAATAGCT
GACATGTGTATGCAAAAGGTGCAGTTTTCTTGGTTATTTTTTGCAGGAGCTATCCCTGTATTTTTTTCATTTTT
TATTGTAACTCTCCTATGCCATTATAATAATTGGGATCCTGTGATGGTGGGAATCAGAAGAATATTTGCTTTTA
TATGCAGAAAACATCGAATTCAGAGAGTTCCAGAAGACAGCGAACAGTGTGAGAGTCTCATTTCTATGCACAGT
GTTTCTCAGGAGGATGGAGCTAGTTAGCTGTCTGTTGTCTGTAGCCCAGCTTGATAATGGAACTATACAGCGAA
GAGACAATCTCTGGCAAGTTTTTGTAGAAAAAATGTTTCAGTGCCTAGTCTGAAAAATAACAGTTTGAGTTCTT
TGAAACTCTAAAATATATTTTTCTCATACCTGTTTTCTTCATTTTCATAATGAAGCACTTTGCTATGTAGCTGT
GTACATATCACTACAGTTATAGGAAGTTTCAGTCTACAGTCCATCCAAAGGACCAACCTGCCTTACACATCTCA
AGGAATTCAGCTGTTGAAATCATTTGAACTAATCAAGGAATAAATCCTAATGTTCTGGGACTTTATTTTCACAT
GTTAAATGCTGGAATATATTATGAAAATGTTTTCAAGAAATCACTTAAGTGTTCATAGACCAGTATTTCTGACA
GGTAAAATGCTAAAATAAGCTACCTGTAATAAGTGTGGATTATATTTTTGGGTTTTGTAGAATATTGCAAATTA
ACCACACAAAAAATGTTTAATTTATGCAACAAGCATGTTTGTGCAAATTTCATGGGACTTTAAAAAGAATAAGT
ATTTGAGAAAATATCTGGTTCACTTACACTACATTTACTGTATTATTCTTTTATAGCATTAGGTGCCTTGTATT
TTAAATCTGTGACAAACCATGGCAAATTTTTAAAGGGGAAGTATTATTATAAAATGAAGAAATATGTATTTCTA
AAGGCTATATTGCTGTAAACTTAATTGATAAAGCTCTGTTTAATTTAGAGTTTTGAAGAAATAGTCTCCCTTCA
ATTAAGAAATTTTCATAATGGAATGATTTAAATTGAAGTGACAAAGAGTATTATTAAAATACAATGTTTATAAA
AAAA
```

FIGURE 56

MVPPRRHRGAGRPGVLSSSPPFRLRSAKFSGIALEDLRRALKTRLQMVCVFVMNRMNSQNSGFTQRRRMALGIV
ILLLVDVIWVASSELTSYVFTQYNKPFFSTFAKTSMFVLYLLGFIIWKPWRQQCTRGLRGKHAAFFADAEGYFA
ACTTDTTMNSSLSEPLYVPVKFHDLPSEKPESTNIDTEKTPKKSRVRFSNIMEIRQLPSSHALEAKLSRMSYPV
KEQESILKTVGKLTATQVAKISFFFCFVWFLANLSYQEALSDTQVAIVNILSSTSGLFTLILAAVFPSNSGDRF
TLSKLLAVILSIGGVVLVNLAGSEKPAGRDTVGSIWSLAGAMLYAVYIVMIKRKVDREDKLDIPMFFGFVGLFN
LLLLWPGFFLLHYTGFEDFEFPNKVVLMCIIINGLIGTVLSEFLWLWGCFLTSSLIGTLALSLTIPLSIIADMC
MQKVQFSWLFFAGAIPVFFSFFIVTLLCHYNNWDPVMVGIRRIFAFICRKHRIQRVPEDSEQCESLISMHSVSQ
EDGAS

Important features:
Transmembrane domain:
amino acids 69-87,105-118,237-256,266-285,300-316,332-346,
364-379,399-419,453-472

N-glycosylation sites:
amino acids 157-161,255-259

N-myristoylation sites:
amino acids 14-20,329-335,404-410,407-413,418-424

FIGURE 57

GGATGCAGCAGAGAGGAGCAGCTGGAAGCCGTGGCTGCGCTCTCTTCCCTCTGCTGGGCG
TCCTGTTCTTCCAGGGTGTTTATATCGTCTTTTCCTTGGAGATTCGTGCAGATGCCCATG
TCCGAGGTTATGTTGGAGAAAAGATCAAGTTGAAATGCACTTTCAAGTCAACTTCAGATG
TCACTGACAAGCTTACTATAGACTGGACATATCGCCCTCCCAGCAGCAGCCACACAGTAT
CAATATTTCATTATCAGTCTTTCCAGTACCCAACCACAGCAGGCACATTTCGGGATCGGA
TTTCCTGGGTTGGAAATGTATACAAAGGGGATGCATCTATAAGTATAAGCAACCCTACCA
TAAAGGACAATGGGACATTCAGCTGTGCTGTGAAGAATCCCCAGATGTGCACCATAATA
TTCCCATGACAGAGCTAACAGTCACAGAAGGGGTTTTGGCACCATGCTTTCCTCTGTGG
CCCTTCTTTCCATCCTTGTCTTTGTGCCCTCAGCCGTGGTGGTTGCTCTGCTGCTGGTGA
GAATGGGGAGGAAGGCTGCTGGGCTGAAGAAGAGGAGCAGGTCTGGCTATAAGAAGTCAT
CTATTGAGGTTTCCGATGACACTGATCAGGAGGAGGAAGAGGCGTGTATGGCGAGGCTTT
GTGTCCGTTGCGCTGAGTGCCTGGATTCAGACTATGAAGAGACATATTGATGAAAGTCTG
TATGACACAAGAAGAGTCACCTAAAGACAGGAAACATCCCATTCCACTGGCAGCTAAAGC
CTGTCAGAGAAAGTGGAGCTGGCCTGGACCATAGCGATGGACAATCCTGGAGATCATCAG
TAAAGACTTTAGGAACCACTTATTTATTGAATAAATGTTCTTGTTGTATTTATAAACTGT
TCAGGAAGTCTCATAAGAGACTCATGACTTCCCCTTTCAATGAATTATGCTGTAATTGAA
TGAAGAAATTCTTTTCCTGAGCA

FIGURE 58

MQQRGAAGSRGCALFPLLGVLFFQGVYIVFSLEIRADAHVRGYVGEKIKLKCTFKSTSD
VTDKLTIDWTYRPPSSSHTVSIFHYQSFQYPTTAGTFRDRISWVGNVYKGDASISISNP
TIKDNGTFSCAVKNPPDVHHNIPMTELTVTERGFGTMLSSVALLSILVFVPSAVVVALL
LVRMGRKAAGLKKRSRSGYKKSSIEVSDDTDQEEEEACMARLCVRCAECLDSDYEETY

Transmembrane domain
    11-30
    157-177

N-glycosylation site
    123-127 cAMP- and cGMP-dependent protein kinase phosphorylation site
    189-193
    197-201

Tyrosine kinase phosphorylation site
    63-71

N-myristoylation site
    5-11
    8-14
    124-130
    153-159

Amidation site
    181-185

FIGURE 59

```
   1    cccttggaag ctggaatcct gcaacaatgg cccagggtgt cctctggatc ctactcggat
  61    tgctactgtg gtcagaccca gggacagcct ccctgcccct gctcatggac tctgtcatcc
 121    aggccctggc tgagctggag cagaaagtgc cagctgccaa gaccagacac acagcttctg
 181    cgtggctgat gtcagctcca aactctggcc cccacaatcg cctctaccac ttcctgctgg
 241    gggcatggag cctcaatgct acagagttgg atccctgccc actaagccca gagctgttag
 301    gcctgaccaa ggaggtggcc cgacatgacg tacgagaagg gaaggaatat ggggtggtgc
 361    tggcacctga tggctcgacc gtggctgtgg agcctctgct ggcggggctg gaggcagggc
 421    tgcaagggcg cagggtcata aatttgccct tggacagcat ggctgcccct tgggagactg
 481    gagatacctt ccagatgtt gtggccattg ctccagatgt aagagccacc tcctccccag
 541    gactcaggga tggctctcca gatgtcacca ctgcagatat tggagccaac actccagatg
 601    ctacaaaagg ctgtccagat gtccaagctt ccttgccaga tgccaaagcc aagtccccac
 661    cgaccatggt ggacagcctc ctggcagtca ccctggctgg aaacctgggc ctgaccttcc
 721    tccgaggttc ccagacccag agccatccag acctgggaac tgagggctgc tgggaccagc
 781    tctctgcccc tcggaccttt acgcttttgg accccaaggc atctctgtta accatggcct
 841    tcctcaatgg cgccctggat ggggtcatcc ttggagacta cctgagccgg actcctgagc
 901    cccggccatc cctcagccac ttgctgagcc agtactatgg gctggggtg gccagagacc
 961    cagggttccg cagcaacttc cgacggcaga acggtgctgc tctgacttca gcctccatcc
1021    tggcccagca ggtgtgggga acccttgtcc ttctacagag gctggagcca gtacacctcc
1081    agcttcagtg catgagccaa gaacagctgg cccaggtggc tgccaatgct accaaggaat
1141    tcactgaggc cttcctggga tgcccggcca tccaccccg ctgccgctgg ggagcggcgc
1201    cttatcgggg ccgcccgaag ctgctgcagc tgccgctggg attcttgtac gtgcatcaca
1261    cctacgtgcc tgcaccaccc tgcacggact tcacgcgctg cgcagccaac atgcgctcca
1321    tgcagcgcta ccaccaggac acgcaaggct ggggagacat cggctacagt ttcgtggtgg
1381    gctcggacgg ctacgtgtac gagggacgcg gctggcactg ggtgggcgcc cacacgctcg
1441    gccacaactc ccggggcttc ggcgtggcca tagtgggcaa ctacaccgcg gcgctgccca
1501    ccgaggccgc tctgcgcacg gtgcgcgaca cgctcccgag ttgtgcggtg cgcgccggcc
1561    tcctgcggcc agactacgcg ctgctgggcc accgccagct ggtgcgcacc gactgccccg
1621    gcgacgcgct cttcgacctg ctgcgcacct ggccgcactt caccgcgact gttaagccaa
1681    gacctgccag gagtgtctct aagagatcca ggagggagcc accccaagg accctgccag
1741    ccacagacct ccaataaaga cagcatggaa acaaaaaaaa aaaaaaaaa aaaa
```

FIGURE 60

```
></usr/seqdb2/sst/DNA/Dnaseqs.min/ss.DNA129542
><subunit 1 of 1, 576 aa, 1 stop
><MW: 62128, pI: 7.41, NX(S/T): 3
MAQGVLWILLGLLLWSDPGTASLPLLMDSVIQALAELEQKVPAAKARHTASAWLMSAPNS
GPHNRLYHFLLGAWSLNATELDPCPLSPELLGLTKEVAQHDVREGKEYGVVLAPDGSTVA
VEPLLAGLEAGLQGRRVINLPLDSMAAPWETGDTFPDVVAIAPDVRATSSPGLRDGSPDV
TTADIGANTPDATKGCPDVQASLPDAKAKSPPTMVDSLLAVTLAGNLGLTFLRGSQTQSH
PDLGTEGCWDQLSAPRTFTLLDPKASLLTKAFLNGALDGVILGDYLSRTPEPRPSLSHLL
SQYYGAGVARDPGFRSNFRRQNGAALTSASILAQQVWGTLVLLQRLEPVHLQLQCMSQEQ
LAQVAANATKEFTEAFLGCPAIHPRCRWGAAPYQGRPKLLQLPLGFLYVHHTYVPAPPCT
DFTRCAANMRSMQRYHQDTQGWGDIGYSFVVGSDGYVYEGRGWHWVGAHTLGHNSRGFGV
AIVGNYTAALPTEAALRTVRDTLPSCAVRAGLLRPDYALLGHRQLVRTDCPGDALFDLLR
TWPHFTATVKPRPARSVSKRSRREPPPRTLPATDLQ
```

FIGURE 61

```
AGTCCCAGACGGGCTTTTCCCAGAGAGCTAAAAGAGAAGGGCCAGAGAATGTCGTCCCAG
CCAGCAGGGAACCAGACCTCCCCCGGGGCCACAGAGGACTACTCCTATGGCAGCTGGTAC
ATCGATGAGCCCCAGGGGGGCGAGGAGCTCCAGCCAGAGGGGGAAGTGCCCTCCTGCCAC
ACCAGCATACCACCCGGCCTGTACCACGCCTGCCTGGCCTCGCTGTCAATCCTTGTGCTG
CTGCTCCTGGCCATGCTGGTGAGGCGCCGCCAGCTCTGGCCTGACTGTGTGCGTGGCAGG
CCCGGCCTGCCCAGCCCTGTGGATTTCTTGGCTGGGGACAGGCCCCGGGCAGTGCCTGCT
GCTGTTTTCATGGTCCTCCTGAGCTCCCTGTGTTTGCTGCTCCCCGACGAGGACGCATTG
CCCTTCCTGACTCTCGCCTCAGCACCCAGCCAAGATGGGAAAACTGAGGCTCCAAGAGGG
GCCTGGAAGATACTGGGACTGTTCTATTATGCTGCCCTCTACTACCCTCTGGCTGCCTGT
GCCACGGCTGGCCACACAGCTGCACACCTGCTCGGCAGCACGCTGTCCTGGGCCCACCTT
GGGGTCCAGGTCTGGCAGAGGGCAGAGTGTCCCCAGGTGCCCAAGATCTACAAGTACTAC
TCCCTGCTGGCCTCCCTGCCTCTCCTGCTGGGCCTCGGATTCCTGAGCCTTTGGTACCCT
GTGCAGCTGGTGAGAAGCTTCAGCCGTAGGACAGGAGCAGGCTCCAAGGGGCTGCAGAGC
AGCTACTCTGAGGAATATCTGAGGAACCTCCTTTGCAGGAAGAAGCTGGGAAGCAGCTAC
CACACCTCCAAGCATGGCTTCCTGTCCTGGGCCCGCGTCTGCTTGAGACACTGCATCTAC
ACTCCACAGCCAGGATTCCATCTCCCGCTGAAGCTGGTGCTTTCAGCTACACTGACAGGG
ACGGCCATTTACCAGGTGGCCCTGCTGCTGCTGGTGGGCGTGGTACCCACTATCCAGAAG
GTGAGGGCAGGGGTCACCACGGATGTCTCCTACCTGCTGGCCGGCTTTGGAATCGTGCTC
TCCGAGGACAAGCAGGAGGTGGTGGAGCTGGTGAAGCACCATCTGTGGGCTCTGGAAGTG
TGCTACATCTCAGCCTTGGTCTTGTCCTGCTTACTCACCTTCCTGGTCCTGATGCGCTCA
CTGGTGACACACAGGACCAACCTTCGAGCTCTGCACCGAGGAGCTGCCCTGGACTTGAGT
CCCTTGCATCGGAGTCCCCATCCCTCCCGCCAAGCCATATTCTGTTGGATGAGCTTCAGT
GCCTACCAGACAGCCTTTATCTGCCTTGGGCTCCTGGTGCAGCAGATCATCTTCTTCCTG
GGAACCACGGCCCTGGCCTTCCTGGTGCTCATGCCTGTGCTCCATGGCAGGAACCTCCTG
CTCTTCCGTTCCCTGGAGTCCTCGTGGCCCTTCTGGCTGACTTTGGCCCTGGCTGTGATC
CTGCAGAACATGGCAGCCCATTGGGTCTTCCTGGAGACTCATGATGGACACCCACAGCTG
ACCAACCGGCGAGTGCTCTATGCAGCCACCTTTCTTCTCTTCCCCCTCAATGTGCTGGTG
GGTGCCATGGTGGCCACCTGGCGAGTGCTCCTCTCTGCCCTCTACAACGCCATCCACCTT
GGCCAGATGGACCTCAGCCTGCTGCCACCGAGAGCCGCCACTCTCGACCCCGGCTACTAC
ACGTACCGAAACTTCTTGAAGATTGAAGTCAGCCAGTCGCATCCAGCCATGACAGCCTTC
TGCTCCCTGCTCCTGCAAGCGCAGAGCCTCCTACCCAGGACCATGGCAGCCCCCCAGGAC
AGCCTCAGACCAGGGGAGGAAGACGAAGGGATGCAGCTGCTACAGACAAAGGACTCCATG
GCCAAGGGAGCTAGGCCCGGGGCCAGCCGCGGCAGGGCTCGCTGGGGTCTGGCCTACACG
CTGCTGCACAACCCAACCCTGCAGGTCTTCCGCAAGACGGCCCTGTTGGGTGCCAATGGT
GCCCAGCCCTGAGGGCAGGGAAGGTCAACCCACCTGCCCATCTGTGCTGAGGCATGTTCC
TGCCTACCATCCTCCTCCCTCCCCGGCTCTCCTCCCAGCATCACACCAGCCATGCAGCCA
GCAGGTCCTCCGGATCACTGTGGTTGGGTGGAGGTCTGTCTGCACTGGGAGCCTCAGGAG
GGCTCTGCTCCACCCACTTGGCTATGGGAGAGCCAGCAGGGGTTCTGGAGAAAAAAACTG
GTGGGTTAGGGCCTTGGTCCAGGAGCCAGTTGAGCCAGGGCAGCCACATCCAGGCGTCTC
CCTACCCTGGCTCTGCCATCAGCCTTGAAGGGCCTCGATGAAGCCTTCTCTGGAACCACT
CCAGCCCAGCTCCACCTCAGCCTTGGCCTTCACGCTGTGGAAGCAGCCAAGGCACTTCCT
```

FIGURE 61 Continued

```
CACCCCCTCAGCGCCACGGACCTCTCTGGGGAGTGGCCGGAAAGCTCCCGGTCCTCTGGC
CTGCAGGGCAGCCCAAGTCATGACTCAGACCAGGTCCCACACTGAGCTGCCCACACTCGA
GAGCCAGATATTTTTGTAGTTTTTATGCCTTTGGCTATTATGAAAGAGGTTAGTGTGTTC
CCTGCAATAAACTTGTTCCTGAGAAAAAAAAAAAAAAAAAAAAAAAAAAAAAAAAAAAAA
AAAAAAAAAAAAAAAAAAAAAAAAAAAAAA
```

MSSQPAGNQTSPGATEDYSYGSWYIDEPQGGEELQPEGEVPSCHTSIPPGLYHACLA
SLSILVLLLLAMLVRRRQLWPDCVRGRPGLPSPVDFLAGDRPRAVPAAVFMVLLSS
LCLLLPDEDALPFLTLASAPSQDGKTEAPRGAWKILGLFYYAALYYPLAACATAGH
TAAHLLGSTLSWAHLGVQVWQRAECPQVPKIYKYYSLLASLPLLLGLGFLSLWYPV
QLVRSFSRRTGAGSKGLQSSYSEEYLRNLLCRKKLGSSYHTSKHGFLSWARVCLRH
CIYTPQPGFHLPLKLVLSATLTGTAIYQVALLLLVGVVPTIQKVRAGVTTDVSYLLA
GFGIVLSEDKQEVVELVKHHLWALEVCYISALVLSCLLTFLVLMRSLVTHRTNLRAL
HRGAALDLSPLHRSPHPSRQAIFCWMSFSAYQTAFICLGLLVQQIIFFLGTTALAFLV
LMPVLHGRNLLLFRSLESSWPFWLTLALAVILQNMAAHWVFLETHDGHPQLTNRR
VLYAATFLLFPLNVLVGAMVATWRVLLSALYNAIHLGQMDLSLLPPRAATLDPGY
YTYRNFLKIEVSQSHPAMTAFCSLLLQAQSLLPRTMAAPQDSLRPGEEDEGMQLLQ
TKDSMAKGARPGASRGRARWGLAYTLLHNPTLQVFRKTALLGANGAQP

Important features of the protein:

Transmembrane domains:

Amino acids   54-69;102-119;148-166;207-222;301-320;
             364-380;431-451;474-489;512-531

N-glycosylation site:

Amino acids   8-12

N-myristoylation sites:

Amino acids   50-56;176-182;241-247;317-323;341-347;525-531;
             627-633;631-637;640-646;661-667

Prokaryotic membrane lipoprotein lipid attachment site:

Amino acids   364-375

ATP/GTP-binding site motif A (P-loop):

Amino acids   132-140

FIGURE 63

```
gatgtggagc tggggtccct gcaagtcatg aacaaaacga gaaagattat ggaacatggg
ggggccacct tcatcaatgc ctttgtgact acacccatgt gctgcccgtc acggtcctcc
atgctcaccg ggaagtatgt gcacaatcac aatgtctaca ccaacaacga gaactgctct
tcccctcgt ggcaggccat gcatgagcct cggacttttg ctgtatatct taacaacact
ggctacagaa cagccttttt tggaaaatac ctcaatgaat ataatggcag ctacatcccc
cctgggtggc gagaatggct tggattaatc aagaattctc gcttctataa ttacactgtt
tgtcgcaatg gcatcaaaga aaagcatgga tttgattatg caaaggacta cttcacagac
ttaatcacta acgagagcat taattacttc aaaatgtcta agagaatgta tccccatagg
cccgttatga tggtgatcag ccacgctgcg ccccacggcc ccgaggactc agccccacag
ttttctaaac tgtaccccaa tgcttcccaa cacataactc ctagttataa ctatgcacca
aatatggata aacactggat tatgcagtac acaggaccaa tgctgcccat ccacatggaa
tttacaaaca ttctacagcg caaaaggctc cagactttga tgtcagtgga tgattctgtg
gagaggctgt ataacatgct cgtggagacg ggggagctgg agaatactta catcatttac
accgccgacc atggttacca tattgggcag tttggactgg tcaaggggaa atccatgcca
tatgactttg atattcgtgt gccttttttt attcgtggtc caagtgtaga accaggatca
atagtcccac agatcgttct caacattgac ttggccccca cgatcctgga tattgctggg
ctcgacacac ctcctgatgt ggacggcaag tctgtcctca aacttctgga cccagaaaag
ccaggtaaca ggtttcgaac aaacaagaag gccaaaattt ggcgtgatac attcctagtg
gaaagaggca aatttctacg taagaaggaa gaatccagca agaatatcca acagtcaaat
cacttgccca aatatgaacg ggtcaaagaa ctatgccagc aggccaggta ccagacagcc
tgtgaacaac cggggcagaa gtggcaatgc attgaggata catctggcaa gcttcgaatt
cacaagtgta aaggacccag tgacctgctc acagtccggc agagcacgcg gaacctctac
gctcgcggct tccatgacaa agacaaagag tgcagttgta gggagtctgg ttaccgtgcc
agcagaagcc aaagaaagag tcaacggcaa ttcttgagaa accaggggac tccaaagtac
aagcccagat ttgtccatac tcggcagaca cgttccttgt ccgtcgaatt tgaaggtgaa
atatatgaca taaatctgga agaagaagaa gaattgcaag tgttgcaacc aagaaacatt
gctaagcgtc atgatgaagg ccacaagggg ccaagagatc tccaggcttc cagtggtggc
aacaggggca ggatgctggc agatagcagc aacgccgtgg gcccacctac cactgtccga
gtgacacaca agtgttttat tcttcccaat gactctatcc attgtgagag agaactgtac
caatcggcca gagcgtggaa ggaccataag gcatacattg acaaagagat tgaagctctg
caagataaaa ttaagaattt aagagaagtg agaggacatc tgaagagaag gaagcctgag
gaatgtagct gcagtaaaca aagctattac aataaagaga aggtgtaaa aaagcaagag
aaattaaaga gccatcttca cccattcaag gaggctgctc aggaagtaga tagcaaactg
caactttca aggagaacaa ccgtaggagg aagaaggaga ggaaggagaa gagacggcag
aggaaggggg aagagtgcag cctgcctggc ctcacttgct tcacgcatga caacaaccac
tggcagacag ccccgttctg gaacctggga tctttctgtg cttgcacgag ttctaacaat
aacacctact ggtgtttgcg tacagttaat gagacgcata atttctttt ctgtgagttt
gctactggct ttttggagta ttttgatatg aatacagatc cttatcagct cacaaataca
gtgcacacgg tagaacgagg cattttgaat cagctacacg tacaactaat ggagctcaga
agctgtcaag gatataagca gtgcaaccca agacctaaga atcttgatgt tggaaataaa
gatggaggaa gctatgacct acacagagga cagttatggg atggatggga aggttaatca
```

FIGURE 63 Continued

```
gccccgtctc actgcagaca tcaactggca aggcctagag gagctacaca gtgtgaatga
aaacatctat gagtacagac aaaactacag acttagtctg gtggactgga ctaattactt
gaaggattta gatagagtat ttgcactgct gaagagtcac tatgagcaaa ataaaacaaa
taagactcaa actgctcaaa gtgacgggtt cttggttgtc tctgctgagc acgctgtgtc
aatggagatg gcctctgctg actcagatga agacccaagg cataaggttg ggaaaacacc
tcatttgacc ttgccagctg accttcaaac cctgcatttg aaccgaccaa cattaagtcc
agagagtaaa cttgaatgga ataacgacat tccagaagtt aatcatttga attctgaaca
ctggagaaaa accgaaaaat ggacggggca tgaagagact aatcatctgg aaaccgattt
cagtggcgat ggcatgacag agctagagct cgggcccagc cccaggctgc agcccattcg
caggcacccg aaagaacttc cccagtatgg tggtcctgga aaggacattt ttgaagatca
actatatctt cctgtgcatt ccgatggaat ttcagttcat cagatgttca ccatggccac
cgcagaacac cgaagtaatt ccagcatagc ggggaagatg ttgaccaagg tggagaagaa
tcacgaaaag gagaagtcac agcacctaga aggcagcgcc tcctcttcac tctcctctga
ttagatgaaa ctgttacctt accctaaaca cagtattcct tttaacttt tttatttgta
aactaataaa ggtaatcaca gccaccaaca ttccaagcta ccctgggtac ctttgtgcag
tagaagctag tgagcatgtg agcaagcggt gtgcacacgg agactcatcg ttataattta
ctatctgcca agagtagaaa gaaggctgg ggatatttgg gttggcttgg ttttgattt
ttgcttgttt gtttgttttg tactaaaaca gtattatctt ttgaatatcg tagggacata
agtatataca tgttatccaa tcaagatggc tagaatggtg cctttctgag tgtctaaaac
ttgacacccc tggtaaatct ttcaacacac ttccactgcc tgcgtaatga agtttgatt
cattttttaac cactggaatt tttcaatgcc gtcattttca gttagatgat tttgcacttt
gagattaaaa tgccatgtct atttgattag tcttattttt ttatttttac aggcttatca
gtctcactgt tggctgtcat tgtgacaaag tcaaataaac ccccaaggac gacacacagt
atggatcaca tattgtttga cattaagctt ttgccagaaa atgttgcatg tgttttacct
cgacttgcta aaatcgatta gcagaaaggc atggctaata atgttggtgg tgaaaataaa
taaataagta aacaaatga agattgcctg ctctctctgt gcctagcctc aaagcgttca
tcatacatca tacctttaag attgctatat tttgggttat tttcttgaca ggagaaaaag
atctaaagat ctttatttt catctttttt ggttttcttg gcatgactaa aagcttaaa
tgttgataaa atatgactag ttttgaattt acaccaagaa cttctcaata aaagaaaatc
atgaatgctc cacaattca acataccaca agagaagtta atttcttaac attgtgttct
atgattattt gtaagacctt caccaagttc tgatatcttt taaagacata gttcaaaatt
gcttttgaaa atctgtattc ttgaaaatat ccttgttgtg tattaggttt ttaaatacca
gctaaaggat tacctcactg agtcatcagt accctcctat tcagctcccc aagatgatgt
gttttttgctt accctaagag aggttttctt cttatttta gataattcaa gtgcttagat
aaattatgtt ttctttaagt gttatggta aactctttta aagaaatttt aatatgttat
agctgaatct ttttggtaac tttaaatctt tatcatagac tctgtacata tgttcaaatt
agctgcttgc ctgatgtgtg tatcatcggt gggatgacag aacaaacata tttatgatca
tgaataatgt gctttgtaaa aagatttcaa gttattagga agcatactct gtttttaat
catgtataat attccatgat acttttatag aacaattctg gcttcaggaa agtctagaag
caatatttct tcaaataaaa ggtgtttaaa cttt
```

FIGURE 64

></usr/seqdb2/sst/DNA/Dnaseqs.min/ss.DNA347767
><subunit 1 of 1, 871 aa, 1 stop
><MW: 101027, pI: 9.39, NX(S/T): 10
MKYSCCALVLAVLGTELLGSLCSTVRSPRFRGRIQQERKNIRPNIILVLTDDQDVELGSL
QVMNKTRKIMEHGGATFINAFVTTPMCCPSRSSMLTGKYVHNHNVYTNNENCSSPSWQAM
HEPRTFAVYLNNTGYRTAFFGKYLNEYNGSYIPPGWREWLGLIKNSRFYNYTVCRNGIKE
KHGFDYAKDYFTDLITNESINYFKMSKRMYPHRPVMMVISHAAPHGPEDSAPQFSKLYPN
ASQHITPSYNYAPNMDKHWIMQYTGPMLPIHMEFTNILQRKRLQTLMSVDDSVERLYNML
VETGELENTYIIYTADHGYHIGQFGLVKGKSMPYDFDIRVPFFIRGPSVEPGSIVPQIVL
NIDLAPTILDIAGLDTPPDVDGKSVLKLLDPEKPGNRFRTNKKAKIWRDTFLVERGKFLR
KKEESSKNIQQSNHLPKYERVKELCQQARYQTACEQPGQKWQCIEDTSGKLRIHKCKGPS
DLLTVRQSTRNLYARGFHDKDKECSCRESGYRASRSQRKSQRQFLRNQGTPKYKPRFVHT
RQTRSLSVEFEGEIYDINLEEEEELQVLQPRNIAKRHDEGHKGPRDLQASSGGNRGRMLA
DSSNAVGPPTTVRVTHKCFILPNDSIHCERELYQSARAWKDHKAYIDKEIEALQDKIKNL
REVRGHLKRRKPEECSCSKQSYYNKEKGVKKQEKLKSHLHPFKEAAQEVDSKLQLFKENN
RRRKKERKEKRRQRKGEECSLPGLTCFTHDNNHWQTAPFWNLGSFCACTSSNNNTYWCLR
TVNETHNFLFCEFATGFLEYFDMNTDPYQLTNTVHTVERGILNQLHVQLMELRSCQGYKQ
CNPRPKNLDVGNKDGGSYDLHRGQLWDGWEG

FIGURE 65

GCGGCCGCGTCGACCGGGCCCTGCGGGCGCGGGGCTGAAGGCGGAACCACGACGGGCAGAGAGCACGGAGCCGG
GAAGCCCCTGGGCGCCCGTCGGAGGGCTATGGAGCAGCGGCCGCGGGGCTGCGCGGCGGTGGCGGCGGCGCTCC
TCCTGGTGCTGCTGGGGGCCCGGGCCCAGGGCGGCACTCGTAGCCCCAGGTGTGACTGTGCCGGTGACTTCCAC
AAGAAGATTGGTCTGTTTTGTTGCAGAGGCTGCCCAGCGGGGCACTACCTGAAGGCCCCTTGCACGGAGCCCTG
CGGCAACTCCACCTGCCTTGTGTGTCCCCAAGACACCTTCTTGGCCTGGGAGAACCACCATAATTCTGAATGTG
CCCGCTGCCAGGCCTGTGATGAGCAGGCCTCCCAGGTGGCGCTGGAGAACTGTTCAGCAGTGGCCGACACCCGC
TGTGGCTGTAAGCCAGGCTGGTTTGTGGAGTGCCAGGTCAGCCAATGTGTCAGCAGTTCACCCTTCTACTGCCA
ACCATGCCTAGACTGCGGGGCCCTGCACCGCCACACACGGCTACTCTGTTCCCGCAGAGATACTGACTGTGGGA
CCTGCCTGCCTGGCTTCTATGAACATGGCGATGGCTGCGTGTCCTGCCCCACGAGCACCCTGGGGAGCTGTCCA
GAGCGCTGTGCCGCTGTCTGTGGCTGGAGGCAGATGTTCTGGGTCCAGGTGCTCCTGGCTGGCCTTGTGGTCCC
CCTCCTGCTTGGGGCCACCCTGACCTACACATACCGCCACTGCTGGCCTCACAAGCCCCTGGTTACTGCAGATG
AAGCTGGGATGGAGGCTCTGACCCCACCACCGGCCACCCATCTGTCACCCTTGGACAGCGCCCACACCCTTCTA
GCACCTCCTGACAGCAGTGAGAAGATCTGCACCGTCCAGTTGGTGGGTAACAGCTGGACCCCTGGCTACCCCGA
GACCCAGGAGGCGCTCTGCCCGCAGGTGACATGGTCCTGGGACCAGTTGCCCAGCAGAGCTCTTGGCCCCGCTG
CTGCGCCCACACTCTCGCCAGAGTCCCCAGCCGGCTCGCCAGCCATGATGCTGCAGCCGGGCCCGCAGCTCTAC
GACGTGATGGACGCGGTCCCAGCGCGGCGCTGGAAGGAGTTCGTGCGCACGCTGGGGCTGCGCGAGGCAGAGAT
CGAAGCCGTGGAGGTGGAGATCGGCCGCTTCCGAGACCAGCAGTACGAGATGCTCAAGCGCTGGCGCCAGCAGC
AGCCCGCGGGCCTCGGAGCCGTTTACGCGGCCCTGGAGCGCATGGGGCTGGACGGCTGCGTGGAAGACTTGCGC
AGCCGCCTGCAGCGCGGCCCGTGACACGGCGCCCACTTGCCACCTAGGCGCTCTGGTGGCCCTTGCAGAAGCCC
TAAGTACGGTTACTTATGCGTGTAGACATTTTATGTCACTTATTAAGCCGCTGGCACGGCCCTGCGTAGCAGCA
CCAGCCGGCCCCACCCCTGCTCGCCCCTATCGCTCCAGCCAAGGCGAAGAAGCACGAACGAATGTCGAGAGGGG
GTGAAGACATTTCTCAACTTCTCGGCCGGAGTTTGGCTGAGATCGCGGTATTAAATCTGTGAAAGAAAACAAAA
AAAAAAAAAAAAAAAAAAAAGTCGACGCGGCCGC

FIGURE 66

```
MEQRPRGCAAVAAALLLVLLGARAQGGTRSPRCDCAGDFHKKIGLFCCRGCPAGHYLKAPCTEPCGNSTCLVCP
QDTFLAWENHHNSECARCQACDEQASQVALENCSAVADTRCGCKPGWFVECQVSQCVSSSPFYCQPCLDCGALH
RHTRLLCSRRDTDCGTCLPGFYEHGDGCVSCPTSTLGSCPERCAAVCGWRQMFWVQVLLAGLVVPLLLGATLTY
TYRHCWPHKPLVTADEAGMEALTPPPATHLSPLDSAHTLLAPPDSSEKICTVQLVGNSWTPGYPETQEALCPQV
TWSWDQLPSRALGPAAAPTLSPESPAGSPAMMLQPGPQLYDVMDAVPARRWKEFVRTLGLREAEIEAVEVEIGR
FRDQQYEMLKRWRQQQPAGLGAVYAALERMGLDGCVEDLRSRLQRGP
```

Signal sequence:                    Amino acids 1-24

Transmembrane domain:               Amino acids 199-219

N-glycosylation sites:              Amino acids 67-71;106-110 cAMP- and cGMP-dependent protein kinase phosphorylation site:
                                    Amino acids 157-161

Tyrosine kinase phosphorylation site:
                                    Amino acids 370-377

N-myristoylation sites:             Amino acids 44-50;50-56;66-72;116-122;
                                                217-223;355-361;391-397;40
                                                1-407

Prokaryotic membrane lipoprotein lipid attachment site:
                                    Amino acids 177-188

GENE DISRUPTIONS, COMPOSITIONS AND METHODS RELATING THERETO

RELATED APPLICATIONS

This application is a US national stage continuation application claiming priority under 35 USC §371 of international application PCT/US2005/029782, filed Aug. 23, 2005, which claims priority under 35 USC §119 to U.S. Provisional Application 60/604,323 filed Aug. 25, 2004, the entire disclosure of which is hereby incorporated by reference.

FIELD OF THE INVENTION

The present invention relates to compositions, including transgenic and knockout animals and methods of using such compositions for the diagnosis and treatment of diseases or disorders.

The disclosure includes a computer program listing appendix, provided on a single compact disc created on Feb. 15, 2011, which is hereby incorporated by reference in its entirety.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietines, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn; received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesion molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immuno-adhesions, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

Given the importance of secreted and membrane-bound proteins in biological and disease processes, in vivo studies and characterizations may provide valuable identification and discovery of therapeutics and/or treatments useful in the prevention, amelioration or correction of diseases or dysfunctions. In this regard, genetically engineered mice have proven to be invaluable tools for the functional dissection of biological processes relevant to human disease, including immunology, cancer, neuro-biology, cardiovascular biology, obesity and many others. Gene knockouts can be viewed as modeling the biological mechanism of drug action by presaging the activity of highly specific antagonists in vivo. Knockout mice have been shown to model drug activity; phenotypes of mice deficient for specific pharmaceutical target proteins can resemble the human clinical phenotype caused by the corresponding antagonist drug. Gene knockouts enable the discovery of the mechanism of action of the target, the predominant physiological role of the target, and mechanism-based side-effects that might result from inhibition of the target in mammals. Examples of this type include mice deficient in the angiotensin converting enzyme (ACE) [Esther, C. R. et al., *Lab. Invest.*, 74:953-965 (1996)] and cyclooxygenase-1 (COX1) genes [Langenbach, R. et al., *Cell*, 83:483-492 (1995)]. Conversely, knocking the gene out in the mouse can have an opposite phenotypic effect to that observed in humans after administration of an agonist drug to the corresponding target. Examples include the erythropoietin knockout [Wu, C. S. et al., *Cell*, 83:59-67 (1996)], in which a consequence of the mutation is deficient red blood cell production, and the GABA(A)-R-β3 knockout [DeLorey, T. M., *J. Neurosci.*, 18:8505-8514 (1998)], in which the mutant mice show hyperactivity and hyper-responsiveness. Both these phenotypes are opposite to the effects of erythropoietin and benzodiazepine administration in humans. A striking example of a target validated using mouse genetics is the ACC2 gene. Although the human ACC2 gene had been identified several years ago, interest in ACC2 as a target for drug development was stimulated only recently after analysis of ACC2 function using a knockout mouse. ACC2 mutant mice eat more than their wild-type littermates, yet burn more fat and store less fat in their adipocytes, making this enzyme a probable target for chemical antagonism in the treatment of obesity [Abu-Elheiga, L. et al., *Science* 291:2613-2616 (2001)].

In the instant application, mutated gene disruptions have resulted in phenotypic observations related to various disease conditions or dysfunctions including: CNS/neurological disturbances or disorders such as anxiety; eye abnormalities and associated diseases; cardiovascular, endothelial or angiogenic disorders including atherosclerosis; abnormal metabolic disorders including diabetes and dyslipidemias associated with elevated serum triglycerides and cholesterol levels; immunological and inflammatory disorders; oncological disorders; bone metabolic abnormalities or disorders such as arthritis, osteoporosis and osteopetrosis; or a developmental disease such as embryonic lethality.

SUMMARY OF THE INVENTION

A. Embodiments

The invention provides an isolated nucleic acid molecule comprising a nucleotide sequence that encodes a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide cDNA as disclosed herein, the coding sequence of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide lacking the signal peptide as disclosed herein, the coding sequence of an extracellular domain of a transmembrane PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect of the invention provides an isolated nucleic acid molecule comprising a nucleotide sequence encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides are contemplated.

The invention also provides fragments of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide coding sequence, or the complement thereof, that may find use as, for example, hybridization probes, for encoding fragments of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide that may optionally encode a polypeptide comprising a binding site for an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody or as antisense oligonucleotide probes. Such nucleic acid fragments usually are or are at least about 10 nucleotides in length, alternatively are or are at least about 15 nucleotides in length, alternatively are or are at least about 20 nucleotides in length, alternatively are or are at least about 30 nucleotides in length, alternatively are or are at least about 40 nucleotides in length, alternatively are or are at least about 50 nucleotides in length, alternatively are or are at least about 60 nucleotides in length, alternatively are or are at least about 70 nucleotides in length, alternatively are or are at least about 80 nucleotides in length, alternatively are or are at least about 90 nucleotides in length, alternatively are or are at least about 100 nucleotides in length, alternatively are or are at least about 110 nucleotides in length, alternatively are or are at least about 120 nucleotides in length, alternatively are or are at least about 130 nucleotides in length, alternatively are or are at least about 140 nucleotides in length, alternatively are or are at least about 150 nucleotides in length, alternatively are or are at least about 160 nucleotides in length, alternatively are or are at least about 170 nucleotides in length, alternatively are or are at least about 180 nucleotides in length, alternatively are or are at least about 190 nucleotides in length, alternatively are or are at least about 200 nucleotides in length, alternatively are or are at least about 250 nucleotides in length, alternatively are or are at least about 300 nucleotides in length, alternatively are or are at least about 350 nucleotides in length, alternatively are or are at least about 400 nucleotides in length, alternatively are or are at least about 450 nucleotides in length, alternatively are or are at least about 500 nucleotides in length, alternatively are or are at least about 600 nucleotides in length, alternatively are or are at least about 700 nucleotides in length, alternatively are or are at least about 800 nucleotides in length, alternatively are or are at least about 900 nucleotides in length and alternatively are or are at least about 1000 nucleotides in length, wherein in this context the term "about" means the referenced nucleotide sequence length plus or minus 10% of that referenced length. It is noted that novel fragments of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-encoding nucleotide sequence may be determined in a routine manner by aligning the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-encoding nucleotide sequence with other known nucleotide sequences using any of a number of well known sequence alignment programs and determining which PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-encoding nucleotide sequence fragment(s) are novel. All of such PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-encoding nucleotide sequences are contemplated herein. Also contemplated are the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide fragments encoded by these nucleotide molecule fragments, preferably those PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide fragments that comprise a binding site for an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention provides isolated PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides encoded by any of the isolated nucleic acid sequences hereinabove identified.

In a certain aspect, the invention concerns an isolated PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In one aspect, the invention concerns PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polypeptides which are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polypeptides will have or have no more than one conservative amino acid substitution as compared to the native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence, alternatively will have or will have no more than 2, 3, 4, 5, 6, 7, 8, 9, or 10 conservative amino acid substitution as compared to the native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence.

In a specific aspect, the invention provides an isolated PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and recovering the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide from the cell culture.

Another aspect the invention provides an isolated PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and recovering the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide from the cell culture.

The invention provides agonists and antagonists of a native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as defined herein. In particular, the agonist or antagonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody or a small molecule.

The invention provides a method of identifying agonists or antagonists to a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide which comprise contacting the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide with a candidate molecule and monitoring a biological activity mediated by said PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Preferably, the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide is a native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

The invention provides a composition of matter comprising a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, or an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as herein described, or an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody, in combination with a carrier. Optionally, the carrier is a pharmaceutically acceptable carrier.

The invention provides the use of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, or an agonist or antagonist thereof as hereinbefore described, or an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody, for the preparation of a medicament useful in the treatment of a condition which is responsive to the anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

The invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

The invention provides an antibody which binds, preferably specifically, to any of the above or below described polypeptides. Optionally, the antibody is a monoclonal antibody, humanized antibody, antibody fragment or single-chain antibody.

The invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

The invention also provides a method of identifying a phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal. In one aspect, the non-human transgenic animal is a mammal. In another aspect, the mammal is a rodent. In still another aspect, the mammal is a rat or a mouse. In one aspect, the non-human transgenic animal is heterozygous for the disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In another aspect, the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In still yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In still another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety-like response during open field activity testing; abnormal circadian rhythm during home-cage activity testing including decreased ambulatory counts; increased exploratory activity during open-field testing; increased stress induced hyperthermia; enhanced motor coordination during inverted screen testing; impaired motor coordination during inverted screen testing; increase in retinal artery tortuosity; retinal degeneration marked by attenuated retinal vessels; opthalmological abnormalities; increased mean systolic blood pressure; increased mean fasting serum glucose levels; decreased mean serum glucose levels; increased mean serum cholesterol levels; increased mean serum triglyceride levels; decreased mean serum cholesterol levels; decreased mean serum triglyceride levels; enhanced glucose tolerance; impaired glucose tolerance; increased mean serum insulin levels; decreased mean serum insulin levels; increased uric acid levels; decreased serum phosphate levels; increased alkaline phosphatase levels and increased alanine amino transferase levels; liver disease; increased mean percentage of CD25+ in both spleen and lymph nodes; decreased mean percentage of natural killer cells; decreased mean percentage of CD21HiCD23Med cells in spleen and lymph nodes; increased mean percentage of CD4 cells and decreased mean percentage of B cells; increased mean percentage of CD8+ cells; decreased mean percentage of eosinophils; decreased mean serum IgG1 response to an ovalbumin challenge; decreased mean serum IgG2a response to an ovalbumin challenge; increased mean serum IgG1 response to an ovalbumin challenge; increased mean serum IgG2a response to an ovalbumin challenge; increased mean serum MCP-1 response to a LPS challenge; increased mean serum TNF-alpha response to a LPS challenge; decreased mean serum MCP-1 response to a LPS challenge; decreased mean serum IL-6 response to a LPS challenge; decreased TNF-alpha response to a LPS challenge; increased mean serum IL6 response to a LPS challenge; increased mean platelet counts; decreased mean total white blood cell (WBC) counts; decreased absolute lymphocyte counts; decreased absolute monocyte counts; decreased skin fibroblast proliferation; increased skin fibroblast proliferation; increased mean percent of total body fat and total fat mass; increased mean body weight; increased mean body length; increased organ weights; increased total tissue mass (TTM); increased lean body mass (LBM); increased bone mineral density (BMD) in total body, femur and vertebrae; increased bone mineral content (BMC) in total body, femur and vertebrae; increased volumetric bone mineral density (vBMD) in total body, femur and vertebrae; increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased bone mineral density (BMD) in total body, femur and vertebrae; decreased bone mineral content (BMC) in total body, femur and vertebrae; decreased volumetric bone mineral density (vBMD) in total body, femur and vertebrae; decreased mean femoral midshaft cortical thickness and cross-sectional area; decreased mean vertebral trabecular bone volume, number and connectivity density; severe depletion of abdominal and subcutaneous body fat deposits; decreased organ weights; growth retardation; hydrocephalus; sebaceous gland hyperplasia and growth retardation; apoptosis of olfactory neuroepithelial cells; lymphoid hyperplasia and tissue inflammation; development abnormalities; male infertility; growth retardation with reduced viability; and embryonic lethality.

The invention also provides an isolated cell derived from a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In one aspect, the isolated cell is a murine cell. In yet another aspect, the murine cell is an embryonic stem cell. In still another aspect, the isolated cell is derived from a non-human transgenic animal which exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality. The invention also provides a method of identifying an agent that modulates a phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

In one aspect, the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In yet another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, BardetBiedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism, or Conradi syndrome.

In still another aspect, the developmental abnormality comprises embryonic lethality or reduced viability.

In still another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety-like response during open field activity testing; abnormal circadian rhythm during home-cage activity testing including decreased ambulatory counts; increased exploratory activity during open-field testing; increased stress induced hyperthermia; enhanced motor coordination during inverted screen testing; impaired motor coordination during inverted screen testing; increase in retinal artery tortuosity; retinal degeneration marked by attenuated retinal vessels; opthalmological abnormalities; increased mean systolic blood pressure; increased mean fasting serum glucose levels; decreased mean serum glucose levels; increased mean serum cholesterol levels; increased mean serum triglyceride levels; decreased mean serum cholesterol levels; decreased mean serum triglyceride levels; enhanced glucose tolerance; impaired glucose tolerance; increased mean serum insulin levels; decreased mean serum insulin levels; increased uric acid levels; decreased serum phosphate levels; increased alkaline phosphatase levels and increased alanine amino transferase levels; liver disease; increased mean percentage of CD25+ in both spleen and lymph nodes; decreased mean percentage of natural killer cells; decreased mean percentage of CD21HiCD23Med cells in spleen and lymph nodes; increased mean percentage of CD4 cells and decreased mean percentage of B cells; increased mean percentage of CD8+ cells; decreased mean percentage of eosinophils; decreased mean serum IgG1 response to an ovalbumin challenge; decreased mean serum IgG2a response to an ovalbumin challenge; increased mean serum IgG1 response to an ovalbumin challenge; increased mean serum IgG2a response to an ovalbumin challenge; increased mean serum MCP-1 response to a LPS challenge; increased mean serum TNF-alpha response to a LPS challenge; decreased mean serum MCP-1 response to a LPS challenge; decreased mean serum IL-6 response to a LPS challenge; decreased TNF-alpha response to a LPS challenge; increased mean serum IL6 response to a LPS challenge; increased mean platelet counts; decreased mean total white blood cell (WBC) counts; decreased absolute lymphocyte counts; decreased absolute monocyte counts; decreased skin fibroblast proliferation; increased skin fibroblast proliferation; increased mean percent of total body fat and total fat mass; increased mean body weight; increased mean body length; increased organ weights; increased total tissue mass (TTM); increased lean body mass (LBM); increased bone mineral density (BMD) in total body, femur and vertebrae; increased bone mineral content (BMC) in total body, femur and vertebrae; increased volumetric bone mineral density (vBMD) in total body, femur and vertebrae; increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased bone mineral density (BMD) in total body, femur and vertebrae; decreased bone mineral content (BMC) in total body, femur and vertebrae; decreased volumetric bone mineral density (vBMD) in total body, femur and vertebrae; decreased mean femoral midshaft cortical thickness and cross-sectional area; decreased mean vertebral trabecular bone volume, number and connectivity density; severe depletion of abdominal and subcutaneous body fat deposits; decreased organ weights; growth retardation; hydrocephalus; sebaceous gland hyperplasia and growth retardation; apoptosis of olfactory neuroepithelial cells; lymphoid hyperplasia and tissue inflammation; development abnormalities; male infertility; growth retardation with reduced viability; and embryonic lethality.

The invention also provides an agent which modulates the phenotype associated with gene disruption. In one aspect, the agent is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody. Instill another aspect, the antagonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention also provides a method of identifying an agent that modulates a physiological characteristic associated with a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

In one aspect, the non-human transgenic animal exhibits at least one of the following physiological characteristics compared with gender matched wild-type littermates:

In another aspect, the non-human transgenic animal exhibits at least one of the following physiological characteristics compared with gender matched wild-type littermates: increased anxiety-like response during open field testing; decreased anxiety-like response during open field activity testing; abnormal circadian rhythm during home-cage activity testing including decreased ambulatory counts; increased exploratory activity during open-field testing; increased stress induced hyperthermia; enhanced motor coordination during inverted screen testing; impaired motor coordination during inverted screen testing; increase in retinal artery tortuosity; retinal degeneration marked by attenuated retinal vessels; opthalmological abnormalities; increased mean systolic blood pressure; increased mean fasting serum glucose levels; decreased mean serum glucose levels; increased mean serum cholesterol levels; increased mean serum triglyceride levels; decreased mean serum cholesterol levels; decreased mean serum triglyceride levels; enhanced glucose tolerance; impaired glucose tolerance; increased mean serum insulin levels; decreased mean serum insulin levels; increased uric acid levels; decreased serum phosphate levels; increased alkaline phosphatase levels and increased alanine amino transferase levels; liver disease; increased mean percentage of CD25+ in both spleen and lymph nodes; decreased mean percentage of natural killer cells; decreased mean percentage of CD21HiCD23Med cells in spleen and lymph nodes; increased mean percentage of CD4 cells and decreased mean percentage of B cells; increased mean percentage of CD8+ cells; decreased mean percentage of eosinophils; decreased mean serum IgG1 response to an ovalbumin challenge; decreased mean serum IgG2a response to an ovalbumin challenge; increased mean serum IgG1 response to an ovalbumin challenge; increased mean serum IgG2a response to an ovalbumin challenge; increased mean serum MCP-1 response to a LPS challenge; increased mean serum TNF-alpha response to a LPS challenge; decreased mean serum MCP-1 response to a LPS challenge; decreased mean serum IL-6 response to a LPS challenge; decreased TNF-alpha response to a LPS challenge; increased mean serum IL6 response to a LPS challenge; increased mean platelet counts; decreased mean total white blood cell (WBC) counts; decreased absolute lymphocyte counts; decreased absolute monocyte counts; decreased skin fibroblast proliferation; increased skin fibroblast proliferation; increased mean percent of total body fat and total fat mass; increased mean body weight; increased mean body length; increased organ weights; increased total tissue mass (TTM); increased lean body mass (LBM); increased bone mineral density (BMD) in total body, femur and vertebrae;

increased bone mineral content (BMC) in total body, femur and vertebrae; increased volumetric bone mineral density (vBMD) in total body, femur and vertebrae; increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased bone mineral density (BMD) in total body, femur and vertebrae; decreased bone mineral content (BMC) in total body, femur and vertebrae; decreased volumetric bone mineral density (vBMD) in total body, femur and vertebrae; decreased mean femoral midshaft cortical thickness and cross-sectional area; decreased mean vertebral trabecular bone volume, number and connectivity density; severe depletion of abdominal and subcutaneous body fat deposits; decreased organ weights; growth retardation; hydrocephalus; sebaceous gland hyperplasia and growth retardation; apoptosis of olfactory neuroepithelial cells; lymphoid hyperplasia and tissue inflammation; development abnormalities; male infertility; growth retardation with reduced viability; and embryonic lethality.

The invention also provides an agent that modulates a physiological characteristic which is associated with gene disruption. In one aspect, the agent is an agonist or antagonist of the phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agent is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody. Instill another aspect, the antagonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention also provides a method of identifying an agent which modulates a behavior associated with a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

In one aspect, the observed behavior is an increased anxiety-like response during open field activity testing. In yet another aspect, the observed behavior is a decreased anxiety-like response during open field activity testing. In yet another aspect, the observed behavior is an abnormal circadian rhythm during home-cage activity testing. In yet another aspect, the observed behavior is an enhanced motor coordination during inverted screen testing. In yet another aspect, the observed behavior is impaired motor coordination during inverted screen testing. In yet another aspect, the observed behavior includes depression, generalized anxiety disorders, attention deficit disorder, sleep disorder, hyperactivity disorder, obsessive compulsive disorder, schizophrenia, cognitive disorders, hyperalgesia and sensory disorders. Such disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histrionic, narcissistic, obsessive-compulsive, schizoid, and schizotypal.

The invention also provides an agent that modulates a behavior which is associated with gene disruption. In one aspect, the agent is an agonist or antagonist of the phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agent is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody. In still another aspect, the antagonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) administering a test agent to said non-human transgenic animal; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality associated with the gene disruption in the non-human transgenic animal.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism, or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety-like response during open field activity testing; abnormal circadian rhythm during home-cage activity testing including decreased ambulatory counts; increased exploratory activity during open-field testing; increased stress induced hyperthermia; enhanced motor coordination during inverted screen testing; impaired motor coordination during inverted screen testing; increase in retinal artery tortuosity; retinal degeneration marked by attenuated retinal vessels; opthalmological abnormalities; increased mean systolic blood pressure; increased mean fasting serum glucose levels; decreased mean serum glucose levels; increased mean serum cholesterol levels; increased mean serum triglyceride levels; decreased mean serum cholesterol levels; decreased mean serum triglyceride levels; enhanced glucose tolerance; impaired glucose tolerance; increased mean serum insulin levels; decreased mean serum insulin levels; increased uric acid levels; decreased serum phosphate levels; increased alkaline phosphatase levels and increased alanine amino transferase levels; liver disease; increased mean percentage of CD25+ in both spleen and lymph nodes; decreased mean percentage of natural killer cells; decreased mean percentage of CD21HiCD23Med cells in spleen and lymph nodes; increased mean percentage of CD4 cells and decreased mean percentage of B cells; increased mean percentage of CD8+ cells; decreased mean percentage of eosinophils; decreased mean serum IgG1 response to an ovalbumin challenge; decreased mean serum IgG2a response to an ovalbumin challenge; increased mean serum IgG1 response to an ovalbumin challenge; increased mean serum IgG2a response to an ovalbumin challenge; increased mean serum MCP-1 response to a LPS challenge; increased mean serum TNF-alpha response to a LPS challenge; decreased mean serum MCP-1 response to a LPS challenge; decreased mean serum IL-6 response to a LPS challenge; decreased TNF-alpha response to a LPS challenge; increased mean serum IL6 response to a LPS challenge; increased mean platelet counts; decreased mean total white blood cell (WBC) counts; decreased absolute lymphocyte counts; decreased absolute monocyte counts; decreased skin fibroblast proliferation; increased skin fibroblast proliferation; increased mean percent of total body fat and total fat mass; increased mean body weight; increased mean body length; increased organ weights; increased total tissue mass (TTM); increased lean body mass (LBM); increased bone mineral density (BMD) in total body, femur and vertebrae; increased bone mineral content (BMC) in total body, femur and vertebrae; increased volumetric bone mineral density (vBMD) in total body, femur and vertebrae; increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased bone mineral density (BMD) in total body, femur and vertebrae; decreased bone mineral content (BMC) in total body, femur and vertebrae; decreased volumetric bone mineral density (vBMD) in total body, femur and vertebrae; decreased mean femoral midshaft cortical thickness and cross-sectional area; decreased mean vertebral trabecular bone volume, number and connectivity density; severe depletion of abdominal and subcutaneous body fat deposits; decreased organ weights; growth retardation; hydrocephalus; sebaceous gland hyperplasia and growth retardation; apoptosis of olfactory neuroepithelial cells; lymphoid hyperplasia and tissue inflammation; development abnormalities; male infertility; growth retardation with reduced viability; and embryonic lethality.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption. In one aspect, the agent is an agonist or antagonist of the phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agent is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody. In still another aspect, the antagonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention also provides a therapeutic agent for the treatment of a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a method of identifying an agent that modulates the expression of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) contacting a test agent with a host cell expressing a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide; and (b) determining whether the test agent modulates the expression of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide by the host cell.

The invention also provides an agent that modulates the expression of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In one aspect, the agent is an agonist or antagonist of the phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agent is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody. In still another aspect, the antagonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention also provides a method of evaluating a therapeutic agent capable of affecting a condition associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

In one aspect, the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a therapeutic agent which is capable of affecting a condition associated with gene disruption. In one aspect, the agent is an agonist or antagonist of the phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agent is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody. Instill another aspect, the antagonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention also provides a pharmaceutical composition comprising a therapeutic agent capable of affecting the condition associated with gene disruption.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject in need of such treatment whom may already have the disorder, or may be prone to have the disorder or may be in whom the disorder is to be prevented, a therapeutically effective amount of a therapeutic agent, or agonists or antagonists thereof, thereby effectively treating or preventing or ameliorating said disorder or disease.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect the therapeutic agent is an agonist or antagonist of the phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agent is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody. In still another aspect, the antagonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal cell culture, each cell of said culture comprising a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) administering a test agent to said cell culture; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said culture. In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing.

In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption in said culture. In one aspect, the agent is an agonist or antagonist of the phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agent is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In yet another aspect, the agonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody. In still another aspect, the antagonist agent is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

The invention also provides a method of modulating a phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject whom may already have the phenotype, or may be prone to have the phenotype or may be in whom the phenotype is to be prevented, an effective amount of an agent identified as modulating said phenotype, or agonists or antagonists thereof, thereby effectively modulating the phenotype.

The invention also provides a method of modulating a physiological characteristic associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject whom may already exhibit the physiological characteristic, or may be prone to exhibit the physiological characteristic or may be in whom the physiological characteristic is to be prevented, an effective amount of an agent identified as modulating said physiological characteristic, or agonists or antagonists thereof, thereby effectively modulating the physiological characteristic.

The invention also provides a method of modulating a behavior associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject whom may already exhibit the behavior, or may be prone to exhibit the behavior or may be in whom the exhibited behavior is to be prevented, an effective amount of an agent identified as modulating said behavior, or agonists or antagonists thereof, thereby effectively modulating the behavior.

The invention also provides a method of modulating the expression of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a host cell expressing said PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, an effective amount of an agent identified as modulating said expression, or agonists or antagonists thereof, thereby effectively modulating the expression of said polypeptide.

The invention also provides a method of modulating a condition associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject whom may have the condition, or may be prone to have the condition or may be in whom the condition is to be prevented, a therapeutically effective amount of a therapeutic agent identified as modulating said condition, or agonists or antagonists thereof, thereby effectively modulating the condition.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a non-human transgenic animal cell culture, each cell of said culture comprising a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, an effective amount of an agent identified as treating or preventing or ameliorating said disorder, or agonists or antagonists thereof, thereby effectively treating or preventing or ameliorating said disorder.

B. Further Embodiments

In yet further embodiments, the invention is directed to the following set of potential claims for this application:

1. A method of identifying a phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal.

2. The method of Claim 1, wherein the non-human transgenic animal is heterozygous for the disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

3. The method of Claim 1, wherein the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

4. The method of Claim 3, wherein the neurological disorder is an increased anxiety-like response during open field activity testing.

5. The method of Claim 3, wherein the neurological disorder is a decreased anxiety-like response during open field activity testing.

6. The method of Claim 3, wherein the neurological disorder is an abnormal circadian rhythm during home-cage activity testing.

7. The method of Claim 3, wherein the neurological disorder is an enhanced motor coordination during inverted screen testing.

8. The method of Claim 3, wherein the neurological disorder is an impaired motor coordination during inverted screen testing.

9. The method of Claim 3, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

10. The method of Claim 3, wherein the eye abnormality is a retinal abnormality.

11. The method of Claim 3, wherein the eye abnormality is consistent with vision problems or blindness.

12. The method of Claim 10, wherein the retinal abnormality is consistent with retinitis pigmentosa.

13. The method of Claim 10, wherein the retinal abnormality is characterized by retinal degeneration or retinal dysplasia.

14. The method of Claim 10, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

15. The method of Claim 3, wherein the eye abnormality is a cataract.

16. The method of Claim 15, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

17. The method of Claim 3, wherein the developmental abnormality comprises embryonic lethality or reduced viability.

18. The method of Claim 3, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

19. The method of Claim 3, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

20. The method of Claim 3, wherein the bone metabolic abnormality or disorder is arthritis, osteoporosis or osteopetrosis.

21. The method of Claim 1, wherein the non-human transgenic animal exhibits at least one of the following physiological characteristics compared with gender matched wild-type littermates: increased anxiety-like response during open field testing; decreased anxiety-like response during open field activity testing; abnormal circadian rhythm during homecage activity testing including decreased ambulatory counts; increased exploratory activity during open-field testing; increased stress induced hyperthermia; enhanced motor coordination during inverted screen testing; impaired motor coordination during inverted screen testing; increase in retinal artery tortuosity; retinal degeneration marked by attenuated retinal vessels; opthalmological abnormalities; increased mean systolic blood pressure; increased mean fasting serum glucose levels; decreased mean serum glucose levels; increased mean serum cholesterol levels; increased mean serum triglyceride levels; decreased mean serum cholesterol levels; decreased mean serum triglyceride levels; enhanced glucose tolerance; impaired glucose tolerance; increased mean serum insulin levels; decreased mean serum insulin levels; increased uric acid levels; decreased serum phosphate levels; increased alkaline phosphatase levels and increased alanine amino transferase levels; liver disease; increased mean percentage of CD25+ in both spleen and lymph nodes; decreased mean percentage of natural killer cells; decreased mean percentage of CD21HiCD23Med cells in spleen and lymph nodes; increased mean percentage of CD4 cells and decreased mean percentage of B cells; increased mean percentage of CD8+ cells; decreased mean percentage of eosinophils; decreased mean serum IgG1 response to an ovalbumin challenge; decreased mean serum IgG2a response to an ovalbumin challenge; increased mean serum IgG1 response to an ovalbumin challenge; increased mean serum IgG2a response to an ovalbumin challenge; increased mean serum MCP-1 response to a LPS challenge; increased mean serum TNF-alpha response to a LPS challenge; decreased mean serum MCP-1 response to a LPS challenge; decreased mean serum IL-6 response to a LPS challenge; decreased TNF-alpha response to a LPS challenge; increased mean serum IL6 response to a LPS challenge; increased mean platelet counts; decreased mean total white blood cell (WBC) counts; decreased absolute lymphocyte counts; decreased absolute monocyte counts; decreased skin fibroblast proliferation; increased skin fibroblast proliferation; increased mean percent of total body fat and total fat mass; increased mean body weight; increased mean body length; increased organ weights; increased total tissue mass (TTM); increased lean body mass (LBM); increased bone mineral density (BMD) in total body, femur and vertebrae; increased bone mineral content (BMC) in total body, femur and vertebrae; increased volumetric bone mineral density (vBMD) in total body, femur and vertebrae; increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased bone mineral density (BMD) in total body, femur and vertebrae; decreased bone mineral content (BMC) in total body, femur and vertebrae; decreased volumetric bone mineral density (vBMD) in total body, femur and vertebrae; decreased mean femoral midshaft cortical thickness and cross-sectional area; decreased mean vertebral trabecular bone volume, number and connectivity density; severe depletion of abdominal and subcutaneous body fat deposits; decreased organ weights; growth retardation; hydrocephalus; sebaceous gland hyperplasia and growth retardation; apoptosis of olfactory neuroepithelial cells; lymphoid hyperplasia and tissue inflammation; development abnormalities; male infertility; growth retardation with reduced viability; and embryonic lethality.

22. An isolated cell derived from a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

23. The isolated cell of Claim 22 which is a murine cell.

24. The isolated cell of Claim 23, wherein the murine cell is an embryonic stem cell.

25. The isolated cell of Claim 22, wherein the non-human transgenic animal exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

26. A method of identifying an agent that modulates a phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

27. The method of Claim 26, wherein the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

28. The method of Claim 27, wherein the neurological disorder is an increased anxiety-like response during open field activity testing.

29. The method of Claim 27, wherein the neurological disorder is a decreased anxiety-like response during open field activity testing.

30. The method of Claim 27, wherein the neurological disorder is an abnormal circadian rhythm during home-cage activity testing.

31. The method of Claim 27, wherein the neurological disorder is an enhanced motor coordination during inverted screen testing.

32. The method of Claim 27, wherein the neurological disorder is an impaired motor coordination during inverted screen testing.

33. The method of Claim 27, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

34. The method of Claim 27, wherein the eye abnormality is a retinal abnormality.

35. The method of Claim 27, wherein the eye abnormality is consistent with vision problems or blindness.

36. The method of Claim 34, wherein the retinal abnormality is consistent with retinitis pigmentosa.

37. The method of Claim 34, wherein the retinal abnormality is characterized by retinal degeneration or retinal dysplasia.

38. The method of Claim 34, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

39. The method of Claim 27, wherein the eye abnormality is a cataract.

40. The method of Claim 39, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

41. The method of Claim 27, wherein the developmental abnormality comprises embryonic lethality or reduced viability.

42. The method of Claim 27, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

43. The method of Claim 27, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation-associated diseases including graft rejection and graft-versus-host disease.

44. The method of Claim 27, wherein said bone metabolic abnormality or disorder is arthritis, osteoporosis or osteopetrosis.

45. The method of Claim 26, wherein the non-human transgenic animal exhibits at least one of the following physiological characteristics compared with gender matched wild-type littermates: increased anxiety-like response during open field testing; decreased anxiety-like response during open field activity testing; abnormal circadian rhythm during home-cage activity testing including decreased ambulatory counts; increased exploratory activity during open-field testing; increased stress induced hyperthermia; enhanced motor coordination during inverted screen testing; impaired motor coordination during inverted screen testing; increase in retinal artery tortuosity; retinal degeneration marked by attenuated retinal vessels; opthalmological abnormalities; increased mean systolic blood pressure; increased mean fasting serum glucose levels; decreased mean serum glucose levels; increased mean serum cholesterol levels; increased mean serum triglyceride levels; decreased mean serum cholesterol levels; decreased mean serum triglyceride levels; enhanced glucose tolerance; impaired glucose tolerance; increased mean serum insulin levels; decreased mean serum insulin levels; increased uric acid levels; decreased serum phosphate levels; increased alkaline phosphatase levels and increased alanine amino transferase levels; liver disease; increased mean percentage of CD25+ in both spleen and lymph nodes; decreased mean percentage of natural killer cells; decreased mean percentage of CD21HiCD23Med cells in spleen and lymph nodes; increased mean percentage of CD4 cells and decreased mean percentage of B cells; increased mean percentage of CD8+ cells; decreased mean percentage of eosinophils; decreased mean serum IgG1 response to an ovalbumin challenge; decreased mean serum IgG2a response to an ovalbumin challenge; increased mean serum IgG1 response to an ovalbumin challenge; increased mean serum IgG2a response to an ovalbumin challenge; increased mean serum MCP-1 response to a LPS challenge; increased mean serum TNF-alpha response to a LPS challenge; decreased mean serum MCP-1 response to a LPS challenge; decreased mean serum IL-6 response to a LPS challenge; decreased TNF-alpha response to a LPS challenge; increased mean serum IL6 response to a LPS challenge; increased mean platelet counts; decreased mean total white blood cell (WBC) counts; decreased absolute lymphocyte counts; decreased absolute monocyte counts; decreased skin fibroblast proliferation; increased skin fibroblast proliferation; increased mean percent of total body fat and total fat mass; increased mean body weight; increased mean body length; increased organ weights; increased total tissue mass (TTM); increased lean body mass (LBM); increased bone mineral density (BMD) in total body, femur and vertebrae; increased bone mineral content (BMC) in total body, femur and vertebrae; increased volumetric bone mineral density (vBMD) in total body, femur and vertebrae; increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased bone mineral density (BMD) in total body, femur and vertebrae; decreased bone mineral content (BMC) in total body, femur and vertebrae; decreased volumetric bone mineral density (vBMD) in total body, femur and vertebrae; decreased mean femoral midshaft cortical thickness and cross-sectional area; decreased mean vertebral trabecular bone volume, number and connectivity density; severe depletion of abdominal and subcutaneous body fat deposits; decreased organ weights; growth retardation; hydrocephalus; sebaceous gland hyperplasia and growth retardation; apoptosis of olfactory neuroepithelial cells; lymphoid hyperplasia and tissue inflammation; development abnormalities; male infertility; growth retardation with reduced viability; and embryonic lethality.

46. An agent identified by the method of Claim 26.

47. The agent of Claim 46 which is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

48. The agent of Claim 47, wherein the agonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

49. The agent of Claim 47, wherein the antagonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

50. A method of identifying an agent that modulates a physiological characteristic associated with a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

51. The method of Claim 50, wherein the non-human transgenic animal exhibits at least one of the following physiological characteristics compared with gender matched wild-type littermates: increased anxiety-like response during open field testing; decreased anxiety-like response during open field activity testing; abnormal circadian rhythm during home-cage activity testing including decreased ambulatory counts; increased exploratory activity during open-field testing; increased stress induced hyperthermia; enhanced motor coordination during inverted screen testing; impaired motor coordination during inverted screen testing; increase in retinal artery tortuosity; retinal degeneration marked by attenuated retinal vessels; opthalmological abnormalities; increased mean systolic blood pressure; increased mean fasting serum glucose levels; decreased mean serum glucose levels; increased mean serum cholesterol levels; increased mean serum triglyceride levels; decreased mean serum cholesterol levels; decreased mean serum triglyceride levels; enhanced glucose tolerance; impaired glucose tolerance; increased mean serum insulin levels; decreased mean serum insulin levels; increased uric acid levels; decreased serum phosphate levels; increased alkaline phosphatase levels and increased alanine amino transferase levels; liver disease; increased mean percentage of CD25+ in both spleen and lymph nodes; decreased mean percentage of natural killer cells; decreased mean percentage of CD21HiCD23Med cells in spleen and lymph nodes; increased mean percentage of CD4 cells and decreased mean percentage of B cells; increased mean percentage of CD8+ cells; decreased mean percentage of eosinophils; decreased mean serum IgG1 response to an ovalbumin challenge; decreased mean serum IgG2a response to an ovalbumin challenge; increased mean serum IgG1 response to an ovalbumin challenge; increased mean serum IgG2a response to an ovalbumin challenge; increased mean serum MCP-1 response to a LPS challenge; increased mean serum TNF-alpha response to a LPS challenge; decreased mean serum MCP-1 response to a LPS challenge; decreased mean serum IL-6 response to a LPS challenge; decreased TNF-alpha response to a LPS challenge; increased mean serum IL6 response to a LPS challenge; increased mean platelet counts; decreased mean total white blood cell (WBC) counts; decreased absolute lymphocyte counts; decreased absolute monocyte counts; decreased skin fibroblast proliferation; increased skin fibroblast proliferation; increased mean percent of total body fat and total fat mass; increased mean body weight; increased mean body length; increased organ weights; increased total tissue mass (TTM); increased lean body mass (LBM); increased bone mineral density (BMD) in total body, femur and vertebrae; increased bone mineral content (BMC) in total body, femur and vertebrae; increased volumetric bone mineral density (vBMD) in total body, femur and vertebrae; increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased bone mineral density (BMD) in total body, femur and vertebrae; decreased bone mineral content (BMC) in total body, femur and vertebrae; decreased volumetric bone mineral density (vBMD) in total body, femur and vertebrae; decreased mean femoral midshaft cortical thickness and cross-sectional area; decreased mean vertebral trabecular bone volume, number and connectivity density; severe depletion of abdominal and subcutaneous body fat deposits; decreased organ weights; growth retardation; hydrocephalus; sebaceous gland hyperplasia and growth retardation; apoptosis of olfactory neuroepithelial cells; lymphoid hyperplasia and tissue inflammation; development abnormalities; male infertility; growth retardation with reduced viability; and embryonic lethality.

52. An agent identified by the method of Claim 50.

53. The agent of Claim 52 which is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

54. The agent of Claim 53, wherein the agonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

55. The agent of Claim 53, wherein the antagonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

56. A method of identifying an agent which modulates a behavior associated with a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

57. The method of Claim 56, wherein the behavior is an increased anxiety-like response during open field activity testing.

58. The method of Claim 56, wherein the behavior is a decreased anxiety-like response during open field activity testing.

59. The method of Claim 56, wherein the behavior is an abnormal circadian rhythm during home-cage activity testing.

60. The method of Claim 56, wherein the behavior is an enhanced motor coordination during inverted screen testing.

61. The method of Claim 56, wherein the behavior is an impaired motor coordination during inverted screen testing.

62. The method of Claim 56, wherein the behavior is depression, generalized anxiety disorders, attention deficit disorder, sleep disorder, hyperactivity disorder, obsessive compulsive disorder, schizophrenia, cognitive disorders, hyperalgesia or sensory disorders.

63. An agent identified by the method of Claim 56.

64. The agent of Claim 63 which is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

65. The agent of Claim 64, wherein the agonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

66. The agent of Claim 64, wherein the antagonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

67. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) administering a test agent to said non-human transgenic animal; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in the non-human transgenic animal.

68. The method of Claim 67, wherein the neurological disorder is an increased anxiety-like response during open field activity testing.

69. The method of Claim 67, wherein the neurological disorder is a decreased anxiety-like response during open field activity testing.

70. The method of Claim 67, wherein the neurological disorder is an abnormal circadian rhythm during home-cage activity testing.

71. The method of Claim 67, wherein the neurological disorder is an enhanced motor coordination during inverted screen testing.

72. The method of Claim 67, wherein the neurological disorder is an impaired motor coordination during inverted screen testing.

73. The method of Claim 73, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

74. The method of Claim 67, wherein the eye abnormality is a retinal abnormality.

75. The method of Claim 67, wherein the eye abnormality is consistent with vision problems or blindness.

76. The method of Claim 74, wherein the retinal abnormality is consistent with retinitis pigmentosa.

77. The method of Claim 74, wherein the retinal abnormality is characterized by retinal degeneration or retinal dysplasia.

78. The method of Claim 74, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

79. The method of Claim 67, wherein the eye abnormality is a cataract.

80. The method of Claim 79, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

81. The method of Claim 67, wherein the developmental abnormality comprises embryonic lethality or reduced viability.

82. The method of Claim 67, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

83. The method of Claim 67, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

84. The method of Claim 67, wherein said bone metabolic abnormality or disorder is arthritis, osteoporosis or osteopetrosis.

85. The method of Claim 67, wherein the non-human transgenic animal exhibits at least one of the following physiological characteristics compared with gender matched wild-type littermates: increased anxiety-like response during open field testing; decreased anxiety-like response during open field activity testing; abnormal circadian rhythm during home-cage activity testing including decreased ambulatory counts; increased exploratory activity during open-field testing; increased stress induced hyperthermia; enhanced motor coordination during inverted screen testing; impaired motor coordination during inverted screen testing; increase in retinal artery tortuosity; retinal degeneration marked by attenuated retinal vessels; opthalmological abnormalities; increased mean systolic blood pressure; increased mean fasting serum glucose levels; decreased mean serum glucose levels; increased mean serum cholesterol levels; increased mean serum triglyceride levels; decreased mean serum cholesterol levels; decreased mean serum triglyceride levels; enhanced glucose tolerance; impaired glucose tolerance; increased mean serum insulin levels; decreased mean serum insulin levels; increased uric acid levels; decreased serum phosphate levels; increased alkaline phosphatase levels and increased alanine amino transferase levels; liver disease; increased mean percentage of CD25+ in both spleen and lymph nodes; decreased mean percentage of natural killer cells; decreased mean percentage of CD21HiCD23Med cells in spleen and lymph nodes; increased mean percentage of CD4 cells and decreased mean percentage of B cells; increased mean percentage of CD8+ cells; decreased mean percentage of eosinophils; decreased mean serum IgG1 response to an ovalbumin challenge; decreased mean serum IgG2a response to an ovalbumin challenge; increased mean serum IgG1 response to an ovalbumin challenge; increased mean serum IgG2a response to an ovalbumin challenge; increased mean serum MCP-1 response to a LPS challenge; increased mean serum TNF-alpha response to a LPS challenge; decreased mean serum MCP-1 response to a LPS challenge; decreased mean serum IL-6 response to a LPS challenge; decreased TNF-alpha response to a LPS challenge; increased mean serum IL6 response to a LPS challenge; increased mean platelet counts; decreased mean total white blood cell (WBC) counts; decreased absolute lymphocyte counts; decreased absolute monocyte counts; decreased skin fibroblast proliferation; increased skin fibroblast proliferation; increased mean percent of total body fat and total fat mass; increased mean body weight; increased mean body length; increased organ weights; increased total tissue mass (TTM); increased lean body mass (LBM); increased bone mineral density (BMD) in total body, femur and vertebrae; increased bone mineral content (BMC) in total body, femur and vertebrae; increased volumetric bone mineral density (vBMD) in total body, femur and vertebrae; increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased bone mineral density (BMD) in total body, femur and vertebrae; decreased bone mineral content (BMC) in total body, femur and vertebrae; decreased volumetric bone mineral density (vBMD) in total body, femur and vertebrae; decreased mean femoral midshaft cortical thickness and cross-sectional area; decreased mean vertebral trabecular bone volume, number and connectivity density; severe depletion of abdominal and subcutaneous body fat deposits; decreased organ weights; growth retardation; hydrocephalus; sebaceous gland hyperplasia and growth retardation; apoptosis of olfactory neuroepithelial cells; lymphoid hyperplasia and tissue inflammation; development abnormalities; male infertility; growth retardation with reduced viability; and embryonic lethality.

86. An agent identified by the method of Claim 67.

87. The agent of Claim 86 which is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

88. The agent of Claim 87, wherein the agonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

89. The agent of Claim 87, wherein the antagonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

90. A therapeutic agent identified by the method of Claim 67.

91. A method of identifying an agent that modulates the expression of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) contacting a test agent with a host cell expressing a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide; and (b) determining whether the test agent modulates the expression of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide by the host cell.

92. An agent identified by the method of Claim 91.

93. The agent of Claim 92 which is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

94. The agent of Claim 93, wherein the agonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

95. The agent of Claim 93, wherein the antagonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

96. A method of evaluating a therapeutic agent capable of affecting a condition associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal whose genome comprises a disruption of the gene which encodes for the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

97. The method of Claim 96, wherein the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

98. A therapeutic agent identified by the method of Claim 96.

99. The therapeutic agent of Claim 98 which is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

100. The therapeutic agent of Claim 99, wherein the agonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

101. The therapeutic agent of Claim 99, wherein the antagonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

102. A pharmaceutical composition comprising the therapeutic agent of Claim 98.

103. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject in need of such treatment whom may already have the disorder, or may be prone to have the disorder or may be in whom the disorder is to be prevented, a therapeutically effective amount of the therapeutic agent of Claim 94, or agonists or antagonists thereof, thereby effectively treating or preventing or ameliorating said disorder.

104. The method of Claim 103, wherein the neurological disorder is an increased anxiety-like response during open field activity testing.

105. The method of Claim 103, wherein the neurological disorder is a decreased anxiety-like response during open field activity testing.

106. The method of Claim 103, wherein the neurological disorder is an abnormal circadian rhythm during home-cage activity testing.

107. The method of Claim 103, wherein the neurological disorder is an enhanced motor coordination during inverted screen testing.

108. The method of Claim 103, wherein the neurological disorder is an impaired motor coordination during inverted screen testing.

109. The method of Claim 103, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

110. The method of Claim 103, wherein the eye abnormality is a retinal abnormality.

111. The method of Claim 103, wherein the eye abnormality is consistent with vision problems or blindness.

112. The method of Claim 110, wherein the retinal abnormality is consistent with retinitis pigmentosa.

113. The method of Claim 110, wherein the retinal abnormality is characterized by retinal degeneration or retinal dysplasia.

114. The method of Claim 110, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

115. The method of Claim 103, wherein the eye abnormality is a cataract.

116. The method of Claim 115, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

117. The method of Claim 103, wherein the developmental abnormality comprises embryonic lethality or reduced viability.

118. The method of Claim 103, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

119. The method of Claim 103, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

120. The method of Claim 103, wherein said bone metabolic abnormality or disorder is arthritis, osteoporosis or osteopetrosis.

121. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising:

(a) providing a non-human transgenic animal cell culture, each cell of said culture comprising a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide;

(b) administering a test agent to said cell culture; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said cell culture.

122. The method of Claim 121, wherein the neurological disorder is an increased anxiety-like response during open field activity testing.

123. The method of Claim 121, wherein the neurological disorder is a decreased anxiety-like response during open field activity testing.

124. The method of Claim 121, wherein the neurological disorder is an abnormal circadian rhythm during home-cage activity testing.

125. The method of Claim 121, wherein the neurological disorder is an enhanced motor coordination during inverted screen testing.

126. The method of Claim 121, wherein the neurological disorder is an impaired motor coordination during inverted screen testing.

127. The method of Claim 121, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

128. The method of Claim 121, wherein the eye abnormality is a retinal abnormality.

129. The method of Claim 121, wherein the eye abnormality is consistent with vision problems or blindness.

130. The method of Claim 128, wherein the retinal abnormality is consistent with retinitis pigmentosa.

131. The method of Claim 128, wherein the retinal abnormality is characterized by retinal degeneration or retinal dysplasia.

132. The method of Claim 128, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

133. The method of Claim 121, wherein the eye abnormality is a cataract.

134. The method of Claim 133, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

135. The method of Claim 121, wherein the developmental abnormality comprises embryonic lethality or reduced viability.

136. The method of Claim 121, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

137. The method of Claim 121, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

138. The method of Claim 121, wherein said bone metabolic abnormality or disorder is arthritis, osteoporosis or osteopetrosis.

139. An agent identified by the method of Claim 121.

140. The agent of Claim 139 which is an agonist or antagonist of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO101102, PRO10282, PRO61709 or PRO779 polypeptide.

141. The agent of Claim 140, wherein the agonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

142. The agent of Claim 140, wherein the antagonist is an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody.

143. A therapeutic agent identified by the method of Claim 121.

144. A method of modulating a phenotype associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject whom may already have the phenotype, or may be prone to have the phenotype or may be in whom the phenotype is to be prevented, an effective amount of the agent of Claim 46, or agonists or antagonists thereof, thereby effectively modulating the phenotype.

145. A method of modulating a physiological characteristic associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject whom may already exhibit the physiological characteristic, or may be prone to exhibit the physiological characteristic or may be in whom the physiological characteristic is to be prevented, an effective amount of the agent of Claim 52, or agonists or antagonists thereof, thereby effectively modulating the physiological characteristic.

146. A method of modulating a behavior associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject whom may already exhibit the behavior, or may be prone to exhibit the behavior or may be in whom the exhibited behavior is to be prevented, an effective amount of the agent of Claim 63, or agonists or antagonists thereof, thereby effectively modulating the behavior.

147. A method of modulating the expression of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a host cell expressing said PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, an effective amount of the agent of Claim 92, or agonists or antagonists thereof, thereby effectively modulating the expression of said polypeptide.

148. A method of modulating a condition associated with a disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a subject whom may have the condition, or may be prone to have the condition or may be in whom the condition is to be prevented, a therapeutically effective amount of the therapeutic agent of Claim 98, or agonists or antagonists thereof, thereby effectively modulating the condition.

149. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the method comprising administering to a non-human transgenic animal cell culture, each cell of said culture comprising a disruption of the gene which encodes for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, a therapeutically effective amount of the agent of Claim 139, or agonists or antagonists thereof, thereby effectively treating or preventing or ameliorating said disorder.

BRIEF DESCRIPTION OF THE DRAWINGS

FIG. 1 shows a nucleotide sequence (SEQ ID NO:1) of a native sequence PRO196 cDNA, wherein SEQ ID NO:1 is a clone designated herein as "DNA22779-1130" (UNQ170).

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO217 cDNA, wherein SEQ ID NO:3 is a clone designated herein as "DNA33094-1131" (UNQ191).

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO231 cDNA, wherein SEQ ID NO:5 is a clone designated herein as "DNA34434-1139" (UNQ205).

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO236 cDNA, wherein SEQ ID NO:7 is a clone designated herein as "DNA35599-1168" (UNQ210).

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO245 cDNA, wherein SEQ ID NO:9 is a clone designated herein as "DNA35638-1141" (UNQ219).

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO246 cDNA, wherein SEQ ID NO:11 is a clone designated herein as "DNA35639-1172" (UNQ220).

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO258 cDNA, wherein SEQ ID NO:13 is a clone designated herein as "DNA35918-1174" (UNQ225).

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO287 cDNA, wherein SEQ ID NO:15 is a clone designated herein as "DNA39969-1185" (UNQ250).

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO328 cDNA, wherein SEQ ID NO:17 is a clone designated herein as "DNA40587-1231" (UNQ289).

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO344 cDNA, wherein SEQ ID NO:19 is a clone designated herein as "DNA40592-1242" (UNQ303).

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO357 cDNA, wherein SEQ ID NO:21 is a clone designated herein as "DNA44804-1248" (UNQ314).

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO526 cDNA, wherein SEQ ID NO:23 is a clone designated herein as "DNA44184-1319" (UNQ330).

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO724 cDNA, wherein SEQ ID NO:25 is a clone designated herein as "DNA49631-1328" (UNQ389).

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO731 cDNA, wherein SEQ ID NO:27 is a clone designated herein as "DNA48331-1329" (UNQ395).

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO732 cDNA, wherein SEQ ID NO:29 is a clone designated herein as "DNA48334-1435" (UNQ396).

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO1003 cDNA, wherein SEQ ID NO:31 is a clone designated herein as "DNA58846-1409" (UNQ487).

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO1104 cDNA, wherein SEQ ID NO:33 is a clone designated herein as "DNA59616-1465" (UNQ547).

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO1151 cDNA, wherein SEQ ID NO:35 is a clone designated herein as "DNA44694-1500" (UNQ581).

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO1244 cDNA, wherein SEQ ID NO:37 is a clone designated herein as "DNA64883-1526" (UNQ628).

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO1298 cDNA, wherein SEQ ID NO:39 is a clone designated herein as "DNA66511-1563" (UNQ666).

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO1313 cDNA, wherein SEQ ID NO:41 is a clone designated herein as "DNA64966-1575" (UNQ679).

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO1570 cDNA, wherein SEQ ID NO:43 is a clone designated herein as "DNA68885-1678" (UNQ776).

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO1886 cDNA, wherein SEQ ID NO:45 is a clone designated herein as "DNA80796-2523" (UNQ870).

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO1891 cDNA, wherein SEQ ID NO:47 is a clone designated herein as "DNA76788-2526" (UNQ873).

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO4409 cDNA, wherein SEQ ID NO:49 is a clone designated herein as "DNA88004-2575" (UNQ1934).

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO5725 cDNA, wherein SEQ ID NO:51 is a clone designated herein as "DNA92265-2669" (UNQ2446).

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO5994 cDNA, wherein SEQ ID NO:53 is a clone designated herein as "DNA98591" (UNQ2506).

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO6097 cDNA, wherein SEQ ID NO:55 is a clone designated herein as "DNA107701-2711" (UNQ2545).

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO7425 cDNA, wherein SEQ ID NO:57 is a clone designated herein as "DNA108792-2753" (UNQ2966).

FIG. 58 shows the amino acid sequence (SEQ ID NO:58) derived from the coding sequence of SEQ ID NO:57 shown in FIG. 57.

FIG. 59 shows a nucleotide sequence (SEQ ID NO:59) of a native sequence PRO10102 cDNA, wherein SEQ ID NO:59 is a clone designated herein as "DNA129542-2808" (UNQ3103).

FIG. 60 shows the amino acid sequence (SEQ ID NO:60) derived from the coding sequence of SEQ ID NO:59 shown in FIG. 59.

FIG. 61 shows a nucleotide sequence (SEQ ID NO:61) of a native sequence PRO10282 cDNA, wherein SEQ ID NO:61 is a clone designated herein as "DNA148380-2827" (UNQ3126).

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO61709 cDNA, wherein SEQ ID NO:63 is a clone designated herein as "DNA347767" (UNQ14964).

FIG. 64 shows the amino acid sequence (SEQ ID NO:64) derived from the coding sequence of SEQ ID NO:63 shown in FIG. 63.

FIG. 65 shows a nucleotide sequence (SEQ ID NO:65) of a native sequence PRO779 cDNA, wherein SEQ ID NO:65 is a clone designated herein as "DNA58801-1052" (UNQ455).

FIG. 66 shows the amino acid sequence (SEQ ID NO:66) derived from the coding sequence of SEQ ID NO:65 shown in FIG. 65.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide" comprises a polypeptide having the same amino acid sequence as the corresponding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide derived from nature. Such native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides can be isolated from nature or can be produced by recombinant or synthetic means. The term "native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide" specifically encompasses naturally-occurring truncated or secreted forms of the specific PRO196, PRO217, PRO231, PRO236, PRO245, PRO246, PRO258, PRO287, PRO328, PRO344, PRO357, PRO526, PRO724, PRO731, PRO732, PRO1003, PRO104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide (e.g., an extracellular domain sequence), naturally-occurring variant forms (e.g., alternatively spliced forms) and naturally-occurring allelic variants of the polypeptide. The invention provides native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides disclosed herein which are mature or full-length native sequence polypeptides comprising the full-length amino acids sequences shown in the accompanying figures. Start and stop codons are shown in bold font and underlined in the figures. However, while the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides.

The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide "extracellular domain" or "ECD" refers to a form of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide which is essentially free of the transmembrane and cytoplasmic domains. Ordinarily, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide ECD will have less than 1% of such transmembrane and/or cytoplasmic domains and preferably, will have less than 0.5% of such domains. It will be understood that any transmembrane domains identified for the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide variant" means a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, preferably an active PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, as defined herein having at least about 80% amino acid sequence identity with a full-length native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO 10102, PRO10282, PRO61709 or PRO779 polypeptide sequence as disclosed herein, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence lacking the signal peptide as disclosed herein, an extracellular domain of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, with or without the signal peptide, as disclosed herein or any other fragment of a full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence as disclosed herein (such as those encoded by a nucleic acid that represents only a portion of the complete coding sequence for a full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide). Such PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide variants include, for instance, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides wherein one or more amino acid residues are added, or deleted, at the N- or C-terminus of the full-length native amino acid sequence. Ordinarily, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide variant will have or will have at least about 80% amino acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence as disclosed herein, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence lacking the signal peptide as disclosed herein, an extracellular domain of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, with or without the signal peptide, as disclosed herein or any other specifically defined fragment of a full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence as disclosed herein. Ordinarily, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polypeptides are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polypeptides will have no more than one conservative amino acid substitution as compared to the native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence, alternatively will have or will have no more than 2, 3, 4, 5, 6, 7, 8, 9, or 10 conservative amino acid substitution as compared to the native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence.

"Percent (%) amino acid sequence identity" with respect to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequences identified herein is defined as the percentage of amino acid residues in a candidate sequence that are identical with the amino acid residues in the specific PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below.

The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X," "Y" and "Z" each represent different hypothetical amino acid residues. Unless specifically stated otherwise, all % amino acid sequence identity values used herein are obtained as described in the immediately preceding paragraph using the ALIGN-2 computer program.

"PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polynucleotide" or "PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant nucleic acid sequence" means a nucleic acid molecule which encodes a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, preferably an active PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, as defined herein and which has at least about 80% nucleic acid sequence identity with a nucleotide acid sequence encoding a full-length native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence as disclosed herein, a full-length native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence lacking the signal peptide as disclosed herein, an extracellular domain of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, with or without the signal peptide, as disclosed herein or any other fragment of a full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence as disclosed herein (such as those encoded by a nucleic acid that represents only a portion of the complete coding sequence for a full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide). Ordinarily, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polynucleotide will have or will have at least about 80% nucleic acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence as disclosed herein, a full-length native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence lacking the signal peptide as disclosed herein, an extracellular domain of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, with or without the signal sequence, as disclosed herein or any other fragment of a full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide sequence as disclosed herein. Variants do not encompass the native nucleotide sequence.

Ordinarily, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polynucleotides are or are at least about 5 nucleotides in length, alternatively are or are at least about 6, 7, 8, 9, 10, 11, 12, 13, 14, 15, 16, 17, 18, 19, 20, 21, 22, 23, 24, 25, 26, 27, 28, 29, 3.0, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-encoding nucleic acid sequences identified herein is defined as the percentage of nucleotides in a candidate sequence that are identical with the nucleotides in the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

The invention also provides PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polynucleotides which are nucleic acid molecules that encode a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and which are capable of hybridizing, preferably under stringent hybridization and wash conditions, to nucleotide sequences encoding a full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as disclosed herein. PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polypeptides may be those that are encoded by a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant polynucleotide.

The term "full-length coding region" when used in reference to a nucleic acid encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide refers to the sequence of nucleotides which encode the full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide of the invention (which is often shown between start and stop codons, inclusive thereof, in the accompanying figures). The term "full-length coding region" when used in reference to an ATCC deposited nucleic acid refers to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-encoding portion of the cDNA that is inserted into the vector deposited with the ATCC (which is often shown between start and stop codons, inclusive thereof, in the accompanying figures).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The invention provides that the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide natural environment will not be present. Ordinarily, however, isolated polypeptide will be prepared by at least one purification step.

An "isolated" PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a proportion that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide which retain a biological and/or an immunological activity of native or naturally-occurring PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, wherein "biological" activity refers to a biological function (either inhibitory or stimulatory) caused by a native or naturally-occurring PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide other than the ability to induce the production of an antibody against an antigenic epitope possessed by a native or naturally-occurring PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and an "immunological" activity refers to the ability to induce the production of an antibody against an antigenic epitope possessed by a native or naturally-occurring PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

The term "antagonist" is used in the broadest sense [unless otherwise qualified], and includes any molecule that partially or fully blocks, inhibits, or neutralizes a biological activity of a native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide disclosed herein. In a similar manner, the term "agonist" is used in the broadest sense [unless otherwise qualified] and includes any molecule that mimics a biological activity of a native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide disclosed herein. Suitable agonist or antagonist molecules specifically include agonist or antagonist antibodies or antibody fragments, fragments or amino acid sequence variants of native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides, peptides, antisense oligonucleotides, small organic molecules, etc. Methods for identifying agonists or antagonists of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may comprise contacting a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide with a candidate agonist or antagonist molecule and measuring a detectable change in one or more biological activities normally associated with the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

"Treating" or "treatment" or "alleviation" refers to both therapeutic treatment and prophylactic or preventative measures, wherein the object is to prevent or slow down (lessen) the targeted pathologic condition or disorder. A subject in need of treatment may already have the disorder, or may be prone to have the disorder or may be in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, rodents such as rats or mice, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. Depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptide, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptide, a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The phrases "cardiovascular, endothelial and angiogenic disorder", "cardiovascular, endothelial and angiogenic dysfunction", "cardiovascular, endothelial or angiogenic disorder" and "cardiovascular, endothelial or angiogenic dysfunction" are used interchangeably and refer in part to systemic disorders that affect vessels, such as diabetes mellitus, as well as diseases of the vessels themselves, such as of the arteries, capillaries, veins, and/or lymphatics. This would include indications that stimulate angiogenesis and/or cardiovascularization, and those that inhibit angiogenesis and/or cardiovascularization. Such disorders include, for example, arterial disease, such as atherosclerosis, hypertension, inflammatory vasculitides, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, tumor angiogenesis, trauma such as wounds, burns, and other injured tissue, implant fixation, scarring, ischemia reperfusion injury, rheumatoid arthritis, cerebrovascular disease, renal diseases such as acute renal failure, or osteoporosis. This would also include angina, myocardial infarctions such as acute myocardial infarctions, cardiac hypertrophy, and heart failure such as CHF.

"Hypertrophy", as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth. Accordingly, "cardiac hypertrophy" is defined as an increase in mass of the heart, which, in adults, is characterized by an increase in myocyte cell size and contractile protein content without concomitant cell division. The character of the stress responsible for inciting the hypertrophy, (e.g., increased preload, increased afterload, loss of myocytes, as in myocardial infarction, or primary depression of contractility), appears to play a critical role in determining the nature of the response. The early stage of cardiac hypertrophy is usually characterized morphologically by increases in the size of myofibrils and mitochondria, as well as by enlargement of mitochondria and nuclei. At this stage, while muscle cells are larger than normal, cellular organization is largely preserved. At a more advanced stage of cardiac hypertrophy, there are preferential increases in the size or number of specific organelles, such as mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase "cardiac hypertrophy" is used to include all stages of the progression of this condition, characterized by various degrees of structural damage of the heart muscle, regardless of the underlying cardiac disorder. Hence, the term also includes physiological conditions instrumental in the development of cardiac hypertrophy, such as elevated blood pressure, aortic stenosis, or myocardial infarction.

"Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

"Congestive heart failure" (CHF) is a progressive pathologic state where the heart is increasingly unable to supply adequate cardiac output (the volume of blood pumped by the heart over time) to deliver the oxygenated blood to peripheral tissues. As CHF progresses, structural and hemodynamic damages occur. While these damages have a variety of manifestations, one characteristic symptom is ventricular hypertrophy. CHF is a common end result of a number of various cardiac disorders.

"Myocardial infarction" generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As a result of the increased stress or strain placed on the heart in prolonged hypertension due, for example, to the increased total peripheral resistance, cardiac hypertrophy has long been associated with "hypertension". A characteristic of the ventricle that becomes hypertrophic as a result of chronic pressure overload is an impaired diastolic performance. Fouad et al., *J. Am. Coll. Cardiol.*, 4: 1500-1506 (1984); Smith et al., *J. Am. Coll. Cardiol.*, 5: 869-874 (1985). A prolonged left ventricular relaxation has been detected in early essential hypertension, in spite of normal or supernormal systolic function. Hartford et al., *Hypertension*, 6: 329-338 (1984). However, there is no close parallelism between blood pressure levels and cardiac hypertrophy. Although improvement in left ventricular function in response to antihypertensive therapy has been reported in humans, patients variously treated with a diuretic (hydrochlorothiazide), a β-blocker (propranolol), or a calcium channel blocker (diltiazem), have shown reversal of left ventricular hypertrophy, without improvement in diastolic function. Inouye et al., *Am. J. Cardiol.*, 53: 1583-7 (1984).

Another complex cardiac disease associated with cardiac hypertrophy is "hypertrophic cardiomyopathy". This condition is characterized by a great diversity of morphologic, functional, and clinical features (Maron et al., *N. Engl. J. Med.*, 316: 780-789 (1987); Spirito et al., *N. Engl. J. Med.*, 320: 749-755 (1989); Louie and Edwards, *Prog. Cardiovasc. Dis.*, 36: 275-308 (1994); Wigle et al., *Circulation*, 92: 1680-1692 (1995)), the heterogeneity of which is accentuated by the fact that it afflicts patients of all ages. Spirito et al., *N. Engl. J. Med.*, 336: 775-785 (1997). The causative factors of hypertrophic cardiomyopathy are also diverse and little understood. In general, mutations in genes encoding sarcomeric proteins are associated with hypertrophic cardiomyopathy. Recent data suggest that β-myosin heavy chain mutations may account for approximately 30 to 40 percent of cases of familial hypertrophic cardiomyopathy. Watkins et al., *N. Engl. J. Med.*, 326: 1108-1114 (1992); Schwartz et al, *Circu-* lation, 91: 532-540 (1995); Marian and Roberts, Circulation, 92: 1336-1347 (1995); Thierfelder et al., Cell, 77:701-712 (1994); Watkins et al., Nat. Gen., 11: 434-437 (1995). Besides β-myosin heavy chain, other locations of genetic mutations include cardiac troponin T, alpha tropomyosin, cardiac myosin binding protein C, essential myosin light chain, and regulatory myosin light chain. See, Malik and Watkins, Curr. Opin. Cardiol., 12: 295-302 (1997).

Supravalvular "aortic stenosis" is an inherited vascular disorder characterized by narrowing of the ascending aorta, but other arteries, including the pulmonary arteries, may also be affected. Untreated aortic stenosis may lead to increased intracardiac pressure resulting in myocardial hypertrophy and eventually heart failure and death. The pathogenesis of this disorder is not fully understood, but hypertrophy and possibly hyperplasia of medial smooth muscle are prominent features of this disorder. It has been reported that molecular variants of the elastin gene are involved in the development and pathogenesis of aortic stenosis. U.S. Pat. No. 5,650,282 issued Jul. 22, 1997.

"Valvular regurgitation" occurs as a result of heart diseases resulting in disorders of the cardiac valves. Various diseases, like rheumatic fever, can cause the shrinking or pulling apart of the valve orifice, while other diseases may result in endocarditis, an inflammation of the endocardium or lining membrane of the atrioventricular orifices and operation of the heart. Defects such as the narrowing of the valve stenosis or the defective closing of the valve result in an accumulation of blood in the heart cavity or regurgitation of blood past the valve. If uncorrected, prolonged valvular stenosis or insufficiency may result in cardiac hypertrophy and associated damage to the heart muscle, which may eventually necessitate valve replacement.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, include systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, or transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis, juvenile rheumatoid arthritis, osteoarthritis, psoriatic arthritis, and ankylosing spondylitis), psoriasis, dermatitis including atopic dermatitis; chronic idiopathic urticaria, including chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), and IBD with co-segregate of pyoderma gangrenosum, erythema nodosum, primary sclerosing cholangitis, and/or episcleritis), respiratory distress syndrome, including adult respiratory distress syndrome (ARDS), meningitis, IgE-mediated diseases such as anaphylaxis and allergic rhinitis, encephalitis such as Rasmussen's encephalitis, uveitis, colitis such as microscopic colitis and collagenous colitis, glomerulonephritis (GN) such as membranous GN, idiopathic membranous GN, membranous proliferative GN (MPGN), including Type I and Type II, and rapidly progressive GN, allergic conditions, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, lupus (including nephritis, cerebritis, pediatric, non-renal, discoid, alopecia), juvenile onset diabetes, multiple sclerosis (MS) such as spino-optical MS, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including Large Vessel vasculitis (including Polymyalgia Rheumatica and Giant Cell (Takayasu's) Arteritis), Medium Vessel vasculitis (including Kawasaki's Disease and Polyarteritis Nodosa), CNS vasculitis, and ANCA-associated vasculitis, such as Churg-Strauss vasculitis or syndrome (CSS)), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, and rejection arising from renal transplantation, liver transplantation, intestinal transplantation, cardiac transplantation, etc.), graft versus host disease (GVHD), pemphigoid bullous, pemphigus (including vulgaris, foliaceus, and pemphigus mucus-membrane pemphigoid), autoimmune polyendocrinopathies, Reiter's disease, stiff-man syndrome, immune complex nephritis, IgM polyneuropathies or IgM mediated neuropathy, idiopathic thrombocytopenic purpura (ITP), thrombotic throbocytopenic purpura (TTP), thrombocytopenia (as developed by myocardial infarction patients, for example), including autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM), including pediatric IDDM, and Sheehan's syndrome; autoimmune hepatitis, Lymphoid interstitial pneumonitis (HIV), bronchiolitis obliterans (non-transplant) vs NSIP, Guillain-Barré Syndrome, Berger's Disease (IgA nephropathy), primary biliary cirrhosis, celiac sprue (gluten enteropathy), refractory sprue with co-segregate dermatitis herpetiformis, cryoglobulinemia, amylotrophic lateral sclerosis (ALS; Lou Gehrig's disease), coronary artery disease, autoimmune inner ear disease (AIED), autoimmune hearing loss, opsoclonus myoclonus syndrome (OMS), polychondritis such as refractory polychondritis, pulmonary alveolar proteinosis, amyloidosis, giant cell hepatitis, scleritis, monoclonal gammopathy of uncertain/unknown significance (MGUS), peripheral neuropathy, paraneoplastic syndrome, channelopathies such as epilepsy, migraine, arrhythmia, muscular disorders, deafness, blindness, periodic paralysis, and channelopathies of the CNS; autism, inflammatory myopathy, and focal segmental glomerulosclerosis (FSGS).

The phrase "anxiety related disorders" refers to disorders of anxiety, mood, and substance abuse, including but not limited to: depression, generalized anxiety disorders, attention deficit disorder, sleep disorder, hyperactivity disorder, obsessive compulsive disorder, schizophrenia, cognitive disorders, hyperalgesia and sensory disorders. Such disorders include the mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

The term "lipid metabolic disorder" refers to abnormal clinical chemistry levels of cholesterol and triglycerides, wherein elevated levels of these lipids is an indication for atherosclerosis. Additionally, abnormal serum lipid levels may be an indication of various cardiovascular diseases including hypertension, stroke, coronary artery diseases, diabetes and/or obesity.

The phrase "eye abnormality" refers to such potential disorders of the eye as they may be related to atherosclerosis or various opthalmological abnormalities. Such disorders include but are not limited to the following: retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis. Cataracts are also considered an eye abnormality and are associated with such systemic diseases as: Human Down's syndrome, Hallerman-Streiff syndrome, Lowe syndrome, galactosemia, Marfan syndrome, Trismoy 13-15 condition, Alport syndrome, myotonic dystrophy, Fabry disease, hypothroidisms, or Conradi syndrome. Other ocular developmental anomalies include: Aniridia, anterior segment and dysgenesis syndrome. Cataracts may also occur as a result of an intraocular infection or inflammation (uveitis).

A "growth inhibitory amount" of an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptide or PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding organic molecule is an amount capable of inhibiting the growth of a cell, especially tumor, e.g., cancer cell, either in vitro or in vivo. A "growth inhibitory amount" of an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptide or PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding organic molecule for purposes of inhibiting neoplastic cell growth may be determined empirically and in a routine manner.

A "cytotoxic amount" of an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptide or PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding organic molecule is an amount capable of causing the destruction of a cell, especially tumor, e.g., cancer cell, either in vitro or in vivo. A "cytotoxic amount" of an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptide or PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding organic molecule for purposes of inhibiting neoplastic cell growth may be determined empirically and in a routine manner.

The term "antibody" is used in the broadest sense and specifically covers, for example, single anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody monoclonal antibodies (including agonist, antagonist, and neutralizing antibodies), anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody compositions with polyepitopic specificity, polyclonal antibodies, single chain anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies, and fragments of anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti- PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The invention provides that the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and a classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptide" is an oligopeptide that binds, preferably specifically, to a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as described herein. PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptides may be chemically synthesized using known oligopeptide synthesis methodology or may be prepared and purified using recombinant technology. PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptides usually are or are at least about 5 amino acids in length, alternatively are or are at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as described herein. PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708, 871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988); Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

A "PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding organic molecule" is an organic molecule other than an oligopeptide or antibody as defined herein that binds, preferably specifically, to a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as described herein. PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding organic molecules may be identified and chemically synthesized using known methodology (see, e.g., PCT Publication Nos. WO00/00823 and WO00/39585). PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding organic molecules are usually less than about 2000 daltons in size, alternatively less than about 1500, 750, 500, 250 or 200 daltons in size, wherein such organic molecules that are capable of binding, preferably specifically, to a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is preferably useful as a diagnostic and/or therapeutic agent in targeting a cell or tissue expressing the antigen, and does not significantly cross-react with other proteins. The extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. The term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a "PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779" or a "growth inhibitory" antibody, oligopeptide or other organic molecule is one which results in measurable growth inhibition of cancer cells expressing or overexpressing the appropriate PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may be a transmembrane polypeptide expressed on the surface of a cancer cell or may be a polypeptide that is produced and secreted by a cancer cell. Preferred growth inhibitory anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies, oligopeptides or organic molecules inhibit growth of PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-expressing tumor cells by or by greater than 20%, preferably from about 20% to about 50%, and even more preferably, by or by greater than 50% (e.g., from about 50% to about 100%) as compared to the appropriate control, the control typically being tumor cells not treated with the antibody, oligopeptide or other organic molecule being tested. Growth inhibition can be measured at an antibody concentration of about 0.1 to 30 µg/ml or about 0.5 nM to 200 nM in cell culture, where the growth inhibition is determined 1-10 days after exposure of the tumor cells to the antibody. Growth inhibition of tumor cells in vivo can be determined in various ways. The antibody is growth inhibitory in vivo if administration of the anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody at about 1 µg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in or in about 2 to 50 fold, preferably in or in about 5 to 50 fold, and most preferably in or in about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. U.S.A.* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD). Preferably, the cancer comprises a tumor that expresses an IGF receptor, more preferably breast cancer, lung cancer, colorectal cancer, or prostate cancer, and most preferably breast or prostate cancer.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma 1I and calicheamicin omegaI1 (see, e.g., Agnew, *Chem. Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, alburnin-engineered nanoparticle formulation of paclitaxel (American Pharmaceutical Partners, Schaumberg, Ill.), and TAXOTERE® doxetaxel (Rhône—Poulenc Rorer, Antony, France); chlorambucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The terms "cell proliferative disorder" and "proliferative disorder" refer to disorders that are associated with some degree of abnormal cell proliferation. In one aspect of the invention, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, preferably a cell that overexpresses a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as compared to a normal cell of the same tissue type. The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may be a transmembrane polypeptide expressed on the surface of a cancer cell or may be a polypeptide that is produced and secreted by a cancer cell. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

As used herein, the term "immunoadhesion" designates antibody-like molecules which combine the binding specificity of a heterologous protein (an "adhesion") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesion part of an immunoadhesion molecule typically is a contiguous amino acid sequence comprising at least the binding site of a receptor or a ligand. The immunoglobulin constant domain sequence in the immunoadhesion may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

"Replication-preventing agent" is an agent wherein replication, function, and/or growth of the cells is inhibited or prevented, or cells are destroyed, no matter what the mechanism, such as by apoptosis, angiostasis, cytosis, tumoricide, mytosis inhibition, blocking cell cycle progression, arresting cell growth, binding to tumors, acting as cellular mediators, etc. Such agents include a chemotherapeutic agent, cytotoxic agent, cytokine, growth-inhibitory agent, or anti-hormonal agent, e.g., an anti-estrogen compound such as tamoxifen, an anti-progesterone such as onapristone (see, EP 616 812); or an anti-androgen such as flutamide, as well as aromidase inhibitors, or a hormonal agent such as an androgen.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

Preferred cytotoxic agents herein for the specific tumor types to use in combination with the antagonists herein are as follows:

1. Prostate cancer: androgens, docetaxel, paclitaxel, estramustine, doxorubicin, mitoxantrone, antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive), AVASTIN™ anti-vascular endothelial growth factor (VEGF), TARCEVA™ OSI-774 (erlotinib) (Genenetech and OSI Pharmaceuticals), or other epidermal growth factor receptor tyrosine kinase inhibitors (EGFR TKI's).
2. Stomach cancer: 5-fluorouracil (5FU), XELODA™ capecitabine, methotrexate, etoposide, cisplatin/carboplatin, pacliitaxel, docetaxel, gemcitabine, doxorubicin, and CPT-11 (camptothecin-11; irinotecan, USA Brand Name: CAMPTOSAR®).
3. Pancreatic cancer: gemcitabine, 5FU, XELODA™ capecitabine, CPT-11, docetaxel, paclitaxel, cisplatin, carboplatin, TARCEVA™ erlotinib, and other EGFR TKI's.
4. Colorectal cancer: 5FU, XELODA™ capecitabine, CPT-11, oxaliplatin, AVASTIN™ anti-VEGF, TARCEVA™ erlotinib and other EGFR TKI's, and ERBITUX™ (formerly known as IMC-C225) human: murine-chimerized monoclonal antibody that binds to EGFR and blocks the ability of EGF to initiate receptor activation and signaling to the tumor.
5. Renal cancer: IL-2, interferon alpha, AVASTIN™ anti-VEGF, MEGACE™ (Megestrol acetate) progestin, vinblastine, TARCEVA™ erlotinib, and other EGFR TKI's.

A "growth inhibitory agent" when used herein refers to a compound or composition which inhibits growth of a cell, especially a PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-expressing cancer cell, either in vitro or in vivo. Thus, the growth inhibitory agent may be one which significantly reduces the percentage of PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

The term "gene" refers to (a) a gene containing at least one of the DNA sequences disclosed herein; (b) any DNA sequence that encodes the amino acid sequence encoded by the DNA sequences disclosed herein and/or; ©) any DNA sequence that hybridizes to the complement of the coding sequences disclosed herein. Preferably, the term includes coding as well as noncoding regions, and preferably includes all sequences necessary for normal gene expression.

The term "gene targeting" refers to a type of homologous recombination that occurs when a fragment of genomic DNA is introduced into a mammalian cell and that fragment locates and recombines with endogenous homologous sequences.

Gene targeting by homologous recombination employs recombinant DNA technologies to replace specific genomic sequences with exogenous DNA of particular design.

The term "homologous recombination" refers to the exchange of DNA fragments between two DNA molecules or chromatics at the site of homologous nucleotide sequences.

The term "target gene" (alternatively referred to as "target gene sequence" or "target DNA sequence") refers to any nucleic acid molecule, polynucleotide, or gene to be modified by homologous recombination. The target sequence includes an intact gene, an exon or intron, a regulatory sequence or any region between genes. The target gene my comprise a portion of a particular gene or genetic locus in the individual's genomic DNA.

"Disruption" of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene occurs when a fragment of genomic DNA locates and recombines with an endogenous homologous sequence wherein the disruption is a deletion of the native gene or a portion thereof, or a mutation in the native gene or wherein the disruption is the functional inactivation of the native gene. Alternatively, sequence disruptions may be generated by nonspecific insertional inactivation using a gene trap vector (i.e. non-human transgenic animals containing and expressing a randomly inserted transgene; see for example U.S. Pat. No. 6,436,707 issued Aug. 20, 2002). These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter the normal gene product by inhibiting its production partially or completely or by enhancing the normal gene product's activity. Preferably, the disruption is a null disruption, wherein there is no significant expression of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene.

The term "native expression" refers to the expression of the full-length polypeptide encoded by the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene, at expression levels present in the wild-type mouse. Thus, a disruption in which there is "no native expression" of the endogenous PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene refers to a partial or complete reduction of the expression of at least a portion of a polypeptide encoded by an endogenous PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene of a single cell, selected cells, or all of the cells of a mammal.

The term "knockout" refers to the disruption of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene wherein the disruption results in: the functional inactivation of the native gene; the deletion of the native gene or a portion thereof; or a mutation in the native gene.

The term "knock-in" refers to the replacement of the mouse ortholog (or other mouse gene) with a human cDNA encoding any of the specific human PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-encoding genes or variants thereof (ie. the disruption results in a replacement of a native mouse gene with a native human gene).

The term "construct" or "targeting construct" refers to an artificially assembled DNA segment to be transferred into a target tissue, cell line or animal. Typically, the targeting construct will include a gene or a nucleic acid sequence of particular interest, a marker gene and appropriate control sequences. As provided herein, the targeting construct comprises a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 targeting construct. A "PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 targeting construct" includes a DNA sequence homologous to at least one portion of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene and is capable of producing a disruption in a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene in a host cell.

The term "transgenic cell" refers to a cell containing within its genome a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene that has been disrupted, modified, altered, or replaced completely or partially by the method of gene targeting.

The term "transgenic animal" refers to an animal that contains within its genome a specific gene that has been disrupted or otherwise modified or mutated by the methods described herein or methods otherwise well known in the art. Preferably the non-human transgenic animal is a mammal. More preferably, the mammal is a rodent such as a rat or mouse. In addition, a "transgenic animal" may be a heterozygous animal (i.e., one defective allele and one wild-type allele) or a homozygous animal (i.e., two defective alleles). An embryo is considered to fall within the definition of an animal. The provision of an animal includes the provision of an embryo or foetus in utero, whether by mating or otherwise, and whether or not the embryo goes to term.

As used herein, the terms "selective marker" and position selection marker" refer to a gene encoding a product that enables only the cells that carry the gene to survive and/or grow under certain conditions. For example, plant and animal cells that express the introduced neomycin resistance (Neo$^r$) gene are resistant to the compound G418. Cells that do not carry the Neo$^r$ gene marker are killed by G418. Other positive selection markers are known to, or are within the purview of, those of ordinary skill in the art.

The term "modulates" or "modulation" as used herein refers to the decrease, inhibition, reduction, amelioration, increase or enhancement of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene function, expression, activity, or alternatively a phenotype associated with PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene.

The term "ameliorates" or "amelioration" as used herein refers to a decrease, reduction or elimination of a condition, disease, disorder, or phenotype, including an abnormality or symptom.

The term "abnormality" refers to any disease, disorder, condition, or phenotype in which PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 is implicated, including pathological conditions and behavioral observations.

TABLE 2

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| PRO | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| PRO-DNA | NNNNNNNNNNNN | (Length = 12 nucleotides) |
|---|---|---|
| Comparison DNA | NNNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO196, PRO217, PRO231, PRO236, PRO245, PRO246, PRO258. PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO0102, PRO10282, PRO61709 or PRO779 Polypeptides The present invention provides newly identified and isolated nucleotide sequences encoding polypeptides referred to in the present application as PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides. In particular, cDNAs encoding various PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides and encoding nucleic acids described herein, Applicants have identified what is believed to be the reading frame best identifiable with the sequence information available at the time.

B. PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 Polypeptide Variants In addition to the full-length native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides described herein, it is contemplated that PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variants can be prepared. PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variants can be prepared by introducing appropriate nucleotide changes into the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 DNA, and/or by synthesis of the desired PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Those skilled in the art will appreciate that amino acid changes may alter post-translational processes of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, such as changing the number or position of glycosylation sites or altering the membrane anchoring characteristics.

Variations in the native full-length sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or in various domains of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide that results in a change in the amino acid sequence of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as compared with the native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Optionally the variation is by substitution of at least one amino acid with any other amino acid in one or more of the domains of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Guidance in determining which amino acid residue may be inserted, substituted or deleted without adversely affecting the desired activity may be found by comparing the sequence of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 fragments may be prepared by any of a number of conventional techniques. Desired peptide fragments may be chemically synthesized. An alternative approach involves generating PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide fragments share at least one biological and/or immunological activity with the native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide disclosed herein.

Conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are preferably introduced and the products screened.

TABLE 6

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isometric amino acid can be used.

C. Modifications of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 Polypeptides Covalent modifications of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides are included within the scope of this invention. One type of covalent modification includes reacting targeted amino acid residues of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide with an organic derivatizing agent that is capable of reacting with selected side chains or the N- or C-terminal residues of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Derivatization with bifunctional agents is useful, for instance, for crosslinking PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides to a water-insoluble support matrix or surface for use in the method for purifying anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide included within the scope of this invention comprises altering the native glycosylation pattern of the polypeptide. "Altering the native glycosylation pattern" is intended for purposes herein to mean deleting one or more carbohydrate moieties found in native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides (either by removing the underlying glycosylation site or by deleting the glycosylation by chemical and/or enzymatic means), and/or adding one or more glycosylation sites that are not present in the native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. In addition, the phrase includes qualitative changes in the glycosylation of the native proteins, involving a change in the nature and proportions of the various carbohydrate moieties present.

Addition of glycosylation sites to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may be accomplished by altering the amino acid sequence. The alteration may be made, for example, by the addition of, or substitution by, one or more serine or threonine residues to the native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO 10102, PRO10282, PRO61709 or PRO779 (for O-linked glycosylation sites). The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 amino acid sequence may optionally be altered through changes at the DNA level, particularly by mutating the DNA encoding the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO 10102, PRO10282, PRO61709 or PRO779 polypeptide at preselected bases such that codons are generated that will translate into the desired amino acids.

Another means of increasing the number of carbohydrate moieties on the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides comprises linking the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides of the present invention may also be modified in a way to form a chimeric molecule comprising the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide fused to another, heterologous polypeptide or amino acid sequence.

Such a chimeric molecule comprises a fusion of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide with a tag polypeptide which provides an epitope to which an anti-tag antibody can selectively bind. The epitope tag is generally placed at the amino- or carboxyl-terminus of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. The presence of such epitope-tagged forms of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide can be detected using an antibody against the tag polypeptide. Also, provision of the epitope tag enables the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide to be readily purified by affinity purification using an anti-tag antibody or another type of affinity matrix that binds to the epitope tag. Various tag polypeptides and their respective antibodies are well known in the art. Examples include polyhistidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

The chimeric molecule may comprise a fusion of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide in place of at least one variable region within an Ig molecule. In a particularly preferred aspect of the invention, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 Polypeptides The description below relates primarily to production of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides by culturing cells transformed or transfected with a vector containing PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 nucleic acid. It is, of course, contemplated that alternative methods, which are well known in the art, may be employed to prepare PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides. For instance, the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may be chemically synthesized separately and combined using chemical or enzymatic methods to produce the full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

1. Isolation of DNA Encoding PRO196, PRO217, PRO231. PRO236, PRO245, PRO246, PRO258, PRO287, PRO328, PRO344, PRO357, PRO526, PRO724, PRO731, PRO732. PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 Polypeptides DNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides may be obtained from a cDNA library prepared from tissue believed to possess the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 mRNA and to express it at a detectable level. Accordingly, human PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-DNA can be conveniently obtained from a cDNA library prepared from human tissue, such as described in the Examples. The PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-encoding gene may also be obtained from a genomic library or by known synthetic procedures (e.g., automated nucleic acid synthesis).

Libraries can be screened with probes (such as antibodies to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac) 169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112: 284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO 10102, PRO10282, PRO61709 or PRO779 polypeptides are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/−DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides.

Still other methods, vectors, and host cells suitable for adaptation to the synthesis of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or against a synthetic peptide based on the DNA sequences provided herein or against exogenous sequence fused to PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 DNA and encoding a specific antibody epitope.

5. Purification of Polypeptide

Forms of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides may be recovered from culture medium or from host cell lysates. If membrane-bound, it can be released from the membrane using a suitable detergent solution (e.g. Triton-X 100) or by enzymatic cleavage. Cells employed in expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides can be disrupted by various physical or chemical means, such as freeze-thaw cycling, sonication, mechanical disruption, or cell lysing agents.

It may be desired to purify PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide produced.

E. Uses for PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 Polypeptides Nucleotide sequences (or their complement) encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides have various applications in the art of molecular biology, including uses as hybridization probes, in chromosome and gene mapping and in the generation of anti-sense RNA and DNA. PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 nucleic acid will also be useful for the preparation of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides by the recombinant techniques described herein.

The full-length native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene, or portions thereof, may be used as hybridization probes for a cDNA library to isolate the full-length PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 cDNA or to isolate still other cDNAs (for instance, those encoding naturally-occurring variants of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides or PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides from other species) which have a desired sequence identity to the native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779. By way of example, a screening method will comprise isolating the coding region of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene using the known DNA sequence to synthesize a selected probe of about 40 bases. Hybridization probes may be labeled by a variety of labels, including radionucleotides such as $^{32}$P or $^{35}$S, or enzymatic labels such as alkaline phosphatase coupled to the probe via avidin/biotin coupling systems. Labeled probes having a sequence complementary to that of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 nucleic acids include antisense or sense oligonucleotides comprising a singe-stranded nucleic acid sequence (either RNA or DNA) capable of binding to target PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 mRNA (sense) or PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 DNA (antisense) sequences. Antisense or sense oligonucleotides, according to the present invention, comprise a fragment of the coding region of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 coding sequences.

Nucleotide sequences encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide can also be used to construct hybridization probes for mapping the gene which encodes that PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 encode a protein which binds to another protein (for example, where the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 is a receptor), the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 can be used to isolate correlative ligand(s). Screening assays can be designed to find lead compounds that mimic the biological activity of a native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or a receptor for PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. The invention provides cDNA encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide which can be used to clone genomic DNA encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide in accordance with established techniques and the genomic sequences used to generate transgenic animals that contain cells which express DNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides. Any technique known in the art may be used to introduce a target gene transgene into animals to produce the founder lines of transgenic animals. Such techniques include, but are not limited to pronuclear microinjection (U.S. Pat. Nos. 4,873,191, 4,736,866 and 4,870,009); retrovirus mediated gene transfer into germ lines (Van der Putten, et al., *Proc. Natl. Acad. Sci., USA,* 82:6148-6152 (1985)); gene targeting in embryonic stem cells (Thompson, et al., *Cell* 56:313-321 (1989)); nonspecific insertional inactivation using a gene trap vector (U.S. Pat. No. 6,436,707); electroporation of embryos (Lo, *Mol. Cell. Biol.,* 3:1803-1814 (1983)); and sperm-mediated gene transfer (Lavitrano, et al., *Cell,* 57:717-723 (1989)); etc. Typically, particular cells would be targeted for a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 transgene incorporation with tissue-specific enhancers. Transgenic animals that include a copy of a transgene encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide introduced into the germ line of the animal at an embryonic stage can be used to examine the effect of increased expression of DNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition. Alternatively, non-human homologues of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides can be used to construct a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 "knock out" animal which has a defective or altered gene encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 proteins as a result of homologous recombination between the endogenous gene encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides and altered genomic DNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides introduced into an embryonic stem cell of the animal. Preferably the knock out animal is a mammal. More preferably, the mammal is a rodent such as a rat or mouse. For example, cDNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides can be used to clone genomic DNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides in accordance with established techniques. A portion of the genomic DNA encoding the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the gene encoding the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

In addition, knockout mice can be highly informative in the discovery of gene function and pharmaceutical utility for a drug target, as well as in the determination of the potential on-target side effects associated with a given target. Gene function and physiology are so well conserved between mice and humans, since they are both mammals and contain similar numbers of genes, which are highly conserved between the species. It has recently been well documented, for example, that 98% of genes on mouse chromosome 16 have a human ortholog (Mural et al., *Science* 296:1661-71 (2002)).

Although gene targeting in embryonic stem (ES) cells has enabled the construction of mice with null mutations in many genes associated with human disease, not all genetic diseases are attributable to null mutations. One can design valuable mouse models of human diseases by establishing a method for gene replacement (knock-in) which will disrupt the mouse locus and introduce a human counterpart with mutation, Subsequently one can conduct in vivo drug studies targeting the human protein (Kitamoto et. Al., *Biochemical and Biophysical Res. Commun.,* 222:742-47 (1996)).

Nucleic acid encoding the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides described herein may also be employed as molecular weight markers for protein electrophoresis purposes and the isolated nucleic acid sequences may be used for recombinantly expressing those markers.

The nucleic acid molecules encoding the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides or fragments thereof described herein are useful for chromosome identification. In this regard, there exists an ongoing need to identify new chromosome markers, since relatively few chromosome marking reagents, based upon actual sequence data are presently available. Each PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 nucleic acid molecule of the present invention can be used as a chromosome marker.

The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides and nucleic acid molecules of the present invention may also be used diagnostically for tissue typing, wherein the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides of the present invention may be differentially expressed in one tissue as compared to another, preferably in a diseased tissue as compared to a normal tissue of the same tissue type. PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 nucleic acid molecules will find use for generating probes for PCR, Northern analysis, Southern analysis and Western analysis.

The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides described herein may also be employed as therapeutic agents. The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides of the present invention can be formulated according to known methods to prepare pharmaceutically useful compositions, whereby the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide is desired in a formulation with release characteristics suitable for the treatment of any disease or disorder requiring administration of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, microencapsulation of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide (agonists) or prevent the effect of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide (antagonists). Agonists that mimic a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide would be especially valuable therapeutically in those instances where a negative phenotype is observed based on findings with the non-human transgenic animal whose genome comprises a disruption of the gene which encodes for the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Antagonists that prevent the effects of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide would be especially valuable therapeutically in those instances where a positive phenotype is observed based upon observations with the non-human transgenic knockout animal. Screening assays for antagonist drug candidates are designed to identify compounds that bind or complex with the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide encoded by the genes identified herein, or otherwise interfere with the interaction of the encoded polypeptide with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide encoded by a nucleic acid identified herein under conditions and for a time sufficient to allow these two components to interact.

In binding assays, the interaction is binding and the complex formed can be isolated or detected in the reaction mixture. The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and drying. Alternatively, an immobilized antibody, e.g., a monoclonal antibody, specific for the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for α-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may be added to a cell along with the compound to be screened for a particular activity and the ability of the compound to inhibit the activity of interest in the presence of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide indicates that the compound is an antagonist to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Alternatively, antagonists may be detected by combining the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and a potential antagonist with membrane-bound PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide receptors or recombinant receptors under appropriate conditions for a competitive inhibition assay. The PRO196, PRO217, PRO231, PRO236, PRO245, PRO246, PRO258, PRO287, PRO328, PRO344, PRO357, PRO526, PRO724, PRO731, PRO732, PRO1063, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide can be labeled, such as by radioactivity, such that the number of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and a cDNA library created from this RNA is divided into pools and used to transfect COS cells or other cells that are not responsive to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Transfected cells that are grown on glass slides are exposed to labeled PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, the labeled PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

Another approach in assessing the effect of an antagonist to a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, would be administering a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 antagonist to a wild-type mouse in order to mimic a known knockout phenotype. Thus, one would initially knockout the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene of interest and observe the resultant phenotype as a consequence of knocking out or disrupting the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene. Subsequently, one could then assess the effectiveness of an antagonist to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide by administering an antagonist to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide to a wild-type mouse. An effective antagonist would be expected to mimic the phenotypic effect that was initially observed in the knockout animal.

Likewise, one could assess the effect of an agonist to a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, by administering a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 agonist to a non-human transgenic mouse in order to ameliorate a known negative knockout phenotype. Thus, one would initially knockout the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 gene of interest and observe the resultant phenotype as a consequence of knocking out or disrupting the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO525, PRO5994, PRO6097, PRO7425, PRO10102, PRO10282, PRO61709 or PRO779 gene. Subsequently, one could then assess the effectiveness of an agonist to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide by administering an agonist to the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide to a the non-human transgenic mouse. An effective agonist would be expected to ameliorate the negative phenotypic effect that was initially observed in the knockout animal.

In another assay for antagonists, mammalian cells or a membrane preparation expressing the receptor would be incubated with a labeled PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide in the presence of the candidate compound. The ability of the compound to enhance or block this interaction could then be measured.

More specific examples of potential antagonists include an oligonucleotide that binds to the fusions of immunoglobulin with the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide that recognizes the receptor but imparts no effect, thereby competitively inhibiting the action of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

Another potential PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. The antisense RNA oligonucleotide hybridizes to the mRNA in vivo and blocks translation of the mRNA molecule into the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, thereby blocking the normal biological activity of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO196, Anti-PRO217, Anti-PRO231, Anti-PRO236, Anti-PRO245, Anti-PRO246, Anti-PRO258. Anti-PRO287, Anti-PRO328, Anti-PRO344, Anti-PRO357, Anti-PRO526, Anti-PRO724, Anti-PRO731 Anti-PRO732, Anti-PRO1003, Anti-PRO1104, Anti-PRO1151, Anti-PRO1244, Anti-PRO1298, Anti-PRO1313, Anti-PRO1570, Anti-PRO1886. Anti-PRO1891, Anti-PRO4409, Anti-PRO5725, Anti-PRO5994, Anti-PRO6097, Anti-PRO7425, Anti-PRO10102, Anti-PRO10282, Anti-PRO61709 or Anti-PRO779 Antibodies The present invention provides anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130: 151-188 (1992).

Monoclonal antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. The antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 protein as described herein. Other such antibodies may combine a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 binding site with a binding site for another protein. Alternatively, an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-expressing cell. Bispecific antibodies may also be used to localize cytotoxic agents to cells which express a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide. These antibodies possess a PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificity (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

The invention provides bispecific antibodies which are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175:

217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et-al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH—CH1-flexible linker-VH—CH1-Fc region chain; or VH—CH1-VH—CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

The invention provides an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody (full length or fragments) which is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK—BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-PRO196, Anti-PRO217, Anti-PRO231, Anti-PRO236, Anti-PRO245, Anti-PRO246. Anti-PRO258, Anti-PRO287, Anti-PRO328, Anti-PRO344, Anti-PRO357, Anti-PRO526. Anti-PRO724, Anti-PRO731, Anti-PRO732, Anti-PRO1003, Anti-PRO1104, Anti-PRO1151, Anti-PRO1244, Anti-PRO1298, Anti-PRO1313, Anti-PRO1570, Anti-PRO1886, Anti-PRO1891. Anti-PRO4409, Anti-PRO5725, Anti-PRO5994, Anti-PRO6097, Anti-PRO7425, Anti-PRO10102, Anti-PRO10282, Anti-PRO61709 or Anti-PRO779 Antibody-Maytansinoid Conjugates (Immunoconjugates)

Anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody-maytansinoid conjugates are prepared by chemically linking an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. The linkage is formed at the C-3 position of maytansinol or a maytansinol analogue.
Calicheamicin Another immunoconjugate of interest comprises an anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$, (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.
Other Cytotoxic Agents Other antitumor agents that can be conjugated to the anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The invention provides that the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

11. Pharmaceutical Compositions of Antibodies

Antibodies specifically binding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide identified herein, as well as other molecules identified by the screening assays disclosed hereinbefore, can be administered for the treatment of various disorders in the form of pharmaceutical compositions.

If the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO196, Anti-PRO217, Anti-PRO231, Anti-PRO236, Anti-PRO245, Anti-PRO246, Anti-PRO258, Anti-PRO287, Anti-PRO328, Anti-PRO344, Anti-PRO357, Anti-PRO526. Anti-PRO724, Anti-PRO731, Anti-PRO732, Anti-PRO1003, Anti-PRO1104, Anti-PRO1151, Anti-PRO1244, Anti-PRO1298, Anti-PRO1313. Anti-PRO1570, Anti-PRO1886, Anti-PRO1891, Anti-PRO4409, Anti-PRO5725, Anti-PRO5994, Anti-PRO6097, Anti-PRO7425, Anti-PRO10102, Anti-PRO10282, Anti-PRO61709 or Anti-PRO779 Antibodies The anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies of the invention have various therapeutic and/or diagnostic utilities for a neurological disorder; a cardiovascular, endothelial or angiogenic disorder; an immunological disorder; an oncological disorder; an embryonic developmental disorder or lethality, or a metabolic abnormality. For example, anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies may be used in diagnostic assays for PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies also are useful for the affinity purification of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides from recombinant cell culture or natural sources. In this process, the antibodies against PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides are immobilized on a suitable support, such a Sephadex resin or filter paper, using methods well known in the art. The immobilized antibody then is contacted with a sample containing the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide to be purified, and thereafter the support is washed with a suitable solvent that will remove substantially all the material in the sample except the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, which is bound to the immobilized antibody. Finally, the support is washed with another suitable solvent that will release the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology*, 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253: 1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI Tinkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, Tinkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL$^+$, SUC$^+$, GAL$^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4-p) or the complex formation of these proteins may also be preferably employed in combination with the amylase-expressing yeast.

Transformation was performed based on the protocol outlined by Gietz et al., *Nucl. Acid. Res.*, 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 mil, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol. <10 μl) in microfuge tubes. The mixture was mixed briefly by vortexing, then 40% PEG/TE (600 μl, 40% polyethylene glycol-4000, mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.*, 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTP's (Perkin Elmer-Cetus); 2.5 μl Kentaq buffer (Clontech); 0.25 μl forward oligo 1; 0.25 μl reverse oligo 2; 12.5 μl distilled water. The sequence of the forward oligonucleotide 1 was:

(SEQ ID NO: 67)
5'-TGTAAAACGACGGCCAGTTAAATAGACCTGCAATTATTAATCT-3'

The sequence of reverse oligonucleotide 2 was:

(SEQ ID NO: 68)
5'-CAGGAAACAGCTATGACCACCTGCACACCTGCAAATCCATT-3'

PCR was then performed as follows:

| a. | | Denature | 92° C., 5 minutes |
|---|---|---|---|
| b. | 3 cycles of: | Denature | 92° C., 30 seconds |
| | | Anneal | 59° C., 30 seconds |
| | | Extend | 72° C., 60 seconds |
| c. | 3 cycles of: | Denature | 92° C., 30 seconds |
| | | Anneal | 57° C., 30 seconds |
| | | Extend | 72° C., 60 seconds |
| d. | 25 cycles of: | Denature | 92° C., 30 seconds |
| | | Anneal | 55° C., 30 seconds |
| | | Extend | 72° C., 60 seconds |
| e. | | Hold | 4° C. |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Using the techniques described in Examples 1 to 3 above, numerous full-length cDNA clones were identified as encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO151, PRO1244, PRO1298, PRO1313, PRO1570, PRO1886, PRO1891, PRO4409, PRO5725, PRO6097, PRO7425, PRO10102, PRO10282, or PRO779 polypeptides as disclosed herein. These cDNAs were then deposited under the terms of the Budapest Treaty with the American Type Culture Collection, 10801 University Blvd., Manassas, Va. 20110-2209, USA (ATCC) as shown in Table 7 below. In addition, the sequence of DNA98591 encoding PRO5994 polypeptides was identified from GenBank accession no.: AF048700; the sequence of DNA347767 encoding PRO61709 polypeptides was identified from GenBank accession no.: AB029000.

TABLE 7

| Material | ATCC Dep. No. | Deposit Date |
|---|---|---|
| DNA22779-1130 | 209280 | Sep. 18, 1997 |
| DNA33094-1131 | 209256 | Sep. 16, 1997 |
| DNA34434-1139 | 209252 | Sep. 16, 1997 |
| DNA35599-1168 | 209373 | Oct. 16, 1997 |
| DNA35638-1141 | 209265 | Sep. 16, 1997 |
| DNA35639-1172 | 209396 | Oct. 17, 1997 |
| DNA35918-1174 | 209402 | Oct. 17, 1997 |
| DNA39969-1185 | 209400 | Oct. 17, 1997 |
| DNA40587-1231 | 209438 | Nov. 7, 1997 |
| DNA40592-1242 | 209492 | Nov. 21, 1997 |
| DNA44804-1248 | 209527 | Dec. 10, 1997 |
| DNA44184-1319 | 209704 | Mar. 26, 1998 |
| DNA49631-1328 | 209806 | Apr. 28, 1998 |
| DNA48331-1329 | 209715 | Mar. 31, 1998 |
| DNA48334-1435 | 209924 | Jun. 2, 1998 |
| DNA58846-1409 | 209957 | Jun. 9, 1998 |
| DNA59616-1465 | 209991 | Jun. 16, 1998 |
| DNA44694-1500 | 203114 | Aug. 11, 1998 |
| DNA64883-1526 | 203253 | Sep. 9, 1998 |
| DNA66511-1563 | 203228 | Sep. 15, 1998 |
| DNA64966-1575 | 203575 | Jan. 12, 1999 |
| DNA68885-1678 | 203311 | Oct. 6, 1998 |
| DNA80796-2523 | 203555 | Dec. 22, 1998 |
| DNA76788-2526 | 203551 | Dec. 22, 1998 |
| DNA88004-2575 | 203890 | Mar. 30, 1999 |
| DNA92265-2669 | PTA-256 | Jun. 22, 1999 |
| DNA107701-2711 | PTA-487 | Aug. 3, 1999 |
| DNA108792-2753 | PTA-617 | Aug. 31, 1999 |
| DNA129542-2808 | PTA-1178 | Jan. 11, 2000 |
| DNA148380-2827 | PTA-1181 | Jan. 11, 2000 |
| DNA58801-1052 | 55820 | Sep. 5, 1996 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 4

Isolation of cDNA Clones Encoding Human PRO196 (NL1) Polypeptides [UNQ170]

NL1 was identified by screening the GenBank database using the computer program BLAST (Altshul et al., *Methods in Enzymology* 266:460-480 (1996)). The NL1 sequence shows homology with known expressed sequence tag (EST) sequences T35448, T11442, and W77823. None of the known EST sequences have been identified as full length sequences, or described as ligands associated with the TIE receptors.

Following its identification, NL1 was cloned from a human fetal lung library prepared from mRNA purchased from Clontech, Inc. (Palo Alto, Calif., USA), catalog #6528-1, following the manufacturer's instructions.

The library was ligated into pRK5B vector, which is a precursor of pRK5D that does not contain the SfiI site; see, Holmes et al., *Science*, 253:1278-1280 (1991). pRK5D, in turn, is a derivative of pRK5 (EP 307,247, published 15 Mar. 1989), with minor differences within the polylinker sequence. The library was screened by hybridization with synthetic oligonucleotide probes:

```
NL1.5-1                                      SEQ. ID. NO: 69
5'-GCTGACGAACCAAGGCAACTACAAACTCCTGGT

NL1.3-1                                      SEQ. ID. NO: 70
5'-TGCGGCCGGACCAGTCCTCCATGGTCACCAGGAGTTTGTAG

NL1.3-2                                      SEQ. ID. NO: 71
5'-GGTGGTGAACTGCTTGCCGTTGTGCCATGTAAA
``` based on the ESTs found in the GenBank database. cDNA sequences were sequenced in their entireties.

The nucleotide and amino acid sequences of NL1 are shown in FIG. 1 (SEQ. ID. NO: 1; DNA22779-1130) and FIG. 2 (SEQ. ID. NO: 2; PRO196), respectively.

NL1 shows a 23% sequence identity with both the TIE1 and the TIE2 ligand.

A clone of NL1 (herein designated DNA22779-1130) was deposited with the American Type Culture Collection (ATCC), 12301 Parklawn Drive, Rockville, Md. 20852, on 18 Sep. 1997, under the terms of the Budapest Treaty, and has been assigned the deposit number ATCC 209280.

NL1 has been mapped to chromosome 9, band arm q13-q21.

Example 5

Isolation of cDNA Clones Encoding Human PRO217 Polypeptides [UNQ191]

A consensus DNA sequence was assembled relative to other EST sequences using phrap as described in Example 1 above. This consensus sequence is designated herein as DNA28760. Based on the assembled DNA28760 consensus sequence, oligonucleotides were synthesized: 1) to identify by PCR a cDNA library that contained the sequence of interest, and 2) for use as probes to isolate a clone of the full-length coding sequence for PRO217.

A pair of PCR primers (forward and reverse) were synthesized:

```
forward PCR primer:
5'-AAAGACGCATCTGCGAGTGTCC-3'    (SEQ ID NO: 72)

reverse PCR primer:
5'-TGCTGATTTCACACTGCTCTCCC-3'   (SEQ ID NO: 73)
```

Additionally, a synthetic oligonucleotide hybridization probe was constructed from the DNA28760 consensus sequence which had the following nucleotide sequence:

```
hybridization probe:
                                (SEQ ID NO: 74)
5'-CCCACGATGTATGAATGGTGGACTTTGTGTGACTCCTGGTTTCTGC
ATC-3'
```

In order to screen several libraries for a source of a full-length clone, DNA from the libraries was screened by PCR amplification with the PCR primer pair identified above. A positive library was then used to isolate clones encoding the PRO217 gene using the probe oligonucleotide and one of the PCR primers. RNA for construction of the cDNA libraries was isolated from human fetal lung tissue.

DNA sequencing of the isolated clones isolated as described above gave the full-length DNA sequence for DNA33094-1131 [FIG. 3, SEQ ID NO:3]; and the derived protein sequence for PRO217.

The entire coding sequence of DNA33094-1131 is included in FIG. 3 (SEQ ID NO:3). Clone DNA33094-1131 contains a single open reading frame with an apparent translational initiation site at nucleotide positions 146-148, and an apparent stop codon at nucleotide positions 1283-1285. The predicted polypeptide precursor is 379 amino acids long with a molecular weight of approximately 41,528 daltons and an estimated pI of about 7.97. Analysis of the full-length PRO217 sequence shown in FIG. 4 (SEQ ID NO:4) evidences the presence of a variety of important polypeptide domains, wherein the locations given for those important polypeptide domains are approximate as described above. Analysis of the full-length PRO217 polypeptide shown in FIG. 4 evidences the presence of the following: a signal peptide from about amino acid 1 to about amino acid 28; N-glycosylation sites from about amino acid 88 to about amino acid 92, and from about amino acid 245 to about amino acid 249; a tyrosine kinase phosphorylation site from about amino acid 370 to about amino acid 378; N-myristoylation sites from about amino acid 184 to about amino acid 190, from about amino acid 185 to about amino acid 191, from about amino acid 189 to about amino acid 195, and from about amino acid 315 to about amino acid 321; an ATP/GTP-binding site motif A (P-loop) from about amino acid 285 to about amino acid 293; and EGF-like domain cysteine pattern signatures from about amino acid 198 to about amino acid 210, from about amino acid 230 to about amino acid 242, from about amino acid 262 to about amino acid 274, from about amino acid 294 to about amino acid 306, and from about amino acid 326 to about amino acid 338. Clone DNA33094-1131 has been deposited with the ATCC on Sep. 16, 1997 and is assigned ATCC deposit no. 209256.

Based on a BLAST and FastA sequence alignment analysis of the full-length sequence shown in FIG. 4 (SEQ ID NO:4), PRO217 appears to be a novel EGF-like homologue.

Example 6

Isolation of cDNA Clones Encoding Human PRO231 Polypeptides [UNQ205]

A consensus DNA sequence was assembled relative to the other identified EST sequences as described in Example 1 above, wherein the consensus sequence was designated herein as DNA30933. Based on the DNA30933 consensus sequence, oligonucleotides were synthesized to identify by PCR a cDNA library that contained the sequence of interest and for use as probes to isolate a clone of the full-length coding sequence for PRO231.

Three PCR primers (two forward and one reverse) were synthesized:

```
forward PCR primer 1
5'-CCAACTACCAAAGCTGCTGGAGCC-3'   (SEQ ID NO: 75)

forward PCR primer 2
5'-GCAGCTCTATTACCACGGGAAGGA-3'   (SEQ ID NO: 76)

reverse PCR primer
5'-TCCTTCCCGTGGTAATAGAGCTGC-3'   (SEQ ID NO: 77)
```

Additionally, a synthetic oligonucleotide hybridization probe was constructed from the consensus DNA30933 sequence which had the following nucleotide sequence

```
hybridization probe
                                (SEQ ID NO: 78)
5'-GGCAGAGAACCAGAGGCCGGAGGAGACTGCCTCTTTACAGCC
AGG-3'
```

In order to screen several libraries for a source of a full-length clone, DNA from the libraries was screened by PCR amplification with the PCR primer pairs identified above. A positive library was then used to isolate clones encoding the PRO231 gene using the probe oligonucleotide and one of the PCR primers.

RNA for construction of the cDNA libraries was isolated from human fetal liver tissue.

DNA sequencing of the clones isolated as described above gave the full-length DNA sequence for PRO231 [herein designated as DNA34434-1139] and the derived protein sequence for PRO231.

The entire nucleotide sequence of DNA34434-1139 is shown in FIG. 5 (SEQ ID NO:5). Clone DNA34434-1139 contains a single open reading frame with an apparent translational initiation site at nucleotide positions 173-175 and ending at the stop codon at nucleotide positions 1457-1459 (FIG. 5; SEQ ID NO:5). The predicted polypeptide precursor is 428 amino acids long (FIG. 6; SEQ ID NO:6). Clone DNA34434-1139 has been deposited with ATCC on Sep. 16, 1997 and is assigned ATCC deposit no. ATCC 209252.

Analysis of the amino acid sequence of the full-length PRO231 suggests that it possesses 30% and 31% amino acid identity with the human and rat prostatic acid phosphatase precursor proteins, respectively.

Example 7

Isolation of cDNA Clones Encoding Human PRO236 Polypeptides [UNQ210]

Consensus DNA sequences were assembled relative to other EST sequences using phrap as described in Example 1 above. This consensus sequences is herein designated DNA30901. Based on the DNA30901 consensus sequence, oligonucleotides were synthesized: 1) to identify by PCR a cDNA library that contained the sequence of interest, and 2) for use as probes to isolate a clone of the full-length coding sequence for PRO236.

Based upon the DNA30901 consensus sequence, a pair of PCR primers (forward and reverse) were synthesized:

```
                                            (SEQ ID NO: 79)
forward PCR primer  5'-TGGCTACTCCAAGACCCTGGCATG-3'

(SEQ ID NO: 80)
reverse PCR primer  5'-TGGACAAATCCCCTTGCTCAGCCC-3'
```

Additionally, a synthetic oligonucleotide hybridization probe was constructed from the consensus DNA30901 sequence which had the following nucleotide sequence

```
hybridization probe
                                            (SEQ ID NO: 81)
5'-GGGCTTCACCGAAGCAGTGGACCTTTATTTTGACCACCTGATGTCCA

GGG-3'
```

In order to screen several libraries for a source of full-length clones, DNA from the libraries was screened by PCR amplification with the PCR primer pairs identified above. Positive libraries were then used to isolate clones encoding the PRO236 gene using the probe oligonucleotides and one of the PCR primers.

RNA for construction of the cDNA libraries was isolated from human fetal lung tissue for PRO236.

DNA sequencing of the clones isolated as described above gave the full-length DNA sequence for PRO236 [herein designated as DNA35599-1168] (SEQ ID NO:7), the derived protein sequence for PRO236.

The entire nucleotide sequence of DNA35599-1168 is shown in FIG. 7 (SEQ ID NO:7). Clone DNA35599-1168 contains a single open reading frame with an apparent translational initiation site at nucleotide positions 69-71 and ending at the stop codon at nucleotide positions 1977-1979 (FIG. 7; SEQ ID NO:7). The predicted polypeptide precursor is 636 amino acids long (FIG. 8; SEQ ID NO:8). Clone DNA35599-1168 has been deposited with ATCC on Oct. 16, 1997 and is assigned ATCC deposit no. ATCC 209373.

Analysis of the amino acid sequence of the full-length PRO236 polypeptide suggests that portions of this polypeptide possesses significant homology to beta-galactosidase proteins derived from various sources, thereby indicating that PRO236 may be a novel beta-galactosidase homolog.

Example 8

Isolation of cDNA Clones Encoding Human PRO245 Polypeptides [UNQ219]

A consensus DNA sequence was assembled relative to the other identified EST sequences as described in Example 1 above, wherein the consensus sequence is designated herein as DNA30954.

Based on the DNA30954 consensus sequence, oligonucleotides were synthesized to identify by PCR a cDNA library that contained the sequence of interest and for use as probes to isolate a clone of the full-length coding sequence for PRO245.

A pair of PCR primers (forward and reverse) were synthesized:

forward PCR primer 5'-ATCGTTGTGAAGTTAGTGC-CCC-3' (SEQ ID NO:82)

reverse PCR primer 5'-ACCTGCGATATCCAACA-GAATTG-3' (SEQ ID NO:83)

Additionally, a synthetic oligonucleotide hybridization probe was constructed from the consensus DNA30954 sequence which had the following nucleotide sequence

```
hybridization probe
                                            (SEQ ID NO: 84)
5'-GGAAGAGGATACAGTCACTCTGGAAGTATTAGTGGCTCCAGCAGT

TCC-3'
```

In order to screen several libraries for a source of a full-length clone, DNA from the libraries was screened by PCR amplification with the PCR primer pair identified above. A positive library was then used to isolate clones encoding the PRO245 gene using the probe oligonucleotide and one of the PCR primers.

RNA for construction of the cDNA libraries was isolated from human fetal liver tissue. DNA sequencing of the clones isolated as described above gave the full-length DNA sequence for PRO245 [herein designated as DNA35638-1141] and the derived protein sequence for PRO245.

The entire nucleotide sequence of DNA35638-1141 is shown in FIG. 9 (SEQ ID NO:9). Clone DNA35638-1141 contains a single open reading frame with an apparent translational initiation site at nucleotide positions 89-91 and ending at the stop codon at nucleotide positions 1025-1027 (FIG. 9; SEQ ID NO:9). The predicted polypeptide precursor is 312 amino acids long (FIG. 10; SEQ ID NO:10). Clone DNA35638-1141 has been deposited with ATCC on Sep. 16, 1997 and is assigned ATCC deposit no. ATCC 209265.

Analysis of the amino acid sequence of the full-length PRO245 suggests that a portion of it possesses 60% amino acid identity with the human c-myb protein and, therefore, may be a new member of the transmembrane protein receptor tyrosine kinase family.

Example 9

Isolation of cDNA Clones Encoding Human PRO246 Polypeptides [UNQ220]

A consensus DNA sequence was assembled relative to other EST sequences using phrap as described in Example 1 above. This consensus sequence is herein designated DNA30955. Based on the DNA30955 consensus sequence, oligonucleotides were synthesized: 1) to identify by PCR a cDNA library that contained the sequence of interest, and 2) for use as probes to isolate a clone of the full-length coding sequence for PRO246.

A pair of PCR primers (forward and reverse) were synthesized:

```
                                          (SEQ ID NO: 85)
forward PCR primer  5'-AGGGTCTCCAGGAGAAAGACTC-3'

(SEQ ID NO: 86)
reverse PCR primer  5'-ATTGTGGGCCTTGCAGACATAGAC-3'
```

Additionally, a synthetic oligonucleotide hybridization probe was constructed from the consensus DNA30955 sequence which had the following nucleotide sequence

```
hybridization probe
                                          (SEQ ID NO: 87)
5'-GGCCACAGCATCAAAACCTTAGAACTCAATGTACTGGTTCCTCCAGC

TCC-3'
```

In order to screen several libraries for a source of a full-length clone, DNA from the libraries was screened by PCR amplification with the PCR primer pair identified above. A positive library was then used to isolate clones encoding the PRO246 gene using the probe oligonucleotide and one of the PCR primers.

RNA for construction of the cDNA libraries was isolated from human fetal liver tissue. DNA sequencing of the clones isolated as described above gave the full-length DNA sequence for PRO246 [herein designated as DNA35639-1172] (SEQ ID NO:11) and the derived protein sequence for PRO246.

The entire nucleotide sequence of DNA35639-1172 is shown in FIG. 11 (SEQ ID NO:11). Clone DNA35639-1172 contains a single open reading frame with an apparent translational initiation site at nucleotide positions 126-128 and ending at the stop codon at nucleotide positions 1296-1298 (FIG. 11). The predicted polypeptide precursor is 390 amino acids long (FIG. 12; SEQ ID NO:12). Clone DNA35639-1172 has been deposited with ATCC on Oct. 17, 1997 and is assigned ATCC deposit no. ATCC 209396.

Analysis of the amino acid sequence of the full-length PRO246 polypeptide suggests that it possess significant homology to the human cell surface protein HCAR, thereby indicating that PRO246 may be a novel cell surface virus receptor.

Example 10

Isolation of cDNA Clones Encoding Human PRO258 Polypeptides [UNQ225]

A consensus DNA sequence was assembled relative to other EST sequences using phrap as described in Example 1 above. This consensus sequence is herein designated DNA28746.

Based on the DNA28746 consensus sequence, oligonucleotides were synthesized: 1) to identify by PCR a cDNA library that contained the sequence of interest, and 2) for use as probes to isolate a clone of the full-length coding sequence for PRO258.

PCR primers (forward and reverse) were synthesized:

```
                                          (SEQ ID NO: 88)
forward PCR primer 5'-GCTAGGAATTCCACAGAAGCCC-3'
```

```
                                          (SEQ ID NO: 89)
reverse PCR primer 5'-AACCTGGAATGTCACCGAGCTG-3'

(SEQ ID NO: 90)
reverse PCR primer 5'-CCTAGCACAGTGACGAGGGACTTGGC-3'
```

Additionally, synthetic oligonucleotide hybridization probes were constructed from the consensus DNA28740 sequence which had the following nucleotide sequence:

```
hybridization probe
                                          (SEQ ID NO: 91)
5'-AAGACACAGCCACCCTAAACTGTCAGTCTTCTGGGAGCAAGCCTGCA

GCC-3'

(SEQ ID NO: 92)
5'-GCCCTGGCAGACGAGGGCGAGTACACCTGCTCAATCTTCACTATGCC

TGT-3'
```

In order to screen several libraries for a source of a full-length clone, DNA from the libraries was screened by PCR amplification with the PCR primer pair identified above. A positive library was then used to isolate clones encoding the PRO258 gene using the probe oligonucleotide and one of the PCR primers.

RNA for construction of the cDNA libraries was isolated from human fetal lung tissue. DNA sequencing of the clones isolated as described above gave the full-length DNA sequence for PRO258 [herein designated as DNA35918-1174] (SEQ ID NO:13) and the derived protein sequence for PRO258.

The entire nucleotide sequence of DNA35918-1174 is shown in FIG. 13 (SEQ ID NO:13). Clone DNA35918-1174 contains a single open reading frame with an apparent translational initiation site at nucleotide positions 147-149 of SEQ ID NO:13 and ending at the stop codon after nucleotide position 1340 of SEQ ID NO:13 (FIG. 13). The predicted polypeptide precursor is 398 amino acids long (FIG. 14; SEQ ID NO:14). Clone DNA35918-1174 has been deposited with ATCC on Oct. 17, 1997 and is assigned ATCC deposit no. ATCC 209402.

Analysis of the amino acid sequence of the full-length PRO258 polypeptide suggests that portions of it possess significant homology to the CRTAM and the poliovirus receptor and have an Ig domain, thereby indicating that PRO258 is a new member of the Ig superfamily.

Example 11

Isolation of cDNA Clones Encoding Human PRO287 Polypeptides [UNQ250]

A consensus DNA sequence encoding PRO287 was assembled relative to the other identified EST sequences as described in Example 1 above, wherein the consensus sequence is designated herein as DNA28728. Based on the DNA28728 consensus sequence, oligonucleotides were synthesized to identify by PCR a cDNA library that contained the sequence of interest and for use as probes to isolate a clone of the full-length coding sequence for PRO287.

A pair of PCR primers (forward and reverse) were synthesized:

```
                                     (SEQ ID NO: 93)
forward PCR primer   5'-CCGATTCATAGACCTCGAGAGT-3'

(SEQ ID NO: 94)
reverse PCR primer   5'-GTCAAGGAGTCCTCCACAATAC-3'
```

Additionally, a synthetic oligonucleotide hybridization probe was constructed from the consensus DNA28728 sequence which had the following nucleotide sequence

```
    hybridization probe
                                     (SEQ ID NO: 95)
    5'-GTGTACAATGGCCATGCCAATGGCCAGCGCATTGGCCGCTTC

TGT-3'
```

In order to screen several libraries for a source of a full-length clone, DNA from the libraries was screened by PCR amplification with the PCR primer pair identified above. A positive library was then used to isolate clones encoding the PRO287 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO287 [herein designated as DNA39969-1185, SEQ ID NO:15] and the derived protein sequence for PRO287.

The entire nucleotide sequence of DNA39969-1185 is shown in FIG. 15 (SEQ ID NO:15). Clone DNA39969-1185 contains a single open reading frame with an apparent translational initiation site at nucleotide positions 307-309 and ending at the stop codon at nucleotide positions 1552-1554 (FIG. 15; SEQ ID NO:15). The predicted polypeptide precursor is 415 amino acids long (FIG. 16; SEQ ID NO:16). Clone DNA39969-1185 has been deposited with ATCC on Oct. 17, 1997 and is assigned ATCC deposit no. ATCC 209400.

Analysis of the amino acid sequence of the full-length PRO287 suggests that it may possess one or more procollagen C-proteinase enhancer protein precursor or procollagen C-proteinase enhancer protein-like domains. Based on a BLAST and FastA sequence alignment analysis of the full-length sequence, PRO287 shows nucleic acid sequence identity to procollagen C-proteinase enhancer protein precursor and procollagen C-proteinase enhancer protein (47 and 54%, respectively).

Example 12

Isolation of cDNA Clones Encoding Human PRO328 Polypeptides [UNQ289]

A consensus DNA sequence was assembled relative to other EST sequences using phrap as described in Example 1 above. This consensus sequence is herein designated DNA35615. Based on the DNA35615 consensus sequence, oligonucleotides were synthesized: 1) to identify by PCR a cDNA library that contained the sequence of interest, and 2) for use as probes to isolate a clone of the full-length coding sequence for PRO328.

Forward and reverse PCR primers were synthesized:

```
                                     (SEQ ID NO: 96)
forward PCR primer   5'-TCCTGCAGTTTCCTGATGC-3'

(SEQ ID NO: 97)
reverse PCR primer   5'-CTCATATTGCACACCAGTAATTCG-3'
```

Additionally, a synthetic oligonucleotide hybridization probe was constructed from the consensus DNA35615 sequence which had the following nucleotide sequence

```
    hybridization nrobe
                                     (SEQ ID NO: 98)
    5'-ATGAGGAGAAACGTTTGATGGTGGAGCTGCACAACCTCTACC

GGG-3'
```

In order to screen several libraries for a source of a full-length clone, DNA from the libraries was screened by PCR amplification with the PCR primer pair identified above. A positive library was then used to isolate clones encoding the PRO328 gene using the probe oligonucleotide and one of the PCR primers.

RNA for construction of the cDNA libraries was isolated from human fetal kidney tissue.

DNA sequencing of the clones isolated as described above gave the full-length DNA sequence for PRO328 [herein designated as DNA40587-1231] (SEQ ID NO:17) and the derived protein sequence for PRO328.

The entire nucleotide sequence of DNA40587-1231 is shown in FIG. 17 (SEQ ID NO:17). Clone DNA40587-1231 contains a single open reading frame with an apparent translational initiation site at nucleotide positions 15-17 and ending at the stop codon at nucleotide positions 1404-1406 (FIG. 17). The predicted polypeptide precursor is 463 amino acids long (FIG. 18; SEQ ID NO:18). Clone DNA40587-1231 has been deposited with ATCC on Nov. 7, 1997 and is assigned ATCC deposit no. ATCC 209438.

Analysis of the amino acid sequence of the full-length PRO328 polypeptide suggests that portions of it possess significant homology to the human glioblastoma protein and to the cysteine rich secretory protein thereby indicating that PRO328 may be a novel glioblastoma protein or cysteine rich secretory protein.

Example 13

Isolation of cDNA Clones Encoding Human PRO344 Polypeptides [UNQ303]

A consensus DNA sequence was assembled relative to other EST sequences as described in Example 1 above. This consensus sequence is herein designated DNA34398. Based on the DNA34398 consensus sequence, oligonucleotides were synthesized: 1) to identify by PCR a cDNA library that contained the sequence of interest, and 2) for use as probes to isolate a clone of the full-length coding sequence for PRO344.

Based on the DNA34398 consensus sequence, forward and reverse PCR primers were synthesized as follows:

```
forward PCR primer
(34398.f1)
                                    (SEQ ID NO: 99)
5'-TACAGGCCCAGTCAGGACCAGGGG-3' forward PCR primer
(34398.f2)
                                    (SEQ ID NO: 100)
5'-AGCCAGCCTCGCTCTCGG-3' forward PCR primer
(34398.f3)
                                    (SEQ ID NO: 101)
5'-GTCTGCGATCAGGTCTGG-3' reverse PCR primer
(34398.r1)
                                    (SEQ ID NO: 102)
5'-GAAAGAGGCAATGGATTCGC-3' reverse PCR primer
(34398.r2)
                                    (SEQ ID NO: 103)
5'-GACTTACACTTGCCAGCACAGCAC-3'
```

Additionally, a synthetic oligonucleotide hybridization probe was constructed from the DNA34398 consensus sequence which had the following nucleotide sequence

```
hybridization probe (34398.p1)
                                    (SEQ ID NO: 104)
5'-GGAGCACCACCAACTGGAGGGTCCGGAGTAGCGAGCGCCCG

AAG-3'
```

In order to screen several libraries for a source of a full-length clone, DNA from the libraries was screened by PCR amplification with one of the PCR primer pairs identified above. A positive library was then used to isolate clones encoding the PRO344 genes using the probe oligonucleotide and one of the PCR primers. RNA for construction of the cDNA libraries was isolated from human fetal kidney tissue.

DNA sequencing of the clones isolated as described above gave the full-length DNA sequence for PRO344 [herein designated as DNA40592-1242] (SEQ ID NO:19) and the derived protein sequence for PRO344.

The entire nucleotide sequence of DNA40592-1242 is shown in FIG. 19 (SEQ ID NO:19). Clone DNA40592-1242 contains a single open reading frame with an apparent translational initiation site at nucleotide positions 227-229 and ending at the stop codon at nucleotide positions 956-958 (FIG. 19). The predicted polypeptide precursor is 243 amino acids long (FIG. 20; SEQ ID NO:20). Important regions of the native PRO344 amino acid sequence include the signal peptide, the start of the mature protein, and two potential N-myristoylation sites as shown in FIG. 20. Clone DNA40592-1242 has been deposited with the ATCC on Nov. 21, 1997 and is assigned ATCC deposit no. ATCC 209492.

Analysis of the amino acid sequence of the full-length PRO344 polypeptides suggests that portions of them possess significant homology to various human and murine complement proteins, thereby indicating that PRO344 may be a novel complement protein.

Example 14

Isolation of cDNA Clones Encoding Human PRO357 Polypeptides [UNQ314]

The sequence expression tag clone no. "2452972" by Incyte Pharmaceuticals, Palo Alto, Calif. was used to begin a data base search. The extracellular domain (ECD) sequences (including the secretion signal, if any) of from about 950 known secreted proteins from the Swiss-Prot public protein database were used to search expressed sequence tag (EST) databases which overlapped with a portion of Incyte EST clone no. "2452972". The EST databases included public EST databases (e.g., GenBank) and a proprietary EST DNA database (LIFESEQ®, Incyte Pharmaceuticals, Palo Alto, Calif.). The search was performed using the computer program BLAST or BLAST2 (Altshul et al., *Methods in Enzmmology* 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

A consensus DNA sequence was then assembled relative to other EST sequences using phrap. This consensus sequence is herein designated DNA37162. In this case, the consensus DNA sequence was extended using repeated cycles of BLAST and phrap to extend the consensus sequence as far as possible using the sources of EST sequences discussed above.

Based on the DNA37162 consensus sequence, oligonucleotides were synthesized: 1) to identify by PCR a cDNA library that contained the sequence of interest, and 2) for use as probes to isolate a clone of the full-length coding sequence for PRO357. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as ber Ausubel et al., *Current Protocols in Molecular Biology*, with the PCR primer pair. A positive library was then used to isolate clones encoding the gene of interest using the probe oligonucleotide and one of the primer pairs.

PCR primers were synthesized as follows:

```
                                    (SEQ ID NO: 105)
forward primer 1: 5'-CCCTCCACTGCCCCACCGACTG-3';

(SEQ ID NO: 106)
reverse primer 1: 5'-CGGTTCTGGGGACGTTAGGGCTCG-3';
and (SEQ ID NO: 107)
forward primer 2: 5'-CTGCCCACCGTCCACCTGCCTCAAT-3'.
```

Additionally, two synthetic oligonucleotide hybridization probes were constructed from the consensus DNA37162 sequence which had the following nucleotide sequences:

```
hybridization probe 1:
                                    (SEQ ID NO: 108)
5'-AGGACTGCCCACCGTCCACCTGCCTCAATGGGGGCACATGCC ACC-3';
and hybridization probe 2:
                                    (SEQ ID NO: 109)
5'-ACGCAAAGCCCTACATCTAAGCCAGAGAGAGACAGGGCAGCT

GGG-3'.
```

In order to screen several libraries for a source of a full-length clone, DNA from the libraries was screened by PCR amplification with a PCR primer pair identified above. A positive library was then used to isolate clones encoding the PRO357 gene using the probe oligonucleotide and one of the PCR primers.

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for PRO357 [herein designated as DNA44804-1248] (SEQ ID NO:21) and the derived protein sequence for PRO357.

The entire nucleotide sequence of DNA44804-1248 is shown in FIG. 21 (SEQ ID NO:21). Clone DNA44804-1248 contains a single open reading frame with an apparent translational initiation site at nucleotide positions 137-139 and ending at the stop codon at nucleotide positions 1931-1933 (FIG. 21). The predicted polypeptide precursor is 598 amino acids long (FIG. 22; SEQ ID NO:22). Clone DNA44804-1248 has been deposited with ATCC on Dec. 10, 1997 and is assigned ATCC deposit no. ATCC 209527.

Analysis of the amino acid sequence of the full-length PRO357 polypeptide therefore suggests that portions of it possess significant homology to ALS, thereby indicating that PRO357 may be a novel leucine rich repeat protein related to ALS.

Example 15

Isolation of cDNA Clones Encoding Human PRO526 Polypeptides [UNQ330]

A consensus sequence was obtained relative to a variety of EST sequences as described in Example 1 above, wherein the consensus sequence obtained is herein designated DNA39626. Based on the DNA39626 consensus sequence, oligonucleotides were synthesized: 1) to identify by PCR a cDNA library that contained the sequence of interest, and 2) for use as probes to isolate a clone of the full-length coding sequence for PRO526.

A pair of PCR primers (forward and reverse) were synthesized:

```
                                       (SEQ ID NO: 110)
forward PCR primer  5'-TGGCTGCCCTGCAGTACCTCTACC-3';

(SEQ ID NO: 111)
reverse PCR primer  5'-CCCTGCAGGTCATTGGCAGCTAGG-3'.
```

Additionally, a synthetic oligonucleotide hybridization probe was constructed from the DNA39626 consensus sequence which had the following nucleotide sequence:

```
hybridization probe
                                       (SEQ ID NO: 112)
5'-AGGCACTGCCTGATGACACCTTCCGCGACCTGGGCAACCTCA

CAC-3'.
```

In order to screen several libraries for a source of a full-length clone, DNA from the libraries was screened by PCR amplification with the PCR primer pair identified above. A positive library was then used to isolate clones encoding the PRO526 gene using the probe oligonucleotide and one of the PCR primers. RNA for construction of the cDNA libraries was isolated from human fetal liver tissue (LIB228).

DNA sequencing of the clones isolated as described above gave the full-length DNA sequence for PRO526 [herein designated as UNQ330 (DNA44184-1319)] (SEQ ID NO:23) and the derived protein sequence for PRO526.

The entire nucleotide sequence of UNQ330 (DNA44184-1319) is shown in FIG. 23 (SEQ ID NO:23). Clone UNQ330 (DNA44184-1319) contains a single open reading frame with an apparent translational initiation site at nucleotide positions 514-516 and ending at the stop codon at nucleotide positions 1933-1935 (FIG. 23). The predicted polypeptide precursor is 473 amino acids long (FIG. 24; SEQ ID NO:24). The full-length PRO526 protein shown in FIG. 24 has an estimated molecular weight of about 50,708 daltons and a pI of about 9.28. Clone UNQ330 (DNA44184-1319) has been deposited with the ATCC on Mar. 26, 1998 under ATCC accession no: 209704. It is understood that the clone contains the actual sequence, whereas the sequences presented herein are representative based on current sequencing techniques.

Analysis of the amino acid sequence of the full-length PRO526 polypeptide suggests that portions of it possess significant homology to the leucine repeat rich proteins including ALS, SLIT, carboxypeptidase and platelet glycoprotein V thereby indicating that PRO526 is a novel protein which is involved in protein-protein interactions.

Still analyzing SEQ ID NO:24, the signal peptide sequence is at about amino acids 1-26. A leucine zipper pattern is at about amino acids 135-156. A glycosaminoglycan attachment is at about amino acids 436-439. N-glycosylation sites are at about amino acids 82-85, 179-182, 237-240 and 423-426. A von Willebrand factor (VWF) type C domain(s) is found at about amino acids 411-425. The skilled artisan can understand which nucleotides correspond to these amino acids based on the sequences provided herein.

Example 16

Isolation of cDNA Clones Encoding Human PRO724 Polypeptides [UNQ389]

A consensus sequence was obtained relative to a variety of EST sequences as described in Example 1 above, wherein the consensus sequence obtained is herein designated DNA35603. Based on the DNA35603 consensus sequence, oligonucleotides were synthesized: 1) to identify by PCR a cDNA library that contained the sequence of interest, and 2) for use as probes to isolate a clone of the full-length coding sequence for PRO724.

Pairs of PCR primers (forward and reverse) were synthesized:

```
                                       (SEQ ID NO: 113)
forward PCR primer 1  5'-GGCTGTCACTGTGGAGACAC-3'

(SEQ ID NO: 114)
forward PCR primer 2  5'-GCAAGGTCATTACAGCTG-3'

(SEQ ID NO: 115)
reverse PCR primer 1  5'-AGAACATAGGAGCAGTCCCACTC-3'
```

-continued reverse PCR primer 2  5'-TGCCTGCTGCTGCACAATCTCAG-3' (SEQ ID NO: 116)

Additionally, a synthetic oligonucleotide hybridization probe was constructed from the consensus DNA35603 sequence which had the following nucleotide sequence hybridization probe
(SEQ ID NO: 117)
5'-GGCTATTGCTTGCCTTGGGACAGACCCTGTGGCTTAGGCTCT
GGC-3'

In order to screen several libraries for a source of a full-length clone, DNA from the libraries was screened by PCR amplification with the PCR primer pairs identified above. A positive library was then used to isolate clones encoding the PRO724 gene using the probe oligonucleotide and one of the PCR primers. RNA for construction of the cDNA libraries was isolated from human fetal lung tissue (LIB26).

DNA sequencing of the clones isolated as described above gave the full-length DNA sequence for PRO724 [herein designated as UNQ389 (DNA49631-1328)] (SEQ ID NO:25) and the derived protein sequence for PRO724.

The entire nucleotide sequence of UNQ389 (DNA49631-1328) is shown in FIG. 25 (SEQ ID NO:25). Clone UNQ389 (DNA49631-1328) contains a single open reading frame with an apparent translational initiation site at nucleotide positions 546-548 and ending at the stop codon at nucleotide positions 2685-2687 (FIG. 25). The predicted polypeptide precursor is 713 amino acids long (FIG. 26; SEQ ID NO:26). The full-length PRO724 protein shown in FIG. 26 has an estimated molecular weight of about 76,193 daltons and a pI of about 5.42. Analysis of the full-length PRO724 amino acid sequence shown in FIG. 26 (SEQ ID NO:26) evidences the presence of the following: a signal peptide from about amino acid 1 to about amino acid 16, a transmembrane domain from about amino acid 442 to about amino acid 462 and LDL receptor class A domain regions from about amino acid 152 to about amino acid 171, about amino acid 331 to about amino acid 350, about amino acid 374 to about amino acid 393 and about amino acid 411 to about amino acid 430. Clone UNQ389 (DNA49631-1328) has been deposited with ATCC on Apr. 28, 1998 and is assigned ATCC deposit no. 209806.

Analysis of the amino acid sequence of the full-length PRO724 polypeptide suggests that it possesses significant sequence similarity to the human LDL receptor protein, thereby indicating that PRO724 may be a novel LDL receptor homolog. More specifically, an analysis of the Dayhoff database (version 35.45 SwissProt 35) evidenced significant homology between the PRO724 amino acid sequence and the following Dayhoff sequences, P_R48547, MMAM2R__1, LRP2_RAT, P_R60517, P_R47861, P_R05533, A44513__1, A30363, P_R74692 and LMLIPOPHO__1.

Example 17

Isolation of cDNA Clones Encoding Human PRO731 Polypeptides [UNQ395]

A database was used to search expressed sequence tag (EST) databases. The EST database used herein was the proprietary EST DNA database LIFESEQ®, of Incyte Pharmaceuticals, Palo Alto, Calif. Incyte clone 2581326 was herein identified and termed DNA42801. Based on the DNA42801 sequence, oligonucleotides were synthesized: 1) to identify by PCR a cDNA library that contained the sequence of interest, and 2) for use as probes to isolate a clone of the full-length coding sequence for PRO731.

A pair of PCR primers (forward and reverse) were synthesized:

forward PCR primer  5'-GTAAGCACATGCCTCCAGAGGTGC-3'; (SEQ ID NO: 118)

reverse PCR primer  5'-GTGACGTGGATGCTTGGGATGTTG-3'. (SEQ ID NO: 119)

Additionally, a synthetic oligonucleotide hybridization probe was constructed from the DNA42801 sequence which had the following nucleotide sequence:

hybridization probe
(SEQ ID NO: 120)
5'-TGGACACCTTCAGTATTGATGCCAAGACAGGCCAGGTCATTCTGCGT
CGA-3'.

In order to screen several libraries for a source of a full-length clone, DNA from the libraries was screened by PCR amplification with the PCR primer pair identified above. A positive library was then used to isolate clones encoding the PRO731 gene using the probe oligonucleotide and one of the PCR primers. RNA for construction of the cDNA libraries was isolated from human bone marrow tissue (LIB255). The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253: 1278-1280 (1991)) in the unique XhoI and NotI sites.

DNA sequencing of the clones isolated as described above gave the full-length DNA sequence for PRO731 [herein designated as UNQ395 (DNA48331-1329)] (SEQ ID NO:27) and the derived protein sequence for PRO731.

The entire nucleotide sequence of UNQ395 (DNA48331-1329) is shown in FIG. 27 (SEQ ID NO:27). Clone UNQ395 (DNA48331-1329) contains a single open reading frame with an apparent translational initiation site at nucleotide positions 329-331 and ending at the stop codon at nucleotide positions 3881-3883 (FIG. 27). The predicted polypeptide precursor is 1184 amino acids long (FIG. 28; SEQ ID NO:28). The full-length PRO731 protein shown in FIG. 28 has an estimated molecular weight of about 129,022 daltons and a pI of about 5.2. Clone UNQ395 (DNA48331-1329) was deposited with the ATCC on Mar. 31, 1998 under ATCC accession no: 209715. Regarding the sequence, it is understood that the deposited clone contains the correct sequence, and the sequences provided herein are based on known sequencing techniques.

Analysis of the amino acid sequence of the full-length PRO731 polypeptide suggests that portions of it possess significant identity and similarity to members of the protocadherin family, thereby indicating that PRO731 may be a novel protocadherin.

Still analyzing the amino acid sequence of SEQ ID NO:28, the putative signal peptide is at about amino acids 1-13 of SEQ ID NO:28. The transmembrane domain is at amino acids 719-739 of SEQ ID NO:28. The N-glycosylation of SEQ ID NO:28 are as follows: 415-418, 582-586, 659-662, 662-665, and 857-860. The cadherin extracellular repeated domain signatures are at about amino acids (of SEQ ID NO:28): 123-133, 232-242, 340-350, 448-458, and 553-563. The corresponding nucleotides can be routinely determined given the sequences provided herein.

Example 18

Isolation of cDNA Clones Encoding Human PRO732 Polypeptides [UNQ396]

A yeast screening assay was employed to identify cDNA clones that encoded potential secreted proteins. Use of this yeast screening assay allowed identification of a single cDNA clone whose sequence (herein designated as DNA42580). The DNA42580 sequence was then compared to a variety of known EST sequences to identify homologies. The EST databases employed included public EST databases (e.g., GenBank) and a proprietary EST DNA database (LIFESEQ®, Incyte Pharmaceuticals, Palo Alto, Calif.). The search was performed using the computer program BLAST or BLAST2 (Altshul et al., *Methods in Enzymology* 266:460-480 (1996)) as a comparison to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

Using the above analysis, a consensus DNA sequence was assembled relative to other EST sequences using phrap. This consensus sequence is herein designated consen01. Proprietary Genentech EST sequences were employed in the consensus assembly and they are herein designated DNA20239, DNA38050 and DNA40683.

Based on the consen01 sequence, oligonucleotides were synthesized: 1) to identify by PCR a cDNA library that contained the sequence of interest, and 2) for use as probes to isolate a clone of the full-length coding sequence for PRO732. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

PCR primers (forward and reverse) were synthesized:

```
forward PCR primer
5'-ATGTTTGTGTGGAAGTGCCCCG-3'      (SEQ ID NO: 121)

forward PCR primer
5'-GTCAACATGCTCCTCTGC-3'           (SEQ ID NO: 122)

reverse PCR primer
5'-AATCCATTGTGCACTGCAGCTCTAGG-3'   (SEQ ID NO: 123)

reverse PCR primer
5'-GAGCATGCCACCACTGGACTGAC-3'      (SEQ ID NO: 124)
```

Additionally, a synthetic oligonucleotide hybridization probe was constructed from the consensus DNA44143 sequence which had the following nucleotide sequence

```
hybridization probe
                                   (SEQ ID NO: 125)
5'-GCCGATGCTGTCCTAGTGGAAACAACTCCACTGTAACTAGATTGATC
TATGCAC-3'
```

In order to screen several libraries for a source of a full-length clone, DNA from the libraries was screened by PCR amplification with the PCR primer pairs identified above. A positive library was then used to isolate clones encoding the PRO732 gene using the probe oligonucleotide and one of the PCR primers.

RNA for construction of the cDNA libraries was isolated from human fetal lung tissue (LIB26). The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science* 253:1278-1280 (1991)) in the unique XhoI and NotI sites.

A full length clone was identified that contained a single open reading frame with an apparent translational initiation site at nucleotide positions 88-90 and ending at the stop codon found at nucleotide positions 1447-1449 (FIG. 29, SEQ ID NO:29). The predicted polypeptide precursor is 453 amino acids long, has a calculated molecular weight of approximately 50,419 daltons and an estimated pI of approximately 5.78. Analysis of the full-length PRO732 sequence shown in FIG. 30 (SEQ ID NO:30) evidences the presence of the following: a signal peptide from about amino acid 1 to about amino acid 28, transmembrane domains from about amino acid 37 to about amino acid 57, from about amino acid 93 to about amino acid 109, from about amino acid 126 to about amino acid 148, from about amino acid 151 to about amino acid 172, from about amino acid 197 to about amino acid 215, from about amino acid 231 to about amino acid 245, from about amino acid 260 to about amino acid 279, from about amino acid 315 to about amino acid 333, from about amino acid 384 to about amino acid 403 and from about amino acid 422 to about amino acid 447, potential N-glycosylation sites from about amino acid 33 to about amino acid 36, from about amino acid 34 to about amino acid 37, from about amino acid 179 to about amino acid 183, from about amino acid 298 to about amino acid 301, from about amino acid 337 to about amino acid 340 and from about amino acid 406 to about amino acid 409, an amino acid block having homology to the MIP family of proteins from about amino acid 119 to about amino acid 149 and an amino acid block having homology to DNA/RNA non-specific endonuclease proteins from about amino acid 279 to about amino acid 286. Clone DNA48334-1435 has been deposited with ATCC on Jun. 2, 1998 and is assigned ATCC deposit no. 209924.

Analysis of the amino acid sequence of the full-length PRO732 polypeptide suggests that it possesses significant sequence similarity to the Diff33 protein, thereby indicating that PRO732 may be a novel Diff33 homolog. More specifically, an analysis of the Dayhoff database (version 35.45 SwissProt 35) evidenced significant homology between the PRO732 amino acid sequence and the following Dayhoff sequences, HS179M20_2, MUSTETU_1, CER11H6_2, RATDRP_1, S51256, E69226, AE000869_1, JC4120, CYB_PARTE and P_R50619.

Example 19

Isolation of cDNA Clones Encoding Human PRO1003 Polypeptides [UNQ487]

Use of the signal sequence algorithm described in Example 3 above allowed identification of a single Incyte EST cluster sequence designated herein as 43055. This sequence was then compared to a variety of EST databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated consen01.

In light of an observed sequence homology between the consensus sequence and an EST sequence encompassed within the Incyte EST clone no. 2849382, the Incyte EST clone 2849382 was purchased and the cDNA insert was obtained and sequenced. It was found that this insert encoded a full-length protein. The sequence of this cDNA insert is shown in FIG. 31.

The entire nucleotide sequence of DNA58846-1409 is shown in FIG. 31 (SEQ ID NO:31). Clone DNA58846-1409 contains a single open reading frame with an apparent translational initiation site at nucleotide positions 41-43 and ending at the stop codon at nucleotide positions 293-295 (FIG. 31). The predicted polypeptide precursor is 84 amino acids long (FIG. 32; SEQ ID NO:32). The full-length PRO1003 protein shown in FIG. 32 has an estimated molecular weight of about 9,408 daltons and a pI of about 9.28. Analysis of the full-length PRO1003 sequence shown in FIG. 32 (SEQ ID NO:32) evidences the presence of a signal peptide at amino acids 1 to about 24, and a cAMP- and cGMP-dependent protein kinase phosphorylation site at about amino acids 58 to about 61. Analysis of the amino acid sequence of the full-length PRO1003 polypeptide using the Dayhoff database (version 35.45 SwissProt 35) evidenced homology between the PRO1003 amino acid sequence and the following Dayhoff sequences: AOPCZA363_3, SRTX_ATREN, A48298, MHVJHMS_1, VGL2_CVMJH, DHDHTC2_2, COR-T_RAT, TAL6_HUMAN, P_W14123, and DVUFI_2.

Example 20

Isolation of cDNA Clones Encoding Human PRO1104 Polypeptides [UNQ547]

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (Lifeseq®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56446.

In light of an observed sequence homology between the DNA56446 sequence and an EST sequence encompassed within the Incyte EST clone no. 2837496, the Incyte EST clone 2837496 was purchased and the cDNA insert was obtained and sequenced. It was found that this insert encoded a full-length protein. The sequence of this cDNA insert is shown in FIG. 33 and is herein designated as DNA59616-1465.

The entire nucleotide sequence of DNA59616-1465 is shown in FIG. 33 (SEQ ID NO:33). Clone DNA59616-1465 contains a single open reading frame with an apparent translational initiation site at nucleotide positions 109-111 and ending at the stop codon at nucleotide positions 1132-1134 of SEQ ID NO:33 (FIG. 33). The predicted polypeptide precursor is 341 amino acids long (FIG. 34; SEQ ID NO:34). The full-length PRO1104 protein shown in FIG. 34 has an estimated molecular weight of about 36,769 daltons and a pI of about 9.03. Clone DNA59616-1465 has been deposited with ATCC on Jun. 16, 1998 under ATCC accession no: 209991. It is understood that the deposited clone has the actual nucleic acid sequence and that the sequences provided herein are based on known sequencing techniques.

Analyzing FIG. 34, a signal peptide is at about amino acids 1-22 of SEQ ID NO:34. N-myristoylation sites are at about amino acids 41-46, 110-115, 133-138, 167-172 and 179-184 of SEQ ID NO:34.

Example 21

Isolation of cDNA Clones Encoding Human PRO1151 Polypeptides [UNQ581]

A consensus DNA sequence was assembled relative to other EST sequences using phrap as described in Example 1 above. This consensus sequence is herein designated DNA40665. Based on the DNA40665 consensus sequence, oligonucleotides were synthesized: 1) to identify by PCR a cDNA library that contained the sequence of interest, and 2) for use as probes to isolate a clone of the full-length coding sequence for PRO1151.

PCR primers (forward and reverse) were synthesized:

```
                                            (SEQ ID NO: 126)
forward PCR primer 5'-CCAGACGCTGCTCTTCGAAAGGGTC-3'

(SEQ ID NO: 127)
reverse PCR primer 5'-GGTCCCCGTAGGCCAGGTCCAGC-3'
```

Additionally, a synthetic oligonucleotide hybridization probe was constructed from the consensus DNA40665 sequence which had the following nucleotide sequence

```
hybridization probe
                                            (SEQ ID NO: 128)
5'-CTACTTCTTCAGCCTCAATGTGCACAGCTGGAATTACAAGGAGACGT
ACG-3'
```

In order to screen several libraries for a source of a full-length clone, DNA from the libraries was screened by PCR amplification with the PCR primer pair identified above. A positive library was then used to isolate clones encoding the PRO1151 gene using the probe oligonucleotide and one of the PCR primers. RNA for construction of the cDNA libraries was isolated from human fetal kidney tissue.

DNA sequencing of the clones isolated as described above gave the full-length DNA sequence for PRO1151 (designated herein as DNA44694-1500 [FIG. 35, SEQ ID NO:35]; and the derived protein sequence for PRO1151.

The entire nucleotide sequence of DNA44694-1500 is shown in FIG. 35 (SEQ ID NO:35). Clone DNA44694-1500 contains a single open reading frame with an apparent translational initiation site at nucleotide positions 272-274 and ending at the stop codon at nucleotide positions 1049-1051 (FIG. 35). The predicted polypeptide precursor is 259 amino acids long (FIG. 36; SEQ ID NO:36). The full-length PRO1151 protein shown in FIG. 36 has an estimated molecular weight of about 28,770 daltons and a pI of about 6.12. Analysis of the full-length PRO1151 sequence shown in FIG. 36 (SEQ ID NO:36) evidences the presence of the following: a signal peptide from about amino acid 1 to about amino acid 20, a potential N-glycosylation site from about amino acid 72 to about amino acid 75 and amino acid sequence blocks having homology to C1q domain-containing proteins from about amino acid 144 to about amino acid 178, from about amino acid 78 to about amino acid 111 and from about amino acid 84 to about amino acid 117. Clone UNQ581 (DNA44694-1500) has been deposited with ATCC on Aug. 11, 1998 and is assigned ATCC deposit no. 203114.

An analysis of the Dayhoff database (version 35.45 SwissProt 35), using a WU-BLAST-2 sequence alignment analysis of the full-length sequence shown in FIG. 36 (SEQ ID NO:36), evidenced significant homology between the PRO1151 amino acid sequence and the following Dayhoff sequences: ACR3_HUMAN, HP25_TAMAS, HUMC1QB2_1, P_R99306, CA1F_HUMAN, JX0369, CA24_HUMAN, S32436, P_R28916 and CA54_HUMAN.

Example 22

Isolation of cDNA Clones Encoding Human PRO1244 Polypeptides [UNQ628]

Use of the signal sequence algorithm described in Example 3 above allowed identification of an EST cluster sequence from the LIFESEQ® database, designated cluster no. 7874. This EST cluster sequence was then compared to a variety of expressed sequence tag (EST) databases which included public EST databases (e.g., GenBank) and a proprietary EST DNA databases (LIFESEQ®, Incyte Pharmaceuticals, Palo Alto, Calif.; Genentech, South San Francisco, Calif.) to identify existing homologies. One or more of the ESTs was derived from a library constructed from tissue of the corpus cavernosum. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated "DNA56011".

In light of the sequence homology between the DNA56011 sequence and an EST sequence contained within Incyte EST No. 3202349, the EST clone no. 3202349 was purchased and the cDNA insert was obtained and sequenced. The sequence of this cDNA insert is shown in FIG. 37 (SEQ ID NO:37) and is herein designated "DNA64883-1526".

The full length clone shown in FIG. 37 contained a single open reading frame with an apparent translational initiation site at nucleotide positions 9-11 and ending at the stop codon found at nucleotide positions 1014-1016 (FIG. 37; SEQ ID NO:37). The predicted polypeptide precursor (FIG. 38, SEQ ID NO:38) is 335 amino acids long. PRO1244 has a calculated molecular weight of approximately 38,037 daltons and an estimated pI of approximately 9.87. Other features include a signal peptide at about amino acids 1-29; transmembrane domains at about amino acids 183-205, 217-237, 271-287, and 301-321; potential N-glycosylation sites at about amino acids 71-74, and 215-218; and a cell attachment sequence at about amino acids 150-152.

An analysis of the Dayhoff database (version 35.45 SwissProt 35), using a WU-BLAST2 sequence alignment analysis of the full-length sequence shown in FIG. 38 (SEQ ID NO:38), revealed homology between the PRO1244 amino acid sequence and the following Dayhoff sequences: AF008554_1, P_485334, G02297, HUMN33S11_1, HUMN33S10_1, YO13_CAEEL, GEN13255, S49758, E70107, and ERP5_MEDSA.

Clone DNA64883-1526 was deposited with the ATCC on Sep. 9, 1998, and is assigned ATCC deposit no. 203253.

Example 23

Isolation of cDNA Clones Encoding Human PRO1298 Polypeptides [UNQ666]

Use of the signal sequence algorithm described in Example 3 above allowed identification of an EST cluster sequence from an Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. One or more of the ESTs was derived from a diseased prostate tissue library. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56389.

In light of the sequence homology between the DNA56389 sequence and an EST sequence contained within an Incyte EST within the assembly from with the consensus sequence was derived, Incyte clone 3355717 was purchased and the cDNA insert was obtained and sequenced. The sequence of this cDNA insert is shown in FIG. 39 and is herein designated as DNA66511-1563.

The full length clone shown in FIG. 39 contained a single open reading frame with an apparent translational initiation site at nucleotide positions 94-96 and ending at the stop codon found at nucleotide positions 1063-1065 (FIG. 39; SEQ ID NO:39). The predicted polypeptide precursor (FIG. 40, SEQ ID NO:40) is 323 amino acids long. The signal peptide is at about amino acids 1-15 of SEQ ID NO:40. PRO1298 has a calculated molecular weight of approximately 37,017 daltons and an estimated pI of approximately 8.83. Clone DNA66511-1563 was deposited with the ATCC on Sep. 15, 1998 and is assigned ATCC deposit no. 203228.

An analysis of the Dayhoff database (version 35.45 SwissProt 35), using a WU-BLAST2 sequence alignment analysis of the full-length sequence shown in FIG. 40 (SEQ ID NO:40), revealed sequence identity between the PRO1298 amino acid sequence and the following Dayhoff sequences (data incorporated herein): ALG2_YEAST, CAPM_STAAU, C69098, C69255, SUS2_MAIZE, A69143, S74778, AB009527_, AF050103_2 and BBA224769_1.

Example 24

Isolation of cDNA Clones Encoding Human PRO1313 Polypeptides [UNQ679]

The extracellular domain (ECD) sequences (including the secretion signal sequence, if any) from about 950 known secreted proteins from the Swiss-Prot public database were used to search EST databases. The EST databases included public EST databases (e.g., GenBank), a proprietary EST database (LIFESEQ®, Incyte Pharmaceuticals, Palo Alto, Calif.), and proprietary ESTs from Genentech. The search was performed using the computer program BLAST or BLAST2 [Altschul et al., *Methods in Enzymology,* 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap. This consensus sequence is herein designated DNA64876. Based on the DNA64876 consensus sequence and upon a search for sequence homology with a proprietary Genentech EST sequence designated as DNA57711, a Merck/Washington University EST sequence designated R80613 was found to have significant homology with DNA64876 and DNA57711. Therefore, the Merck/Washington University EST clone no. R80613 was purchased and the insert thereof obtained and sequence, thereby giving rise to the DNA64966-1575 sequence shown in FIG. 41.

DNA sequencing of the R80613 insert obtained as described above gave the full-length DNA sequence for PRO1313 (designated herein as DNA64966-1575 [FIG. 41, SEQ ID NO: 41]; (UNQ679) and the derived protein sequence for PRO1313.

The entire nucleotide sequence of UNQ679 (DNA64966-1575) is shown in FIG. 41 (SEQ ID NO:41). Clone UNQ679 (DNA64966-1575) contains a single open reading frame with an apparent translational initiation site at nucleotide positions 115-117 and ending at the stop codon at nucleotide positions 1036-1038 (FIG. 41). The predicted polypeptide precursor is 307 amino acids long (FIG. 42; SEQ ID NO:42). The full-length PRO1313 protein shown in FIG. 42 has an estimated molecular weight of about 35,098 daltons and a pI of about 8.11. Analysis of the full-length PRO1313 sequence shown in FIG. 42 (SEQ ID NO:42) evidences the presence of the following: a signal peptide from about amino acid 1 to about amino acid 15, transmembrane domains from about amino acid 134 to about amino acid 157, from about amino acid 169 to about amino acid 189, from about amino acid 230 to about amino acid 248 and from about amino acid 272 to about amino acid 285, potential N-glycosylation sites from about amino acid 34 to about amino acid 37, from about amino acid 135 to about amino acid 138 and from about amino acid 203 to about amino acid 206 and ATP/GTP binding site motif A from about amino acid 53 to about amino acid 60. Clone UNQ679 (DNA64966-1575) has been deposited with ATCC on Jan. 12, 1999 and is assigned ATCC deposit no. 203575.

An analysis of the Dayhoff database (version 35.45 SwissProt 35), using a WU-BLAST2 sequence alignment analysis of the full-length sequence shown in FIG. 42 (SEQ ID NO:42), evidenced significant homology between the PRO1313 amino acid sequence and the following Dayhoff sequences: CELT27A1_3, CEF09C6_7, U93688_9, H64896, YDCX_ECOLI and RNU06101_1.

Example 25

Isolation of cDNA Clones Encoding Human PRO1570 Polypeptides [UNQ776]

A consensus DNA sequence encoding PRO1570 was assembled relative to other EST sequences using phrap as described in Example 1 above to form an assembly. This consensus sequence is designated herein as "DNA65415". Based on the DNA65415 consensus sequence and other discoveries and information provided herein, the clone including Incyte EST 3232285 (from a uterine/colon cancer tissue library) was purchased and sequenced in full which gave SEQ ID NO:43.

The entire coding sequence of PRO1570 is included in FIG. 43 (SEQ ID NO:43). Clone DNA68885-1678 contains a single open reading frame with an apparent translational initiation site at nucleotide positions 210-212 and an apparent stop codon at nucleotide positions 1506-1508 of SEQ ID NO:43. The predicted polypeptide precursor is 432 amino acids long. FIG. 44 (SEQ ID NO:44) shows a number of motifs. Clone DNA68885-1678 has been deposited with the ATCC on Oct. 6, 1998 and is assigned ATCC deposit no. 203311. The full-length PRO1570 protein shown in FIG. 44 has an estimated molecular weight of about 47,644 daltons and a pI of about 5.18.

An analysis of the Dayhoff database (version 35.45 SwissProt 35), using a WU-BLAST2 sequence alignment analysis of the full-length sequence shown in FIG. 44 (SEQ ID NO:44), revealed sequence identity between the PRO1570 amino acid sequence and the following Dayhoff sequences (incorporated herein): P_W22986, TMS2_HUMAN, HEPS_HUMAN, P_R89435, AB002134_1, KAL_MOUSE, ACRO_HUMAN, GEN12917, AF045649_1, and P_W34285.

Example 26

Isolation of cDNA Clones Encoding Human PRO1886 Polypeptides [UNQ870]

An initial DNA sequence was identified using a yeast screen, in a human aortic endothelial cDNA library that preferentially represents the 5' ends of the primary cDNA clones. This sequence was compared to ESTs from public databases (e.g., GenBank, Merck/Wash U.), and a proprietary EST database (LIFESEQ®, Incyte Pharmaceuticals, Palo Alto, Calif.), using the computer program BLAST or BLAST2 [Altschul et al., *Methods in Enzymology,* 266:460-480 (1996)]. The ESTs were clustered and assembled into a consensus DNA sequence using the computer program "phrap" (Phil Green, University of Washington, Seattle, Wash.; http://bozeman-.mbt.washington.edu/phrap.docs/phrap.html). This consensus sequence is designated herein as "DNA78722". Other novel sequences were identified in the alignment of sequences which formed DNA78722. Based on the DNA78722 consensus sequence, oligonucleotides were synthesized for use as probes to isolate a clone of the full-length coding sequence for PRO1886 from a human aortic endothelial cells cDNA library.

The full length DNA80796-2523 clone shown in FIG. 45 contained a single open reading frame with an apparent translational initiation site at nucleotide positions 73-75 and ending at the stop codon found at nucleotide positions 1022-1025 (FIG. 45; SEQ ID NO:45). The predicted polypeptide precursor (FIG. 46, SEQ ID NO:46) is 316 amino acids long. Other features are indicated in FIG. 46. PRO1886 has a calculated molecular weight of approximately 36045 daltons and an estimated pI of approximately 8.18. Clone DNA80796-2523 (UNQ870), designated as DNA80796-2523 has been deposited with the ATCC on Dec. 22, 1998 and is assigned ATCC deposit no. 203555.

An analysis of the Dayhoff database (version 35.45 SwissProt 35), using a WU-BLAST2 sequence alignment analysis of the full-length sequence shown in FIG. 46 (SEQ ID NO:46), revealed sequence identity between the PRO1886 amino acid sequence and the following Dayhoff sequences: CELT26A8_2 and S43230.

Example 27

Isolation of cDNA Clones Encoding Human PRO1891 Polypeptides [UNQ873]

The extracellular domain (ECD) sequences (including the secretion signal sequence, if any) from about 950 known secreted proteins from the Swiss-Prot public database were used to search EST databases. The EST databases included public EST databases (e.g., GenBank), and a proprietary EST database (LIFESEQ®, Incyte Pharmaceuticals, Palo Alto, Calif.). The search was performed using the computer program BLAST or BLAST2 [Altschul et al., *Methods in Enzymology*, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence encoding PRO1891 was assembled relative to other EST sequences using phrap. This consensus sequence is designated herein "DNA44813"

Based on the DNA44813 consensus sequence, oligonucleotides were synthesized: 1) to identify by PCR a cDNA library that contained the sequence of interest, and 2) for use as probes to isolate a clone of the full-length coding sequence for PRO1891. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

PCR primers (forward and reverse) were synthesized:
forward PCR primers:
(44813.f1; SEQ ID NO: 129)
GCTGCTTTGCTCACAACTGCTCGC, (44813.f2; SEQ ID NO: 130)
CATGACACCTTCCTGCTG
and (44813.f3; SEQ ID NO: 131)
CAGCCATGGGTGACTGTGACCTCC reverse PCR primers:
(44813.r1; SEQ ID NO: 132)
CTCCTGGGAGTCGGTAGCAACACC, (44813.r2; SEQ ID NO: 133)
GGGAGGTCACAGTCACCC
and (44813.r3; SEQ ID NO: 134)
GGCTGGGCTTTCCACCCTGGCAC.

Additionally, a synthetic oligonucleotide hybridization probe was constructed from the consensus DNA44813 sequence which had the following nucleotide sequence:

hybridization probe:
(44813.p1; SEQ ID NO: 135)
CAGCCATGGGTGACTGTGACCTCCCTGAGTTTTGCACGGG.

In order to screen several libraries for a source of a full-length clone, DNA from the libraries was screened by PCR amplification with the PCR primer pair identified above. A positive library was then used to isolate clones encoding the PRO1891 gene using the probe oligonucleotide and one of the PCR primers.

RNA for construction of the cDNA libraries was isolated human bone marrow. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

DNA sequencing of the clones isolated as described above gave the full-length DNA sequence for PRO1891, designated herein as "DNA76788-2526" (FIG. 47; SEQ ID NO:47), and the derived protein sequence for PRO1891.

The entire coding sequence of PRO1891 is shown in FIG. 47 (SEQ ID NO:47). Clone DNA76788-2526 contains a single open reading frame with an apparent translational initiation site at nucleotide positions 114-116, and an apparent stop codon at nucleotide positions 2553-2555. The predicted polypeptide precursor is 813 amino acids long. The full-length PRO1891 protein shown in FIG. 48 (SEQ ID NO:48) has an estimated molecular weight of about 87,739 daltons and a pI of about 6.94. Additional features include a signal peptide at about amino acids 1-27; a transmembrane domain at about amino acids 702-720; potential N-glycosylation sites at about amino acids 109-112, 145-148, 231-234, 276-279, and 448-451; a tyrosine kinase phosphorylation site at about amino acids 236-243; potential N-myristoylation sites at about amino acids 29-34, 285-190, 195-200, 308-313, 318-323, 326-331, 338-343, 370-375, 400-405, 402-407, 454-

459, 504-509, 510-515, 517-522, 580-585, 601-606, 661-666, 687-692, 717-722, and 719-724; an amidation site at about amino acids 200-203; and a neutral zinc metallopeptidases, zinc-binding region signature at about amino acids 342-351.

An analysis of the Dayhoff database (version 35.45 SwissProt 35), using a WU-BLAST2 sequence alignment analysis of the full-length sequence shown in FIG. 48 (SEQ ID NO:48), revealed significant homology between the PRO1891 amino acid sequence and the following Dayhoff sequences: XLU66003_1, P_W25716, AF023477_1, P_WO1825, P_R99801, P_W25722, P_W44120, P_R67759, AF029899_1, and P_W14772.

Clone DNA76788 (UNQ873), designated as DNA76788-2526 was deposited with the ATCC on Dec. 22, 1998 and is assigned ATCC deposit no. 203551.

Example 28

Isolation of cDNA Clones Encoding Human PRO4409 Polypeptides [UNQ1934]

DNA88004-2575 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash. The consensus sequence obtained therefrom is herein designated DNA79305. In light of DNA79305, a human brain library cDNA library was screened with the following two primers to identify DNA88004-2575: 5'GAGCTGAAGT-CAGCCTTTGAG3' (SEQ ID NO:136, forward) and 5'CTCTGCAGAAGTCTCGTTCC3' (SEQ ID NO:137, reverse).

The full length clone shown in FIG. 49 contained a single open reading frame with an apparent translational initiation site at nucleotide positions 337-339 and ending at the stop codon found at nucleotide positions 1171-1173 (FIG. 49; SEQ ID NO:49). The predicted polypeptide precursor (FIG. 50, SEQ ID NO:50) is 278 amino acids long. PRO4409 has a calculated molecular weight of approximately 30748 daltons and an estimated pI of approximately 5.47.

An analysis of the Dayhoff database (version 35.45 SwissProt 35), using a WU-BLAST2 sequence alignment analysis of the full-length sequence shown in FIG. 50 (SEQ ID NO:50), revealed homology between the PRO4409 amino acid sequence and the following Dayhoff sequences (sequences nad related text incorporated herein): HGS_RF300, HSU80744_1, CEC11H1_7, CEVK04G11_2, HGS_RF177, CEF09E8_2, AF034802_1, P_R51227, I46014 and CYL2_BOVIN.

Clone DNA88004-2575 (UNQ1934), designated as DNA88004-2575 was deposited with the ATCC on Mar. 30, 1999 and is assigned ATCC deposit no. 203890.

Example 29

Isolation of cDNA Clones Encoding Human PRO5725 Polypeptides [UNQ2446]

An expressed sequence tag (EST) DNA database (LIFESEQ®, Incyte Pharmaceuticals, Palo Alto, Calif.) was searched and an EST was identified which showed homology to Neuritin. EST clone no. 3705684 was then purchased from LIFESEQ®, Incyte Pharmaceuticals, Palo Alto, Calif. and the cDNA insert of that clone was obtained and sequenced in entirety.

The entire nucleotide sequence of the clone, designated herein as DNA92265-2669, is shown in FIG. 51 (SEQ ID NO: 51). The DNA92265-2669 clone contains a single open reading frame with an apparent translational initiation site at nucleotide positions 27-29 and a stop signal at nucleotide positions 522-524 (FIG. 51, SEQ ID NO:51). The predicted polypeptide precursor is 165 amino acids long, has a calculated molecular weight of approximately 17,786 daltons and an estimated pI of approximately 8.43. Analysis of the full-length PRO5725 sequence shown in FIG. 52 (SEQ ID NO:52) evidences the presence of a variety of important polypeptide domains as shown in FIG. 52, wherein the locations given for those important polypeptide domains are approximate as described above. Clone DNA92265-2669 has been deposited with ATCC on Jun. 22, 1999 and is assigned ATCC deposit no. PTA-256.

An analysis of the Dayhoff database (version 35.45 SwissProt 35), using the ALIGN-2 sequence alignment analysis of the full-length sequence shown in FIG. 52 (SEQ ID NO:52), evidenced sequence identity between the PRO5725 amino acid sequence and the following Dayhoff sequences: RNU88958_1; P_W37859; P_W37858; JC6305; HGS_RE778; HGS_RE777; P_W27652; P_W44088; HGS_RE776; and HGS_RE425.

Example 30

Isolation of cDNA Clones Encoding Human PRO6097 Polypeptides [UNQ2545]

1. Preparation of Oligo dT Primed cDNA Library mRNA was isolated from human SK-Lu-1 adenocarcinoma cell line tissue using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY. 0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with the amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL+, SUC+, GAL+. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4-p) or the complex formation of these proteins may also be preferably employed in combination with the amylase-expressing yeast.

Transformation was performed based on the protocol outlined by Gietz et al., *Nucl. Acid. Res.*, 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about 2×10$^6$ cells/ml (approx. OD$_{600}$=0.1) into fresh YEPD broth (500 ml) and regrown to 1×10$^7$ cells/ml (approx. OD$_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM Li$_2$OOCCH$_3$), and resuspended into LiAc/TE (2.5 ml).

Transformation took place by mixing the prepared cells (100 µl) with freshly denatured single stranded salmon testes DNA (Lofstrand Labs, Gaithersburg, Md.) and transforming DNA (1 µg, vol. <10 µl) in microfuge tubes. The mixture was mixed briefly by vortexing, then 40% PEG/TE (600 µl, 40% polyethylene glycol-4000, 10 mM Tris-HCl, 1 mM EDTA, 100 mM Li$_2$OOCCH$_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 µl, 10 mM Tris-HCl, 1 mM EDTA pH 7.5) followed by recentrifugation. The cells were then diluted into TE (1 ml) and aliquots (200 µl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.*, 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing: 0.5 µl Klentaq (Clontech, Palo Alto, Calif.); 4.0 µl 10 mM dNTP's (Perkin Elmer-Cetus); 2.5 µl Klentaq buffer (Clontech); 0.25 µl forward oligo 1; 0.25 µl reverse oligo 2; 12.5 µl distilled water. The sequence of the forward oligonucleotide 1 was:

(SEQ ID NO: 67)
5'-TGTAAAACGACGGCCAGT<u>TAAATAGACCTGCAATTATTAATCT</u>-3'

The sequence of reverse oligonucleotide 2 was:

(SEQ ID NO: 68)
5'-CAGGAAACAGCTATGACC<u>ACCTGCACACCTGCAAATCCATT</u>-3'

PCR was then performed as follows:

| a. |  | Denature | 92° C., 5 minutes |
|---|---|---|---|
| b. | 3 cycles of: | Denature | 92° C., 30 seconds |
|  |  | Anneal | 59° C., 30 seconds |
|  |  | Extend | 72° C., 60 seconds |
| c. | 3 cycles of: | Denature | 92° C., 30 seconds |
|  |  | Anneal | 57° C., 30 seconds |
|  |  | Extend | 72° C., 60 seconds |
| d. | 25 cycles of: | Denature | 92° C., 30 seconds |
|  |  | Anneal | 55° C., 30 seconds |
|  |  | Extend | 72° C., 60 seconds |
| e. |  | Hold | 4° C. |

The underlined regions of the oligonucleotides disclosed above annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 µl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

5. Identification of Full-length Clone

A cDNA sequence isolated in the above screen is herein designated DNA84712. Probes were then generated from the sequence of the DNA84712 molecule and used to screen a human SK-Lu-1 adenocarcinoma cell line library (247) prepared as described in paragraph 1 above. The cloning vector was pRK5B (pRK5B is a precursor of pRK5D that does not contain the SfiI site; see, Holmes et al., *Science*, 253:1278-1280 (1991)), and the cDNA size cut was less than 2800 bp. The oligonucleotides probes were synthesized: 1) to identify by PCR a cDNA library that contained the sequence of interest, and 2) for use as probes to isolate a clone of the full-length coding sequence for PRO6097. Forward and reverse PCR primers generally range from 20 to 30 nucleotides and are often designed to give a PCR product of about 100-1000 bp in length. The probe sequences are typically 40-55 bp in length. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

The oligonucleotide probes employed were as follows:

```
forward PCR primer
                                        (SEQ ID NO: 138)
5'-CTGACCGGTCCGCTCATGG-3' reverse PCR primer
                                        (SEQ ID NO: 139)
5'-CAGCATGCTTTCCGCGAAGTC-3' hybridization probe
```

```
                                        (SEQ ID NO: 140)
5'-GGCAGGAAGGCCAGGGGTGCTGAGTTCTTCACCTCCTTTT

AGACTG3'
```

A full length clone was identified that contained a single open reading frame with an apparent translational initiation site at nucleotide positions 158-160 and a stop signal at nucleotide positions 1727-1729 (FIG. 55, SEQ ID NO: 55). The predicted polypeptide precursor is 523 amino acids long, has a calculated molecular weight of approximately 58,887 daltons and an estimated pI of approximately 9.57. Analysis of the full-length PRO6097 sequence shown in FIG. 56 (SEQ ID NO: 56) evidences the presence of a variety of important polypeptide domains as shown in FIG. 56, wherein the locations given for those important polypeptide domains are approximate as described above. Clone DNA107701-2711 has been deposited with ATCC on Aug. 3, 1999 and is assigned ATCC Deposit No. PTA-487.

An analysis of the Dayhoff database (version 35.45 SwissProt 35), using the ALIGN-2 sequence alignment analysis of the full-length sequence shown in FIG. 56 (SEQ ID NO: 56), evidenced sequence identity between the PRO6097 amino acid sequence and the following Dayhoff sequences: YMB8_YEAST; S49759; ATF10N7_5; SPBC405_3; S69718; H69798; D71226; U95370_5; A69780; B69461.

Example 31

Isolation of cDNA Clones Encoding Human PRO7425 Polypeptides [UNQ2966]

The extracellular domain (ECD) sequences (including the secretion signal sequence, if any) from about 950 known secreted proteins from the Swiss-Prot public database were used to search EST databases. The EST databases included (1) public EST databases (e.g., Merck/Washington University), (2) a proprietary EST database (LIFESEQ®, Incyte Pharmaceuticals, Palo Alto, Calif.), (3) a proprietary EST database from Genentech. The search was performed using the computer program BLAST or BLAST2 [Altschul et al., *Methods in Enzymology*, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA86620. In some cases, the DNA86620 consensus sequence derives from an intermediate consensus DNA sequence which was extended using repeated cycles of BLAST and phrap to extend that intermediate consensus sequence as far as possible using the sources of EST sequences discussed above.

Based on the DNA86620 consensus sequence, and in light of an observed sequence homology between the DNA86620 sequence and an EST sequence encompassed within clone no. 4797137 from the LIFESEQ®, Incyte Pharmaceuticals, Palo Alto, Calif. database, clone no. 4797137 was purchased and the cDNA insert was obtained and sequenced. It was found herein that that cDNA insert encoded a full-length protein. The sequence of this cDNA insert is shown in FIG. 57 and is herein designated as DNA108792-2753.

The full length clone identified above contained a single open reading frame with an apparent translational initiation site at nucleotide positions 3-5 and a stop signal at nucleotide positions 708-710 (FIG. 57, SEQ ID NO: 57). The predicted polypeptide precursor is 235 amino acids long, has a calculated molecular weight of approximately 25989 daltons and an estimated pI of approximately 8.32. Analysis of the full-length PRO7425 sequence shown in FIG. 58 (SEQ ID NO: 58) evidences the presence of a variety of important polypeptide domains as shown in FIG. 58, wherein the locations given for those important polypeptide domains are approximate as described above. Clone DNA108792-2753 has been deposited with ATCC on Aug. 31, 1999 and is assigned ATCC Deposit No. PTA-617.

An analysis of the Dayhoff database (version 35.45 SwissProt 35), using the ALIGN-2 sequence alignment analysis of the full-length sequence shown in FIG. 58 (SEQ ID NO: 58), evidenced sequence identity between the PRO7425 amino acid sequence and the following Dayhoff sequences: P_Y11831; P_Y11619; MYP0_HUMAN; MYP0_MOUSE; HSPMPO2__1; AF087020__1; GEN13751; AF007783__1; P_W14146; XLU43330__1.

Example 32

Isolation of cDNA Clones Encoding Human PRO10102 Polypeptides [UNQ3103]

DNA 129542-2808 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the LIFESEQ® (Incyte Pharmaceuticals, Inc., Palo Alto, Calif.) database, designated herein as 166950H1. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA112560.

In light of an observed sequence homology between the DNA112560 sequence and an EST sequence encompassed within clone no. 166950 from LIFESEQ® (Incyte Pharmaceuticals, Inc., Palo Alto, Calif.) database, clone no. 166950 was purchased and the cDNA insert was obtained and sequenced. It was found herein that that cDNA insert encoded a full-length protein. The sequence of this cDNA insert is shown in FIG. 59 and is herein designated as DNA129542-2808.

Clone DNA129542-2808 contains a single open reading frame with an apparent translational initiation site at nucleotide positions 58-60 and ending at the stop codon at nucleotide positions 1786-1788 (FIG. 59; SEQ ID NO:59). The predicted polypeptide precursor is 576 amino acids long (FIG. 60; SEQ ID NO:60). The full-length PRO10102 protein shown in FIG. 60 has an estimated molecular weight of about 62128 daltons and a pI of about 7.41. Analysis of the full-length PRO10102 sequence shown in FIG. 60 (SEQ ID NO:60) evidences the presence of a variety of important polypeptide domains as shown in FIG. 60, wherein the locations given for those important polypeptide domains are approximate as described above. Clone DNA129542-2808 has been deposited with ATCC on Feb. 23, 2000 and is assigned ATCC deposit no. PTA-1405.

An analysis of the Dayhoff database (version 35.45 SwissProt 35), using the ALIGN-2 sequence alignment analysis of the full-length sequence shown in FIG. 60 (SEQ ID NO:60), evidenced sequence identity between the PRO10102 amino acid sequence and the following Dayhoff sequences: rTNFSF3L__1, P_Y00771, AC007785__2, AF076483__1, P_W23722, P_W37837, P_Y00770 and AB016605__1. The PRO10102 polypeptide is much longer than the sequences with which it shares homology. For example, it has 378 amino acid residues at the N-terminal end that are not homologous to rTNFSF3L__1 and P_Y00771.

Example 33

Isolation of cDNA Clones Encoding Human PRO10282 Polypeptides [UNQ3126]

AcDNA clone (DNA148380-2827) encoding a native human PRO10282 polypeptide was identified using a yeast screen, in a human cDNA library that preferentially represents the 5' ends of the primary cDNA clones. Clone DNA148380-2827-1 contains a single open reading frame with an apparent translational initiation site at nucleotide positions 49-51 and ending at the stop codon at nucleotide positions 2050-2052 (FIG. 61; SEQ ID NO:61). The predicted polypeptide precursor is 667 amino acids long (FIG. 62; SEQ ID NO:62). The full-length PRO10282 protein shown in FIG. 62 has an estimated molecular weight of about 73502 daltons and apI of about 9.26. Analysis of the full-length PRO10282 sequence shown in FIG. 62 (SEQ ID NO:62) evidences the presence of a variety of important polypeptide domains as shown in FIG. 62, wherein the locations given for those important polypeptide domains are approximate as described above. Clone DNA148380-2827 has been deposited with ATCC on Jan. 11, 2000 and is assigned ATCC deposit no. PTA-1181.

An analysis of the Dayhoff database (version 35.45 SwissProt 35), using the ALIGN-2 sequence alignment analysis of the full-length sequence shown in FIG. 62 (SEQ ID NO:62), evidenced sequence identity between the PRO10282 amino acid sequence and the following Dayhoff sequences: AF062476, P_W88559 and HGS_RE259.

Example 34

Isolation of cDNA Clones Encoding Human PRO779 Polypeptides [UNQ455]

Human fetal heart and human fetal lung 1gt10 bacteriophage cDNA libraries (both purchased from Clontech) were screened by hybridization with synthetic oligonucleotide probes based on an EST (GenBank locus W71984), which showed some degree of homology to the intracellular domain (ICD) of human TNFR1 and CD95. W71984 is a 523 bp EST, which in its −1 reading frame has 27 identities to a 43 amino acid long sequence in the ICD of human TNFR1. The oligonucleotide probes used in the screening were 27 and 25 bp long, respectively, with the following sequences:

5'-GGCGCTCTGGTGGCCCTTGCAGAAGCC-3'    (SEQ ID NO: 141)

5'-TTCGGCCGAGAAGTTGAGAAATGTC-3'    (SEQ ID NO: 142)

Hybridization was done with a 1:1 mixture of the two probes overnight at room temperature in buffer containing 20% formamide, 5×SSC, 10% dextran sulfate, 0.1% NaPiPO4,) 0.05 M NaPO4, 0.05 mg salmon sperm DNA, and 0.1% sodium dodecyl sulfate (SDS), followed consecutively by one wash at room temperature in 6×SSC, two washes at 37 C in 1×SSC/0.1% SDS, two washes at 37 C in 0.5×SSC/0.1% SDS, and two washes at 37 C in 0.2×SSC/0.1% SDS. One positive clone from each of the fetal heart (FH20A.57) and fetal lung (FL8A.53) libraries were confirmed to be specific by PCR using the respective above hybridization probes as primers. Single phage plaques containing each of the positive clones were isolated by limiting dilution and the DNA was purified using a Wizard lambda prep DNA purification kit (Promega).

The cDNA inserts were excised from the lambda vector arms by digestion with EcoRI, gel-purified, and subcloned into pRK5 that was predigested with EcoRI. The clones were then sequenced in entirety.

Clone (FH20A.57) DNA58801-1052 (also referred to as Apo 3 clone FH20.57 deposited as ATCC 55820, as indicated below) contains a single open reading frame with an apparent translational initiation site at nucleotide positions 103-105 and ending at the stop codon found at nucleotide positions 1354-1356 [FIG. 65, SEQ ID NO:65]. The predicted polypeptide precursor is 417 amino acids long (FIG. 66; SEQ ID NO:66). The full-length PRO779 protein shown in FIG. 66 has an estimated molecular weight of about 45,000 daltons and a pI of about 6.40. Analysis of the full-length PRO779 sequence shown in FIG. 66 (SEQ ID NO:66) evidences the presence of a variety of important polypeptide domains, wherein the locations given for those important polypeptide domains are approximate as described above. Analysis of the full-length PRO779 sequence shown in FIG. 66 evidences the presence of the following: a signal peptide from about amino acid 1 to about amino acid 24; a transmembrane domain from about amino acid 199 to about amino acid 219; N-glycosylation sites from about amino acid 67 to about amino acid 71 and from about amino acid 106 to about amino acid 110; a cAMP- and cGMP-dependent protein kinase phosphorylation site from about amino acid 157 to about amino acid 161; a tyrosine kinase phosphorylation site from about amino acid 370 to about amino acid 377; N-myristoylation sites from about amino acid 44 to about amino acid 50, from about amino acid 50 to about amino acid 56, from about amino acid 66 to about amino acid 72, from about amino acid 116 to about amino acid 122, from about amino acid 217 to about amino acid 223, from about amino acid 355 to about amino acid 361, from about amino acid 391 to about amino acid 397, and from about amino acid 401 to about amino acid 407; and a prokaryotic membrane lipoprotein lipid attachment site from about amino acid 177 to about amino acid 188. Clone DNA58801-1052 has been deposited with ATCC on Sep. 5, 1996 and is assigned ATCC deposit no. 55820.

The ECD contains 4 cysteine-rich repeats which resemble the corresponding regions of human TNFR1 (4 repeats), of human CD95 (3 repeats) and of the other known TNFR family members. The ICD contains a death domain sequence that resembles the death domains found in the ICD of TNFR1 and CD95 and in the cytoplasmic death signaling proteins such as human FADD/MORT1, TRADD, RIP, and *Drosophila* Reaper. Both globally and in individual regions, PRO779 (Apo 3) is more closely related to TNFR1 than to CD95; the respective amino acid identities are 29.3% and 22.8% overall, 28.2% and 24.7% in the ECD, 31.6% and 18.3% in the ICD, and 47.5% and 20% in the death domain.

Example 35

Generation and Analysis of Mice Comprising PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244. PRO1298, PRO1313, PRO1570, PRO1886, PRO1891, PRO4409, PRO5725, PRO5994, PRO6097, PRO7425, PRO10102, PRO10282, PRO61709 or PRO779 Gene Disruptions To investigate the role of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides, disruptions in PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 genes were produced by homologous recombination or retroviral insertion techniques. Specifically, transgenic mice comprising disruptions in PRO196, PRO217, PRO231, PRO236, PRO245, PRO246, PRO258, PRO287, PRO328, PRO344, PRO357, PRO526, PRO724, PRO731, PRO732, PRO1003, PRO104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 genes (i.e., knockout mice) were created by either gene targeting or gene trapping. Mutations were confirmed by southern blot analysis to confirm correct targeting on both the 5' and 3' ends. Gene-specific genotyping was also performed by genomic PCR to confirm the loss of the endogenous native transcript as demonstrated by RT-PCR using primers that anneal to exons flanking the site of insertion. Targeting vectors were electroporated into 129 strain ES cells and targeted clones were identified. Targeted clones were microinjected into host blastocysts to produce chimeras. Chimeras were bred with C57 animals to produce F1 heterozygotes. Heterozygotes were intercrossed to produce F2 wild-type, heterozygote and homozygote cohorts which were used for phenotypic analysis. Rarely, if not enough F1 heterozygotes were produced, the F1 hets were bred to wild-type C57 mice to produce sufficient heterozygotes to breed for cohorts to be analyzed for a phenotype. All phenotypic analysis was performed from 12-16 weeks after birth.

Overall Summary of Results

35.1. Generation and Analysis of Mice Comprising DNA22779-1130 (UNQ170) Gene Disruptions In these knockout experiments, the gene encoding PRO196 polypeptides (designated as DNA22779-1130) (UNQ170) was disrupted. The gene specific information for these studies is as follows: the mutated mouse gene corresponds to nucleotide reference: NM_011923 or ACCESSION:NM_011923 NID: gi 6753119 ref NM_011923.1 *Mus musculus* angiopoietin-like 2 (Angptl2); protein reference: Q9R045 or ACCESSION:Q9R045 NID: *Mus musculus* (Mouse). ANGIOPOIETIN-RELATED PROTEIN 2 PRECURSOR (ANGIOPOIETIN-LIKE 2). MOUSESPTRNRDB; the human gene sequence reference: NM_012098 or ACCESSION:NM_012098 NID: gi 6912235 ref NM_012098.1 *Homo sapiens* angiopoietin-like 2 (ANGPTL2); the human protein sequence corresponds to reference: Q9UKU9 or ACCESSION:Q9UKU9 NID: *Homo sapiens* (Human). ANGIOPOIETIN-RELATED PROTEIN 2 PRECURSOR (ANGIOPOIETIN-LIKE 2). HUMANSPTRNRDB.

The mouse gene of interest is angiopoietin-like 2 (Angptl2), ortholog of human ANGPTL2. Aliases include angiopoietin related protein 2 (Arp2), HARP, and MGC8889. Angptl2 is a secreted glycoprotein hormone expressed in vascular endothelial cells, vascular smooth muscle, heart, small intestine, spleen, stomach, colon, ovary, adrenal gland, skeletal muscle, and prostate. Although Angptl2 is structurally similar to the angiopoietin family of hormones, Angptl2 does not bind to angiopoietin receptors Tie1 and Tie2. Angptl2 induces sprouting in endothelial cells, which is consistent with the role of angiopoietins in blood vessel formation (Kim et al., *J Biol Chem*, 274(37):26523-8 (1999)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation.

|          | wt   | het | hom  | Total |
|----------|------|-----|------|-------|
| Observed | 23   | 32  | 23   | 78    |
| Expected | 19.5 | 39  | 19.5 | 78    |

Chi-Sq. = 2.51
Significance = 0.28467
(hom/n) = 0.29
Avg. Litter Size = 8

Mutation Type: Homologous Recombination (standard).

Coding exon 1 was targeted (NCBI accession NM_011923.1).

Wild-type expression of the target gene was detected in embryonic stem (ES) cells and in all 13 adult tissue samples tested by RT-PCR, except skeletal muscle, bone, and adipose. Disruption of the target gene was confirmed by Southern hybridization analysis.

35.1.1. Phenotypic Analysis (for Disrupted Gene: DNA22779-1130 (UNQ170)

(a) Overall Phenotypic Summary:

Mutation of the gene encoding the ortholog of human angiopoietin-like 2 (ANGPTL2) resulted in decreased mean serum MCP-1, TNF-alpha, and IL-6 responses to LPS challenge in (−/−) mice. The (−/−) mice also exhibited significant growth retardation marked by decreased total tissue mass, total body fat, decreased body weight and length as well as decreased mean vertebral trabecular bone measurements. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACScalibur instrument.

Results:

The (−/−) mice exhibited a decreased mean serum MCP-1, IL-6 and TNF-alpha response to LPS challenge when compared with their (+/+) littermates and the historical mean.

Analyzed wt/het/hom: 6/4/10

In summary, the LPS endotoxin challenge demonstrated that knockout mice deficient in the gene encoding PRO196 polypeptides exhibit immunological abnormalities when compared with their wild-type littermates. In particular, the mutant mice exhibited a decreased ability to elicit an immunological response (MCP-1, TNF-alpha and IL-6 production) when challenged with the LPS endotoxin indicating a deficiency in the proinflammatory response. IL-6 contributes to the later stages of B cell activation. In addition, IL-6 plays a critical role in inducing the acute phase response and systemic inflammation. This suggests that PRO196 polypeptides or agonists thereof would stimulate the immune system and would find utility in the cases wherein this effect would be beneficial to the individual such as in the case of leukemia, and other types of cancer, and in immunocompromised patients, such as AIDS sufferers. Accordingly, inhibitors or antagonists to PRO196 polypeptides would play a role in inhibiting the immune response and would be useful candidates for suppressing harmful immune responses, e.g. in the case of graft rejection or graft-versus-host diseases.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited decreased mean body weight and mean body length (at least two (2) standard deviations (SD) below normal especially in the first eight (8) weeks) when compared with their gender-matched (+/+) littermates and the historical means.

Analyzed wt/het/hom: 23/32/23

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included: DEXA for measurement of bone mineral density on femur and vertebra MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited decreased mean total tissue mass and total body fat when compared with their gender-matched (+/+) littermates and the historical means.

Micro-CT: The (−/−) mice exhibited a decreased mean vertebral trabecular bone volume, thickness, and connectivity density when compared with their gender-matched (+/+) littermates and the historical means.

Analyzed wt/het/hom: 4/4/10

Summary

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO196 polypeptides or agonists thereof play a role in maintaining bone homeostasis. In addition, PRO196 or its encoding gene would be useful in bone healing or useful for the treatment of osteoarthritis or osteoporosis; whereas antagonists to PRO196 or its encoding gene would lead to abnormal or pathological bone disorders including inflammatory diseases associated with abnormal bone metabolism such as arthritis, osteoporosis, and osteopenia.

The (−/−) mice analyzed by DEXA exhibited significant growth retardation marked by a notably decreased total tissue mass and total body fat as well as reduction in body weight and length when compared with their (+/+) littermates. These results may be due to problems associated with the hypothalamic-pituitary axis which can affect bone growth. This in conjunction with the observations of decreased bone measurements suggest a tissue wasting condition such as cachexia. Thus, PRO196 polypeptides or agonists thereof would be useful in the treatment of bone disorders but would also be useful for treating growth disorders or for the prevention of cachexia or other tissue wasting diseases.

35.2. Generation and Analysis of Mice Comprising DNA33094-1131 (UNQ191) Gene Disruptions In these knockout experiments, the gene encoding PRO217 polypeptides (designated as DNA33094-1131) (UNQ191) was disrupted. The gene specific information for these studies is as follows: the mutated mouse gene corresponds to nucleotide reference: NM_011915 or ACCESSION:NM_011915 NID:6755998 Mus musculus Mus musculus Wnt inhibitory factor 1 (Wif1); protein reference: Q9WUA1 or ACCESSION:Q9WUA1 NID: Mus musculus (Mouse). WNT INHIBITORY FACTOR 1 PRECURSOR (WIF-1). MOUSESPTRNRDB; the human gene sequence reference: NM_007191 or ACCESSION:NM_007191 NID:18379354 Homo sapiens Homo sapiens WNT inhibitory factor 1 (WIF1); the human protein sequence corresponds to reference: Q9Y5W5 or ACCESSION:Q9Y5W5 NID: Homo sapiens (Human). Wnt inhibitory factor 1 precursor (WIF-1). HUMANSPTRNRDB.

The mouse gene of interest is Wif1 (Wnt inhibitory factor 1), ortholog of human WIF1. Aliases include WIF-1 and Wnt inhibitory factor-1. WIF1 is a secreted protein expressed during embryonic development that binds with Wnt proteins, disrupting activation of their cognate receptors. Wnt proteins are extracellular signaling molecules involved in developmental processes (Hseih et al., Nature, 398(6726):431-6 (1999). WIF1 is down-regulated in prostate, breast, lung, and bladder cancer but up-regulated in colon adenocarcinoma cell lines, suggesting that alterations in WIF1 expression may be related to tumorigenesis in these tissues (Wissmann et al., J. Pathol, 201(2):204-12 (2003); Cebrat et al., Cancer Lett, 206(1):107-13 (2004)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation.

|  | wt | het | hom | Total |
|---|---|---|---|---|
| Observed | 24 | 35 | 20 | 79 |
| Expected | 19.75 | 39.5 | 19.75 | 79 |

Chi-Sq. = 1.43
Significance = 0.48910
(hom/n) = 0.25
Avg. Litter Size = 8

Mutation Type: Homologous Recombination (standard)
Coding exon 1 was targeted (NCBI accession NM_011915.1).
Wild-type expression of the target gene was detected in brain, spinal cord, eye, and heart among the 13 adult tissue samples tested by RT-PCR.
Disruption of the target gene was confirmed by Southern hybridization analysis.

35.2.1. Phenotypic Analysis (for Disrupted Gene: DNA33094-1131 (UNQ191)

(a) Overall Phenotypic Summary:

Mutation of the gene encoding the ortholog of human Wnt inhibitory factor 1 (WIF1) resulted in growth retardation accompanied by decreased bone measurements in (−/−) mice. In addition, mutant (−/−) mice exhibited an increased IgG2a response to an ovalbumin challenge. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immuno-dominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Analyzed wt/het/hom: 8/4/9

Results of this Challenge:

The (−/−) mice exhibited an increased mean serum IgG2a response to ovalbumin challenge when compared with their (+/+) littermates and the historical means. Thus, these knockout mice exhibited an increased ability to elicit an OVA-specific antibody response to the T-cell dependent OVA antigen or a positive immunological phenotype (proinflammatory response). Thus, the gene encoding PRO217 polypeptides would be expected to lead to inhibition of the proinflammatory response which could be caused by Th, B or plasma cell defects.

In summary, the ovalbumin challenge studies indicate that knockout mice deficient in the gene encoding PRO217 polypeptides exhibit immunological abnormalities when compared with their wild-type littermates. In particular, the mutant mice exhibited an increased ability to elicit an immunological response when challenged with the T-cell dependent OVA antigen. Thus, inhibitors or antagonists of PRO217 polypeptides would be useful for stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO217 polypeptides or agonists thereof would be useful for inhibiting the immune response and thus would be useful candidates for suppressing harmful immune responses, e.g. in the case of graft rejection or graft-versus-host diseases.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited decreased mean body weight and mean body length (one (1) standard deviation (SD) below historic mean in weight and two (2) standard deviations (SD) below historical mean in length) when compared with their gender-matched (+/+) littermates and the historical means.

Heart Rate: The heart rate decreased 1-2 standard deviations relative to the historic controls in both male and female knockout (−/−) mice.

Fertility: The single male (−/−) mouse (M-151) available for analysis was infertile.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

The (−/−) mice exhibited decreased mean total tissue mass and lean body mass and decreased mean bone mineral content and bone mineral content when compared with their gender-matched (+/+) littermates and the historical means. Analyzed wt/het/hom: 4/4/8

Summary

The (−/−) mice analyzed by DEXA exhibited notably decreased total tissue mass and lean body mass as well as decreased bone measurements when compared with their (+/+) littermates, suggestive of growth retardation in these mutants. This in conjunction with the observations of decreased body weight and length suggest a tissue wasting condition such as cachexia or other growth related disorders. Thus, PRO217 polypeptides or agonists thereof would be useful in the treatment or prevention of growth disorders including cachexia or other tissue wasting diseases.

35.3. Generation and Analysis of Mice Comprising DNA34434-1139 (UNQ205) Gene Disruptions In these knockout experiments, the gene encoding PRO231 polypeptides (designated as DNA34434-1139) (UNQ205) was disrupted. The gene specific information for these studies is as follows: the mutated mouse gene corresponds to nucleotide reference: NM_019800 or ACCESSION:NM_019800 NID:9790058 *Mus musculus Mus musculus* acid phosphatase 6, lysophosphatidic (Acp6); protein reference: Q9JMG5 or ACCESSION:Q9JMG5 NID: *Mus musculus* (Mouse). MPACPL1. MOUSESPTRNRDB; the human gene sequence reference: NM_016361 or ACCESSION:NM_016361 NID: 21359910 *Homo sapiens Homo sapiens* LPAP for lysophosphatidic acid phosphatase (LOC51205); the human protein sequence corresponds to reference: Q9NPH0 or ACCESSION:Q9NPH0 NID: *Homo sapiens* (Human). HPACPL1 (cDNA FLJ20650 FIS, CLONE KAT01962) (LPAP FOR LYSOPHOSPHATIDIC ACID PHOSPHATASE) (LYSOPHOSPHATIDIC ACID PHOSPHATASE PRECURSOR). HUMANSPTRNRDB.

The targeted mouse gene is Acp6 (acid phosphatase 6, lysophosphatidic), which is the ortholog of human ACP6. Aliases include: ACPL1; mPACPL1; 5730559A09Rik; acid phosphatase like 1; LPAP; PACPL1; and likely ortholog of mouse acid phosphatase 6, lysophosphatidic. ACP6 is a cytoplasmic or mitochondrial enzyme that catalyzes the hydrolysis of lysophosphatidic acid to monoacylglycerol and phosphate. Expression of ACP6 is detected in a wide variety of tissues but is particularly high in kidney, heart, small intestine, muscle, and liver. The enzyme also has been detected in the cytosolic fraction of brain homogenates and in interstitial cells of Cajal (ICC), which function as pacemakers and mediators of motor neurotransmission in gastrointestinal smooth muscle. ACP6 may play a role in lipid metabolism (Hiroyama and Takenawa, *Biochem J*, 336 (Pt 2):483-9 (1998); Hiroyama and Takenawa, *J Biol Chem*, 274(41):29172-80 (1999); Takayama et al., *Gut* 50(6):790-6 (2002)).

Genetics Information:

|  | wt | het | hom | Total |
|---|---|---|---|---|
| Observed | 19 | 39 | 23 | 81 |
| Expected | 20.25 | 40.5 | 20.25 | 81 |

Chi-Sq. = 0.51
Significance = 0.77640
(hom/n) = 0.28
Avg. Litter Size = 8

Mutation Type: Retroviral Insertion (OST).
Retroviral insertion occurred in the intron between coding exons 1 and 2 (Accession: NM_019800.1).
Wild-type expression of the target gene was detected in all 13 adult tissue samples tested by RT-PCR, except skeletal muscle, bone, and adipose.
RT-PCR analysis revealed that the transcript was absent in the (−/−) mouse analyzed (M-46). Disruption of the target gene was confirmed by Inverse PCR.

35.3.1. Phenotypic Analysis (for Disrupted Gene: DNA34434-1139 (UNQ205)

(a) Overall Phenotypic Summary:

Mutation of the gene encoding the ortholog of human acid phosphatase 6, lysophosphatidic (ACP6) resulted in the observation of an increased mean platelet count in the (−/−) mutant mice compared with the wild-type (+/+) littermates. In addition, the (−/−) mutant mice appeared to have decreased total body fat (% and gram) as well as decreased total tissue mass indicative of tissue wasting diseases. Transcript was absent by RT-PCR.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

The (−/−) mice exhibited an increased mean platelet count when compared with their (+/+) littermates and the historical mean. Analyzed wt/het/hom: 7/5/8

Thus, mutant mice deficient in the DNA34434-1139 gene resulted in a phenotype related to coagulation disorders. In this regard, inhibitors or antagonists of PRO231 polypeptides would be useful in treating disorders related to abnormal blood coagulation such as hemophilia.

(c) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The (−/−) mice exhibited a decreased total body fat (% and g) and total tissue mass when compared with their gender-matched (+/+) littermates and the historical means.

Summary

These results demonstrate that knockout mutant mice exhibit abnormal body measurements with significant decreased body fat and mass suggestive of tissue wasting diseases. The (−/−) mice analyzed by DEXA exhibited notably decreased total tissue mass and lean body mass when compared with their (+/+) littermates, suggestive of growth retardation in these mutants. Thus, PRO231 polypeptides or agonists thereof would be useful for treating growth disorders or for the prevention of cachexia or other tissue wasting diseases.

35.4. Generation and Analysis of Mice Comprising DNA35599-1168 (UNQ210) Gene Disruptions In these knockout experiments, the gene encoding PRO236 polypeptides (designated as DNA35599-1168) (UNQ210) was disrupted. The gene specific information for these studies is as follows: the mutated mouse gene corresponds to nucleotide reference: NM_153803 or ACCESSION:NM_153803 NID: gi 24418924 ref NM_153803.1 *Mus musculus* hypothetical protein MGC47419 (MGC47419); protein reference: Q8CFT1 or ACCESSION:Q8CFT1 NID: *Mus musculus* (Mouse). Similar to RIKEN cDNA4921509F24 gene; the human gene sequence reference: NM_138342 or ACCESSION:NM_138342 NID: gi 24308391 ref NM_138342.1 *Homo sapiens* hypothetical protein BC008326 (LOC89944); the human protein sequence corresponds to reference: Q81W92 or ACCESSION:Q81W92 NID: *Homo sapiens* (Human). Hypothetical protein BC008326.

The mouse gene of interest is "cDNA sequence BC038479" (BC038479), ortholog of human "hypothetical protein BC008326." Aliases include hypothetical protein MGC47419.

BC038479 is a putative lysosomal enzyme that contains a glycosyl hydrolase family 35 domain. Proteins with this domain include beta-galactosidase, a lysosomal enzyme that catalyzes the cleavage of the terminal galactose from gangliosides, glycoproteins, and glycosaminoglycans (Pfam accession PF01301).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation.

|  | wt | het | hom | Total |
|---|---|---|---|---|
| Observed | 22 | 25 | 26 | 73 |
| Expected | 18.25 | 36.5 | 18.25 | 73 |

Chi-Sq. = 7.68
Significance = 0.02144
(hom/n) = 0.36
Avg. Litter Size = 7

Mutation Type: Homologous Recombination (standard)
Coding exon 1 was targeted (NCBI accession NM_153803.1).
Wild-type expression of the target gene was detected in embryonic stem (ES) cells and in all 13 adult tissue samples tested by RT-PCR.
Disruption of the target gene was confirmed by Southern hybridization analysis.

35.4.1. Phenotypic Analysis (for Disrupted Gene: DNA35599-1168 (UNQ210)

(a) Overall Phenotypic Summary:

Mutation of the gene encoding the ortholog of a hypothetical human protein (BC008326) resulted in decreased mean white blood cell (WBC) and lymphocyte counts and a decreased mean percentage of natural killer cells in (−/−) mice. The (−/−) mice also exhibited impaired glucose tolerance. In addition, the (−/−) mutant mice exhibited abnormal bone measurements indicative of osteoporosis. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

(1) Flourescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

(2) Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

The (−/−) mice exhibited decreased mean total white blood cell and absolute lymphocyte counts when compared with their (+/+) littermates and the historical means.

FACS analysis also demonstrated that (−/−) mice exhibited a decreased mean percentage of natural killer cells when compared with their (+/+) littermates and the historical mean. Analyzed wt/het/hom: 7/5/8

In summary, the hematology and FACS results indicate that the homozygous mutant mice have an impaired immune system, especially in view of the decreased total white blood cell count and absolute lymphocyte counts. Furthermore, the decreased mean percentage of natural killer cells is an additional indicator of a negative phenotype associated with knocking out the DNA35599-1168 gene which encodes PRO236 polypeptides. Natural killer cells are the first line of defense to viral infection since these cells have been implicated in viral immunity and in defense against tumors. Natural killer cells or NK cells act as effectors in antibody-dependent cell-mediated cytotoxicity and have been identified by their ability to kill certain lymphoid tumor cell lines in vitro without the need for prior immunization or activation. However, their known function in host defense is in the early phases of infection with several intracellular pathogens, particularly herpes viruses. Thus, PRO236 polypeptides and agonists thereof would be important for a healthy immune system and would be useful in stimulating the immune system especially against viral infections.

(c) Bone Metabolism & Body Diagnostics: Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro-CT: The (−/−) mice exhibited decreased bone measurements in the $5^{th}$ lumbar vertebrae (decreased mean vertebral trabecular bone volume and thickness) when compared with their gender-matched (+/+) littermates and the historical means.

Summary

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO236 polypeptides or agonists thereof play a role in maintaining bone homeostasis. In addition, PRO236 or its encoding gene would be useful in bone healing or useful for the treatment of arthritis or osteoporosis; whereas antagonists to PRO236 or its encoding gene would lead to abnormal or pathological bone disorders including inflammatory diseases associated with abnormal bone metabolism such as arthritis, osteoporosis, and osteopenia.

(d) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygote mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

During the glucose tolerance test the (−/−) mice exhibited impaired glucose tolerance when compared with their gender-matched (+/+) littermates and the historical means.

These studies indicated that (−/−) mice exhibit a decreased glucose tolerance in the presence of normal fasting glucose at all 3 intervals tested when compared with their gender-matched (+/+) littermates and the historical means. Thus, knockout mice exhibited the phenotypic pattern of an impaired glucose homeostasis. In light of this observation, PRO236 polypeptides (or agonists thereof) or its encoding gene would play be useful in the treatment of impaired glucose homeostasis and/or various cardiovascular diseases, including the treatment of diabetes.

35.5. Generation and Analysis of Mice Comprising DNA35638-1141 (UNQ219) Gene Disruptions In these knockout experiments, the gene encoding PRO245 polypeptides (designated as DNA35638-1141) (UNQ219) was disrupted. The gene specific information for these studies is as follows: the mutated mouse gene corresponds to nucleotide reference: NM_023844 or Mus musculus RIKEN cDNA 1110002N23 gene (1110002N23Rik); protein reference: Q9JI59 or VASCULAR ENDOTHELIAL JUNCTION-ASSOCIATED MOLECULE (JUNCTIONAL ADHESION MOLECULE-3) (2410030G21RIK PROTEIN); the human gene sequence reference: NM_021219 or ACCESSION:NM_021219 NID: gi 21704284 ref NM_021219.2 Homo sapiens junctional adhesion molecule 2 (JAM2); the human protein sequence corresponds to reference: P57087 or ACCESSION:P57087 NID: Homo sapiens (Human). JUNCTIONAL ADHESION MOLECULE 2 PRECURSOR (VASCULAR ENDOTHELIAL JUNCTION-ASSOCIATED MOLECULE) (VE-JAM) HUMANSPTRNRDB.

The disrupted mouse gene is Jam2 (junction adhesion molecule 2), the ortholog of human JAM2. Aliases include VEJAM, VE-JAM, JAM-2, Jcam2, C21orf43, chromosome 21 open reading frame 43, vascular endothelial junction-associated molecule, and junction cell adhesion molecule 2.

JAM2, an Ig superfamily member, is a membrane-lodged extracellular protein. JAM2 is specifically localized at junctions of lymphatic endothelial cells and high endothelial venules within lymph nodes and Peyer patches (Johnson-Leger et al., Blood, 100(7):2479-86 (2002)). JAM2 binds T, NK, and dendritic cells via interactions with alpha-4-beta1 integrin and JAM3 (Liang et al., J Immunol, 168(4):1618-26 (2002)). JAM2 apparently plays a central role in tight junction formation, transendothelial and lymphocyte migration, and the establishment of cell polarity in endothelial tissue (Ebnet et al., J Cell Sci, 116(Pt 19):3879-91 (2003), Aurrand-Lions et al., Cells Tissues Organs, 172(3):152-60 (2002)).

Genetics Information:

|  | wt | het | hom | Total |
|---|---|---|---|---|
| Observed | 18 | 32 | 22 | 72 |
| Expected | 18 | 36 | 18 | 72 |

Chi-Sq. = 1.33
Significance = 0.51342
(hom/n) = 0.31
Avg. Litter Size = 7

Mutation Type: Retroviral Insertion (OST)
Retroviral insertion occurred between coding exons 3 and 4 (Accession: NM_023844).
Wild-type expression of the target gene was detected in embryonic stem (ES) cells and in all 13 adult tissue samples tested by RT-PCR, except adipose.
RT-PCR analysis revealed that the transcript was absent in the (−/−) mouse analyzed (F-58).

35.5.1. Phenotypic Analysis (for Disrupted Gene: DNA35638-1141 (UNQ219)

(a) Overall Phenotypic Summary:

Mutation of the gene encoding the ortholog of human junction adhesion molecule 2 (JAM2) resulted in an increased anxiety-related response in (−/−) mice. In addition, mutant (−/−) mice demonstrated a decreased ovalbumin response compared with their (+/+) wild-type littermates. Also, the (−/−) mutant mice showed opthalmological abnormalities associated with an increase in retinal artery tortuosity. Transcript was absent by RT-PCR.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immuno-dominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Analyzed wt/het/hom: 8/4/9

Results of this Challenge:

The (−/−) mice exhibited a decreased mean serum IgG2a response to ovalbumin challenge when compared with their (+/+) littermates and the historical means. Thus, these knockout mice exhibited a decreased ability to elicit an OVA-specific antibody response to the T-cell dependent OVA antigen.

In summary, the ovalbumin challenge studies indicate that knockout mice deficient in the gene encoding PRO245 polypeptides exhibit immunological abnormalities when compared with their wild-type littermates. In particular, the mutant mice exhibited a decreased ability to elicit an immunological response when challenged with the T-cell dependent OVA antigen. Thus, PRO245 polypeptides or agonists thereof, would be useful for stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, inhibitors (antagonists) of PRO245 polypeptides would be useful for inhibiting the immune response and thus would be useful candidates for suppressing harmful immune responses, e.g. in the case of graft rejection or graft-versus-host diseases.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., *Nature.* 1996 Feb. 15; 379(6566):606-12), and the GABA receptor (Homanics et al., *Proc Natl Acad Sci USA.* 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value. Analyzed wt/het/hom: 5/4/8

Results:

The (−/−) mice exhibited a decreased median sum time-in-center during open field testing when compared with their gender-matched (+/+) littermates and the historical mean, suggesting an increased anxiety-like response in the mutants. As noted above, a notable difference was observed during open field activity testing. The (−/−) mice exhibited a decreased median sum time in the center area when compared with their gender-matched (+/+) littermates. This type of behavior is consistent with an increased anxiety like response. Thus, the knockout mice demonstrated a phenotype consistent with anxiety related disorders which are associated with mild to moderate anxiety, anxiety due to a general medical condition, and/or bipolar disorders; hyperactivity; sensory disorders; obsessive-compulsive disorders, schizophrenia or a paranoid personality. Thus, PRO245 polypeptides or agonists thereof would be useful in the treatment of such neurological disorders or the amelioration of the symptoms associated with anxiety disorders.

(d) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to opthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct opthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Ophthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wild-type (+/+) littermates would be indicative of such pathological conditions.

Results:

Pathological microscopic observations showed an increase in retinal artery tortuosity in the (−/−) mice analyzed. In addition, corneal inflammation and ulceration was also noted in the (−/−) mutant mice. Analyzed wt/het/hom: 0/1/4

In summary, in this study, (−/−) mice showed opthalmological abnormalities which would lead to attenuated retinal vessels and possibly retinal degeneration when compared with their (+/+) littermates. In summary, by knocking out the gene identified as DNA35638-1141 encoding PRO245 polypeptides, homozygous mutant progeny exhibit phenotypes which are associated with retinal artery abnormalities. Such detected retinal changes are most commonly associated with cardiovascular systemic diseases or disorders that may be related to the vascular disease of hypertension (and any disease that causes hypertension, e.g. atherosclerosis), diabetes or other ocular diseases corresponding to opthalmological disorders such as retinal degeneration. Thus, antagonists of PRO245 encoding genes would lead to similar pathological retinal changes, whereas agonists would be useful as therapeutic agents in the treatment of hypertension, atherosclerosis or other opthalmological disorders including retinal degeneration and diseases associated with this condition (as indicated above).

35.6. Generation and Analysis of Mice Comprising DNA35639-1172 (UNQ220) Gene Disruptions In these knockout experiments, the gene encoding PRO246 polypeptides (designated as DNA35639-1172) (UNQ220) was disrupted. The gene specific information for these studies is as follows: the mutated mouse gene corresponds to nucleotide reference: NM_0271020R ACCESSION:NM_027102 NID:22094994 *Mus musculus Mus musculus* endothelial cell-selective adhesion molecule; protein reference: Q925F2 or ACCESSION:Q925F2 NID: *Mus musculus* (Mouse). ENDOTHELIAL CELL-SELECTIVE ADHESION MOLECULE. MOUSESPTRNRDB; the human gene sequence reference: NM_138961 or ACCESSION:NM_138961 NID:20452463 *Homo sapiens Homo sapiens* similar to endothelial cell-selective adhesion molecule; the human protein sequence corresponds to reference: Q96AP7 or ACCESSION:Q96AP7 NID: *Homo sapiens* (Human). Hypothetical protein PLACE1000456.

The disrupted mouse gene is Esam1 (endothelial cell-specific adhesion molecule), ortholog of human ESAM. Aliases include W117m, 2310008D05Rik, and HUEL (C4orf1)-interacting protein.

ESAM is a cell adhesion molecule of the immunoglobulin receptor family expressed at tight junctions on endothelial cells. ESAM is likely to play a role in inter endothelial cell adhesion (Hirata et al., *J Biol Chem,* 276(19): 16223-31 (2001); Nasdala et al, *J Biol Chem,* 277(18): 16294-303 (2002)). Ishida and colleagues, [*J Biol Chem,* 278(36):34598-604 (2003)] showed that tumor volume of ESAM homozygous null mice was notably smaller than that of wild-type mice. By matrigel plug assay, Ishida and colleagues also showed that neovascularization was notably lower in ESAM homozygous null mice than in wild-type mice. They concluded that ESAM played a role in pathological angiogenic processes such as tumor growth.

Targeted or gene trap mutations were generated in strain 129SvEv$^{Bvd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation.

|  | wt | het | hom | Total |
|---|---|---|---|---|
| Observed | 18 | 26 | 15 | 59 |
| Expected | 14.75 | 29.5 | 14.75 | 59 |

Chi-Sq. = 1.14
Significance = 0.56677
(hom/n) = 0.25
Avg. Litter Size = 7

Mutation Type: Retroviral Insertion (OST)
Retroviral insertion occurred in the intron between coding exons 2 and 3 (accession: NM_027102.1).
Wild-type expression of the target gene was detected in embryonic stem (ES) cells and in all 13 adult tissue samples tested by RT-PCR, except adipose.
RT-PCR analysis revealed that the transcript was absent in the (−/−) mouse analyzed (M-156). Disruption of the target gene was confirmed by Inverse PCR.

35.6.1. Phenotypic Analysis (for disrupted gene: DNA35639-1172 (UNQ220)

(a) Overall Phenotypic Summary:

Mutation of the gene encoding the ortholog of human endothelial cell-specific adhesion molecule (ESAM) resulted in an increased mean serum glucose levels and a decreased or impaired glucose tolerance. In addition, (−/−) mice exhibited a decreased heart rate (one standard deviation below the historic mean). Transcript was absent by RT-PCR.

(b) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

The (−/−) mice exhibited an increased mean serum glucose level [two (2) standard deviations (SD) above the historic mean] when compared with their gender-matched (+/+) littermates and the historical mean. In addition, the (−/−) mice exhibited impaired glucose tolerance when compared with their gender-matched (+/+) littermates and the historical means.

Analyzed wt/het/hom: 4/4/8

These studies indicated that (−/−) mice exhibit a decreased or impaired glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefor PRO246 polypeptides (or agonists thereof) or its encoding gene would be useful in the treatment of conditions associated with an impaired glucose homeostasis and/or various cardiovascular diseases, including diabetes.

35.7. Generation and Analysis of Mice Comprising DNA35918-1174 (UNQ225) Gene Disruptions In these knockout experiments, the gene encoding PRO258 polypeptides (designated as DNA35918-1174) (UNQ225) was disrupted. The gene specific information for these studies is as follows: the mutated mouse gene corresponds to nucleotide reference: NM_053199 or *Mus musculus* immunoglobulin superfamily, member 4B (Igsf4b); protein reference: Q99N28 or ACCESSION:Q99N28 NID: *Mus musculus* (Mouse). NECTIN-LIKE PROTEIN 1. MOUSESPTRN-RDB; the human gene sequence reference: NM_021189 or *Homo sapiens* immunoglobulin superfamily, member 4B (IGSF4B); the human protein sequence corresponds to reference: Q9UJP1 or ACCESSION:Q9UJP1 NID: *Homo sapiens* (Human). BK134P22.1 (NOVEL PROTEIN SIMILAR TO MOUSE IMMUNOSUPERFAMILY PROTEIN BL2) (NECTIN-LIKE PROTEIN 1). HUMANSPTRNRDB.

The mouse gene of interest is Igsf4b (immunoglobulin superfamily, member 4B), ortholog of human IGSF4B. Aliases include BIgR, Necl1, Tsll1, FLJ10698, nectin-like 1, TSLC1-like 1, nectin-like protein 1, and brain immunoglobulin receptor precursor.

IGSF4B is a type I plasma membrane protein expressed primarily in neurogenic cells that likely functions as a cell adhesion molecule. The protein contains a signal peptide, three immunoglobulin-like domains (Pfam accession PF00047), a transmembrane segment, and a short cytoplasmic C terminus. IGSF4B is structurally similar to TSLC1, a tumor suppressor in human non-small cell lung carcinomas, and IGSF4B expression is lost or markedly reduced in many glioma cell lines, suggesting that IGSF4B may also function as a tumor suppressor (Fukuhara et al., *Oncogene*, 20(38): 5401-7 (2001); Shingai et al, *J Biol Chem*, 278(37):35421-7 (2003); Fukami et al, *Gene*, 323:11-8 (2003)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation.

|          | wt    | het  | hom   | Total |
|----------|-------|------|-------|-------|
| Observed | 17    | 30   | 22    | 69    |
| Expected | 17.25 | 34.5 | 17.25 | 69    |

Chi-Sq. = 1.90
Significance = 0.38702
(hom/n) = 0.32
Avg. Litter Size = 7

Mutation Type: Homologous Recombination (standard)
Coding exon 1 was targeted (NCBI accession NM_053199.2).
Wild-type expression of the target gene was detected in all 13 adult tissue samples tested by RT-PCR, except brain and eye. Disruption of the target gene was confirmed by Southern hybridization analysis.

35.7.1. Phenotypic Analysis (for Disrupted Gene: DNA35918-1174 (UNQ225)

(a) Overall Phenotypic Summary:

Mutation of the gene encoding the ortholog of human immunoglobulin superfamily, member 4B (IGSF4B) resulted in numerous immunological abnormalities in (−/−) mice. The (−/−) mice also exhibited enhanced motor coordination. However, circadian rhythm testing showed decreased ambulation for the (−/−) mice. In addition, the mutant (−/−) mice showed a significant increase in mean serum cholesterol levels and mean serum glucose levels. MicroCT observations indicated decreased $5^{th}$ lumbar bone measurements. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Hematology Analysis:

Test Description Blood tests are carried out by Abbott's Cell-Dyn 3500R, an automated hematology analyzer. Some of its features include a five-part WBC differential. 'Patient' reports can cover over 22 parameters in all.

Results:

The (−/−) mice exhibited decreased mean total white blood cell, absolute lymphocyte, and absolute monocyte counts when compared with their (+/+) littermates and the historical means.

Analyzed wt/het/hom: 7/4/8

Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

The (−/−) mice exhibited an increased mean percentage of CD4 cells and a decreased mean percentage of B cells when compared with their (+/+) littermates and the historical means.

Analyzed wt/het/hom: 7/4/8

Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immuno-dominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Analyzed wt/het/hom: 7/4/8

Results of this challenge: The (−/−) mice exhibited a decreased (virtually absent) mean serum IgG2a response to the ovalbumin challenge when compared with their (+/+) littermates. Thus, these knockout mice exhibited an decreased ability to elicit an OVA-specific antibody response to the T-cell dependent OVA antigen more than likely due to a defect in Th cells. PRO258 polypeptides or agonists thereof would therefore be expected to stimulate the immune system and would find utility in the cases wherein this effect would be beneficial to the individual such as in the case of leukemia, and other types of cancer, and in immunocompromised patients, such as AIDS sufferers. Accordingly, inhibitors or antagonists of PRO258 polypeptides would play a role in inhibiting the immune response and would be useful candidates for suppressing harmful immune responses, e.g. in the case of graft rejection or graft-versus-host diseases.

Overall Summary of Immunological Observations

In summary, the ovalbumin challenge studies, hematology and FACS results indicate that the homozygous mutant mice have an impaired immune system, especially in view of the decreased total white blood cell count and absolute lymphocyte and monocyte counts as well as an inability to elicit an OVA-specific antibody response. These studies all serve as an indicator of a negative phenotype associated with knocking out the DNA35918-1174 gene which encodes PRO258 polypeptides. Thus, PRO258 polypeptides and agonists thereof would be important for a healthy immune system and would be useful in stimulating or inducing the immune system's protective functions.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

The (−/−) mice exhibited decreased ambulatory counts during the 1-hour habituation period of home-cage activity testing when compared with their gender-matched (+/+) littermates and the historical mean. These results are indicative of a suppression of circadian rhythm especially since there was a marked decrease in the dark period relative to the littermate controls.

Analyzed wt/het/hom: 6/4/12

Inverted Screen Testing:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Inverted Screen Test Data:

The Inverted Screen is used to measure motor strength/coordination. Untrained mice were placed individually on top of a square (7.5 cm×7.5 cm) wire screen which was mounted horizontally on a metal rod. The rod was then rotated 180 degrees so that the mice were on the bottom of the screens. The following behavioral responses were recorded over a 1 min testing session: fell off, did not climb, and climbed up.

| Genotype | Ratio Fell Down | % | Ratio Climbed up | % |
|---|---|---|---|---|
| +/+ (n = 4) | 0/4 | 0 | 0/4 | 0 |
| +/− (n = 4) | 0/4 | 0 | 4/4 | 100* |
| −/− (n = 8) | 1/8 | 13 | 7/8 | 88* |

*coding indicates a notable difference.

A motor strength deficit is apparent when there is a 50% point difference between (−/−) or (+/−) mice and (+/+) mice for the fell down response. 0/8 or 1/8 (−/−) or (+/−) mice not climbing indicates impaired motor coordination. 7/8 or 8/8(−/−) or (+/−) mice climbing up indicates enhanced motor coordination.

Results:

The Inverted Screen Test is designed to measure basic sensory & motor observations: Enhanced motor coordination was observed in the (−/−) mice during inverted screen testing when 7/8 (−/−) mice climbed up the screen, whereas 0/4 (+/+) mice climbed up.

Analyzed wt/het/hom: 6/4/12

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche). Analyzed wt/het/hom: 4/4/8

Results:

(1) The (−/−) mice exhibited an increased mean serum cholesterol level when compared with their gender-matched (+/+) littermates and the historical mean. The mean serum cholesterol values were significantly above the normal range. (2) The (−/−) mice also exhibited a significantly increased mean serum glucose level. During the glucose tolerance test, the (−/−) mice exhibited an increased mean fasting serum glucose level when compared with their gender-matched (+/+) littermates and the historical mean.

In summary, these knockout mutant mice exhibited a negative phenotype with regards to lipid metabolism. Thus, mutant mice deficient in the PRO258 gene can serve as a model for treatment of cardiovascular disease. PRO258 polypeptides, agonists thereof or the encoding gene for PRO258 would be useful in regulating blood lipids and in particular in maintaining normal cholesterol metabolism. Thus, such agents would be useful in the treatment of such cardiovascular diseases associated with dyslipidemia as: hypertension, atherosclerosis, heart failure, stroke, various coronary artery diseases, and/or obesity.

In concurrence, knockout mice exhibited the phenotypic pattern of an impaired glucose homeostasis with elevated levels of fasting serum glucose indicative of diabetes or a pre-diabetic condition. Based on these results, PRO258 (or agonists thereof) or its encoding gene would be useful in the treatment of an impaired glucose metabolism and/or diabetes.

(e) Bone Metabolism & Body Diagnostics: Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro-CT: The (−/−) mice exhibited decreased bone measurements in the $5^{th}$ lumbar vertebrae (decreased mean vertebral trabecular bone volume, number, thickness, and connectivity density) when compared with their gender-matched (+/+) littermates and the historical means. The midshaft femur showed a decreased total area. In addition, the mutant (−/−) mice exhibited a decreased heart rate which was two (2) standard deviations below the mean.

Summary

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO258 polypeptides or agonists thereof play a role in maintaining bone homeostasis. In addition, PRO258 or its encoding gene would be useful in bone healing or useful for the treatment of arthritis or osteoporosis; whereas antagonists to PRO258 or its encoding gene would lead to abnormal or pathological bone disorders including inflammatory diseases associated with abnormal bone metabolism such as arthritis, osteoporosis, and osteopenia.

35.8. Generation and Analysis of Mice Comprising DNA39969-1185 (UNQ250) Gene Disruptions In these knockout experiments, the gene encoding PRO287 polypeptides (designated as DNA39969-1185) (UNQ250) was disrupted. The gene specific information for these studies is as follows: the mutated mouse gene corresponds to nucleotide reference: NM_029620 or ACCESSION:NM_029620 NID: gi 22095010 ref NM_029620.1 *Mus musculus* procollagen C-endopeptidase enhancer 2 (Pcolce2); protein reference: NP_083896 or ACCESSION:NP_083896 NID: gi 22095011 ref NP_083896.1 (NM_029620) procollagen C-endopeptidase enhancer 2 [*Mus musculus*]; the human gene sequence reference: NM_013363 or ACCESSION: NM_013363 NID: gi 16904386 ref NM_013363.2 *Homo sapiens* procollagen C-endopeptidase enhancer 2 (PCOLCE2); the human protein sequence corresponds to reference: NP_037495 or ACCESSION:NP_037495 NID: gi 7019483 ref NP_037495.1 (NM_013363) procollagen C-endopeptidase enhancer 2 [*Homo sapiens*].

The mouse gene of interest is Pcolce2 (procollagen C-endopeptidase enhancer 2), ortholog of human PCOLCE2. Aliases include PCPE2.

PCOLCE2 is a secreted glycoprotein that binds with the C terminus of type I procollagen, enhancing cleavage of procollagen by C-proteinases such as bone morphogenic protein-1. Trabecular meshwork, lungs, heart, brain, liver, skeletal muscle, kidney, pancreas, and placenta express PCOLCE2 mRNA; however, PCOLCE2 protein is detected mainly in trabecular network. PCOLCE2 is likely to play a role in cartilage formation in different tissues during development (Steiglitz et al., *J Biol Chem*, 277(51):49820-30 (2002); Xu et al., *Genomics*, 66(3):264-73 (2000)).

Genetics Information:

|  | wt | het | hom | Total |
|---|---|---|---|---|
| Observed | 25 | 39 | 18 | 82 |
| Expected | 20.5 | 41 | 20.5 | 82 |

Chi-Sq. = 1.39
Significance = 0.49901
(hom/n) = 0.22
Avg. Litter Size = 8

Mutation Type: Retroviral Insertion (OST)

Retroviral insertion occurred in the intron between coding exons 1 and 2 (NCBI accession NM_029620.1).

Wild-type expression of the target gene was detected in brain, spinal cord, eye, thymus, spleen, and lung among the 13 adult tissue samples tested by RT-PCR.

RT-PCR analysis revealed that the transcript was absent in the (−/−) mouse analyzed (M-201).

35.8.1. Phenotypic Analysis (for Disrupted Gene: DNA39969-1185 (UNQ250)

(a) Overall Phenotypic Summary:

Mutation of the gene encoding the ortholog of human procollagen C-endopeptidase enhancer 2 (PCOLCE2) resulted in growth retardation and decreased bone measurements in (−/−) mice. Increased uric acid levels and decreased serum phosphate levels were also observed in the mutant (−/−) mice. Transcript was absent by RT-PCR.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited decreased mean body weight and mean body length when compared with their gender-matched (+/+) littermates and the historical means. Analyzed wt/het/hom: 37/54/28

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and mid-shaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited decreased mean total tissue mass and lean body mass when compared with their gender-matched (+/+) littermates and the historical means. These mutant mice also exhibited decreased mean bone mineral content and bone mineral density.

Micro-CT: The (−/−) mice exhibited decreased mean vertebral trabecular bone volume, number, thickness, and connectivity density and decreased mean femoral mid-shaft cross-sectional area when compared with their gender-matched (+/+) littermates and the historical means. Analyzed wt/het/hom: 4/4/8

In addition, the (−/−) mice had a significant decrease in body fat.

Summary

These results demonstrate that knockout mutant mice exhibit abnormal bone metabolism with significant bone loss similar to osteoporosis characterized by decrease in bone mass with decreased density and possibly fragility leading to bone fractures. This in conjunction with blood chemistry analysis (see below) wherein increased uric acid levels and decreased serum phosphate levels were observed. Thus, it appears that PRO287 or agonists thereof would be useful in maintaining bone homeostasis. In addition, PRO287 or its encoding gene would be important in bone healing or for the treatment of arthritis or osteoporosis; whereas antagonists to PRO287 would lead to abnormal or pathological bone disorders including inflammatory diseases associated with abnormal bone metabolism including arthritis, osteoporosis, and osteopenia. In addition, the (−/−) mice analyzed by DEXA exhibited notably decreased total tissue mass and lean body mass wand decreased body fat when compared with their (+/+) littermates, suggestive of growth retardation in these mutants. This in conjunction with the observations of decreased body weight and length suggest a tissue wasting condition such as cachexia or other growth disorder. Thus, PRO287 polypeptides or agonists thereof would be useful in the treatment or prevention of growth disorders such as cachexia and/or other tissue wasting diseases.

(c) Blood Chemistry—Uric Acid and Serum Phosphate Levels

Blood chemistry analysis was performed using the COBAS Integra 400 (mfr: Roche) in its clinical settings for running blood chemistry tests on mice.

Results: Mutant (−/−) mice exhibited increased uric acid levels as well as decreased serumphosphate levels compared to their control wild-type littermates.

35.9. Generation and Analysis of Mice Comprising DNA40587-1231 (UNQ289) Gene Disruptions In these knockout experiments, the gene encoding PRO328 polypeptides (designated as DNA40587-1231) (UNQ289) was disrupted. The gene specific information for these studies is as follows: the mutated mouse gene corresponds to nucleotide reference: NM_023734 or ACCESSION:NM_023734 NID:12963802 *Mus musculus Mus musculus* RIKEN cDNA 1200009H11 gene (1200009H11Rik); protein reference: Q9ET66 or ACCESSION:Q9ET66 NID: *Mus musculus* (Mouse). CYSTEINE-RICH PROTEASE INHIBITOR. MOUSESPTRNRDB; the human gene sequence reference: NM_153370 or *Homo sapiens* protease inhibitor 16 (PI16); the human protein sequence corresponds to reference: Q8NBK0 or ACCESSION:Q8NBK0 NID: *Homo sapiens* (Human). Hypothetical protein PLACE1010482.

The mouse gene of interest encodes a hypothetical secreted protein, which is the ortholog of human P116 (protease inhibitor 16).

PI16 contains a signal peptide, an SCP-like extracellular protein (SCP) domain, and several internal repeats. SCP domains are found in extracellular proteins from many different species. Examples include insect venom allergens, mammalian testis-specific proteins, and plant pathogenesis-related proteins (Pfam accession PF00188). PI16 is a homolog of protease inhibitor 15 (PI15), which also contains an SCP domain and functions as a secreted serine protease (trypsin) inhibitor (Yamakawa et al., *Biochim Biophys Acta*, 1395(2):202-8 (1998)). The function of PI16 has not been demonstrated experimentally.

Genetics Information:

|  | wt | het | hom | Total |
|---|---|---|---|---|
| Observed | 16 | 45 | 22 | 83 |
| Expected | 20.75 | 41.5 | 20.75 | 83 |

Chi-Sq. = 1.46
Significance = 0.48243
(hom/n) = 0.27
Avg. Litter Size = 8

Mutation Type Retroviral Insertion (OST)
Retroviral insertion occurred in the intron between coding exons 2 and 3 (NCBI accession NM_023734.2).
Wild-type expression of the target gene was detected in embryonic stem (ES) cells and in all 13 adult tissue samples tested by RT-PCR.
RT-PCR analysis revealed that the transcript was absent in the (−/−) mouse analyzed (M-97).

35.9.1. Phenotypic Analysis (for Disrupted Gene: DNA40587-1231 (UNQ289)

(a) Overall Phenotypic Summary:

Mutation of the gene encoding the ortholog of human protease inhibitor 16 (PI16) resulted in a immunological phenotype in (−/−) mice. An enhanced glucose tolerance was also observed during the glucose tolerance testing for the (−/−) mice. Changes in lumbar 5 vertebrae were also noted (decreased measurements compared to littermate controls). Transcript was absent by RT-PCR.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:
Hematology Analysis:
Test Description: Blood tests are carried out by Abbott's Cell-Dyn 3500R, an automated hematology analyzer. Some of its features include a five-part WBC differential. 'Patient' reports can cover over 22 parameters in all.
Results:
Hematology:
The (−/−) mice exhibited an increased mean red cell distribution width when compared with their (+/+) littermates and the historical mean.
Analyzed wt/het/hom: 9/4/14
Flourescence-Activated Cell-Sorting (FACS) Analysis/Tissue Specific FACS
Procedure:
FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

Tissue Specific FACS: The (−/−) mice exhibited a decreased mean percentage of CD21Hi CD23Med cells in the spleen and lymph nodes. Increased mean percentages of CD25+ cells in both spleen and lymph nodes were also noted in the (−/−) mice.

Analyzed wt/het/hom: 9/4/14

In summary, knocking out DNA40587-1231 (the gene which encodes PRO328 polypeptides) resulted in a a decrease in a subset of B cells—marginal zone B cells—that contain a pool of memory cells and participate in fast immune responses. Thus, antagonists or inhibitors of PRO328 polypeptides would be expected to demonstrate the same phenotype. PRO328 polypeptides would be useful in the development or production of marginal zone B cells useful for participating in fast immune responses.

(c) Phenotypic Analysis: Metabolism—Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

The (−/−) mice exhibited an enhanced glucose tolerance when compared with their gender-matched (+/+) littermates and the historical means. Thus, knockout mice exhibited the opposite phenotypic pattern of an impaired glucose homeostasis, and as such antagonists to PRO328 or its encoding gene would be useful in the treatment of impaired glucose homeostasis and diseases associated with abnormal glucose metabolism.

(d) Bone Metabolism & Body Diagnostics: Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and mid-shaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro-CT: The (−/−) mice exhibited decreased mean vertebral trabecular bone volume, number, thickness, and connectivity density and decreased mean femoral mid-shaft cross-sectional area when compared with their gender-matched (+/+) littermates and the historical means. Analyzed wt/het/hom: 4/4/8

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO328 or agonists thereof would be useful in maintaining bone homeostasis. In addition, PRO328 or its encoding gene would be important in bone healing or for the treatment of arthritis or osteoporosis; whereas antagonists to PRO328 would lead to abnormal or pathological bone disorders including inflammatory diseases associated with abnormal bone metabolism including arthritis, osteoporosis, and osteopenia.

35.10. Generation and Analysis of Mice Comprising DNA40592-1242 (UNQ303) Gene Disruptions In these knockout experiments, the gene encoding PRO344 polypeptides (designated as DNA40592-1242) (UNQ303) was disrupted. The gene specific information for these studies is as follows: the mutated mouse gene corresponds to nucleotide reference: BC023068 or *Mus musculus* C1q and tumor necrosis factor related protein 5; protein reference: Q8R002 or ACCESSION:Q8R002NID: *Mus musculus* (Mouse). Similar to DKFZP586B0621 protein (Hypothetical protein); the human gene sequence reference: NM_015645 or *Homo sapiens* C1q and tumor necrosis factor related protein 5 (C1QTNF5); the human protein sequence corresponds to reference: Q9BXJ0 or ACCESSION:Q9BXJ0 NID: *Homo sapiens* (Human). Complement C1q tumor necrosis factor-related protein 5 precursor.

The disrupted mouse gene is C1qtnf5 (C1q and tumor necrosis factor related protein 5), which is the ortholog of human C1QTNF5. Aliases include CTRP5 and complement-c1q tumor necrosis factor-related protein 5.

C1QTNF5 is a hypothetical secreted protein, containing a signal peptide, a collagen triple helix repeat (Pfam accession PF01391), and a complement component C1q domain (SMART accession SM00110). C1q domains are globular structures found in many collagens and in the C1 enzyme complex that activates the serum complement system. The fold of this domain is similar to that of tumor necrosis factor. The molecular function and biological role of C1QTNF5 is not known.
Genetics Information:

|  | wt | het | hom | Total |
|---|---|---|---|---|
| Observed | 19 | 31 | 16 | 66 |
| Expected | 16.5 | 33 | 16.5 | 66 |

Chi-Sq. = 0.52
Significance = 0.77292
(hom/n) = 0.24
Avg. Litter Size = 7

Mutation Type Retroviral Insertion (OST)
Retroviral insertion occurred between coding exons 1 and 2 (Accession: NM_145613.2).
Wild-type expression of the target gene was detected in brain, spinal cord, eye, lung, kidney, skeletal muscle, and heart among the 13 adult tissue samples tested by RT-PCR. The larger bands are unspliced gene-specific transcripts.
PCR analysis revealed that the transcript was absent in the (−/−) mouse analyzed (M-131).
35.10.1. Phenotypic Analysis (for Disrupted Gene: DNA40592-1242 (UNQ303).
(a) Overall Phenotypic Summary:
Mutation of the gene encoding the ortholog of human C1q and tumor necrosis factor related protein 5 (C1QTNF5) resulted in retinal degeneration in (−/−) mice. In addition, the (−/−) mice exhibited abnormal bone measurements with decreased measurements in lumbar 5. The knockout mice also showed a significant decrease in total body fat and showed increased uric acid levels. Transcript was absent by RT-PCR.
(b) Cardiovascular Phenotypic Analysis:
In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to opthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct opthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Ophthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wild-type (+/+) littermates would be indicative of such pathological conditions.

Results:
Fundus: Of the 7 non-albino (−/−) mice analyzed, 6 (F-134, F-155, F-158, M-164, M-171, and F-183) exhibited multiple white spots covering the entire retina with attenuated retinal arteries, suggesting retinal degeneration in the mutants similar to flecked retinal disease in humans. Analyzed wt/het/hom: 4/4/8

Pathological microscopic observations showed signs of retinal degeneration in the 4 (−/−) mice analyzed (M-173, M-188, F-197, and F-199). Histological changes were noted wherein the retina showed increased apoptotic cells in the outer nuclear layer. Gene expression analysis could not be performed for this project.

In summary, in this study, optic fundus photography showed that (−/−) mice exhibited signs of severe retinal degeneration, namely notably attenuated retinal vessels when compared with their (+/+) littermates. Angiograms demonstrated that the mutant (−/−) mice showed attenuated retinal vessels with micro aneurysms. Likewise, microscopic observations showed bilateral retinal degeneration in the mutant (−/−) mice. In summary, by knocking out the gene identified as DNA40592-1242 encoding PRO344 polypeptides, homozygous mutant progeny exhibit phenotypes which are associated with retinal degeneration. Such detected retinal changes are most commonly associated with cardiovascular systemic diseases or disorders that may be related to the vascular disease of hypertension (and any disease that causes hypertension, e.g. atherosclerosis), diabetes or other ocular diseases corresponding to opthalmological disorders such as retinal degeneration. Thus, antagonists of PRO344 encoding genes would lead to similar pathological retinal changes, whereas agonists would be useful as therapeutic agents in the treatment of hypertension, atherosclerosis or other opthalmological disorders including retinal degeneration and diseases associated with this condition (as indicated above).

(c) Bone Metabolism & Body Diagnostics: Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mutant mice showed a significant decrease in total body fat content compared to their littermate controls. In addition, uric acid levels were elevated in the (−/−) mutant mice (as observed in blood chemistry analysis).

Micro-CT: The (−/−) mice exhibited decreased mean vertebral trabecular bone volume, number, thickness, and connectivity density and decreased mean femoral mid-shaft cross-sectional area when compared with their gender-matched (+/+) littermates and the historical means. Analyzed wt/het/hom: 4/4/8

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO344 or agonists thereof would be useful in maintaining bone homeostasis. In addition, PRO344 or its encoding gene would be important in bone healing or for the treatment of arthritis or osteoporosis; whereas antagonists to PRO344 would lead to abnormal or pathological bone disorders including inflammatory diseases associated with abnormal bone metabolism including osteoarthritis, osteoporosis, and osteopenia. In addition, the decrease in total body fat in the (−/−) mice was indicative of a tissue wasting disease.

35.11. Generation and Analysis of Mice Comprising DNA44804-1248 (UNQ314) Gene Disruptions In these knockout experiments, the gene encoding PRO357 polypeptides (designated as DNA44804-1248) (UNQ312) was disrupted. The gene specific information for these studies is as follows: the mutated mouse gene corresponds to nucleotide reference: NM_139307 or *Mus musculus* Slit-like 2 (*Drosophila*) (Slitl2); protein reference: NP_647468 or Slit-like 2 [*Mus musculus*]; the human gene sequence reference: BC013767 or ACCESSION:BC013767 NID:15489338 *Homo sapiens Homo sapiens*, Similar to RIKEN cDNA 2610528G05 gene, clone IMAGE:3875837; the human protein sequence corresponds to reference: Q96CX1 or ACCESSION:Q96CX1 NID: *Homo sapiens* (Human). SIMILAR TO RIKEN CDNA 2610528G05 GENE (FRAGMENT). HUMANSPTRNRDB.

The disrupted mouse gene is Slitl2 (Slit-like 2 [*Drosophila*]), the ortholog of human hypothetical protein LOC114990. Aliases include hypothetical protein BC013767 and 2610528G05Rik.

Slit-type proteins (e.g., SLIT1) are extracellular proteins that play a critical role in developmental processes, especially nervous and endocrine system formation. Slit-type proteins are thought to assist in cellular movement (Piper and Little, *Bioessays*, 25(1):32-8 (2003)). Thus, by homology, LOC114990 is likely secreted or mostly extracellular and assists in developmental processes.

Genetics Information:

|  | wt | het | hom | Total |
|---|---|---|---|---|
| Observed | 15 | 33 | 13 | 61 |
| Expected | 15.25 | 30.5 | 15.25 | 61 |

Chi-Sq. = 0.54
Significance = 0.76300
(hom/n) = 0.21
Avg. Litter Size = 4

Mutation Type: Retroviral Insertion (OST)

Retroviral insertion disrupted the gene in coding exon 2 (Accession: NM_139307).

Wild-type expression of the target gene was detected in embryonic stem (ES) cells and, among the 13 adult tissue samples tested by RT-PCR, in kidney, skeletal muscle, and heart.

RT-PCR analysis revealed that the transcript was absent in the (−/−) mouse analyzed (F-59). Disruption of the target gene was confirmed by Inverse PCR.

35.11.1. Phenotypic Analysis (for Disrupted Gene: DNA44804-1248 (UNQ314)

(a) Overall Phenotypic Summary:

Mutation of the gene encoding the ortholog of a human hypothetical protein (BC013767) resulted in an increased mean bone mineral content, volumetric bone mineral density and bone mineral density in total body, femur and vertebrae. Several (−/−) mice were smaller than their (+/+) littermates and died early (by 19 days after birth). The (+/−) mice also showed diminished size and died early. Male (−/−) mice exhibited infertility. The knockout mice showed increase in serum triglycerides, ketone bodies and glucose levels and had elevated blood pressure. The (−/−) mice also showed increased bone measurements and increased total body fat. Transcript was absent by RT-PCR.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Several (−/−) mice were smaller than their (+/+) littermates, and 2 died by 19 days after birth. The remaining (−/−) mice seemed healthy. A number of (+/−) mice were also small, exhibited reduced organ weights and died early. The 2 male (−/−) mice available for analysis exhibited increased mean systolic blood pressure when compared with their gender-matched (+/+) littermates and the historical mean. Analyzed wt/het/hom: 14/27/10

Fertility: The male (−/−) mouse analyzed (M-106) was infertile.

Pathology: Microscopic observations for the single (−/−) mouse available for analysis (M-106) showed a sero purulent exudate from the middle ear on one side. Additionally, a cyst was noted on the testis along with degeneration unilaterally. Analyzed wt/het/hom: 0/2/1

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µLCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited increased mean bone mineral content, volumetric bone mineral density, and bone mineral density in total body, femur, and vertebrae when compared with their gender-matched (+/+) littermates and the historical means. The mutant mice also showed increased total body fat content and a corresponding increase in blood triglycerides indicative of dyslipidemia. Analyzed wt/het/hom: 4/8/8

MicroCT: The (−/−) mice increased lumbar 5 vertebrae measurements compared to their wild-type littermates.

Summary

Several (−/−) mice showed signs of growth retardation since several mutant mice were much smaller than their (+/+) littermates. In addition, the heterozygous (+/−) mice showed signs of decreased growth and reduced viability being small and not surviving as long as their (+/+) littermates. Furthermore, the (−/−) mice exhibited increased mean bone mineral content, volumetric bone mineral density and total body and femoral bone mineral density when compared with their gender-matched (+/+) littermates. These results indicate that the knockout mutants not only showed signs of growth deficiencies and reduced viability but also exhibited bone abnormalities associated with such bone diseases as osteopetrosis. Osteopetrosis is a condition characterized by abnormal thickening and hardening of bone and abnormal fragility of the bones. As such, PRO357 polypeptides or agonists thereof would be important for normal growth and normal bone metabolism and would be useful for the treatment of osteopetrosis or other related bone disorders. In addition, the male (−/−) mice showed signs of infertility and degenerate testes. Thus, PRO357 polypeptides or agonists thereof would be useful in the prevention and/or treatment of such bone disorders and also would play a role in maintaining normal growth and development.

(c) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results:

The (−/−) mice exhibited increased mean serum triglyceride, ketone bodies and glucose levels when compared with their gender-matched (+/+) littermates and the historical means. In addition, the (−/−) mice exhibited elevated blood pressure.

As summarized above, the (−/−) mice exhibited notably increased triglyceride levels when compared with their gender-matched (+/+) littermates and the historical means for the male (+/+) mice. In addition, the increased mean serum glucose levels suggesting diabetes. The elevated mean systolic blood pressure along with the blood chemistry is indicative of hypertension or other cardiovascular disease. Thus, mutant mice deficient in the PRO357 gene can serve as a model for cardiovascular disease including diabetes. PRO357 polypeptides or its encoding gene would be useful in regulating normal blood lipid levels such as triglycerides and/or blood sugars. Thus, PRO357 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

35.12. Generation and Analysis of Mice Comprising DNA44184-1319 (UNQ330) Gene Disruptions In these knockout experiments, the gene encoding PRO526 polypeptides (designated as DNA44184-1319) (UNQ330) was disrupted. The gene specific information for these studies is as follows: the mutated mouse gene corresponds to nucleotide reference: NM_022982 or ACCESSION:NM_022982 NID: gi 12667793 ref NM_022982.1 *Mus musculus* reticulon 4 receptor (Rtn4r); protein reference: Q99PI8 or Reticulon 4 receptor precursor (Nogo receptor) (NgR) (Nogo-66 receptor); the human gene sequence reference: NM_023004 or *Homo sapiens* reticulon 4 receptor (RTN4R); the human protein sequence corresponds to reference: Q9BZR6 or Reticulon 4 receptor precursor (Nogo receptor) (NgR) (Nogo-66 receptor) (UNQ330/PRO526).

The mouse gene of interest is Rtn4r (reticulon 4 receptor), ortholog of human RTN4R. Aliases include NgR, NOGOR, nogo receptor, and Nogo-66 receptor.

RTN4R is a glycosylphosphatidylinositol-anchored extracellular protein that functions as a receptor for reticulon 4 (RTN4; also known as NOGO), oligodendrocyte myelin glycoprotein (OMG), and myelin-associated glycoprotein (MAG), which mediate inhibition of axonal growth (Fournier et al, *Nature*, 409(6818):341-6 (2001); Wang, Koprivica et al., *Nature*, 417(6892):941-4 (2002); Liu et al., *Science*, 297 (5584):1190-3 (2002)). Upon binding with these ligands, RTN4R associates with p75, a transmembrane protein and receptor of the neurotrophin growth factor family, and LINGO-1, a nervous system-specific transmembrane protein. This association transduces the signal to the interior of the cell (Wang, Kim et al., *Nature*, 420(6911):74-8 (2002); Wong et al., *Nat Neurosci*, 5(12):1302-8 (2002); Mi et al., *Nat. Neurosci.* 7(3):221-8 (2004)). RTN4R is involved in axonal guidance and nervous system development. Moreover, RTN4R and its signaling components are targets for inhibitors that enable axonal regeneration following injury to the central nervous system (Fisher et al., *J Neurosci*, 24(7): 1646-51 (2004); Song et al., *J Neurosci*, 24(2):542-6 (2004); Lee et al., *Nat Rev Drug Discov*, 2(11):872-8 (2003)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation.

|  | wt | het | hom | Total |
|---|---|---|---|---|
| Observed | 20 | 36 | 22 | 78 |
| Expected | 19.5 | 39 | 19.5 | 78 |

Chi-Sq. = 0.56
Significance = 0.75424
(hom/n) = 0.28
Avg. Litter Size = 8

Mutation Type Homologous Recombination (standard)
Coding exon 2 was targeted (NCBI accession NM_022982.1).
Wild-type expression of the target gene was detected in embryonic stem (ES) cells and in all 13 adult tissue samples tested by RT-PCR.
Disruption of the target gene was confirmed by Southern hybridization analysis.

35.12.1. Phenotypic Analysis (for Disrupted Gene: DNA44184-1319 (UNQ330)

(a) Overall Phenotypic Summary:

Mutation of the gene encoding the ortholog of human reticulon 4 receptor (RTN4R) resulted in enhanced glucose tolerance and decreased mean serum cholesterol, triglycerides and glucose levels in (−/−) mice. The male (−/−) mutant mice exhibited an increased lean body mass, increased bone mineral density, and increased bone mineral content in total body, femurs and vertebrae, as well as increased mean body weight. The mutant mice also exhibited a highly elevated TNF-alpha and IL-6 response to the LPS challenge. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 µL sterile saline using a 26 gauge needle. The doses were based on the average weight of the mice tested at 1 µg/g body weight 3 hours after injection; a 100 ul blood sample was then taken and analyzed for the presence of TNFa, MCP-1, and IL-6 on the FACSCalibur instrument.

Results:

The (−/−) mice exhibited a highly elevated mean serum IL-6 and TNF-alpha response to LPS challenge when compared with their (+/+) littermates and the historical mean.

In summary, the LPS endotoxin challenge demonstrated that knockout mice deficient in the gene encoding PRO526 polypeptides exhibit immunological abnormalities when compared with their wild-type littermates. In particular, the mutant mice exhibited an increased ability to elicit an immunological response (TNF-alpha and IL-6 production) when challenged with the LPS endotoxin indicating a strong proinflammatory response. IL-6 and TNF-alpha contribute to the later stages of B cell activation. In addition, IL-6 plays a critical role in inducing the acute phase response and systemic inflammation. This suggests that inhibitors or antagonists of PRO526 polypeptides or its encoding gene would stimulate the immune system and would find utility in the cases wherein this effect would be beneficial to the individual such as in the case of leukemia, and other types of cancer, and in immuno-compromised patients, such as AIDS sufferers. Accordingly, PRO526 polypeptides or agonists thereof thereof would play a role in inhibiting the immune response and would be useful candidates for suppressing harmful immune responses, e.g. in the case of graft rejection or graft-versus-host diseases.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The mutant (−/−) mice exhibited a significant increased body weight compared to their wild-type littermate controls.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited increased mean lean body mass and increased mean bone mineral content and bone mineral density in total body, femurs, and vertebrae when compared with their gender-matched (+/+) littermates and the historical means.

MicroCT: The (−/−) mice increased trabecular connectivity density compared to their wild-type littermates and the historical mean.

Summary

In summary, the male (−/−) mice exhibited increased mean lean body mass, bone mineral content, and total body and femoral bone mineral density when compared with their gender-matched (+/+) littermates. These results indicate that the knockout mutant phenotype may be associated with such bone abnormalities as osteopetrosis. Osteopetrosis is a condition characterized by abnormal thickening and hardening of bone and abnormal fragility of the bones. As such, PRO526 polypeptides or agonists thereof would be beneficial for the treatment of osteopetrosis or other osteo diseases. On the other hand, inhibitors or antagonists of PRO526 polypeptides would be useful in bone healing. Analyzed wt/het/hom: 4/4/8

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results:

The (−/−) mice exhibited decreased mean serum cholesterol, triglyceride and glucose levels when compared with their gender-matched (+/+) littermates and the historical mean. In summary, these knockout mutant mice exhibited a positive phenotype with regards to lipid and/or glucose metabolism. Thus, mutant mice deficient in the PRO526 gene can serve as a model for treatment of cardiovascular disease. Antagonists to PRO526 or its encoding gene would be useful in regulating blood lipids and in particular in maintaining normal cholesterol metabolism. Such inhibitors or antagonists to PRO526 polypeptides would be useful in the treatment of such cardiovascular diseases associated with dyslipidemia as: hypertension, atherosclerosis, heart failure, stroke, various coronary artery diseases, obesity and/or diabetes.

(e) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

The (−/−) mice exhibited an enhanced glucose tolerance when compared with their gender-matched (+/+) littermates and the historical means. Thus, knockout mice exhibited the opposite phenotypic pattern of an impaired glucose homeostasis, and as such antagonists to PRO526 or its encoding gene would be useful in the treatment of impaired glucose homeostasis and diseases associated with abnormal glucose metabolism.

35.13. Generation and Analysis of Mice Comprising DNA49631-1328 (UNQ389) Gene Disruptions In these knockout experiments, the gene encoding PRO724 polypeptides (designated as DNA49631-1328) (UNQ389) was disrupted. The gene specific information for these studies is as follows: the mutated mouse gene corresponds to nucleotide reference: NM_022993 or ACCESSION:NM_022993 NID:12667805 *Mus musculus Mus musculus* low-density lipoprotein receptor-related protein 10 (Lrp10); protein reference: Q9EPE8 or ACCESSION:Q9EPE8 NID: *Mus musculus* (Mouse). LOW-DENSITY LIPOPROTEIN RECEPTOR-RELATED PROTEIN 9. MOUSESPTRNRDB; the human gene sequence reference: NM_014045 or ACCESSION:NM_014045 NID:13027587 *Homo sapiens Homo sapiens* DKFZP564C1940 protein (DKFZP564C1940); the human protein sequence corresponds to reference: Q86T02. ACCESSION:Q86T02NID: *Homo sapiens* (Human). Human full-length cDNA clone CS0DK002YO06 of HeLa cells of *Homo sapiens* (Human).

The mouse gene of interest is Lrp10 (low-density lipoprotein receptor-related protein 10), ortholog of human LRP10. Aliases include Lrp9, MGC8675, and DKFZP564C1940.

LRP10 is a predicted type I plasma membrane protein expressed primarily in liver that mediates the uptake of apolipoprotein E-enriched beta-VLDL in vitro and, thus, likely functions as a receptor for low-density lipoproteins in vivo. In addition to liver, LRP10 is also found in kidney and brain, with particularly high levels occurring in vascular walls. LRP10 may play a role in apoE-containing lipoprotein uptake (Sugiyama et al., *Biochemistry*, 39(51):15817-25 (2000)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation.

|          | wt    | het  | hom   | Total |
|----------|-------|------|-------|-------|
| Observed | 17    | 29   | 17    | 63    |
| Expected | 15.75 | 31.5 | 15.75 | 63    |

Chi-Sq. = 0.40
Significance = 0.82003
(hom/n) = 0.27
Avg. Litter Size = 6

Mutation Type: Homologous Recombination (standard)
Coding exons 3 through 7 were targeted (NCBI accession NM_022993.2).
Wild-type expression of the target gene was detected in embryonic stem (ES) cells and in all 13 adult tissue samples tested by RT-PCR.
Disruption of the target gene was confirmed by Southern hybridization analysis.

35.13.1. Phenotypic Analysis (for disrupted gene: DNA49631-1328 (UNQ389)
(a) Overall Phenotypic Summary:
Mutation of the gene encoding the ortholog of human low-density lipoprotein receptor-related protein 10 (LRP10) resulted in a dramatically decreased skin fibroblast proliferation rate in (−/−) mice. In addition, (−/−) mice exhibited increased bone measurements. An impaired glucose tolerance was also noted for the mutant mice. Also, the mutant (−/−) mice exhibited immunological abnormalities marked by decreased levels of eosinophils and monocytes but also increased levels of CD8+ cells. Gene disruption was confirmed by Southern blot.

(b) Immunology Phenotypic Analysis
Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:
(1) Flourescence-Activated Cell-Sorting (FACS) Analysis
Procedure:
FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

(2) Hematology Analysis:
Test Description: Blood tests are carried out by Abbott's Cell-Dyn 3500R, an automated hematology analyzer. Some of its features include a five-part WBC differential. 'Patient' reports can cover over 22 parameters in all.

Results:
The (−/−) mice exhibited decreased eosinophils and monocytes when compared with their (+/+) littermates and the historical means.
FACS analysis also demonstrated that (−/−) mice exhibit an increased mean percentage of CD8+ cells when compared with their (+/+) littermates and the historical mean.
Analyzed wt/het/hom: 7/5/8

In summary, the hematology and FACS results indicate that the homozygous mutant mice exhibited decreased eosinophil and monocyte counts compared to their littermate controls indicating low levels of precursors of macrophages. However, the (−/−) mutant mice also showed an increased percentage of CD8+ cells. CD8+ molecules are the co-receptor molecules which cooperate with the T-cell receptor in antigen recognition and in particular specifically bind only to the invariant parts of the MHC class 1 molecule. During antigen recognition, the CD8+ molecules associate on the T-cell surface with components of the T-cell receptor to form the cytotoxic CD8+ T-cell. Thus, inhibitors or antagonists of PRO724 polypeptides would be important in the T-cell mediated response involving the MHC class I pathway and would be beneficial in those instances wherein cytotoxic T cells are required in host defense against cytosolic pathogens. In contrast, PRO724 polypeptides or agonists thereof, would be expected to mimic a negative phenotype resulting in a deficiency in the mean percentage of CD8+ cells and therefore an MHC class I deficiency would result. One such disease model occurs when there is an almost complete absence of cell-surface MHC class I molecules. Patients with this condition have normal levels of mRNA encoding MHC class I molecules and normal levels of production of MHC class I proteins. However, these individuals are immunodeficient, specifically owing to the lack of CD8+ T cells. This results in a severe immunodeficiency disease wherein the response to nearly all pathogens is critically suppressed.

(c) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 mil/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited increased mean bone mineral density when compared with their gender-matched (+/+) littermates and the historical means.

Micro-CT: The (−/−) mice exhibited increased mean vertebral trabecular bone volume, number, and connectivity density when compared with their gender-matched (+/+) littermates and the historical means.

Analyzed wt/het/hom: 4/4/9

In summary, the (−/−) mice exhibited increased mean bone mineral content, and total body and femoral bone mineral density when compared with their gender-matched (+/+) littermates. These results indicate that the knockout mutant phenotype is associated with bone abnormalities such as osteopetrosis. Osteopetrosis is a condition characterized by abnormal thickening and hardening of bone and abnormal fragility of the bones. As such, PRO724 polypeptides or agonists thereof would be beneficial for the treatment of osteopetrosis or other osteo diseases. On the other hand, inhibitors or antagonists of PRO724 polypeptides would be useful in bone healing.

(d) Oncology Phenotypic Analysis

In the area of oncology, targets were identified herein for the treatment of solid tumors, lymphomas and leukemia.

Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

The (−/−) mice exhibited a dramatically decreased mean skin fibroblast proliferation rate when compared with their gender-matched (+/+) littermates and the historical mean. Thus, homozygous mutant mice demonstrated a hypo-proliferative phenotype. As suggested by these observations, antagonists of a PRO724 polypeptide or its encoding gene would be useful in decreasing abnormal cell proliferation such as tumor cell growth.

(e) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygote mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

The (−/−) mice exhibited an increased mean serum glucose level when compared with their gender-matched (+/+) littermates and the historical mean. In addition, the (−/−) mice exhibited impaired glucose tolerance when compared with their gender-matched (+/+) littermates and the historical means.

Analyzed wt/het/hom: 4/4/8

These studies indicated that (−/−) mice exhibit a decreased glucose tolerance in the presence of normal fasting glucose at all 3 intervals tested when compared with their gender-matched (+/+) littermates and the historical means. Thus, knockout mutant mice exhibited the phenotypic pattern of an impaired glucose homeostasis, and therefor PRO724 polypeptides (or agonists thereof) or its encoding gene would be useful in the treatment of impaired glucose homeostasis and/or various cardiovascular diseases, including diabetes.

35.14. Generation and Analysis of Mice Comprising DNA48331-1329 (UNQ395) Gene Disruptions In these knockout experiments, the gene encoding PRO731 polypeptides (designated as DNA48331-1329) (UNQ395) was disrupted. The gene specific information for these studies is as follows: the mutated mouse gene corresponds to nucleotide reference: NM_017378 or ACCESSION:NM_017378 NID:8393915 *Mus musculus Mus musculus* protocadherin 12 (Pcdh12); protein reference: 055134 or ACCESSION: 055134 NID: *Mus musculus* (Mouse). VASCULAR CADHERIN-2. MOUSESPTRNRDB; the human gene sequence reference: NM_016580 or ACCESSION:NM_016580 NID: 14589925 *Homo sapiens Homo sapiens* protocadherin 12 (PCDH12); the human protein sequence corresponds to reference: Q9NPG4 or ACCESSION:Q9NPG4 NID: *Homo sapiens* (Human). Protocadherin 12 precursor (Vascular cadherin-2) (Vascular endothelial cadherin-2) (VE-cadherin-2) (VE-cad-2). HUMANSPTRNRDB.

The mouse gene of interest is Pcdh12 (protocadherin 12), ortholog of human PCDH12. Aliases include Pcdh14, VE-cad-2, VE-cadherin-2, VECAD2, protocadherin 14, and vascular endothelial cadherin-2.

PCDH12 is a type I membrane protein expressed in vascular endothelium that likely functions as a cadherin family cell adhesion molecule. The protein consists of an extracellular domain containing six cadherin repeats, a transmembrane segment, and a cytoplasmic C terminus. Unlike vascular endothelial cadherin-1, PCDH12 neither interacts with catenins nor affects cell migration or growth. PCDH12 promotes homotypic calcium-dependent adhesion and aggregation clusters at intercellular junctions (Telo et al., *J Biol Chem*, 273(28):17565-72 (1998); Wu and Maniatis, *Proc Natl Acad Sci USA*, 97(7):3124-9 (2000)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation.

|  | wt | het | hom | Total |
|---|---|---|---|---|
| Observed | 20 | 40 | 19 | 79 |
| Expected | 19.75 | 39.5 | 19.75 | 79 |

Chi-Sq. = 0.04
Significance = 0.98119
(hom/n) = 0.24
Avg. Litter Size = 8

Mutation Type: Homologous Recombination (standard)
Coding exon 1 was targeted (NCBI accession NM_017378.1).

Wild-type expression of the target gene was detected in all 13 adult tissue samples tested by RT-PCR, except stomach, small intestine, and colon.

Disruption of the target gene was confirmed by Southern hybridization analysis.

35.14.1. Phenotypic Analysis (for Disrupted Gene: DNA48331-1329 (UNQ395)

(a) Overall Phenotypic Summary:

Mutation of the gene encoding the ortholog of human protocadherin 12 (PCDH12) resulted in larger (−/−) mice, exhibiting increased body weight, total tissue mass, and lean body mass as well increased bone related measurements. The (−/−) mice exhibited increased organ weight, total body fat and total fat mass. In addition, the (−/−) mice exhibited a decreased percentage of natural killer cells and blood eosinophils. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

Flourescence-Activated Cell-Sorting (FACS) Analysis
Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS: The (−/−) mice exhibited a decreased mean percentage of natural killer cells and blood eosinophils when compared with their (+/+) littermates and the historical mean. Analyzed wt/het/hom: 7/4/8

In summary, the FACS results indicate that the homozygous mutant mice have an impaired immune system, especially in view of the decreased mean percentage of natural killer cells which is an indicator of a negative phenotype associated with knocking out the DNA48331-1329 gene which encodes PRO731 polypeptides. Natural killer cells are the first line of defense to viral infection since these cells have been implicated in viral immunity and in defense against tumors. Natural killer cells or NK cells act as effectors in antibody-dependent cell-mediated cytotoxicity and have been identified by their ability to kill certain lymphoid tumor cell lines in vitro without the need for prior immunization or activation. However, their known function in host defense is in the early phases of infection with several intracellular pathogens, particularly herpes viruses. Thus, PRO731 polypeptides and agonists thereof would be important for a healthy immune system and would be useful in stimulating the immune system particularly during viral infections.

(c) Bone Metabolism & Body Diagnostics (1) Tissue Mass & Lean Body Mass Measurements—Dexa
Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):
Body Measurements: A measurement of body length and weight was performed at approximately 16 weeks of age.
Results:

The (−/−) mice exhibited increased mean body weight when compared with their gender-matched (+/+) littermates and the historical means. Organ weights were also significantly increased. Analyzed wt/het/hom: 28/58/33

Pathology: Microscopic observations revealed apoptosis of the olfactory neuro epithelial cells in 3/6 (−/−) and 1/2 (+/+) mice.

Gene Expression: LacZ activity was not detected in the panel of tissues by immuno histochemical analysis. Analyzed wt/het/hom: 4/2/13

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited increased mean total tissue mass, lean body mass, total body bone mineral density, and volumetric bone mineral density when compared with their gender-matched (+/+) littermates and the historical means. In addition, the (−/−) mice exhibited increased mean percent total body fat and total fat mass.

Micro-CT: The (−/−) mice exhibited increased mean vertebral trabecular bone volume, number and connectivity density and increased mean femoral mid-shaft cortical thickness and cross-sectional area when compared with their gender-matched (+/+) littermates and the historical means.

Analyzed wt/het/hom: 4/4/8

In summary, the (−/−) mice exhibited increased body weight, increased body fat, increased mean lean body mass, increased bone mineral content, and increased total body and femoral bone mineral density when compared with their gender-matched (+/+) littermates. The observations of an increased body weight, body fat and mean lean body mass in the (−/−) mutant mice suggests an obesity phenotype. These data suggest that the DNA48331-1329 gene encoding PRO731 polypeptides serves to negatively regulate proliferation and growth (cell/organ size) and would be important for cellular survival. In addition, the abnormal bone measurements indicate that the knockout mutant phenotype is associated with bone abnormalities such as osteopetrosis. Osteopetrosis is a condition characterized by abnormal thickening and hardening of bone and abnormal fragility of the bones. As such, PRO731 polypeptides or agonists thereof would be beneficial for the treatment of osteopetrosis or other osteo diseases. On the other hand, inhibitors or antagonists of PRO731 polypeptides would be useful in bone healing.

38.15. Generation and Analysis of Mice Comprising DNA48334-1435 (UNQ396) Gene Disruptions In these knockout experiments, the gene encoding PRO732 polypeptides (designated as DNA48334-1435) (UNQ396) was disrupted. The gene specific information for these studies is as follows: the mutated mouse gene corresponds to nucleotide reference: NM_019760 or ACCESSION:NM_019760 NID: gi 9790268 ref NM_019760.1 *Mus musculus* tumor differentially expressed 1, like (Tde1l); protein reference: Q9QZI8 or ACCESSION:Q9QZI8 NID: *Mus musculus* (Mouse). Tumor differentially expressed 1 protein like (Membrane protein TMS-2). MOUSESPTRNRDB; the human gene sequence reference: NM_020755 or ACCESSION:NM_020755 NID: gi 24308212 ref NM_020755.1 *Homo sapiens* likely ortholog of mouse tumor differentially expressed 1, like (TDE1L); the human protein sequence corresponds to reference: Q9NRX5 or ACCESSION:Q9NRX5 NID: *Homo sapiens* (Human). Tumor differentially expressed 1 protein like. HUMANSPTRNRDB.

The mouse gene of interest is Tde2 (tumor differentially expressed 2), ortholog of human TDE2. Aliases include Tms2, TMS-2, Tde1l, AIGP2, membrane protein TMS-2, and tumor differentially expressed 1-like. TDE2 is a putative integral plasma membrane protein expressed in neurons of the central nervous system (Grossman et al., *J Exp Biol* 203 Pt 3:447-57 (2000)) and in several other tissues, such as bladder, kidney, and muscle (Player et al, *Int J Cancer*, 107(2):238-43 (2003)). The protein consists of several transmembrane segments contained within a "TMS membrane protein/tumor differentially expressed protein (TDE)" domain. This domain is found in several other proteins, constituting a family that is differentially expressed in various tumor and cell lines (Pfam accession PF03348). For example, TDE2 expression tends to be higher in non small cell lung cancers than in adjacent normal tissue. In contrast, TDE2 expression in lung tumors tends to be lower than that in adjacent nonmalignant bronchiole epithelium (Player et al., *Int J Cancer*, 107(2):238-43 (2003)). The function of this protein is not known.

Genetics Information:

|  | wt | het | hom | Total |
| --- | --- | --- | --- | --- |
| Observed | 13 | 32 | 9 | 54 |
| Expected | 13.5 | 27 | 13.5 | 54 |

Chi-Sq. = 2.44
Significance = 0.29457
(hom/n) = 0.17
Avg. Litter Size = 6

Mutation Type Retroviral Insertion (OST)

Retroviral insertion occurred in the intron between coding exons 1 and 2 (NCBI accession NM_019760.1).

Wild-type expression of the target gene was detected in all 13 adult tissue samples tested by RT-PCR, except bone.

RT-PCR analysis revealed that the transcript was absent in the (−/−) mouse analyzed (M-133). Disruption of the target gene was confirmed by Inverse PCR.

35.15.1. Phenotypic Analysis (for Disrupted Gene: DNA48334-1435 (UNQ396)

(a) Overall Phenotypic Summary:

Mutation of the gene encoding the ortholog of human tumor differentially expressed 2 (TDE2) resulted in growth retardation as well as bone abnormalities (decreased bone measurements) in (−/−) mice. The (−/−) mice also exhibited an increased mean serum glucose level and impaired glucose tolerance. Hydrocephalus was noted in several of the (−/−) mutant mice. In addition, open field testing revealed increased activity during open field testing in the mutant (−/−) mice. Transcript was absent by RT-PCR.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Both the male and female (−/−) mice exhibited decreased mean body weight and mean body length when compared with their gender-matched (+/+) littermates and the historical means. The difference was more notable in the males. Analyzed wt/het/hom: 20/45/10

Pathology/Microscopic Observations: Hydrocephalus was noted in several (−/−) mice available for analysis.

Gene Expression: LacZ activity was not detected in the panel of tissues by immunohistochemical analysis. Analyzed wt/het/hom: 2/2/6

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited decreased mean total tissue mass and lean body mass when compared with their gender-matched (+/+) littermates and the historical means. These mutant animals also exhibited decreased mean bone mineral content and bone mineral density-related measurements.

Micro-CT: The (−/−) mice exhibited decreased mean vertebral trabecular bone volume, number, thickness, and connectivity density and decreased mean femoral mid-shaft cortical thickness when compared with their gender-matched (+/+) littermates and the historical means. Analyzed wt/het/hom: 4/4/8

Summary

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO732 or agonists thereof would play a role in maintaining bone homeostasis. In addition, PRO732 or its encoding gene would be useful for maintaining bone homeostasis and for bone healing or for the treatment of arthritis or osteoporosis; whereas antagonists to PRO732 or its encoding gene would lead to abnormal or pathological bone disorders including inflammatory diseases associated with abnormal bone metabolism including arthritis, osteoporosis, and osteopenia.

The (−/−) mice analyzed by DEXA exhibited notably decreased total tissue mass and lean body mass when compared with their (+/+) littermates, suggestive of growth retardation in these mutants. This in conjunction with the observations of abnormal bone measurements suggest a tissue wasting condition or other growth related disorders such as cachexia. Thus, PRO732 polypeptides or agonists thereof would be useful in the treatment of bone disorders but also would be useful for the prevention of growth related disorders such as cachexia and/or other tissue wasting diseases.

(c) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results:

Blood Chemistry: The (−/−) mice exhibited an increased mean serum glucose level when compared with their gender-matched (+/+) littermates and the historical mean. In the glucose tolerance test: 4 (−/−) mice analyzed, 2 (M-157 and M-167), exhibited increased fasting serum glucose levels when compared with their gender-matched (+/+) littermates and the historical mean. Analyzed wt/het/hom: 4/5/8

These studies indicated that (−/−) mice exhibit a decreased glucose tolerance in the presence of normal fasting glucose at all 3 intervals tested when compared with their gender-matched (+/+) littermates and the historical means. Thus, knockout mice exhibited the phenotypic pattern of an impaired glucose homeostasis, and therefor PRO732 polypeptides (or agonists thereof) or its encoding gene would be useful in the treatment of impaired glucose homeostasis.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., *Nature.* 1996 Feb. 15; 379(6566):606-12), and the GABA receptor (Homanics et al., *Proc Natl Acad Sci USA.* 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value. Analyzed wt/het/hom: 5/4/8

Results:

The (−/−) mice exhibited a decreased median sum time-in-center during open field testing when compared with their gender-matched (+/+) littermates and the historical mean, suggesting an increased anxiety-like response in the mutants.

As noted above, a notable difference was observed during open field activity testing. The (−/−) mice exhibited a decreased median sum time in the center area when compared with their gender-matched (+/+) littermates. This type of behavior is consistent with an increased anxiety like response. Thus, the knockout mice demonstrated a phenotype consistent with anxiety related disorders which are associated with mild to moderate anxiety, anxiety due to a general medical condition, and/or bipolar disorders; hyperactivity; sensory disorders; obsessive-compulsive disorders, schizophrenia or a paranoid personality. Thus, PRO732 polypeptides or agonists thereof would be useful in the treatment of such neurological disorders or the amelioration of the symptoms associated with anxiety disorders.

35.16. Generation and Analysis of Mice Comprising DNA58846-1409 (UNQ487) Gene Disruptions In these knockout experiments, the gene encoding PRO1003 polypeptides (designated as DNA58846-1409) (UNQ487) was disrupted. The gene specific information for these studies is as follows: the mutated mouse gene corresponds to nucleotide reference: NM_032541 or ACCESSION:NM_032541 NID: gi 14211541 ref NM_032541.1 *Mus musculus* hepcidin antimicrobial peptide (Hamp); protein reference: Q9EQ21 or ACCESSION:Q9EQ21 NID: *Mus musculus* (Mouse). PROHEPCIDIN (HEPCIDIN ANTIMICROBIAL PEPTIDE). MOUSESPTRNRDB; the human gene sequence reference: NM_021175 or ACCESSION: NM_021175 NID: gi 10863972 ref NM_021175.1 *Homo sapiens* hepcidin antimicrobial peptide (HAMP); the human protein sequence corresponds to reference: P81172 or ACCESSION:P81172 NID: *Homo sapiens* (Human). ANTIMICROBIAL PEPTIDE HEPCIDIN PRECURSOR (LIVER-EXPRESSED ANTIMICROBIAL PEPTIDE) (LEAP-1) (PUTATIVE LIVER TUMOR REGRESSOR) (PLTR) [CONTAINS: HEPCIDIN 25 (HEPC25); HEPCIDIN 20 (HEPC20)]. HUMANSPTRNRDB.

The disrupted mouse gene is hepcidin antimicrobial peptide (Hamp), ortholog of human HAMP. Aliases include HEPC1, HEPC, HFE2, LEAP1, LEAP-1, and liver-expressed antimicrobial peptide.

HAMP is a protein secreted mainly from liver that functions as an iron regulatory hormone and mediator of innate immunity. The 84-amino acid protein contains a signal peptide, a propeptide, and a 25-amino acid hepcidin core at the C-terminus. The positively charged hydrophilic residues and the hydrophobic residues of the mature 25 amino acid hepcidin core peptide are spatially separated, enabling the peptide to disrupt microbial membranes (Ganz Tomas., *Blood,* 102 (3):783-8 (2003)).

HAMP is involved in iron homeostasis. Increases in iron load increase HAMP expression, resulting in decreased dietary iron absorption, transplacental iron transport, and iron mobilization from splenic and hepatic macrophages. Mutations in the HAMP gene can cause juvenile hereditary hemochromatosis, leading to iron overload, cirrhosis, cardiomyopathy, arthritis, and endocrine failure. HAMP has strong antimicrobial activity against bacteria and some fungi. However, individuals lacking active HAMP still have the ability to prevent infection, suggesting that the role of HAMP as an antimicrobial is not critical (Roetto et al., *Nat Genet,* 33(1): 21-2 (2003)). Inflammation upregulates HAMP, possibly resulting in iron disorders and anemia in response to inflammatory diseases such as infectious disease, osteoarticular diseases, and malignancies (Ganz Tomas, *Blood,* 102(3):783-8 (2003)).

Nicolas and colleagues, *Proc Natl Acad Sci USA*, 98(15): 8780-5 (2001) showed that HAMP-deficient mice (caused by knockout of a transcription factor gene that regulates HAMP expression) develop multivisceral iron overload. In a mouse model of hemochromatosis, Nicolas and colleagues, *Nat Genet,* 34(1):97-101 (2003) showed that iron accumulation normally occurring in these mice was inhibited by overexpression of HAMP. In wild-type mice, Nicolas and colleagues, *Proc Natl Acad Sci USA,* 99(7):4596-601 (2002) showed that HAMP overexpression produced mice with pale skin that died a few hours after birth. These animals had decreased body iron levels and presented severe microcytic hypochromic anemia.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation

|          | wt    | het  | hom   | Total |
|----------|-------|------|-------|-------|
| Observed | 20    | 33   | 24    | 77    |
| Expected | 19.25 | 38.5 | 19.25 | 77    |

Chi-Sq. = 1.99
Significance = 0.37028
(hom/n) = 0.31
Avg. Litter Size = 8

Mutation Type Homologous Recombination (standard)
Coding exons 1 and 2 were targeted (NCBI accession NM_032541.1).
Wild-type expression of the target gene was detected in embryonic stem (ES) cells and, in all 13 adult tissues samples tested by RT-PCR, except liver, heart and adipose.
Disruption of the target gene was confirmed by Southern hybridization analysis.

35.16.1. Phenotypic Analysis (for disrupted gene: DNA58846-1409 (UNQ487))

(a) Overall Phenotypic Summary:

Mutation of the gene encoding the ortholog of human hepcidin antimicrobial peptide (HAMP) resulted in enhanced glucose tolerance in (−/−) mice. The knockout mice (−/−) also showed elevated levels of serum uric acid. Gene disruption was confirmed by Southern blot.

(b) Phenotypic Analysis: Metabolism-Blood Chemistry/ Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/9

Results:

The (−/−) mice exhibited enhanced glucose tolerance and a significant decrease in mean serum glucose when compared with their gender-matched (+/+) littermates and the historical means. Thus, knockout mice exhibited the opposite phenotypic pattern of an impaired glucose homeostasis, and as such antagonists to PRO1003 or its encoding gene would be useful in the treatment of impaired glucose homeostasis and/or any associated metabolic disorder. In addition, the knockout mutant mice (−/−) exhibited elevated serum uric acid levels (greater than 2 SD above the historical mean). However, there were no other indices of renal compromise.

35.17. Generation and Analysis of Mice Comprising DNA59616-1465 (UNQ547) Gene Disruptions In these knockout experiments, the gene encoding PRO1104 polypeptides (designated as DNA59616-1465) (UNQ547) was disrupted. The gene specific information for these studies is as follows: the mutated mouse gene corresponds to nucleotide reference: XM_131066 or *Mus musculus* similar to hypothetical protein FLJ20519 (LOC229588); protein reference: XP_131066 or similar to hypothetical protein FLJ20519 [*Mus musculus*]; the human gene sequence reference: NM_017860 or *Homo sapiens* hypothetical protein FLJ20519 (FLJ20519); the human protein sequence corresponds to reference: NP_060330 or hypothetical protein FLJ20519 [*Homo sapiens*]. The disrupted mouse gene is a hypothetical protein (interim name, LOC229588), which is orthologous to human hypothetical protein FLJ20519.

A signal peptide-like region is predicted at the N-terminus through bioinformatic analysis. Overall, the protein is predicted to be secreted or to reside in the plasma membrane.
Genetics Information:

|          | wt    | het  | hom   | Total |
|----------|-------|------|-------|-------|
| Observed | 8     | 19   | 20    | 47    |
| Expected | 11.75 | 23.5 | 11.75 | 47    |

Chi-Sq. = 7.85
Significance = 0.01973
(hom/n) = 0.43
Avg. Litter Size = 7

Mutation Type: Retroviral Insertion (OST)
Retroviral insertion occurred in the first coding exon (Accession: XM_131066).
Wild-type expression of the target gene was detected in embryonic stem (ES) cells and, among the 13 adult tissue samples tested by RT-PCR, in spinal cord, eye, thymus, and lung.
RT-PCR analysis revealed that the transcript was absent in the (−/−) mouse analyzed (M-104). Disruption of the target gene was confirmed by Inverse PCR.

35.17.1. Phenotypic Analysis (for Disrupted Gene: DNA59616-1465 (UNQ547)

(a) Overall Phenotypic Summary:

Mutation of the gene encoding the ortholog of a human hypothetical protein (FLJ2519) resulted in an increased body weight and length measurements as well as increased body mass and femoral bone measurements. The ovalbumin (OVA) challenge resulted in reduced anti-OVA titers in the homozygous knockout mice. In addition, the (−/−) mice showed an enhanced glucose tolerance compared with their wild-type littermates. Transcript was absent by RT-PCR.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immuno-dominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Analyzed wt/het/hom: 7/4/8

Results of this challenge: The (−/−) mice exhibited a decreased mean serum IgG2a response to the ovalbumin challenge when compared with their (+/+) littermates. Thus, these knockout mice exhibited an decreased ability to elicit an OVA-specific antibody response to the T-cell dependent OVA antigen more than likely due to a defect in Th cells. PRO1104 polypeptides or agonists thereof would therefore be expected to stimulate the immune system and would find utility in the cases wherein this effect would be beneficial to the individual such as in the case of leukemia, and other types of cancer, and in immunocompromised patients, such as AIDS sufferers. Accordingly, inhibitors or antagonists of PRO1104 polypeptides would play a role in inhibiting the immune response and would be useful candidates for suppressing harmful immune responses, e.g. in the case of graft rejection or graft-versus-host diseases.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited increased mean body weight and increased mean body length (by at least one (1) standard deviation heavier than controls before 8 weeks of age) when compared with their gender-matched (+/+) littermates and the historical mean. Analyzed wt/het/hom: 15/22/16

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited increased mean total tissue mass and lean body mass when compared with their gender-matched (+/+) littermates and the historical means.

Micro-CT: The (−/−) mice exhibited increased mean femoral mid-shaft cross-sectional area when compared with their gender-matched (+/+) littermates and the historical means. Analyzed wt/het/hom: 4/4/8

In summary, the (−/−) mice exhibited increased body weight and length, increased mean total tissue mass and lean body mass and increased bone cross-sectional measurements when compared with their gender-matched (+/+) littermates. These observations suggests an obesity and/or growth disorder type phenotype. In addition, the mutant (−/−) mice exhibited an abnormal bone development. Thus, PRO1104 polypeptides or agonists thereof, would be useful for normal growth and bone development and would play a role in the treatment of related growth or metabolic disorders associated with obesity and/or bone disorders.

(d) Phenotypic Analysis: Metabolism-Blood Chemistry/ Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/9

Results:

The (−/−) mice exhibited enhanced glucose tolerance and a significant decrease in mean serum glucose when compared with their gender-matched (+/+) littermates and the historical means. Thus, knockout mice exhibited the opposite phenotypic pattern of an impaired glucose homeostasis, and as such antagonists to PRO1104 or its encoding gene would be useful in the treatment of impaired glucose homeostasis and/or any associated metabolic disorder.

35.18. Generation and Analysis of Mice Comprising DNA44694-1500 (UNQ581) Gene Disruptions In these knockout experiments, the gene encoding PRO1151 polypeptides (designated as DNA44694-1500) (UNQ581) was disrupted. The gene specific information for these studies is as follows: the mutated mouse gene corresponds to nucleotide reference: NM_028331 or *Mus musculus* C1q and tumor necrosis factor related protein 6 (C1qtnf6); proteinreference: Q8BKR0 or ACCESSION:Q8BKR0 NID: *Mus musculus* (Mouse). Weakly similar to complement-C1Q tumor necrosis factor-related protein; the human gene sequence reference: NM_031910 or *Homo sapiens* C1q and tumor necrosis factor related protein 6 (C1QTNF6), transcript variant 1; the human protein sequence corresponds to reference: NP_114116 or C1q and tumor necrosis factor related protein 6; complement-c1q tumor necrosis factor-related protein 6 [*Homo sapiens*] gi|32967300|ref|NP_872292.1| C1q and tumor necrosis factor related protein 6; complement-c1q tumor necrosis factor-related protein 6 [*Homo sapiens*] gi|13274531|gb|AAK17966.1| complement-c1q tumor necrosis factor-related protein [*Homo sapiens*].

The mouse gene of interest is C1qtnf6 (C1q and tumor necrosis factor related protein 6), ortholog of human C1QTNF6. Aliases include CTRP6, ZACRP6, and complement-c1q tumor necrosis factor-related protein 6.

C1QTNF6 is a putative secreted protein, consisting of a signal peptide, a collagen triple helix repeat, and a "complement component C1q" domain. Collagen triple helix repeats are most often found in collagens, which are generally extracellular structural proteins (Pfam accession PF01391). C1q domains are found in many collagens and in the C1q subunit of C1 enzyme complex, which activates the serum complement system. C1q and tumor necrosis factor fold similarly (SMART accession SM0010). The function of this protein is not known.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 18 | 25 | 13 | 56 |
| Expected | 14 | 28 | 14 | 56 |

Chi-Sq. = 1.54
Significance = 0.46401
(hom/n) = 0.23
Avg. Litter Size = 8

Mutation Type Homologous Recombination (standard)
Coding exon 2 was targeted (NCBI accession NM_028331.2).
Wild-type expression of the target gene was detected in embryonic stem (ES) cells and in all 13 adult tissue samples tested by RT-PCR, except skeletal muscle.
Disruption of the target gene was confirmed by Southern hybridization analysis.

35.18.1. Phenotypic Analysis (for Disrupted Gene: DNA44694-1500 (UNQ581)

(a) Overall Phenotypic Summary:

Mutation of the gene encoding the ortholog of human C1q and tumor necrosis factor related protein 6 (C1QTNF6) resulted in decreased bone mineral density measurements. Gene disruption was confirmed by Southern blot.

(b) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited decreased mean bone mineral density in total body and femur when compared with their gender-matched (+/+) littermates and the historical means.

Micro-CT: The (−/−) mice exhibited decreased mean femoral midshaft cortical thickness when compared with their gender-matched (+/+) littermates and the historical means.

Analyzed wt/het/hom: 5/4/8

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO1151 or agonists thereof would be useful in maintaining bone homeostasis. In addition, PRO1151 or its encoding gene would be useful in bone healing or for the treatment of arthritis or osteoporosis; whereas antagonists to PRO1151 or its encoding gene would lead to abnormal or pathological bone disorders including inflammatory diseases associated with abnormal bone metabolism including arthritis, osteoporosis, and osteopenia.

35.19. Generation and Analysis of Mice Comprising DNA64883-1526 (UNQ628) Gene Disruptions In these knockout experiments, the gene encoding PRO1244 polypeptides (designated as DNA64883-1526) (UNQ628) was disrupted. The gene specific information for these studies is as follows: the mutated mouse gene corresponds to nucleotide reference: NM_025952 or *Mus musculus* RIKEN cDNA 2610529C04 gene (2610529C04Rik); protein reference: NP_080228 or implantation-associated protein [*Mus musculus*]; the human gene sequence reference: NM_032121 or *Homo sapiens* implantation-associated protein (DKFZp564K142); the human protein sequence corresponds to reference: NP_115497 or implantation-associated protein [*Homo sapiens*].

The disrupted mouse gene encodes a hypothetical protein, which is the ortholog of human FLJ14726. Aliases include 2610529C04Rik, IAG2, 2410001C15Rik, PRO0756, DKFZp564K142, implantation-associated protein, and implantation-associated uterine protein.

FLJ14726 contains an OST3/OST6 motif (Pfam PF04756) suggesting that it might be an oligosaccharide transferase and might be located in the endoplasmic reticulum. Proteins with similar function have been described and studied in yeast (Knauer and Lehle, *J Biol Chem,* 274(24):17249-56 (1999).

This project is X-linked, hemizygotes have no notable phenotype.

Summary of X-linked Gene Distribution by Sex and Genotype
(Only the agouti pups from the male chimeras are included.)

| Summary of X-linked Gene Distributions for Sex by Genotype | | | | | | |
|---|---|---|---|---|---|---|
| Progeny | Agouti F1 (M chimera × wt) | | Progeny | F1a (F het × wt) | | |
| Sex | wt | het | Sex | wt | het | hemi |
| M | 24 | 0 | M | 32 | n/a | 23 |
| F | 16 | 11 | F | 18 | 18 | n/a |

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEV$^{Brd}$/C57 hybrid mice to yield additional heterozygous animals for the intercross to generate the F2 mice. Level I phenotypic analysis is performed on mice from this generation.

| | wt | het | hom | Total |
|---|---|---|---|---|
| Observed | 22 | 18 | 30 | 70 |
| Expected | 17.5 | 35 | 17.5 | 70 |

Chi-Sq. = 18.34
Significance = 0.00010
(hom/n) = 0.43
Avg. Litter Size = 7

Mutation Type: Retroviral Insertion (OST)
Retroviral insertion occurred between coding exons 1 and 2 (Accession: NM_025952).
Wild-type expression of the target gene was detected in all 13 adult tissue samples tested by RT-PCR, except skeletal muscle, bone, and adipose.
RT-PCR analysis revealed that the transcript was absent in the (0/−) mouse analyzed (M-97).

35.19.1. Phenotypic Analysis (for Disrupted Gene: DNA64883-1526 (UNQ628)

(a) Overall Phenotypic Summary:

Mutation of the gene encoding the ortholog of human implantation-associated protein (DKFZp564K142) protein resulted in an increased mean serum glucose level. Transcript was absent by RT-PCR.

(b) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/12

Results:

Blood Chemistry: The (−/−) mice exhibited an increased mean serum glucose level when compared with their gender-matched (+/+) littermates and the historical mean.

Thus, knockout mice exhibited the phenotypic pattern of an impaired glucose homeostasis, and as such PRO1244 polypeptides or agonists thereof, would be useful in the treatment of impaired glucose homeostasis and/or any associated metabolic disease.

35.20. Generation and Analysis of Mice Comprising DNA66511-1563 (UNQ666) Gene Disruptions In these knockout experiments, the gene encoding PRO1298 polypeptides (designated as DNA66511-1563) (UNQ666) was disrupted. The gene specific information for these studies is as follows: the mutated mouse gene corresponds to nucleotide reference: NM_019998 or ACCESSION:NM_019998 NID:9910439 *Mus musculus Mus musculus* RIKEN cDNA 1300013N08 gene (1300013N08Rik); protein reference: Q9JJA8 or Q9JJA8 Q9JJA8 BRAIN CDNA, CLONE MNCB-5081; the human gene sequence reference: NM_033087 or ACCESSION:NM_033087 NID: 14861835 *Homo sapiens Homo sapiens* hypothetical protein FLJ14511 (FLJ14511); the human protein sequence corresponds to reference: Q9H553 or Q9H553 Q9H553 BA13B9.1 NOVEL PROTEIN SIMILAR TO A GLYCOS.

The mouse gene of interest is Alg2 (asparagine-linked glycosylation 2 homolog [yeast, alpha-1,3-mannosyltransferase]), ortholog of human ALG2. Aliases include ALPG2, CDGIi, MNCb-5081, hALPG2, FLJ14511, homolog of yeast ALG2, and GDP-Man:Man(1)GlcNAc(2)-PP-dolichol mannosyltransferase.

ALG2 is an alpha 1,3-mannosyltransferase located in the lumen of the endoplasmic reticulum that catalyzes the formation of Manalpha1,3-ManGlcNAc2-PP dolichol from Man1GlcNAc2-PP-dolichol and GDP-mannose. ALG2 appears to play an important role in glycoprotein biosynthesis. Loss-of-function mutations in ALG2 cause congenital disorder of glycosylation type Ii. Individuals with this mutation are normal at birth but develop a multisystemic disorder in the first year of life. The disorder includes mental retardation, seizures, coloboma of the iris, hypomyelination, hepatomegaly, and coagulation abnormalities (Thiel et al., *J Biol Chem*, 278(25):22498-505 (2003)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|  | wt | het | hom | Total |
|---|---|---|---|---|
| Observed | 10 | 37 | 0 | 47 |
| Expected | 11.75 | 23.5 | 11.75 | 47 |

Chi-Sq. = 19.77
Significance = 0.00005
(hom/n) = 0.00
Avg. Litter Size = 5

Mutation Type: Homologous Recombination (standard)
Coding exon 2 was targeted (NCBI accession NM_019998.2).
Wild-type expression of the target gene was detected in embryonic stem (ES) cells and in all 13 adult tissue samples tested by RT-PCR, except lung, bone, and adipose.
Disruption of the target gene was confirmed by Southern hybridization analysis.

35.20.1. Phenotypic Analysis (for Disrupted Gene: DNA66511-1563 (UNQ666)
  (a) Overall Phenotypic Summary:
  Mutation of the gene encoding the ortholog of human asparagine-linked glycosylation 2 homolog (ALG2) resulted in lethality of (−/−) mutants. The (+/−) mice exhibited a decreased skin fibroblast proliferation rate. The heterozygous (+/−) mice exhibited an increased total tissue mass, increased fat %, and increased BMC/LBM ration, as well as increased trabecular bone measurements. Gene disruption was confirmed by Southern blot.
  Discussion Related to Embryonic Developmental Abnormality of Lethality:
  Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.
  (b) Pathology
  Microscopic Observations: Not tested due to embryonic lethality. At 12.5 days, 40 embryos were observed: 28 (+/−) embryos, 6 (+/+) embryos, 4 resorption moles, and 2 inconclusive.
  Gene Expression: LacZ activity was not detected in the panel of tissues by immunohistochemical analysis.
  (c) Oncology Phenotypic Analysis
  In the area of oncology, targets were identified herein for the treatment of solid tumors, lymphomas and leukemia.
  Adult Skin Cell Proliferation:
  Procedure: Skin cells were isolated from 16 week old animals (2 wild type and 4 heterozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.
  Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.
  Results:
  The (+/−) mice exhibited a decreased mean skin fibroblast proliferation rate when compared with their gender-matched (+/+) littermates and the historical mean. Thus, heterozygous mutant mice demonstrated a hypo-proliferative phenotype. As suggested by these observations, antagonists of a PRO1298 polypeptide or its encoding gene would be useful in the treatment of diseases associated with abnormal cell proliferation.
  (d) Bone Metabolism & Body Diagnostics: Bone Metabolism: Radiology Phenotypic Analysis
  In the area of bone metabolism, targets were identified herein for the treatment of arthritis, osteoporosis, osteopenia and osteopetrosis as well as identifying targets that promote bone healing. Tests included:
  DEXA for measurement of bone mineral density on femur and vertebra
  MicroCT for very high resolution and very high sensitivity measurements of bone mineral density for both trabecular and cortical bone.
  Dexa Analysis—Test Description:
  Procedure: Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.
  The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].
  Bone microCT Analysis:
  Procedure: MicroCT was also used to get very sensitive measurements of BMD. One vertebra and 1 femur were taken from a cohort of 4 wild type and 8 heterozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.
  Results:
  DEXA: The (+/−) mice exhibited increased mean total tissue mass and increased total body fat (% and gram), and an increased BMC/LBM ratio when compared with their gender-matched (+/+) littermates and the historical means.
  Micro-CT: The (+/−) mice exhibited increased trabecular bone volume, number, thickness, and connectivity density as well as mean femoral mid-shaft cortical thickness area when compared with their gender-matched (+/+) littermates and the historical means.

In summary, the (+/−) mice exhibited increased mean total tissue mass and total body fat and increased trabecular bone and femoral mid-shaft bone measurements when compared with their gender-matched (+/+) littermates. These observations suggest an obesity and/or growth disorder type phenotype. In addition, the mutant (+/−) mice exhibited an abnormal bone development. Thus, PRO1298 polypeptides or agonists thereof, would be useful for normal growth and bone development and would play a role in the treatment of related growth or metabolic disorders associated with obesity and/or bone disorders.

35.21. Generation and Analysis of Mice Comprising DNA64966-1575 (UNQ679) Gene Disruptions In these knockout experiments, the gene encoding PRO1313 polypeptides (designated as DNA64966-1575) (UNQ679) was disrupted. The gene specific information for these studies is as follows: the mutated mouse gene corresponds to nucleotide reference: NM__175187 or *Mus musculus* RIKEN cDNA 2810446P07 gene; protein reference: NP__780396 or RIKEN cDNA 2810446P07 [*Mus musculus*]; the human gene sequence reference: NM__153354 or *Homo sapiens* hypothetical protein MGC33214 (MGC33214); the human protein sequence corresponds to reference: NP__699185 or hypothetical protein MGC33214 [*Homo sapiens*].

The mouse gene of interest encodes a hypothetical membrane protein (2810446P07Rik), which is the ortholog of a human hypothetical membrane protein (MGC33214).

MGC33214 is likely to be a membrane protein, containing seven transmembrane domains. The function of this protein is currently unknown. MGC33214 is most similar to other hypothetical proteins from a wide variety of species, including a very large (5722 amino acids) rat hypothetical protein annotated as "similar to ATP binding cassette transporter A13." Bioinformatic analysis suggests that the protein may be located on the plasma membrane; however, endoplasmic reticulum and nuclear membrane are also possible cell locations.

Genetics Information:

|  | wt | het | hom | Total |
| --- | --- | --- | --- | --- |
| Observed | 22 | 41 | 8 | 71 |
| Expected | 17.75 | 35.5 | 17.75 | 71 |

Chi-Sq. = 7.23
Significance = 0.02698
(hom/n) = 0.11
Avg. Litter Size = 8

Mutation Type: Retroviral Insertion (OST)
Retroviral insertion occurred in the intron between coding exons 1 and 2 (NCBI accession number NM__175187.3).
Wild-type expression of the target gene was detected in embryonic stem (ES) cells and in all 13 adult tissue samples tested by RT-PCR.
Due to lethality, transcript expression analysis was not performed. Disruption of the target gene was confirmed by Inverse PCR.

35.21.1. Phenotypic Analysis (for Disrupted Gene: DNA64966-1575 (UNQ679)

(a) Overall Phenotypic Summary:

Mutation of the gene encoding the ortholog of a human hypothetical membrane protein (MGC33214) resulted in lethality of (−/−) mutants. No notable phenotype was observed for the (+/−) mice. All (−/−) pups were dead at the time of genotyping.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(b) Embryonic Expression Studies
In Situ Hybridization (ISH) Studies:

Using a probe made to base pairs 969-1407 from the initiating ATG of NM__175187 (exons 10-12), specific and ubiquitous staining was observed in the embryonic placenta of (+/+) mice at E6.5d, E7.5d, E9.5d, E10.5d, E11.5d and E12.5D. Yet another probe showed UNQ679 staining specific to the dorsal midline (ubiquitous staining) (probe was made to base pairs 1317-1888 from the initiating ATG of NM__175187 (exon 12 to start of 3' UTR). On the other hand, UNQ679 homozygous (−/−) mice were shown to be anemic and much smaller compared to the wild-type (+/+) control mice at E13.5d. Similar results were noted at E18.5d. A placental defect was notably displayed in the mutant (−/−) mice at 14.5d compared to the wild-type embryos at E14.5d. In addition, the head and eyes of the UNQ679 (−/−) embryos at E16.5d were improperly formed. UNQ679 (−/−) mutant embryos were smaller, anemic and have malformed hearts at E15.5d. See EXAMPLE 44 for ISH protocol. Thus, UNQ679 is essential for placenta development and normal development. The observed anemia in the mutant (−/−) embryos at E13.5d was more than likely a result of the defective placental development.

35.22. Generation and Analysis of Mice Comprising DNA68885-1678 (UNQ776) Gene Disruptions In these knockout experiments, the gene encoding PRO1570 polypeptides (designated as DNA68885-1678) (UNQ776) was disrupted. The gene specific information for these studies is as follows: the mutated mouse gene corresponds to nucleotide reference: NM__145403 or ACCESSION:NM__145403 NID:21703805 *Mus musculus Mus musculus* similar to Transmembrane protease, serine 4 (Membrane-type serine protease 2) (MT-SP2) (LOC214523); protein reference: Q8VCA5 or ACCESSION:Q8VCA5 NID: *Mus musculus* (Mouse). SIMILAR TO TRANSMEMBRANE PROTEASE, SERINE 4. MOUSESPTRNRDB; the human gene sequence reference: NM__019894 or ACCESSION:NM__019894 NID:15451939 *Homo sapiens Homo sapiens* transmembrane protease, serine 4 (TMPRSS4); the human protein sequence corresponds to reference: Q9NRS4 or ACCESSION:Q9NRS4 NID: *Homo sapiens* (Human). TRANSMEMBRANE PROTEASE, SERINE 4 (EC 3.4.21.-) (MEMBRANE-TYPE SERINE PROTEASE 2) (MT-SP2). HUMANSPTRNRDB.

The mouse gene of interest is Tmprss4 (transmembrane protease, serine 4), ortholog of human TMPRSS4. Aliases include membrane-type serine protease 2, MT-SP2, transmembrane serine protease 3, and TMPRSS3.

TMPRSS4 is a type II membrane protein that is likely to function as a serine protease of the chymotrypsin family. The protein contains a signal anchor and an extracellular trypsin-like serine protease domain. TMPRSS4 is overexpressed in pancreatic cancer but not in normal pancreas, suggesting that TMPRSS4 may be involved in metastasis (Wallrapp et al., *Cancer Res*, 60(10):2602-6 (2000); Gress et al., *Genes Chromosomes Cancer*, 19(2):97-103 (1997)). TMPRSS4 may regulate renal sodium transport by activating the epithelial sodium channel (ENaC) expressed in collecting tubules (Vuagniaux et al., *J Gen Physiol*, 120(2):191-201 (2002)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 24 | 33 | 14 | 71 |
| Expected | 17.75 | 35.5 | 17.75 | 71 |

Chi-Sq. = 3.17
Significance = 0.20505
(hom/n) = 0.20
Avg. Litter Size = 8

Mutation Type Homologous Recombination (standard)
Coding exons 3 through 5 were targeted (NCBI accession NM_145403.1).
Wild-type expression of the target gene was detected in all 13 adult tissue samples tested by RT-PCR, except spinal cord, thymus, bone, and adipose.
Disruption of the target gene was confirmed by Southern hybridization analysis.

35.22.1. Phenotypic Analysis (for Disrupted Gene: DNA68885-16778 (UNQ776)

(a) Overall Phenotypic Summary:

Mutation of the gene encoding the ortholog of human transmembrane protease, serine 4 (TMPRSS4) resulted in an increased anxiety-related response in (−/−) mice. The (−/−) mice also exhibited an increased skin fibroblast proliferation rate. Mutant (−/−) mice also exhibited increased mean serum triglyceride levels, and increased mean serum glucose levels with an impaired glucose tolerance. An increased response to the LPS challenge was also observed in the (−/−) mice. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 µL sterile saline using a 26 gauge needle. The doses were based on the average weight of the mice tested at 1 µg/g body weight 3 hours after injection; a 100 ul blood sample was then taken and analyzed for the presence of TNFa, MCP-1, and IL-6 on the FACSCalibur instrument.

Results:

The (−/−) mice exhibited an increased mean serum MCP-1 response to LPS challenge when compared with their (+/+) littermates and the historical mean.
Analyzed wt/het/hom: 7/4/11

In summary, the LPS endotoxin challenge results indicate that knockout mice deficient in the gene encoding PRO1570 polypeptides exhibit immunological abnormalities when compared with their wild-type littermates. In one instance, the mutant mice exhibited an increased ability to elicit an immunological response (MCP-1 production) when challenged with the LPS endotoxin indicating a proinflammatory response. MCP-1 contributes to the later stages of B cell activation. In addition, MCP-1 plays a critical role in inducing the acute phase response and systemic inflammation. This finding suggests that inhibitors or antagonists to PRO1570 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO1570 polypeptides or agonists thereof would be useful in inhibiting the immune response and would be useful candidates for suppressing harmful immune responses, e.g. in the case of graft rejection or graft-versus-host diseases.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value. Analyzed wt/het/hom: 4/4/8

Results:

The (−/−) mice exhibited decreased median sum time-in-center and hole poke activity during open field testing when compared with their gender-matched (+/+) littermates and the historical mean, suggesting an increased anxiety-like response in the mutants.

As noted above, a notable difference was observed during open field activity testing. The (−/−) mice exhibited a decreased median sum time in the center area when compared with their gender-matched (+/+) littermates. This type of behavior is consistent with an increased anxiety like response. Thus, the knockout mice demonstrated a phenotype consistent with anxiety related disorders which are associated with mild to moderate anxiety, anxiety due to a general medical condition, and/or bipolar disorders; hyperactivity; sensory disorders; obsessive-compulsive disorders, schizophrenia or a paranoid personality. Thus, PRO1570 polypeptides or agonists thereof would be useful in the treatment of such neurological disorders or the amelioration of the symptoms associated with anxiety disorders.

(d) Oncology Phenotypic Analysis

In the area of oncology, targets were identified herein for the treatment of solid tumors, lymphomas and leukemia.

Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results:

The (−/−) mice exhibited an increased mean skin fibroblast proliferation rate when compared with their gender-matched (+/+) littermates and the historical mean. Thus, homozygous mutant mice demonstrated a hyper-proliferative phenotype. As suggested by these observations, PRO1570 polypeptides or agonists thereof would be useful in decreasing abnormal cell proliferation such as tumor cell growth.

(e) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results:

The (−/−) mice exhibited increased mean serum triglyceride and glucose levels when compared with their gender-matched (+/+) littermates and the historical means.

As summarized above, the (−/−) mice exhibited notably increased triglyceride levels when compared with their gender-matched (+/+) littermates and the historical means for the male (+/+) mice. In addition, the increased mean serum glucose levels suggesting diabetes. Thus, mutant mice deficient in the PRO1570 gene can serve as a model for cardiovascular disease including diabetes. PRO1570 polypeptides or its encoding gene would be useful in regulating normal blood lipid levels such as triglycerides. Thus, PRO1570 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

35.23. Generation and Analysis of Mice Comprising DNA80796-2523 (UNQ870) Gene Disruptions In these knockout experiments, the gene encoding PRO1886 polypeptides (designated as DNA80796-2523) (UNQ870) was disrupted. The gene specific information for these studies is as follows: the mutated mouse gene corresponds to nucleotide reference: XM_134593 or *Mus musculus* hypothetical protein 4932417I16 (4932417I16); protein reference: XP_134593 or similar to predicted CDS, putative protein of bilateral origin (4J193) [*Mus musculus*]; the human gene sequence reference: AK025820 or *Homo sapiens* cDNA: FLJ22167 fis, clone HRC00584; the human protein sequence corresponds to reference: BAB15244 or unnamed protein product [*Homo sapiens*].

The disrupted mouse gene encodes a hypothetical protein (4932417I16Rik), which is orthologous to human hypothetical protein FLJ22167. Aliases include hypothetical protein 4932417I16 (murine).

Bioinformatic analyses of FLJ22167 indicate that it is a transmembrane protein, possibly located in the plasma membrane or the endoplasmic reticulum. In human, some FLJ22167 transcripts overlap those of an adjacent gene (CHST5), but such overlap is not observed in mouse. The overlap has sometimes led to misidentification of FLJ22167 as a possible enzyme (isoform of CHST5). No critically evaluated information suggests that FLJ22167 is an enzyme.

Genetics Information:

|          | wt    | het  | hom   | Total |
|----------|-------|------|-------|-------|
| Observed | 29    | 28   | 0     | 57    |
| Expected | 14.25 | 28.5 | 14.25 | 57    |

Chi-Sq. = 29.53
Significance = 0.00000
(hom/n) = 0.00
Avg. Litter Size = 6

Mutation Type: Retroviral Insertion (OST)

Retroviral insertion occurred within the intron proceeding coding exon 1 (NCBI Accession AK030046).

Wild-type expression of the target gene was detected in embryonic stem (ES) cells and in all 13 adult tissue samples tested by RT-PCR.

Due to lethality, transcript expression analysis was not performed. Disruption of the target gene was confirmed by Inverse PCR.

35.23.1. Phenotypic Analysis (for Disrupted Gene: DNA80796-2523 (UNQ870)

(a) Overall Phenotypic Summary:

Mutation of the gene encoding the ortholog of a human hypothetical protein (FLJ22167) resulted in lethality of (−/−) mutants. One fourth (¼) of the UNQ870 pups make it to birth. The (+/−) mice exhibited increased total body fat (% and gram) and increased mean total tissue mass. In addition, a reduced fibroblast proliferation was observed in the (+/−) mice.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(b) Further Expression and Embryonic Observations

UNQ 870 is upregulated in endometrial adenocarcinoma (See EXAMPLES 41 and 42 for protocol).

Microscopic observations showed one third (⅓) of the heterozygous (+/−) mice to have hydronephrosis of the right kidney.

The UNQ870 homozygous (−/−) embryos showed heart defects at E15.5d.

Three fourths (¾) of UNQ870 homozygous (−/−) embryos are anemic and have abnormal eyes at E14.5d. One fourth (¼) of the UNQ870 (−/−) embryos are anemic and have eyes at E15.5d but no eyelid closure. Normal eyelid development results in an eyelid primordia at E12.5d, a fused eyelid between 15.5d-16.5d and eyes open at P12-14d. There is a parallel between eyelid closure and wound healing (progressive events run in parallel). Also other factors such as FGF8 expression, neurogenin 2 expression, Gli3 and Dlx2 expression, as well as EyaI expression all appear to be altered in the (−/−) mutant embryos. [FGF8 expression is reduced in UNQ870 (−/−) at E10.5d; reduced staining in the telencephalic vescicle and nasal placode in UNQ870 (−/−). Neurogenin 2 expression is reduced in UNQ870 (−/−) at E10.5d; reduced staining in telencephalon of UNQ870 (−/−) or reduced or missing ventral staining in UNQ870 (−/−). Gli3 expression is altered in UNQ870 (−/−) at E10.5d; (reduced staining in telencephalon, branchial arches, and optic vesicles). Dlx2 expression is altered in UNQ870 (−/−) at E9.5d; tighter domain of staining at AER of limb bud in wild-type (+/+). EyaI expression is altered in UNQ870 (−/−) at E9.5d; reduced staining in branchial arches and otic vesicles. See EXAMPLE 44 for ISH protocol.

Pax6 knockouts are similar to UNQ870 knockouts. Small eye (Sey) is a semidominant mutation in the Pax6 gene. Homozygotes (−/−) result in the complete lack of eyes and nasal primordia. On the basis of comparative mapping studies and on phenotypic similarities, Sey has been suggested to be homologous to congenital aniridia (lack of iris) in humans.

(c) Bone Metabolism & Body Diagnostics (1) Tissue Mass & Lean Body Mass Measurements—Dexa Dexa Analysis—Test Description:

Procedure: Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (+/−) mice exhibited increased mean body weight when compared with their gender-matched (+/+) littermates and the historical means.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The (+/−) mice exhibited increased mean total tissue mass, percent total body fat, and total fat mass when compared with their gender-matched (+/+) littermates and the historical means.

These studies suggest that mutant (+/−) non-human transgenic animals exhibit a negative phenotype that may be associated with obesity. Thus, PRO1886 polypeptides or agonists thereof are essential for normal growth and metabolic processes and especially would be important in the prevention and/or treatment of obesity.

(d) Oncology Phenotypic Analysis

In the area of oncology, targets were identified herein for the treatment of solid tumors, lymphomas and leukemia.

Adult Skin Cell Proliferation:

Procedure: Skin cells were isolated from 16 week old animals (2 wild type and 4 heterozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and (+/−) mutant mice. Duplicate or triplicate cultures of 0.05 million cells were plated and allowed to grow for six days. At the end of the culture period, the number of cells present in the culture was determined using a electronic particle counter.

Results:

The (+/−) mice exhibited a decreased mean skin fibroblast proliferation rate when compared with their gender-matched (+/+) littermates and the historical mean. Thus, heterozygous mutant mice demonstrated a hypo-proliferative phenotype. As suggested by these observations, antagonists of a PRO1886 polypeptide or its encoding gene would be useful in decreasing abnormal cell proliferation such as tumor cell growth.

35.24. Generation and Analysis of Mice Comprising DNA76788-2526 (UNQ873) Gene Disruptions In these knockout experiments, the gene encoding PRO1891 polypeptides (designated as DNA76788-2526) (UNQ873) was disrupted. The gene specific information for these studies is as follows: the mutated mouse gene corresponds to nucleotide reference: NM_033615 or ACCESSION:NM_033615 NID: gi 23956237 ref NM_033615.1 *Mus musculus* a disintegrin and metalloprotease domain 33 (Adam33); protein reference: Q923W9 or ACCESSION: Q923W9 NID: *Mus musculus* (Mouse). ADAM 33 PRECURSOR (EC 3.4.24.) (A DISINTEGRIN AND METALLOPROTEINASE DOMAIN 33). MOUSESPTRNRDB; the human gene sequence reference: NM_025220 or ACCESSION:NM_025220 NID:18252044 *Homo sapiens Homo sapiens* a disintegrin and metalloproteinase domain 33 (ADAM33); the human protein sequence corresponds to reference: Q9BZ11 or ACCESSION:Q9BZ11 NID: *Homo sapiens* (Human). ADAM 33 PRECURSOR (EC 3.4.24.-) (A DISINTEGRIN AND METALLOPROTEINASE DOMAIN 33). HUMANSPTRNRDB.

The mouse gene of interest is Adam33 (a disintegrin and metalloprotease domain 33), ortholog of human ADAM33.

Aliases include Adam1, metalloprotease disintegrin, and disintegrin and reprolysin metalloproteinase family protein.

ADAM33 is a type I integral membrane protein that likely functions as a zinc metalloprotease and cell adhesion molecule. The protein consists of a large extracellular domain, a transmembrane segment, and a short cytoplasmic C-terminus. The large extracellular domain contains a propeptide, a zinc metalloprotease catalytic domain, a disintegrin domain, a cysteine rich region, and an EGF-like domain. The propeptide is cleaved to form the mature protein. ADAM33 is widely expressed, with particularly high expression in placenta, lung, spleen, and veins. Expression of ADAM33 appears to be absent in liver (Yoshinaka et al., *Gene*, 282(1-2):227-36 (2002); Van Eerdewegh et al., *Nature*, 418(6896):426-30 (2002); Garlisi et al., *Biochem Biophys Res Commun*, 301(1): 35-43 (2003)). The biological role of ADAM33 and ADAM family members in general are not clearly known; however, they have been implicated in processes such as fertilization, neurogenesis, myogenesis, embryonic TGF-alpha release, and the inflammatory response (Primakoff and Myles, *Trends Genet*, 16(2):83-7 (2000)).

ADAM33 has been implicated in asthma and bronchial hyper responsiveness. The protease is expressed in human lung fibroblasts and bronchial smooth muscle, which play a central role in airway remodeling. Damage to airway epithelial cells by activated T cells leads to smooth muscle hyperplasia, fibroblast proliferation, increased matrix deposition, and conversion of bronchial smooth muscle from the quiescent, contractile type to the proliferative, synthetic type. Alterations in ADAM33 activity or expression may underlie abnormalities in airway remodeling in bronchial hyper responsiveness (Van Eerdewegh et al., *Nature*, 418(6896): 426-30 (2002)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 15 | 48 | 21 | 84 |
| Expected | 21 | 42 | 21 | 84 |

Chi-Sq. = 2.57
Significance = 0.27645
(hom/n) = 0.25
Avg. Litter Size = 9

Mutation Type Homologous Recombination (standard)
Coding exons 12 through 16 were targeted (NCBI accession NM_033615.1).
Wild-type expression of the target gene was detected in all 13 adult tissue samples tested by RT-PCR, except adipose.
Disruption of the target gene was confirmed by Southern hybridization analysis.

35.24.1. Phenotypic Analysis (for Disrupted Gene: DNA76788-2526 (UNQ873)

(a) Overall Phenotypic Summary:
Mutation of the gene encoding the ortholog of human a disintegrin and metalloprotease domain 33 (ADAM33) resulted in an increased IgG1 response to ovalbumin challenge in (−/−) mice. The (−/−) mice exhibited increased serum triglycerides, increased mean serum insulin and decreased bone density measurements. In addition, glucose tolerance testing suggested insulin resistance. Immunological abnormalities were also observed in the (−/−) mice. Gene disruption was confirmed by Southern blot.

(b) Immunology Phenotypic Analysis
Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Analyzed wt/het/hom: 9/4/14

Results of this challenge: The (−/−) mice exhibited an increased mean serum IgG1 response to the ovalbumin challenge when compared with their (+/+) littermates. Thus, these knockout mice exhibited an increased ability to elicit an OVA-specific antibody response to the T-cell dependent OVA antigen. Inhibitors (antagonists) of PRO1891 polypeptides would be expected to also stimulate the immune system and would find utility in the cases wherein this effect would be beneficial to the individual such as in the case of leukemia, and other types of cancer, and in immunocompromised patients, such as AIDS sufferers. Accordingly, PRO1891 polypeptides or agonists thereof would be useful in inhibiting the immune response and would be useful candidates for suppressing harmful immune responses, e.g. in the case of graft rejection or graft-versus-host diseases.

(c) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Both the male and female (−/−) mice exhibited decreased mean bone mineral content, bone mineral density, and volumetric bone mineral density when compared with their gender-matched (+/+) littermates and the historical means.

Micro-CT: The (−/−) mice exhibited decreased mean vertebral trabecular bone volume, number, thickness, and connectivity density when compared with their gender-matched (+/+) littermate and the historical means.

Analyzed wt/het/hom: 4/4/8

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO1891 or agonists thereof would be useful in maintaining bone homeostasis. In addition, PRO1891 or its encoding gene would be useful in bone healing or for the treatment of arthritis or osteoporosis; whereas antagonists to PRO1891 or its encoding gene would lead to abnormal or pathological bone disorders including inflammatory diseases associated with abnormal bone metabolism including arthritis, osteoporosis, and osteopenia.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results:

The (−/−) mice exhibited an increased mean serum triglyceride level when compared with their gender-matched (+/+) littermates and the historical mean.

As summarized above, the (−/−) mice exhibited notably increased triglyceride levels when compared with their gender-matched (+/+) littermates and the historical means for the male (+/+) mice. Thus, mutant mice deficient in the PRO1891 gene can serve as a model for cardiovascular disease.

PRO1891 polypeptides or its encoding gene would be useful in regulating blood lipids such as triglycerides. Thus, PRO1891 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

(e) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Insulin Data:

Test Description: Lexicon Genetics uses the Cobra II Series Auto-Gamma Counting System in its clinical settings for running quantitative Insulin assays on mice.

Results:

The (−/−) mice exhibited an increased mean serum insulin level when compared with their gender-matched (+/+) littermates and the historical mean.

However, blood chemistry testing showed (−/−) mice exhibiting an increased mean serum glucose level when compared with their gender-matched (+/+) littermates and the historical mean. During the glucose tolerance test, the (−/−) mice exhibited an increased mean fasting serum glucose level when compared with their gender-matched (+/+) littermates and the historical mean.

Thus, knockout mice exhibited the phenotypic pattern of an impaired glucose homeostasis with elevated levels of fasting serum glucose indicative of diabetes or a pre-diabetic condition even in the presence of increased insulin levels. Based on these results, PRO1891 (or agonists thereof) or its encoding gene would be useful in the treatment of an impaired glucose metabolism (marked by insulin resistance) and/or diabetes.

35.25. Generation and Analysis of Mice Comprising DNA88004-2575 (UNQ1934) Gene Disruptions In these knockout experiments, the gene encoding PRO4409 polypeptides (designated as DNA88004-2575) (UNQ1934) was disrupted. The gene specific information for these studies is as follows: the mutated mouse gene corresponds to nucleotide reference: NM_028065 or ACCESSION:NM_028065 NID: gi 21312509 ref NM_028065.1 *Mus musculus* RIKEN cDNA 1600025D17 gene (1600025D17Rik); protein reference: Q9DAU1 or ACCESSION:Q9DAU1 NID: *Mus musculus* (Mouse). 1600025D17Rik protein (Putative retinoic acid-regulated protein) (RIKEN cDNA 1600025D17 gene). MOUSESPTRNRDB; the human gene sequence reference: NM_006586 or *Homo sapiens* trinucleotide repeat containing 5 (TNRC5); the human protein sequence corresponds to reference: Q9BT09 or ACCESSION:Q9BT09 NID: *Homo sapiens* (Human). Hypothetical protein (DJ475N16.1) (CTG4A). HUMANSPTRNRDB.

The mouse gene of interest encodes a hypothetical protein (1600025D17Rik), which is the ortholog of human protein TNRC5 (trinucleotide repeat containing 5). Aliases include CAG repeat containing expanded repeat domain and CAG/CTG 5.

TNRC5 is a hypothetical protein containing CAG repeats, which are likely to be involved in specific diseases, most with neuropsychiatric features (Margolis et al., *Hum Genet*, 100 (1): 114-22 (1997)). The protein contains a signal peptide but no other identifiable domains. The cell location of TNRC5 is ambiguous; bioinformatic analysis suggests that the protein may be secreted or located in the endoplasmic reticulum. TNRC5 gene transcription is likely to be under the control of retinoids, which play an important role in development and physiology (Glozak et al., *Mol Endocrinol*, 17(1):27-41 (2003)).

Genetics Information:

|  | wt | het | hom | Total |
|---|---|---|---|---|
| Observed | 20 | 37 | 10 | 67 |
| Expected | 16.75 | 33.5 | 16.75 | 67 |

Chi-Sq. = 3.72
Significance = 0.15595
(hom/n) = 0.15
Avg. Litter Size = 8

Mutation Type: Retroviral Insertion (OST)

Retroviral insertion occurred in the intron between coding exons 1 and 2 (NCBI accession NM_028065.2).

Wild-type expression of the target gene was detected in embryonic stem (ES) cells and, among the 13 adult tissue samples tested by RT-PCR, in kidney; stomach, small intestine, and colon; and adipose.

Due to reduced viability, transcript expression analysis was not performed. Disruption of the target gene was confirmed by Inverse PCR.

35.25.1. Phenotypic Analysis (for Disrupted Gene: DNA88004-2575 (UNQ1934)

(a) Overall Phenotypic Summary:

Mutation of the gene encoding the ortholog of human trinucleotide repeat containing 5 (TNRC5) resulted in small (−/−) mice that failed to thrive. UNQ1934 was shown to be ubiquitously expressed between 7.5d-12.5d of embryo development in wild-type pups. The (−/−) mutants were euthanized or transferred to necropsy by 3 weeks of age. 40% fewer than expected homozygotes were present at genotyping. Heterozygous (+/−) mice exhibited decreased total tissue mass and fat (% and gram) compared to their wild-type littermate controls and the historical mean.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(b) Body Diagnostics—Tissue Mass & Lean Body Mass Measurements—Dexa (1) Dexa Analysis—Test Description:

Procedure: Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

General Observations: The (−/−) mice were small, failed to thrive, and were euthanized or sent to pathology for analysis by 3 weeks of age.

Weight: The (−/−) mice exhibited decreased mean body weight at the 2 week measurement when compared with their gender-matched (+/+) littermates and the historical means.

Pathology:

Microscopic Observations: Though the (−/−) mice were smaller than their (+/+) littermates and died before 4 weeks of age, no histopathological lesions were observed that explained the early mortality.

Gene Expression: Expression of the neo transcript was not detected in the panel of tissues analyzed by in situ hybridization.

Summary

The (−/−) mice analyzed exhibited notably decreased viability shown by a failure to survive past four weeks of age when compared with their (+/+) littermates. The (−/−) mice were quite small in size and showed a notable decrease in body weight suggestive of growth retardation in these mutants. Although pathology observations failed to reveal any histopathological lesions, the negative phenotype is indicative of a tissue wasting condition with severe growth retardation. Thus, PRO4409 polypeptides or agonists thereof must be essential for normal growth and/or growth metabolism and therefore would be useful in the treatment or prevention of growth disorders such as cachexia or other tissue wasting diseases.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The (+/−) mice exhibited decreased mean total tissue mass, percent total body fat, and total fat mass when compared with their gender-matched (+/+) littermates and the historical means.

These studies suggest that mutant (+/−) non-human transgenic animals exhibit a negative phenotype that may be associated with tissue wasting diseases. Thus, PRO4409 polypeptides or agonists thereof are essential for normal growth and metabolic processes and especially would be important in the prevention and/or treatment of growth disorders and/or tissue wasting diseases.

35.26. Generation and Analysis of Mice Comprising DNA92265-2669 (UNQ2446) Gene Disruptions In these knockout experiments, the gene encoding PRO5725 polypeptides (designated as DNA92265-2669) (UNQ2446) was disrupted. The gene specific information for these studies is as follows: the mutated mouse gene corresponds to nucleotide reference: NM_175024 or *Mus musculus* RIKEN cDNA G630049C14 gene (G630049C14Rik); protein reference: Q8BN06 or ACCESSION:Q8BN06 NID: *Mus musculus* (Mouse). Hypothetical protein; the human gene sequence reference: NM_198443 or *Homo sapiens* MRCC2446 (UNQ2446); the human protein sequence corresponds to reference: NP_940845 or MRCC2446 [*Homo sapiens*] gi|37182683|gb|AAQ89142.1| MRCC2446 [*Homo sapiens*].

The targeted mouse gene encodes a hypothetical protein (G630049C14Rik), which is the ortholog of hypothetical human protein MRCC2446. The human gene is also known as UNQ2446.

The human and mouse genes encode putative secreted proteins. The mouse hypothetical protein contains a signal peptide, a C-terminal transmembrane segment, and no other identifiable domains. The human protein contains a signal peptide and no other identifiable domains. Both proteins appear to be distantly similar to neuritin, an extracellular protein anchored on the plasma membrane of neurons that is likely to be involved in neuritogenesis (Naeve et al., *Proc Natl Acad Sci USA*, 94(6):2648-53 (1997)).

Genetics Information:

|  | wt | het | hom | Total |
|---|---|---|---|---|
| Observed | 20 | 30 | 15 | 65 |
| Expected | 16.25 | 32.5 | 16.25 | 65 |

Chi-Sq. = 1.15
Significance = 0.56162
(hom/n) = 0.23
Avg. Litter Size = 7

Mutation Type: Retroviral Insertion (OST)
Retroviral insertion occurred in coding exon 2 (Accession: NM_175024.1).
Wild-type expression of the target gene was detected in embryonic stem (ES) cells and in all 13 adult tissue samples tested by RT-PCR, except skeletal muscle.
RT-PCR analysis revealed that the transcript was absent in the (−/−) mouse analyzed (M-121).

35.26.1. Phenotypic Analysis (for Disrupted Gene: DNA92265-2669 (UNQ2446)
(a) Overall Phenotypic Summary:
Mutation of the gene encoding the ortholog of a hypothetical human protein resulted in the observation of decreased body weight, decreased lean body mass, bone mineral density and bone mineral content as well as decreased lumbar 5 measurements. Transcript was absent by RT-PCR.
(b) Body Diagnostics—Tissue Mass & Lean Body Mass Measurements—Dexa
Dexa Analysis—Test Description:
Procedure: A cohort of 4 wild type, 4 heterozygotes and 8 homozygotes were tested in this assay. Dual Energy X-ray Absorptiometry (DEXA) has been used successfully to identify changes in total tissue mass (TTM).
The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).
Body Measurements (Body Length & Weight):
Body Measurements: A measurement of body length and weight was performed at approximately 16 weeks of age.
Results:
The male and female (−/−) mice exhibited decreased mean body weight when compared with their gender-matched (+/+) littermates and the historical means. Analyzed wt/het/hom: 28/36/22
The (−/−) mice were quite small in size and showed a notable decrease in body weight suggestive of growth retardation in these mutants. Although pathology observations failed to reveal any histopathological lesions, the negative phenotype suggested growth retardation. Thus, PRO5725 polypeptides or agonists thereof must be essential for normal growth and/or growth metabolism and therefore would be useful in the treatment or prevention of growth related disorders.
(2) Bone Metabolism: Radiology Phenotypic Analysis
In the area of bone metabolism, targets were identified herein for the treatment of arthritis, osteoporosis, osteopenia and osteopetrosis as well as identifying targets that promote bone healing. Tests included:
DEXA for measurement of bone mineral density on femur and vertebra
MicroCT for very high resolution and very high sensitivity measurements of bone mineral density for both trabecular and cortical bone.
Dexa Analysis—Test Description:
Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].
Bone microCT Analysis:
Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and mid-shaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.
Results:
DEXA: The (−/−) mice exhibited decreased mean lean body mass, bone mineral content and bone mineral density when compared with their gender-matched (+/+) littermates and the historical means.
Micro-CT: The (−/−) mice exhibited decreased mean vertebral trabecular bone volume, number, thickness, and connectivity density and decreased mean femoral mid-shaft cortical thickness when compared with their gender-matched (+/+) littermates and the historical means.
Analyzed wt/het/hom: 4/4/8
Summary
These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO5725 or agonists thereof would play a role in maintaining bone homeostasis. In addition, PRO5725 or its encoding gene would be useful for maintaining bone homeostasis and for bone healing or for the treatment of arthritis or osteoporosis; whereas antagonists to PRO5725 or its encoding gene would lead to abnormal or pathological bone disorders including inflammatory diseases associated with abnormal bone metabolism including arthritis, osteoporosis, and osteopenia.
The (−/−) mice analyzed by DEXA exhibited notably decreased lean body mass when compared with their (+/+) littermates, suggestive of growth retardation in these mutants. This in conjunction with the observations of abnormal bone measurements suggest a tissue wasting condition or other growth related disorders such as cachexia. Thus, PRO5725 polypeptides or agonists thereof would be useful in the treatment of bone disorders but also would be useful for the prevention of growth related disorders such as cachexia and/or other tissue wasting diseases.

35.27. Generation and Analysis of Mice Comprising DNA98591 (UNQ2506) Gene Disruptions
In these knockout experiments, the gene encoding PRO5994 polypeptides (designated as DNA98591 (UNQ2506) was disrupted. The gene specific information for these studies is as follows: the mutated mouse gene corresponds to nucleotide reference: NM_011463 or *Mus musculus* serine protease inhibitor, Kazal type 4 (Spink4); protein reference: 035679 or ACCESSION:035679 NID: *Mus musculus* (Mouse). SERINE PROTEASE INHIBITOR KAZAL-TYPE 4 PRECURSOR (PEPTIDE PEC-60 HOMOLOG) (MPGC60 PROTEIN). MOUSESPTRNRDB; the human gene sequence reference: NM_014471 or ACCESSION: NM_014471 NID: gi 7657452 ref NM_014471.1 *Homo sapiens* serine protease inhibitor, Kazal type 4 (SPINK4); the human protein sequence corresponds to reference: 060575 or ACCESSION:060575 NID: *Homo sapiens* (Human). SERINE PROTEASE INHIBITOR KAZAL-TYPE 4 PRECURSOR (PEPTIDE PEC-60 HOMOLOG). HUMANSPTRNRDB.

The mouse gene of interest is Spink4 (serine protease inhibitor, Kazal type 4), ortholog of human SPINK4. Aliases include MPGC60, PEC-60, and gastrointestinal peptide.

SPINK4 is a putative secreted serine protease inhibitor expressed predominantly in the intestinal tract (Krause et al., *Differentiation*, 63(5):285-94 (1998)). SPINK4 is the apparent human ortholog of porcine PEC-60 (SwissProt P37109), which has been shown to inhibit glucose-induced insulin secretion. PEC-60 has been isolated from brains of rat and pig (Norberg et al., *Cell Mol Life Sci*, 60(2):378-81 (2003)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation

|          | wt    | het  | hom   | Total |
|----------|-------|------|-------|-------|
| Observed | 21    | 41   | 27    | 89    |
| Expected | 22.25 | 44.5 | 22.25 | 89    |

Chi-Sq. = 1.36
Significance = 0.50673
(hom/n) = 0.30
Avg. Litter Size = 9

Mutation Type: Homologous Recombination (standard)
Coding exon 1 was targeted (NCBI accession NM_011463.1).
Wild-type expression of the target gene was detected in all 13 adult tissue samples tested by RT-PCR, except brain, lung, and skeletal muscle.
Disruption of the target gene was confirmed by Southern hybridization analysis.

35.27.1. Phenotypic Analysis (for Disrupted Gene: DNA98591 (UNQ2506)
  (a) Overall Phenotypic Summary:
  Mutation of the gene encoding the ortholog of human serine protease inhibitor, Kazal type 4 (SPINK4) resulted in decreased body weight and length as well as decreased tissue mass measurements. In addition, the (−/−) mice exhibit lymphoid hyperplasia and tissue inflammation at an increased incidence. Gene disruption was confirmed by Southern blot.
  (b) Bone Metabolism & Body Diagnostics
  (1) Tissue Mass & Lean Body Mass Measurements—Dexa
  Dexa Analysis—Test Description:
  Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):
Body Measurements: A measurement of body length and weight was performed at approximately 16 weeks of age.
Results:
General Observations: The agouti (−/−) mouse is much smaller than its black (+/+) littermate.
The (−/−) mice exhibited decreased mean body weight and decreased body length when compared with the historical means.
(2) Bone Metabolism: Radiology Phenotypic Analysis
In the area of bone metabolism, targets were identified herein for the treatment of arthritis, osteoporosis, osteopenia and osteopetrosis as well as identifying targets that promote bone healing. Tests included:
DEXA for measurement of bone mineral density on femur and vertebra
MicroCT for very high resolution and very high sensitivity measurements of bone mineral density for both trabecular and cortical bone.
Dexa Analysis—Test Description:
Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].
Results:
DEXA: The (−/−) mice exhibited decreased mean total tissue mass and lean body mass when compared with their gender-matched (+/+) littermates and the historical means.
Analyzed wt/het/hom: 4/4/8
Summary
These results demonstrate that the knockout mutant (−/−) mice analyzed by DEXA were quite small in size and exhibited a decrease in body weight and length as well as a decrease in total tissue, lean body mass suggestive of growth retardation in these mutants. Thus, PRO5994 polypeptides or agonists thereof must be essential for normal growth and/or growth metabolism and therefore would be useful in the treatment or prevention of growth disorders, cachexia or other tissue wasting diseases.
  (c) Pathological Observations
  The knockout (−/−) mice exhibited lymphoid hyperplasia and tissue inflammation at an increased incidence.

35.28. Generation and Analysis of Mice Comprising DNA107701-2711 (UNQ2545) Gene Disruptions In these knockout experiments, the gene encoding PRO6097 polypeptides (designated as DNA107701-2711) (UNQ2545) was disrupted. The gene specific information for these studies is as follows: the mutated mouse gene corresponds to nucleotide reference: NM_028787 or *Mus musculus* solute carrier family 35, member F5 (Slc35f5); protein reference: Q9 DBK9 or Q9 DBK9 Q9 DBK9 1300003P13RIK PROTEIN; the human gene sequence reference: NM_025181 or *Homo sapiens* solute carrier family 35, member F5 (SLC35F5); the human protein sequence corresponds to reference: Q8WV83 or ACCESSION: Q8WV83 NID: *Homo sapiens* (Human). Similar to RIKEN cDNA 1300003P13 gene (NS5ATP3).

The mouse gene of interest is Slc35f5 (solute carrier family 35, member F5), ortholog of human SLC35F5. Aliases include 1300003P13Rik and FLJ22004.

SLC35F5 is a predicted integral plasma membrane protein of unknown function, containing 10 transmembrane segments. Most of the transmembrane segments are contained within a domain that has weak similarity to that found in carbohydrate/phosphate translocators (KOG 4313) and drug permeases (COG0697) (Marchler-Bauer et al., *Nucleic Acids Res*, 31(1):383-7 (2003).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 17 | 35 | 12 | 64 |
| Expected | 16 | 32 | 16 | 64 |

Chi-Sq. = 1.34
Significance = 0.51075
(hom/n) = 0.19
Avg. Litter Size = 7

Mutation Type Homologous Recombination (standard)
Coding exons 1 through 3 were targeted (NCBI accession NM_028787.2).
Wild-type expression of the target gene was detected in embryonic stem (ES) cells and in all 13 adult tissue samples tested by RT-PCR, except bone.
Disruption of the target gene was confirmed by Southern hybridization analysis.

35.28.1. Phenotypic Analysis (for Disrupted Gene: DNA107701-2711 (UNQ2545)

(a) Overall Phenotypic Summary:

Mutation of the gene encoding the ortholog of human solute carrier family 35, member F5 (SLC35F5) resulted in larger (−/−) mice, exhibiting increased body weight, total tissue mass, lean body mass and bone measurements. In addition, the mutant knockout mice exhibited a decreased or reduced IgG2a response to an ovalbumin challenge. Also, additional immunological abnormalities were exhibited by observing an increased percentage of T cells, with decreased natural killer cells and B cells and an increased percentage of CD4 T cells in the mutant (−/−) mice compared with their littermate controls. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Analyzed wt/het/hom: 8/4/9

Results of this Challenge:

The (−/−) mice exhibited a decreased mean serum IgG2a response to ovalbumin challenge when compared with their (+/+) littermates and the historical means. Thus, these knockout mice exhibited a decreased ability to elicit an OVA-specific antibody response to the T-cell dependent OVA antigen.

In summary, the ovalbumin challenge studies indicate that knockout mice deficient in the gene encoding PRO6097 polypeptides exhibit immunological abnormalities when compared with their wild-type littermates. In particular, the mutant mice exhibited a decreased ability to elicit an immunological response when challenged with the T-cell dependent OVA antigen. Thus, PRO6097 polypeptides or agonists thereof, would be useful for stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, inhibitors (antagonists) of PRO6097 polypeptides would be useful for inhibiting the immune response and thus would be useful candidates for suppressing harmful immune responses, e.g. in the case of graft rejection or graft-versus-host diseases.

Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

FACS: The (−/−) mice exhibited an increased percentage of T cells (increased % of CD4 T cells) with a decreased mean percentage of natural killer cells and B cells when compared with their (+/+) littermates and the historical mean. Analyzed wt/het/hom: 7/4/8

In summary, the FACS results indicate that the homozygous mutant mice demonstrate immunological abnormalities marked by increased T cell population but a decreased mean percentage of natural killer cells and B cells. [Natural killer cells are the first line of defense to viral infection since these cells have been implicated in viral immunity and in defense against tumors]. Natural killer cells or NK cells act as effectors in antibody-dependent cell-mediated cytotoxicity and have been identified by their ability to kill certain lymphoid tumor cell lines in vitro without the need for prior immunization or activation. However, their known function in host defense is in the early phases of infection with several intracellular pathogens, particularly herpes viruses]. On the otherhand, by knocking out the gene which encodes PRO6097 polypeptides a beneficial effect is shown by the increase in the T cell population. Thus, PRO6097 polypeptides or the gene encoding PRO6097 appears to act as a negative regulator of T cell proliferation. An opposite effect was shown for the B cell and natural killer cell population.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited increased mean body weight when compared with their gender-matched (+/+) littermates and the historical mean. Analyzed wt/het/hom: 21/40/15

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited increased mean total tissue mass, lean body mass, bone mineral content, and bone mineral density in total body and femur when compared with their gender-matched (+/+) littermates and the historical means. Analyzed wt/het/hom: 4/4/8

MicroCT: The knockouts (−/−) exhibited an increased trabecular bone volume, number, and connectivity density compared with their littermate controls.

In summary, the (−/−) mice exhibited increased body weight and length, increased mean total tissue mass and lean body mass and increased bone mineral density measurements and trabecular bone measurements when compared with their gender-matched (+/+) littermates. The heterozygous mice (+/−) exhibited similar bone effects but the increased measurement values were between the wild-type and homozygous values. These observations suggest an obesity and/or growth disorder type phenotype. In addition, the mutant (−/−) mice exhibited abnormal bone measurements. Thus, PRO6097 polypeptides or agonists thereof, would be useful for normal growth and bone development and would play a role in the treatment of related growth or metabolic disorders associated with obesity and/or bone disorders such as osteopetrosis.

35.29. Generation and Analysis of Mice Comprising DNA108792-2753 (UNQ2966) Gene Disruptions In these knockout experiments, the gene encoding PRO7425 polypeptides (designated as DNA108792-2753) (UNQ2966) was disrupted. The gene specific information for these studies is as follows: the mutated mouse gene corresponds to nucleotide reference: NM_176993 or *Mus musculus* RIKEN cDNA A53006517 gene (A530065I17Rik); protein reference: NP_795967 or RIKEN cDNA A530065I17 gene [*Mus musculus*]; the human gene sequence reference: NM_198275 or *Homo sapiens* hypothetical protein LOC196264 (LOC196264); the human protein sequence corresponds to reference: NP_938016 or hypothetical protein LOC196264 [*Homo sapiens*].

The disrupted mouse gene is a hypothetical protein (interim name, A530065I17Rik), which is the ortholog of human hypothetical protein FLJ38080. Aliases for the human locus include LOC196264 and QQRG2966.

Analysis of FLJ38080 indicates that two transmembrane domains (1 near each end) flank a central Igv-type motif (InterPro IPR0003596). Such features suggest the protein may be partially or completely extracellular, and perhaps participates in signaling or protein-protein interactions.

Genetics Information:

|  | wt | het | hom | Total |
|---|---|---|---|---|
| Observed | 16 | 32 | 20 | 68 |
| Expected | 17 | 34 | 17 | 68 |

Chi-Sq. = 0.71
Significance = 0.70262
(hom/n) = 0.29
Avg. Litter Size = 8

Mutation Type Retroviral Insertion (OST)

Retroviral insertion occurred in the intron between coding exons 2 and 3 (NCBI accession BQ713326).

Wild-type expression of the target gene was detected in all 13 adult tissues samples tested by RT-PCR, except thymus, lung, skeletal muscle and adipose.

RT-PCR analysis revealed that the transcript was absent in the (−/−) mouse analyzed (M-75).

35.29.1. Phenotypic Analysis (for Disrupted Gene: DNA108792-7425 (UNQ2966)

(a) Overall Phenotypic Summary:

Mutation of the gene encoding the ortholog of a human hypothetical protein (FLJ38080) resulted in sebaceous gland hyperplasia and severe growth retardation in (−/−) mice. In addition, the (−/−) mice exhibited decreased mean body mass-related measurements and decreased bone measurements. The (−/−) mice also exhibited severe depletion of body fat depots and enlarged kidneys. Lower insulin levels were also observed in the (−/−) mice as well as abnormal changes in alkaline phosphatase (most likely due to decreased bone mineralization) and mean serum ALT (alanine amino transaminase) suggestive of liver disease. Furthermore, the mutant (−/−) mice exhibited severe hypoactivity in the circadian rhythm test. Transcript was absent by RT-PCR.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., *Nature.* 1996 Feb. 15; 379(6566):606-12), and the GABA receptor (Homanics et al., *Proc Natl Acad Sci USA.* 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

The (−/−) mice exhibited a decreased normalized slope during open field activity testing when compared with their (+/+) littermates, suggesting an abnormal habituation response to a novel environment in the mutants.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period. Thus, the mutant (−/−) mice exhibited severe hypoactivity. Analyzed wt/het/hom: 4/4/8

Results:

The (−/−) mice exhibited abnormal activity during the 1-hour habituation, the 12-hour habituation, and all light and dark periods of home cage activity testing when compared with their gender-matched (+/+) littermates and the historical means. The (−/−) mice exhibited no diurnal alternations during the 3-day testing period.

As summarized above, notable differences were observed during home-cage activity testing. The (−/−) mice exhibited decreased ambulatory counts during the day 2 light period when compared with their (+/+) littermates. In addition, the homozygous (−/−) mice exhibited decreased light-to-dark and light-to-total activity ratios when compared with their (+/+) littermates, suggesting an abnormal circadian rhythms response in the mutants. These results are consistent with the findings during open field testing and indicate that the homozygous mutant mice exhibit circadian rhythms which are usually associated with lethargy or depressive disorders. Thus, PRO7425 polypeptides or its encoded gene would be useful in the treatment of such neurological disorders including depressive disorders or other decreased anxiety-like symptoms.

Functional Observational Battery (FOB) Test

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

Basic Sensory & Motor Observations: All 8 (−/−) mice exhibited thinning fur with bald patches during the functional observational battery testing when compared with their (+/+) littermates.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

General Observations: The (−/−) mice are much smaller with oily thinning fur with bald patches and exhibited darker, stickier feces than their (+/+) littermates.

Both the male and female (−/−) mice exhibited decreased mean body weight and decreased mean body length when compared with their gender-matched (+/+) littermates and the historical means.

The (−/−) mice also exhibited a decreased mean heart rate when compared with their gender-matched (+/+) littermates and the historical mean.

Analyzed wt/het/hom: 12/23/17

Pathology:

Microscopic Observations: The (−/−) mice exhibited diffuse, but enhanced sebaceous gland hyperplasia. The skin lesions in the mutants varied in severity from one area to another and were generally not associated with inflammation. The majority of sebaceous glands were active and hyperplastic, even in areas containing anagenic hair follicles.

Gene Expression: Expression of the neo transcript was not detected in the panel of tissues analyzed by in situ hybridization. Analyzed wt/het/hom: 2/1/6

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

CAT-Scan Protocol:

Mice were injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for ~10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed.

Three dimensional images were reconstructed by the Feldkamp algorithm in a cluster of workstations using an ImTek 3D RECON software.

Results:

DEXA: Both the male and female (−/−) mice exhibited decreased mean body mass-related measurements (total tissue mass, lean body mass, total fat mass, and percent total body fat) and decreased mean bone mineral-related measurements (bone mineral content, volumetric bone mineral density, and bone mineral density in total body, vertebrae, and femur) when compared with their gender-matched (+/+) littermates and the historical means, suggesting severe growth retardation in the mutants.

Micro-CT: The (−/−) mice exhibited decreased mean vertebral trabecular bone volume, number, thickness, and connective density and decreased mean femoral mid-shaft cortical thickness and cross-sectional area when compared with their gender-matched (+/+) littermates and the historical means.

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO7425 or agonists thereof would be useful in maintaining bone homeostasis. In addition, PRO7425 or its encoding gene would be useful in bone healing or for the treatment of arthritis or osteoporosis; whereas antagonists to PRO7425 or its encoding gene would lead to abnormal or pathological bone disorders including inflammatory diseases associated with abnormal bone metabolism including arthritis, osteoporosis, and osteopenia.

CAT-Scan: All 3 (−/−) mice available for testing exhibited generally decreased body size and severe depletion of abdominal and subcutaneous body fat depots. Bilaterally enlarged kidneys were noted in 2 mutants (M-83 and M-121) when compared with their (+/+) and (+/−) littermates of normal body size. However, no obvious lesion was observed in the kidneys. Analyzed wt/het/hom: 4/4/9

Thus in summary, the (−/−) mice analyzed by DEXA were quite small in size and exhibited a notable decrease in body weight and length as well as a notable depletion of body fat depots, decrease in total tissue, lean body mass and decreased bone mineral content and density suggestive of growth retardation in these mutants. These observations are consistent with a tissue wasting condition and/or growth retardation. Thus, PRO7425 polypeptides or agonists thereof must be essential for normal growth and/or growth metabolism and therefore would be useful in the treatment or prevention of growth disorders, cachexia or other tissue wasting diseases.

(d) Phenotypic Analysis: Metabolism-Blood Chemistry

In the area of metabolism, targets may be identified for the treatment of diabetes. Blood chemistry phenotypic analysis includes measuring serum insulin levels as an indicator of changes in glucose metabolism. Abnormal glucose metabolism can be related to the following disorders or conditions: Diabetes Type 1 and Type 2, Syndrome X, various cardiovascular diseases and/or obesity.

Insulin Data:

Test Description: Lexicon Genetics uses the Cobra II Series Auto-Gamma Counting System in its clinical settings for running quantitative Insulin assays on mice.

Results:

The (−/−) mice exhibited a decreased mean serum insulin level when compared with their gender-matched (+/+) littermates and the historical mean. In addition, other Blood Chemistry analysis indicated that the mutant (−/−) mice showed increased serum alkaline phosphatase and mean serum ALT (alanine amino transaminase) suggestive of liver disease. Ketones were also noted in the urine of the mutant mice. These results indicate a diabetic phenotype.

35.30. Generation and Analysis of Mice Comprising DNA129542-2808 (UNQ3103) Gene Disruptions In these knockout experiments, the gene encoding PRO10102 polypeptides (designated as DNA129542-2808) (UNQ3103) was disrupted. The gene specific information for these studies is as follows: the mutated mouse gene corresponds to nucleotide reference: NM_021319 or *Mus musculus* peptidoglycan recognition protein-like (Pglyrpl-pending); protein reference: NP_067294 or peptidoglycan recognition protein-like; TAG-like [*Mus musculus*]; the human gene sequence reference: NM_052890 or *Homo sapiens* peptidoglycan recognition protein L precursor (PGRP-L); the human protein sequence corresponds to reference: NP_443122 or peptidoglycan recognition protein L precursor [*Homo sapiens*].

The targeted mouse gene is peptidoglycan recognition protein-like (Pglyrpl-pending), ortholog of human peptidoglycan recognition protein L precursor (PGRP-L). Aliases include TAGL, tagL, PGRP-L, TAGL-beta, tagl-beta, TAGL-alpha, tagL-alpha, PGLYRPL, TAGL-like, and TAG-like.

PGRP-L is an evolutionarily conserved N-acetylmuramoyl-L-alanine amidase expressed in liver that cleaves the lactylamide bond in bacterial cell wall peptidoglycan (Gelius et al., *Biochem Biophys Res Commun*, 306(4):988-94 (2003)). Bioinformatic analysis of PGRP-L suggests that the protein is secreted, containing a signal peptide and a C-terminal "N-acetylmuramoyl-L-alanine amidase" domain (Pfam 01510). However, PGRP-L may be an integral membrane protein (Kibardin et al., *J Mol Biol*, 326(2):467-74 (2003)).

Variants lacking the C-terminal amidase catalytic domain are still able to bind with gram-positive bacteria, gram-negative bacteria, and peptidoglycan, indicating that the catalytic and peptidoglycan-binding domains are separate (Kibardin et al, 2003). PGRP-L is likely to play a role in innate immunity, recognizing and degrading bacteria in liver (Gelius et al., *Biochem Biophys Res Commun*, 306(4):988-94 (2003); Kibardin et al., *J Mol Biol*, 326(2):467-74 (2003)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 17 | 35 | 16 | 68 |
| Expected | 17 | 34 | 17 | 68 |

Chi-Sq. = 0.09
Significance = 0.95684
(hom/n) = 0.24
Avg. Litter Size = 7

Mutation Type Homologous Recombination (standard)
Exons 1 and 2 were targeted (NCBI NM_021319).
Wild-type expression of the target gene was detected in embryonic stem (ES) cells and in all 13 adult tissue samples tested by RT-PCR, except kidney, testis, and bone.
Disruption of the target gene was confirmed by Southern hybridization analysis.

35.30.1. Phenotypic Analysis (for Disrupted Gene: DNA129542-2808 (UNQ3103)

(a) Overall Phenotypic Summary:

Mutation of the gene encoding the ortholog of human peptidoglycan recognition protein L precursor (PGRP-L) resulted in a decreased anxiety-related response in female (−/−) mice. However, the male (−/−) mice did not exhibit the same response. There was a strong trend towards stress-induced hyperthermia noted for the mutant (−/−) mice. These observations show an anxiety-related phenotype but a liver specific expression pattern does not suggest these behavioral effects. Gene disruption was confirmed by Southern blot.

(b) Expression Pattern

UNQ3103 shows a very specific expression in the liver (see EXAMPLE 41 for protocol)

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histrionic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., *Nature*. 1996 Feb. 15; 379(6566):606-12), and the GABA receptor (Homanics et al., *Proc Natl Acad Sci USA*. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

A difference was found during open field testing. The female (−/−) mice exhibited an increased median sum time in center when compared with their gender-matched (+/+) littermates and the historical mean, suggesting a decreased anxiety-like response in the mutants. Male (−/−) mice did not exhibit the same response.

As noted above, a difference was observed during open field activity testing. The female (−/−) mice exhibited an increased median sum time in the center area when compared with their gender-matched (+/+) littermates, which is indicative of a decreased anxiety-like response in the mutants. Thus, knockout mice demonstrated a phenotype consistent with depressive disorders, schizophrenia and/or bipolar disorders. Thus, PRO10102 polypeptides and agonists thereof would be useful for the treatment or amelioration of the symptoms associated with depressive disorders.

Functional Observational Battery (FOB) Test

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

The mutant (−/−) mice showed a strong trend towards increased stress induced hyperthermia (three-fourths 3/4 (−/−) mice tested showed increases two standard deviations (2 SD) above the historical mean).

35.31. Generation and Analysis of Mice Comprising DNA148380-2827 (UNQ3126) Gene Disruptions In these knockout experiments, the gene encoding PRO10282 polypeptides (designated as DNA148380-2827) (UNQ3126) was disrupted. The gene specific information for these studies is as follows: the mutated mouse gene corresponds to nucleotide reference: NM_009291 or ACCESSION:NM_009291 NID: gi 6678170 ref NM_009291.1 Mus musculus stimulated by retinoic acid gene 6 (Stra6); protein reference: 070491 or ACCESSION:070491 NID: Mus musculus (Mouse). Retinoic acid-responsive protein. MOUSESPTRNRDB; the human gene sequence reference: NM_022369 or ACCESSION:NM_022369 NID: gi 21314699 ref NM_022369.2 Homo sapiens hypothetical protein FLJ12541 similar to Stra6 (FLJ12541); the human protein sequence corresponds to reference: Q9BX79 or ACCESSION:Q9BX79 NID: Homo sapiens (Human). STRA6 isoform 1. HUMANSPTRNRDB.

The mouse gene of interest is Stra6 (stimulated by retinoic acid gene 6), ortholog of human "stimulated by retinoic acid gene 6." Aliases include FLJ12541.

Stra6 is a likely integral plasma membrane protein induced by retinoic acid. The protein contains eight transmembrane segments but no other discernable domain. Stra6 is often located at blood-organ barriers and may function as a component of a transport apparatus. Stra6 is expressed in Sertoli cells during specific stages of spermatocyte development (Bouillet et al., *Mech Dev,* 63(2):173-86 (1997)) and in developing mouse limbs (Chazaud et al., *Dev Genet,* 19(1):66-73 (1996)). Wnt-1 potentiates retinoid-induced Stra6 expression, and Stra6 mRNA may be overexpressed in human colorectal cancers as well as other tumors driven by activation of the Wnt-1/beta-catenin pathway (Szeto et al., *Cancer Res,* 61(10):4197-205 (2001); Tice et al., *J Biol Chem,* 277(16): 14329-35 (2002)).

Genetics Information:

|  | wt | het | hom | Total |
| --- | --- | --- | --- | --- |
| Observed | 16 | 34 | 19 | 69 |
| Expected | 17.25 | 34.5 | 17.25 | 69 |

Chi-Sq. = 0.28
Significance = 0.87138
(hom/n) = 0.28
Avg. Litter Size = 7

Mutation Type: Retroviral Insertion (OST)

Retroviral insertion occurred in the intron between coding exons 1 and 2 (NCBI accession NM_009291.1).

Wild-type expression of the target gene was detected in brain, eye, thymus, and lung among the 13 adult tissue samples tested by RT-PCR.

RT-PCR analysis revealed that the transcript was absent in the (−/−) mouse analyzed (M-76). Disruption of the target gene was confirmed by Inverse PCR.

35.31.1. Phenotypic Analysis (for Disrupted Gene: DNA148380-2827 (UNQ3126)

(a) Overall Phenotypic Summary:

Mutation of the gene encoding the ortholog of human putative "stimulated by retinoic acid gene 6" (STRA6) resulted in growth retardation and decreased bone measurements in (−/−) mice. An increased level of mean serum glucose was also observed in (−/−) mice. Transcript was absent by RT-PCR.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan.

Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited decreased mean body weight and decreased mean body weight when compared with their gender-matched (+/+) littermates and the historical means. Analyzed wt/het/hom: 16/37/19

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The (−/−) mice exhibited decreased mean total tissue mass and lean body mass when compared with their gender-matched (+/+) littermates and the historical means. In addition to these changes noted, fat (% and gram), bone mineral density and bone mineral content were all lower relative to their wild-type littermates consistent with the decreased size of the (−/−) mice.

Micro-CT: The (−/−) mice exhibited decreased mean vertebral trabecular bone volume, number, thickness, and connective density and decreased mean femoral mid-shaft cortical thickness and cross-sectional area when compared with their gender-matched (+/+) littermates and the historical means.

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO10282 or agonists thereof would be useful in maintaining bone homeostasis. In addition, PRO10282 or its encoding gene would be useful in bone healing or for the treatment of arthritis or osteoporosis; whereas antagonists to PRO10282 or its encoding gene would lead to abnormal or pathological bone disorders including inflammatory diseases associated with abnormal bone metabolism including arthritis, osteoporosis, and osteopenia.

Thus in summary, the (−/−) mice analyzed by DEXA were quite small in size and exhibited a notable decrease in body weight and length as well as a notable depletion of body fat depots, decrease in total tissue mass, lean body mass and decreased bone mineral content and density suggestive of growth retardation in these mutants. Thus, PRO10282 polypeptides or agonists thereof must be essential for normal growth and/or growth metabolism and therefore would be useful in the treatment or prevention of growth disorders, cachexia or other tissue wasting diseases.

(c) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

Blood Chemistry: The (−/−) mice exhibited an increased mean serum glucose level when compared with their gender-matched (+/+) littermates and the historical mean. During the glucose tolerance test, the (−/−) mice exhibited an increased mean fasting serum glucose level when compared with their gender-matched (+/+) littermates and the historical mean.

Thus, knockout mice exhibited the phenotypic pattern of an impaired glucose homeostasis with elevated levels of fasting serum glucose indicative of diabetes or a pre-diabetic condition. Based on these results, PRO10282 (or agonists thereof) or its encoding gene would be useful in the treatment of an impaired glucose metabolism and/or diabetes.

35.32. Generation and Analysis of Mice Comprising DNA347767 (UNQ14964) Gene Disruptions In these knockout experiments, the gene encoding PRO61709 polypeptides (designated as DNA347767 (UNQ14964) was disrupted. The gene specific information for these studies is as follows: the mutated mouse gene corresponds to nucleotide reference: NM_172294 or *Mus mus-*

*culus* sulfatase 1 (Sulf1); protein reference: Q8K007 or ACCESSION:Q8K007 NID: *Mus musculus* (Mouse). Extracellular sulfatase Sulf-1 precursor (EC 3.1.6.-) (MSulf-1); the human gene sequence reference: NM_015170 or *Homo sapiens* sulfatase 1 (SULF1); the human protein sequence corresponds to reference: Q81WU6 or Extracellular sulfatase Sulf-1 precursor (HSulf-1) gi|27356932|gb|AAM76860.1| extracellular sulfatase SULF-1 [*Homo sapiens*].

The disrupted mouse gene is Sulf1 (sulfatase 1), ortholog of human SULF1. Aliases include AW121680, extracellular sulfatase SULF-1, SULF-1, HSULF-1, KIAA1077, and sulfatase FP.

SULF1 is a secreted arylsulfatase with the ability to remove sulfate from glucosamine within subregions of heparin. This action on heparin is likely to inhibit signaling by heparin-dependent growth factors, thereby inhibiting cell proliferation and facilitating apoptosis (Morimoto-Tomita, et al., *J Biol Chem*, 277(51):49175-85 (2002); Lai et al., *J Biol Chem*, 278(25):23107-17 (2003); Lai et al., *Gastroenterology*, 126(1):231-48 (2004)). Down-regulation of SULF1 may be a mechanism by which certain types of cancer cells enhance growth factor signaling (Lai et al., *J Biol Chem*, 278(25):23107-17 (2003)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 31 | 44 | 19 | 94 |
| Expected | 23.5 | 47 | 23.5 | 94 |

Chi-Sq. = 3.45
Significance = 0.17846
(hom/n) = 0.20
Avg. Litter Size = 9

Mutation Type Retroviral Insertion (OST)
Retroviral insertion occurred in the intron preceding coding exon 1 (NCBI accession NM_172294.1).
Wild-type expression of the target gene was detected in embryonic stem (ES) cells and in all 13 adult tissue samples tested by RT-PCR.
RT-PCR analysis revealed that the transcript was absent in the (−/−) mouse analyzed (M-208).

35.32.1. Phenotypic Analysis (for Disrupted Gene: DNA347767 (UNQ14964)

(a) Overall Phenotypic Summary:

Mutation of the gene encoding the ortholog of human sulfatase 1 (SULF1) resulted in a decreased IL-6, TNF alpha and MCP-1 response to LPS challenge in (−/−) mice. Transcript was absent by RT-PCR.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Acute Phase Response:
Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFα, MCP-1, and IL-6 on the FACSCalibur instrument.

Results:

The (−/−) mice exhibited a decreased mean serum IL-6 response (as well as TNF-alpha and MCP-1) to LPS challenge when compared with their (+/+) littermates. Analyzed wt/het/hom: 8/4/8

In summary, the LPS endotoxin challenge demonstrated that knockout mice deficient in the gene encoding PRO61709 polypeptides exhibit immunological abnormalities when compared with their wild-type littermates. In particular, the mutant mice exhibited a decreased ability to elicit an immunological response (TNF-alpha, MCP-1 and IL-6 production) when challenged with the LPS endotoxin indicating a proinflammatory response. IL-6, MCP-1 and TNF alpha contribute to the later stages of B cell activation. In addition, they play a critical role in inducing the acute phase response and systemic inflammation. This suggests that PRO61709 polypeptides or agonists thereof would stimulate the immune system and would find utility in the cases wherein this effect would be beneficial to the individual such as in the case of leukemia, and other types of cancer, and in immunocompromised patients, such as AIDS sufferers. Accordingly, inhibitors or antagonists to PRO61709 polypeptides thereof would be useful in inhibiting the immune response and would be useful candidates for suppressing harmful immune responses, e.g. in the case of graft rejection or graft-versus-host diseases.

35.33. Generation and Analysis of Mice Comprising DNA58801-1052 (UNQ455) Gene Disruptions In these knockout experiments, the gene encoding PRO779 polypeptides (designated as DNA58801-1052 (UNQ455) was disrupted. The gene specific information for these studies is as follows: the mutated mouse gene corresponds to nucleotide reference: NM_033042 or ACCESSION:NM_033042 NID:14719437 *Mus musculus Mus musculus* tumor necrosis factor receptor superfamily, member 12 (Tnfrsf12); protein reference: Q99MM1 or Q99MM1 Q99MM1 WSL-1-LIKE PROTEIN; the human gene sequence reference: NM_003790 or ACCESSION:NM_003790 NID:4507568 *Homo sapiens Homo sapiens* tumor necrosis factor receptor superfamily, member 12 (translocating chain-association membrane protein) (TNFRSF12); the human protein sequence corresponds to reference: Q93038 or TR12_HUMAN Q93038 WSL-1 PROTEIN PRECURSOR APOPTOSIS-MEDI.

The mouse gene of interest is Tnfrsf25 (tumor necrosis factor receptor superfamily, member 25), ortholog of human TNFRSF25. Aliases include DR3, TR3, Wsl, DDR3, LARD, APO-3, TRAMP, WSL-1, WSL-LR, Tnfrsf12, WSL-1 protein, death receptor beta, death domain receptor 3, apoptosis inducing receptor, apoptosis-mediating receptor, death domain receptor 3 soluble form, lymphocyte associated receptor of death, translocating chain-association membrane protein, and tumor necrosis factor receptor superfamily member 12. TNFRSF25 is a type I plasma membrane protein expressed in thymocytes and lymphocytes that functions as a receptor for the ligands TNFSF12 (tumor necrosis factor (ligand) superfamily, member 12) and TNFSF15 (tumor necrosis factor (ligand) superfamily, member 15). Activation of TNFRSF25 can stimulate apoptosis or, conversely, promote T cell expansion by a nuclear factor kappa-B-mediated process (Chinnaiyan et al, *Science* 274(5289):990-2 (1996); Kitson et al, *Nature* 384(6607):372-5 (1996); Migone et al, *Immunity* 16(3):479-92 (2002); Wen et al, *J Biol Chem* 278 (40):39251-8 (2003)). TNFRSF25 appears to play a role in lymphocyte homeostasis. Wang et al., *Mol Cell Biol* 21(10): 3451-61 (2001) showed that negative selection and anti-CD3-induced apoptosis are impaired in TNFRSF25 homozygous null mice but not in wild-type mice, suggesting that TNFRSF25 plays a non redundant role in removal of self-reactive T cells in the thymus.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis is performed on mice from this generation

|  | wt | het | hom | Total |
|---|---|---|---|---|
| Observed | 21 | 42 | 21 | 84 |
| Expected | 21 | 42 | 21 | 84 |

Chi-Sq. = 0.00
Significance = 1.00000
(hom/n) = 0.25
Avg. Litter Size = 8

Mutation Type: Homologous Recombination (standard)
Coding exons 1 through 5 were targeted (NCBI accession NM_033042.2).
Wild-type expression of the target gene was detected in embryonic stem (ES) cells and in all 13 adult tissue samples tested by RT-PCR.
RT-PCR analysis revealed that the transcript was absent in the (−/−) mouse analyzed (M-208).

35.33.1. Phenotypic Analysis (for Disrupted Gene: DNA58801-1052 (UNQ455)

(a) Overall Phenotypic Summary:

Mutation of the gene encoding the ortholog of human tumor necrosis factor receptor superfamily, member 25 (TNFRSF25) resulted in decreased lumbar 5 vertebra measurements in the (−/−) mice compared to the wild-type littermate controls and historical means. In addition, the mutant knockout mice exhibited an enhanced IgG responses to an ovalbumin challenge.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:
Ovalbumin Challenge
Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Analyzed wt/het/hom: 8/4/9
Results of this Challenge:
The (−/−) mice exhibited an increased mean serum IgG2a response to ovalbumin challenge when compared with their (+/+) littermates and the historical means. Thus, these knockout mice exhibited an increased ability to elicit an OVA-specific antibody response to the T-cell dependent OVA antigen.

In summary, the ovalbumin challenge studies indicate that knockout mice deficient in the gene encoding PRO779 polypeptides exhibit immunological abnormalities when compared with their wild-type littermates. In particular, the mutant mice exhibited an increased ability to elicit an immunological response when challenged with the T-cell dependent OVA antigen. Thus, inhibitors or antagonists of PRO779 polypeptides would be useful for stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO779 polypeptides or agonists thereof would be useful for inhibiting the immune response and thus would be useful candidates for suppressing harmful immune responses, e.g. in the case of graft rejection or graft-versus-host diseases.

(c) Bone Metabolism & Body Diagnostics: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:
Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:
Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:
Micro-CT: The (−/−) mice exhibited a decreased lumbar 5 vertebra measurements in bone volume, trabecular number and connectivity density when compared with their gender-matched (+/+) littermates and the historical means. These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO779 polypeptides or agonists thereof play a role in maintaining bone homeostasis. In addition, PRO779 or its encoding gene would be useful in maintaining bone homeostasis and would be important in bone healing or useful for the treatment of osteoarthritis or osteoporosis; whereas antagonists to PRO779 or its encoding gene would lead to abnormal or pathological bone disorders including inflammatory diseases associated with abnormal bone metabolism including arthritis, osteoporosis, and osteopenia.

Example 36

Use of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 as a Hybridization Probe The following method describes use of a nucleotide sequence encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide as a hybridization probe.

DNA comprising the coding sequence of full-length or mature PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides as disclosed herein is employed as a probe to screen for homologous DNAs (such as those encoding naturally-occurring variants of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides) in human tissue cDNA libraries or human tissue genomic libraries.

Hybridization and washing of filters containing either library DNAs is performed under the following high stringency conditions. Hybridization of radiolabeled PRO196-, PRO217-, PRO231-, PRO236-, PRO245-, PRO246-, PRO258-, PRO287-, PRO328-, PRO344-, PRO357-, PRO526-, PRO724-, PRO731-, PRO732-, PRO1003-, PRO1104-, PRO1151-, PRO1244-, PRO1298-, PRO1313-, PRO1570-, PRO1886-, PRO1891-, PRO4409-, PRO5725-, PRO5994-, PRO6097-, PRO7425-, PRO10102-, PRO10282-, PRO61709- or PRO779-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides can then be identified using standard techniques known in the art.

Example 37

Expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 in *E. coli*

This example illustrates preparation of an unglycosylated form of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides by recombinant expression in *E. coli*.

The DNA sequence encoding a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 protein can then be purified using a metal chelating column under conditions that allow tight binding of the protein.

PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 may be expressed in *E. coli* in a poly-His tagged form, using the following procedure. The DNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 38

Expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 in Mammalian Cells This example illustrates preparation of a potentially glycosylated form of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide by recombinant expression in mammalian cells.

The vector, pRK5 (see EP 307,247, published Mar. 15, 1989), is employed as the expression vector. Optionally, the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 DNA is ligated into pRK5 with selected restriction enzymes to allow insertion of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 DNA using ligation methods such as described in Sambrook et al., supra. The resulting vector is called pRK5-PRO196, pRK5-PRO217, pRK5-PRO231, pRK5-PRO236, pRK5-PRO245, pRK5-PRO246, pRK5-PRO258, pRK5-PRO287, pRK5-PRO328, pRK5-PRO344, pRK5-PRO357, pRK5-PRO526, pRK5-PRO724, pRK5-PRO731, pRK5-PRO732, pRK5-PRO1003, pRK5-PRO1104, pRK5-PRO1151, pRK5-PRO1244, pRK5-PRO1298, pRK5-PRO1313, pRK5-PRO1570, pRK5-PRO1886, pRK5-PRO1891, pRK5-PRO4409, pRK5-PRO5725, pRK5-PRO5994, pRK5-PRO6097, pRK5-PRO7425, pRK5-PRO10102, pRK5-PRO10282, pRK5-PRO61709 or pRK5-PRO779.

The selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO196, pRK5-PRO217, pRK5-PRO231, pRK5-PRO236, pRK5-PRO245, pRK5-PRO246, pRK5-PRO258, pRK5-PRO287, pRK5-PRO328, pRK5-PRO344, pRK5-PRO357, pRK5-PRO526, pRK5-PRO724, pRK5-PRO731, pRK5-PRO732, pRK5-PRO1003, pRK5-PRO1104, pRK5-PRO1151, pRK5-PRO1244, pRK5-PRO1298, pRK5-PRO1313, pRK5-PRO1570, pRK5-PRO1886, pRK5-PRO1891, pRK5-PRO4409, pRK5-PRO5725, pRK5-PRO5994, pRK5-PRO6097, pRK5-PRO7425, pRK5-PRO10102, pRK5-PRO10282, pRK5-PRO61709 or pRK5-PRO779 DNA is mixed with about 1 µg DNA encoding the VA RNA gene [Thimmappaya et al., *Cell*, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides. The cultures containing transfected cells may undergo further incubation (in serum free medium) and the medium is tested in selected bioassays.

In an alternative technique, PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5-PRO196, pRK5-PRO217, pRK5-PRO231, pRK5-PRO236, pRK5-PRO245, pRK5-PRO246, pRK5-PRO258, pRK5-PRO287, pRK5-PRO328, pRK5-PRO344, pRK5-PRO357, pRK5-PRO526, pRK5-PRO724, pRK5-PRO731, pRK5-PRO732, pRK5-PRO1003, pRK5-PRO1104, pRK5-PRO1151, pRK5-PRO1244, pRK5-PRO1298, pRK5-PRO1313, pRK5-PRO1570, pRK5-PRO1886, pRK5-PRO1891, pRK5-PRO4409, pRK5-PRO5725, pRK5-PRO5994, pRK5-PRO6097, pRK5-PRO7425, pRK5-PRO10102, pRK5-PRO10282, pRK5-PRO61709 or pRK5-PRO779 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 can then be concentrated and purified by any selected method, such as dialysis and/or column chromatography.

PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 can be expressed in CHO cells. The pRK5-PRO196, pRK5-PRO217, pRK5-PRO231, pRK5-PRO236, pRK5-PRO245, pRK5-PRO246, pRK5-PRO258, pRK5-PRO287, pRK5-PRO328, pRK5-PRO344, pRK5-PRO357, pRK5-PRO526, pRK5-PRO724, pRK5-PRO731, pRK5-PRO732, pRK5-PRO1003, pRK5-PRO1104, pRK5-PRO1151, pRK5-PRO1244, pRK5-PRO1298, pRK5-PRO1313, pRK5-PRO1570, pRK5-PRO1886, pRK5-PRO1891, pRK5-PRO4409, pRK5-PRO5725, pRK5-PRO5994, pRK5-PRO6097, pRK5-PRO7425, pRK5-PRO10102, pRK5-PRO10282, pRK5-PRO61709 or pRK5-PRO779 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the culture medium may be replaced with serum free medium. Preferably, the cultures are incubated for about 6 days, and then the conditioned medium is harvested. The medium containing the expressed PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 can then be concentrated and purified by any selected method.

Epitope-tagged PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 may also be expressed in host CHO cells. The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 may be subcloned out of the pRK5 vector. The subclone insert can undergo PCR to fuse in frame with a selected epitope tag such as a poly-his tag into a Baculovirus expression vector. The poly-his tagged PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 can then be concentrated and purified by any selected method, such as by $Ni^{2+}$-chelate affinity chromatography.

PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 39

Expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 in Yeast The following method describes recombinant expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 in yeast.

First, yeast expression vectors are constructed for intracellular production or secretion of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 from the ADH2/GAPDH promoter. DNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 and the promoter is inserted into suitable restriction enzyme sites in the selected plasmid to direct intracellular expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779. For secretion, DNA encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 can be cloned into the selected plasmid, together with DNA encoding the ADH2/GAPDH promoter, a native PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 signal peptide or other mammalian signal peptide, or, for example, a yeast alpha-factor or invertase secretory signal/leader sequence, and linker sequences (if needed) for expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 can subsequently be isolated and purified by removing the yeast cells from the fermentation medium by centrifugation and then concentrating the medium using selected cartridge filters. The concentrate containing PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 may further be purified using selected column chromatography resins.

Example 40

Expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 in Baculovirus-Infected Insect Cells The following method describes recombinant expression of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 in Baculovirus-infected insect cells.

The sequence coding for PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 or the desired portion of the coding sequence of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 are pooled and dialyzed against loading buffer.

Alternatively, purification of the IgG tagged (or Fc tagged) PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 can be performed using known chromatography techniques, including for instance, Protein A or protein G column chromatography.

Example 41

Tissue Expression Profiling Using GeneExpress®

A proprietary database containing gene expression information (GeneExpress®, Gene Logic Inc., Gaithersburg, Md.) was analyzed in an attempt to identify polypeptides (and their encoding nucleic acids) whose expression is significantly upregulated in a particular tumor tissue(s) of interest as compared to other tumor(s) and/or normal tissues. Specifically, analysis of the GeneExpress® database was conducted using either software available through Gene Logic Inc., Gaithersburg, Md., for use with the GeneExpress® database or with proprietary software written and developed at Genentech, Inc. for use with the GeneExpress® database. The rating of positive hits in the analysis is based upon several criteria including, for example, tissue specificity, tumor specificity and expression level in normal essential and/or normal proliferating tissues. The following is a list of molecules whose tissue expression profile as determined from an analysis of the GeneExpress® database evidences high tissue expression and significant upregulation of expression in a specific tumor or tumors as compared to other tumor(s) and/or normal tissues and optionally relatively low expression in normal essential and/or normal proliferating tissues. Tissue expression profiling was performed on several UNQ genes the results of which are disclosed in Example 35.

Example 42

Microarray Analysis to Detect Upregulation of UNQ Genes in Cancerous Tumors

Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In one example, the specific preparation of nucleic acids for hybridization and probes, slides, and hybridization conditions are all detailed in PCT Patent Application Serial No. PCT/US01/10482, filed on Mar. 30, 2001 and which is herein incorporated by reference.

In the present example, cancerous tumors derived from various human tissues were studied for upregulated gene expression relative to cancerous tumors from different tissue types and/or non-cancerous human tissues in an attempt to identify those polypeptides which are overexpressed in a particular cancerous tumor(s). In certain experiments, cancerous human tumor tissue and non-cancerous human tumor tissue of the same tissue type (often from the same patient) were obtained and analyzed for UNQ polypeptide expression. Additionally, cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described UNQ polypeptide-encoding nucleic acid sequences were used in the creation of the microarray and RNA from various tumor tissues were used for the hybridization thereto. Below is shown the results of these experiments, demonstrating that various UNQ polypeptides of the present invention are significantly overexpressed in various human tumor tissues as compared to their normal counterpart tissue(s). Moreover, all of the molecules shown below are significantly overexpressed in their specific tumor tissue(s) as compared to in the "universal" epithelial control. As described above, these data demonstrate that the UNQ polypeptides of the present invention are useful not only as diagnostic markers for the presence of one or more cancerous tumors, but also serve as therapeutic targets for the treatment of those tumors. Microarray analysis was performed on several UNQ genes the results of which are disclosed in Example 35.

Example 43

Quantitative Analysis of UNQ mRNA Expression

In this assay, a 5' nuclease assay (for example, TaqMan®) and real-time quantitative PCR (for example, ABI Prizm 7700 Sequence Detection System® (Perkin Elmer, Applied Biosystems Division, Foster City, Calif.)), were used to find genes that are significantly overexpressed in a cancerous tumor or tumors as compared to other cancerous tumors or normal non-cancerous tissue. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The starting material for the screen was mRNA isolated from a variety of different cancerous tissues. The mRNA is quantitated precisely, e.g., fluorometrically. As a negative control, RNA was isolated from various normal tissues of the same tissue type as the cancerous tissues being tested.

5' nuclease assay data are initially expressed as Ct, or the threshold cycle. This is defined as the cycle at which the reporter signal accumulates above the background level of fluorescence. The $\Delta$Ct values are used as quantitative measurement of the relative number of starting copies of a particular target sequence in a nucleic acid sample when comparing cancer mRNA results to normal human mRNA results. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively measure the relative fold increase in mRNA expression between two or more different tissues. Using this technique, the molecules have been identified as being significantly overexpressed in a particular tumor(s) as compared to their normal non-cancerous counterpart tissue(s) (from both the same and different tissue donors) and thus, represent excellent polypeptide targets for the diagnosis and therapy of cancer in mammals. Specific results for a UNQ gene are disclosed in Example 35.

Example 44

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:
  2.0 µl 5× transcription buffer
  1.0 µl DTT (100 mM)
  2.0 µl NTP mix (2.5 mM: 101; each of 10 mM GTP, CTP & ATP+10 µl H$_2$O)
  1.0 µl UTP (50 µM)
  1.0 µl Rnasin
  1.0 µl DNA template (1 µg)
  1.0 µl H$_2$O
  1.0 µl RNA polymerase (for PCR products T3=AS, T7=S, usually)

The tubes were incubated at 37° C. for one hour. 1.0 µl RQ1 DNase were added, followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5 µl of RNA Mrk III were added to 3 µL of loading buffer. After heating on a 95° C. heat block for three minutes, the probe was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{33}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+ 975 ml SQ H$_2$O). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-Embedded Sections

The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8× proteinase K (100 µl in 250 ml Rnase buffer, 37° C., 30 minutes)— formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper.

D. Hybridization 1.0×10$^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

E. Washes

Washing was done 2×10 minutes with 2×SSC, EDTA at room temperature (400 ml 20×SSC+16 ml 0.25M EDTA, V$_f$=4 L), followed by RNaseA treatment at 37° C. for 30 minutes (500 µl of 10 mg/ml in 250 ml Rnase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, V$_f$=4 L).

F. Oligonucleotides

In situ analysis was performed on a variety of DNA sequences disclosed herein. The oligonucleotides employed for these analyses were obtained so as to be complementary to the nucleic acids (or the complements thereof) as shown in the accompanying figures.

G. Results

In situ analysis was performed on a variety of DNA sequences disclosed herein the results of which are disclosed in Example 35.

Example 45

Preparation of Antibodies that Bind PRO196, PRO217, PRO231, PRO236, PRO245, PRO246, PRO258, PRO287, PRO328, PRO344, PRO357, PRO526, PRO724, PRO731, PRO732, PRO1003, PRO1104 PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779

This example illustrates preparation of monoclonal antibodies which can specifically bind PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779.

Techniques for producing the monoclonal antibodies are known in the art and are described, for instance, in Goding, supra. Immunogens that may be employed include purified PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides, fusion proteins containing PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151; PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides, and cells expressing recombinant PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides on the cell surface. Selection of the immunogen can be made by the skilled artisan without undue experimentation.

Mice, such as Balb/c, are immunized with the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 antibodies.

After a suitable antibody titer has been detected, the animals "positive" for antibodies can be injected with a final intravenous injection of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779. Determination of "positive" hybridoma cells secreting the desired monoclonal antibodies against PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 is within the skill in the art.

The positive hybridoma cells can be injected intraperitoneally into syngeneic Balb/c mice to produce ascites containing the anti-PRO196, anti-PRO217, anti-PRO231, anti-PRO236, anti-PRO245, anti-PRO246, anti-PRO258, anti-PRO287, anti-PRO328, anti-PRO344, anti-PRO357, anti-PRO526, anti-PRO724, anti-PRO731, anti-PRO732, anti-PRO1003, anti-PRO1104, anti-PRO1151, anti-PRO1244, anti-PRO1298, anti-PRO1313, anti-PRO1570, anti-PRO1886, anti-PRO1891, anti-PRO4409, anti-PRO5725, anti-PRO5994, anti-PRO6097, anti-PRO7425, anti-PRO10102, anti-PRO10282, anti-PRO61709 or anti-PRO779 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 46

Purification of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 Polypeptides Using Specific Antibodies Native or recombinant PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides may be purified by a variety of standard techniques in the art of protein purification. For example, pro-PRO196, pro-PRO217, pro-PRO231, pro-PRO236, pro-PRO245, pro-PRO246, pro-PRO258, pro-PRO287, pro-PRO328, pro-PRO344, pro-PRO357, pro-PRO526, pro-PRO724, pro-PRO731, pro-PRO732, pro-PRO1003, pro-PRO1104, pro-PRO1151, pro-PRO1244, pro-PRO1298, pro-PRO1313, pro-PRO1570, pro-PRO1886, pro-PRO1891, pro-PRO4409, pro-PRO5725, pro-PRO5994, pro-PRO6097, pro-PRO7425, pro-PRO10102, pro-PRO10282, pro-PRO61709 or pro-PRO779 polypeptide, mature PRO196, mature PRO217, mature PRO231, mature PRO236, mature PRO245, mature PRO246, mature PRO258, mature PRO287, mature PRO328, mature PRO344, mature PRO357, mature PRO526, mature PRO724, mature PRO731, mature PRO732, mature PRO1003, mature PRO1104, mature PRO1151, mature PRO1244, mature PRO1298, mature PRO1313, mature PRO1570, mature PRO1886, mature PRO1891, mature PRO4409, mature PRO5725, mature PRO5994, mature PRO6097, mature PRO7425, mature PRO10102, mature PRO10282, mature PRO61709 or mature PRO779 polypeptide, or pre-PRO196, pre-PRO217, pre-PRO231, pre-PRO236, pre-PRO245, pre-PRO246, pre-PRO258, pre-PRO287, pre-PRO328, pre-PRO344, pre-PRO357, pre-PRO526, pre-PRO724, pre-PRO731, pre-PRO732, pre-PRO1003, pre-PRO1104, pre-PRO1151, pre-PRO1244, pre-PRO1298, pre-PRO1313, pre-PRO1570, pre-PRO1886, pre-PRO1891, pre-PRO4409, pre-PRO5725, pre-PRO5994, pre-PRO6097, pre-PRO7425, pre-PRO10102, pre-PRO10282, pre-PRO61709 or pre-PRO779 polypeptide is purified by immunoaffinity chromatography using antibodies specific for the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide of interest. In general, an immunoaffinity column is constructed by covalently coupling the anti-PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide by preparing a fraction from cells containing PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide in a soluble form. This preparation is derived by solubilization of the whole cell or of a subcellular fraction obtained via differential centrifugation by the addition of detergent or by other methods well known in the art. Alternatively, soluble polypeptide containing a signal sequence may be secreted in useful quantity into the medium in which the cells are grown.

A soluble PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-containing preparation is passed over the immunoaffinity column, and the column is washed under conditions that allow the preferential absorbance of PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide (e.g., high ionic strength buffers in the presence of detergent). Then, the column is eluted under conditions that disrupt antibody/PRO196, antibody/PRO217, antibody/PRO231, antibody/PRO236, antibody/PRO245, antibody/PRO246, antibody/PRO258, antibody/PRO287, antibody/PRO328, antibody/PRO344, antibody/PRO357, antibody/PRO526, antibody/PRO724, antibody/PRO731, antibody/PRO732, antibody/PRO1003, antibody/PRO1104, antibody/PRO1151, antibody/PRO1244, antibody/PRO1298, antibody/PRO1313, antibody/PRO1570, antibody/PRO1886, antibody/PRO1891, antibody/PRO4409, antibody/PRO5725, antibody/PRO5994, antibody/PRO6097, antibody/PRO7425, antibody/PRO10102, antibody/PRO10282, antibody/PRO61709 or antibody/PRO779 polypeptide binding (e.g., a low pH buffer such as approximately pH 2-3, or a high concentration of a chaotrope such as urea or thiocyanate ion), and PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide is collected.

Example 47

Drug Screening

This invention is particularly useful for screening compounds by using PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptides or binding fragment thereof in any of a variety of drug screening techniques. The PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or fragment. Drugs are screened against such transformed cells in competitive binding assays. Such cells, either in viable or fixed form, can be used for standard binding assays. One may measure, for example, the formation of complexes between PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or a fragment and the agent being tested. Alternatively, one can examine the diminution in complex formation between the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and its target cell or target receptors caused by the agent being tested.

Thus, the present invention provides methods of screening for drugs or any other agents which can affect a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-associated disease or disorder. These methods comprise contacting such an agent with an PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or fragment thereof and assaying (I) for the presence of a complex between the agent and the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or fragment, or (ii) for the presence of a complex between the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or fragment and the cell, by methods well known in the art. In such competitive binding assays, the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or fragment is typically labeled. After suitable incubation, free PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or fragment is separated from that present in bound form, and the amount of free or uncomplexed label is a measure of the ability of the particular agent to bind to PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or to interfere with the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, the peptide test compounds are reacted with PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide and washed. Bound PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide is detected by methods well known in the art. Purified PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide specifically compete with a test compound for binding to PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or fragments thereof. In this manner, the antibodies can be used to detect the presence of any peptide which shares one or more antigenic determinants with PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide.

Example 48

Rational Drug Design

The goal of rational drug design is to produce structural analogs of biologically active polypeptide of interest (i.e., a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide) or of small molecules with which they interact, e.g., agonists, antagonists, or inhibitors. Any of these examples can be used to fashion drugs which are more active or stable forms of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide or which enhance or interfere with the function of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide in vivo (cf., Hodgson, *Bio/Technology*, 9: 19-21 (1991)).

In one approach, the three-dimensional structure of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide, or of a PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-inhibitor complex, is determined by x-ray crystallography, by computer modeling or, most typically, by a combination of the two approaches. Both the shape and charges of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide must be ascertained to elucidate the structure and to determine active site(s) of the molecule. Less often, useful information regarding the structure of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may be gained by modeling based on the structure of homologous proteins. In both cases, relevant structural information is used to design analogous PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide-like molecules or to identify efficient inhibitors. Useful examples of rational drug design may include molecules which have improved activity or stability as shown by Braxton and Wells, *Biochemistry*, 31:7796-7801 (1992) or which act as inhibitors, agonists, or antagonists of native peptides as shown by Athauda et al., *J. Biochem.* 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide may be made available to perform such analytical studies as X-ray crystallography. In addition, knowledge of the PRO196, PRO217, PRO231, PRO236, PRO245, PRO246, PRO258, PRO287, PRO328, PRO344, PRO357, PRO526, PRO724, PRO731, PRO732, PRO1003, PRO1104, PRO1151, PRO1244, PRO1298, PRO1313, PRO1570, PRO1886, PRO1891, PRO4409, PRO5725, PRO5994, PRO6097, PRO7425, PRO10102, PRO10282, PRO61709 or PRO779 polypeptide amino acid sequence provided herein will provide guidance to those employing computer modeling techniques in place of or in addition to x-ray crystallography.

What is claimed is:

1. A method of identifying an agent that modulates a characteristic of a bone metabolic abnormality or disorder, the method comprising: (a) providing a transgenic mouse whose genome comprises a homozygous disruption of a gene which encodes for the PRO1891 polypeptide (SEQ ID NO: 48) and which, compared with gender matched wild-type littermates, exhibits a characteristic of a bone metabolic abnormality or disorder selected from group of characteristics consisting of: decreased bone mineral density (BMD) in total body, femur and vertebrae; decreased bone mineral content (BMC) in total body, femur and vertebrae; decreased volumetric bone mineral density (vBMD) in total body, femur and vertebrae; and decreased mean vertebral trabecular bone volume, number and connectivity density; (b) measuring said characteristic of the transgenic mouse of (a); (c) comparing the measured characteristic of (b) with that of a gender matched wild-type mouse; (d) administering a test agent to the transgenic mouse of (a); and (e) determining whether the test agent modulates the characteristic of a bone metabolic abnormality or disorder.

2. A method of identifying an agent that ameliorates a characteristic of a bone metabolic abnormality or disorder, the method comprising: (a) providing a transgenic mouse whose genome comprises a homozygous disruption of a gene which encodes for a PRO1891 polypeptide (SEQ ID NO 48) and which, compared with gender matched wild-type littermates, exhibits a characteristic of a bone metabolic abnormality or disorder selected from the group consisting of decreased bone mineral density (BMD) in total body, femur and vertebrae; decreased bone mineral content (BMC) in total body, femur and vertebrae; decreased volumetric bone mineral density (vBMD) in total body, femur and vertebrae; and decreased mean vertebral trabecular bone volume, number and connectivity density; (b) administering a test agent to said transgenic mouse; and (c) determining whether said test agent ameliorates said characteristic of a bone metabolic abnormality or disorder.

* * * * *

SEQUENCE LISTING

```
<160> NUMBER OF SEQ ID NOS: 142

<210> SEQ ID NO 1
<211> LENGTH: 2290
<212> TYPE: DNA
<213> ORGANISM: Homo sapiens

<400> SEQUENCE: 1
ggctgagggg aggcccggag cctttctggg gcctggggga tcctcttgca          50
ctggtgggtg gagagaagcg cctgcagcca accagggtca ggctgtgctc         100
```

```
acagtttcct ctggcggcat gtaaaggctc cacaaaggag ttgggagttc        150
aaatgaggct gctgcggacg gcctgaggat ggaccccaag ccctggacct        200
gccgagcgtg gcactgaggc agcggctgac gctactgtga gggaaagaag        250
gttgtgagca gccccgcagg acccctggcc agccctggcc ccagcctctg        300
ccggagccct ctgtggaggc agagccagtg gagcccagtg aggcagggct        350
gcttggcagc caccggcctg caactcagga accoctccag aggccatgga        400 caggctgccc cgctgacggc cagggtgaag catgtgagga gccgccccgg        450
agccaagcag gagggaagag gctttcatag attctattca caaagaataa        500
ccaccatttt gcaaggacca tgaggccact gtgcgtgaca tgctggtggc        550
tcggactgct ggctgccatg ggagctgttg caggccagga ggacggtttt        600
gagggcactg aggagggctc gccaagagag ttcatttacc taaacaggta        650
caagcgggcg ggcgagtccc aggacaagtg cacctacacc ttcattgtgc        700
cccagcagcg ggtcacgggt gccatctgcg tcaactccaa ggagcctgag        750
gtgcttctgg agaaccgagt gcataagcag gagctagagc tgctcaacaa        800
tgagctgctc aagcagaagc ggcagatcga gacgctgcag cagctggtgg        850
aggtggacgg cggcattgtg agcgaggtga agctgctgcg caaggagagc        900
cgcaacatga actcgcgggt cacgcagctc tacatgcagc tcctgcacga        950
gatcatccgc aagcgggaca acgcgttgga gctctcccag ctggagaaca       1000
ggatcctgaa ccagacagcc gacatgctgc agctggccag caagtacaag       1050
gacctggagc acaagtacca gcacctggcc acactggccc acaaccaatc       1100
agagatcatc gcgcagcttg aggagcactg ccagagggtg ccctcggcca       1150
ggcccgtccc ccagccaccc cccgctgccc cgccccgggt ctaccaacca       1200
cccacctaca accgcatcat caaccagatc tctaccaacg agatccagag       1250
tgaccagaac ctgaaggtgc tgccacccac tctgccccact atgcccactc       1300 tcaccagcct cccatcttcc accgacaagc cgtcgggccc atggagagac       1350
tgcctgcagg ccctggagga tggccacgac accagctcca tctacctggt       1400
gaagccggag aacaccaacc gcctcatgca ggtgtggtgc gaccagagac       1450
acgaccccgg gggctggacc gtcatccaga gacgcctgga tggctctgtt       1500
aacttcttca ggaactggga gacgtacaag caagggtttg gaacattga        1550 cggcgaatac tggctgggcc tggagaacat ttactggctg acgaaccaag       1600
gcaactacaa actcctggtg accatggagg actggtccgg ccgcaaagtc       1650
tttgcagaat acgccagttt ccgcctggaa cctgagagcg agtattataa       1700
gctgcggctg gggcgctacc atggcaatgc gggtgactcc tttacatggc       1750
acaacggcaa gcagttcacc accctggaca gagatcatga tgtctacaca       1800
ggaaactgtg cccactacca gaagggaggc tggtggtata cgcctgtgc        1850 ccactccaac ctcaacgggg tctggtaccg cggggccat taccggagcc        1900 gctaccagga cggagtctac tgggctgagt tccgaggagg ctcttactca       1950
ctcaagaaag tggtgatgat gatccgaccg aaccccaaca ccttccacta       2000
agccagctcc ccctcctgac ctctcgtggc cattgccagg agcccaccct       2050
ggtcacgctg gccacagcac aaagaacaac tcctcaccag ttcatcctga       2100
```

```
ggctgggagg accgggatgc tggattctgt tttccgaagt cactgcagcg        2150
gatgatggaa ctgaatcgat acggtgtttt ctgtccctcc tactttcctt        2200
cacaccagac agcccctcat gtctccagga caggacagga ctacagacaa        2250
ctctttcttt aaataaatta agtctctaca ataaaaaaaa                   2290
```

<210> SEQ ID NO 2
<211> LENGTH: 493
<212> TYPE: PRT
<213> ORGANISM: Homo sapiens

<400> SEQUENCE: 2

```
Met Arg Pro Leu Cys Val Thr Cys Trp Trp Leu Gly Leu Leu Ala
 1               5                  10                   15

Ala Met Gly Ala Val Ala Gly Gln Glu Asp Gly Phe Glu Gly Thr
                20                  25                   30

Glu Glu Gly Ser Pro Arg Glu Phe Ile Tyr Leu Asn Arg Tyr Lys
             35                  40                   45

Arg Ala Gly Glu Ser Gln Asp Lys Cys Thr Tyr Thr Phe Ile Val
         50                  55                   60

Pro Gln Gln Arg Val Thr Gly Ala Ile Cys Val Asn Ser Lys Glu
     65                  70                   75

Pro Glu Val Leu Leu Glu Asn Arg Val His Lys Gln Glu Leu Glu
         80                  85                   90

Leu Leu Asn Asn Glu Leu Leu Lys Gln Lys Arg Gln Ile Glu Thr
         95                 100                  105

Leu Gln Gln Leu Val Glu Val Asp Gly Gly Ile Val Ser Glu Val
        110                 115                  120

Lys Leu Leu Arg Lys Glu Ser Arg Asn Met Asn Ser Arg Val Thr
        125                 130                  135

Gln Leu Tyr Met Gln Leu Leu His Glu Ile Ile Arg Lys Arg Asp
        140                 145                  150

Asn Ala Leu Glu Leu Ser Gln Leu Glu Asn Arg Ile Leu Asn Gln
        155                 160                  165

Thr Ala Asp Met Leu Gln Leu Ala Ser Lys Tyr Lys Asp Leu Glu
        170                 175                  180

His Lys Tyr Gln His Leu Ala Thr Leu Ala His Asn Gln Ser Glu
        185                 190                  195

Ile Ile Ala Gln Leu Glu Glu His Cys Gln Arg Val Pro Ser Ala
        200                 205                  210

Arg Pro Val Pro Gln Pro Pro Ala Ala Pro Pro Arg Val Tyr
        215                 220                  225

Gln Pro Pro Thr Tyr Asn Arg Ile Ile Asn Gln Ile Ser Thr Asn
        230                 235                  240

Glu Ile Gln Ser Asp Gln Asn Leu Lys Val Leu Pro Pro Pro Leu
        245                 250                  255

Pro Thr Met Pro Thr Leu Thr Ser Leu Pro Ser Ser Thr Asp Lys
        260                 265                  270

Pro Ser Gly Pro Trp Arg Asp Cys Leu Gln Ala Leu Glu Asp Gly
        275                 280                  285

His Asp Thr Ser Ser Ile Tyr Leu Val Lys Pro Glu Asn Thr Asn
        290                 295                  300

Arg Leu Met Gln Val Trp Cys Asp Gln Arg His Asp Pro Gly Gly
        305                 310                  315
```

```
Trp Thr Val Ile Gln Arg Arg Leu Asp Gly Ser Val Asn Phe Phe
            320                 325                 330

Arg Asn Trp Glu Thr Tyr Lys Gln Gly Phe Gly Asn Ile Asp Gly
            335                 340                 345

Glu Tyr Trp Leu Gly Leu Glu Asn Ile Tyr Trp Leu Thr Asn Gln
            350                 355                 360

Gly Asn Tyr Lys Leu Leu Val Thr Met Glu Asp Trp Ser Gly Arg
            365                 370                 375

Lys Val Phe Ala Glu Tyr Ala Ser Phe Arg Leu Glu Pro Glu Ser
            380                 385                 390

Glu Tyr Tyr Lys Leu Arg Leu Gly Arg Tyr His Gly Asn Ala Gly
            395                 400                 405

Asp Ser Phe Thr Trp His Asn Gly Lys Gln Phe Thr Thr Leu Asp
            410                 415                 420

Arg Asp His Asp Val Tyr Thr Gly Asn Cys Ala His Tyr Gln Lys
            425                 430                 435

Gly Gly Trp Trp Tyr Asn Ala Cys Ala His Ser Asn Leu Asn Gly
            440                 445                 450

Val Trp Tyr Arg Gly Gly His Tyr Arg Ser Arg Tyr Gln Asp Gly
            455                 460                 465

Val Tyr Trp Ala Glu Phe Arg Gly Gly Ser Tyr Ser Leu Lys Lys
            470                 475                 480

Val Val Met Met Ile Arg Pro Asn Pro Asn Thr Phe His
            485                 490

<210> SEQ ID NO 3
<211> LENGTH: 2033
<212> TYPE: DNA
<213> ORGANISM: Homo sapiens

<400> SEQUENCE: 3
ccaggccggg aggcgacgcg cccagccgtc taaacgggaa cagccctggc          50
tgagggagct gcagcgcagc agagtatctg acggcgccag gttgcgtagg         100
tgcggcacga ggagttttcc cggcagcgag gaggtcctga gcagcatggc         150
ccggaggagc gccttccctg ccgccgcgct ctggctctgg agcatcctcc         200
tgtgcctgct ggcactgcgg gcggaggccg gccgccgcca ggaggagagc         250
ctgtacctat ggatcgatgc tcaccaggca agagtactca taggatttga         300
agaagatatc ctgattgttt cagagggaaa atggcacct tttacacatg          350 atttcagaaa agcgcaacag agaatgccag ctattcctgt caatatccat         400
tccatgaatt ttacctggca agctgcaggg caggcagaat acttctatga         450
attcctgtcc ttgcgctccc tggataaagg catcatggca gatccaaccg         500
tcaatgtccc tctgctggga acagtgcctc acaaggcatc agttgttcaa         550
gttggtttcc catgtcttgg aaaacaggat ggggtggcag catttgaagt         600
ggatgtgatt gttatgaatt ctgaaggcaa caccattctc caaacacctc         650
aaaatgctat cttctttaaa acatgtcaac aagctgagtg cccaggcggg         700
tgccgaaatg gaggcttttg taatgaaaga cgcatctgcg agtgtcctga         750
tgggttccac ggacctcact gtgagaaagc cctttgtacc ccacgatgta         800
tgaatggtgg actttgtgtg actcctggtt tctgcatctg cccacctgga         850
ttctatggag tgaactgtga caaagcaaac tgctcaacca cctgctttaa         900
```

```
tggagggacc tgtttctacc ctggaaaatg tatttgccct ccaggactag         950
agggagagca gtgtgaaatc agcaaatgcc cacaaccctg tcgaaatgga        1000
ggtaaatgca ttggtaaaag caaatgtaag tgttccaaag gttaccaggg        1050
agacctctgt tcaaagcctg tctgcgagcc tggctgtggt gcacatggaa        1100
cctgccatga acccaacaaa tgccaatgtc aagaaggttg gcatggaaga        1150
cactgcaata aaaggtacga agccagcctc atacatgccc tgaggccagc        1200
aggcgcccag ctcaggcagc acacgccttc acttaaaaag gccgaggagc        1250
ggcgggatcc acctgaatcc aattacatct ggtgaactcc gacatctgaa        1300
acgttttaag ttacaccaag ttcatagcct ttgttaacct ttcatgtgtt        1350
gaatgttcaa ataatgttca ttacacttaa gaatactggc ctgaatttta        1400
ttagcttcat tataaatcac tgagctgata tttactcttc cttttaagtt        1450
ttctaagtac gtctgtagca tgatggtata gattttcttg tttcagtgct        1500
ttgggacaga ttttatatta tgtcaattga tcaggttaaa attttcagtg        1550
tgtagttggc agatattttc aaaattacaa tgcatttatg gtgtctgggg        1600 gcagggaac atcagaaagg ttaaattggg caaaaatgcg taagtcacaa         1650
gaatttggat ggtgcagtta atgttgaagt tacagcattt cagattttat        1700
tgtcagatat ttagatgttt gttacatttt taaaaattgc tcttaatttt        1750
taaactctca atacaatata ttttgacctt accattattc cagagattca        1800
gtattaaaaa aaaaaaaatt acactgtggt agtggcattt aaacaatata        1850
atatattcta aacacaatga aatagggaat ataatgtatg aacttttgc         1900 attggcttga agcaatataa tatattgtaa acaaaacaca gctcttacct        1950
aataaacatt ttatactgtt tgtatgtata aaataaaggt gctgctttag        2000 tttttttggaa aaaaaaaaaa aaaaaaaaa  aaa                         2033
```

<210> SEQ ID NO 4
<211> LENGTH: 379
<212> TYPE: PRT
<213> ORGANISM: Homo sapiens

<400> SEQUENCE: 4

Met Ala Arg Arg Ser Ala Phe Pro Ala Ala Leu Trp Leu Trp
 1               5                  10                  15

Ser Ile Leu Leu Cys Leu Leu Ala Leu Arg Ala Glu Ala Gly Pro
                20                  25                  30

Pro Gln Glu Glu Ser Leu Tyr Leu Trp Ile Asp Ala His Gln Ala
                35                  40                  45

Arg Val Leu Ile Gly Phe Glu Glu Asp Ile Leu Ile Val Ser Glu
                50                  55                  60

Gly Lys Met Ala Pro Phe Thr His Asp Phe Arg Lys Ala Gln Gln
                65                  70                  75

Arg Met Pro Ala Ile Pro Val Asn Ile His Ser Met Asn Phe Thr
                80                  85                  90

Trp Gln Ala Ala Gly Gln Ala Glu Tyr Phe Tyr Glu Phe Leu Ser
                95                  100                 105

Leu Arg Ser Leu Asp Lys Gly Ile Met Ala Asp Pro Thr Val Asn
                110                 115                 120

Val Pro Leu Leu Gly Thr Val Pro His Lys Ala Ser Val Val Gln
                125                 130                 135

| | | | | | | | | | | |
|---|---|---|---|---|---|---|---|---|---|---|
| Val | Gly | Phe | Pro | Cys | Leu | Gly | Lys | Gln | Asp | Gly | Val | Ala | Ala | Phe |
| | | | 140 | | | | | 145 | | | | | 150 | |

Val Gly Phe Pro Cys Leu Gly Lys Gln Asp Gly Val Ala Ala Phe
            140                 145                 150

Glu Val Asp Val Ile Val Met Asn Ser Glu Gly Asn Thr Ile Leu
            155                 160                 165

Gln Thr Pro Gln Asn Ala Ile Phe Phe Lys Thr Cys Gln Gln Ala
            170                 175                 180

Glu Cys Pro Gly Gly Cys Arg Asn Gly Gly Phe Cys Asn Glu Arg
            185                 190                 195

Arg Ile Cys Glu Cys Pro Asp Gly Phe His Gly Pro His Cys Glu
            200                 205                 210

Lys Ala Leu Cys Thr Pro Arg Cys Met Asn Gly Gly Leu Cys Val
            215                 220                 225

Thr Pro Gly Phe Cys Ile Cys Pro Pro Gly Phe Tyr Gly Val Asn
            230                 235                 240

Cys Asp Lys Ala Asn Cys Ser Thr Thr Cys Phe Asn Gly Gly Thr
            245                 250                 255

Cys Phe Tyr Pro Gly Lys Cys Ile Cys Pro Pro Gly Leu Glu Gly
            260                 265                 270

Glu Gln Cys Glu Ile Ser Lys Cys Pro Gln Pro Cys Arg Asn Gly
            275                 280                 285

Gly Lys Cys Ile Gly Lys Ser Lys Cys Lys Cys Ser Lys Gly Tyr
            290                 295                 300

Gln Gly Asp Leu Cys Ser Lys Pro Val Cys Glu Pro Gly Cys Gly
            305                 310                 315

Ala His Gly Thr Cys His Glu Pro Asn Lys Cys Gln Cys Gln Glu
            320                 325                 330

Gly Trp His Gly Arg His Cys Asn Lys Arg Tyr Glu Ala Ser Leu
            335                 340                 345

Ile His Ala Leu Arg Pro Ala Gly Ala Gln Leu Arg Gln His Thr
            350                 355                 360

Pro Ser Leu Lys Lys Ala Glu Glu Arg Arg Asp Pro Pro Glu Ser
            365                 370                 375

Asn Tyr Ile Trp

<210> SEQ ID NO 5
<211> LENGTH: 1514
<212> TYPE: DNA
<213> ORGANISM: Homo sapiens

<400> SEQUENCE: 5
ggggtctccc tcagggccgg gaggcacagc ggtccctgct tgctgaaggg         50
ctggatgtac gcatccgcag gttcccgcgg acttggggc gcccgctgag         100 ccccggcgcc cgcagaagac ttgtgtttgc ctcctgcagc ctcaacccgg         150
agggcagcga gggcctacca ccatgatcac tggtgtgttc agcatgcgct         200
tgtggacccc agtgggcgtc ctgacctcgc tggcgtactg cctgcaccag         250
cggcgggtgg ccctggccga gctgcaggag gccgatggcc agtgtccggt         300
cgaccgcagc ctgctgaagt tgaaaatggt gcaggtcgtg tttcgacacg         350
gggctcggag tcctctcaag ccgctcccgc tggaggagca ggtagagtgg         400 aaccccagc tattagaggt cccaccccaa actcagtttg attacacagt         450
caccaatcta gctggtggtc cgaaaccata ttctccttac gactctcaat         500
accatgagac caccctgaag gggggcatgt ttgctgggca gctgaccaag         550

```
gtgggcatgc agcaaatgtt tgccttggga gagagactga ggaagaacta         600
tgtggaagac attccctttc tttcaccaac cttcaaccca caggaggtct         650
ttattcgttc cactaacatt tttcggaatc tggagtccac ccgttgtttg         700
ctggctgggc ttttccagtg tcagaaagaa ggacccatca tcatccacac         750
tgatgaagca gattcagaag tcttgtatcc caactaccaa agctgctgga         800
gcctgaggca gagaaccaga ggccggaggc agactgcctc tttacagcca         850
ggaatctcag aggatttgaa aaggtgaag acaggatgg gcattgacag           900 tagtgataaa gtggacttct tcatcctcct ggacaacgtg gctgccgagc         950
aggcacacaa cctcccaagc tgccccatgc tgaagagatt tgcacggatg         1000
atcgaacaga gagctgtgga cacatccttg tacatactgc ccaaggaaga        1050
cagggaaagt cttcagatgg cagtaggccc attcctccac atcctagaga        1100
gcaacctgct gaaagccatg gactctgcca ctgcccccga caagatcaga        1150
aagctgtatc tctatgcggc tcatgatgtg accttcatac cgctcttaat        1200
gaccctgggg attttgacc acaaatggcc accgttttgct gttgacctga        1250 ccatggaact ttaccagcac ctggaatcta aggagtggtt tgtgcagctc        1300
tattaccacg ggaaggagca ggtgccgaga ggttgccctg atgggctctg        1350
cccgctggac atgttcttga atgccatgtc agtttatacc ttaagcccag        1400
aaaaatacca tgcactctgc tctcaaactc aggtgatgga agttggaaat        1450
gaagagtaac tgatttataa aagcaggatg tgttgatttt aaaataaagt        1500
gcctttatac  aatg                                              1514
```

<210> SEQ ID NO 6
<211> LENGTH: 428
<212> TYPE: PRT
<213> ORGANISM: Homo sapiens

<400> SEQUENCE: 6

Met Ile Thr Gly Val Phe Ser Met Arg Leu Trp Thr Pro Val Gly
1               5                   10                  15

Val Leu Thr Ser Leu Ala Tyr Cys Leu His Gln Arg Arg Val Ala
                20                  25                  30

Leu Ala Glu Leu Gln Glu Ala Asp Gly Gln Cys Pro Val Asp Arg
                35                  40                  45

Ser Leu Leu Lys Leu Lys Met Val Gln Val Val Phe Arg His Gly
                50                  55                  60

Ala Arg Ser Pro Leu Lys Pro Leu Pro Leu Glu Glu Gln Val Glu
                65                  70                  75

Trp Asn Pro Gln Leu Leu Glu Val Pro Pro Gln Thr Gln Phe Asp
                80                  85                  90

Tyr Thr Val Thr Asn Leu Ala Gly Gly Pro Lys Pro Tyr Ser Pro
                95                  100                 105

Tyr Asp Ser Gln Tyr His Glu Thr Thr Leu Lys Gly Gly Met Phe
                110                 115                 120

Ala Gly Gln Leu Thr Lys Val Gly Met Gln Gln Met Phe Ala Leu
                125                 130                 135

Gly Glu Arg Leu Arg Lys Asn Tyr Val Glu Asp Ile Pro Phe Leu
                140                 145                 150

Ser Pro Thr Phe Asn Pro Gln Glu Val Phe Ile Arg Ser Thr Asn

```
                155                 160                 165
Ile Phe Arg Asn Leu Glu Ser Thr Arg Cys Leu Leu Ala Gly Leu
            170                 175                 180

Phe Gln Cys Gln Lys Glu Gly Pro Ile Ile Ile His Thr Asp Glu
            185                 190                 195

Ala Asp Ser Glu Val Leu Tyr Pro Asn Tyr Gln Ser Cys Trp Ser
            200                 205                 210

Leu Arg Gln Arg Thr Arg Gly Arg Gln Thr Ala Ser Leu Gln
            215                 220                 225

Pro Gly Ile Ser Glu Asp Leu Lys Lys Val Lys Asp Arg Met Gly
            230                 235                 240

Ile Asp Ser Ser Asp Lys Val Asp Phe Phe Ile Leu Leu Asp Asn
            245                 250                 255

Val Ala Ala Glu Gln Ala His Asn Leu Pro Ser Cys Pro Met Leu
            260                 265                 270

Lys Arg Phe Ala Arg Met Ile Glu Gln Arg Ala Val Asp Thr Ser
            275                 280                 285

Leu Tyr Ile Leu Pro Lys Glu Asp Arg Glu Ser Leu Gln Met Ala
            290                 295                 300

Val Gly Pro Phe Leu His Ile Leu Glu Ser Asn Leu Leu Lys Ala
            305                 310                 315

Met Asp Ser Ala Thr Ala Pro Asp Lys Ile Arg Lys Leu Tyr Leu
            320                 325                 330

Tyr Ala Ala His Asp Val Thr Phe Ile Pro Leu Leu Met Thr Leu
            335                 340                 345

Gly Ile Phe Asp His Lys Trp Pro Pro Phe Ala Val Asp Leu Thr
            350                 355                 360

Met Glu Leu Tyr Gln His Leu Glu Ser Lys Glu Trp Phe Val Gln
            365                 370                 375

Leu Tyr Tyr His Gly Lys Glu Gln Val Pro Arg Gly Cys Pro Asp
            380                 385                 390

Gly Leu Cys Pro Leu Asp Met Phe Leu Asn Ala Met Ser Val Tyr
            395                 400                 405

Thr Leu Ser Pro Glu Lys Tyr His Ala Leu Cys Ser Gln Thr Gln
            410                 415                 420

Val Met Glu Val Gly Asn Glu Glu
            425

<210> SEQ ID NO 7
<211> LENGTH: 3106
<212> TYPE: DNA
<213> ORGANISM: Homo sapiens
<220> FEATURE:
<221> NAME/KEY: Unsure
<222> LOCATION: 1683
<223> OTHER INFORMATION: Unknown base

<400> SEQUENCE: 7
aggctcccgc gcgcggctga gtgcggactg gagtgggaac ccgggtcccc            50
gcgcttagag aacacgcgat gaccacgtgg agcctccggc ggaggccggc            100
ccgcacgctg ggactcctgc tgctggtcgt cttgggcttc ctggtgctcc            150
gcaggctgga ctggagcacc ctggtccctc tgcggctccg ccatcgacag            200
ctggggctgc aggccaaggg ctggaacttc atgctggagg attccacctt            250
ctggatcttc gggggctcca tccactattt ccgtgtgccc agggagtact            300
```

```
ggagggaccg cctgctgaag atgaaggcct gtggcttgaa caccctcacc      350
acctatgttc cgtggaacct gcatgagcca gaaagaggca aatttgactt      400
ctctgggaac ctggacctgg aggccttcgt cctgatggcc gcagagatcg      450
ggctgtgggt gattctgcgt ccaggcccct acatctgcag tgagatggac      500
ctcgggggct tgcccagctg gctactccaa gaccctggca tgaggctgag      550
gacaacttac aagggcttca ccgaagcagt ggacctttat tttgaccacc      600
tgatgtccag ggtggtgcca ctccagtaca agcgtggggg acctatcatt      650
gccgtgcagg tggagaatga atatggttcc tataataaag accccgcata      700
catgccctac gtcaagaagg cactggagga ccgtggcatt gtggaactgc      750
tcctgacttc agacaacaag gatgggctga gcaaggggat tgtccaggga      800
gtcttggcca ccatcaactt gcagtcaaca cacgagctgc agctactgac      850
cacctttctc ttcaacgtcc agggactca gcccaagatg gtgatggagt      900
actgacgggg tggtttgac tcgtggggag ccctcacaa tatcttggat      950
tcttctgagg ttttgaaaac cgtgtctgcc attgtggacg ccggctcctc     1000
catcaacctc tacatgttcc acggaggcac caactttggc ttcatgaatg     1050
gagccatgca cttccatgac tacaagtcag atgtcaccag ctatgactat     1100
gatgctgtgc tgacagaagc cggcgattac acggccaagt acatgaagct     1150
tcgagacttc ttcggctcca tctcaggcat ccctctccct cccccaccctg    1200
accttcttcc caagatgccg tatgagccct taacgccagt cttgtacctg     1250
tctctgtggg acgccctcaa gtacctgggg gagccaatca gtctgaaaa     1300
gcccatcaac atgagaaacc tgccagtcaa tgggggaaat ggacagtcct     1350
tcgggtacat tctctatgag accagcatca cctcgtctgg catcctcagt     1400
ggccacgtgc atgatcgggg gcaggtgttt gtgaacacag tatccatagg     1450
attcttggac tacaagacaa cgaagattgc tgtcccctg atccagggtt     1500
acaccgtgct gaggatcttg gtggagaatc gtgggcgagt caactatggg     1550
gagaatattg atgaccagcg caaaggctta attggaaatc tctatctgaa     1600
tgattcaccc ctgaaaaact tcagaatcta tagcctggat atgaagaaga     1650
gcttctttca gaggttcggc ctggacaaat ggngttccct cccagaaaca     1700
cccacattac ctgcttctt cttgggtagc ttgtccatca gctccacgcc     1750
ttgtgacacc tttctgaagc tggagggctg ggagaagggg gttgtattca     1800
tcaatggcca gaaccttgga cgttactgga acattggacc ccagaagacg     1850
ctttacctcc caggtccctg gttgagcagc ggaatcaacc aggtcatcgt     1900
ttttgaggag acgatggcgg gccctgcatt acagttcacg gaaaccccccc    1950
acctgggcag gaaccagtac attaagtgag cggtggcacc ccctcctgct     2000
ggtgccagtg ggagactgcc gcctcctctt gacctgaagc ctggtggctg     2050
ctgccccacc cctcactgca aaagcatctc cttaagtagc aacctcaggg     2100
actgggggct acagtctgcc cctgtctcag ctcaaaaccc taagcctgca     2150
gggaaaggtg ggatggctct gggcctggct tgttgatga tggctttcct      2200
acagccctgc tcttgtgccg aggctgtcgg gctgtctcta gggtgggagc     2250
agctaatcag atcgcccagc ctttggccct cagaaaaagt gctgaaacgt     2300
```

-continued

| | |
|---|---|
| gcccttgcac cggacgtcac agccctgcga gcatctgctg gactcaggcg | 2350 |
| tgctctttgc tggttcctgg gaggcttggc cacatccctc atggccccat | 2400 |
| tttatccccg aaatcctggg tgtgtcacca gtgtagaggg tggggaaggg | 2450 |
| gtgtctcacc tgagctgact tgttcttcc ttcacaacct tctgagcctt | 2500 |
| ctttgggatt ctggaaggaa ctcggcgtga gaaacatgtg acttcccctt | 2550 |
| tcccttccca ctcgctgctt cccacagggt gacaggctgg gctggagaaa | 2600 |
| cagaaatcct caccctgcgt cttcccaagt tagcaggtgt ctctggtgtt | 2650 |
| cagtgaggag gacatgtgag tcctggcaga agccatggcc catgtctgca | 2700 |
| catccaggga ggaggacaga aggcccagct cacatgtgag tcctggcaga | 2750 |
| agccatggcc catgtctgca catccaggga ggaggacaga aggcccagct | 2800 |
| cacatgtgag tcctggcaga agccatggcc catgtctgca catccaggga | 2850 |
| ggaggacaga aggcccagct cacatgtgag tcctggcaga agccatggcc | 2900 |
| catgtctgca catccaggga ggaggacaga aggcccagct cagtggcccc | 2950 |
| cgctccccac cccccacgcc cgaacagcag gggcagagca gccctccttc | 3000 |
| gaagtgtgtc caagtccgca tttgagcctt gttctggggc ccagcccaac | 3050 |
| acctggcttg ggctcactgt cctgagttgc agtaaagcta taaccttgaa | 3100 |
| tcacaa | 3106 |

<210> SEQ ID NO 8
<211> LENGTH: 636
<212> TYPE: PRT
<213> ORGANISM: Homo sapiens
<220> FEATURE:
<221> NAME/KEY: Unsure
<222> LOCATION: 539
<223> OTHER INFORMATION: Unknown amino acid

<400> SEQUENCE: 8

Met Thr Thr Trp Ser Leu Arg Arg Pro Ala Arg Thr Leu Gly
1               5                   10                  15

Leu Leu Leu Leu Val Val Leu Gly Phe Leu Val Leu Arg Arg Leu
                20                  25                  30

Asp Trp Ser Thr Leu Val Pro Leu Arg Leu Arg His Arg Gln Leu
            35                  40                      45

Gly Leu Gln Ala Lys Gly Trp Asn Phe Met Leu Glu Asp Ser Thr
        50                  55                      60

Phe Trp Ile Phe Gly Gly Ser Ile His Tyr Phe Arg Val Pro Arg
65                  70                      75

Glu Tyr Trp Arg Asp Arg Leu Leu Lys Met Lys Ala Cys Gly Leu
                80                  85                      90

Asn Thr Leu Thr Thr Tyr Val Pro Trp Asn Leu His Glu Pro Glu
                95                  100                 105

Arg Gly Lys Phe Asp Phe Ser Gly Asn Leu Asp Leu Glu Ala Phe
            110                 115                     120

Val Leu Met Ala Ala Glu Ile Gly Leu Trp Val Ile Leu Arg Pro
        125                 130                     135

Gly Pro Tyr Ile Cys Ser Glu Met Asp Leu Gly Gly Leu Pro Ser
    140                 145                     150

Trp Leu Leu Gln Asp Pro Gly Met Arg Leu Arg Thr Thr Tyr Lys
                155                 160                 165

Gly Phe Thr Glu Ala Val Asp Leu Tyr Phe Asp His Leu Met Ser

```
                       170                 175                 180
Arg Val Val Pro Leu Gln Tyr Lys Arg Gly Gly Pro Ile Ile Ala
                   185                 190                 195
Val Gln Val Glu Asn Glu Tyr Gly Ser Tyr Asn Lys Asp Pro Ala
                   200                 205                 210
Tyr Met Pro Tyr Val Lys Lys Ala Leu Glu Asp Arg Gly Ile Val
                   215                 220                 225
Glu Leu Leu Leu Thr Ser Asp Asn Lys Asp Gly Leu Ser Lys Gly
                   230                 235                 240
Ile Val Gln Gly Val Leu Ala Thr Ile Asn Leu Gln Ser Thr His
                   245                 250                 255
Glu Leu Gln Leu Leu Thr Thr Phe Leu Phe Asn Val Gln Gly Thr
                   260                 265                 270
Gln Pro Lys Met Val Met Glu Tyr Trp Thr Gly Trp Phe Asp Ser
                   275                 280                 285
Trp Gly Gly Pro His Asn Ile Leu Asp Ser Ser Glu Val Leu Lys
                   290                 295                 300
Thr Val Ser Ala Ile Val Asp Ala Gly Ser Ser Ile Asn Leu Tyr
                   305                 310                 315
Met Phe His Gly Gly Thr Asn Phe Gly Phe Met Asn Gly Ala Met
                   320                 325                 330
His Phe His Asp Tyr Lys Ser Asp Val Thr Ser Tyr Asp Tyr Asp
                   335                 340                 345
Ala Val Leu Thr Glu Ala Gly Asp Tyr Thr Ala Lys Tyr Met Lys
                   350                 355                 360
Leu Arg Asp Phe Phe Gly Ser Ile Ser Gly Ile Pro Leu Pro Pro
                   365                 370                 375
Pro Pro Asp Leu Leu Pro Lys Met Pro Tyr Glu Pro Leu Thr Pro
                   380                 385                 390
Val Leu Tyr Leu Ser Leu Trp Asp Ala Leu Lys Tyr Leu Gly Glu
                   395                 400                 405
Pro Ile Lys Ser Glu Lys Pro Ile Asn Met Glu Asn Leu Pro Val
                   410                 415                 420
Asn Gly Gly Asn Gly Gln Ser Phe Gly Tyr Ile Leu Tyr Glu Thr
                   425                 430                 435
Ser Ile Thr Ser Ser Gly Ile Leu Ser Gly His Val His Asp Arg
                   440                 445                 450
Gly Gln Val Phe Val Asn Thr Val Ser Ile Gly Phe Leu Asp Tyr
                   455                 460                 465
Lys Thr Thr Lys Ile Ala Val Pro Leu Ile Gln Gly Tyr Thr Val
                   470                 475                 480
Leu Arg Ile Leu Val Glu Asn Arg Gly Arg Val Asn Tyr Gly Glu
                   485                 490                 495
Asn Ile Asp Asp Gln Arg Lys Gly Leu Ile Gly Asn Leu Tyr Leu
                   500                 505                 510
Asn Asp Ser Pro Leu Lys Asn Phe Arg Ile Tyr Ser Leu Asp Met
                   515                 520                 525
Lys Lys Ser Phe Phe Gln Arg Phe Gly Leu Asp Lys Trp Xaa Ser
                   530                 535                 540
Leu Pro Glu Thr Pro Thr Leu Pro Ala Phe Phe Leu Gly Ser Leu
                   545                 550                 555
Ser Ile Ser Ser Thr Pro Cys Asp Thr Phe Leu Lys Leu Glu Gly
                   560                 565                 570
```

```
Trp Glu Lys Gly Val Val Phe Ile Asn Gly Gln Asn Leu Gly Arg
            575                 580                 585

Tyr Trp Asn Ile Gly Pro Gln Lys Thr Leu Tyr Leu Pro Gly Pro
            590                 595                 600

Trp Leu Ser Ser Gly Ile Asn Gln Val Ile Val Phe Glu Glu Thr
            605                 610                 615

Met Ala Gly Pro Ala Leu Gln Phe Thr Glu Thr Pro His Leu Gly
            620                 625                 630

Arg Asn Gln Tyr Ile Lys
            635

<210> SEQ ID NO 9
<211> LENGTH: 1295
<212> TYPE: DNA
<213> ORGANISM: Homo sapiens

<400> SEQUENCE: 9
cccagaagtt caagggcccc cggcctcctg cgctcctgcc gccgggaccc         50
tcgacctcct cagagcagcc ggctgccgcc ccgggaagat ggcgaggagg        100
agccgccacc gctcctcct gctgctgctg cgctacctgg tggtcgccct         150
gggctatcat aaggcctatg gttttctgc cccaaaagac caacaagtag         200
tcacagcagt agagtaccaa gaggctattt tagcctgcaa aaccccaaag        250
aagactgttt cctccagatt agagtggaag aaactgggtc ggagtgtctc        300
ctttgtctac tatcaacaga ctcttcaagg tgattttaaa aatcgagctg        350
agatgataga tttcaatatc cggatcaaaa atgtgacaag aagtgatgcg        400
gggaaatatc gttgtgaagt tagtgcccca tctgagcaag gccaaaacct        450
ggaagaggat acagtcactc tggaagtatt agtggctcca gcagttccat        500
catgtgaagt accctcttct gctctgagtg gaactgtggt agagctacga        550
tgtcaagaca agaagggaaa tccagctcct gaatacacat ggtttaagga        600
tggcatccgt ttgctagaaa atcccagact tggctcccaa gcaccaaca         650 gctcatacac aatgaataca aaaactggaa ctctgcaatt taatactgtt        700
tccaaactgg acactggaga atattcctgt gaagcccgca attctgttgg        750
atatcgcagg tgtcctggga acgaatgca agtagatgat ctcaacataa         800
gtggcatcat agcagccgta gtagttgtgg ccttagtgat ttccgtttgt        850
ggccttggtg tatgctatgc tcagaggaaa ggctactttt caaaagaaac        900
ctccttccag aagagtaatt cttcatctaa agccacgaca atgagtgaaa        950
atgtgcagtg gctcacgcct gtaatcccag cactttggaa ggccgcggcg       1000
ggcggatcac gaggtcagga gttctagacc agtctggcca atatggtgaa       1050
accccatctc tactaaaata caaaaattag ctgggcatgg tggcatgtgc       1100
ctgcagttcc agctgcttgg gagacaggag aatcacttga acccgggagg       1150
cggaggttgc agtgagctga gatcacgcca ctgcagtcca gcctgggtaa       1200
cagagcaaga ttccatctca aaaaataaaa taaataaata aataaatact       1250 ggttttttacc tgtagaattc ttacaataaa tatagcttga  tattc          1295

<210> SEQ ID NO 10
<211> LENGTH: 312
<212> TYPE: PRT
<213> ORGANISM: Homo sapiens
```

<400> SEQUENCE: 10

| | | | | | | | | | | | | | | | |
|---|---|---|---|---|---|---|---|---|---|---|---|---|---|---|---|
| Met | Ala | Arg | Arg | Ser | Arg | His | Arg | Leu | Leu | Leu | Leu | Leu | Leu | Arg | |
| 1 | | | | 5 | | | | | 10 | | | | | 15 | |

Tyr Leu Val Val Ala Leu Gly Tyr His Lys Ala Tyr Gly Phe Ser
           20                 25                30

Ala Pro Lys Asp Gln Gln Val Val Thr Ala Val Glu Tyr Gln Glu
           35                 40                45

Ala Ile Leu Ala Cys Lys Thr Pro Lys Thr Val Ser Ser Arg
           50                 55                60

Leu Glu Trp Lys Lys Leu Gly Arg Ser Val Ser Phe Val Tyr Tyr
           65                 70                75

Gln Gln Thr Leu Gln Gly Asp Phe Lys Asn Arg Ala Glu Met Ile
           80                 85                90

Asp Phe Asn Ile Arg Ile Lys Asn Val Thr Arg Ser Asp Ala Gly
           95                100              105

Lys Tyr Arg Cys Glu Val Ser Ala Pro Ser Glu Gln Gly Gln Asn
          110              115              120

Leu Glu Glu Asp Thr Val Thr Leu Glu Val Leu Val Ala Pro Ala
          125              130              135

Val Pro Ser Cys Glu Val Pro Ser Ser Ala Leu Ser Gly Thr Val
          140              145              150

Val Glu Leu Arg Cys Gln Asp Lys Glu Gly Asn Pro Ala Pro Glu
          155              160              165

Tyr Thr Trp Phe Lys Asp Gly Ile Arg Leu Leu Glu Asn Pro Arg
          170              175              180

Leu Gly Ser Gln Ser Thr Asn Ser Ser Tyr Thr Met Asn Thr Lys
          185              190              195

Thr Gly Thr Leu Gln Phe Asn Thr Val Ser Lys Leu Asp Thr Gly
          200              205              210

Glu Tyr Ser Cys Glu Ala Arg Asn Ser Val Gly Tyr Arg Arg Cys
          215              220              225

Pro Gly Lys Arg Met Gln Val Asp Asp Leu Asn Ile Ser Gly Ile
          230              235              240

Ile Ala Ala Val Val Val Val Ala Leu Val Ile Ser Val Cys Gly
          245              250              255

Leu Gly Val Cys Tyr Ala Gln Arg Lys Gly Tyr Phe Ser Lys Glu
          260              265              270

Thr Ser Phe Gln Lys Ser Asn Ser Ser Ser Lys Ala Thr Thr Met
          275              280              285

Ser Glu Asn Val Gln Trp Leu Thr Pro Val Ile Pro Ala Leu Trp
          290              295              300

Lys Ala Ala Ala Gly Gly Ser Arg Gly Gln Glu Phe
          305              310

<210> SEQ ID NO 11
<211> LENGTH: 1813
<212> TYPE: DNA
<213> ORGANISM: Homo sapiens

<400> SEQUENCE: 11

| | | |
|---|---|---|
| ggagccgccc tgggtgtcag cggctcggct cccgcgcacg ctccggccgt | 50 |
| cgcgcagcct cggcacctgc aggtccgtgc gtccgcgggc tggcgcccct | 100 |
| gactccgtcc cggccaggga gggccatgat ttccctcccg gggcccctgg | 150 |

```
tgaccaactt gctgcggttt ttgttcctgg ggctgagtgc cctcgcgccc      200
ccctcgcggg cccagctgca actgcacttg cccgccaacc ggttgcaggc      250
ggtggaggga ggggaagtgg tgcttccagc gtggtacacc ttgcacgggg      300
aggtgtcttc atcccagcca tgggaggtgc cctttgtgat gtggttcttc      350
aaacagaaag aaaaggagga tcaggtgttg tcctacatca atggggtcac      400
aacaagcaaa cctggagtat ccttggtcta ctccatgccc tcccggaacc      450
tgtccctgcg gctggagggt ctccaggaga aagactctgg cccctacagc      500
tgctccgtga atgtgcaaga caaacaaggc aaatctaggg gccacagcat      550 caaaaccta gaactcaatg tactggttcc tccagctcct ccatcctgcc       600
gtctccaggg tgtgccccat gtgggggcaa acgtgaccct gagctgccag      650
tctccaagga gtaagcccgc tgtccaatac cagtgggatc ggcagcttcc      700
atccttccag actttctttg caccagcatt agatgtcatc cgtgggtctt      750
taagcctcac caacctttcg tcttccatgg ctggagtcta tgtctgcaag      800
gcccacaatg aggtgggcac tgcccaatgt aatgtgacgc tggaagtgag      850
cacagggcct ggagctgcag tggttgctgg agctgttgtg ggtaccctgg      900
ttggactggg gttgctggct gggctggtcc tcttgtacca ccgccggggc      950
aaggccctgg aggagccagc caatgatatc aaggaggatg ccattgctcc     1000
ccggaccctg ccctggccca agagctcaga cacaatctcc aagaatggga     1050 cccttcctc tgtcacctcc gcacgagccc tccggccacc ccatggccct      1100
cccaggcctg gtgcattgac ccccacgccc agtctctcca gccaggccct     1150
gccctcacca agactgccca cgacagatgg ggcccaccct caaccaatat     1200 ccccatccc tggtggggtt tcttcctctg gcttgagccg catgggtgct      1250
gtgcctgtga tggtgcctgc ccagagtcaa gctggctctc tggtatgatg     1300
accccaccac tcattggcta aaggatttgg ggtctctcct tcctataagg     1350
gtcacctcta gcacagaggc ctgagtcatg ggaaagagtc acactcctga     1400
cccttagtac tctgcccca cctctcttta ctgtgggaaa accatctcag       1450
taagacctaa gtgtccagga gacagaagga gaagaggaag tggatctgga     1500
attgggagga gcctccaccc acccctgact cctccttatg aagccagctg     1550
ctgaaattag ctactcacca agagtgaggg gcagagactt ccagtcactg     1600
agtctcccag gccccttga tctgtacccc accctatct aacaccaccc        1650 ttggctccca ctccagctcc ctgtattgat ataacctgtc aggctggctt     1700
ggttaggttt tactggggca gaggataggg aatctcttat taaaactaac     1750
atgaaatatg tgttgttttc atttgcaaat ttaaataaag atacataatg     1800
tttgtatgaa aaa                                              1813
```

<210> SEQ ID NO 12
<211> LENGTH: 390
<212> TYPE: PRT
<213> ORGANISM: Homo sapiens

<400> SEQUENCE: 12

Met Ile Ser Leu Pro Gly Pro Leu Val Thr Asn Leu Leu Arg Phe
1               5                   10                  15

Leu Phe Leu Gly Leu Ser Ala Leu Ala Pro Pro Ser Arg Ala Gln

```
              20                  25                  30
Leu Gln Leu His Leu Pro Ala Asn Arg Leu Gln Ala Val Glu Gly
              35                  40                  45
Gly Glu Val Val Leu Pro Ala Trp Tyr Thr Leu His Gly Glu Val
              50                  55                  60
Ser Ser Ser Gln Pro Trp Glu Val Pro Phe Val Met Trp Phe Phe
              65                  70                  75
Lys Gln Lys Glu Lys Glu Asp Gln Val Leu Ser Tyr Ile Asn Gly
              80                  85                  90
Val Thr Thr Ser Lys Pro Gly Val Ser Leu Val Tyr Ser Met Pro
              95                 100                 105
Ser Arg Asn Leu Ser Leu Arg Leu Glu Gly Leu Gln Glu Lys Asp
             110                 115                 120
Ser Gly Pro Tyr Ser Cys Ser Val Asn Val Gln Asp Lys Gln Gly
             125                 130                 135
Lys Ser Arg Gly His Ser Ile Lys Thr Leu Glu Leu Asn Val Leu
             140                 145                 150
Val Pro Pro Ala Pro Pro Ser Cys Arg Leu Gln Gly Val Pro His
             155                 160                 165
Val Gly Ala Asn Val Thr Leu Ser Cys Gln Ser Pro Arg Ser Lys
             170                 175                 180
Pro Ala Val Gln Tyr Gln Trp Asp Arg Gln Leu Pro Ser Phe Gln
             185                 190                 195
Thr Phe Phe Ala Pro Ala Leu Asp Val Ile Arg Gly Ser Leu Ser
             200                 205                 210
Leu Thr Asn Leu Ser Ser Ser Met Ala Gly Val Tyr Val Cys Lys
             215                 220                 225
Ala His Asn Glu Val Gly Thr Ala Gln Cys Asn Val Thr Leu Glu
             230                 235                 240
Val Ser Thr Gly Pro Gly Ala Ala Val Ala Gly Ala Val Val
             245                 250                 255
Gly Thr Leu Val Gly Leu Gly Leu Ala Gly Leu Val Leu Leu
             260                 265                 270
Tyr His Arg Arg Gly Lys Ala Leu Glu Glu Pro Ala Asn Asp Ile
             275                 280                 285
Lys Glu Asp Ala Ile Ala Pro Arg Thr Leu Pro Trp Pro Lys Ser
             290                 295                 300
Ser Asp Thr Ile Ser Lys Asn Gly Thr Leu Ser Ser Val Thr Ser
             305                 310                 315
Ala Arg Ala Leu Arg Pro Pro His Gly Pro Pro Arg Pro Gly Ala
             320                 325                 330
Leu Thr Pro Thr Pro Ser Leu Ser Ser Gln Ala Leu Pro Ser Pro
             335                 340                 345
Arg Leu Pro Thr Thr Asp Gly Ala His Pro Gln Pro Ile Ser Pro
             350                 355                 360
Ile Pro Gly Gly Val Ser Ser Ser Gly Leu Ser Arg Met Gly Ala
             365                 370                 375
Val Pro Val Met Val Pro Ala Gln Ser Gln Ala Gly Ser Leu Val
             380                 385                 390

<210> SEQ ID NO 13
<211> LENGTH: 1685
<212> TYPE: DNA
<213> ORGANISM: Homo sapiens
```

<400> SEQUENCE: 13

```
cccacgcgtc cgcacctcgg ccccgggctc cgaagcggct cgggggcgcc        50
ctttcggtca acatcgtagt ccacccctc cccatcccca gccccgggg         100
attcaggctc gccagcgccc agccagggag ccggccggga agcgcgatgg       150
gggccccagc cgcctcgctc ctgctcctgc tcctgctgtt cgcctgctgc       200
tgggcgcccg gcggggccaa cctctcccag gacgacagcc agccctggac       250
atctgatgaa acagtggtgg ctggtggcac cgtggtgctc aagtgccaag       300
tgaaagatca cgaggactca tccctgcaat ggtctaaccc tgctcagcag       350
actctctact ttggggagaa gagagcctt cgagataatc gaattcagct        400
ggttacctct acgccccacg agctcagcat cagcatcagc aatgtggccc       450
tggcagacga gggcgagtac acctgctcaa tcttcactat gcctgtgcga       500
actgccaagt ccctcgtcac tgtgctagga attccacaga agcccatcat       550
cactggttat aaatcttcat tacgggaaaa agacacagcc accctaaact       600
gtcagtcttc tgggagcaag cctgcagccc ggctcacctg gagaaagggt       650
gaccaagaac tccacggaga accaacccgc atacaggaag atcccaatgg       700
taaaaccttc actgtcagca gctcggtgac attccaggtt acccgggagg       750
atgatggggc gagcatcgtg tgctctgtga accatgaatc tctaaaggga       800
gctgacagat ccacctctca acgcattgaa gttttataca caccaactgc       850
gatgattagg ccagaccctc cccatcctcg tgagggccag aagctgttgc       900
tacactgtga gggtcgcggc aatccagtcc cccagcagta cctatgggag       950
aaggagggca gtgtgccacc cctgaagatg acccaggaga gtgccctgat      1000
cttccctttc ctcaacaaga gtgacagtgg cacctacggc tgcacagcca      1050
ccagcaacat gggcagctac aaggcctact acacccctcaa tgttaatgac    1100
cccagtccgg tgcctcctc ctccagcacc taccacgcca tcatcggtgg      1150
gatcgtggct ttcattgtct tcctgctgct catcatgctc atcttccttg      1200
gccactactt gatccggcac aaaggaacct acctgacaca tgaggcaaaa      1250
ggctccgacg atgctccaga cgcggacacg gccatcatca atgcagaagg      1300
cgggcagtca ggaggggacg acaagaagga atatttcatc tagaggcgcc      1350
tgcccacttc ctgcgccccc caggggccct gtggggactg ctggggccgt     1400
caccaacccg gacttgtaca gagcaaccgc agggccgccc ctcccgcttg      1450
ctccccagcc cacccacccc cctgtacaga atgtctgctt tgggtgcggt      1500
tttgtactcg gtttggaatg gggagggag agggcggggg gaggggaggg       1550
ttgccctcag ccctttccgt ggcttctctg catttgggtt attattattt      1600
ttgtaacaat cccaaatcaa atctgtctcc aggctggaga ggcaggagcc      1650
ctggggtgag aaaagcaaaa aacaaacaaa aaaca                     1685
```

<210> SEQ ID NO 14
<211> LENGTH: 398
<212> TYPE: PRT
<213> ORGANISM: Homo sapiens

<400> SEQUENCE: 14

```
Met Gly Ala Pro Ala Ala Ser Leu Leu Leu Leu Leu Leu Phe
 1               5                  10                  15
```

-continued

Ala Cys Cys Trp Ala Pro Gly Gly Ala Asn Leu Ser Gln Asp Asp
                20                  25                  30

Ser Gln Pro Trp Thr Ser Asp Glu Thr Val Val Ala Gly Gly Thr
                35                  40                  45

Val Val Leu Lys Cys Gln Val Lys Asp His Glu Asp Ser Ser Leu
                50                  55                  60

Gln Trp Ser Asn Pro Ala Gln Gln Thr Leu Tyr Phe Gly Glu Lys
                65                  70                  75

Arg Ala Leu Arg Asp Asn Arg Ile Gln Leu Val Thr Ser Thr Pro
                80                  85                  90

His Glu Leu Ser Ile Ser Ile Ser Asn Val Ala Leu Ala Asp Glu
                95                 100                 105

Gly Glu Tyr Thr Cys Ser Ile Phe Thr Met Pro Val Arg Thr Ala
               110                 115                 120

Lys Ser Leu Val Thr Val Leu Gly Ile Pro Gln Lys Pro Ile Ile
               125                 130                 135

Thr Gly Tyr Lys Ser Ser Leu Arg Glu Lys Asp Thr Ala Thr Leu
               140                 145                 150

Asn Cys Gln Ser Ser Gly Ser Lys Pro Ala Ala Arg Leu Thr Trp
               155                 160                 165

Arg Lys Gly Asp Gln Glu Leu His Gly Glu Pro Thr Arg Ile Gln
               170                 175                 180

Glu Asp Pro Asn Gly Lys Thr Phe Thr Val Ser Ser Ser Val Thr
               185                 190                 195

Phe Gln Val Thr Arg Glu Asp Asp Gly Ala Ser Ile Val Cys Ser
               200                 205                 210

Val Asn His Glu Ser Leu Lys Gly Ala Asp Arg Ser Thr Ser Gln
               215                 220                 225

Arg Ile Glu Val Leu Tyr Thr Pro Thr Ala Met Ile Arg Pro Asp
               230                 235                 240

Pro Pro His Pro Arg Glu Gly Gln Lys Leu Leu Leu His Cys Glu
               245                 250                 255

Gly Arg Gly Asn Pro Val Pro Gln Gln Tyr Leu Trp Glu Lys Glu
               260                 265                 270

Gly Ser Val Pro Pro Leu Lys Met Thr Gln Glu Ser Ala Leu Ile
               275                 280                 285

Phe Pro Phe Leu Asn Lys Ser Asp Ser Gly Thr Tyr Gly Cys Thr
               290                 295                 300

Ala Thr Ser Asn Met Gly Ser Tyr Lys Ala Tyr Tyr Thr Leu Asn
               305                 310                 315

Val Asn Asp Pro Ser Pro Val Pro Ser Ser Ser Thr Tyr His
               320                 325                 330

Ala Ile Ile Gly Gly Ile Val Ala Phe Ile Val Phe Leu Leu Leu
               335                 340                 345

Ile Met Leu Ile Phe Leu Gly His Tyr Leu Ile Arg His Lys Gly
               350                 355                 360

Thr Tyr Leu Thr His Glu Ala Lys Gly Ser Asp Asp Ala Pro Asp
               365                 370                 375

Ala Asp Thr Ala Ile Ile Asn Ala Glu Gly Gly Gln Ser Gly Gly
               380                 385                 390

Asp Asp Lys Lys Glu Tyr Phe Ile
               395

<210> SEQ ID NO 15
<211> LENGTH: 2026
<212> TYPE: DNA
<213> ORGANISM: Homo sapiens

<400> SEQUENCE: 15

| | | | | | |
|---|---|---|---|---|---|
| cggacgcgtg | ggattcagca | gtggcctgtg | gctgccagag | cagctcctca | 50 |
| ggggaaacta | agcgtcgagt | cagacggcac | cataatcgcc | tttaaaagtg | 100 |
| cctccgccct | gccggccgcg | tatccccgg | ctacctgggc | cgccccgcgg | 150 |
| cggtgcgcgc | gtgagaggga | gcgcgcgggc | agccgagcgc | cggtgtgagc | 200 |
| cagcgctgct | gccagtgtga | gcggcggtgt | gagcgcggtg | ggtgcggagg | 250 |
| ggcgtgtgtg | ccggcgcgcg | cgccgtgggg | tgcaaacccc | gagcgtctac | 300 |
| gctgccatga | ggggcgcgaa | cgcctgggcg | ccactctgcc | tgctgctggc | 350 |
| tgccgccacc | cagctctcgc | ggcagcagtc | cccagagaga | cctgttttca | 400 |
| catgtggtgg | cattcttact | ggagagtctg | gatttattgg | cagtgaaggt | 450 |
| tttcctggag | tgtaccctcc | aaatagcaaa | tgtacttgga | aaatcacagt | 500 |
| tcccgaagga | aaagtagtcg | ttctcaattt | ccgattcata | gacctcgaga | 550 |
| gtgacaacct | gtgccgctat | gactttgtgg | atgtgtacaa | tggccatgcc | 600 |
| aatggccagc | gcattggccg | cttctgtggc | actttccggc | ctggagccct | 650 |
| tgtgtccagt | ggcaacaaga | tgatggtgca | gatgattttct | gatgccaaca | 700 |
| cagctggcaa | tggcttcatg | gccatgttct | ccgctgctga | accaaacgaa | 750 |
| agaggggatc | agtattgtgg | aggactcctt | gacagacctt | ccggctcttt | 800 |
| taaaaccccc | aactggccag | accgggatta | ccctgcagga | gtcacttgtg | 850 |
| tgtggcacat | tgtagcccca | aagaatcagc | ttatagaatt | aaagtttgag | 900 |
| aagtttgatg | tggagcgaga | taactactgc | cgatatgatt | atgtggctgt | 950 |
| gtttaatggc | ggggaagtca | acgatgctag | aagaattgga | aagtattgtg | 1000 |
| gtgatagtcc | acctgcgcca | attgtgtctg | agagaaatga | acttcttatt | 1050 |
| cagttttttat | cagacttaag | tttaactgca | gatgggttta | ttggtcacta | 1100 |
| catattcagg | ccaaaaaaac | tgcctacaac | tacagaacag | cctgtcacca | 1150 |
| ccacattccc | tgtaaccacg | ggtttaaaac | ccaccgtggc | cttgtgtcaa | 1200 |
| caaaagtgta | gacggacggg | gactctggag | ggcaattatt | gttcaagtga | 1250 |
| ctttgtatta | gccggcactg | ttatcacaac | catcactcgc | gatgggagtt | 1300 |
| tgcacgccac | agtctcgatc | atcaacatct | acaaagaggg | aaatttggcg | 1350 |
| attcagcagg | cgggcaagaa | catgagtgcc | aggctgactg | tcgtctgcaa | 1400 |
| gcagtgccct | ctcctcagaa | gaggtctaaa | ttacattatt | atgggccaag | 1450 |
| taggtgaaga | tgggcgaggc | aaaatcatgc | caaacagctt | tatcatgatg | 1500 |
| ttcaagacca | agaatcagaa | gctcctggat | gccttaaaaa | ataagcaatg | 1550 |
| ttaacagtga | actgtgtcca | tttaagctgt | attctgccat | tgcctttgaa | 1600 |
| agatctatgt | tctctcagta | gaaaaaaaaa | tacttataaa | attacatatt | 1650 |
| ctgaaagagg | attccgaaag | atgggactgg | ttgactcttc | acatgatgga | 1700 |
| ggtatgaggc | ctccgagata | gctgagggaa | gttcttttgcc | tgctgtcaga | 1750 |
| ggagcagcta | tctgattgga | aacctgccga | cttagtgcgg | tgataggaag | 1800 |
| ctaaaagtgt | caagcgttga | cagcttggaa | gcgtttattt | atacatctct | 1850 |

```
gtaaaaggat attttagaat tgagttgtgt gaagatgtca aaaaaagatt          1900
ttagaagtgc aatatttata gtgttatttg tttcaccttc aagcctttgc          1950
cctgaggtgt tacaatcttg tcttgcgttt tctaaatcaa tgcttaataa          2000 aatatttta aaggaaaaaa aaaaaa                                    2026

<210> SEQ ID NO 16
<211> LENGTH: 415
<212> TYPE: PRT
<213> ORGANISM: Homo sapiens

<400> SEQUENCE: 16

Met Arg Gly Ala Asn Ala Trp Ala Pro Leu Cys Leu Leu Ala
  1               5                  10                  15

Ala Ala Thr Gln Leu Ser Arg Gln Gln Ser Pro Glu Arg Pro Val
             20                  25                  30

Phe Thr Cys Gly Gly Ile Leu Thr Gly Glu Ser Gly Phe Ile Gly
             35                  40                  45

Ser Glu Gly Phe Pro Gly Val Tyr Pro Asn Ser Lys Cys Thr
             50                  55                  60

Trp Lys Ile Thr Val Pro Glu Gly Lys Val Val Leu Asn Phe
             65                  70                  75

Arg Phe Ile Asp Leu Glu Ser Asp Asn Leu Cys Arg Tyr Asp Phe
             80                  85                  90

Val Asp Val Tyr Asn Gly His Ala Asn Gly Gln Arg Ile Gly Arg
             95                 100                 105

Phe Cys Gly Thr Phe Arg Pro Gly Ala Leu Val Ser Ser Gly Asn
            110                 115                 120

Lys Met Met Val Gln Met Ile Ser Asp Ala Asn Thr Ala Gly Asn
            125                 130                 135

Gly Phe Met Ala Met Phe Ser Ala Ala Glu Pro Asn Glu Arg Gly
            140                 145                 150

Asp Gln Tyr Cys Gly Gly Leu Leu Asp Arg Pro Ser Gly Ser Phe
            155                 160                 165

Lys Thr Pro Asn Trp Pro Asp Arg Asp Tyr Pro Ala Gly Val Thr
            170                 175                 180

Cys Val Trp His Ile Val Ala Pro Lys Asn Gln Leu Ile Glu Leu
            185                 190                 195

Lys Phe Glu Lys Phe Asp Val Glu Arg Asp Asn Tyr Cys Arg Tyr
            200                 205                 210

Asp Tyr Val Ala Val Phe Asn Gly Gly Glu Val Asn Asp Ala Arg
            215                 220                 225

Arg Ile Gly Lys Tyr Cys Gly Asp Ser Pro Pro Ala Pro Ile Val
            230                 235                 240

Ser Glu Arg Asn Glu Leu Leu Ile Gln Phe Leu Ser Asp Leu Ser
            245                 250                 255

Leu Thr Ala Asp Gly Phe Ile Gly His Tyr Ile Phe Arg Pro Lys
            260                 265                 270

Lys Leu Pro Thr Thr Thr Glu Gln Pro Val Thr Thr Phe Pro
            275                 280                 285

Val Thr Thr Gly Leu Lys Pro Thr Val Ala Leu Cys Gln Gln Lys
            290                 295                 300

Cys Arg Arg Thr Gly Thr Leu Glu Gly Asn Tyr Cys Ser Ser Asp
            305                 310                 315
```

-continued

```
Phe Val Leu Ala Gly Thr Val Ile Thr Thr Ile Thr Arg Asp Gly
            320                 325                 330
Ser Leu His Ala Thr Val Ser Ile Ile Asn Ile Tyr Lys Glu Gly
            335                 340                 345
Asn Leu Ala Ile Gln Gln Ala Gly Lys Asn Met Ser Ala Arg Leu
            350                 355                 360
Thr Val Val Cys Lys Gln Cys Pro Leu Leu Arg Arg Gly Leu Asn
            365                 370                 375
Tyr Ile Ile Met Gly Gln Val Gly Glu Asp Gly Arg Gly Lys Ile
            380                 385                 390
Met Pro Asn Ser Phe Ile Met Met Phe Lys Thr Lys Asn Gln Lys
            395                 400                 405
Leu Leu Asp Ala Leu Lys Asn Lys Gln Cys
            410                 415

<210> SEQ ID NO 17
<211> LENGTH: 1875
<212> TYPE: DNA
<213> ORGANISM: Homo sapiens

<400> SEQUENCE: 17
gacggctggc caccatgcac ggctcctgca gtttcctgat gcttctgctg          50
ccgctactgc tactgctggt ggccaccaca ggccccgttg agccctcac           100 agatgaggag aaacgtttga tggtggagct gcacaacctc taccgggccc          150
aggtatcccc gacggcctca gacatgctgc acatgagatg ggacgaggag          200
ctggccgcct tcgccaaggc ctacgcacgg cagtgcgtgt ggggccacaa          250
caaggagcgc gggcgccgcg cgagaatctg ttcgccatc acagacgagg           300 gcatggacgt gccgctggcc atggaggagt ggcaccacga gcgtgagcac          350
tacaacctca cgccgccac ctgcagccca ggccagatgt gcggccacta           400
cacgcaggtg gtatgggcca agacagagag gatcggctgt ggttcccact          450
tctgtgagaa gctccagggt gttgaggaga ccaacatcga attactggtg          500
tgcaactatg agcctccggg gaacgtgaag gggaaacggc cctaccagga          550
ggggactccg tgctcccaat gtccctctgg ctaccactgc aagaactccc          600
tctgtgaacc catcggaagc ccggaagatg ctcaggattt gccttacctg          650
gtaactgagg ccccatcctt ccgggcgact gaagcatcag actctaggaa          700
aatgggtact ccttcttccc tagcaacggg gattccggct ttcttggtaa          750
cagaggtctc aggctccctg gcaaccaagg ctctgcctgc tgtggaaacc          800
caggccccaa cttccttagc aacgaaagac ccgccctcca tggcaacaga          850
ggctccacct gcgtaacaa ctgaggtccc ttccattttg gcagctcaca           900
gcctgccctc cttggatgag gagccagtta ccttccccaa atcgacccat          950
gttcctatcc caaaatcagc agacaaagtg acagacaaaa caaaagtgcc          1000
ctctaggagc ccagagaact ctctggaccc caagatgtcc ctgacagggg          1050
caagggaact cctaccccat gcccaggagg aggctgaggc tgaggctgag          1100
ttgcctcctt ccagtgaggt cttggcctca gttttccag cccaggacaa           1150 gccaggtgag ctgcaggcca cactggacca cacggggcac acctcctcca          1200
agtccctgcc caatttcccc aatacctctg ccaccgctaa tgccacgggt          1250
gggcgtgccc tggctctgca gtcgtccttg ccaggtgcag agggccctga          1300
```

```
caagcctagc gttgtgtcag ggctgaactc gggccctggt catgtgtggg        1350
gccctctcct gggactactg ctcctgcctc ctctggtgtt ggctggaatc        1400
ttctgaatgg gataccactc aaagggtgaa gaggtcagct gtcctcctgt        1450
catcttcccc accctgtccc cagcccctaa acaagatact tcttggttaa        1500
ggccctccgg aagggaaagg ctacggggca tgtgcctcat cacaccatcc        1550
atcctggagg cacaaggcct ggctggctgc gagctcagga ggccgcctga        1600
ggactgcaca ccgggcccac acctctcctg cccctccctc ctgagtcctg        1650
ggggtgggag gatttgaggg agctcactgc ctacctggcc tggggctgtc        1700
tgcccacaca gcatgtgcgc tctccctgag tgcctgtgta gctggggatg        1750
gggattccta ggggcagatg aaggacaagc cccactggag tggggttctt        1800 tgagtgggggg aggcagggac gagggaagga aagtaactcc tgactctcca        1850
ataaaaacct gtccaacctg tgaaa                                   1875
```

<210> SEQ ID NO 18
<211> LENGTH: 463
<212> TYPE: PRT
<213> ORGANISM: Homo sapiens

<400> SEQUENCE: 18

```
Met His Gly Ser Cys Ser Phe Leu Met Leu Leu Pro Leu Leu
  1               5                  10                  15

Leu Leu Leu Val Ala Thr Thr Gly Pro Val Gly Ala Leu Thr Asp
             20                  25                  30

Glu Glu Lys Arg Leu Met Val Glu Leu His Asn Leu Tyr Arg Ala
             35                  40                  45

Gln Val Ser Pro Thr Ala Ser Asp Met Leu His Met Arg Trp Asp
             50                  55                  60

Glu Glu Leu Ala Ala Phe Ala Lys Ala Tyr Ala Arg Gln Cys Val
             65                  70                  75

Trp Gly His Asn Lys Glu Arg Gly Arg Arg Gly Glu Asn Leu Phe
             80                  85                  90

Ala Ile Thr Asp Glu Gly Met Asp Val Pro Leu Ala Met Glu Glu
             95                 100                 105

Trp His His Glu Arg Glu His Tyr Asn Leu Ser Ala Ala Thr Cys
            110                 115                 120

Ser Pro Gly Gln Met Cys Gly His Tyr Thr Gln Val Val Trp Ala
            125                 130                 135

Lys Thr Glu Arg Ile Gly Cys Gly Ser His Phe Cys Glu Lys Leu
            140                 145                 150

Gln Gly Val Glu Glu Thr Asn Ile Glu Leu Leu Val Cys Asn Tyr
            155                 160                 165

Glu Pro Pro Gly Asn Val Lys Gly Lys Arg Pro Tyr Gln Glu Gly
            170                 175                 180

Thr Pro Cys Ser Gln Cys Pro Ser Gly Tyr His Cys Lys Asn Ser
            185                 190                 195

Leu Cys Glu Pro Ile Gly Ser Pro Glu Asp Ala Gln Asp Leu Pro
            200                 205                 210

Tyr Leu Val Thr Glu Ala Pro Ser Phe Arg Ala Thr Glu Ala Ser
            215                 220                 225

Asp Ser Arg Lys Met Gly Thr Pro Ser Ser Leu Ala Thr Gly Ile
            230                 235                 240
```

```
Pro Ala Phe Leu Val Thr Glu Val Ser Gly Ser Leu Ala Thr Lys
            245                 250                 255
Ala Leu Pro Ala Val Glu Thr Gln Ala Pro Thr Ser Leu Ala Thr
            260                 265                 270
Lys Asp Pro Pro Ser Met Ala Thr Glu Ala Pro Pro Cys Val Thr
            275                 280                 285
Thr Glu Val Pro Ser Ile Leu Ala Ala His Ser Leu Pro Ser Leu
            290                 295                 300
Asp Glu Glu Pro Val Thr Phe Pro Lys Ser Thr His Val Pro Ile
            305                 310                 315
Pro Lys Ser Ala Asp Lys Val Thr Asp Lys Thr Lys Val Pro Ser
            320                 325                 330
Arg Ser Pro Glu Asn Ser Leu Asp Pro Lys Met Ser Leu Thr Gly
            335                 340                 345
Ala Arg Glu Leu Leu Pro His Ala Gln Glu Glu Ala Glu Ala Glu
            350                 355                 360
Ala Glu Leu Pro Pro Ser Ser Glu Val Leu Ala Ser Val Phe Pro
            365                 370                 375
Ala Gln Asp Lys Pro Gly Glu Leu Gln Ala Thr Leu Asp His Thr
            380                 385                 390
Gly His Thr Ser Ser Lys Ser Leu Pro Asn Phe Pro Asn Thr Ser
            395                 400                 405
Ala Thr Ala Asn Ala Thr Gly Gly Arg Ala Leu Ala Leu Gln Ser
            410                 415                 420
Ser Leu Pro Gly Ala Glu Gly Pro Asp Lys Pro Ser Val Val Ser
            425                 430                 435
Gly Leu Asn Ser Gly Pro Gly His Val Trp Gly Pro Leu Leu Gly
            440                 445                 450
Leu Leu Leu Leu Pro Pro Leu Val Leu Ala Gly Ile Phe
            455                 460

<210> SEQ ID NO 19
<211> LENGTH: 1377
<212> TYPE: DNA
<213> ORGANISM: Homo sapiens

<400> SEQUENCE: 19
gactagttct cttggagtct gggaggagga aagcggagcc ggcagggagc        50
gaaccaggac tggggtgacg gcagggcagg gggcgcctgg ccggggagaa       100
gcgcgggggc tggagcacca ccaactggag ggtccggagt agcgagcgcc       150
ccgaaggagg ccatcgggga gccgggaggg gggactgcga gaggaccccg       200
gcgtccgggc tcccggtgcc agcgctatga ggccactcct cgtcctgctg       250
ctcctgggcc tggcggccgg ctcgccccca ctggacgaca caagatccc        300 cagcctctgc ccggggcacc ccggccttcc aggcacgccg gccaccatg        350 gcagccaggg cttgccgggc gcgatggcc gcgacgccg cgacggcgcg         400 cccgggggctc cgggagagaa aggcgagggc gggaggccgg gactgccggg      450
acctcgaggg gaccccggc gcgaggaga ggcgggaccc gcggggccca         500
ccgggcctgc cggggagtgc tcggtgcctc cgcgatccgc cttcagcgcc       550
aagcgctccg agagcggggt gcctccgccg tctgacgcac ccttgccctt       600
cgaccgcgtg ctggtgaacg agcagggaca ttacgacgcc gtcaccggca       650
```

```
agttcacctg ccaggtgcct ggggtctact acttcgccgt ccatgccacc      700
gtctaccggg ccagcctgca gtttgatctg gtgaagaatg gcgaatccat      750
tgcctctttc ttccagtttt tcggggggtg gcccaagcca gcctcgctct      800
cgggggggc catggtgagg ctggagcctg aggaccaagt gtgggtgcag       850
gtgggtgtgg gtgactacat tggcatctat gccagcatca agacagacag      900
caccttctcc ggatttctgg tgtactccga ctggcacagc tccccagtct      950
ttgcttagtg cccactgcaa agtgagctca tgctctcact cctagaagga     1000
gggtgtgagg ctgacaacca ggtcatccag gagggctggc cccctggaa      1050
tattgtgaat gactagggag gtggggtaga gcactctccg tcctgctgct     1100
ggcaaggaat gggaacagtg gctgtctgcg atcaggtctg gcagcatggg     1150
gcagtggctg gatttctgcc caagaccaga ggagtgtgct gtgctggcaa     1200
gtgtaagtcc cccagttgct ctggtccagg agcccacggt ggggtgctct     1250
cttcctggtc ctctgcttct ctggatcctc cccaccccct cctgctcctg     1300
gggccggccc ttttctcaga gatcactcaa taaacctaag aaccctcata     1350
aaaaaaaaaa aaaaaaaaa  aaaaaaa                              1377

<210> SEQ ID NO 20
<211> LENGTH: 243
<212> TYPE: PRT
<213> ORGANISM: Homo sapiens

<400> SEQUENCE: 20

Met Arg Pro Leu Leu Val Leu Leu Leu Gly Leu Ala Ala Gly
  1               5                  10                  15

Ser Pro Pro Leu Asp Asp Asn Lys Ile Pro Ser Leu Cys Pro Gly
                 20                  25                  30

His Pro Gly Leu Pro Gly Thr Pro Gly His His Gly Ser Gln Gly
             35                  40                  45

Leu Pro Gly Arg Asp Gly Arg Asp Gly Arg Asp Gly Ala Pro Gly
             50                  55                  60

Ala Pro Gly Glu Lys Gly Glu Gly Gly Arg Gly Leu Pro Gly
             65                  70                  75

Pro Arg Gly Asp Pro Gly Pro Arg Gly Glu Ala Gly Pro Ala Gly
             80                  85                  90

Pro Thr Gly Pro Ala Gly Glu Cys Ser Val Pro Pro Arg Ser Ala
             95                 100                 105

Phe Ser Ala Lys Arg Ser Glu Ser Arg Val Pro Pro Pro Ser Asp
            110                 115                 120

Ala Pro Leu Pro Phe Asp Arg Val Leu Val Asn Glu Gln Gly His
            125                 130                 135

Tyr Asp Ala Val Thr Gly Lys Phe Thr Cys Gln Val Pro Gly Val
            140                 145                 150

Tyr Tyr Phe Ala Val His Ala Thr Val Tyr Arg Ala Ser Leu Gln
            155                 160                 165

Phe Asp Leu Val Lys Asn Gly Glu Ser Ile Ala Ser Phe Phe Gln
            170                 175                 180

Phe Phe Gly Gly Trp Pro Lys Pro Ala Ser Leu Ser Gly Gly Ala
            185                 190                 195

Met Val Arg Leu Glu Pro Glu Asp Gln Val Trp Val Gln Val Gly
            200                 205                 210
```

```
Val Gly Asp Tyr Ile Gly Ile Tyr Ala Ser Ile Lys Thr Asp Ser
            215                 220                 225

Thr Phe Ser Gly Phe Leu Val Tyr Ser Asp Trp His Ser Ser Pro
            230                 235                 240

Val Phe Ala

<210> SEQ ID NO 21
<211> LENGTH: 2555
<212> TYPE: DNA
<213> ORGANISM: Homo sapiens

<400> SEQUENCE: 21
```

| | | | | | |
|---|---|---|---|---|---|
| ggggcgggtg | gacgcggact | cgaacgcagt | tgcttcggga | cccaggaccc | 50 |
| cctcgggccc | gacccgccag | gaaagactga | ggccgcggcc | tgccccgccc | 100 |
| ggctccctgc | gccgccgccg | cctccgggga | cagaagatgt | gctccagggt | 150 |
| ccctctgctg | ctgccgctgc | tcctgctact | ggccctgggg | cctggggtgc | 200 |
| agggctgccc | atccggctgc | cagtgcagcc | agccacagac | agtcttctgc | 250 |
| actgcccgcc | aggggaccac | ggtgccccga | gacgtgccac | ccgacacggt | 300 |
| ggggctgtac | gtctttgaga | acggcatcac | catgctcgac | gcaagcagct | 350 |
| ttgccggcct | gccgggcctg | cagctcctgg | acctgtcaca | gaaccagatc | 400 |
| gccagcctgc | gcctgccccg | cctgctgctg | ctggacctca | gccacaacag | 450 |
| cctcctggcc | ctggagcccg | gcatcctgga | cactgccaac | gtggaggcgc | 500 |
| tgcggctggc | tggtctgggg | ctgcagcagc | tggacgaggg | gctcttcagc | 550 |
| cgcttgcgca | acctccacga | cctggatgtg | tccgacaacc | agctggagcg | 600 |
| agtgccacct | gtgatccgag | gcctccgggg | cctgacgcgc | ctgcggctgg | 650 |
| ccggcaacac | ccgcattgcc | cagtgcggc | ccgaggacct | ggccggcctg | 700 |
| gctgccctgc | aggagctgga | tgtgagcaac | ctaagcctgc | aggccctgcc | 750 |
| tggcgacctc | tcgggcctct | tcccccgcct | gcggctgctg | gcagctgccc | 800 |
| gcaacccctt | caactgcgtg | tgcccccctga | gctggtttgg | ccctggggtg | 850 |
| cgcgagagcc | acgtcacact | ggccagcccc | gaggagacgc | gctgccactt | 900 |
| cccgccaag | aacgctggcc | ggctgctcct | ggagcttgac | tacgccgact | 950 |
| ttggctgccc | agccaccacc | accacagcca | cagtgcccac | cacgaggccc | 1000 |
| gtggtgcggg | agcccacagc | cttgtcttct | agcttggctc | ctacctggct | 1050 |
| tagccccaca | gcgccggcca | ctgaggcccc | cagcccgccc | tccactgccc | 1100 |
| caccgactgt | agggcctgtc | cccagcccc | aggactgccc | accgtccacc | 1150 |
| tgcctcaatg | ggggcacatg | ccacctgggg | acacggcacc | acctggcgtg | 1200 |
| cttgtgcccc | gaaggcttca | cgggcctgta | ctgtgagagc | cagatggggc | 1250 |
| agggacacg | gcccagccct | acaccagtca | cgccgaggcc | accacggtcc | 1300 |
| ctgaccctgg | gcatcgagcc | ggtgagcccc | acctccctgc | gcgtggggct | 1350 |
| gcagcgctac | ctccagggga | gctccgtgca | gctcaggagc | ctccgtctca | 1400 |
| cctatcgcaa | cctatcgggc | cctgataagc | ggctggtgac | gctgcgactg | 1450 |
| cctgcctcgc | tcgctgagta | cacggtcacc | cagctgcggc | ccaacgccac | 1500 |
| ttactccgtc | tgtgtcatgc | ctttgggggcc | cgggcgggtg | ccggagggcg | 1550 |
| aggaggcctg | cggggaggcc | catacacccc | cagccgtcca | ctccaaccac | 1600 |

-continued

```
gccccagtca cccaggcccg cgagggcaac ctgccgctcc tcattgcgcc      1650
cgccctggcc gcggtgctcc tggccgcgct ggctgcggtg ggggcagcct      1700
actgtgtgcg gcggggggcgg gccatggcag cagcggctca ggacaaaggg     1750
caggtggggc caggggctgg gcccctggaa ctggagggga tgaaggtccc      1800
cttggagcca ggcccgaagg caacagaggg cggtggagag gccctgccca      1850
gcgggtctga gtgtgaggtg ccactcatgg gcttcccagg gcctggcctc      1900
cagtcacccc tccacgcaaa gccctacatc taagccagag agagacaggg      1950
cagctggggc cgggctctca gccagtgaga tggccagccc cctcctgctg      2000
ccacaccacg taagttctca gtcccaacct cggggatgtg tgcagacagg      2050
gctgtgtgac cacagctggg ccctgttccc tctggacctc ggtctcctca      2100
tctgtgagat gctgtggccc agctgacgag ccctaacgtc cccagaaccg      2150
agtgcctatg aggacagtgt ccgccctgcc ctccgcaacg tgcagtccct      2200
gggcacggcg ggccctgcca tgtgctggta acgcatgcct gggccctgct      2250
gggctctccc actccaggcg gaccctgggg gccagtgaag gaagctcccg      2300
gaaagagcag agggagagcg ggtaggcggc tgtgtgactc tagtcttggc      2350
cccaggaagc gaaggaacaa agaaactgg aaaggaagat gctttaggaa       2400
catgttttgc ttttttaaaa tatatatata tttataagag atccttttccc     2450
atttattctg ggaagatgtt tttcaaactc agagacaagg actttggttt     2500
ttgtaagaca aacgatgata tgaaggcctt ttgtaagaaa aataaaaaa      2550
aaaaa                                                        2555
```

<210> SEQ ID NO 22
<211> LENGTH: 598
<212> TYPE: PRT
<213> ORGANISM: Homo sapiens

<400> SEQUENCE: 22

```
Met Cys Ser Arg Val Pro Leu Leu Pro Leu Leu Leu Leu Leu
  1               5                  10                  15

Ala Leu Gly Pro Gly Val Gln Gly Cys Pro Ser Gly Cys Gln Cys
            20                  25                  30

Ser Gln Pro Gln Thr Val Phe Cys Thr Ala Arg Gln Gly Thr Thr
            35                  40                  45

Val Pro Arg Asp Val Pro Pro Asp Thr Val Gly Leu Tyr Val Phe
            50                  55                  60

Glu Asn Gly Ile Thr Met Leu Asp Ala Ser Ser Phe Ala Gly Leu
            65                  70                  75

Pro Gly Leu Gln Leu Leu Asp Leu Ser Gln Asn Gln Ile Ala Ser
            80                  85                  90

Leu Arg Leu Pro Arg Leu Leu Leu Asp Leu Ser His Asn Ser
            95                 100                 105

Leu Leu Ala Leu Glu Pro Gly Ile Leu Asp Thr Ala Asn Val Glu
           110                 115                 120

Ala Leu Arg Leu Ala Gly Leu Gly Leu Gln Gln Leu Asp Glu Gly
           125                 130                 135

Leu Phe Ser Arg Leu Arg Asn Leu His Asp Leu Asp Val Ser Asp
           140                 145                 150

Asn Gln Leu Glu Arg Val Pro Pro Val Ile Arg Gly Leu Arg Gly
           155                 160                 165
```

```
Leu Thr Arg Leu Arg Leu Ala Gly Asn Thr Arg Ile Ala Gln Leu
                170                 175                 180

Arg Pro Glu Asp Leu Ala Gly Leu Ala Ala Leu Gln Glu Leu Asp
                185                 190                 195

Val Ser Asn Leu Ser Leu Gln Ala Leu Pro Gly Asp Leu Ser Gly
                200                 205                 210

Leu Phe Pro Arg Leu Arg Leu Leu Ala Ala Arg Asn Pro Phe
                215                 220                 225

Asn Cys Val Cys Pro Leu Ser Trp Phe Gly Pro Trp Val Arg Glu
                230                 235                 240

Ser His Val Thr Leu Ala Ser Pro Glu Glu Thr Arg Cys His Phe
                245                 250                 255

Pro Pro Lys Asn Ala Gly Arg Leu Leu Leu Glu Leu Asp Tyr Ala
                260                 265                 270

Asp Phe Gly Cys Pro Ala Thr Thr Thr Thr Ala Thr Val Pro Thr
                275                 280                 285

Thr Arg Pro Val Val Arg Glu Pro Thr Ala Leu Ser Ser Ser Leu
                290                 295                 300

Ala Pro Thr Trp Leu Ser Pro Thr Ala Pro Ala Thr Glu Ala Pro
                305                 310                 315

Ser Pro Pro Ser Thr Ala Pro Pro Thr Val Gly Pro Val Pro Gln
                320                 325                 330

Pro Gln Asp Cys Pro Pro Ser Thr Cys Leu Asn Gly Gly Thr Cys
                335                 340                 345

His Leu Gly Thr Arg His His Leu Ala Cys Leu Cys Pro Glu Gly
                350                 355                 360

Phe Thr Gly Leu Tyr Cys Glu Ser Gln Met Gly Gln Gly Thr Arg
                365                 370                 375

Pro Ser Pro Thr Pro Val Thr Pro Arg Pro Pro Arg Ser Leu Thr
                380                 385                 390

Leu Gly Ile Glu Pro Val Ser Pro Thr Ser Leu Arg Val Gly Leu
                395                 400                 405

Gln Arg Tyr Leu Gln Gly Ser Ser Val Gln Leu Arg Ser Leu Arg
                410                 415                 420

Leu Thr Tyr Arg Asn Leu Ser Gly Pro Asp Lys Arg Leu Val Thr
                425                 430                 435

Leu Arg Leu Pro Ala Ser Leu Ala Glu Tyr Thr Val Thr Gln Leu
                440                 445                 450

Arg Pro Asn Ala Thr Tyr Ser Val Cys Val Met Pro Leu Gly Pro
                455                 460                 465

Gly Arg Val Pro Glu Gly Glu Glu Ala Cys Gly Glu Ala His Thr
                470                 475                 480

Pro Pro Ala Val His Ser Asn His Ala Pro Val Thr Gln Ala Arg
                485                 490                 495

Glu Gly Asn Leu Pro Leu Leu Ile Ala Pro Ala Leu Ala Ala Val
                500                 505                 510

Leu Leu Ala Ala Leu Ala Ala Val Gly Ala Ala Tyr Cys Val Arg
                515                 520                 525

Arg Gly Arg Ala Met Ala Ala Ala Gln Asp Lys Gly Gln Val
                530                 535                 540

Gly Pro Gly Ala Gly Pro Leu Glu Leu Glu Gly Val Lys Val Pro
                545                 550                 555

Leu Glu Pro Gly Pro Lys Ala Thr Glu Gly Gly Gly Glu Ala Leu
```

```
                    560             565             570
Pro Ser Gly Ser Glu Cys Glu Val Pro Leu Met Gly Phe Pro Gly
            575             580                 585
Pro Gly Leu Gln Ser Pro Leu His Ala Lys Pro Tyr Ile
            590             595

<210> SEQ ID NO 23
<211> LENGTH: 2236
<212> TYPE: DNA
<213> ORGANISM: Homo sapiens

<400> SEQUENCE: 23
ggcgccggtg caccgggcgg gctgagcgcc tcctgcggcc cggcctgcgc        50
gccccggccc gccgcgccgc ccacgcccca accccggccc gcgcccccta       100
gcccccgccc gggcccgcgc ccgcgcccgc gcccaggtga gcgctccgcc       150
cgccgcgagg ccccgccccg gcccgccccc gccccgcccc ggccggcggg       200
ggaaccgggc ggattcctcg cgcgtcaaac cacctgatcc cataaaacat       250
tcatcctccc ggcggccgc gctgcgagcc cccgccagt ccgcgccgcc         300 gccgccctcg ccctgtgcgc cctgcgcgcc ctgcgcaccc gcggcccgag       350
cccagccaga gccgggcgga gcggagcgcg ccgagcctcg tcccgcggcc       400
gggccggggc cgggccgtag cggcggcgcc tggatgcgga cccggccgcg       450
gggagacggg cgcccgcccc gaaacgactt tcagtccccg acgcgccccg       500 cccaaccccct acgatgaaga gggcgtccgc tggagggagc cggctgctgg      550
catgggtgct gtggctgcag gcctggcagg tggcagcccc atgcccaggt       600
gcctgcgtat gctacaatga gcccaaggtg acgacaagct gcccccagca       650
gggcctgcag gctgtgcccg tgggcatccc tgctgccagc cagcgcatct       700
tcctgcacgg caaccgcatc tcgcatgtgc cagctgccag cttccgtgcc       750
tgccgcaacc tcaccatcct gtggctgcac tcgaatgtgc tggcccgaat       800
tgatgcggct gccttcactg gcctggccct cctggagcag ctggacctca       850
gcgataatgc acagctccgg tctgtggacc ctgccacatt ccacggcctg       900
ggccgcctac acacgctgca cctggaccgc tgcggcctgc aggagctggg       950
cccggggctg ttccgcggcc tggctgccct gcagtacctc tacctgcagg      1000
acaacgcgct gcaggcactg cctgatgaca ccttccgcga cctgggcaac      1050
ctcacacacc tcttcctgca cggcaaccgc atctccagcg tgcccgagcg      1100
cgccttccgt gggctgcaca gcctcgaccg tctcctactg caccagaacc      1150
gcgtggccca tgtgcacccg catgccttcc gtgaccttgg ccgcctcatg      1200
acactctatc tgtttgccaa caatctatca gcgctgccca ctgaggccct      1250 ggccccctg cgtgccctgc agtacctgag gctcaacgac aaccctgggg      1300
tgtgtgactg ccgggcacgc ccactctggg cctggctgca gaagttccgc      1350
ggctcctcct ccgaggtgcc ctgcagcctc ccgcaacgcc tggctggccg      1400
tgacctcaaa cgcctagctg ccaatgacct gcagggctgc gctgtggcca      1450
ccggccctta ccatcccatc tggaccggca gggccaccga tgaggagccg      1500
ctggggcttc ccaagtgctg ccagccagat gccgctgaca aggcctcagt      1550
actggagcct ggaagaccag cttcggcagg caatgcgctg aagggacgcg      1600
```

-continued

| | |
|---|---|
| tgccgcccgg tgacagcccg ccgggcaacg gctctggccc acggcacatc | 1650 |
| aatgactcac cctttgggac tctgcctggc tctgctgagc ccccgctcac | 1700 |
| tgcagtgcgg cccgagggct ccgagccacc agggttcccc acctcgggcc | 1750 |
| ctcgccggag gccaggctgt tcacgcaaga accgcacccg cagccactgc | 1800 |
| cgtctgggcc aggcaggcag cggggtggc gggactggtg actcagaagg | 1850 |
| ctcaggtgcc ctacccagcc tcacctgcag cctcaccccc ctgggcctgg | 1900 |
| cgctggtgct gtggacagtg cttgggccct gctgaccccc agcggacaca | 1950 |
| agagcgtgct cagcagccag gtgtgtgtac atacggggtc tctctccacg | 2000 |
| ccgccaagcc agccgggcgg ccgacccgtg gggcaggcca ggccaggtcc | 2050 |
| tccctgatgg acgcctgccg cccgccaccc ccatctccac cccatcatgt | 2100 |
| ttacagggtt cggcggcagc gtttgttcca gaacgccgcc tcccacccag | 2150 |
| atcgcggtat atagagatat gcattttatt ttacttgtgt aaaaatatcg | 2200 |
| gacgacgtgg aataaagagc tcttttctta aaaaaa | 2236 |

<210> SEQ ID NO 24
<211> LENGTH: 473
<212> TYPE: PRT
<213> ORGANISM: Homo sapiens

<400> SEQUENCE: 24

Met Lys Arg Ala Ser Ala Gly Gly Ser Arg Leu Leu Ala Trp Val
 1               5                  10                  15

Leu Trp Leu Gln Ala Trp Gln Val Ala Ala Pro Cys Pro Gly Ala
                20                  25                  30

Cys Val Cys Tyr Asn Glu Pro Lys Val Thr Thr Ser Cys Pro Gln
                35                  40                  45

Gln Gly Leu Gln Ala Val Pro Val Gly Ile Pro Ala Ala Ser Gln
                50                  55                  60

Arg Ile Phe Leu His Gly Asn Arg Ile Ser His Val Pro Ala Ala
                65                  70                  75

Ser Phe Arg Ala Cys Arg Asn Leu Thr Ile Leu Trp Leu His Ser
                80                  85                  90

Asn Val Leu Ala Arg Ile Asp Ala Ala Ala Phe Thr Gly Leu Ala
                95                 100                 105

Leu Leu Glu Gln Leu Asp Leu Ser Asp Asn Ala Gln Leu Arg Ser
               110                 115                 120

Val Asp Pro Ala Thr Phe His Gly Leu Gly Arg Leu His Thr Leu
               125                 130                 135

His Leu Asp Arg Cys Gly Leu Gln Glu Leu Gly Pro Gly Leu Phe
               140                 145                 150

Arg Gly Leu Ala Ala Leu Gln Tyr Leu Tyr Leu Gln Asp Asn Ala
               155                 160                 165

Leu Gln Ala Leu Pro Asp Asp Thr Phe Arg Asp Leu Gly Asn Leu
               170                 175                 180

Thr His Leu Phe Leu His Gly Asn Arg Ile Ser Ser Val Pro Glu
               185                 190                 195

Arg Ala Phe Arg Gly Leu His Ser Leu Asp Arg Leu Leu Leu His
               200                 205                 210

Gln Asn Arg Val Ala His Val His Pro His Ala Phe Arg Asp Leu
               215                 220                 225

Gly Arg Leu Met Thr Leu Tyr Leu Phe Ala Asn Asn Leu Ser Ala

```
                        230                 235                 240
Leu Pro Thr Glu Ala Leu Ala Pro Leu Arg Ala Leu Gln Tyr Leu
                245                 250                 255
Arg Leu Asn Asp Asn Pro Trp Val Cys Asp Cys Arg Ala Arg Pro
                260                 265                 270
Leu Trp Ala Trp Leu Gln Lys Phe Arg Gly Ser Ser Glu Val
                275                 280                 285
Pro Cys Ser Leu Pro Gln Arg Leu Ala Gly Arg Asp Leu Lys Arg
                290                 295                 300
Leu Ala Ala Asn Asp Leu Gln Gly Cys Ala Val Ala Thr Gly Pro
                305                 310                 315
Tyr His Pro Ile Trp Thr Gly Arg Ala Thr Asp Glu Glu Pro Leu
                320                 325                 330
Gly Leu Pro Lys Cys Cys Gln Pro Asp Ala Ala Asp Lys Ala Ser
                335                 340                 345
Val Leu Glu Pro Gly Arg Pro Ala Ser Ala Gly Asn Ala Leu Lys
                350                 355                 360
Gly Arg Val Pro Pro Gly Asp Ser Pro Pro Gly Asn Gly Ser Gly
                365                 370                 375
Pro Arg His Ile Asn Asp Ser Pro Phe Gly Thr Leu Pro Gly Ser
                380                 385                 390
Ala Glu Pro Pro Leu Thr Ala Val Arg Pro Glu Gly Ser Glu Pro
                395                 400                 405
Pro Gly Phe Pro Thr Ser Gly Pro Arg Arg Pro Gly Cys Ser
                410                 415                 420
Arg Lys Asn Arg Thr Arg Ser His Cys Arg Leu Gly Gln Ala Gly
                425                 430                 435
Ser Gly Gly Gly Gly Thr Gly Asp Ser Glu Gly Ser Gly Ala Leu
                440                 445                 450
Pro Ser Leu Thr Cys Ser Leu Thr Pro Leu Gly Leu Ala Leu Val
                455                 460                 465
Leu Trp Thr Val Leu Gly Pro Cys
                470

<210> SEQ ID NO 25
<211> LENGTH: 3240
<212> TYPE: DNA
<213> ORGANISM: Homo sapiens

<400> SEQUENCE: 25
cggacgcgtg gcggacgcg tgggcctggg caagggccgg ggcgccgggc           50
cgagccacct cttcccctcc cccgcttccc tgtcgcgctc cgctggctgg          100
acgcgctgga ggagtggagc agcacccggc cggccctggg ggctgacagt          150
cggcaaagtt tggcccgaag aggaagtggt ctcaaacccc ggcaggtggc          200
gaccaggcca gaccagggc gctcgctgcc tgcgggcggg ctgtaggcga           250
gggcgcgccc cagtgccgag acccgggct tcaggagccg ccccgggag            300 agaagagtgc ggcggcggac ggagaaaaca actccaaagt tggcgaaagg          350 caccgccccct actcccgggc tgccgccgcc tcccgccccc cagccctggc         400
atccagagta cgggtcgagc ccgggccatg gagccccct ggggaggcgg           450 caccagggag cctgggcgcc cggggctccg ccgcgacccc atcgggtaga           500
ccacagaagc tccgggaccc ttccggcacc tctggacagc ccaggatgct          550
```

-continued

| | |
|---|---|
| gttggccacc ctcctcctcc tcctccttgg aggcgctctg gcccatccag | 600 |
| accggattat ttttccaaat catgcttgtg aggaccccc agcagtgctc | 650 |
| ttagaagtgc agggcacctt acagaggccc ctggtccggg acagccgcac | 700 |
| ctcccctgcc aactgcacct ggctcatcct gggcagcaag aacagactg | 750 |
| tcaccatcag gttccagaag ctacacctgg cctgtggctc agagcgctta | 800 |
| accctacgct cccctctcca gccactgatc tccctgtgtg aggcacctcc | 850 |
| cagccctctg cagctgcccg ggggcaacgt caccatcact tacagctatg | 900 |
| ctggggccag agcacccatg gccagggct tcctgctctc ctacagccaa | 950 |
| gattggctga tgtgcctgca ggaagagttt cagtgcctga ccaccgctg | 1000 |
| tgtatctgct gtccagcgct gtgatggggt tgatgcctgt ggcgatggct | 1050 |
| ctgatgaagc aggttgcagc tcagaccct tccctggcct accccaaga | 1100 |
| cccgtccct ccctgccttg caatgtcacc ttggaggact tctatggggt | 1150 |
| cttctcctct cctggatata cacacctagc ctcagtctcc cacccccagt | 1200 |
| cctgccattg gctgctggac ccccatgatg gccggcggct ggccgtgcgc | 1250 |
| ttcacagccc tggacttggg cttttggagat gcagtgcatg tgtatgacgg | 1300 |
| ccctgggccc cctgagagct cccgactact gcgtagtctc acccacttca | 1350 |
| gcaatggcaa ggctgtcact gtggagacac tgtctggcca ggctgttgtg | 1400 |
| tcctaccaca cagttgcttg gagcaatggt cgtggcttca atgccaccta | 1450 |
| ccatgtgcgg ggctattgct tgccttggga cagaccctgt ggcttaggct | 1500 |
| ctggcctggg agctggcgaa ggcctaggtg agcgctgcta cagtgaggca | 1550 |
| cagcgctgtg acggctcatg ggactgtgct gacggcacag atgaggagga | 1600 |
| ctgcccaggc tgcccacctg gacacttccc ctgtggggct gctggcacct | 1650 |
| ctggtgccac agcctgctac ctgcctgctg accgctgcaa ctaccagact | 1700 |
| ttctgtgctg atggagcaga tgagagacg tgtcggcatt gccagcctgg | 1750 |
| caatttccga tgccgggacg agaagtgcgt gtatgagacg tgggtgtgcg | 1800 |
| atgggcagcc agactgtgcg gacggcagtg atgagtggga ctgctcctat | 1850 |
| gttctgcccc gcaaggtcat tacagctgca gtcattggca gcctagtgtg | 1900 |
| cggcctgctc ctggtcatcg ccctgggctg cacctgcaag ctctatgcca | 1950 |
| ttcgcacca ggagtacagc atctttgccc ccctctcccg gatggaggct | 2000 |
| gagattgtgc agcagcaggc acccccttcc tacgggcagc tcattgccca | 2050 |
| gggtgccatc ccacctgtag aagactttcc tacagagaat cctaatgata | 2100 |
| actcagtgct gggcaacctg cgttctctgc tacagatctt acgccaggat | 2150 |
| atgactccag gaggtggccc aggtgcccgc cgtcgtcagc ggggccgctt | 2200 |
| gatgcgacgc ctggtacgcc gtctccgccg ctggggcttg ctccctcgaa | 2250 |
| ccaacacccc ggctcgggcc tctgaggcca gatcccaggt cacaccttct | 2300 |
| gctgctcccc ttgaggccct agatggtggc acaggtccag cccgtgaggg | 2350 |
| cggggcagtg ggtgggcaag atggggagca ggcacccca ctgcccatca | 2400 |
| aggctcccct cccatctgct agcacgtctc cagccccac tactgtccct | 2450 |
| gaagccccag ggccactgcc ctcactgccc ctagagccat cactattgtc | 2500 |
| tggagtggtg caggccctgc gaggccgcct gttgcccagc ctggggcccc | 2550 |

-continued

```
caggaccaac ccggagcccc cctggacccc acacagcagt cctggccctg      2600
gaagatgagg acgatgtgct actggtgcca ctggctgagc cggggggtgtg     2650
ggtagctgag gcagaggatg agccactgct tacctgaggg gacctggggg      2700
ctctactgag gcctctcccc tgggggctct actcatagtg gcacaacctt      2750
ttagaggtgg gtcagcctcc cctccaccac ttccttccct gtccctggat      2800
ttcagggact tggtgggcct cccgttgacc ctatgtagct gctataaagt      2850
taagtgtccc tcaggcaggg agagggctca cagagtctcc tctgtacgtg      2900
gccatggcca gacaccccag tcccttcacc accacctgct ccccacgcca      2950
ccaccatttg ggtggctgtt tttaaaaagt aaagttctta gaggatcata      3000
ggtctggaca ctccatcctt gccaaacctc tacccaaaag tggccttaag      3050
caccggaatg ccaattaact agagaccctc agccccccaa ggggaggatt      3100
tgggcagaac ctgaggtttt gccatccaca atccctccta cagggcctgg      3150
ctcacaaaaa gagtgcaaca aatgcttcta ttccatagct acggcattgc      3200
tcagtaagtt gaggtcaaaa ataaaggaat catacatctc                 3240
```

<210> SEQ ID NO 26
<211> LENGTH: 713
<212> TYPE: PRT
<213> ORGANISM: Homo sapiens

<400> SEQUENCE: 26

```
Met Leu Leu Ala Thr Leu Leu Leu Leu Leu Gly Gly Ala Leu
  1               5                  10                  15

Ala His Pro Asp Arg Ile Ile Phe Pro Asn His Ala Cys Glu Asp
                 20                  25                  30

Pro Pro Ala Val Leu Leu Glu Val Gln Gly Thr Leu Gln Arg Pro
                 35                  40                  45

Leu Val Arg Asp Ser Arg Thr Ser Pro Ala Asn Cys Thr Trp Leu
                 50                  55                  60

Ile Leu Gly Ser Lys Glu Gln Thr Val Thr Ile Arg Phe Gln Lys
                 65                  70                  75

Leu His Leu Ala Cys Gly Ser Glu Arg Leu Thr Leu Arg Ser Pro
                 80                  85                  90

Leu Gln Pro Leu Ile Ser Leu Cys Glu Ala Pro Pro Ser Pro Leu
                 95                 100                 105

Gln Leu Pro Gly Gly Asn Val Thr Ile Thr Tyr Ser Tyr Ala Gly
                110                 115                 120

Ala Arg Ala Pro Met Gly Gln Gly Phe Leu Leu Ser Tyr Ser Gln
                125                 130                 135

Asp Trp Leu Met Cys Leu Gln Glu Glu Phe Gln Cys Leu Asn His
                140                 145                 150

Arg Cys Val Ser Ala Val Gln Arg Cys Asp Gly Val Asp Ala Cys
                155                 160                 165

Gly Asp Gly Ser Asp Glu Ala Gly Cys Ser Ser Asp Pro Phe Pro
                170                 175                 180

Gly Leu Thr Pro Arg Pro Val Pro Ser Leu Pro Cys Asn Val Thr
                185                 190                 195

Leu Glu Asp Phe Tyr Gly Val Phe Ser Ser Pro Gly Tyr Thr His
                200                 205                 210

Leu Ala Ser Val Ser His Pro Gln Ser Cys His Trp Leu Leu Asp
                215                 220                 225
```

```
Pro His Asp Gly Arg Arg Leu Ala Val Arg Phe Thr Ala Leu Asp
            230                 235                 240

Leu Gly Phe Gly Asp Ala Val His Val Tyr Asp Gly Pro Gly Pro
            245                 250                 255

Pro Glu Ser Ser Arg Leu Leu Arg Ser Leu Thr His Phe Ser Asn
            260                 265                 270

Gly Lys Ala Val Thr Val Glu Thr Leu Ser Gly Gln Ala Val Val
            275                 280                 285

Ser Tyr His Thr Val Ala Trp Ser Asn Gly Arg Gly Phe Asn Ala
            290                 295                 300

Thr Tyr His Val Arg Gly Tyr Cys Leu Pro Trp Asp Arg Pro Cys
            305                 310                 315

Gly Leu Gly Ser Gly Leu Gly Ala Gly Glu Gly Leu Gly Glu Arg
            320                 325                 330

Cys Tyr Ser Glu Ala Gln Arg Cys Asp Gly Ser Trp Asp Cys Ala
            335                 340                 345

Asp Gly Thr Asp Glu Glu Asp Cys Pro Gly Cys Pro Pro Gly His
            350                 355                 360

Phe Pro Cys Gly Ala Ala Gly Thr Ser Gly Ala Thr Ala Cys Tyr
            365                 370                 375

Leu Pro Ala Asp Arg Cys Asn Tyr Gln Thr Phe Cys Ala Asp Gly
            380                 385                 390

Ala Asp Glu Arg Arg Cys Arg His Cys Gln Pro Gly Asn Phe Arg
            395                 400                 405

Cys Arg Asp Glu Lys Cys Val Tyr Glu Thr Trp Val Cys Asp Gly
            410                 415                 420

Gln Pro Asp Cys Ala Asp Gly Ser Asp Glu Trp Asp Cys Ser Tyr
            425                 430                 435

Val Leu Pro Arg Lys Val Ile Thr Ala Ala Val Ile Gly Ser Leu
            440                 445                 450

Val Cys Gly Leu Leu Leu Val Ile Ala Leu Gly Cys Thr Cys Lys
            455                 460                 465

Leu Tyr Ala Ile Arg Thr Gln Glu Tyr Ser Ile Phe Ala Pro Leu
            470                 475                 480

Ser Arg Met Glu Ala Glu Ile Val Gln Gln Ala Pro Pro Ser
            485                 490                 495

Tyr Gly Gln Leu Ile Ala Gln Gly Ala Ile Pro Pro Val Glu Asp
            500                 505                 510

Phe Pro Thr Glu Asn Pro Asn Asp Asn Ser Val Leu Gly Asn Leu
            515                 520                 525

Arg Ser Leu Leu Gln Ile Leu Arg Gln Asp Met Thr Pro Gly Gly
            530                 535                 540

Gly Pro Gly Ala Arg Arg Gln Arg Gly Arg Leu Met Arg Arg
            545                 550                 555

Leu Val Arg Arg Leu Arg Arg Trp Gly Leu Leu Pro Arg Thr Asn
            560                 565                 570

Thr Pro Ala Arg Ala Ser Glu Ala Arg Ser Gln Val Thr Pro Ser
            575                 580                 585

Ala Ala Pro Leu Glu Ala Leu Asp Gly Gly Thr Gly Pro Ala Arg
            590                 595                 600

Glu Gly Gly Ala Val Gly Gly Gln Asp Gly Glu Gln Ala Pro Pro
            605                 610                 615

Leu Pro Ile Lys Ala Pro Leu Pro Ser Ala Ser Thr Ser Pro Ala
```

```
            620                 625                 630
Pro Thr Thr Val Pro Glu Ala Pro Gly Pro Leu Pro Ser Leu Pro
            635                 640                 645
Leu Glu Pro Ser Leu Leu Ser Gly Val Val Gln Ala Leu Arg Gly
            650                 655                 660
Arg Leu Leu Pro Ser Leu Gly Pro Pro Gly Pro Thr Arg Ser Pro
            665                 670                 675
Pro Gly Pro His Thr Ala Val Leu Ala Leu Glu Asp Glu Asp Asp
            680                 685                 690
Val Leu Leu Val Pro Leu Ala Glu Pro Gly Val Trp Val Ala Glu
            695                 700                 705
Ala Glu Asp Glu Pro Leu Leu Thr
            710

<210> SEQ ID NO 27
<211> LENGTH: 4313
<212> TYPE: DNA
<213> ORGANISM: Homo sapiens

<400> SEQUENCE: 27
gtcccacatc ctgctcaact gggtcaggtc cctcttagac cagctcttgt           50
ccatcatttg ctgaagtgga ccaactagtt ccccagtagg gggtctcccc          100
tggcaattct tgatcggcgt ttggacatct cagatcgctt ccaatgaaga          150
tggccttgcc ttggggtcct gcttgtttca taatcatcta actatgggac          200
aaggttgtgc cggcagctct gggggaagga gcacggggct gatcaagcca          250
tccaggaaac actggaggac ttgtccagcc ttgaaagaac tctagtggtt          300
tctgaatcta gcccacttgg cggtaagcat gatgcaactt ctgcaacttc          350
tgctggggct tttggggcca ggtggctact tatttctttt aggggattgt          400
caggaggtga ccactctcac ggtgaaatac caagtgtcag aggaagtgcc          450
atctggtaca gtgatcggga agctgtccca ggaactgggc cgggaggaga          500
ggcggaggca agctggggcc gccttccagg tgttgcagct gcctcaggcg          550
ctccccattc aggtggactc tgaggaaggc ttgctcagca caggcaggcg          600
gctggatcga gagcagctgt gccgacagtg ggatccctgc ctggtttcct          650
ttgatgtgct tgccacaggg gatttggctc tgatccatgt ggagatccaa          700
gtgctggaca tcaatgacca ccagccacgg tttcccaaag cgagcagga           750 gctggaaatc tctgagagcg cctctctgcg aacccggatc cccctggaca          800
gagctcttga cccagacaca ggccctaaca ccctgcacac ctacactctg          850
tctcccagtg agcactttgc cttggatgtc attgtgggcc ctgatgagac          900
caaacatgca gaactcatag tggtgaagga gctggacagg gaaatccatt          950
cattttttga tctggtgtta actgcctatg acaatgggaa cccccccaag         1000
tcaggtacca gcttggtcaa ggtcaacgtc ttggactcca atgacaatag         1050
ccctgcgttt gctgagagtt cactggcact ggaaatccaa gaagatgctg         1100
cacctggtac gcttctcata aaactgaccg ccacagaccc tgaccaaggc         1150
cccaatgggg aggtggagtt cttcctcagt aagcacatgc ctccagaggt         1200
gctggacacc ttcagtattg atgccaagac aggccaggtc attctgcgtc         1250
gacctctaga ctatgaaaag aaccctgcct acgaggtgga tgttcaggca         1300
```

```
agggacctgg gtcccaatcc tatcccagcc cattgcaaag ttctcatcaa    1350
ggttctggat gtcaatgaca acatcccaag catccacgtc acatgggcct    1400
cccagccatc actggtgtca gaagctcttc ccaaggacag ttttattgct    1450
cttgtcatgg cagatgactt ggattcagga cacaatggtt tggtccactg    1500
ctggctgagc caagagctgg gccacttcag gctgaaaaga actaatggca    1550
acacatacat gttgctaacc aatgccacac tggacagaga gcagtggccc    1600
aaatatacccc tcactctgtt agcccaagac caaggactcc agcccttatc    1650
agccaagaaa cagctcagca ttcagatcag tgacatcaac gacaatgcac    1700
ctgtgtttga gaaaagcagg tatgaagtct ccacgcggga aaacaactta    1750
ccctctcttc acctcattac catcaaggct catgatgcag acttgggcat    1800
taatggaaaa gtctcatacc gcatccagga ctccccagtt gctcacttag    1850
tagctattga ctccaacaca ggagaggtca ctgctcagag gtcactgaac    1900
tatgaagaga tggccggctt tgagttccag gtgatcgcag aggacagcgg    1950
gcaacccatg cttgcatcca gtgtctctgt gtgggtcagc ctcttggatg    2000
ccaatgataa tgccccagag gtggtccagc ctgtgctcag cgatggaaaa    2050
gccagcctct ccgtgcttgt gaatgcctcc acaggccacc tgctggtgcc    2100
catcgagact cccaatggct tgggcccagc gggcactgac acacctccac    2150
tggccactca cagctcccgg ccattccttt tgacaaccat tgtggcaaga    2200
gatgcagact cgggggcaaa tggagagccc ctctacagca tccgcaatgg    2250
aaatgaagcc cacctcttca tcctcaaccc tcatacgggg cagctgttcg    2300
tcaatgtcac caatgccagc agcctcattg ggagtgagtg ggagctggag    2350
atagtagtag aggaccaggg aagccccccc ttacagaccc gagccctgtt    2400
gagggtcatg tttgtcacca gtgtggacca cctgagggac tcagcccgca    2450
agcctggggc cttgagcatg tcgatgctga cggtgatctg cctggctgta    2500
ctgttgggca tcttcgggtt gatcctggct ttgttcatgt ccatctgccg    2550
gacagaaaag aaggacaaca gggcctacaa ctgtcgggag gccgagtcca    2600
cctaccgcca gcagcccaag aggccccaga aacacattca gaaggcagac    2650
atccacctcg tgcctgtgct caggggtcag gcaggtgagc cttgtgaagt    2700
cgggcagtcc cacaaagatg tggacaagga ggcgatgatg gaagcaggct    2750
gggacccctg cctgcaggcc cccttccacc tcaccccgac cctgtacagg    2800
acgctgcgta atcaaggcaa ccaggagca ccggcggaga gccgagaggt    2850
gctgcaagac acggtcaacc tccttttcaa ccatcccagg cagaggaatg    2900
cctcccggga gaacctgaac cttcccgagc ccagcctgc acaggccag    2950
ccacgttcca ggcctctgaa ggttgcaggc agccccacag ggaggctggc    3000
tggagaccag ggcagtgagg aagcccccaca gaggccacca gcctcctctg    3050
caaccctgag acggcagcga catctcaatg gcaaagtgtc ccctgagaaa    3100
gaatcagggc cccgtcagat cctgcggagc ctggtccggc tgtctgtggc    3150
tgccttcgcc gagcggaacc ccgtggagga gctcactgtg gattctcctc    3200
ctgttcagca aatctcccag ctgctgtcct tgctgcatca gggccaattc    3250
cagcccaaac caaccaccg aggaaataag tacttggcca agccaggagg    3300
```

| | |
|---|---:|
| cagcaggagt gcaatcccag acacagatgg cccaagtgca agggctggag | 3350 |
| gccagacaga cccagaacag gaggaagggc ctttggatcc tgaagaggac | 3400 |
| ctctctgtga agcaactgct agaagaagag ctgtcaagtc tgctggaccc | 3450 |
| cagcacaggt ctggccctgg accggctgag cgcccctgac ccggcctgga | 3500 |
| tggcgagact ctctttgccc ctcaccacca actaccgtga caatgtgatc | 3550 |
| tccccggatg ctgcagccac ggaggagccg aggaccttcc agacgttcgg | 3600 |
| caaggcagag gcaccagagc tgagcccaac aggcacgagg ctggccagca | 3650 |
| cctttgtctc ggagatgagc tcactgctgg agatgctgct ggaacagcgc | 3700 |
| tccagcatgc ccgtggaggc cgcctccgag gcgctgcggc ggctctcggt | 3750 |
| ctgcggagg accctcagtt tagacttggc caccagtgca gcctcaggca | 3800 |
| tgaaagtgca aggggaccca ggtggaaaga cggggactga gggcaagagc | 3850 |
| agaggcagca gcagcagcag caggtgcctg tgaacatacc tcagacgcct | 3900 |
| ctggatccaa gaaccagggg cctgaggatc tgtggacaag agctggtttc | 3950 |
| taaaatcttg taactcacta gctagcggcg gcctgagaac tttagggtga | 4000 |
| ctgatgctac ccccacagag gaggcaagag ccccaggact aacagctgac | 4050 |
| tgaccaaagc agcccccttgt aagcagctct gagtctttg gaggacaggg | 4100 |
| acggtttgtg gctgagataa gtgtttcctg gcaaaacata tgtggagcac | 4150 |
| aaagggtcag tcctctggca gaacagatgc cacggagtat cacaggcagg | 4200 |
| aaagggtggc cttcttgggt agcaggagtc aggggggctgt accctggggg | 4250 |
| tgccaggaaa tgctctctga cctatcaata aaggaaaagc agtaaaaaaa | 4300 |
| aaaaaaaaaa aaa | 4313 |

<210> SEQ ID NO 28
<211> LENGTH: 1184
<212> TYPE: PRT
<213> ORGANISM: Homo sapiens

<400> SEQUENCE: 28

```
Met Met Gln Leu Leu Gln Leu Leu Gly Leu Leu Pro Gly
  1               5                  10                  15

Gly Tyr Leu Phe Leu Leu Gly Asp Cys Gln Glu Val Thr Thr Leu
                 20                  25                  30

Thr Val Lys Tyr Gln Val Ser Glu Glu Val Pro Ser Gly Thr Val
                 35                  40                  45

Ile Gly Lys Leu Ser Gln Glu Leu Gly Arg Glu Glu Arg Arg
                 50                  55                  60

Gln Ala Gly Ala Ala Phe Gln Val Leu Gln Leu Pro Gln Ala Leu
                 65                  70                  75

Pro Ile Gln Val Asp Ser Glu Glu Gly Leu Leu Ser Thr Gly Arg
                 80                  85                  90

Arg Leu Asp Arg Glu Gln Leu Cys Arg Gln Trp Asp Pro Cys Leu
                 95                 100                 105

Val Ser Phe Asp Val Leu Ala Thr Gly Asp Leu Ala Leu Ile His
                110                 115                 120

Val Glu Ile Gln Val Leu Asp Ile Asn Asp His Gln Pro Arg Phe
                125                 130                 135

Pro Lys Gly Glu Gln Glu Leu Glu Ile Ser Glu Ser Ala Ser Leu
                140                 145                 150
```

```
Arg Thr Arg Ile Pro Leu Asp Arg Ala Leu Asp Pro Asp Thr Gly
            155                 160                 165

Pro Asn Thr Leu His Thr Tyr Thr Leu Ser Pro Ser Glu His Phe
            170                 175                 180

Ala Leu Asp Val Ile Val Gly Pro Asp Glu Thr Lys His Ala Glu
            185                 190                 195

Leu Ile Val Val Lys Glu Leu Asp Arg Glu Ile His Ser Phe Phe
            200                 205                 210

Asp Leu Val Leu Thr Ala Tyr Asp Asn Gly Asn Pro Pro Lys Ser
            215                 220                 225

Gly Thr Ser Leu Val Lys Val Asn Val Leu Asp Ser Asn Asp Asn
            230                 235                 240

Ser Pro Ala Phe Ala Glu Ser Ser Leu Ala Leu Glu Ile Gln Glu
            245                 250                 255

Asp Ala Ala Pro Gly Thr Leu Leu Ile Lys Leu Thr Ala Thr Asp
            260                 265                 270

Pro Asp Gln Gly Pro Asn Gly Glu Val Glu Phe Phe Leu Ser Lys
            275                 280                 285

His Met Pro Pro Glu Val Leu Asp Thr Phe Ser Ile Asp Ala Lys
            290                 295                 300

Thr Gly Gln Val Ile Leu Arg Arg Pro Leu Asp Tyr Glu Lys Asn
            305                 310                 315

Pro Ala Tyr Glu Val Asp Val Gln Ala Arg Asp Leu Gly Pro Asn
            320                 325                 330

Pro Ile Pro Ala His Cys Lys Val Leu Ile Lys Val Leu Asp Val
            335                 340                 345

Asn Asp Asn Ile Pro Ser Ile His Val Thr Trp Ala Ser Gln Pro
            350                 355                 360

Ser Leu Val Ser Glu Ala Leu Pro Lys Asp Ser Phe Ile Ala Leu
            365                 370                 375

Val Met Ala Asp Asp Leu Asp Ser Gly His Asn Gly Leu Val His
            380                 385                 390

Cys Trp Leu Ser Gln Glu Leu Gly His Phe Arg Leu Lys Arg Thr
            395                 400                 405

Asn Gly Asn Thr Tyr Met Leu Leu Thr Asn Ala Thr Leu Asp Arg
            410                 415                 420

Glu Gln Trp Pro Lys Tyr Thr Leu Thr Leu Leu Ala Gln Asp Gln
            425                 430                 435

Gly Leu Gln Pro Leu Ser Ala Lys Lys Gln Leu Ser Ile Gln Ile
            440                 445                 450

Ser Asp Ile Asn Asp Asn Ala Pro Val Phe Glu Lys Ser Arg Tyr
            455                 460                 465

Glu Val Ser Thr Arg Glu Asn Asn Leu Pro Ser Leu His Leu Ile
            470                 475                 480

Thr Ile Lys Ala His Asp Ala Asp Leu Gly Ile Asn Gly Lys Val
            485                 490                 495

Ser Tyr Arg Ile Gln Asp Ser Pro Val Ala His Leu Val Ala Ile
            500                 505                 510

Asp Ser Asn Thr Gly Glu Val Thr Ala Gln Arg Ser Leu Asn Tyr
            515                 520                 525

Glu Glu Met Ala Gly Phe Glu Phe Gln Val Ile Ala Glu Asp Ser
            530                 535                 540

Gly Gln Pro Met Leu Ala Ser Ser Val Ser Val Trp Val Ser Leu
            545                 550                 555
```

-continued

```
Leu Asp Ala Asn Asp Asn Ala Pro Glu Val Val Gln Pro Val Leu
            560                 565                 570
Ser Asp Gly Lys Ala Ser Leu Ser Val Leu Val Asn Ala Ser Thr
            575                 580                 585
Gly His Leu Leu Val Pro Ile Glu Thr Pro Asn Gly Leu Gly Pro
            590                 595                 600
Ala Gly Thr Asp Thr Pro Pro Leu Ala Thr His Ser Ser Arg Pro
            605                 610                 615
Phe Leu Leu Thr Thr Ile Val Ala Arg Asp Ala Asp Ser Gly Ala
            620                 625                 630
Asn Gly Glu Pro Leu Tyr Ser Ile Arg Asn Gly Asn Glu Ala His
            635                 640                 645
Leu Phe Ile Leu Asn Pro His Thr Gly Gln Leu Phe Val Asn Val
            650                 655                 660
Thr Asn Ala Ser Ser Leu Ile Gly Ser Glu Trp Glu Leu Glu Ile
            665                 670                 675
Val Val Glu Asp Gln Gly Ser Pro Pro Leu Gln Thr Arg Ala Leu
            680                 685                 690
Leu Arg Val Met Phe Val Thr Ser Val Asp His Leu Arg Asp Ser
            695                 700                 705
Ala Arg Lys Pro Gly Ala Leu Ser Met Ser Met Leu Thr Val Ile
            710                 715                 720
Cys Leu Ala Val Leu Leu Gly Ile Phe Gly Leu Ile Leu Ala Leu
            725                 730                 735
Phe Met Ser Ile Cys Arg Thr Glu Lys Lys Asp Asn Arg Ala Tyr
            740                 745                 750
Asn Cys Arg Glu Ala Glu Ser Thr Tyr Arg Gln Gln Pro Lys Arg
            755                 760                 765
Pro Gln Lys His Ile Gln Lys Ala Asp Ile His Leu Val Pro Val
            770                 775                 780
Leu Arg Gly Gln Ala Gly Glu Pro Cys Glu Val Gly Gln Ser His
            785                 790                 795
Lys Asp Val Asp Lys Glu Ala Met Met Glu Ala Gly Trp Asp Pro
            800                 805                 810
Cys Leu Gln Ala Pro Phe His Leu Thr Pro Thr Leu Tyr Arg Thr
            815                 820                 825
Leu Arg Asn Gln Gly Asn Gln Gly Ala Pro Ala Glu Ser Arg Glu
            830                 835                 840
Val Leu Gln Asp Thr Val Asn Leu Leu Phe Asn His Pro Arg Gln
            845                 850                 855
Arg Asn Ala Ser Arg Glu Asn Leu Asn Leu Pro Glu Pro Gln Pro
            860                 865                 870
Ala Thr Gly Gln Pro Arg Ser Arg Pro Leu Lys Val Ala Gly Ser
            875                 880                 885
Pro Thr Gly Arg Leu Ala Gly Asp Gln Gly Ser Glu Glu Ala Pro
            890                 895                 900
Gln Arg Pro Pro Ala Ser Ser Ala Thr Leu Arg Arg Gln Arg His
            905                 910                 915
Leu Asn Gly Lys Val Ser Pro Glu Lys Glu Ser Gly Pro Arg Gln
            920                 925                 930
Ile Leu Arg Ser Leu Val Arg Leu Ser Val Ala Ala Phe Ala Glu
            935                 940                 945
Arg Asn Pro Val Glu Glu Leu Thr Val Asp Ser Pro Pro Val Gln
```

```
                    950                  955                  960
Gln Ile Ser Gln Leu Leu Ser Leu Leu His Gln Gly Gln Phe Gln
                965                  970                  975
Pro Lys Pro Asn His Arg Gly Asn Lys Tyr Leu Ala Lys Pro Gly
                980                  985                  990
Gly Ser Arg Ser Ala Ile Pro Asp Thr Asp Gly Pro Ser Ala Arg
                995                 1000                 1005
Ala Gly Gly Gln Thr Asp Pro Glu Gln Glu Glu Gly Pro Leu Asp
               1010                 1015                 1020
Pro Glu Glu Asp Leu Ser Val Lys Gln Leu Leu Glu Glu Glu Leu
               1025                 1030                 1035
Ser Ser Leu Leu Asp Pro Ser Thr Gly Leu Ala Leu Asp Arg Leu
               1040                 1045                 1050
Ser Ala Pro Asp Pro Ala Trp Met Ala Arg Leu Ser Leu Pro Leu
               1055                 1060                 1065
Thr Thr Asn Tyr Arg Asp Asn Val Ile Ser Pro Asp Ala Ala Ala
               1070                 1075                 1080
Thr Glu Glu Pro Arg Thr Phe Gln Thr Phe Gly Lys Ala Glu Ala
               1085                 1090                 1095
Pro Glu Leu Ser Pro Thr Gly Thr Arg Leu Ala Ser Thr Phe Val
               1100                 1105                 1110
Ser Glu Met Ser Ser Leu Leu Glu Met Leu Leu Glu Gln Arg Ser
               1115                 1120                 1125
Ser Met Pro Val Glu Ala Ala Ser Glu Ala Leu Arg Arg Leu Ser
               1130                 1135                 1140
Val Cys Gly Arg Thr Leu Ser Leu Asp Leu Ala Thr Ser Ala Ala
               1145                 1150                 1155
Ser Gly Met Lys Val Gln Gly Asp Pro Gly Gly Lys Thr Gly Thr
               1160                 1165                 1170
Glu Gly Lys Ser Arg Gly Ser Ser Ser Ser Arg Cys Leu
               1175                 1180

<210> SEQ ID NO 29
<211> LENGTH: 3127
<212> TYPE: DNA
<213> ORGANISM: Homo sapiens

<400> SEQUENCE: 29
tctcgcagat agtaaataat ctcggaaagg cgagaaagaa gctgtctcca          50
tcttgtctgt atccgctgct cttgtgacgt tgtggagatg gggagcgtcc         100
tggggctgtg ctccatggcg agctggatac catgtttgtg tggaagtgcc         150
ccgtgtttgc tatgccgatg ctgtcctagt ggaaacaact ccactgtaac         200
tagattgatc tatgcacttt tcttgcttgt tggagtatgt gtagcttgtg         250
taatgttgat accaggaatg gaagaacaac tgaataagat tcctggattt         300
tgtgagaatg agaaaggtgt tgtcccttgt aacattttgg ttggctataa         350
agctgtatat cgtttgtgct ttggtttggc tatgttctat cttcttctct         400
ctttactaat gatcaaagtg aagagtagca gtgatcctag agctgcagtg         450
cacaatggat tttggttctt taaatttgct gcagcaattg caattattat         500
tggggcattc ttcattccag aaggaacttt tacaactgtg tggttttatg         550
taggcatggc aggtgccttt tgtttcatcc tcatacaact agtcttactt         600
attgattttg cacattcatg gaatgaatcg tgggttgaaa aaatggaaga         650
```

-continued

| | |
|---|---|
| agggaactcg agatgttggt atgcagcctt gttatcagct acagctctga | 700 |
| attatctgct gtctttagtt gctatcgtcc tgttctttgt ctactacact | 750 |
| catccagcca gttgttcaga aaacaaggcg ttcatcagtg tcaacatgct | 800 |
| cctctgcgtt ggtgcttctg taatgtctat actgccaaaa atccaagaat | 850 |
| cacaaccaag atctggtttg ttacagtctt cagtaattac agtctacaca | 900 |
| atgtatttga catggtcagc tatgaccaat gaaccagaaa caaattgcaa | 950 |
| cccaagtcta ctaagcataa ttggctacaa tacaacaagc actgtcccaa | 1000 |
| aggaagggca gtcagtccag tggtggcatg ctcaaggaat tataggacta | 1050 |
| attctctttt tgttgtgtgt attttattcc agcatccgta cttcaaacaa | 1100 |
| tagtcaggtt aataaactga ctctaacaag tgatgaatct acattaatag | 1150 |
| aagatggtgg agctagaagt gatggatcac tggaggatgg ggacgatgtt | 1200 |
| caccgagctg tagataatga aagggatggt gtcacttaca gttattcctt | 1250 |
| ctttcacttc atgcttttcc tggcttcact ttatatcatg atgacccttta | 1300 |
| ccaactggtc caggtatgaa ccctctcgtg agatgaaaag tcagtggaca | 1350 |
| gctgtctggg tgaaaatctc ttccagttgg attggcatcg tgctgtatgt | 1400 |
| ttggacactc gtggcaccac ttgttcttac aaatcgtgat tttgactgag | 1450 |
| tgagacttct agcatgaaag tcccactttg attattgctt atttgaaaac | 1500 |
| agtattccca acttttgtaa agttgtgtat gttttttgctt cccatgtaac | 1550 |
| ttctccagtg ttctggcatg aattagattt tactgcttgt cattttgtta | 1600 |
| ttttcttacc aagtgcattg atatgtgaag tagaatgaat tgcagaggaa | 1650 |
| agttttatga atatggtgat gagttagtaa aagtggccat tattgggctt | 1700 |
| attctctgct ctatagttgt gaaatgaaga gtaaaaacaa atttgtttga | 1750 |
| ctattttaaa attatattag accttaagct gttttagcaa gcattaaagc | 1800 |
| aaatgtatgg ctgccttttg aaatatttga tgtgttgcct ggcaggatac | 1850 |
| tgcaaagaac atggtttatt ttaaaattta taaacaagtc acttaaatgc | 1900 |
| cagttgtctg aaaaatctta taaggtttta cccttgatac ggaatttaca | 1950 |
| caggtaggga gtgtttagtg gacaatagtg taggttatgg atggaggtgt | 2000 |
| cggtactaaa ttgaataacg agtaaataat cttacttggg tagagatggc | 2050 |
| cttttgccaac aaagtgaact gttttggttg ttttaaactc atgaagtatg | 2100 |
| ggttcagtgg aaatgtttgg aactctgaag gatttagaca aggttttgaa | 2150 |
| aaggataatc atgggttaga aggaagtgtt ttgaaagtca ctttgaaagt | 2200 |
| tagttttggg cccagcacgg tagctcaccc ttggtaatcc cagcactttg | 2250 |
| ggagcttaag tgggtagatt acttgagccc aggaattcag accagcttgg | 2300 |
| cacatggtga acctgttcta taaaaataat ctggctttga gcatatgcct | 2350 |
| gtggtccagc actgagaggc tagtgaagat tgctgagccc agagccaaag | 2400 |
| gttgcagtga gcaagtcacg tcactgcact ctagctggca cagagtaagc | 2450 |
| caaaaaaata tatatatt gaaatcaagg aggcaaaatt ttgacaggga | 2500 |
| aggaagtaac tgcaaaacca ctaggcttta gtaggtactt atataaaatc | 2550 |
| tagtccagtt ctctcattta aaaaaatgaa gacactgaaa tacagactta | 2600 |
| aatagctcag atagctaatt aggaaatttc aagttggcca ataatagcat | 2650 |

-continued

```
tctctctgac atttaaaaat aatttctatt caaaatacat gcatattgat        2700
ttacacctca tactgtgata attaatgtga tgtggattgc tggtgtccag        2750
catgacccat aaacaggtca gaagaatgat ggaatgtttt agaataaact        2800
cctgcttata gtatactaca cagttcaaaa gatgtttaaa atgcttttgt        2850
atttactgcc atgtaattga aatatataga ttattgtaac ctttcaacct        2900
gaaaatcaag cagtatgaga gtttagttat ttgtatgtgt cactagtgtc        2950
taatgaagct tttaaaatct acaatttctt ctttaaaaat atttattaat        3000
gtgaatggaa tataacaatt cagcttaatt ccccaacctt attctgtgtg        3050
tagacattgt attccacaat tttgaatggc tgtgttttac ctctaaataa        3100
atgaattcag agaaaaaaaa aaaaaaa                                 3127
```

<210> SEQ ID NO 30
<211> LENGTH: 453
<212> TYPE: PRT
<213> ORGANISM: Homo sapiens

<400> SEQUENCE: 30

```
Met Gly Ser Val Leu Gly Leu Cys Ser Met Ala Ser Trp Ile Pro
 1               5                  10                  15

Cys Leu Cys Gly Ser Ala Pro Cys Leu Cys Arg Cys Cys Pro
            20                  25                  30

Ser Gly Asn Asn Ser Thr Val Thr Arg Leu Ile Tyr Ala Leu Phe
            35                  40                  45

Leu Leu Val Gly Val Cys Val Ala Cys Val Met Leu Ile Pro Gly
            50                  55                  60

Met Glu Glu Gln Leu Asn Lys Ile Pro Gly Phe Cys Glu Asn Glu
            65                  70                  75

Lys Gly Val Val Pro Cys Asn Ile Leu Val Gly Tyr Lys Ala Val
            80                  85                  90

Tyr Arg Leu Cys Phe Gly Leu Ala Met Phe Tyr Leu Leu Ser
            95                  100                 105

Leu Leu Met Ile Lys Val Lys Ser Ser Ser Asp Pro Arg Ala Ala
            110                 115                 120

Val His Asn Gly Phe Trp Phe Phe Lys Phe Ala Ala Ile Ala
            125                 130                 135

Ile Ile Ile Gly Ala Phe Phe Ile Pro Glu Gly Thr Phe Thr Thr
            140                 145                 150

Val Trp Phe Tyr Val Gly Met Ala Gly Ala Phe Cys Phe Ile Leu
            155                 160                 165

Ile Gln Leu Val Leu Leu Ile Asp Phe Ala His Ser Trp Asn Glu
            170                 175                 180

Ser Trp Val Glu Lys Met Glu Glu Gly Asn Ser Arg Cys Trp Tyr
            185                 190                 195

Ala Ala Leu Leu Ser Ala Thr Ala Leu Asn Tyr Leu Leu Ser Leu
            200                 205                 210

Val Ala Ile Val Leu Phe Phe Val Tyr Tyr Thr His Pro Ala Ser
            215                 220                 225

Cys Ser Glu Asn Lys Ala Phe Ile Ser Val Asn Met Leu Leu Cys
            230                 235                 240

Val Gly Ala Ser Val Met Ser Ile Leu Pro Lys Ile Gln Glu Ser
            245                 250                 255
```

```
Gln Pro Arg Ser Gly Leu Leu Gln Ser Ser Val Ile Thr Val Tyr
            260                 265                 270

Thr Met Tyr Leu Thr Trp Ser Ala Met Thr Asn Glu Pro Glu Thr
            275                 280                 285

Asn Cys Asn Pro Ser Leu Leu Ser Ile Ile Gly Tyr Asn Thr Thr
            290                 295                 300

Ser Thr Val Pro Lys Glu Gly Gln Ser Val Gln Trp Trp His Ala
            305                 310                 315

Gln Gly Ile Ile Gly Leu Ile Leu Phe Leu Leu Cys Val Phe Tyr
            320                 325                 330

Ser Ser Ile Arg Thr Ser Asn Asn Ser Gln Val Asn Lys Leu Thr
            335                 340                 345

Leu Thr Ser Asp Glu Ser Thr Leu Ile Glu Asp Gly Gly Ala Arg
            350                 355                 360

Ser Asp Gly Ser Leu Glu Asp Gly Asp Val His Arg Ala Val
            365                 370                 375

Asp Asn Glu Arg Asp Gly Val Thr Tyr Ser Tyr Ser Phe Phe His
            380                 385                 390

Phe Met Leu Phe Leu Ala Ser Leu Tyr Ile Met Met Thr Leu Thr
            395                 400                 405

Asn Trp Ser Arg Tyr Glu Pro Ser Arg Glu Met Lys Ser Gln Trp
            410                 415                 420

Thr Ala Val Trp Val Lys Ile Ser Ser Ser Trp Ile Gly Ile Val
            425                 430                 435

Leu Tyr Val Trp Thr Leu Val Ala Pro Leu Val Leu Thr Asn Arg
            440                 445                 450

Asp Phe Asp

<210> SEQ ID NO 31
<211> LENGTH: 485
<212> TYPE: DNA
<213> ORGANISM: Homo sapiens

<400> SEQUENCE: 31
gctcaagacc cagcagtggg acagccagac agacggcacg atggcactga        50
gctcccagat ctgggccgct tgcctcctgc tcctcctcct cctcgccagc       100
ctgaccagtg gctctgtttt cccacaacag acgggacaac ttgcagagct       150
gcaaccccag gacagagctg gagccagggc cagctggatg cccatgttcc       200
agaggcgaag gaggcgagac acccacttcc ccatctgcat tttctgctgc       250
ggctgctgtc atcgatcaaa gtgtgggatg tgctgcaaga cgtagaacct       300
acctgccctg cccccgtccc ctcccttcct tatttattcc tgctgcccca       350
gaacataggt cttggaataa aatggctggt tcttttgttt tccaaaaaaa       400
aaaaaaaaaa aaaaaaaaaa aaaaaaaaaa aaaaaaaaaa aaaaaaaaaa       450
aaaaaaaaaa aaaaaaaaaa aaaaaaaaaa  aaaaa                     485

<210> SEQ ID NO 32
<211> LENGTH: 84
<212> TYPE: PRT
<213> ORGANISM: Homo sapiens

<400> SEQUENCE: 32

Met Ala Leu Ser Ser Gln Ile Trp Ala Ala Cys Leu Leu Leu Leu
  1               5                  10                  15
```

```
Leu Leu Leu Ala Ser Leu Thr Ser Gly Ser Val Phe Pro Gln Gln
            20                  25                  30

Thr Gly Gln Leu Ala Glu Leu Gln Pro Gln Asp Arg Ala Gly Ala
            35                  40                  45

Arg Ala Ser Trp Met Pro Met Phe Gln Arg Arg Arg Arg Arg Asp
            50                  55                  60

Thr His Phe Pro Ile Cys Ile Phe Cys Cys Gly Cys Cys His Arg
            65                  70                  75

Ser Lys Cys Gly Met Cys Cys Lys Thr
            80

<210> SEQ ID NO 33
<211> LENGTH: 1245
<212> TYPE: DNA
<213> ORGANISM: Homo sapiens

<400> SEQUENCE: 33
ggcctcggtt caaacgaccc ggtgggtcta cagcggaagg gagggagcga        50
aggtaggagg cagggcttgc ctcactggcc accctcccaa ccccaagagc       100
ccagccccat ggtccccgcc gccggcgcgc tgctgtgggt cctgctgctg       150
aatctgggtc cccgggcggc gggggcccaa ggcctgaccc agactccgac       200
cgaaatgcag cgggtcagtt tacgctttgg gggccccatg acccgcagct       250
accggagcac cgcccggact ggtcttcccc ggaagacaag gataatccta       300
gaggacgaga atgatgccat ggccgacgcc gaccgcctgg ctggaccagc       350
ggctgccgag ctcttggccg ccacggtgtc caccggcttt agccggtcgt       400
ccgccattaa cgaggaggat gggtcttcag aagagggggt tgtgattaat       450
gccggaaagg atagcaccag cagagagctt cccagtgcga ctcccaatac       500
agcggggagt tccagcacga ggtttatagc aatagtcag gagcctgaaa        550 tcaggctgac ttcaagcctg ccgcgctccc ccgggaggtc tactgaggac       600
ctgccaggct cgcaggccac cctgagccag tggtccacac ctgggtctac       650
cccgagccgg tggccgtcac cctcacccac agccatgcca tctcctgagg       700
atctgcggct ggtgctgatg ccctgggggcc cgtggcactg ccactgcaag      750
tcgggcacca tgagccggag ccggtctggg aagctgcacg gcctttccgg       800
gcgccttcga gttggggcgc tgagccagct ccgcacggag cacaagcctt       850
gcacctatca acaatgtccc tgcaaccgac ttcgggaaga gtgcccctg        900 gacacaagtc tctgtactga caccaactgt gcctctcaga gcaccaccag       950
taccaggacc accactaccc ccttccccac catccacctc agaagcagtc      1000
ccagcctgcc accgccagc ccctgcccag ccctggcttt ttggaaacgg       1050
gtcaggattg gcctggagga tatttggaat agcctctctt cagtgttcac       1100
agagatgcaa ccaatagaca gaaaccagag gtaatggcca cttcatccac       1150
atgaggagat gtcagtatct caacctctct tgcccttca atcctagcac        1200 ccactagata ttttagtac agaaaaacaa aactggaaaa cacaa            1245

<210> SEQ ID NO 34
<211> LENGTH: 341
<212> TYPE: PRT
<213> ORGANISM: Homo sapiens

<400> SEQUENCE: 34
```

```
Met Val Pro Ala Ala Gly Ala Leu Leu Trp Val Leu Leu Leu Asn
  1               5                  10                  15

Leu Gly Pro Arg Ala Ala Gly Ala Gln Gly Leu Thr Gln Thr Pro
             20                  25                  30

Thr Glu Met Gln Arg Val Ser Leu Arg Phe Gly Gly Pro Met Thr
             35                  40                  45

Arg Ser Tyr Arg Ser Thr Ala Arg Thr Gly Leu Pro Arg Lys Thr
             50                  55                  60

Arg Ile Ile Leu Glu Asp Glu Asn Asp Ala Met Ala Asp Ala Asp
             65                  70                  75

Arg Leu Ala Gly Pro Ala Ala Ala Glu Leu Leu Ala Ala Thr Val
             80                  85                  90

Ser Thr Gly Phe Ser Arg Ser Ser Ala Ile Asn Glu Glu Asp Gly
             95                 100                 105

Ser Ser Glu Glu Gly Val Val Ile Asn Ala Gly Lys Asp Ser Thr
            110                 115                 120

Ser Arg Glu Leu Pro Ser Ala Thr Pro Asn Thr Ala Gly Ser Ser
            125                 130                 135

Ser Thr Arg Phe Ile Ala Asn Ser Gln Glu Pro Glu Ile Arg Leu
            140                 145                 150

Thr Ser Ser Leu Pro Arg Ser Pro Gly Arg Ser Thr Glu Asp Leu
            155                 160                 165

Pro Gly Ser Gln Ala Thr Leu Ser Gln Trp Ser Thr Pro Gly Ser
            170                 175                 180

Thr Pro Ser Arg Trp Pro Ser Pro Ser Thr Ala Met Pro Ser
            185                 190                 195

Pro Glu Asp Leu Arg Leu Val Leu Met Pro Trp Gly Pro Trp His
            200                 205                 210

Cys His Cys Lys Ser Gly Thr Met Ser Arg Ser Arg Ser Gly Lys
            215                 220                 225

Leu His Gly Leu Ser Gly Arg Leu Arg Val Gly Ala Leu Ser Gln
            230                 235                 240

Leu Arg Thr Glu His Lys Pro Cys Thr Tyr Gln Gln Cys Pro Cys
            245                 250                 255

Asn Arg Leu Arg Glu Glu Cys Pro Leu Asp Thr Ser Leu Cys Thr
            260                 265                 270

Asp Thr Asn Cys Ala Ser Gln Ser Thr Thr Ser Thr Arg Thr Thr
            275                 280                 285

Thr Thr Pro Phe Pro Thr Ile His Leu Arg Ser Ser Pro Ser Leu
            290                 295                 300

Pro Pro Ala Ser Pro Cys Pro Ala Leu Ala Phe Trp Lys Arg Val
            305                 310                 315

Arg Ile Gly Leu Glu Asp Ile Trp Asn Ser Leu Ser Ser Val Phe
            320                 325                 330

Thr Glu Met Gln Pro Ile Asp Arg Asn Gln Arg
            335                 340
```

<210> SEQ ID NO 35
<211> LENGTH: 3089
<212> TYPE: DNA
<213> ORGANISM: Homo sapiens

<400> SEQUENCE: 35
caggaaccct ctctttgggt ctggattggg acccctttcc agtaccattt         50

| | |
|---|---|
| tttctagtga accacgaagg gacgatacca gaaaacaccc tcaacccaaa | 100 |
| ggaaatagac tacagcccca attggctgac tttggctata gaaaaaagaa | 150 |
| aggaacgaaa agagacagtt ttttttggaa agctaagtct tccctttatc | 200 |
| gagtcaagaa acccccccctt cttgagctat ttacagcttt taacaattga | 250 |
| gtaaagtacg ctccggtcac catggtgaca gccgccctgg gtcccgtctg | 300 |
| ggcagcgctc ctgctctttc tcctgatgtg tgagatccgt atggtggagc | 350 |
| tcacctttga cagagctgtg gccagcggct gccaacggtg ctgtgactct | 400 |
| gaggaccccc tggatcctgc ccatgtatcc tcagcctctt cctccggccg | 450 |
| cccccacgcc ctgcctgaga tcagacccta cattaatatc accatcctga | 500 |
| agggtgacaa aggggaccca ggcccaatgg gcctgcagg gtacatgggc | 550 |
| agggagggtc cccaagggga gcctggccct cagggcagca agggtgacaa | 600 |
| gggggagatg ggcagccccg gcgccccgtg ccagaagcgc ttcttcgcct | 650 |
| tctcagtggg ccgcaagacg gccctgcaca gcggcgagga cttccagacg | 700 |
| ctgctcttcg aaagggtctt tgtgaacctt gatgggtgct ttgacatggc | 750 |
| gaccggccag tttgctgctc ccctgcgtgg catctacttc ttcagcctca | 800 |
| atgtgcacag ctggaattac aaggagacgt acgtgcacat tatgcataac | 850 |
| cagaaagagg ctgtcatcct gtacgcgcag cccagcgagc gcagcatcat | 900 |
| gcagagccaa agtgtgatgc tggacctggc ctacggggac cgcgtctggg | 950 |
| tgcggctctt caagcgccag cgcgagaacg ccatctacag caacgacttc | 1000 |
| gacacctaca tcaccttcag cggccacctc atcaaggccg aggacgactg | 1050 |
| agggcctctg ggccaccctc ccggctggag agctcaggtg ctggtcccgt | 1100 |
| cccctgcagg gctcagtttg cactgctgtg aagcaggaag gccagggagg | 1150 |
| tccccgggga cctggcattc tggggagacc ctgcttctat cttggctgcc | 1200 |
| atcatccctc ccagcctatt tctgctcctc tcttctctct tggacctatt | 1250 |
| ttaagaagct tgctaaccta aatattctag aactttccca gcctcgtagc | 1300 |
| ccagcacttc tcaaacttgg aaatgcatgc gaatcacccg gggttcgtgt | 1350 |
| taaatgcaga ttctgactca gcaggtctga gtgggtccag gattctgtgt | 1400 |
| ttctcatatg ttcctgggtg atgctgatgg ggtcagtcta tgaaccacac | 1450 |
| tggagcaacc aggttctagg actttctcaa tattctagta cttttctgaac | 1500 |
| attctggaat cctccccaca ttctagaatt ctcccaacat tttttttttct | 1550 |
| tgagacagag tcttgctctg ttgcccaggc tagagtgcag tggtgcaatc | 1600 |
| tcagttcact gcaacctctg cctcccgggt tcaagcgatt cttctgcctc | 1650 |
| agcctcccta gtggctggga ttacaggcgc ctgctaccat gcctggctaa | 1700 |
| ttttgtatt tttagtagag atggggtttc accatattgg ccaggctggt | 1750 |
| cttgaactcc tgacttcagg tgacccaccc gcctcggcct ctcaaaatgc | 1800 |
| tgggattaca ggtgtgagcc accgtgcctg gccaattcca acattcttaa | 1850 |
| attctctcat ccctccaggg ctcccgtgc tatgttctct ttaccccttc | 1900 |
| cccctcttct cttgctcagg cctgcaccac tgcagccacc gttcatttat | 1950 |
| tcattcatta aacactgagc actcactctg tgctgggtcc cgggaagggt | 2000 |
| gaggggtca gacacaggcc ctgccectgc cctcagtgac tggccagtcc | 2050 |

-continued

```
agcccaggcg gggagagatg tgtacatagg ttttaaagca gacccagagc         2100 tcatggggc ctgtgttctg ggtgttcagg tgctgctggt cctccattac          2150
ccactgctcc ccaaggctgg tgggacgggg tcccggtggc aggggcaggt         2200
atctccttcc cgttcctcat ccacctgccc agtgctcatc gttacagcaa         2250
accccagggg gccttggcca ggtcaagggt tctgtgagga gaggacccag         2300
gagtgtgggg gcatttgggg ggtgaagtgg cccccgaaga atggaaccca         2350
cacccatagc tctccccaca gctgatacgg catcctgcga aagacctgc          2400 cctcctcact gggatcccct tcctgcctcc tcccagggct ctgccagggc         2450
cttgctcagt cccttccacc aaagtcatct gaacttccgt ttccccaggg         2500
cctccagctg ccctcagaca ctgatgtctg tccccaggtg ctctctgccc         2550
ctcatgcccc tctcaccggc ccagtgcccc gactctccag gctttatcaa         2600
ggtgctaagg cccgggtggg cagctcctcg tctcagagcc ctcctccggc         2650
ctggtgctgc ctttacaaac acctgcagga aagggccac ggaagcccca          2700 ggctttagag ccctcagcag gtctggggag ctagagcaaa ggagggacct         2750
caggccttcc gtttcttctt ccagggtggg gtggcctggt gttcccctag         2800
ccttccaaac ccaggtggcc tgcccttctc cccagaggga ggcggcctcc         2850
gcccattggt gctcatgcag actctggggc tgaggtgccc cgggggtga          2900 tctctggtgc tcacagccga gggagccgtg gctccatggc cagatgacgg         2950
aaacagggtc tgaccaagtg ccaggaagac ctgtgctata aaccaccctg         3000
cctgatcctg cccctgcctg accccgccac gccctgccgt ccagcatgat         3050
taaagaatgc tgtctcctct tggaaaaaaa aaaaaaaaa                     3089
```

<210> SEQ ID NO 36
<211> LENGTH: 259
<212> TYPE: PRT
<213> ORGANISM: Homo sapiens

<400> SEQUENCE: 36

```
Met Val Thr Ala Ala Leu Gly Pro Val Trp Ala Ala Leu Leu Leu
 1               5                  10                  15

Phe Leu Leu Met Cys Glu Ile Arg Met Val Glu Leu Thr Phe Asp
                20                  25                  30

Arg Ala Val Ala Ser Gly Cys Gln Arg Cys Cys Asp Ser Glu Asp
                35                  40                  45

Pro Leu Asp Pro Ala His Val Ser Ser Ala Ser Ser Ser Gly Arg
                50                  55                  60

Pro His Ala Leu Pro Glu Ile Arg Pro Tyr Ile Asn Ile Thr Ile
                65                  70                  75

Leu Lys Gly Asp Lys Gly Asp Pro Gly Pro Met Gly Leu Pro Gly
                80                  85                  90

Tyr Met Gly Arg Glu Gly Pro Gln Gly Glu Pro Gly Pro Gln Gly
                95                 100                 105

Ser Lys Gly Asp Lys Gly Glu Met Gly Ser Pro Gly Ala Pro Cys
               110                 115                 120

Gln Lys Arg Phe Phe Ala Phe Ser Val Gly Arg Lys Thr Ala Leu
               125                 130                 135

His Ser Gly Glu Asp Phe Gln Thr Leu Leu Phe Glu Arg Val Phe
               140                 145                 150
```

```
Val Asn Leu Asp Gly Cys Phe Asp Met Ala Thr Gly Gln Phe Ala
            155                 160                 165

Ala Pro Leu Arg Gly Ile Tyr Phe Phe Ser Leu Asn Val His Ser
            170                 175                 180

Trp Asn Tyr Lys Glu Thr Tyr Val His Ile Met His Asn Gln Lys
            185                 190                 195

Glu Ala Val Ile Leu Tyr Ala Gln Pro Ser Glu Arg Ser Ile Met
            200                 205                 210

Gln Ser Gln Ser Val Met Leu Asp Leu Ala Tyr Gly Asp Arg Val
            215                 220                 225

Trp Val Arg Leu Phe Lys Arg Gln Arg Glu Asn Ala Ile Tyr Ser
            230                 235                 240

Asn Asp Phe Asp Thr Tyr Ile Thr Phe Ser Gly His Leu Ile Lys
            245                 250                 255

Ala Glu Asp Asp

<210> SEQ ID NO 37
<211> LENGTH: 2213
<212> TYPE: DNA
<213> ORGANISM: Homo sapiens

<400> SEQUENCE: 37
```

| | | | | | |
|---|---|---|---|---|---|
| gagcgaacat | ggcagcgcgt | tggcggtttt | ggtgtgtctc | tgtgaccatg | 50 |
| gtggtggcgc | tgctcatcgt | ttgcgacgtt | ccctcagcct | ctgcccaaag | 100 |
| aaagaaggag | atggtgttat | ctgaaaaggt | tagtcagctg | atggaatgga | 150 |
| ctaacaaaag | acctgtaata | agaatgaatg | agacaagtt | ccgtcgcctt | 200 |
| gtgaaagccc | caccgagaaa | ttactccgtt | atcgtcatgt | tcactgctct | 250 |
| ccaactgcat | agacagtgtg | tcgtttgcaa | gcaagctgat | gaagaattcc | 300 |
| agatcctggc | aaactcctgg | cgatactcca | gtgcattcac | caacaggata | 350 |
| tttttttgcca | tggtggattt | tgatgaaggc | tctgatgtat | ttcagatgct | 400 |
| aaacatgaat | tcagctccaa | cttttcatcaa | ctttcctgca | aaagggaaac | 450 |
| ccaaacgggg | tgatacatat | gagttacagg | tgcggggttt | ttcagctgag | 500 |
| cagattgccc | ggtggatcgc | cgacagaact | gatgtcaata | ttagagtgat | 550 |
| tagacccca | aattatgctg | gtccccttat | gttgggattg | cttttggctg | 600 |
| ttattggtgg | acttgtgtat | cttcgaagaa | gtaatatgga | atttctcttt | 650 |
| aataaaactg | gatgggcttt | tgcagctttg | tgttttgtgc | ttgctatgac | 700 |
| atctggtcaa | atgtggaacc | atataagagg | accaccatat | gcccataaga | 750 |
| atccccacac | gggacatgtg | aattatatcc | atggaagcag | tcaagcccag | 800 |
| tttgtagctg | aaacacacat | tgttcttctg | tttaatggtg | gagttacctt | 850 |
| aggaatggtg | ctttatgtg | aagctgctac | ctctgacatg | gatattggaa | 900 |
| agcgaaagat | aatgtgtgtg | gctggtattg | gacttgttgt | attattcttc | 950 |
| agttggatgc | tctctatttt | tagatctaaa | tatcatggct | acccatacag | 1000 |
| ctttctgatg | agttaaaaag | gtcccagaga | tatatagaca | ctggagtact | 1050 |
| ggaaattgaa | aaacgaaaat | cgtgtgtgtt | tgaaagaag | aatgcaactt | 1100 |
| gtatattttg | tattacctct | ttttttcaag | tgatttaaat | agttaatcat | 1150 |
| ttaaccaaag | aagatgtgta | gtgccttaac | aagcaatcct | ctgtcaaaat | 1200 |
| ctgaggtatt | tgaaaataat | tatcctctta | accttctctt | cccagtgaac | 1250 |

-continued

```
tttatggaac atttaattta gtacaattaa gtatattata aaaattgtaa        1300
aactactact ttgttttagt tagaacaaag ctcaaaacta ctttagttaa        1350
cttggtcatc tgattttata ttgccttatc caaagatggg gaaagtaagt        1400
cctgaccagg tgttcccaca tatgcctgtt acagataact acattaggaa        1450
ttcattctta gcttcttcat ctttgtgtgg atgtgtatac tttacgcatc        1500
tttccttttg agtagagaaa ttatgtgtgt catgtggtct tctgaaaatg        1550
gaacaccatt cttcagagca cacgtctagc cctcagcaag acagttgttt        1600
ctcctcctcc ttgcatattt cctactgcgc tccagcctga gtgatagagt        1650
gagactctgt ctcaaaaaaa agtatctcta aatacaggat tataatttct        1700
gcttgagtat ggtgttaact accttgtatt tagaaagatt tcagattcat        1750
tccatctcct tagttttctt ttaaggtgac ccatctgtga taaaaatata        1800
gcttagtgct aaaatcagtg taacttatac atggcctaaa atgtttctac        1850
aaattagagt ttgtcactta ttccatttgt acctaagaga aaaataggct        1900
cagttagaaa aggactccct ggccaggcgc agtgacttac gcctgtaatc        1950
tcagcacttt gggaggccaa ggcaggcaga tcacgaggtc aggagttcga        2000
gaccatcctg gccaacatgg tgaaaccccg tctctactaa aaatataaaa        2050
attagctggg tgtggtggca ggagcctgta atcccagcta cacaggaggc        2100
tgaggcacga gaatcacttg aactcaggag atggaggttt cagtgagccg        2150
agatcacgcc actgcactcc agcctggcaa cagagcgaga ctccatctca        2200
aaaaaaaaaa aaa                                               2213
```

<210> SEQ ID NO 38
<211> LENGTH: 335
<212> TYPE: PRT
<213> ORGANISM: Homo sapiens

<400> SEQUENCE: 38

```
Met Ala Ala Arg Trp Arg Phe Trp Cys Val Ser Val Thr Met Val
 1               5                  10                  15

Val Ala Leu Leu Ile Val Cys Asp Val Pro Ser Ala Ser Ala Gln
                20                  25                  30

Arg Lys Lys Glu Met Val Leu Ser Glu Lys Val Ser Gln Leu Met
                35                  40                  45

Glu Trp Thr Asn Lys Arg Pro Val Ile Arg Met Asn Gly Asp Lys
                50                  55                  60

Phe Arg Arg Leu Val Lys Ala Pro Pro Arg Asn Tyr Ser Val Ile
                65                  70                  75

Val Met Phe Thr Ala Leu Gln Leu His Arg Gln Cys Val Val Cys
                80                  85                  90

Lys Gln Ala Asp Glu Glu Phe Gln Ile Leu Ala Asn Ser Trp Arg
                95                 100                 105

Tyr Ser Ser Ala Phe Thr Asn Arg Ile Phe Phe Ala Met Val Asp
               110                 115                 120

Phe Asp Glu Gly Ser Asp Val Phe Gln Met Leu Asn Met Asn Ser
               125                 130                 135

Ala Pro Thr Phe Ile Asn Phe Pro Ala Lys Gly Lys Pro Lys Arg
               140                 145                 150

Gly Asp Thr Tyr Glu Leu Gln Val Arg Gly Phe Ser Ala Glu Gln
```

```
                 155                 160                 165
Ile Ala Arg Trp Ile Ala Asp Arg Thr Asp Val Asn Ile Arg Val
            170                 175                 180
Ile Arg Pro Pro Asn Tyr Ala Gly Pro Leu Met Leu Gly Leu Leu
            185                 190                 195
Leu Ala Val Ile Gly Gly Leu Val Tyr Leu Arg Arg Ser Asn Met
            200                 205                 210
Glu Phe Leu Phe Asn Lys Thr Gly Trp Ala Phe Ala Ala Leu Cys
            215                 220                 225
Phe Val Leu Ala Met Thr Ser Gly Gln Met Trp Asn His Ile Arg
            230                 235                 240
Gly Pro Pro Tyr Ala His Lys Asn Pro His Thr Gly His Val Asn
            245                 250                 255
Tyr Ile His Gly Ser Ser Gln Ala Gln Phe Val Ala Glu Thr His
            260                 265                 270
Ile Val Leu Leu Phe Asn Gly Gly Val Thr Leu Gly Met Val Leu
            275                 280                 285
Leu Cys Glu Ala Ala Thr Ser Asp Met Asp Ile Gly Lys Arg Lys
            290                 295                 300
Ile Met Cys Val Ala Gly Ile Gly Leu Val Val Leu Phe Phe Ser
            305                 310                 315
Trp Met Leu Ser Ile Phe Arg Ser Lys Tyr His Gly Tyr Pro Tyr
            320                 325                 330
Ser Phe Leu Met Ser
            335

<210> SEQ ID NO 39
<211> LENGTH: 1648
<212> TYPE: DNA
<213> ORGANISM: Homo sapiens

<400> SEQUENCE: 39
caggccattt gcatcccact gtccttgtgt tcggagccag gccacaccgt          50
cctcagcagt gtcatgtgtt aaaaacgcca agctgaatat atcatgcccc         100
tattaaaact tgtacatggc tccccattgg tttttggaga aaagttcaag         150 cttttttacct tggtgtctgc ctgtatccca gtgttcaggc tggctagacg        200
gcggaagaag atcctatttt actgtcactt cccagatctg cttctcacca         250
agagagattc ttttcttaaa cgactataca gggccccaat tgactggata         300
gaggaataca ccacaggcat ggcagactgc atcttagtca acagccagtt         350
cacagctgct gttttaagg aaacattcaa gtccctgtct cacatagacc          400
ctgatgtcct ctatccatct ctaaatgtca ccagctttga ctcagttgtt         450
cctgaaaagc tggatgacct agtccccaag gggaaaaaat tcctgctgct         500
ctccatcaac agatacgaaa ggaagaaaaa tctgactttg gcactggaag         550
ccctagtaca gctgcgtgga agattgacat cccaagattg ggagagggtt         600
catctgatcg tggcaggtgg ttatgacgag agagtcctgg agaatgtgga         650
acattatcag gaattgaaga aaatggtcca acagtccgac cttggccagt         700
atgtgacctt cttgaggtct ttctcagaca acagaaaat ctccctcctc          750 cacagctgca cgtgtgtgct ttacacacca agcaatgagc actttggcat         800
tgtccctctg gaagccatgt acatgcagtg cccagtcatt gctgttaatt         850
```

-continued

| | |
|---|---|
| cgggtggacc cttggagtcc attgaccaca gtgtcacagg gtttctgtgt | 900 |
| gagcctgacc cggtgcactt ctcagaagca atagaaaagt tcatccgtga | 950 |
| accttcctta aaagccacca tgggcctggc tggaagagcc agagtgaagg | 1000 |
| aaaaattttc ccctgaagca tttacagaac agctctaccg atatgttacc | 1050 |
| aaactgctgg tataatcaga ttgttttttaa gatctccatt aatgtcattt | 1100 |
| ttatggattg tagacccagt tttgaaacca aaaagaaac ctagaatcta | 1150 |
| atgcagaaga gatcttttaa aaaataaact tgagtcttga atgtgagcca | 1200 |
| ctttcctata taccacacct ccctgtccac ttttcagaaa aaccatgtct | 1250 |
| tttatgctat aatcattcca aattttgcca gtgttaagtt acaaatgtgg | 1300 |
| tgtcattcca tgttcagcag agtattttaa ttatattttc tcgggattat | 1350 |
| tgctcttctg tctataaatt ttgaatgata ctgtgcctta attggttttc | 1400 |
| atagtttaag tgtgtatcat tatcaaagtt gattaatttg gcttcatagt | 1450 |
| ataatgagag cagggctatt gtagttccca gattcaatcc accgaagtgt | 1500 |
| tcactgtcat ctgttaggga attttttgttt gtcctgtctt tgcctggatc | 1550 |
| catagcgaga gtgctctgta ttttttttaa gataatttgt attttttgcac | 1600 |
| actgagatat aataaaaggt gtttatcata aaaaaaaaa aaaaaaaa | 1648 |

<210> SEQ ID NO 40
<211> LENGTH: 323
<212> TYPE: PRT
<213> ORGANISM: Homo sapiens

<400> SEQUENCE: 40

```
Met Pro Leu Leu Lys Leu Val His Gly Ser Pro Leu Val Phe Gly
 1               5                  10                  15

Glu Lys Phe Lys Leu Phe Thr Leu Val Ser Ala Cys Ile Pro Val
                20                  25                  30

Phe Arg Leu Ala Arg Arg Lys Lys Ile Leu Phe Tyr Cys His
            35                  40                  45

Phe Pro Asp Leu Leu Leu Thr Lys Arg Asp Ser Phe Leu Lys Arg
            50                  55                  60

Leu Tyr Arg Ala Pro Ile Asp Trp Ile Glu Glu Tyr Thr Thr Gly
        65                  70                  75

Met Ala Asp Cys Ile Leu Val Asn Ser Gln Phe Thr Ala Ala Val
                80                  85                  90

Phe Lys Glu Thr Phe Lys Ser Leu Ser His Ile Asp Pro Asp Val
            95                 100                 105

Leu Tyr Pro Ser Leu Asn Val Thr Ser Phe Asp Ser Val Val Pro
           110                 115                 120

Glu Lys Leu Asp Asp Leu Val Pro Lys Gly Lys Lys Phe Leu Leu
           125                 130                 135

Leu Ser Ile Asn Arg Tyr Glu Arg Lys Lys Asn Leu Thr Leu Ala
           140                 145                 150

Leu Glu Ala Leu Val Gln Leu Arg Gly Arg Leu Thr Ser Gln Asp
           155                 160                 165

Trp Glu Arg Val His Leu Ile Val Ala Gly Gly Tyr Asp Glu Arg
           170                 175                 180

Val Leu Glu Asn Val Glu His Tyr Gln Glu Leu Lys Lys Met Val
           185                 190                 195

Gln Gln Ser Asp Leu Gly Gln Tyr Val Thr Phe Leu Arg Ser Phe
```

```
                  200                 205                 210
Ser Asp Lys Gln Lys Ile Ser Leu Leu His Ser Cys Thr Cys Val
                  215                 220                 225

Leu Tyr Thr Pro Ser Asn Glu His Phe Gly Ile Val Pro Leu Glu
                  230                 235                 240

Ala Met Tyr Met Gln Cys Pro Val Ile Ala Val Asn Ser Gly Gly
                  245                 250                 255

Pro Leu Glu Ser Ile Asp His Ser Val Thr Gly Phe Leu Cys Glu
                  260                 265                 270

Pro Asp Pro Val His Phe Ser Glu Ala Ile Glu Lys Phe Ile Arg
                  275                 280                 285

Glu Pro Ser Leu Lys Ala Thr Met Gly Leu Ala Gly Arg Ala Arg
                  290                 295                 300

Val Lys Glu Lys Phe Ser Pro Glu Ala Phe Thr Glu Gln Leu Tyr
                  305                 310                 315

Arg Tyr Val Thr Lys Leu Leu Val
                  320

<210> SEQ ID NO 41
<211> LENGTH: 1181
<212> TYPE: DNA
<213> ORGANISM: Homo sapiens

<400> SEQUENCE: 41
aagaccctct ctttcgctgt ttgagagtct ctcggctcaa ggaccgggag           50
gtaagaggtt tgggactgcc ccggcaactc cagggtgtct ggtccacgac          100
ctatcctagg cgccatgggt gtgataggta tacagctggt tgttaccatg          150
gtgatggcca gtgtcatgca gaagattata cctcactatt ctcttgctcg          200
atggctactc tgtaatggca gtttgaggtg gtatcaacat cctacagaag          250
aagaattaag aattcttgca gggaaacaac aaaaagggaa aaccaaaaaa          300
gataggaaat ataatggtca cattgaaagt aagccattaa ccattccaaa          350
ggatattgac cttcatctag aaacaaagtc agttacagaa gtggatactt          400
tagcattgca ttactttcca gaataccagt ggctggtgga tttcacagtg          450
gctgctacag ttgtgtatct agtaactgaa gtctactaca attttatgaa          500
gcctacacag gaaatgaata tcagcttagt ctggtgccta cttgttttgt          550
cttttgcaat caaagttcta ttttcattaa ctacacacta ttttaaagta          600
gaagatggtg gtgaaagatc tgtttgtgtc acctttggat ttttttttctt         650 tgtcaaagca atggcagtgt tgattgtaac agaaaattat ctggaatttg          700
gacttgaaac agggtttaca aattttttcag acagtgcgat gcagtttctt         750
gaaaagcaag gttagaatc tcagagtcct gttttcaaaac ttactttcaa          800 attttttcctg gctattttct gttcattcat tggggctttt ttgacatttc         850
ctggattacg actggctcaa atgcatctgg atgccctgaa tttggcaaca          900
gaaaaaatta cacaaacttt acttcatatc aacttcttgg cacctttatt          950
tatggttttg ctctgggtaa aaccaatcac caaagactac attatgaacc         1000
caccactggg caaagaaatt tccccatctg gaagatgaag ataatagtat         1050
ctaactcaca aggttatcat tggaataaat gaaagaacac atgtaatgca         1100
accagctgga attaagtgct taataaatgt tcttttcact gctttgcctc         1150
```
atcagaatta aaatagaaat acttgactag t    1181

<210> SEQ ID NO 42
<211> LENGTH: 307
<212> TYPE: PRT
<213> ORGANISM: Homo sapiens

<400> SEQUENCE: 42

```
Met Gly Val Ile Gly Ile Gln Leu Val Val Thr Met Val Met Ala
 1               5                  10                  15

Ser Val Met Gln Lys Ile Ile Pro His Tyr Ser Leu Ala Arg Trp
                20                  25                  30

Leu Leu Cys Asn Gly Ser Leu Arg Trp Tyr Gln His Pro Thr Glu
                35                  40                  45

Glu Glu Leu Arg Ile Leu Ala Gly Lys Gln Lys Gly Lys Thr
                50                  55                  60

Lys Lys Asp Arg Lys Tyr Asn Gly His Ile Glu Ser Lys Pro Leu
                65                  70                  75

Thr Ile Pro Lys Asp Ile Asp Leu His Leu Glu Thr Lys Ser Val
                80                  85                  90

Thr Glu Val Asp Thr Leu Ala Leu His Tyr Phe Pro Glu Tyr Gln
                95                 100                 105

Trp Leu Val Asp Phe Thr Val Ala Ala Thr Val Val Tyr Leu Val
               110                 115                 120

Thr Glu Val Tyr Tyr Asn Phe Met Lys Pro Thr Gln Glu Met Asn
               125                 130                 135

Ile Ser Leu Val Trp Cys Leu Leu Val Leu Ser Phe Ala Ile Lys
               140                 145                 150

Val Leu Phe Ser Leu Thr Thr His Tyr Phe Lys Val Glu Asp Gly
               155                 160                 165

Gly Glu Arg Ser Val Cys Val Thr Phe Gly Phe Phe Phe Val
               170                 175                 180

Lys Ala Met Ala Val Leu Ile Val Thr Glu Asn Tyr Leu Glu Phe
               185                 190                 195

Gly Leu Glu Thr Gly Phe Thr Asn Phe Ser Asp Ser Ala Met Gln
               200                 205                 210

Phe Leu Glu Lys Gln Gly Leu Glu Ser Gln Ser Pro Val Ser Lys
               215                 220                 225

Leu Thr Phe Lys Phe Phe Leu Ala Ile Phe Cys Ser Phe Ile Gly
               230                 235                 240

Ala Phe Leu Thr Phe Pro Gly Leu Arg Leu Ala Gln Met His Leu
               245                 250                 255

Asp Ala Leu Asn Leu Ala Thr Glu Lys Ile Thr Gln Thr Leu Leu
               260                 265                 270

His Ile Asn Phe Leu Ala Pro Leu Phe Met Val Leu Leu Trp Val
               275                 280                 285

Lys Pro Ile Thr Lys Asp Tyr Ile Met Asn Pro Pro Leu Gly Lys
               290                 295                 300

Glu Ile Ser Pro Ser Gly Arg
               305
```

<210> SEQ ID NO 43
<211> LENGTH: 2063
<212> TYPE: DNA
<213> ORGANISM: Homo sapiens

<400> SEQUENCE: 43

-continued

| | |
|---|---|
| gagagaggca gcagcttgct cagcggacaa ggatgctggg cgtgagggac | 50 |
| caaggcctgc cctgcactcg ggcctcctcc agccagtgct gaccagggac | 100 |
| ttctgacctg ctggccagcc aggacctgtg tggggaggcc ctcctgctgc | 150 |
| cttggggtga caatctcagc tccaggctac agggagaccg ggaggatcac | 200 |
| agagccagca tgttacagga tcctgacagt gatcaacctc tgaacagcct | 250 |
| cgatgtcaaa cccctgcgca aaccccgtat ccccatggag accttcagaa | 300 |
| aggtggggat cccatcatc atagcactac tgagcctggc gagtatcatc | 350 |
| attgtggttg tcctcatcaa ggtgattctg gataaatact acttcctctg | 400 |
| cgggcagcct ctccacttca tcccgaggaa gcagctgtgt gacggagagc | 450 |
| tggactgtcc cttgggggag gacgaggagc actgtgtcaa gagcttcccc | 500 |
| gaagggcctg cagtggcagt ccgcctctcc aaggaccgat ccacactgca | 550 |
| ggtgctggac tcggccacag ggaactggtt ctctgcctgt ttcgacaact | 600 |
| tcacagaagc tctcgctgag acagcctgta ggcagatggg ctacagcaga | 650 |
| gctgtggaga ttggcccaga ccaggatctg gatgttgttg aaatcacaga | 700 |
| aaacagccag gagcttcgca tgcggaactc aagtgggccc tgtctctcag | 750 |
| gctccctggt ctccctgcac tgtcttgcct gtgggaagag cctgaagacc | 800 |
| ccccgtgtgg tgggtgggga ggaggcctct gtggattctt ggccttggca | 850 |
| ggtcagcatc cagtacgaca aacagcacgt ctgtggaggg agcatcctgg | 900 |
| accccactg ggtcctcacg gcagcccact gcttcaggaa acataccgat | 950 |
| gtgttcaact ggaaggtgcg ggcaggctca gacaaactgg gcagcttccc | 1000 |
| atccctggct gtggccaaga tcatcatcat tgaattcaac cccatgtacc | 1050 |
| ccaaagacaa tgacatcgcc ctcatgaagc tgcagttccc actcactttc | 1100 |
| tcaggcacag tcaggcccat ctgtctgccc ttctttgatg aggagctcac | 1150 |
| tccagccacc ccactctgga tcattggatg gggctttacg aagcagaatg | 1200 |
| gagggaagat gtctgacata ctgctgcagg cgtcagtcca ggtcattgac | 1250 |
| agcacacggt gcaatgcaga cgatgcgtac caggggaag tcaccgagaa | 1300 |
| gatgatgtgt gcaggcatcc cggaaggggg tgtggacacc tgccagggtg | 1350 |
| acagtggtgg gccctgatg taccaatctg accagtggca tgtggtgggc | 1400 |
| atcgttagct ggggctatgg ctgcggggc ccgagcaccc caggagtata | 1450 |
| caccaaggtc tcagcctatc tcaactggat ctacaatgtc tggaaggctg | 1500 |
| agctgtaatg ctgctgcccc tttgcagtgc tgggagccgc ttccttcctg | 1550 |
| ccctgcccac ctggggatcc cccaaagtca gacacagagc aagagtcccc | 1600 |
| ttgggtacac ccctctgccc acagcctcag catttcttgg agcagcaaag | 1650 |
| ggcctcaatt cctgtaagag accctcgcag cccagaggcg cccagaggaa | 1700 |
| gtcagcagcc ctagctcggc cacacttggt gctcccagca tcccagggag | 1750 |
| agacacagcc cactgaacaa ggtctcaggg gtattgctaa gccaagaagg | 1800 |
| aactttccca cactactgaa tggaagcagg ctgtcttgta aaagcccaga | 1850 |
| tcactgtggg ctggagagga gaaggaaagg gtctgcgcca gccctgtccg | 1900 |
| tcttcaccca tccccaagcc tactagagca agaaaccagt tgtaatataa | 1950 |
| aatgcactgc cctactgttg gtatgactac cgttacctac tgttgtcatt | 2000 |

```
gttattacag ctatggccac tattattaaa gagctgtgta acatctctgg          2050
caaaaaaaaa aaa                                                   2063
```

<210> SEQ ID NO 44
<211> LENGTH: 432
<212> TYPE: PRT
<213> ORGANISM: Homo sapiens

<400> SEQUENCE: 44

```
Met Leu Gln Asp Pro Asp Ser Asp Gln Pro Leu Asn Ser Leu Asp
  1               5                  10                  15

Val Lys Pro Leu Arg Lys Pro Arg Ile Pro Met Glu Thr Phe Arg
                 20                  25                  30

Lys Val Gly Ile Pro Ile Ile Ile Ala Leu Leu Ser Leu Ala Ser
                 35                  40                  45

Ile Ile Ile Val Val Leu Ile Lys Val Ile Leu Asp Lys Tyr
                 50                  55                  60

Tyr Phe Leu Cys Gly Gln Pro Leu His Phe Ile Pro Arg Lys Gln
                 65                  70                  75

Leu Cys Asp Gly Glu Leu Asp Cys Pro Leu Gly Glu Asp Glu Glu
                 80                  85                  90

His Cys Val Lys Ser Phe Pro Glu Gly Pro Ala Val Ala Val Arg
                 95                 100                 105

Leu Ser Lys Asp Arg Ser Thr Leu Gln Val Leu Asp Ser Ala Thr
                110                 115                 120

Gly Asn Trp Phe Ser Ala Cys Phe Asp Asn Phe Thr Glu Ala Leu
                125                 130                 135

Ala Glu Thr Ala Cys Arg Gln Met Gly Tyr Ser Arg Ala Val Glu
                140                 145                 150

Ile Gly Pro Asp Gln Asp Leu Asp Val Val Glu Ile Thr Glu Asn
                155                 160                 165

Ser Gln Glu Leu Arg Met Arg Asn Ser Ser Gly Pro Cys Leu Ser
                170                 175                 180

Gly Ser Leu Val Ser Leu His Cys Leu Ala Cys Gly Lys Ser Leu
                185                 190                 195

Lys Thr Pro Arg Val Val Gly Glu Glu Ala Ser Val Asp Ser
                200                 205                 210

Trp Pro Trp Gln Val Ser Ile Gln Tyr Asp Lys Gln His Val Cys
                215                 220                 225

Gly Gly Ser Ile Leu Asp Pro His Trp Val Leu Thr Ala Ala His
                230                 235                 240

Cys Phe Arg Lys His Thr Asp Val Phe Asn Trp Lys Val Arg Ala
                245                 250                 255

Gly Ser Asp Lys Leu Gly Ser Phe Pro Ser Leu Ala Val Ala Lys
                260                 265                 270

Ile Ile Ile Ile Glu Phe Asn Pro Met Tyr Pro Lys Asp Asn Asp
                275                 280                 285

Ile Ala Leu Met Lys Leu Gln Phe Pro Leu Thr Phe Ser Gly Thr
                290                 295                 300

Val Arg Pro Ile Cys Leu Pro Phe Phe Asp Glu Glu Leu Thr Pro
                305                 310                 315

Ala Thr Pro Leu Trp Ile Ile Gly Trp Gly Phe Thr Lys Gln Asn
                320                 325                 330

Gly Gly Lys Met Ser Asp Ile Leu Leu Gln Ala Ser Val Gln Val
```

```
                      335                 340                 345
Ile Asp Ser Thr Arg Cys Asn Ala Asp Asp Ala Tyr Gln Gly Glu
                350                 355                 360
Val Thr Glu Lys Met Met Cys Ala Gly Ile Pro Glu Gly Gly Val
            365                 370                 375
Asp Thr Cys Gln Gly Asp Ser Gly Gly Pro Leu Met Tyr Gln Ser
        380                 385                 390
Asp Gln Trp His Val Val Gly Ile Val Ser Trp Gly Tyr Gly Cys
    395                 400                 405
Gly Gly Pro Ser Thr Pro Gly Val Tyr Thr Lys Val Ser Ala Tyr
410                 415                 420
Leu Asn Trp Ile Tyr Asn Val Trp Lys Ala Glu Leu
            425                 430

<210> SEQ ID NO 45
<211> LENGTH: 2714
<212> TYPE: DNA
<213> ORGANISM: Homo sapiens

<400> SEQUENCE: 45
cggacgcgtg ggtggcaacc aggagaagcc aaacttggtc ccccggctcg          50
cggagtgcct gcgagcggtg ctcatggcgc tctatgaggt cttctctcac         100
ccggtcgagc gcagttaccg cgcggggctc tgctccaaag ccgcgctgtt         150
cctgctgctg gccgctgcgc tcacgtacat cccgccgctg ctggtggcct         200
tccggagcca cgggttttgg ctgaagcgga gcagctacga ggagcagccg         250
accgtgcgct ccaacacca ggtgctgctc gtggccctgc tcggacccga          300
aagcgacggg ttcctcgcct ggagcacgtt ccccgccttc aaccggctgc         350
aaggggatcg cctgcgcgtc ccgctcgttt cgactagaga agaagacagg         400
aaccaggatg ggaagacgga catgttacat tttaagctgg agcttcccct         450
gcagtccacg gagcacgttc tcggtgtgca gctcatcctg actttctcct         500
atcgattaca caggatggcg accctcgtga tgcagagcat ggcgtttctc         550
cagtcctcct ttcctgtccc gggatccag ttatacgtga acggagacct          600
gaggctgcag cagaagcagc cgctgagctg tggtggccta gatgcccgat         650
acaacatatc cgtgatcaac gggaccagcc ctttgcctta tgactacgac         700
ctcacccata ttgttgctgc ctaccaggag aggaacgtta ccaccgtcct         750
gaatgatccc aaccccatct ggctggtggg cagggccgca gatgctccat         800 tgtgattaa tgctatcatc cgataccctg tggaagtcat ttcttatcag          850
ccaggattct gggagatggt aaagttcgcc tgggtacagt atgtcagcat         900
cctgcttatc ttcctctggg tgtttgaaag aatcaagatc ttcgtgtttc         950
agaatcaggt ggtgaccacc attcctgtga cagtgacgcc ccggggagac        1000
ttgtgtaagg agcacttatc ctagaaaggc catttctgaa gactcagcag        1050
gaccgtggct gcctcattgt catcttctgg aacatcttaa gaccttttg         1100 aaagagccca cgcgacacct gcgggcttgt gtgcttttcc ctcagagaca        1150
acggttcttt ccggttttgc tctacacagt tccgtatctt cagagctcct        1200
gcagaattgt cagggactag tttgtggaaa ggtctgagag ttcctggagg        1250
ctataattag cttttggggt tttccttctt tgccttagcg ttgaatttca        1300
```

```
ggagaaaatt gcagtcagtt cagacatctt ggaaagagtc ccatctctgg        1350
tcaagcagag acttttcctc tgttgaactg aggaacacac tgtgcatttc        1400
ttccttctgt tgtgagccac tcttactctt ttcagggctc tcttgtgaca        1450
aacatgccaa tcactagcac tttgcacccc tgggcttctc catttcccat        1500
tcacagcttt gatttccaga gctgaggcct ttaactggag acctggaggg        1550
gcagggccca agggcaaggg ccgcattagc acaggcaatc agggagggcc        1600
gctgaaggac acttggaccg tccacctgcc ccagcccaac agtcagtcat        1650
ctgtcatcag ctcagctgag cagccctgga tctttgccgt actgtgactg        1700
ggctctttgc cctattttc cctctgtctg tgcccctgga tggcaggctg         1750
aagtcagagg ggctgtttca ttctcagccc cctcagcagc actgggggaa        1800
gaaagcattg tcaacagg ttctttctgg ccctcaccca acagcctggg          1850
cacttggccc tcctcctcct tgacagccct cccccttcct gcaaaggaca        1900
ggggcgacag gggttggtgt tgggattggc tcccgctgcc tgacaaccac        1950
aagtttattt ggaaggctag cgggaagccc agcggctggc gtttcccttg        2000
actaaggaac agggtgccca tcagagtggg gcgggcagct ttgggaagga        2050
cacaagaagc agtaagagtg taaagaggat gctggcctgg gcaggccagt        2100
ccagcctggc cactagcaga ataccaagca gtccagtgga ttaccctcgt        2150
ggctaagcaa gtgtctgcag gagcagagat ggctggaagg ggcctctgca        2200
cacggaagat ggcttgttca gcccattcac ctcctgagga tgtgggcagt        2250
ctcctccaag aacacatgga gctgcttcct gatcccaagc aggtcattgc        2300
cactggaagg acatggcccc ggtgatccat gcttcatgcc cacccagaaa        2350 cacaccctc agtgtgtgcc tcagtttact ttggagatca gttgtcgttt         2400
ttagtgctcc tttaggctta ctaaaacagt tttggaaaca aagctatttt        2450
gaagtattca agcagaggaa ttccctaaca ctgaccccct tgtctttttt        2500
taatattcag gctgttttat atgcctaaat tttttctta agatctaaac         2550 gaaaaatagt ttcttgttta aattcacata aggcaatgag atatggaaag        2600
atgacaagat acgtataaac attggtttgc atcttattaa attattctaa        2650
tgcaaatctt gtataaagaa cccatgatgt tttgtaactt tctaattaaa        2700
atgttcaaaa tgag                                              2714
```

<210> SEQ ID NO 46
<211> LENGTH: 316
<212> TYPE: PRT
<213> ORGANISM: Homo sapiens

<400> SEQUENCE: 46

Met Ala Leu Tyr Glu Val Phe Ser His Pro Val Glu Arg Ser Tyr
1               5                   10                  15

Arg Ala Gly Leu Cys Ser Lys Ala Ala Leu Phe Leu Leu Leu Ala
                20                  25                  30

Ala Ala Leu Thr Tyr Ile Pro Pro Leu Leu Val Ala Phe Arg Ser
                35                  40                  45

His Gly Phe Trp Leu Lys Arg Ser Ser Tyr Glu Glu Gln Pro Thr
                50                  55                  60

Val Arg Phe Gln His Gln Val Leu Leu Val Ala Leu Leu Gly Pro
                65                  70                  75

```
Glu Ser Asp Gly Phe Leu Ala Trp Ser Thr Phe Pro Ala Phe Asn
             80                  85                  90
Arg Leu Gln Gly Asp Arg Leu Arg Val Pro Leu Val Ser Thr Arg
             95                 100                 105
Glu Glu Asp Arg Asn Gln Asp Gly Lys Thr Asp Met Leu His Phe
            110                 115                 120
Lys Leu Glu Leu Pro Leu Gln Ser Thr Glu His Val Leu Gly Val
            125                 130                 135
Gln Leu Ile Leu Thr Phe Ser Tyr Arg Leu His Arg Met Ala Thr
            140                 145                 150
Leu Val Met Gln Ser Met Ala Phe Leu Gln Ser Ser Phe Pro Val
            155                 160                 165
Pro Gly Ser Gln Leu Tyr Val Asn Gly Asp Leu Arg Leu Gln Gln
            170                 175                 180
Lys Gln Pro Leu Ser Cys Gly Gly Leu Asp Ala Arg Tyr Asn Ile
            185                 190                 195
Ser Val Ile Asn Gly Thr Ser Pro Phe Ala Tyr Asp Tyr Asp Leu
            200                 205                 210
Thr His Ile Val Ala Ala Tyr Gln Glu Arg Asn Val Thr Thr Val
            215                 220                 225
Leu Asn Asp Pro Asn Pro Ile Trp Leu Val Gly Arg Ala Ala Asp
            230                 235                 240
Ala Pro Phe Val Ile Asn Ala Ile Ile Arg Tyr Pro Val Glu Val
            245                 250                 255
Ile Ser Tyr Gln Pro Gly Phe Trp Glu Met Val Lys Phe Ala Trp
            260                 265                 270
Val Gln Tyr Val Ser Ile Leu Leu Ile Phe Leu Trp Val Phe Glu
            275                 280                 285
Arg Ile Lys Ile Phe Val Phe Gln Asn Gln Val Val Thr Thr Ile
            290                 295                 300
Pro Val Thr Val Thr Pro Arg Gly Asp Leu Cys Lys Glu His Leu
            305                 310                 315
Ser

<210> SEQ ID NO 47
<211> LENGTH: 3582
<212> TYPE: DNA
<213> ORGANISM: Homo sapiens

<400> SEQUENCE: 47
cggacgcgtg ggtccggcgg cctgaggctg caccgggcac gggtcggccg          50
caatccagcc tgggcggagc cggagttgcg agccgctgcc tagaggccga         100
ggagctcaca gctatgggct ggaggccccg gagagctcgg ggacccccgt         150
tgctgctgct gctactactg ctgctgctct ggccagtgcc aggcgccggg         200
gtgcttcaag acatatccc tgggcagcca gtcaccccgc actgggtcct          250
ggatggacaa ccctggcgca ccgtcagcct ggaggagccg gtctcgaagc         300
cagacatggg gctggtggcc ctggaggctg aaggccagga gctcctgctt         350
gagctggaga agaaccacag gctgctggcc ccaggataca tagaaaccca         400
ctacggccca gatgggcagc cagtggtgct ggcccccaac cacacggatc         450
attgccacta ccaagggcga gtaaggggct tcccgactc ctgggtagtc          500
ctctgcacct gctctgggat gagtggcctg atcaccctca gcaggaatgc         550
```

```
cagctattat ctgcgtccct ggccaccccg gggctccaag gacttctcaa        600
cccacgagat ctttcggatg gagcagctgc tcacctggaa aggaacctgt        650
ggccacaggg atcctgggaa caaagcgggc atgaccagcc ttcctggtgg        700
tccccagagc aggggcaggc gagaagcgcg caggacccgg aagtacctgg        750
aactgtacat tgtggcagac cacaccctgt tcttgactcg gcaccgaaac        800
ttgaaccaca ccaaacagcg tctcctggaa gtcgccaact acgtggacca        850
gcttctcagg actctggaca ttcaggtggc gctgaccggc ctggaggtgt        900
ggaccgagcg ggaccgcagc cgcgtcacgc aggacgccaa cgccacgctc        950
tgggccttcc tgcagtggcg ccgggggctg tgggcgcagc ggccccacga       1000
ctccgcgcag ctgctcacgg gccgcgcctt ccagggcgcc acagtgggcc       1050
tggcgcccgt cgagggcatg tgccgcgccg agagctcggg aggcgtgagc       1100
acggaccact cggagctccc catcggcgcc gcagccacca tgcccatga        1150 gatcggccac agcctcggcc tcagccacga ccccgacggc tgctgcgtgg       1200
aggctgcggc cgagtccgga ggctgcgtca tggctgcggc caccgggcac       1250
ccgtttccgc gcgtgttcag cgcctgcagc cgccgccagc tgcgcgcctt       1300
cttccgcaag gggggcggcg cttgcctctc caatgccccg gaccccggac       1350
tcccggtgcc gccggcgctc tgcgggaacg gcttcgtgga agcgggcgag       1400
gagtgtgact gcgccctgg ccaggagtgc cgcgacctct gctgctttgc       1450
tcacaactgc tcgctgcgcc cgggggccca gtgcgcccac ggggactgct       1500
gcgtgcgctg cctgctgaag ccggctggag cgctgtgccg ccaggccatg       1550
ggtgactgtg acctccctga gttttgcacg ggcacctcct cccactgtcc       1600
cccagacgtt tacctactgg acggctcacc ctgtgccagg ggcagtggct       1650
actgctggga tggcgcatgt cccacgctgg agcagcagtg ccagcagctc       1700
tgggggcctg gctcccaccc agctcccgag gcctgtttcc aggtggtgaa       1750
ctctgcggga gatgctcatg gaaactgcgg ccaggacagc gagggccact       1800
tcctgccctg tgcagggagg gatgcccctgt gtgggaagct gcagtgccag       1850
ggtggaaagc ccagcctgct cgcaccgcac atggtgccag tggactctac       1900
cgttcaccta gatggccagg aagtgacttg tcggggagcc ttggcactcc       1950
ccagtgccca gctggacctg cttggcctgg gcctggtaga gccaggcacc       2000
cagtgtggac ctagaatggt gtgccagagc aggcgctgca ggaagaatgc       2050
cttccaggag cttcagcgct gcctgactgc ctgccacagc cacggggttt       2100
gcaatagcaa ccataactgc cactgtgctc caggctgggc tccacccttc       2150
tgtgacaagc caggctttgg tggcagcatg gacagtggcc ctgtgcaggc       2200
tgaaaaccat gacaccttcc tgctggccat gctcctcagc gtcctgctgc       2250
ctctgctccc aggggccggc ctggcctggt gttgctaccg actcccagga       2300
gcccatctgc agcgatgcag ctggggctgc agaagggacc ctgcgtgcag       2350
tggccccaaa gatggcccac acagggacca cccctgggc ggcgttcacc        2400 ccatggagtt gggccccaca gccactggac agcctggcc cctggaccct        2450 gagaactctc atgagcccag cagccaccct gagaagcctc tgccagcagt       2500
ctcgcctgac ccccaagcag atcaagtcca gatgccaaga tcctgcctct       2550
```

```
ggtgagaggt agctcctaaa atgaacagat ttaaagacag gtggccactg        2600
acagccactc caggaacttg aactgcaggg gcagagccag tgaatcaccg        2650
gacctccagc acctgcaggc agcttggaag tttcttcccc gagtggagct        2700
tcgacccacc cactccagga acccagagcc acattagaag ttcctgaggg        2750
ctggagaaca ctgcttgggc acactctcca gctcaataaa ccatcagtcc        2800
cagaagcaaa ggtcacacag cccctgacct ccctcaccag tggaggctgg        2850
gtagtgctgg ccatcccaaa agggctctgt cctgggagtc tggtgtgtct        2900
cctacatgca atttccacgg acccagctct gtggagggca tgactgctgg        2950
ccagaagcta gtggtcctgg ggccctatgg ttcgactgag tccacactcc        3000
cctgcagcct ggctggcctc tgcaaacaaa cataattttg ggaccttcc         3050 ttcctgtttc ttcccaccct gtcttctccc ctaggtggtt cctgagcccc        3100
cacccccaat cccagtgcta cacctgaggt tctggagctc agaatctgac        3150
agcctctccc ccattctgtg tgtgtccggg ggacagaggg aaccatttaa        3200
gaaaagatac caaagtagaa gtcaaaagaa agacatgttg gctataggcg        3250
tggtggctca tgcctataat cccagcactt gggaagccg  gggtaggagg        3300 atcaccagag gccagcaggt ccacaccagc ctgggcaaca cagcaagaca        3350
ccgcatctac agaaaaattt taaaattagc tgggcgtggt ggtgtgtacc        3400
tgtaggccta gctgctcagg aggctgaagc aggaggatca cttgagcctg        3450
agttcaacac tgcagtgagc tatggtggca ccactgcact ccagcctggg        3500
tgacagagca agaccctgtc tctaaaataa attttaaaag gacttaaaaa        3550
aaaaaaaaaa aaaaaaaaaa aaaaaagaa  aa                           3582
```

<210> SEQ ID NO 48
<211> LENGTH: 813
<212> TYPE: PRT
<213> ORGANISM: Homo sapiens

<400> SEQUENCE: 48

Met Gly Trp Arg Pro Arg Arg Ala Arg Gly Thr Pro Leu Leu Leu
 1               5                  10                  15

Leu Leu Leu Leu Leu Leu Trp Pro Val Pro Gly Ala Gly Val
                20                  25                  30

Leu Gln Gly His Ile Pro Gly Gln Pro Val Thr Pro His Trp Val
                35                  40                  45

Leu Asp Gly Gln Pro Trp Arg Thr Val Ser Leu Glu Glu Pro Val
                50                  55                  60

Ser Lys Pro Asp Met Gly Leu Val Ala Leu Glu Ala Glu Gly Gln
                65                  70                  75

Glu Leu Leu Leu Glu Leu Glu Lys Asn His Arg Leu Leu Ala Pro
                80                  85                  90

Gly Tyr Ile Glu Thr His Tyr Gly Pro Asp Gly Gln Pro Val Val
                95                  100                 105

Leu Ala Pro Asn His Thr Asp His Cys His Tyr Gln Gly Arg Val
                110                 115                 120

Arg Gly Phe Pro Asp Ser Trp Val Val Leu Cys Thr Cys Ser Gly
                125                 130                 135

Met Ser Gly Leu Ile Thr Leu Ser Arg Asn Ala Ser Tyr Tyr Leu
                140                 145                 150

```
Arg Pro Trp Pro Pro Arg Gly Ser Lys Asp Phe Ser Thr His Glu
            155                 160                 165

Ile Phe Arg Met Glu Gln Leu Leu Thr Trp Lys Gly Thr Cys Gly
            170                 175                 180

His Arg Asp Pro Gly Asn Lys Ala Gly Met Thr Ser Leu Pro Gly
            185                 190                 195

Gly Pro Gln Ser Arg Gly Arg Arg Glu Ala Arg Arg Thr Arg Lys
            200                 205                 210

Tyr Leu Glu Leu Tyr Ile Val Ala Asp His Thr Leu Phe Leu Thr
            215                 220                 225

Arg His Arg Asn Leu Asn His Thr Lys Gln Arg Leu Leu Glu Val
            230                 235                 240

Ala Asn Tyr Val Asp Gln Leu Leu Arg Thr Leu Asp Ile Gln Val
            245                 250                 255

Ala Leu Thr Gly Leu Glu Val Trp Thr Glu Arg Asp Arg Ser Arg
            260                 265                 270

Val Thr Gln Asp Ala Asn Ala Thr Leu Trp Ala Phe Leu Gln Trp
            275                 280                 285

Arg Arg Gly Leu Trp Ala Gln Arg Pro His Asp Ser Ala Gln Leu
            290                 295                 300

Leu Thr Gly Arg Ala Phe Gln Gly Ala Thr Val Gly Leu Ala Pro
            305                 310                 315

Val Glu Gly Met Cys Arg Ala Glu Ser Ser Gly Gly Val Ser Thr
            320                 325                 330

Asp His Ser Glu Leu Pro Ile Gly Ala Ala Ala Thr Met Ala His
            335                 340                 345

Glu Ile Gly His Ser Leu Gly Leu Ser His Asp Pro Asp Gly Cys
            350                 355                 360

Cys Val Glu Ala Ala Ala Glu Ser Gly Gly Cys Val Met Ala Ala
            365                 370                 375

Ala Thr Gly His Pro Phe Pro Arg Val Phe Ser Ala Cys Ser Arg
            380                 385                 390

Arg Gln Leu Arg Ala Phe Phe Arg Lys Gly Gly Gly Ala Cys Leu
            395                 400                 405

Ser Asn Ala Pro Asp Pro Gly Leu Pro Val Pro Pro Ala Leu Cys
            410                 415                 420

Gly Asn Gly Phe Val Glu Ala Gly Glu Glu Cys Asp Cys Gly Pro
            425                 430                 435

Gly Gln Glu Cys Arg Asp Leu Cys Cys Phe Ala His Asn Cys Ser
            440                 445                 450

Leu Arg Pro Gly Ala Gln Cys Ala His Gly Asp Cys Cys Val Arg
            455                 460                 465

Cys Leu Leu Lys Pro Ala Gly Ala Leu Cys Arg Gln Ala Met Gly
            470                 475                 480

Asp Cys Asp Leu Pro Glu Phe Cys Thr Gly Thr Ser Ser His Cys
            485                 490                 495

Pro Pro Asp Val Tyr Leu Leu Asp Gly Ser Pro Cys Ala Arg Gly
            500                 505                 510

Ser Gly Tyr Cys Trp Asp Gly Ala Cys Pro Thr Leu Glu Gln Gln
            515                 520                 525

Cys Gln Gln Leu Trp Gly Pro Gly Ser His Pro Ala Pro Glu Ala
            530                 535                 540

Cys Phe Gln Val Val Asn Ser Ala Gly Asp Ala His Gly Asn Cys
```

545                 550                 555
Gly Gln Asp Ser Glu Gly His Phe Leu Pro Cys Ala Gly Arg Asp
            560                 565                 570
Ala Leu Cys Gly Lys Leu Gln Cys Gln Gly Gly Lys Pro Ser Leu
        575                 580                 585
Leu Ala Pro His Met Val Pro Val Asp Ser Thr Val His Leu Asp
    590                 595                 600
Gly Gln Glu Val Thr Cys Arg Gly Ala Leu Ala Leu Pro Ser Ala
605                 610                 615
Gln Leu Asp Leu Leu Gly Leu Gly Leu Val Glu Pro Gly Thr Gln
            620                 625                 630
Cys Gly Pro Arg Met Val Cys Gln Ser Arg Arg Cys Arg Lys Asn
        635                 640                 645
Ala Phe Gln Glu Leu Gln Arg Cys Leu Thr Ala Cys His Ser His
    650                 655                 660
Gly Val Cys Asn Ser Asn His Asn Cys His Cys Ala Pro Gly Trp
665                 670                 675
Ala Pro Pro Phe Cys Asp Lys Pro Gly Phe Gly Gly Ser Met Asp
            680                 685                 690
Ser Gly Pro Val Gln Ala Glu Asn His Asp Thr Phe Leu Leu Ala
        695                 700                 705
Met Leu Leu Ser Val Leu Leu Pro Leu Leu Pro Gly Ala Gly Leu
    710                 715                 720
Ala Trp Cys Cys Tyr Arg Leu Pro Gly Ala His Leu Gln Arg Cys
725                 730                 735
Ser Trp Gly Cys Arg Arg Asp Pro Ala Cys Ser Gly Pro Lys Asp
            740                 745                 750
Gly Pro His Arg Asp His Pro Leu Gly Val His Pro Met Glu
        755                 760                 765
Leu Gly Pro Thr Ala Thr Gly Gln Pro Trp Pro Leu Asp Pro Glu
    770                 775                 780
Asn Ser His Glu Pro Ser Ser His Pro Glu Lys Pro Leu Pro Ala
785                 790                 795
Val Ser Pro Asp Pro Gln Ala Asp Gln Val Gln Met Pro Arg Ser
            800                 805                 810
Cys Leu Trp

<210> SEQ ID NO 49
<211> LENGTH: 1675
<212> TYPE: DNA
<213> ORGANISM: Homo sapiens

<400> SEQUENCE: 49
ggcacgaggg agcctccgtt aggggtggg aaaggacttt gccataggtc         50
gctgaggcca ccatctgctc tcttactggc caagggcgta aaaagatagt        100
cttcccatta gctagagagc aaacccccaga aagcctattg gctgcgccgt       150
ccgcgggcct tggtccgctt tgaaggcggg ctgcggctgc gagaggaggg        200
cgggcgggag gctagctgtt gtcgtggttg ctcggaggca cgtgtgcagt        250
cccggaagcg gcgagggaa actgctccgc gcgcgccgcg ggaggaggaa         300
ccgcccggtc ctttagggtc cgggcccggc cgggccatgg attcaatgcc        350
tgagcccgcg tccgctgtc ttctgcttct tcccttgctg ctgctgctgc         400
tgctgctgct gccggccccg gagctgggcc cgagccaggc cggagctgag        450

-continued

```
gagaacgact gggttcgcct gcccagcaaa tgcgaagtgt gtaaatatgt      500
tgctgtggag ctgaagtcag cctttgagga aaccggcaag accaaggagg      550
tgattggcac gggctatggc atcctggacc agaaggcctc tggagtcaaa      600
tacaccaagt cggacttgcg gttaatcgaa gtcactgaga ccatttgcaa      650
gaggctcctg gattatagcc tgcacaagga gaggaccggc agcaatcgat      700
ttgccaaggg catgtcagag acctttgaga cattacacaa cctggtacac      750
aaaggggtca aggtggtgat ggacatcccc tatgagctgt ggaacgagac      800
ttctgcagag gtggctgacc tcaagaagca gtgtgatgtg ctggtggaag      850
agtttgagga ggtgatcgag gactggtaca ggaaccacca ggaggaagac      900
ctgactgaat tcctctgcgc caaccacgtg ctgaagggaa aagacaccag      950
ttgcctggca gagcagtggt ccggcaagaa gggagacaca gctgccctgg     1000
gagggaagaa gtccaagaag aagagcagca gggccaaggc agcaggcggc     1050
aggagtagca gcagcaaaca aaggaaggag ctgggtggcc ttgagggaga     1100
ccccagcccc gaggaggatg agggcatcca gaaggcatcc cctctcacac     1150 acagccccc  tgatgagctc tgagcccacc cagcatcctc tgtcctgaga     1200
cccctgattt tgaagctgag gagtcagggg catggctctg caggccggga     1250
atggccccgc agccttcagc ccctccttgc cttggctgtg ccctcttctg     1300
ccaaggaaag acacaagccc caggaagaac tcagagccgt catgggtagc     1350
ccacgccgtc ctttcccctc cccaagtgtt tctctcctga cccagggttc     1400
aggcaggcct tgtggtttca ggactgcaag gactccagtg tgaactcagg     1450
aggggcaggt gtcagaactg gcaccaggac tggagcccc  tccggagac      1500 caaactcacc atccctcagt cctccccaac agggtactag gactgcagcc     1550
ccctgtagct cctctctgct taccctcct  gtggacacct tgcactctgc      1600
ctggcccttc ccagagccca aagagtaaaa atgttctggt tctgatttct     1650
gaaaaaaaaa aaaaaaaaa  ttcct                                 1675
```

<210> SEQ ID NO 50
<211> LENGTH: 278
<212> TYPE: PRT
<213> ORGANISM: Homo sapiens

<400> SEQUENCE: 50

```
Met Asp Ser Met Pro Glu Pro Ala Ser Arg Cys Leu Leu Leu Leu
 1               5                  10                  15

Pro Leu Leu Leu Leu Leu Leu Leu Leu Pro Ala Pro Glu Leu
                20                  25                  30

Gly Pro Ser Gln Ala Gly Ala Glu Glu Asn Asp Trp Val Arg Leu
                35                  40                  45

Pro Ser Lys Cys Glu Val Cys Lys Tyr Val Ala Val Glu Leu Lys
                50                  55                  60

Ser Ala Phe Glu Glu Thr Gly Lys Thr Lys Glu Val Ile Gly Thr
                65                  70                  75

Gly Tyr Gly Ile Leu Asp Gln Lys Ala Ser Gly Val Lys Tyr Thr
                80                  85                  90

Lys Ser Asp Leu Arg Leu Ile Glu Val Thr Glu Thr Ile Cys Lys
                95                 100                 105
```

```
Arg Leu Leu Asp Tyr Ser Leu His Lys Glu Arg Thr Gly Ser Asn
            110                 115                 120

Arg Phe Ala Lys Gly Met Ser Glu Thr Phe Glu Thr Leu His Asn
            125                 130                 135

Leu Val His Lys Gly Val Lys Val Val Met Asp Ile Pro Tyr Glu
            140                 145                 150

Leu Trp Asn Glu Thr Ser Ala Glu Val Ala Asp Leu Lys Lys Gln
            155                 160                 165

Cys Asp Val Leu Val Glu Glu Phe Glu Val Ile Glu Asp Trp
            170                 175                 180

Tyr Arg Asn His Gln Glu Glu Asp Leu Thr Glu Phe Leu Cys Ala
            185                 190                 195

Asn His Val Leu Lys Gly Lys Asp Thr Ser Cys Leu Ala Glu Gln
            200                 205                 210

Trp Ser Gly Lys Lys Gly Asp Thr Ala Ala Leu Gly Gly Lys Lys
            215                 220                 225

Ser Lys Lys Lys Ser Ser Arg Ala Lys Ala Ala Gly Gly Arg Ser
            230                 235                 240

Ser Ser Ser Lys Gln Arg Lys Glu Leu Gly Gly Leu Glu Gly Asp
            245                 250                 255

Pro Ser Pro Glu Glu Asp Glu Gly Ile Gln Lys Ala Ser Pro Leu
            260                 265                 270

Thr His Ser Pro Pro Asp Glu Leu
            275

<210> SEQ ID NO 51
<211> LENGTH: 633
<212> TYPE: DNA
<213> ORGANISM: Homo sapiens

<400> SEQUENCE: 51
ctcctgcact aggctctcag ccagggatga tgcgctgctg ccgccgccgc         50
tgctgctgcc ggcaaccacc ccatgccctg aggccgttgc tgttgctgcc        100
cctcgtcctt ttacctcccc tggcagcagc tgcagcgggc ccaaaccgat        150
gtgacaccat ataccagggc ttcgccgagt gtctcatccg cttgggggac        200
agcatgggcc gcggaggcga gctggagacc atctgcaggt cttggaatga        250
cttccatgcc tgtgcctctc aggtcctgtc aggctgtccg gaggaggcag        300
ctgcagtgtg ggaatcacta cagcaagaag ctcgccaggc cccccgtccg        350
aataacttgc acactctgtg cggtgccccg gtgcatgttc gggagcgcgg        400
cacaggctcc gaaaccaacc aggagacgct gcgggctaca gcgcctgcac        450
tccccatggc ccctgcgccc ccactgctgg cggctgctct ggctctggcc        500
tacctcctga ggcctctggc ctagcttgtt gggttgggta gcagcgcccg        550
tacctccagc cctgctctgg cggtggttgt ccaggctctg cagagcgcag        600
cagggctttt cattaaaggt atttatattt gta                          633

<210> SEQ ID NO 52
<211> LENGTH: 165
<212> TYPE: PRT
<213> ORGANISM: Homo sapiens

<400> SEQUENCE: 52

Met Met Arg Cys Cys Arg Arg Cys Cys Cys Arg Gln Pro Pro
  1                 5                  10                  15
```

```
His Ala Leu Arg Pro Leu Leu Leu Pro Leu Val Leu Leu Pro
         20                  25                  30

Pro Leu Ala Ala Ala Ala Gly Pro Asn Arg Cys Asp Thr Ile
         35                  40                  45

Tyr Gln Gly Phe Ala Glu Cys Leu Ile Arg Leu Gly Asp Ser Met
    50                  55                  60

Gly Arg Gly Gly Glu Leu Glu Thr Ile Cys Arg Ser Trp Asn Asp
         65                  70                  75

Phe His Ala Cys Ala Ser Gln Val Leu Ser Gly Cys Pro Glu Glu
         80                  85                  90

Ala Ala Ala Val Trp Glu Ser Leu Gln Gln Glu Ala Arg Gln Ala
         95                 100                 105

Pro Arg Pro Asn Asn Leu His Thr Leu Cys Gly Ala Pro Val His
        110                 115                 120

Val Arg Glu Arg Gly Thr Gly Ser Glu Thr Asn Gln Glu Thr Leu
        125                 130                 135

Arg Ala Thr Ala Pro Ala Leu Pro Met Ala Pro Ala Pro Pro Leu
        140                 145                 150

Leu Ala Ala Ala Leu Ala Leu Ala Tyr Leu Leu Arg Pro Leu Ala
        155                 160                 165

<210> SEQ ID NO 53
<211> LENGTH: 386
<212> TYPE: DNA
<213> ORGANISM: Homo sapiens

<400> SEQUENCE: 53
ccaggatcag catggccgtc cgccagtggg taatcgccct ggccttggct        50
gccctccttg ttgtggacag ggaagtgcca gtggcagcag gaaagctccc       100
tttctcaaga atgcccatct gtgaacacat ggtagagtct ccaacctgtt       150
cccagatgtc caacctggtc tgcggcactg atgggctcac atatacgaat       200
gaatgccagc tctgcttggc ccggataaaa accaaacagg acatccagat       250
catgaaagat ggcaaatgct gatcccacag gagcacctca agccatgaag       300
tgtcagctgg agaacagtgg tgggcatgga gaggatatga catgaaataa       350
aagatccagc ccaactgaaa aaaaaaaaaa  aaaaaa                     386

<210> SEQ ID NO 54
<211> LENGTH: 86
<212> TYPE: PRT
<213> ORGANISM: Homo sapiens

<400> SEQUENCE: 54

Met Ala Val Arg Gln Trp Val Ile Ala Leu Ala Leu Ala Ala Leu
 1               5                  10                  15

Leu Val Val Asp Arg Glu Val Pro Val Ala Ala Gly Lys Leu Pro
         20                  25                  30

Phe Ser Arg Met Pro Ile Cys Glu His Met Val Glu Ser Pro Thr
         35                  40                  45

Cys Ser Gln Met Ser Asn Leu Val Cys Gly Thr Asp Gly Leu Thr
         50                  55                  60

Tyr Thr Asn Glu Cys Gln Leu Cys Leu Ala Arg Ile Lys Thr Lys
         65                  70                  75

Gln Asp Ile Gln Ile Met Lys Asp Gly Lys Cys
         80                  85
```

<210> SEQ ID NO 55
<211> LENGTH: 2594
<212> TYPE: DNA
<213> ORGANISM: Homo sapiens

<400> SEQUENCE: 55

| | | | | |
|---|---|---|---|---|
| gtggagttgg | gtggtgtcgg | gagcctctcc | ctgaggggca | ccgcgtcttc | 50 |
| aggagctggg | cctccagtgc | ggcgcgatgt | caggcgcggt | gacagctctg | 100 |
| tgagtccgag | gccgcggccg | tggcgctggg | cggctgcggg | gcctgaccgg | 150 |
| tccgctcatg | gtgccgccac | gacgccatcg | cggggcagga | aggccagggg | 200 |
| tgctgagttc | ttcacctcct | tttagactga | gatctgccaa | gttttccggc | 250 |
| attgctcttg | aggatctcag | aagggctctt | aagacaagac | tgcaaatggt | 300 |
| gtgtgtattt | gtcatgaacc | gaatgaattc | ccagaacagt | ggtttcactc | 350 |
| agcgcaggcg | aatggctctt | gggattgtta | ttcttctgct | tgttgatgtg | 400 |
| atatgggttg | cttcctctga | acttacttcg | tatgttttta | cccagtacaa | 450 |
| caaaccattc | ttcagcacct | tgcaaaaac | atctatgttt | gttttgtacc | 500 |
| ttttgggctt | tattatttgg | aagccatgga | gacaacagtg | tacaagagga | 550 |
| cttcgcggaa | agcatgctgc | ttttttttgca | gatgctgaag | gttactttgc | 600 |
| tgcttgcaca | acagatacaa | ctatgaatag | ttctttgagt | gaacctctgt | 650 |
| atgtgcctgt | gaaattccat | gatcttccaa | gtgaaaaacc | tgagagcaca | 700 |
| aacattgata | ctgaaaaaac | ccccaaaaag | tctcgtgtga | ggttcagtaa | 750 |
| tatcatggag | attcgacagc | ttccgtcaag | tcatgcattg | gaagcaaagt | 800 |
| tgtctcgcat | gtcatatcct | gtgaaagaac | aagaatccat | actgaaaact | 850 |
| gtggggaaac | ttactgcaac | tcaagtagcg | aaaattagct | ttttttttg | 900 |
| ctttgtgtgg | ttttttggcaa | atttgtcata | tcaagaagca | ctttcagaca | 950 |
| cacaagttgc | tatagttaat | attttatctt | caacttccgg | acttttacc | 1000 |
| ttaatccttg | ctgcagtatt | tccaagtaac | agtggagata | gatttaccct | 1050 |
| ttctaaacta | ttagctgtaa | ttttaagcat | tggaggcgtt | gtactggtaa | 1100 |
| acctggcagg | gtctgaaaaa | cctgctggaa | gagacacagt | aggttccatt | 1150 |
| tggtctcttg | ctggagccat | gctctatgct | gtctatattg | ttatgattaa | 1200 |
| gagaaaagta | gatagagaag | acaagttgga | tattccaatg | ttctttggtt | 1250 |
| ttgtaggttt | gtttaatctg | ctgctcttat | ggccaggttt | cttttactt | 1300 |
| cattatactg | gatttgagga | cttcgagttt | cccaataaag | tagtattaat | 1350 |
| gtgcattatc | attaatggcc | ttattggaac | agtactctca | gagttcctgt | 1400 |
| ggttgtgggg | ctgctttctt | acctcatcat | tgataggcac | acttgcacta | 1450 |
| agccttacaa | tacctctgtc | cataatagct | gacatgtgta | tgcaaaaggt | 1500 |
| gcagttttct | tggttatttt | ttgcaggagc | tatccctgta | ttttttcat | 1550 |
| ttttattgt | aactctccta | tgccattata | ataattggga | tcctgtgatg | 1600 |
| gtgggaatca | gaagaatatt | tgcttttata | tgcagaaaac | atcgaattca | 1650 |
| gagagttcca | gaagacagcg | aacagtgtga | gagtctcatt | tctatgcaca | 1700 |
| gtgtttctca | ggaggatgga | gctagttagc | tgtctgttgt | ctgtagccca | 1750 |
| gcttgataat | ggaactatac | agcgaagaga | caatctctgg | caagttttg | 1800 |

-continued

```
tagaaaaaat gtttcagtgc ctagtctgaa aaataacagt ttgagttctt        1850
tgaaactcta aaatatattt ttctcatacc tgttttcttc attttcataa        1900
tgaagcactt tgctatgtag ctgtgtacat atcactacag ttataggaag        1950
tttcagtcta cagtccatcc aaaggaccaa cctgccttac acatctcaag        2000
gaattcagct gttgaaatca tttgaactaa tcaaggaata aatcctaatg        2050
ttctgggact ttattttcac atgttaaatg ctggaatata ttatgaaaat        2100
gttttcaaga aatcacttaa gtgttcatag accagtattt ctgacaggta        2150
aaatgctaaa ataagctacc tgtaataagt gtggattata ttttgggtt         2200 ttgtagaata ttgcaaatta accacacaaa aaatgtttaa tttatgcaac        2250
aagcatgttt gtgcaaattt catgggactt taaaaagaat aagtatttga        2300
gaaaatatct ggttcactta cactacattt actgtattat tcttttatag        2350
cattaggtgc cttgtatttt aaatctgtga caaaccatgg caaattttta        2400
aaggggaagt attattataa aatgaagaaa tatgtatttc taaaggctat        2450
attgctgtaa acttaattga taaagctctg tttaatttag agttttgaag        2500
aaatagtctc ccttcaatta agaaattttc ataatggaat gatttaaatt        2550
gaagtgacaa agagtattat taaaatacaa tgtttataaa  aaaa             2594
```

<210> SEQ ID NO 56
<211> LENGTH: 523
<212> TYPE: PRT
<213> ORGANISM: Homo sapiens

<400> SEQUENCE: 56

```
Met Val Pro Pro Arg Arg His Arg Gly Ala Gly Arg Pro Gly Val
  1               5                  10                  15

Leu Ser Ser Ser Pro Pro Phe Arg Leu Arg Ser Ala Lys Phe Ser
                 20                  25                  30

Gly Ile Ala Leu Glu Asp Leu Arg Arg Ala Leu Lys Thr Arg Leu
                 35                  40                  45

Gln Met Val Cys Val Phe Val Met Asn Arg Met Asn Ser Gln Asn
                 50                  55                  60

Ser Gly Phe Thr Gln Arg Arg Arg Met Ala Leu Gly Ile Val Ile
                 65                  70                  75

Leu Leu Leu Val Asp Val Ile Trp Val Ala Ser Ser Glu Leu Thr
                 80                  85                  90

Ser Tyr Val Phe Thr Gln Tyr Asn Lys Pro Phe Phe Ser Thr Phe
                 95                 100                 105

Ala Lys Thr Ser Met Phe Val Leu Tyr Leu Leu Gly Phe Ile Ile
                110                 115                 120

Trp Lys Pro Trp Arg Gln Gln Cys Thr Arg Gly Leu Arg Gly Lys
                125                 130                 135

His Ala Ala Phe Phe Ala Asp Ala Glu Gly Tyr Phe Ala Ala Cys
                140                 145                 150

Thr Thr Asp Thr Thr Met Asn Ser Ser Leu Ser Glu Pro Leu Tyr
                155                 160                 165

Val Pro Val Lys Phe His Asp Leu Pro Ser Glu Lys Pro Glu Ser
                170                 175                 180

Thr Asn Ile Asp Thr Glu Lys Thr Pro Lys Lys Ser Arg Val Arg
                185                 190                 195
```

```
Phe Ser Asn Ile Met Glu Ile Arg Gln Leu Pro Ser Ser His Ala
            200                 205                 210

Leu Glu Ala Lys Leu Ser Arg Met Ser Tyr Pro Val Lys Glu Gln
            215                 220                 225

Glu Ser Ile Leu Lys Thr Val Gly Lys Leu Thr Ala Thr Gln Val
            230                 235                 240

Ala Lys Ile Ser Phe Phe Phe Cys Phe Val Trp Phe Leu Ala Asn
            245                 250                 255

Leu Ser Tyr Gln Glu Ala Leu Ser Asp Thr Gln Val Ala Ile Val
            260                 265                 270

Asn Ile Leu Ser Ser Thr Ser Gly Leu Phe Thr Leu Ile Leu Ala
            275                 280                 285

Ala Val Phe Pro Ser Asn Ser Gly Asp Arg Phe Thr Leu Ser Lys
            290                 295                 300

Leu Leu Ala Val Ile Leu Ser Ile Gly Gly Val Val Leu Val Asn
            305                 310                 315

Leu Ala Gly Ser Glu Lys Pro Ala Gly Arg Asp Thr Val Gly Ser
            320                 325                 330

Ile Trp Ser Leu Ala Gly Ala Met Leu Tyr Ala Val Tyr Ile Val
            335                 340                 345

Met Ile Lys Arg Lys Val Asp Arg Glu Asp Lys Leu Asp Ile Pro
            350                 355                 360

Met Phe Phe Gly Phe Val Gly Leu Phe Asn Leu Leu Leu Leu Trp
            365                 370                 375

Pro Gly Phe Phe Leu Leu His Tyr Thr Gly Phe Glu Asp Phe Glu
            380                 385                 390

Phe Pro Asn Lys Val Val Leu Met Cys Ile Ile Ile Asn Gly Leu
            395                 400                 405

Ile Gly Thr Val Leu Ser Glu Phe Leu Trp Leu Trp Gly Cys Phe
            410                 415                 420

Leu Thr Ser Ser Leu Ile Gly Thr Leu Ala Leu Ser Leu Thr Ile
            425                 430                 435

Pro Leu Ser Ile Ile Ala Asp Met Cys Met Gln Lys Val Gln Phe
            440                 445                 450

Ser Trp Leu Phe Phe Ala Gly Ala Ile Pro Val Phe Phe Ser Phe
            455                 460                 465

Phe Ile Val Thr Leu Leu Cys His Tyr Asn Asn Trp Asp Pro Val
            470                 475                 480

Met Val Gly Ile Arg Arg Ile Phe Ala Phe Ile Cys Arg Lys His
            485                 490                 495

Arg Ile Gln Arg Val Pro Glu Asp Ser Glu Gln Cys Glu Ser Leu
            500                 505                 510

Ile Ser Met His Ser Val Ser Gln Glu Asp Gly Ala Ser
            515                 520

<210> SEQ ID NO 57
<211> LENGTH: 983
<212> TYPE: DNA
<213> ORGANISM: Homo sapiens

<400> SEQUENCE: 57
ggatgcagca gagaggagca gctggaagcc gtggctgcgc tctcttccct          50
ctgctgggcg tcctgttctt ccagggtgtt tatatcgtct tttccttgga         100
gattcgtgca gatgcccatg tccgaggtta tgttggagaa aagatcaagt         150
```

```
tgaaatgcac tttcaagtca acttcagatg tcactgacaa gcttactata      200
gactggacat atcgccctcc cagcagcagc cacacagtat caatatttca      250
ttatcagtct ttccagtacc caaccacagc aggcacattt cgggatcgga      300
tttcctgggt tggaaatgta tacaaagggg atgcatctat aagtataagc      350
aaccctacca taaaggacaa tgggacattc agctgtgctg tgaagaatcc      400
cccagatgtg caccataata ttcccatgac agagctaaca gtcacagaaa      450
ggggttttgg caccatgctt tcctctgtgg cccttctttc catccttgtc      500
tttgtgccct cagccgtggt ggttgctctg ctgctggtga aatgggggag      550
gaaggctgct gggctgaaga agaggagcag gtctggctat aagaagtcat      600
ctattgaggt ttccgatgac actgatcagg aggaggaaga ggcgtgtatg      650
gcgaggcttt gtgtccgttg cgctgagtgc ctggattcag actatgaaga      700
gacatattga tgaaagtctg tatgacacaa gaagagtcac ctaaagacag      750
gaaacatccc attccactgg cagctaaagc ctgtcagaga aagtggagct      800
ggcctggacc atagcgatgg acaatcctgg agatcatcag taaagacttt      850
aggaaccact tatttattga ataaatgttc ttgttgtatt tataaactgt      900
tcaggaagtc tcataagaga ctcatgactt cccctttcaa tgaattatgc      950
tgtaattgaa tgaagaaatt cttttcctga gca                        983
```

<210> SEQ ID NO 58
<211> LENGTH: 235
<212> TYPE: PRT
<213> ORGANISM: Homo sapiens

<400> SEQUENCE: 58

```
Met Gln Gln Arg Gly Ala Ala Gly Ser Arg Gly Cys Ala Leu Phe
 1               5                  10                  15

Pro Leu Leu Gly Val Leu Phe Phe Gln Gly Val Tyr Ile Val Phe
                20                  25                  30

Ser Leu Glu Ile Arg Ala Asp Ala His Val Arg Gly Tyr Val Gly
            35                  40                  45

Glu Lys Ile Lys Leu Lys Cys Thr Phe Lys Ser Thr Ser Asp Val
        50                  55                  60

Thr Asp Lys Leu Thr Ile Asp Trp Thr Tyr Arg Pro Pro Ser Ser
    65                  70                  75

Ser His Thr Val Ser Ile Phe His Tyr Gln Ser Phe Gln Tyr Pro
            80                  85                  90

Thr Thr Ala Gly Thr Phe Arg Asp Arg Ile Ser Trp Val Gly Asn
            95                 100                 105

Val Tyr Lys Gly Asp Ala Ser Ile Ser Ile Ser Asn Pro Thr Ile
           110                 115                 120

Lys Asp Asn Gly Thr Phe Ser Cys Ala Val Lys Asn Pro Pro Asp
           125                 130                 135

Val His His Asn Ile Pro Met Thr Glu Leu Thr Val Thr Glu Arg
           140                 145                 150

Gly Phe Gly Thr Met Leu Ser Ser Val Ala Leu Leu Ser Ile Leu
           155                 160                 165

Val Phe Val Pro Ser Ala Val Val Val Ala Leu Leu Leu Val Arg
           170                 175                 180

Met Gly Arg Lys Ala Ala Gly Leu Lys Lys Arg Ser Arg Ser Gly
           185                 190                 195
```

Tyr Lys Lys Ser Ser Ile Glu Val Ser Asp Asp Thr Asp Gln Glu
            200                 205                 210

Glu Glu Glu Ala Cys Met Ala Arg Leu Cys Val Arg Cys Ala Glu
            215                 220                 225

Cys Leu Asp Ser Asp Tyr Glu Glu Thr Tyr
            230                 235

<210> SEQ ID NO 59
<211> LENGTH: 1794
<212> TYPE: DNA
<213> ORGANISM: Homo sapiens

<400> SEQUENCE: 59

| | | | |
|---|---|---|---|
| cccttggaag ctggaatcct gcaacaatgg cccagggtgt cctctggatc | | | 50 |
| ctactcggat tgctactgtg gtcagaccca gggacagcct ccctgcccct | | | 100 |
| gctcatggac tctgtcatcc aggccctggc tgagctggag cagaaagtgc | | | 150 |
| cagctgccaa gaccagacac acagcttctg cgtggctgat gtcagctcca | | | 200 |
| aactctggcc cccacaatcg cctctaccac ttcctgctgg gggcatggag | | | 250 |
| cctcaatgct acagagttgg atccctgccc actaagccca gagctgttag | | | 300 |
| gcctgaccaa ggaggtggcc cgacatgacg tacgagaagg gaaggaatat | | | 350 |
| ggggtggtgc tggcacctga tggctcgacc gtggctgtgg agcctctgct | | | 400 |
| ggcggggctg gaggcagggc tgcaagggcg cagggtcata aatttgccct | | | 450 |
| tggacagcat ggctgcccct gggagactg gagatacctt tccagatgtt | | | 500 |
| gtggccattg ctccagatgt aagagccacc tcctccccag gactcaggga | | | 550 |
| tggctctcca gatgtcacca ctgcagatat tggagccaac actccagatg | | | 600 |
| ctacaaaagg ctgtccagat gtccaagctt ccttgccaga tgccaaagcc | | | 650 |
| aagtccccac cgaccatggt ggacagcctc ctggcagtca cctggctgg | | | 700 |
| aaacctgggc ctgaccttcc tccgaggttc ccagacccag agccatccag | | | 750 |
| acctgggaac tgagggctgc tgggaccagc tctctgcccc tcggaccttt | | | 800 |
| acgcttttgg accccaaggc atctctgtta accatggcct tcctcaatgg | | | 850 |
| cgccctggat ggggtcatcc ttggagacta cctgagccgg actcctgagc | | | 900 |
| cccggccatc cctcagccac ttgctgagcc agtactatgg ggctggggtg | | | 950 |
| gccagagacc cagggttccg cagcaacttc cgacggcaga acgtgctgc | | | 1000 |
| tctgacttca gcctccatcc tggcccagca ggtgtgggga acccttgtcc | | | 1050 |
| ttctacagag gctggagcca gtacacctcc agcttcagtg catgagccaa | | | 1100 |
| gaacagctgg cccaggtggc tgccaatgct accaaggaat tcactgaggc | | | 1150 |
| cttcctggga tgcccggcca tccacccccg ctgccgctgg ggagcggcgc | | | 1200 |
| cttatcgggg ccgcccgaag ctgctgcagc tgccgctggg attcttgtac | | | 1250 |
| gtgcatcaca cctacgtgcc tgcaccaccc tgcacggact tcacgcgctg | | | 1300 |
| cgcagccaac atgcgctcca tgcagcgcta ccaccaggac acgcaaggct | | | 1350 |
| ggggagacat cggctacagt ttcgtggtgg gctcggacgg ctacgtgtac | | | 1400 |
| gagggacgcg gctggcactg ggtgggcgcc cacacgctcg gccacaactc | | | 1450 |
| ccggggcttc ggcgtggcca tagtgggcaa ctacaccgcg cgcgctgccca | | | 1500 |
| ccgaggccgc tctgcgcacg gtgcgcgaca cgctcccgag ttgtgcggtg | | | 1550 |

-continued

```
cgcgccggcc tcctgcggcc agactacgcg ctgctgggcc accgccagct          1600
ggtgcgcacc gactgccccg gcgacgcgct cttcgacctg ctgcgcacct          1650
ggccgcactt caccgcgact gttaagccaa gacctgccag gagtgtctct          1700
aagagatcca ggagggagcc accccaagg accctgccag ccacagacct           1750
ccaataaaga cagcatggaa acaaaaaaaa aaaaaaaaa  aaaa                1794
```

<210> SEQ ID NO 60
<211> LENGTH: 576
<212> TYPE: PRT
<213> ORGANISM: Homo sapiens

<400> SEQUENCE: 60

```
Met Ala Gln Gly Val Leu Trp Ile Leu Leu Gly Leu Leu Leu Trp
  1               5                  10                  15

Ser Asp Pro Gly Thr Ala Ser Leu Pro Leu Met Asp Ser Val
                 20                  25                  30

Ile Gln Ala Leu Ala Glu Leu Glu Gln Lys Val Pro Ala Ala Lys
                 35                  40                  45

Ala Arg His Thr Ala Ser Ala Trp Leu Met Ser Ala Pro Asn Ser
                 50                  55                  60

Gly Pro His Asn Arg Leu Tyr His Phe Leu Leu Gly Ala Trp Ser
                 65                  70                  75

Leu Asn Ala Thr Glu Leu Asp Pro Cys Pro Leu Ser Pro Glu Leu
                 80                  85                  90

Leu Gly Leu Thr Lys Glu Val Ala Gln His Asp Val Arg Glu Gly
                 95                 100                 105

Lys Glu Tyr Gly Val Val Leu Ala Pro Asp Gly Ser Thr Val Ala
                110                 115                 120

Val Glu Pro Leu Leu Ala Gly Leu Glu Ala Gly Leu Gln Gly Arg
                125                 130                 135

Arg Val Ile Asn Leu Pro Leu Asp Ser Met Ala Ala Pro Trp Glu
                140                 145                 150

Thr Gly Asp Thr Phe Pro Asp Val Val Ala Ile Ala Pro Asp Val
                155                 160                 165

Arg Ala Thr Ser Ser Pro Gly Leu Arg Asp Gly Ser Pro Asp Val
                170                 175                 180

Thr Thr Ala Asp Ile Gly Ala Asn Thr Pro Asp Ala Thr Lys Gly
                185                 190                 195

Cys Pro Asp Val Gln Ala Ser Leu Pro Asp Ala Lys Ala Lys Ser
                200                 205                 210

Pro Pro Thr Met Val Asp Ser Leu Leu Ala Val Thr Leu Ala Gly
                215                 220                 225

Asn Leu Gly Leu Thr Phe Leu Arg Gly Ser Gln Thr Gln Ser His
                230                 235                 240

Pro Asp Leu Gly Thr Glu Gly Cys Trp Asp Gln Leu Ser Ala Pro
                245                 250                 255

Arg Thr Phe Thr Leu Leu Asp Pro Lys Ala Ser Leu Leu Thr Lys
                260                 265                 270

Ala Phe Leu Asn Gly Ala Leu Asp Gly Val Ile Leu Gly Asp Tyr
                275                 280                 285

Leu Ser Arg Thr Pro Glu Pro Arg Pro Ser Leu Ser His Leu Leu
                290                 295                 300

Ser Gln Tyr Tyr Gly Ala Gly Val Ala Arg Asp Pro Gly Phe Arg
                305                 310                 315
```

```
Ser Asn Phe Arg Arg Gln Asn Gly Ala Ala Leu Thr Ser Ala Ser
            320                 325                 330

Ile Leu Ala Gln Gln Val Trp Gly Thr Leu Val Leu Leu Gln Arg
        335                 340                 345

Leu Glu Pro Val His Leu Gln Leu Gln Cys Met Ser Gln Glu Gln
    350                 355                 360

Leu Ala Gln Val Ala Ala Asn Ala Thr Lys Glu Phe Thr Glu Ala
365                 370                 375

Phe Leu Gly Cys Pro Ala Ile His Pro Arg Cys Arg Trp Gly Ala
        380                 385                 390

Ala Pro Tyr Gln Gly Arg Pro Lys Leu Leu Gln Leu Pro Leu Gly
    395                 400                 405

Phe Leu Tyr Val His His Thr Tyr Val Pro Ala Pro Pro Cys Thr
410                 415                 420

Asp Phe Thr Arg Cys Ala Ala Asn Met Arg Ser Met Gln Arg Tyr
        425                 430                 435

His Gln Asp Thr Gln Gly Trp Gly Asp Ile Gly Tyr Ser Phe Val
    440                 445                 450

Val Gly Ser Asp Gly Tyr Val Tyr Glu Gly Arg Gly Trp His Trp
455                 460                 465

Val Gly Ala His Thr Leu Gly His Asn Ser Arg Gly Phe Gly Val
        470                 475                 480

Ala Ile Val Gly Asn Tyr Thr Ala Ala Leu Pro Thr Glu Ala Ala
    485                 490                 495

Leu Arg Thr Val Arg Asp Thr Leu Pro Ser Cys Ala Val Arg Ala
500                 505                 510

Gly Leu Leu Arg Pro Asp Tyr Ala Leu Leu Gly His Arg Gln Leu
        515                 520                 525

Val Arg Thr Asp Cys Pro Gly Asp Ala Leu Phe Asp Leu Leu Arg
    530                 535                 540

Thr Trp Pro His Phe Thr Ala Thr Val Lys Pro Arg Pro Ala Arg
545                 550                 555

Ser Val Ser Lys Arg Ser Arg Arg Glu Pro Pro Pro Arg Thr Leu
        560                 565                 570

Pro Ala Thr Asp Leu Gln
        575

<210> SEQ ID NO 61
<211> LENGTH: 2732
<212> TYPE: DNA
<213> ORGANISM: Homo sapiens

<400> SEQUENCE: 61
agtcccagac gggcttttcc cagagagcta aaagagaagg gccagagaat          50
gtcgtcccag ccagcaggga accagacctc ccccggggcc acagaggact         100
actcctatgg cagctggtac atcgatgagc ccagggggg cgaggagctc          150 cagccagagg gggaagtgcc ctcctgccac accagcatac cacccggcct         200
gtaccacgcc tgcctggcct cgctgtcaat ccttgtgctg ctgctcctgg         250
ccatgctggt gaggcgccgc cagctctggc ctgactgtgt cgtggcagg          300 cccggcctgc ccagccctgt ggatttcttg gctggggaca ggccccgggc         350
agtgcctgct gctgttttca tggtcctcct gagctccctg tgtttgctgc         400
tccccgacga ggacgcattg cccttcctga ctctcgcctc agcacccagc         450
```

-continued

| | |
|---|---|
| caagatggga aaactgaggc tccaagaggg gcctggaaga tactgggact | 500 |
| gttctattat gctgccctct actaccctct ggctgcctgt gccacggctg | 550 |
| gccacacagc tgcacacctg ctcggcagca cgctgtcctg ggcccacctt | 600 |
| ggggtccagg tctggcagag ggcagagtgt ccccaggtgc caagatcta | 650 |
| caagtactac tccctgctgg cctccctgcc tctcctgctg ggcctcggat | 700 |
| tcctgagcct ttggtaccct gtgcagctgg tgagaagctt cagccgtagg | 750 |
| acaggagcag gctccaaggg gctgcagagc agctactctg aggaatatct | 800 |
| gaggaacctc ctttgcagga agaagctggg aagcagctac cacacctcca | 850 |
| agcatggctt cctgtcctgg gcccgcgtct gcttgagaca ctgcatctac | 900 |
| actccacagc caggattcca tctcccgctg aagctggtgc tttcagctac | 950 |
| actgacaggg acggccattt accaggtggc cctgctgctg ctggtgggcg | 1000 |
| tggtacccac tatccagaag gtgagggcag gggtcaccac ggatgtctcc | 1050 |
| tacctgctgg ccggctttgg aatcgtgctc tccgaggaca agcaggaggt | 1100 |
| ggtggagctg gtgaagcacc atctgtgggc tctggaagtg tgctacatct | 1150 |
| cagccttggt cttgtcctgc ttactcacct tcctggtcct gatgcgctca | 1200 |
| ctggtgacac acaggaccaa ccttcgagct ctgaccgag gagctgccct | 1250 |
| ggacttgagt cccttgcatc ggagtcccca tccctcccgc caagccatat | 1300 |
| tctgttggat gagcttcagt gcctaccaga cagcctttat ctgccttggg | 1350 |
| ctcctggtgc agcagatcat cttcttcctg ggaaccacgg ccctggcctt | 1400 |
| cctggtgctc atgcctgtgc tccatggcag gaacctcctg ctcttccgtt | 1450 |
| ccctggagtc ctcgtggccc ttctggctga ctttggccct ggctgtgatc | 1500 |
| ctgcagaaca tggcagccca ttgggtcttc ctggagactc atgatggaca | 1550 |
| cccacagctg accaaccggc gagtgctcta tgcagccacc tttcttctct | 1600 |
| tcccccctcaa tgtgctggtg ggtgccatgg tggccacctg gcgagtgctc | 1650 |
| ctctctgccc tctacaacgc catccacctt ggccagatgg acctcagcct | 1700 |
| gctgccaccg agagccgcca ctctcgaccc cggctactac acgtaccgaa | 1750 |
| acttcttgaa gattgaagtc agccagtcgc atccagccat gacagccttc | 1800 |
| tgctcccctgc tcctgcaagc gcagagcctc ctacccagga ccatggcagc | 1850 |
| ccccccaggac agcctcagac caggggagga agacgaaggg atgcagctgc | 1900 |
| tacagacaaa ggactccatg gccaagggag ctaggcccgg ggccagccgc | 1950 |
| ggcagggctc gctggggtct ggcctacacg ctgctgcaca acccaaccct | 2000 |
| gcaggtcttc cgcaagacgg ccctgttggg tgccaatggt gcccagccct | 2050 |
| gagggcaggg aaggtcaacc cacctgccca tctgtgctga ggcatgttcc | 2100 |
| tgcctaccat cctcctccct ccccggctct cctcccagca tcacaccagc | 2150 |
| catgcagcca gcaggtcctc cggatcactg tggttgggtg gaggtctgtc | 2200 |
| tgcactggga gcctcaggag ggctctgctc cacccacttg gctatgggag | 2250 |
| agccagcagg ggttctggag aaaaaaactg gtgggttagg gccttggtcc | 2300 |
| aggagccagt tgagccaggg cagccacatc caggcgtctc cctaccctgg | 2350 |
| ctctgccatc agccttgaag ggcctcgatg aagccttctc tggaaccact | 2400 |
| ccagcccagc tccacctcag ccttggcctt cacgctgtgg aagcagccaa | 2450 |

```
ggcacttcct cacccctca gcgccacgga cctctctggg gagtggccgg        2500
aaagctcccg gtcctctggc ctgcagggca gcccaagtca tgactcagac        2550
caggtcccac actgagctgc ccacactcga gagccagata ttttttgtagt      2600 tttatgcct ttggctatta tgaaagaggt tagtgtgttc cctgcaataa         2650
acttgttcct gagaaaaaaa aaaaaaaaaa aaaaaaaaaa aaaaaaaaaa        2700
aaaaaaaaaa aaaaaaaaaa aaaaaaaaaa aa                           2732
```

<210> SEQ ID NO 62
<211> LENGTH: 667
<212> TYPE: PRT
<213> ORGANISM: Homo sapiens

<400> SEQUENCE: 62

```
Met Ser Ser Gln Pro Ala Gly Asn Gln Thr Ser Pro Gly Ala Thr
 1               5                  10                  15

Glu Asp Tyr Ser Tyr Gly Ser Trp Tyr Ile Asp Glu Pro Gln Gly
                20                  25                  30

Gly Glu Glu Leu Gln Pro Glu Gly Glu Val Pro Ser Cys His Thr
                35                  40                  45

Ser Ile Pro Pro Gly Leu Tyr His Ala Cys Leu Ala Ser Leu Ser
                50                  55                  60

Ile Leu Val Leu Leu Leu Ala Met Leu Val Arg Arg Arg Gln
65                  70                  75

Leu Trp Pro Asp Cys Val Arg Gly Arg Pro Gly Leu Pro Ser Pro
                80                  85                  90

Val Asp Phe Leu Ala Gly Asp Arg Pro Arg Ala Val Pro Ala Ala
                95                 100                 105

Val Phe Met Val Leu Leu Ser Ser Leu Cys Leu Leu Leu Pro Asp
               110                 115                 120

Glu Asp Ala Leu Pro Phe Leu Thr Leu Ala Ser Ala Pro Ser Gln
               125                 130                 135

Asp Gly Lys Thr Glu Ala Pro Arg Gly Ala Trp Lys Ile Leu Gly
               140                 145                 150

Leu Phe Tyr Tyr Ala Ala Leu Tyr Tyr Pro Leu Ala Ala Cys Ala
               155                 160                 165

Thr Ala Gly His Thr Ala Ala His Leu Leu Gly Ser Thr Leu Ser
               170                 175                 180

Trp Ala His Leu Gly Val Gln Val Trp Gln Arg Ala Glu Cys Pro
               185                 190                 195

Gln Val Pro Lys Ile Tyr Lys Tyr Tyr Ser Leu Leu Ala Ser Leu
               200                 205                 210

Pro Leu Leu Leu Gly Leu Gly Phe Leu Ser Leu Trp Tyr Pro Val
               215                 220                 225

Gln Leu Val Arg Ser Phe Ser Arg Arg Thr Gly Ala Gly Ser Lys
               230                 235                 240

Gly Leu Gln Ser Ser Tyr Ser Glu Glu Tyr Leu Arg Asn Leu Leu
               245                 250                 255

Cys Arg Lys Lys Leu Gly Ser Ser Tyr His Thr Ser Lys His Gly
               260                 265                 270

Phe Leu Ser Trp Ala Arg Val Cys Leu Arg His Cys Ile Tyr Thr
               275                 280                 285

Pro Gln Pro Gly Phe His Leu Pro Leu Lys Leu Val Leu Ser Ala
               290                 295                 300
```

Thr Leu Thr Gly Thr Ala Ile Tyr Gln Val Ala Leu Leu Leu
            305                 310                 315
Val Gly Val Val Pro Thr Ile Gln Lys Val Arg Ala Gly Val Thr
            320                 325                 330
Thr Asp Val Ser Tyr Leu Leu Ala Gly Phe Gly Ile Val Leu Ser
            335                 340                 345
Glu Asp Lys Gln Glu Val Val Glu Leu Val Lys His His Leu Trp
            350                 355                 360
Ala Leu Glu Val Cys Tyr Ile Ser Ala Leu Val Leu Ser Cys Leu
            365                 370                 375
Leu Thr Phe Leu Val Leu Met Arg Ser Leu Val Thr His Arg Thr
            380                 385                 390
Asn Leu Arg Ala Leu His Arg Gly Ala Ala Leu Asp Leu Ser Pro
            395                 400                 405
Leu His Arg Ser Pro His Pro Ser Arg Gln Ala Ile Phe Cys Trp
            410                 415                 420
Met Ser Phe Ser Ala Tyr Gln Thr Ala Phe Ile Cys Leu Gly Leu
            425                 430                 435
Leu Val Gln Gln Ile Ile Phe Phe Leu Gly Thr Thr Ala Leu Ala
            440                 445                 450
Phe Leu Val Leu Met Pro Val Leu His Gly Arg Asn Leu Leu Leu
            455                 460                 465
Phe Arg Ser Leu Glu Ser Ser Trp Pro Phe Trp Leu Thr Leu Ala
            470                 475                 480
Leu Ala Val Ile Leu Gln Asn Met Ala Ala His Trp Val Phe Leu
            485                 490                 495
Glu Thr His Asp Gly His Pro Gln Leu Thr Asn Arg Arg Val Leu
            500                 505                 510
Tyr Ala Ala Thr Phe Leu Leu Phe Pro Leu Asn Val Leu Val Gly
            515                 520                 525
Ala Met Val Ala Thr Trp Arg Val Leu Ser Ala Leu Tyr Asn
            530                 535                 540
Ala Ile His Leu Gly Gln Met Asp Leu Ser Leu Leu Pro Pro Arg
            545                 550                 555
Ala Ala Thr Leu Asp Pro Gly Tyr Tyr Thr Tyr Arg Asn Phe Leu
            560                 565                 570
Lys Ile Glu Val Ser Gln Ser His Pro Ala Met Thr Ala Phe Cys
            575                 580                 585
Ser Leu Leu Leu Gln Ala Gln Ser Leu Leu Pro Arg Thr Met Ala
            590                 595                 600
Ala Pro Gln Asp Ser Leu Arg Pro Gly Glu Glu Asp Glu Gly Met
            605                 610                 615
Gln Leu Leu Gln Thr Lys Asp Ser Met Ala Lys Gly Ala Arg Pro
            620                 625                 630
Gly Ala Ser Arg Gly Arg Ala Arg Trp Gly Leu Ala Tyr Thr Leu
            635                 640                 645
Leu His Asn Pro Thr Leu Gln Val Phe Arg Lys Thr Ala Leu Leu
            650                 655                 660
Gly Ala Asn Gly Ala Gln Pro
            665

<210> SEQ ID NO 63
<211> LENGTH: 4834
<212> TYPE: DNA

<213> ORGANISM: Homo sapiens

<400> SEQUENCE: 63

| | | | | |
|---|---|---|---|---|
| gatgtggagc | tggggtccct | gcaagtcatg | aacaaaacga | gaaagattat | 50 |
| ggaacatggg | ggggccacct | tcatcaatgc | ctttgtgact | acacccatgt | 100 |
| gctgcccgtc | acggtcctcc | atgctcaccg | ggaagtatgt | gcacaatcac | 150 |
| aatgtctaca | ccaacaacga | gaactgctct | tccccctcgt | ggcaggccat | 200 |
| gcatgagcct | cggacttttg | ctgtatatct | taacaacact | ggctacagaa | 250 |
| cagccttttt | tggaaaatac | ctcaatgaat | ataatggcag | ctacatcccc | 300 |
| cctgggtggc | gagaatggct | tggattaatc | aagaattctc | gcttctataa | 350 |
| ttacactgtt | tgtcgcaatg | gcatcaaaga | aaagcatgga | tttgattatg | 400 |
| caaaggacta | cttcacagac | ttaatcacta | acgagagcat | taattacttc | 450 |
| aaaatgtcta | agagaatgta | tccccatagg | cccgttatga | tggtgatcag | 500 |
| ccacgctgcg | ccccacggcc | ccgaggactc | agccccacag | ttttctaaac | 550 |
| tgtaccccaa | tgcttcccaa | cacataactc | ctagttataa | ctatgcacca | 600 |
| aatatggata | acactggat | tatgcagtac | acaggaccaa | tgctgcccat | 650 |
| ccacatggaa | tttacaaaca | ttctacagcg | caaaaggctc | cagactttga | 700 |
| tgtcagtgga | tgattctgtg | gagaggctgt | ataacatgct | cgtggagacg | 750 |
| ggggagctgg | agaatactta | catcatttac | accgccgacc | atggttacca | 800 |
| tattgggcag | tttggactgg | tcaaggggaa | atccatgcca | tatgactttg | 850 |
| atattcgtgt | gccttttttt | attcgtggtc | caagtgtaga | accaggatca | 900 |
| atagtcccac | agatcgttct | caacattgac | ttggccccca | cgatcctgga | 950 |
| tattgctggg | ctcgacacac | ctcctgatgt | ggacggcaag | tctgtcctca | 1000 |
| aacttctgga | cccagaaaag | ccaggtaaca | ggtttcgaac | aaacaagaag | 1050 |
| gccaaaattt | ggcgtgatac | attcctagtg | gaaagaggca | aatttctacg | 1100 |
| taagaaggaa | gaatccagca | agaatatcca | acagtcaaat | cacttgccca | 1150 |
| aatatgaacg | ggtcaaagaa | ctatgccagc | aggccaggta | ccagacagcc | 1200 |
| tgtgaacaac | cggggcagaa | gtggcaatgc | attgaggata | catctggcaa | 1250 |
| gcttcgaatt | cacaagtgta | aaggacccag | tgacctgctc | acagtccggc | 1300 |
| agagcacgcg | gaacctctac | gctcgcggct | tccatgacaa | agacaaagag | 1350 |
| tgcagttgta | gggagtctgg | ttaccgtgcc | agcagaagcc | aaagaaagag | 1400 |
| tcaacggcaa | ttcttgagaa | accaggggac | tccaaagtac | aagcccagat | 1450 |
| ttgtccatac | tcggcagaca | cgttccttgt | ccgtcgaatt | tgaaggtgaa | 1500 |
| atatatgaca | taaatctgga | agaagaagaa | gaattgcaag | tgttgcaacc | 1550 |
| aagaaacatt | gctaagcgtc | atgatgaagg | ccacaagggg | ccaagagatc | 1600 |
| tccaggcttc | cagtggtggc | aacaggggca | ggatgctggc | agatagcagc | 1650 |
| aacgccgtgg | gcccacctac | cactgtccga | gtgacacaca | agtgttttat | 1700 |
| tcttcccaat | gactctatcc | attgtgagag | agaactgtac | caatcggcca | 1750 |
| gagcgtggaa | ggaccataag | gcatacattg | acaaagagat | tgaagctctg | 1800 |
| caagataaaa | ttaagaattt | aagagaagtg | agaggacatc | tgaagagaag | 1850 |
| gaagcctgag | gaatgtagct | gcagtaaaca | aagctattac | aataaagaga | 1900 |

-continued

```
aaggtgtaaa aaagcaagag aaattaaaga gccatcttca cccattcaag      1950
gaggctgctc aggaagtaga tagcaaactg caacttttca aggagaacaa      2000
ccgtaggagg aagaaggaga ggaaggagaa gagacggcag aggaaggggg      2050
aagagtgcag cctgcctggc ctcacttgct tcacgcatga caacaaccac      2100
tggcagacag ccccgttctg gaacctggga tctttctgtg cttgcacgag      2150
ttctaacaat aacacctact ggtgtttgcg tacagttaat gagacgcata      2200
attttctttt ctgtgagttt gctactggct ttttggagta ttttgatatg      2250
aatacagatc cttatcagct cacaaataca gtgcacacgg tagaacgagg      2300
cattttgaat cagctacacg tacaactaat ggagctcaga agctgtcaag      2350
gatataagca gtgcaaccca agacctaaga atcttgatgt tggaaataaa      2400
gatggaggaa gctatgacct acacagagga cagttatggg atggatggga      2450
aggttaatca gccccgtctc actgcagaca tcaactggca aggcctagag      2500
gagctacaca gtgtgaatga aaacatctat gagtacagac aaaactacag      2550
acttagtctg gtggactgga ctaattactt gaaggattta gatagagtat      2600
ttgcactgct gaagagtcac tatgagcaaa ataaaacaaa taagactcaa      2650
actgctcaaa gtgacgggtt cttggttgtc tctgctgagc acgctgtgtc      2700
aatggagatg gcctctgctg actcagatga agacccaagg cataaggttg      2750
ggaaaacacc tcatttgacc ttgccagctg accttcaaac cctgcatttg      2800
aaccgaccaa cattaagtcc agagagtaaa cttgaatgga ataacgacat      2850
tccagaagtt aatcatttga attctgaaca ctggagaaaa accgaaaaat      2900
ggacggggca tgaagagact aatcatctgg aaaccgattt cagtggcgat      2950
ggcatgacag agctagagct cgggcccagc cccaggctgc agcccattcg      3000
caggcacccg aaagaacttc cccagtatgg tggtcctgga aaggacattt      3050
ttgaagatca actatatctt cctgtgcatt ccgatggaat ttcagttcat      3100
cagatgttca ccatggccac cgcagaacac cgaagtaatt ccagcatagc      3150
ggggaagatg ttgaccaagg tggagaagaa tcacgaaaag gagaagtcac      3200
agcacctaga aggcagcgcc tcctcttcac tctcctctga ttagatgaaa      3250
ctgttacctt accctaaaca cagtatttct ttttaacttt tttatttgta      3300
aactaataaa ggtaatcaca gccaccaaca ttccaagcta ccctgggtac      3350
ctttgtgcag tagaagctag tgagcatgtg agcaagcggt gtgcacacgg      3400
agactcatcg ttataattta ctatctgcca agagtagaaa gaaaggctgg      3450
ggatatttgg gttggcttgg ttttgatttt ttgcttgttt gtttgttttg      3500
tactaaaaca gtattatctt ttgaatatcg tagggacata agtatataca      3550
tgttatccaa tcaagatggc tagaatggtg cctttctgag tgtctaaaac      3600
ttgacacccc tggtaaatct ttcaacacac ttccactgcc tgcgtaatga      3650
agttttgatt cattttaac cactggaatt tttcaatgcc gtcattttca       3700
gttagatgat tttgcacttt gagattaaaa tgccatgtct atttgattag      3750
tcttattttt ttatttttac aggcttatca gtctcactgt tggctgtcat      3800
tgtgacaaag tcaaataaac ccccaaggac gacacacagt atggatcaca      3850
tattgtttga cattaagctt ttgccagaaa atgttgcatg tgttttacct      3900
```

-continued

| | |
|---|---|
| cgacttgcta aaatcgatta gcagaaaggc atggctaata atgttggtgg | 3950 |
| tgaaaataaa taaataagta aacaaaatga agattgcctg ctctctctgt | 4000 |
| gcctagcctc aaagcgttca tcatacatca tacctttaag attgctatat | 4050 |
| tttgggttat tttcttgaca ggagaaaaag atctaaagat cttttatttt | 4100 |
| catctttttt ggttttcttg gcatgactaa gaagcttaaa tgttgataaa | 4150 |
| atatgactag ttttgaattt acaccaagaa cttctcaata aaagaaaatc | 4200 |
| atgaatgctc cacaatttca acataccaca agagaagtta atttcttaac | 4250 |
| attgtgttct atgattattt gtaagacctt caccaagttc tgatatcttt | 4300 |
| taaagacata gttcaaaatt gcttttgaaa atctgtattc ttgaaaatat | 4350 |
| ccttgttgtg tattaggttt ttaaatacca gctaaaggat tacctcactg | 4400 |
| agtcatcagt accctcctat tcagctcccc aagatgatgt gttttttgctt | 4450 |
| accctaagag aggttttctt cttatttttta gataattcaa gtgcttagat | 4500 |
| aaattatgtt ttctttaagt gtttatggta aactcttttta aagaaaattt | 4550 |
| aatatgttat agctgaatct ttttggtaac tttaaatctt tatcatagac | 4600 |
| tctgtacata tgttcaaatt agctgcttgc ctgatgtgtg tatcatcggt | 4650 |
| gggatgacag aacaaacata tttatgatca tgaataatgt gctttgtaaa | 4700 |
| aagatttcaa gttattagga agcatactct gttttttaat catgtataat | 4750 |
| attccatgat acttttatag aacaattctg gcttcaggaa agtctagaag | 4800 |
| caatatttct tcaaataaaa ggtgtttaaa cttt | 4834 |

<210> SEQ ID NO 64
<211> LENGTH: 871
<212> TYPE: PRT
<213> ORGANISM: Homo sapiens

<400> SEQUENCE: 64

Met Lys Tyr Ser Cys Cys Ala Leu Val Leu Ala Val Leu Gly Thr
 1               5                  10                  15

Glu Leu Leu Gly Ser Leu Cys Ser Thr Val Arg Ser Pro Arg Phe
                20                  25                  30

Arg Gly Arg Ile Gln Gln Glu Arg Lys Asn Ile Arg Pro Asn Ile
                35                  40                  45

Ile Leu Val Leu Thr Asp Asp Gln Asp Val Glu Leu Gly Ser Leu
                50                  55                  60

Gln Val Met Asn Lys Thr Arg Lys Ile Met Glu His Gly Gly Ala
                65                  70                  75

Thr Phe Ile Asn Ala Phe Val Thr Thr Pro Met Cys Cys Pro Ser
                80                  85                  90

Arg Ser Ser Met Leu Thr Gly Lys Tyr Val His Asn His Asn Val
                95                 100                 105

Tyr Thr Asn Asn Glu Asn Cys Ser Ser Pro Ser Trp Gln Ala Met
               110                 115                 120

His Glu Pro Arg Thr Phe Ala Val Tyr Leu Asn Asn Thr Gly Tyr
               125                 130                 135

Arg Thr Ala Phe Phe Gly Lys Tyr Leu Asn Glu Tyr Asn Gly Ser
               140                 145                 150

Tyr Ile Pro Pro Gly Trp Arg Glu Trp Leu Gly Leu Ile Lys Asn
               155                 160                 165

Ser Arg Phe Tyr Asn Tyr Thr Val Cys Arg Asn Gly Ile Lys Glu

```
            170                 175                 180
Lys His Gly Phe Asp Tyr Ala Lys Asp Tyr Phe Thr Asp Leu Ile
            185                 190                 195
Thr Asn Glu Ser Ile Asn Tyr Phe Lys Met Ser Lys Arg Met Tyr
            200                 205                 210
Pro His Arg Pro Val Met Met Val Ile Ser His Ala Ala Pro His
            215                 220                 225
Gly Pro Glu Asp Ser Ala Pro Gln Phe Ser Lys Leu Tyr Pro Asn
            230                 235                 240
Ala Ser Gln His Ile Thr Pro Ser Tyr Asn Tyr Ala Pro Asn Met
            245                 250                 255
Asp Lys His Trp Ile Met Gln Tyr Thr Gly Pro Met Leu Pro Ile
            260                 265                 270
His Met Glu Phe Thr Asn Ile Leu Gln Arg Lys Arg Leu Gln Thr
            275                 280                 285
Leu Met Ser Val Asp Ser Val Glu Arg Leu Tyr Asn Met Leu
            290                 295                 300
Val Glu Thr Gly Glu Leu Glu Asn Thr Tyr Ile Ile Tyr Thr Ala
            305                 310                 315
Asp His Gly Tyr His Ile Gly Gln Phe Gly Leu Val Lys Gly Lys
            320                 325                 330
Ser Met Pro Tyr Asp Phe Asp Ile Arg Val Pro Phe Phe Ile Arg
            335                 340                 345
Gly Pro Ser Val Glu Pro Gly Ser Ile Val Pro Gln Ile Val Leu
            350                 355                 360
Asn Ile Asp Leu Ala Pro Thr Ile Leu Asp Ile Ala Gly Leu Asp
            365                 370                 375
Thr Pro Pro Asp Val Asp Gly Lys Ser Val Leu Lys Leu Leu Asp
            380                 385                 390
Pro Glu Lys Pro Gly Asn Arg Phe Arg Thr Asn Lys Lys Ala Lys
            395                 400                 405
Ile Trp Arg Asp Thr Phe Leu Val Glu Arg Gly Lys Phe Leu Arg
            410                 415                 420
Lys Lys Glu Glu Ser Ser Lys Asn Ile Gln Gln Ser Asn His Leu
            425                 430                 435
Pro Lys Tyr Glu Arg Val Lys Glu Leu Cys Gln Gln Ala Arg Tyr
            440                 445                 450
Gln Thr Ala Cys Glu Gln Pro Gly Gln Lys Trp Gln Cys Ile Glu
            455                 460                 465
Asp Thr Ser Gly Lys Leu Arg Ile His Lys Cys Lys Gly Pro Ser
            470                 475                 480
Asp Leu Leu Thr Val Arg Gln Ser Thr Arg Asn Leu Tyr Ala Arg
            485                 490                 495
Gly Phe His Asp Lys Asp Lys Glu Cys Ser Cys Arg Glu Ser Gly
            500                 505                 510
Tyr Arg Ala Ser Arg Ser Gln Arg Lys Ser Gln Arg Gln Phe Leu
            515                 520                 525
Arg Asn Gln Gly Thr Pro Lys Tyr Lys Pro Arg Phe Val His Thr
            530                 535                 540
Arg Gln Thr Arg Ser Leu Ser Val Glu Phe Glu Gly Glu Ile Tyr
            545                 550                 555
Asp Ile Asn Leu Glu Glu Glu Glu Leu Gln Val Leu Gln Pro
            560                 565                 570
```

```
Arg Asn Ile Ala Lys Arg His Asp Glu Gly His Lys Gly Pro Arg
                575                 580                 585

Asp Leu Gln Ala Ser Ser Gly Gly Asn Arg Gly Arg Met Leu Ala
                590                 595                 600

Asp Ser Ser Asn Ala Val Gly Pro Pro Thr Thr Val Arg Val Thr
                605                 610                 615

His Lys Cys Phe Ile Leu Pro Asn Asp Ser Ile His Cys Glu Arg
                620                 625                 630

Glu Leu Tyr Gln Ser Ala Arg Ala Trp Lys Asp His Lys Ala Tyr
                635                 640                 645

Ile Asp Lys Glu Ile Glu Ala Leu Gln Asp Lys Ile Lys Asn Leu
                650                 655                 660

Arg Glu Val Arg Gly His Leu Lys Arg Arg Lys Pro Glu Glu Cys
                665                 670                 675

Ser Cys Ser Lys Gln Ser Tyr Tyr Asn Lys Glu Lys Gly Val Lys
                680                 685                 690

Lys Gln Glu Lys Leu Lys Ser His Leu His Pro Phe Lys Glu Ala
                695                 700                 705

Ala Gln Glu Val Asp Ser Lys Leu Gln Leu Phe Lys Glu Asn Asn
                710                 715                 720

Arg Arg Arg Lys Lys Glu Arg Lys Glu Lys Arg Arg Gln Arg Lys
                725                 730                 735

Gly Glu Glu Cys Ser Leu Pro Gly Leu Thr Cys Phe Thr His Asp
                740                 745                 750

Asn Asn His Trp Gln Thr Ala Pro Phe Trp Asn Leu Gly Ser Phe
                755                 760                 765

Cys Ala Cys Thr Ser Ser Asn Asn Asn Thr Tyr Trp Cys Leu Arg
                770                 775                 780

Thr Val Asn Glu Thr His Asn Phe Leu Phe Cys Glu Phe Ala Thr
                785                 790                 795

Gly Phe Leu Glu Tyr Phe Asp Met Asn Thr Asp Pro Tyr Gln Leu
                800                 805                 810

Thr Asn Thr Val His Thr Val Glu Arg Gly Ile Leu Asn Gln Leu
                815                 820                 825

His Val Gln Leu Met Glu Leu Arg Ser Cys Gln Gly Tyr Lys Gln
                830                 835                 840

Cys Asn Pro Arg Pro Lys Asn Leu Asp Val Gly Asn Lys Asp Gly
                845                 850                 855

Gly Ser Tyr Asp Leu His Arg Gly Gln Leu Trp Asp Gly Trp Glu
                860                 865                 870

Gly

<210> SEQ ID NO 65
<211> LENGTH: 1662
<212> TYPE: DNA
<213> ORGANISM: Homo sapiens

<400> SEQUENCE: 65
gcggccgcgt cgaccgggcc ctgcgggcgc ggggctgaag gcggaaccac          50
gacgggcaga gagcacggag ccgggaagcc cctgggcgcc cgtcggaggg         100
ctatggagca gcggccgcgg ggctgcgcgg cggtggcggc ggcgctcctc         150
ctggtgctgc tggggccccg ggcccagggc ggcactcgta gcccaggtg          200 tgactgtgcc ggtgacttcc acaagaagat tggtctgttt gttgcagag          250
```

-continued

| | |
|---|---|
| gctgcccagc gggcactac ctgaaggccc cttgcacgga gccctgcggc | 300 |
| aactccacct gccttgtgtg tccccaagac accttcttgg cctgggagaa | 350 |
| ccaccataat tctgaatgtg cccgctgcca ggcctgtgat gagcaggcct | 400 |
| cccaggtggc gctggagaac tgttcagcag tggccgacac ccgctgtggc | 450 |
| tgtaagccag gctggtttgt ggagtgccag gtcagccaat gtgtcagcag | 500 |
| ttcacccttc tactgccaac catgcctaga ctgcggggcc ctgcaccgcc | 550 |
| acacacggct actctgttcc cgcagagata ctgactgtgg gacctgcctg | 600 |
| cctggcttct atgaacatgg cgatggctgc gtgtcctgcc ccacgagcac | 650 |
| cctggggagc tgtccagagc gctgtgccgc tgtctgtggc tggaggcaga | 700 |
| tgttctgggt ccaggtgctc ctggctggcc ttgtggtccc cctcctgctt | 750 |
| ggggccaccc tgacctacac ataccgccac tgctggcctc acaagcccct | 800 |
| ggttactgca gatgaagctg ggatggaggc tctgacccca ccaccggcca | 850 |
| cccatctgtc acccttggac agcgcccaca cccttctagc acctcctgac | 900 |
| agcagtgaga gatctgcac cgtccagttg gtgggtaaca gctggacccc | 950 |
| tggctacccc gagacccagg aggcgctctg cccgcaggtg acatggtcct | 1000 |
| gggaccagtt gcccagcaga gctcttggcc ccgctgctgc gcccacactc | 1050 |
| tcgccagagt ccccagccgg ctcgccagcc atgatgctgc agccgggccc | 1100 |
| gcagctctac gacgtgatgg acgcggtccc agcgcggcgc tggaaggagt | 1150 |
| tcgtgcgcac gctggggctg cgcgaggcag agatcgaagc cgtggaggtg | 1200 |
| gagatcggcc gcttccgaga ccagcagtac gagatgctca gcgctggcg | 1250 |
| ccagcagcag cccgcgggcc tcggagccgt ttacgcggcc ctggagcgca | 1300 |
| tggggctgga cggctgcgtg gaagacttgc gcagccgcct gcagcgcggc | 1350 |
| ccgtgacacg gcgcccactt gccacctagg cgctctggtg gcccttgcag | 1400 |
| aagccctaag tacggttact tatgcgtgta gacatttat gtcacttatt | 1450 |
| aagccgctgg cacggccctg cgtagcagca ccagccggcc ccaccctgc | 1500 |
| tcgcccctat cgctccagcc aaggcgaaga agcacgaacg aatgtcgaga | 1550 |
| gggggtgaag acatttctca acttctcggc cggagtttgg ctgagatcgc | 1600 |
| ggtattaaat ctgtgaaaga aacaaaaaaa aaaaaaaaa aaaaaaaagt | 1650 |
| cgacgcggcc gc | 1662 |

<210> SEQ ID NO 66
<211> LENGTH: 417
<212> TYPE: PRT
<213> ORGANISM: Homo sapiens

<400> SEQUENCE: 66

Met Glu Gln Arg Pro Arg Gly Cys Ala Ala Val Ala Ala Ala Leu
1               5                   10                  15

Leu Leu Val Leu Leu Gly Ala Arg Ala Gln Gly Gly Thr Arg Ser
                20                  25                  30

Pro Arg Cys Asp Cys Ala Gly Asp Phe His Lys Lys Ile Gly Leu
        35                  40                  45

Phe Cys Cys Arg Gly Cys Pro Ala Gly His Tyr Leu Lys Ala Pro
        50                  55                  60

Cys Thr Glu Pro Cys Gly Asn Ser Thr Cys Leu Val Cys Pro Gln
        65                  70                  75

Asp Thr Phe Leu Ala Trp Glu Asn His His Asn Ser Glu Cys Ala
            80                  85                  90

Arg Cys Gln Ala Cys Asp Glu Gln Ala Ser Gln Val Ala Leu Glu
        95                 100                 105

Asn Cys Ser Ala Val Ala Asp Thr Arg Cys Gly Cys Lys Pro Gly
            110                 115                 120

Trp Phe Val Glu Cys Gln Val Ser Gln Cys Val Ser Ser Ser Pro
        125                 130                 135

Phe Tyr Cys Gln Pro Cys Leu Asp Cys Gly Ala Leu His Arg His
        140                 145                 150

Thr Arg Leu Leu Cys Ser Arg Arg Asp Thr Asp Cys Gly Thr Cys
            155                 160                 165

Leu Pro Gly Phe Tyr Glu His Gly Asp Gly Cys Val Ser Cys Pro
            170                 175                 180

Thr Ser Thr Leu Gly Ser Cys Pro Glu Arg Cys Ala Ala Val Cys
            185                 190                 195

Gly Trp Arg Gln Met Phe Trp Val Gln Val Leu Leu Ala Gly Leu
            200                 205                 210

Val Val Pro Leu Leu Leu Gly Ala Thr Leu Thr Tyr Thr Tyr Arg
            215                 220                 225

His Cys Trp Pro His Lys Pro Leu Val Thr Ala Asp Glu Ala Gly
            230                 235                 240

Met Glu Ala Leu Thr Pro Pro Ala Thr His Leu Ser Pro Leu
            245                 250                 255

Asp Ser Ala His Thr Leu Leu Ala Pro Pro Asp Ser Ser Glu Lys
            260                 265                 270

Ile Cys Thr Val Gln Leu Val Gly Asn Ser Trp Thr Pro Gly Tyr
            275                 280                 285

Pro Glu Thr Gln Glu Ala Leu Cys Pro Gln Val Thr Trp Ser Trp
            290                 295                 300

Asp Gln Leu Pro Ser Arg Ala Leu Gly Pro Ala Ala Ala Pro Thr
            305                 310                 315

Leu Ser Pro Glu Ser Pro Ala Gly Ser Pro Ala Met Met Leu Gln
            320                 325                 330

Pro Gly Pro Gln Leu Tyr Asp Val Met Asp Ala Val Pro Ala Arg
            335                 340                 345

Arg Trp Lys Glu Phe Val Arg Thr Leu Gly Leu Arg Glu Ala Glu
            350                 355                 360

Ile Glu Ala Val Glu Val Glu Ile Gly Arg Phe Arg Asp Gln Gln
            365                 370                 375

Tyr Glu Met Leu Lys Arg Trp Arg Gln Gln Pro Ala Gly Leu
            380                 385                 390

Gly Ala Val Tyr Ala Ala Leu Glu Arg Met Gly Leu Asp Gly Cys
            395                 400                 405

Val Glu Asp Leu Arg Ser Arg Leu Gln Arg Gly Pro
            410                 415

<210> SEQ ID NO 67
<211> LENGTH: 43
<212> TYPE: DNA
<213> ORGANISM: Artificial sequence
<220> FEATURE:
<223> OTHER INFORMATION: oligonucleotide probe

<400> SEQUENCE: 67

```
tgtaaaacga cggccagtta aatagacctg caattattaa tct          43
```

<210> SEQ ID NO 68
<211> LENGTH: 41
<212> TYPE: DNA
<213> ORGANISM: Artificial sequence
<220> FEATURE:
<223> OTHER INFORMATION: oligonucleotide probe

<400> SEQUENCE: 68

```
caggaaacag ctatgaccac ctgcacacct gcaaatccat t            41
```

<210> SEQ ID NO 69
<211> LENGTH: 33
<212> TYPE: DNA
<213> ORGANISM: Artificial sequence
<220> FEATURE:
<223> OTHER INFORMATION: oligonucleotide probe

<400> SEQUENCE: 69

```
gctgacgaac caaggcaact acaaactcct ggt                     33
```

<210> SEQ ID NO 70
<211> LENGTH: 41
<212> TYPE: DNA
<213> ORGANISM: Artificial sequence
<220> FEATURE:
<223> OTHER INFORMATION: oligonucleotide probe

<400> SEQUENCE: 70

```
tgcggccgga ccagtcctcc atggtcacca ggagtttgta g            41
```

<210> SEQ ID NO 71
<211> LENGTH: 33
<212> TYPE: DNA
<213> ORGANISM: Artificial sequence
<220> FEATURE:
<223> OTHER INFORMATION: oligonucleotide probe

<400> SEQUENCE: 71

```
ggtggtgaac tgcttgccgt tgtgccatgt aaa                     33
```

<210> SEQ ID NO 72
<211> LENGTH: 22
<212> TYPE: DNA
<213> ORGANISM: Artificial sequence
<220> FEATURE:
<223> OTHER INFORMATION: oligonucleotide probe

<400> SEQUENCE: 72

```
aaagacgcat ctgcgagtgt cc                                 22
```

<210> SEQ ID NO 73
<211> LENGTH: 23
<212> TYPE: DNA
<213> ORGANISM: Artificial sequence
<220> FEATURE:
<223> OTHER INFORMATION: oligonucleotide probe

<400> SEQUENCE: 73

```
tgctgatttc acactgctct ccc                                23
```

<210> SEQ ID NO 74
<211> LENGTH: 49
<212> TYPE: DNA
<213> ORGANISM: Artificial sequence
<220> FEATURE:

```
<223> OTHER INFORMATION: oligonucleotide probe

<400> SEQUENCE: 74
cccacgatgt atgaatggtg gactttgtgt gactcctggt  ttctgcatc           49

<210> SEQ ID NO 75
<211> LENGTH: 24
<212> TYPE: DNA
<213> ORGANISM: Artificial sequence
<220> FEATURE:
<223> OTHER INFORMATION: oligonucleotide probe

<400> SEQUENCE: 75
ccaactacca aagctgctgg  agcc                                       24

<210> SEQ ID NO 76
<211> LENGTH: 24
<212> TYPE: DNA
<213> ORGANISM: Artificial sequence
<220> FEATURE:
<223> OTHER INFORMATION: oligonucleotide probe

<400> SEQUENCE: 76
gcagctctat taccacggga  agga                                       24

<210> SEQ ID NO 77
<211> LENGTH: 24
<212> TYPE: DNA
<213> ORGANISM: Artificial sequence
<220> FEATURE:
<223> OTHER INFORMATION: oligonucleotide probe

<400> SEQUENCE: 77
tccttcccgt ggtaatagag  ctgc                                       24

<210> SEQ ID NO 78
<211> LENGTH: 45
<212> TYPE: DNA
<213> ORGANISM: Artificial sequence
<220> FEATURE:
<223> OTHER INFORMATION: oligonucleotide probe

<400> SEQUENCE: 78
ggcagagaac cagaggccgg aggagactgc ctctttacag  ccagg                45

<210> SEQ ID NO 79
<211> LENGTH: 24
<212> TYPE: DNA
<213> ORGANISM: Artificial sequence
<220> FEATURE:
<223> OTHER INFORMATION: oligonucleotide probe

<400> SEQUENCE: 79
tggctactcc aagaccctgg  catg                                       24

<210> SEQ ID NO 80
<211> LENGTH: 24
<212> TYPE: DNA
<213> ORGANISM: Artificial sequence
<220> FEATURE:
<223> OTHER INFORMATION: oligonucleotide probe

<400> SEQUENCE: 80
tggacaaatc cccttgctca  gccc                                       24

<210> SEQ ID NO 81
```

```
<211> LENGTH: 50
<212> TYPE: DNA
<213> ORGANISM: Artificial sequence
<220> FEATURE:
<223> OTHER INFORMATION: oligonucleotide probe

<400> SEQUENCE: 81
gggcttcacc gaagcagtgg acctttattt tgaccacctg atgtccaggg        50

<210> SEQ ID NO 82
<211> LENGTH: 22
<212> TYPE: DNA
<213> ORGANISM: Artificial sequence
<220> FEATURE:
<223> OTHER INFORMATION: oligonucleotide probe

<400> SEQUENCE: 82
atcgttgtga agttagtgcc  cc                                     22

<210> SEQ ID NO 83
<211> LENGTH: 23
<212> TYPE: DNA
<213> ORGANISM: Artificial sequence
<220> FEATURE:
<223> OTHER INFORMATION: oligonucleotide probe

<400> SEQUENCE: 83
acctgcgata tccaacagaa  ttg                                    23

<210> SEQ ID NO 84
<211> LENGTH: 48
<212> TYPE: DNA
<213> ORGANISM: Artificial sequence
<220> FEATURE:
<223> OTHER INFORMATION: oligonucleotide probe

<400> SEQUENCE: 84
ggaagaggat acagtcactc tggaagtatt agtggctcca  gcagttcc         48

<210> SEQ ID NO 85
<211> LENGTH: 22
<212> TYPE: DNA
<213> ORGANISM: Artificial sequence
<220> FEATURE:
<223> OTHER INFORMATION: oligonucleotide probe

<400> SEQUENCE: 85
agggtctcca ggagaaagac  tc                                     22

<210> SEQ ID NO 86
<211> LENGTH: 24
<212> TYPE: DNA
<213> ORGANISM: Artificial sequence
<220> FEATURE:
<223> OTHER INFORMATION: oligonucleotide probe

<400> SEQUENCE: 86
attgtgggcc ttgcagacat  agac                                   24

<210> SEQ ID NO 87
<211> LENGTH: 50
<212> TYPE: DNA
<213> ORGANISM: Artificial sequence
<220> FEATURE:
<223> OTHER INFORMATION: oligonucleotide probe

<400> SEQUENCE: 87
```
ggccacagca tcaaaacctt agaactcaat gtactggttc ctccagctcc                50

<210> SEQ ID NO 88
<211> LENGTH: 22
<212> TYPE: DNA
<213> ORGANISM: Artificial sequence
<220> FEATURE:
<223> OTHER INFORMATION: oligonucleotide probe

<400> SEQUENCE: 88
gctaggaatt ccacagaagc cc                                              22

<210> SEQ ID NO 89
<211> LENGTH: 22
<212> TYPE: DNA
<213> ORGANISM: Artificial sequence
<220> FEATURE:
<223> OTHER INFORMATION: oligonucleotide probe

<400> SEQUENCE: 89
aacctggaat gtcaccgagc tg                                              22

<210> SEQ ID NO 90
<211> LENGTH: 26
<212> TYPE: DNA
<213> ORGANISM: Artificial sequence
<220> FEATURE:
<223> OTHER INFORMATION: oligonucleotide probe

<400> SEQUENCE: 90
cctagcacag tgacgaggga cttggc                                          26

<210> SEQ ID NO 91
<211> LENGTH: 50
<212> TYPE: DNA
<213> ORGANISM: Artificial sequence
<220> FEATURE:
<223> OTHER INFORMATION: oligonucleotide probe

<400> SEQUENCE: 91
aagacacagc caccctaaac tgtcagtctt ctgggagcaa gcctgcagcc                50

<210> SEQ ID NO 92
<211> LENGTH: 50
<212> TYPE: DNA
<213> ORGANISM: Artificial sequence
<220> FEATURE:
<223> OTHER INFORMATION: oligonucleotide probe

<400> SEQUENCE: 92
gccctggcag acgagggcga gtacacctgc tcaatcttca ctatgcctgt                50

<210> SEQ ID NO 93
<211> LENGTH: 22
<212> TYPE: DNA
<213> ORGANISM: Artificial sequence
<220> FEATURE:
<223> OTHER INFORMATION: oligonucleotide probe

<400> SEQUENCE: 93
ccgattcata gacctcgaga gt                                              22

<210> SEQ ID NO 94
<211> LENGTH: 22
<212> TYPE: DNA
<213> ORGANISM: Artificial sequence
<220> FEATURE:

```
<223> OTHER INFORMATION: oligonucleotide probe

<400> SEQUENCE: 94
gtcaaggagt cctccacaat ac                                      22

<210> SEQ ID NO 95
<211> LENGTH: 45
<212> TYPE: DNA
<213> ORGANISM: Artificial sequence
<220> FEATURE:
<223> OTHER INFORMATION: oligonucleotide probe

<400> SEQUENCE: 95
gtgtacaatg gccatgccaa tggccagcgc attggccgct tctgt             45

<210> SEQ ID NO 96
<211> LENGTH: 19
<212> TYPE: DNA
<213> ORGANISM: Artificial sequence
<220> FEATURE:
<223> OTHER INFORMATION: oligonucleotide probe

<400> SEQUENCE: 96
tcctgcagtt tcctgatgc                                          19

<210> SEQ ID NO 97
<211> LENGTH: 24
<212> TYPE: DNA
<213> ORGANISM: Artificial sequence
<220> FEATURE:
<223> OTHER INFORMATION: oligonucleotide probe

<400> SEQUENCE: 97
ctcatattgc acaccagtaa ttcg                                    24

<210> SEQ ID NO 98
<211> LENGTH: 45
<212> TYPE: DNA
<213> ORGANISM: Artificial sequence
<220> FEATURE:
<223> OTHER INFORMATION: oligonucleotide probe

<400> SEQUENCE: 98
atgaggagaa acgtttgatg gtggagctgc acaacctcta ccggg             45

<210> SEQ ID NO 99
<211> LENGTH: 24
<212> TYPE: DNA
<213> ORGANISM: Artificial sequence
<220> FEATURE:
<223> OTHER INFORMATION: oligonucleotide probe

<400> SEQUENCE: 99
tacaggccca gtcaggacca gggg                                    24

<210> SEQ ID NO 100
<211> LENGTH: 18
<212> TYPE: DNA
<213> ORGANISM: Artificial sequence
<220> FEATURE:
<223> OTHER INFORMATION: oligonucleotide probe

<400> SEQUENCE: 100
agccagcctc gctctcgg                                           18

<210> SEQ ID NO 101
```

```
<211> LENGTH: 18
<212> TYPE: DNA
<213> ORGANISM: Artificial sequence
<220> FEATURE:
<223> OTHER INFORMATION: oligonucleotide probe

<400> SEQUENCE: 101
gtctgcgatc aggtctgg                                                  18

<210> SEQ ID NO 102
<211> LENGTH: 20
<212> TYPE: DNA
<213> ORGANISM: Artificial sequence
<220> FEATURE:
<223> OTHER INFORMATION: oligonucleotide probe

<400> SEQUENCE: 102
gaaagaggca atggattcgc                                                20

<210> SEQ ID NO 103
<211> LENGTH: 24
<212> TYPE: DNA
<213> ORGANISM: Artificial sequence
<220> FEATURE:
<223> OTHER INFORMATION: oligonucleotide probe

<400> SEQUENCE: 103
gacttacact tgccagcaca gcac                                           24

<210> SEQ ID NO 104
<211> LENGTH: 45
<212> TYPE: DNA
<213> ORGANISM: Artificial sequence
<220> FEATURE:
<223> OTHER INFORMATION: oligonucleotide probe

<400> SEQUENCE: 104
ggagcaccac caactggagg gtccggagta gcgagcgccc cgaag                    45

<210> SEQ ID NO 105
<211> LENGTH: 22
<212> TYPE: DNA
<213> ORGANISM: Artificial sequence
<220> FEATURE:
<223> OTHER INFORMATION: oligonucleotide probe

<400> SEQUENCE: 105
ccctccactg ccccaccgac tg                                             22

<210> SEQ ID NO 106
<211> LENGTH: 24
<212> TYPE: DNA
<213> ORGANISM: Artificial sequence
<220> FEATURE:
<223> OTHER INFORMATION: oligonucleotide probe

<400> SEQUENCE: 106
cggttctggg gacgttaggg ctcg                                           24

<210> SEQ ID NO 107
<211> LENGTH: 25
<212> TYPE: DNA
<213> ORGANISM: Artificial sequence
<220> FEATURE:
<223> OTHER INFORMATION: oligonucleotide probe

<400> SEQUENCE: 107
```

```
ctgcccaccg tccacctgcc tcaat                                      25

<210> SEQ ID NO 108
<211> LENGTH: 45
<212> TYPE: DNA
<213> ORGANISM: Artificial sequence
<220> FEATURE:
<223> OTHER INFORMATION: oligonucleotide probe

<400> SEQUENCE: 108
aggactgccc accgtccacc tgcctcaatg ggggcacatg ccacc                45

<210> SEQ ID NO 109
<211> LENGTH: 45
<212> TYPE: DNA
<213> ORGANISM: Artificial sequence
<220> FEATURE:
<223> OTHER INFORMATION: oligonucleotide probe

<400> SEQUENCE: 109
acgcaaagcc ctacatctaa gccagagaga gacagggcag ctggg                45

<210> SEQ ID NO 110
<211> LENGTH: 24
<212> TYPE: DNA
<213> ORGANISM: Artificial sequence
<220> FEATURE:
<223> OTHER INFORMATION: oligonucleotide probe

<400> SEQUENCE: 110
tggctgccct gcagtacctc tacc                                       24

<210> SEQ ID NO 111
<211> LENGTH: 24
<212> TYPE: DNA
<213> ORGANISM: Artificial sequence
<220> FEATURE:
<223> OTHER INFORMATION: oligonucleotide probe

<400> SEQUENCE: 111
ccctgcaggt cattggcagc tagg                                       24

<210> SEQ ID NO 112
<211> LENGTH: 45
<212> TYPE: DNA
<213> ORGANISM: Artificial sequence
<220> FEATURE:
<223> OTHER INFORMATION: oligonucleotide probe

<400> SEQUENCE: 112
aggcactgcc tgatgacacc ttccgcgacc tgggcaacct cacac                45

<210> SEQ ID NO 113
<211> LENGTH: 20
<212> TYPE: DNA
<213> ORGANISM: Artificial sequence
<220> FEATURE:
<223> OTHER INFORMATION: oligonucleotide probe

<400> SEQUENCE: 113
ggctgtcact gtggagacac                                            20

<210> SEQ ID NO 114
<211> LENGTH: 18
<212> TYPE: DNA
<213> ORGANISM: Artificial sequence
<220> FEATURE:
```

<223> OTHER INFORMATION: oligonucleotide probe

<400> SEQUENCE: 114
gcaaggtcat tacagctg                                              18

<210> SEQ ID NO 115
<211> LENGTH: 23
<212> TYPE: DNA
<213> ORGANISM: Artificial sequence
<220> FEATURE:
<223> OTHER INFORMATION: oligonucleotide probe

<400> SEQUENCE: 115
agaacatagg agcagtccca ctc                                        23

<210> SEQ ID NO 116
<211> LENGTH: 23
<212> TYPE: DNA
<213> ORGANISM: Artificial sequence
<220> FEATURE:
<223> OTHER INFORMATION: oligonucleotide probe

<400> SEQUENCE: 116
tgcctgctgc tgcacaatct cag                                        23

<210> SEQ ID NO 117
<211> LENGTH: 45
<212> TYPE: DNA
<213> ORGANISM: Artificial sequence
<220> FEATURE:
<223> OTHER INFORMATION: oligonucleotide probe

<400> SEQUENCE: 117
ggctattgct tgccttggga cagaccctgt ggcttaggct ctggc                45

<210> SEQ ID NO 118
<211> LENGTH: 24
<212> TYPE: DNA
<213> ORGANISM: Artificial sequence
<220> FEATURE:
<223> OTHER INFORMATION: oligonucleotide probe

<400> SEQUENCE: 118
gtaagcacat gcctccagag gtgc                                       24

<210> SEQ ID NO 119
<211> LENGTH: 24
<212> TYPE: DNA
<213> ORGANISM: Artificial sequence
<220> FEATURE:
<223> OTHER INFORMATION: oligonucleotide probe

<400> SEQUENCE: 119
gtgacgtgga tgcttgggat gttg                                       24

<210> SEQ ID NO 120
<211> LENGTH: 50
<212> TYPE: DNA
<213> ORGANISM: Artificial sequence
<220> FEATURE:
<223> OTHER INFORMATION: oligonucleotide probe

<400> SEQUENCE: 120
tggacacctt cagtattgat gccaagacag gccaggtcat tctgcgtcga           50

<210> SEQ ID NO 121

-continued

```
<211> LENGTH: 22
<212> TYPE: DNA
<213> ORGANISM: Artificial sequence
<220> FEATURE:
<223> OTHER INFORMATION: oligonucleotide probe

<400> SEQUENCE: 121
atgtttgtgt ggaagtgccc cg                                              22

<210> SEQ ID NO 122
<211> LENGTH: 18
<212> TYPE: DNA
<213> ORGANISM: Artificial sequence
<220> FEATURE:
<223> OTHER INFORMATION: oligonucleotide probe

<400> SEQUENCE: 122
gtcaacatgc tcctctgc                                                   18

<210> SEQ ID NO 123
<211> LENGTH: 26
<212> TYPE: DNA
<213> ORGANISM: Artificial sequence
<220> FEATURE:
<223> OTHER INFORMATION: oligonucleotide probe

<400> SEQUENCE: 123
aatccattgt gcactgcagc tctagg                                          26

<210> SEQ ID NO 124
<211> LENGTH: 23
<212> TYPE: DNA
<213> ORGANISM: Artificial sequence
<220> FEATURE:
<223> OTHER INFORMATION: oligonucleotide probe

<400> SEQUENCE: 124
gagcatgcca ccactggact gac                                             23

<210> SEQ ID NO 125
<211> LENGTH: 54
<212> TYPE: DNA
<213> ORGANISM: Artificial sequence
<220> FEATURE:
<223> OTHER INFORMATION: oligonucleotide probe

<400> SEQUENCE: 125
gccgatgctg tcctagtgga aacaactcca ctgtaactag attgatctat                50
gcac                                                                  54

<210> SEQ ID NO 126
<211> LENGTH: 25
<212> TYPE: DNA
<213> ORGANISM: Artificial sequence
<220> FEATURE:
<223> OTHER INFORMATION: oligonucleotide probe

<400> SEQUENCE: 126
ccagacgctg ctcttcgaaa gggtc                                           25

<210> SEQ ID NO 127
<211> LENGTH: 23
<212> TYPE: DNA
<213> ORGANISM: Artificial sequence
<220> FEATURE:
<223> OTHER INFORMATION: oligonucleotide probe
```

```
<400> SEQUENCE: 127
ggtccccgta ggccaggtcc agc                                              23

<210> SEQ ID NO 128
<211> LENGTH: 50
<212> TYPE: DNA
<213> ORGANISM: Artificial sequence
<220> FEATURE:
<223> OTHER INFORMATION: oligonucleotide probe

<400> SEQUENCE: 128
ctacttcttc agcctcaatg tgcacagctg gaattacaag gagacgtacg                 50

<210> SEQ ID NO 129
<211> LENGTH: 24
<212> TYPE: DNA
<213> ORGANISM: Artificial sequence
<220> FEATURE:
<223> OTHER INFORMATION: oligonucleotide probe

<400> SEQUENCE: 129
gctgctttgc tcacaactgc tcgc                                             24

<210> SEQ ID NO 130
<211> LENGTH: 18
<212> TYPE: DNA
<213> ORGANISM: Artificial sequence
<220> FEATURE:
<223> OTHER INFORMATION: oligonucleotide probe

<400> SEQUENCE: 130
catgacacct tcctgctg                                                    18

<210> SEQ ID NO 131
<211> LENGTH: 24
<212> TYPE: DNA
<213> ORGANISM: Artificial sequence
<220> FEATURE:
<223> OTHER INFORMATION: oligonucleotide probe

<400> SEQUENCE: 131
cagccatggg tgactgtgac ctcc                                             24

<210> SEQ ID NO 132
<211> LENGTH: 24
<212> TYPE: DNA
<213> ORGANISM: Artificial sequence
<220> FEATURE:
<223> OTHER INFORMATION: oligonucleotide probe

<400> SEQUENCE: 132
ctcctgggag tcggtagcaa cacc                                             24

<210> SEQ ID NO 133
<211> LENGTH: 18
<212> TYPE: DNA
<213> ORGANISM: Artificial sequence
<220> FEATURE:
<223> OTHER INFORMATION: oligonucleotide probe

<400> SEQUENCE: 133
gggaggtcac agtcaccc                                                    18

<210> SEQ ID NO 134
<211> LENGTH: 23
<212> TYPE: DNA
```

```
<213> ORGANISM: Artificial sequence
<220> FEATURE:
<223> OTHER INFORMATION: oligonucleotide probe

<400> SEQUENCE: 134
ggctgggctt tccaccctgg cac                                        23

<210> SEQ ID NO 135
<211> LENGTH: 40
<212> TYPE: DNA
<213> ORGANISM: Artificial sequence
<220> FEATURE:
<223> OTHER INFORMATION: oligonucleotide probe

<400> SEQUENCE: 135
cagccatggg tgactgtgac ctccctgagt tttgcacggg                      40

<210> SEQ ID NO 136
<211> LENGTH: 21
<212> TYPE: DNA
<213> ORGANISM: Artificial sequence
<220> FEATURE:
<223> OTHER INFORMATION: oligonucleotide probe

<400> SEQUENCE: 136
gagctgaagt cagcctttga g                                          21

<210> SEQ ID NO 137
<211> LENGTH: 20
<212> TYPE: DNA
<213> ORGANISM: Artificial sequence
<220> FEATURE:
<223> OTHER INFORMATION: oligonucleotide probe

<400> SEQUENCE: 137
ctctgcagaa gtctcgttcc                                            20

<210> SEQ ID NO 138
<211> LENGTH: 19
<212> TYPE: DNA
<213> ORGANISM: Artificial sequence
<220> FEATURE:
<223> OTHER INFORMATION: oligonucleotide probe

<400> SEQUENCE: 138
ctgaccggtc cgctcatgg                                             19

<210> SEQ ID NO 139
<211> LENGTH: 21
<212> TYPE: DNA
<213> ORGANISM: Artificial sequence
<220> FEATURE:
<223> OTHER INFORMATION: oligonucleotide probe

<400> SEQUENCE: 139
cagcatgctt tccgcgaagt c                                          21

<210> SEQ ID NO 140
<211> LENGTH: 46
<212> TYPE: DNA
<213> ORGANISM: Artificial sequence
<220> FEATURE:
<223> OTHER INFORMATION: oligonucleotide probe

<400> SEQUENCE: 140
ggcaggaagg ccaggggtgc tgagttcttc acctcctttt agactg                46
```

```
<210> SEQ ID NO 141
<211> LENGTH: 27
<212> TYPE: DNA
<213> ORGANISM: Artificial sequence
<220> FEATURE:
<223> OTHER INFORMATION: oligonucleotide probe

<400> SEQUENCE: 141
ggcgctctgg tggcccttgc agaagcc                                    27

<210> SEQ ID NO 142
<211> LENGTH: 25
<212> TYPE: DNA
<213> ORGANISM: Artificial sequence
<220> FEATURE:
<223> OTHER INFORMATION: oligonucleotide probe

<400> SEQUENCE: 142
ttcggccgag aagttgagaa atgtc                                      25
```